US010806737B2

(12) United States Patent
Crew et al.

(10) Patent No.: US 10,806,737 B2
(45) Date of Patent: Oct. 20, 2020

(54) COMPOUNDS AND METHODS FOR THE TARGETED DEGRADATION OF FETAL LIVER KINASE POLYPEPTIDES

(71) Applicants: Arvinas Operations, Inc., New Haven, CT (US); Yale University, New Haven, CT (US)

(72) Inventors: Andrew P. Crew, Guilford, CT (US); Keith R. Hornberger, Southbury, CT (US); Craig M. Crews, New Haven, CT (US); George Burslem, Sandwich (GB)

(73) Assignees: Arvinas Operations, Inc., New Haven, CT (US); Yale University, New Haven, CT (US)

( * ) Notice: Subject to any disclaimer, the term of this patent is extended or adjusted under 35 U.S.C. 154(b) by 0 days.

(21) Appl. No.: 15/840,950

(22) Filed: Dec. 13, 2017

(65) Prior Publication Data
US 2018/0256586 A1 Sep. 13, 2018

Related U.S. Application Data

(60) Provisional application No. 62/450,716, filed on Jan. 26, 2017, provisional application No. 62/438,844, filed on Dec. 23, 2016.

(51) Int. Cl.
*A61K 31/529* (2006.01)
*C07D 417/12* (2006.01)
*C07D 498/08* (2006.01)
*C07D 405/14* (2006.01)
*C07D 471/04* (2006.01)
*C07D 519/00* (2006.01)
*C07D 513/04* (2006.01)
*A61P 35/00* (2006.01)
*A61K 47/54* (2017.01)
*C07D 401/14* (2006.01)
*C07D 498/22* (2006.01)
*A61P 35/02* (2006.01)
*A61K 31/429* (2006.01)
*A61K 31/454* (2006.01)
*A61K 45/06* (2006.01)

(52) U.S. Cl.
CPC .......... *A61K 31/529* (2013.01); *A61K 31/429* (2013.01); *A61K 31/454* (2013.01); *A61K 45/06* (2013.01); *A61K 47/555* (2017.08); *A61P 35/00* (2018.01); *A61P 35/02* (2018.01); *C07D 401/14* (2013.01); *C07D 405/14* (2013.01); *C07D 417/12* (2013.01); *C07D 471/04* (2013.01); *C07D 498/08* (2013.01); *C07D 498/22* (2013.01); *C07D 513/04* (2013.01); *C07D 519/00* (2013.01)

(58) Field of Classification Search
CPC .................................................. C07D 513/04
See application file for complete search history.

(56) References Cited

U.S. PATENT DOCUMENTS

| 6,306,663 | B1 | 10/2001 | Kenten et al. |
|---|---|---|---|
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Sakamoto et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,915,293 | B2 | 3/2011 | Ramesh |
| 9,500,653 | B2 | 11/2016 | Crews et al. |
| 9,632,089 | B2 | 4/2017 | Crews et al. |
| 2006/0128632 | A1 | 6/2006 | Sharma et al. |
| 2006/0281768 | A1 | 12/2006 | Gaul |
| 2007/0149572 | A1 | 6/2007 | Ballentine et al. |
| 2007/0281907 | A1 | 12/2007 | Watkins |
| 2008/0051432 | A1 | 2/2008 | Zhang |
| 2008/0214501 | A1 | 9/2008 | Pan et al. |

(Continued)

FOREIGN PATENT DOCUMENTS

| CN | 1844118 A | 10/2006 |
|---|---|---|
| CN | 103688176 A | 3/2014 |

(Continued)

OTHER PUBLICATIONS

Zawilska. Pharmacological Reports, 2013, 65, 1-14 (Year: 2013).*
Sanz. Current Opinion in Oncology, 2009, 21, 594-600 (Year: 2009).*
"Stereoisomer", PAC, 1996, 68, 1213, attached as PDF (Year: 1996).*
Ahn, et al., "HIF-lalpha peptide derivatives with modifications at the hydroxyproline residue as activators of HIF-lalpha", Bioorg Med Chem Lett. 19(15), 2009, 4403-4405.
Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).
Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).

(Continued)

*Primary Examiner* — Noble E Jarrell
(74) *Attorney, Agent, or Firm* — Bryan D. Zerhusen, Esq.; Nicholas R. Herrel, Esq.; Cantor Colburn LLP

(57) ABSTRACT

The present disclosure relates to bifunctional compounds, which find utility as modulators of FLT3 (target protein). In particular, the present disclosure is directed to bifunctional compounds, which contain on one end a Von Hppel-Lindau, cereblon, ligand which binds to the E3 ubiquitin ligase and on the other end a moiety which binds the target protein FLT3, such that the target protein is placed in proximity to the ubiquitin ligase to effect degradation (and inhibition) of target protein. The present disclosure exhibits a broad range of pharmacological activities associated with degradation/ inhibition of the target protein. Diseases or disorders that result from aggregation or accumulation of the target protein are treated or prevented with compounds and compositions of the present disclosure.

23 Claims, 9 Drawing Sheets

(56) References Cited

U.S. PATENT DOCUMENTS

| | | |
|---|---|---|
| 2008/0269140 A1 | 10/2008 | Wang et al. |
| 2009/0054358 A1 | 2/2009 | Small et al. |
| 2010/0203012 A1 | 8/2010 | Laurent et al. |
| 2011/0195043 A1 | 8/2011 | Sun et al. |
| 2012/0270800 A1 | 10/2012 | Verdine et al. |
| 2013/0274259 A1 | 10/2013 | Zhang et al. |
| 2014/0088143 A1 | 3/2014 | Jain |
| 2014/0235629 A1 | 8/2014 | Bartberger et al. |
| 2014/0243372 A1 | 8/2014 | Rew |
| 2014/0275168 A1 | 9/2014 | Nam et al. |
| 2014/0302523 A1 | 10/2014 | Crews et al. |
| 2014/0329800 A1 | 11/2014 | Gao et al. |
| 2014/0356322 A1 | 12/2014 | Crews et al. |
| 2015/0045339 A1 | 2/2015 | Takasaki et al. |
| 2015/0119421 A1 | 4/2015 | Jain |
| 2015/0119435 A1 | 4/2015 | Crews et al. |
| 2015/0259288 A1 | 9/2015 | Nam et al. |
| 2015/0291562 A1 | 10/2015 | Crew et al. |
| 2015/0344473 A1 | 10/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0303109 A1 | 10/2016 | Jain |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1* | 5/2017 | Crews ................ C07K 5/06034 |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |

FOREIGN PATENT DOCUMENTS

| | | |
|---|---|---|
| EP | 2985285 | 2/2016 |
| JP | A 2004-525889 | 8/2004 |
| JP | A 2010-502627 | 1/2010 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 2000/066119 | 11/2000 |
| WO | WO 2002/066512 | 8/2002 |
| WO | WO 2002/100845 | 12/2002 |
| WO | WO 2003/013541 | 2/2003 |
| WO | WO 2005/097791 | 10/2005 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/008260 | 1/2011 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2013/071035 | 5/2013 |
| WO | WO 2013/071039 | 5/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2015/000868 | 1/2015 |
| WO | WO 2015/006524 | 1/2015 |
| WO | WO 2015/160845 | 10/2015 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/011590 | 1/2017 |
| WO | WO 2017/030814 | 2/2017 |
| WO | WO 2017/046036 | 3/2017 |
| WO | WO 2017/079267 | 5/2017 |
| WO | WO 2017/161119 | 9/2017 |
| WO | WO 2017/185036 | 10/2017 |
| WO | WO 2017/197051 | 11/2017 |
| WO | WO 2018/098280 | 5/2018 |
| WO | WO 2018/148440 | 8/2018 |

OTHER PUBLICATIONS

Bargagna-Mohan, et al., "Use of PROTACS as molecular probes of angiogenesis", Bioorg Med Chem Left. 15(11) 2005, 2724-2727.

Bondeson, et al., (2017) "Targeted Protein Degradation by Small Molecules." *Annu Rev Pharmacol Toxicol* 57:107-123.

Bondeson, et al., "Catalytic in vivo protein knockdown by small-molecule PROTACS", National Chem Biol. 11(8) Aug. 2015, 611-617.

Buckley, et al., "HaloPROTACS: use of small molecule PROTACS to induce degradation of HaloTag fusion proteins", ACS Chem Biol. 10(8), 2015, 1831-1837.

Buckley, et al., "Small-molecule inhibitors of the interaction between the E3 ligase VHL and HIF1a", Angew Chem Int Ed Engl.51(46), Nov. 12, 2012, 11463-11467.

Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

Burslem, et al., (2017) "Small-Molecule Modulation of Protein Homeostasis." *Chem Rev* 117(17):11269-11301.

Capitosti, S., et al., "Thalidomide analogues demonstrate dual inhibition of both angiogenesis and prostate cancer", Bioorganic & Medicinal Chemistry 12, (2004) 327-336.

Carmony, KC, et al., "PROTAC-Induced Proteolytic Targeting", Methods Mol. Biol., 2012, vol. 832, pp. 627-638.

Cas Registry No. 1004933-70-3, which entered STN on Feb. 21, 2008.

(56) References Cited

OTHER PUBLICATIONS

Cas Registry No. 871986-52-6 entered STN Jan. 16, 2006.
Chene, P., et al., "Inhibiting the p53-MDM2 interaction: an important target for cancer therapy" Nat. Rev. Cancer (2003), 3, 102-109.
CID16125106—"4-(4-aminophenyl)-1H-indazol-3-amine", (2007) National Center for Biotechnology Information. PubChem Compound Database; CID=16125106, https://pubchem.ncbi.nlm.nih.gov/compound/16125106.
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antagonists of inhibitors of apoptosis proteins based on thiazole amide isosteres", Bioorg. Med. Chem. Lett., 20(7), 2229-2233 (2010).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al, "Two-Headed Protac: An Effective New Tool for Targeted Protein Degradation," Chembiochem., 2010, vol. 11, pp. 1531-1534.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).
Dixon, S. J. et al., "Identifying druggable disease-modifying gene products",. *Curr Opin Chem Biol* 13, 549-555, doi:S1367-5931(09)00107-0 [pii] 10.1016/j.cbpa.2009.08.003 (2009).
El-Shami, et al., "FLT3 inhibitors in acute myeloid leukemia", Expert Rev. Hematol. 1(2) 153-160 (2008).
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 (2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Gschwind, A., et al., "The discovery of receptor tyrosine kinases: targets for cancer therapy", Nat Rev Cancer 4, 361-370 (2004).
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Ho, K. et al., "Discovery of 4-phenyl-2-phenylaminopyridine based TNIK inhibitors", Bioorganic and Medicinal Chemistry Letters 2013, 23, 569-573.
Hon, et al., "Structural basis for the recognition of hydroxyproline in Hlf-1 alpha by pVHL", Nature 417, Jun. 27, 2002, 975-978.
Huang, et al., (2016) "Drugging the undruggables: exploring the ubiquitin system for drug development." *Cell Res* 26(4):484-498.
Hughes, et al., (2017) "Molecular recognition of ternary complexes: a new dimension in the structure-guided design of chemical degraders." *Essays Biochem* 61(5):505-516.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Kim, K.S., "Discovery of tetrahydroisoquinoline-based bivalent heterodimeric IAP antagonists", Bioorg. Med. Chem. Lett. 24(21), 5022-5029 (2014).
Kiyoi, "FLT3 inhibitors; recent advances and problems for clinical application", Nagoya J Med, Sci. 77. 7-17 (2015).
Knott, Edward (1955). "Compounds containing sulphur chromophores. Part I. The action of bases on heterocyclic sulphide quarternary salts", Journal of the Chemical Society (resumed). 10.1039/jr9550000916. 949-954.
Kronke, et al, "Lenalidomide Causes Selective Degradation of IKZF1 and IKZF3 in Multiple Myeloma Cells", Science 343, 301-305 (2014).
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Lemmon, M.A., et al., "Cell Signaling by Receptor Tyrosine Kinases", Cell 141, 1117-1134 (2010).
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012.
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Maniaci C, et al. (2017) "Homo-PROTACs: bivalent small-molecule dimerizers of the VHL E3 ubiquitin ligase to induce self-degradation." *Nat Commun* 8(1):830 1-13.
Mannhold, R., et al., "IAP antagonists: promising candidates for cancer therapy", Drug Discov. Today, 15 (5-6), 210-219 (2010).

(56) References Cited

OTHER PUBLICATIONS

Medline Plus Trusted Health Information for You, www.nlm.nih. gov/medlineplus/cancer.html pp. 1-10, (2007).
Min, Jung-hyun, et al., "Structure of an HIV-1-alpha—pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., "Amino-Substituted Thalodomide Analogs: Potent Inhibitors of TNF-α Production", Bioorganic & Medicinal Chemistry Letters 9 (1999) 1625-1630.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138-144 (2017).
Nikolovska-Coleska, et al., "Interaction of a cyclic, Bivalent Smac Mimetic with the X-linked inhibitor of apoptosis protein", Biochemistry, 2008, 47(37), pp. 9811-9824.
Ohoka, N. et al. Sniper(TACC3) induces cytoplasmic vacuolization and sensitizes cancer cells to Bortezomib. Cancer Sci. 108, 1032-1041 (2017).
Oost, T.K. et al., "Discovery of potent antagonists of the antiapoptotic protein XIAP for the treatment of cancer", Journal of Medicinal Chemistry 2004, 47, 4417-4426.
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Perez, HL," Discovery of potent heterodimeric antagonists of inhibitor of apoptosis proteins (IAPs) with sustained antitumor activity", J. Med. Chem. 58(3), 1556-1562 (2015).
Pratz, K.W., et al., "A pharmacodynamic study of the FLT3 inhibitor KW-2449 yields insight into the basis for clinical response", Blood 113, 3938-3946 (2009).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/ jm501550p. Epub Dec. 4, 2014. PubMed PMID: 25384157.
Richters, A., et al., "Identification and further development of potent TBK1 inhibitors", ACS Chemical Biology, vol. 10, No. 1, Jan. 16, 2015, pp. 289-298 (2015).
Rodriguez-Gonzalez, et al., "Targeting steroid hormone receptors for ubiquitination and degradation in breast and prostate cancer", Oncogene. 27(57), Dec. 4, 2008, 7201-7211.
Rosania et al., "Targeting hyperproliferative disorders with cyclin dependent kinase inhibitors", Exp. Opin. Ther. Patents (2000) 10(2):215-230.
Rotili, D., et al., "Photoactivable peptides for identifying enzyme-substrate and protein-protein interactions", Chem Commun (Carob) 47(5), Feb. 2011, 1488-1490.

Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1 -Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).
Sargent, et al., "Synthesis of the cyclophane tetramethoxyturriane: a derivative of the phenolic cyclophanes of Grevillea striata R. Br.", J. Chem. Soc., Perkin Trans. 1, 1990, 129-132 (Abstract).
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017 "Compounds containing sulfur Chromophores v. Complex cyanines".
Stoppler, Melissa Conrad., Endometriosis [online], "Endometriosis Definition and Facts" URL http://www.medicinenet.com/endometriosis/ article.htm, retrieved on Apr. 5, 2017.
Stoppler, Melissa Conrad., Endometriosis [online], "What about surgery for Endometriosis?" URL http://www.medicinenet.com/ endometriosis/article.htm, retrieved on Apr. 5, 2017.
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/ jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Toure, et al., (2016) "Small-Molecule PROTACS: New Approaches to Protein Degradation." *Angew Chem Int Ed Engl* 55(6):1966-1973.
Trewartha D, Carter K. "Advances in prostate cancer treatment", Nat Rev Drug Discov. Nov. 2013;12(11):823-824. doi: 10.1038/ nrd4068. PubMed PMID: 24172327.
Turk, B. E., "Binding of thalidomide to alpha1-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor la protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.
Vazquez, A. et al., "The genetics of the p53 pathway, apoptosis and cancer therapy", Nat. Rev. Drug. Dis., 7, 979-982 (2008).
Vu, B. et al. "Discovery of RG7112: a small-molecule MDM2 inhibitor in clinical development", ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).

(56) References Cited

OTHER PUBLICATIONS

Wang, S., et al. "Small-molecule inhibitors of the MDM2-p53 protein-protein interaction (MDM2 inhibitors) in clinical trials for cancer treatment", J. Med. Chem. (2015) 58, 1038-1052.

Wang, S., et al. "Temporal activation of p53 by a specific MDM2 inhibitor is selectively toxic to tumors and leads to complete tumor growth inhabitation", PNAS USA (2008) 105, 3933-3938.

Weisberg, et al. "Discovery and characterization of novel mutant FLT3 kinase inhibitors", Mol Cancer Ther. Sep. 2010; 9(9): 2468-2477. Doi:10.1158/1535-7163.MCT-10-0232.

William, A.D., et al., " Discovery of the Macrocycle 11-(2-Pyrrolidin-1-yl-ethoxy)-14,19-dioxa-5,7,26-triaza-tetracyclo[19.3.1.1(2,6). 1(8,12)]heptacosa-1(25),2(26),3,5,8,10,12(27),16,21,23-decaene (SB1518), a Potent Janus Kinase 2/Fms-Like Tyrosine Kinase-3 (JAK2/FLT3) Inhibitor for the Treatment of Myelofibrosis and Lymphoma", Journal of Medicinal Chemistry, 2011, vol. 54., pp, 4638-4658.

Winter, et al., "Phthalimide Conjugation as a strategy for in vivo target protein degradation", Science, 2015 vol. 348 (6241), pp. 1376-1381 [Pub online: May 21, 2015].

Zengerle, et al., "Selective Small Molecule Induced Degradation of the BET Bromodomain Protein BRD4" ACS Chemical Biology, Jun. 2, 2015, vol. 10, pp. 1770-1777.

Zhang B.et al., "Small-molecule MDM2-p53 inhibitors: recent advances", Future Med. Chem. (2015) 7, 631-645.

Zhang, D. et al., "Targeted Degradation of Proteins by Small Molecules: A Novel Tool for Functional Proteomics," comb Chem. High Throughput Screen., 2004, vol. 7, No. 7, pp. 689-697.

\* cited by examiner

PROTAC-34

COMPOUNDS AND METHODS FOR THE TARGETED DEGRADATION OF FETAL LIVER KINASE POLYPEPTIDES

CROSS-REFERENCE TO RELATED APPLICATIONS

The present disclosure claims priority to U.S. Provisional Patent Application 62/438,844, filed 23 Dec. 2016, titled: COMPOUNDS AND METHODS FOR THE TARGETED DEGRADATION OF FETAL LIVER KINASE POLYPEPTIDES, and U.S. Provisional Patent Application 62/450,716, filed 26 Jan. 2017, titled: COMPOUNDS AND METHODS FOR THE TARGETED DEGRADATION OF FETAL LIVER KINASE POLYPEPTIDES, both of which are incorporated herein by reference in their entireties for all purposes.

STATEMENT REGARDING FEDERALLY FUNDED RESEARCH

This invention was made with government support under grant number NIH R35CA197589, as issued by the National Institutes of Health. The government has certain rights in the invention.

INCORPORATION BY REFERENCE

U.S. patent application Ser. No. 15/230,354, filed on Aug. 5, 2016; and U.S. patent application Ser. No. 15/206,497 filed 11 Jul. 2016; and U.S. patent application Ser. No. 15/209,648 filed 13 Jul. 2016; and U.S. Patent Application Ser. No. 62/406,888, filed on Oct. 11, 2016; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639, are incorporated herein by reference in their entirety. Furthermore, all references cited herein are incorporated by reference herein in their entirety.

FIELD OF THE INVENTION

The description provides bifunctional compounds comprising a target protein binding moiety for FMS-like receptor tyrosine kinase (FLT3) or mutant versions thereof and a E3 ubiquitin ligase binding moiety, and associated methods of use. The bifunctional compounds are useful as modulators of targeted ubiquitination of FLT3 (and mutants thereof), which is degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

Tumor suppressor gene p53 plays an important role in cell growth arrest and apoptosis in response to DNA damage or stress (A. Vazquez, et al. *Nat. Rev. Drug. Dis.* (2008), 7, 979-982), and inactivation of p53 has been suggested as one of the major pathway for tumor cell survival (A. J. Levine, et al. *Nature* (2000), 408, 307-310). In cancer patients, about 50% were found with p53 mutation (M. Hollstein, et al. *Science* (1991), 233, 49-53), while patients with wild type p53 were often found p53 down regulation by MDM2 through the protein-protein interaction of p53 and MDM2 (P. Chene, et al. *Nat. Rev. Cancer* (2003), 3, 102-109). Under normal cell condition without oncogenic stress signal, MDM2 keeps p53 at low concentration. In response to DNA damage or cellular stress, p53 level increases, and that also causes increase in MDM2 due to the feedback loop from p53/MDM2 auto regulatory system. In other words, p53 regulates MDM2 at the transcription level, and MDM2 regulates p53 at its activity level (A. J. Levine, et al. *Genes Dev.* (1993) 7, 1126-1132).

Several mechanisms can explain p53 down regulation by MDM2. First, MDM2 binds to N-terminal domain of p53 and blocks expression of p53-responsive genes (J. Momand, et al. Cell (1992), 69, 1237-1245). Second, MDM2 shuttles p53 from nucleus to cytoplasm to facilitate proteolytic degradation (J. Roth, et al. *EMBO J.* (1998), 17, 554-564). Lastly, MDM2 carries intrinsic E3 ligase activity of conjugating ubiquitin to p53 for degradation through ubiquitin-dependent 26s proteasome system (UPS) (Y. Haupt, et al. *Nature* (1997) 387, 296-299). As such, because MDM2 functions as E3 ligase, recruiting MDM2 to a disease causing protein and effectuating its ubiquitination and degradation is an approach of high interest for drug discovery.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Inhibitors of Apotosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspace-9) that implement apoptosis. As such, through the binding of caspases, IAPs inhibit cell death. However, pro-apoptotic stimuli can result in the release of mitochondrial proteins DIABLO (also known as second mitrochondria-derived activator of caspases or SMAC) and HTRA2 (also known as Omi). Binding of DIABLO and HTRA2 appears to block IAP activity.

SMAC interacts with essentially all known IAPs including XIAP, c-IAP1, c-IAP2, NIL-IAP, Bruce, and survivin. The first four amino acids (AVPI) of mature SMAC bind to a portion of IAPs, which is believed to be essential for blocking the anti-apoptotic effects of IAPs.

Bifunctional compounds such as those that are described in U.S. Patent Application Publications 2015-0291562 and 2014-0356322 (incorporated herein by reference), function to recruit endogenous proteins to an E3 ubiquiuin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

FMS-like tyrosine kinase 3 (FLT3) is a class III receptor tyrosine kinase. It is activated by the FLT3 ligand and signals through the PI3K, RAS, and JAK/STAT pathways. FLT3 plays a role in early hematopoiesis and FLT3 deficient mice have reduced numbers of progenitors of multiple lymphoid lineages. FLT3 and FLT3 ligand have been shown to play a role in a number of human leukocyte malignancies including acute myelogenous leukemia (AML), acute pro-myelocytic leukemia (APL), B and T cell acute lymphoblastic leukemia (ALL), chronic myelogenous leukemia (CML), and myelodysplasia (MDS). This may result from constitutive activation of the receptor due to mutations, resulting in cellular proliferation and blocking of myeloid differentiation.

For example, activating mutations in FLT3 are found in approximately 30% of AML patients, representing the most frequent genetic alteration in the disease. About 75% of the activating mutations are internal tandem duplications (ITD) and 25% are point mutations in the activation loop of the kinase domain. The most frequently identified activating point mutation is D835Y. However, mutations have also been found at N841I and Y842C. Additional point mutations have been identified in the juxtamembrane domain and kinase domain, although these have been shown to result in lower transforming potential.

Murine bone marrow transplanted with a retrovirus expressing the FLT3-ITD has been shown to result in the production of a lethal myeloproliferative disease in mice characterized by leukocytosis consisting of mature neutrophils. This disease did not show a block in differentiation as seen in human AML suggesting that FLT3 mutations confer a proliferative or survival advantage to the cells.

An ongoing need exists in the art for effective treatments for disease associated with overexpression or aggregation of FLT3. However, non-specific effects, and the inability to specifically target and modulate FLT3, remain as obstacles to the development of effective treatments. As such, small-molecule therapeutic agents that target FLT3 and leverage or potentiate VHL's, cereblon's, MDM2's, and IAPs' substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., acute myeloid leukemia (AML).

As such, in one aspect the disclosure provides bifunctional or PROTAC compounds, which comprise an E3 ubiquitin ligase binding moiety (i.e., a ligand for an E3 ubquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein. In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM), or an IAP E3 ubiquitin ligase binding moiety (i.e., a "ILM"). For example, the structure of the bifunctional compound can be depicted as:

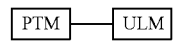

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

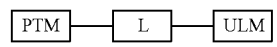

where PTM is a protein/polypeptide targeting moiety, L is a linker, e.g., a bond or a chemical group coupling PTM to ULM, and ULM is a IAP E3 ubiquitin ligase binding moiety, or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the biofunctional compound can be depicted as:

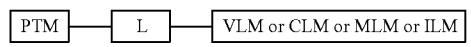

wherein: PTM is a protein/polypeptide targeting moiety; "L" is a linker (e.g. a bond or a chemical linker group) coupling the PTM and at least one of VLM, CLM, MLM, ILM, or a combination thereif; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety; and ILM is a IAP binding moiety which binds to IAP;

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (I) or their unnatural mimetics, respectively. In additional embodiments, the amino acids of the AVPI tetrapeptide fragment are connected to each other through amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Pub. No. 2014-03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication US 2015-0291562, which is incorporated herein in its entirety.

In certain embodiments, MLM can be nutlin or a derivative thereof. Furthermore, other contemplated MLMs are included in U.S. patent application Ser. No. 15/206,497 filed 11 Jul. 2016, which as discussed above, is incorporated herein in its entirety. In certain additional embodiments, the MLM of the bifunctional compound comprises chemical moieties such as substituted imidazolines, substituted spiroindolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In yet another aspect, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, wherein PTM is coupled to VLM or CLM or MLM or ILM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figures 1A, 1B:
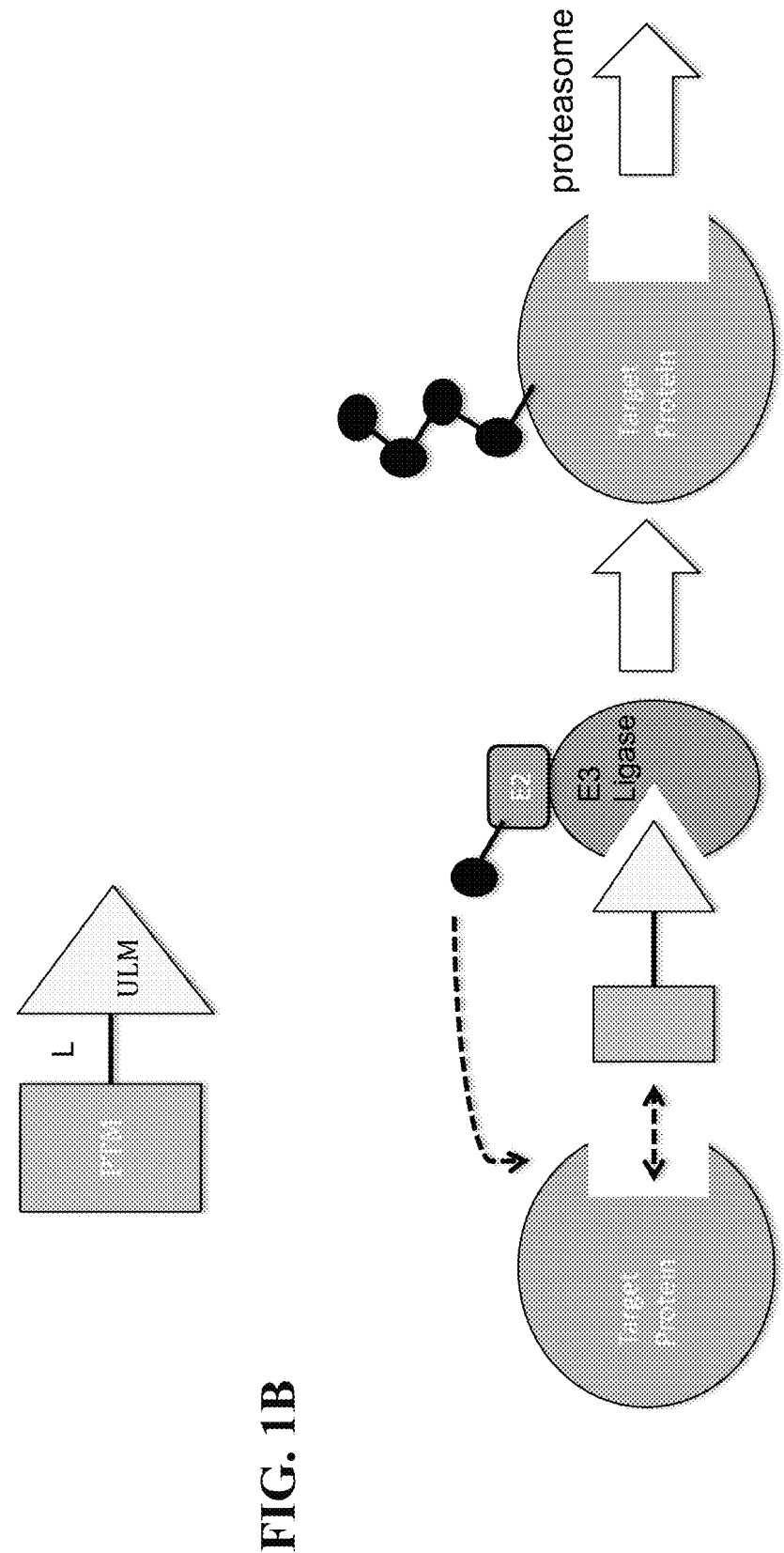
FIGS. 1A and 1B. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 ubiquitin ligase, and the PTM binds and recruits a target protein, such as FMS-like receptor tyrosine kinase (FLT3), bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degration by the proteosomal machinery of the cell.

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein (such as FMS-like receptor tyrosine kinase [FLT3]), which leads to degradation of the target protein by the proteasome (see FIGS. 1A and 1B). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse bould minute 2 homologue (MDM2) E3 ubiquitin ligase binding moiety (MLM). In an exemplary embodiment, the ULM is coupled to a target protein binding moiety (PTM) via a chemical linker (L) according to the structure:

PTM-L-ULM    (A)

wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitin ligase binding moieties, the term VLM is inclusive of all possible VHL binding moieties, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

PTM-ILM    (B)

PTM-CLM    (C)

PTM-VLM    (D)

PTM-MLM    (E)

In certain embodiments, the bifunctional compound further comprises a chemical linker ("L"). For example, the bifunctional compound can be depicted as:

PTM-L-ILM    (F)

PTM-L-CLM    (G)

PTM-L-VLM    (H)

PTM-L-MLM    (I)

wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 µM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 µM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the aspects of embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ILMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

Exemplary ILMs

AVPI Tetrapeptide Fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

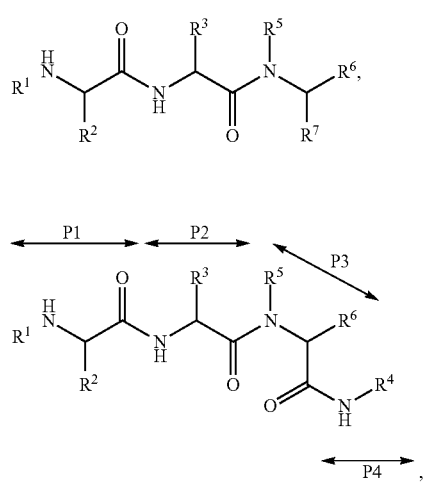

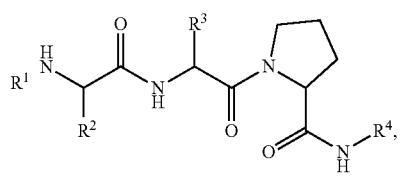

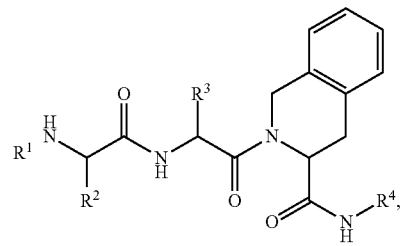

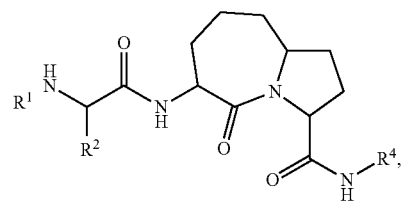

wherein:
R$^1$ for Formulas (I), (II), (III), (IV), and (V) is selected from H or alkyl;
R$^2$ for Formulas (I), (II), (III), (IV), and (V) is selected from H or alkyl;
R$^3$ for Formulas (I), (II), (III), (IV), and (V) is selected from H, alkyl, cycloalkyl and heterocycloalkyl;
R$^5$ and R$^6$ for Formulas (I), (II), (III), (IV), and (V) are independently selected from H, alkyl, cycloalkyl, heterocycloalkyl, or more preferably, R$^5$ and R$^6$ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;
R$^3$ and R$^5$ for Formulas (I), (II), (III), (IV), and (V) taken together can form a 5-8-membered ring further optionally fused to 1-2 cycloalkyl, heterocycloalkyl, aryl or heteroaryl rings;
R$^7$ for Formulas (I), (II), (III), (IV), and (V) is selected from cycloalkyl, cycloalkylalkyl, heterocycloalkyl, heterocycloalkylalkyl, aryl, arylalkyl, heteroaryl or heteroarylalkyl, each one further optionally substituted with 1-3 substituents selected from halogen, alkyl, haloalkyl, hydroxyl, alkoxy, cyano, (hetero)cycloalkyl or (hetero)aryl, or R$^7$ is —C(O) NH—R$^4$; and
R$^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above.

As shown above, P1, P2, P3, and P4 of Formula (II) correlate with A, V, P, and I, respectively, of the AVPI tetrapeptide fragment or an unnatural mimetic thereof. Similarly, each of Formulas (I) and (III) through (V) have portions correlating with A, V, P, and I of the AVPI tetrapeptide fragment or an unnatural mimetic thereof.

In any of the compounds described herein, the ILM can have the structure of Formula (VI), which is a derivative of IAP antagonists described in WO Pub. No. 2008/014236, or an unnatural mimetic thereof:

wherein:
R$_1$ of Formula (VI) is, independently selected from H, C$_1$-C$_4$-alkynyl or C$_3$-C$_{10}$-cycloalkyl which are unsubstituted or substituted;
R$_2$ of Formula (VI) is, independently selected from H, C$_1$-C$_4$-alkyl, C$_1$-C$_4$-alkenyl, C$_1$-C$_4$-alkynyl or C$_3$-C$_{10}$-cycloalkyl which are unsubstituted or substituted;
R$_3$ of Formula (VI) is, independently selected from H, —CF$_3$, —C$_2$H$_5$, C$_1$-C$_4$ alkyl, C$_1$-C$_4$-alkenyl, C$_1$-C$_4$-alkyl, —CH$_2$—Z or any R$_2$ and R$_3$ together form a heterocyclic ring;
each Z of Formula (VI) is, independently selected from H, —OH, F, Cl, —CH$_3$, —CF$_3$, —CH$_2$Cl, —CH$_2$F or —CH$_2$OH;
R$_4$ of Formula (VI) is, independently selected from C$_1$-C$_{16}$ straight or branched alkyl, C$_1$-C$_{16}$-alkenyl, C$_1$-C$_{16}$-alkynyl, C$_3$-C$_{10}$-cycloalkyl, —(CH$_2$)$_{0-6}$—Z$_1$, —(CH$_2$)$_{0-6}$-aryl, and —(CH$_2$)$_{0-6}$-het, wherein alkyl, cycloalkyl, and phenyl are unsubstituted or substituted;
R$_5$ of Formula (VI) is, independently selected from H, C$_{1-10}$-alkyl, aryl, phenyl, C$_{3-7}$-cycloalkyl, —(CH$_2$)$_{1-6}$—C$_{3-7}$-cycloalkyl, —C$_{1-10}$-alkyl-aryl, —(CH$_2$)$_{0-6}$—C$_{3-7}$-cycloalkyl-(CH$_2$)$_{0-6}$-phenyl, —(CH$_2$)$_{0-4}$—CH[(CH$_2$)$_{1-4}$-phenyl]$_2$, indanyl, —C(O)—C$_{1-10}$-alkyl, —C(O)—(CH$_2$)$_{1-6}$—C$_{3-7}$-cycloalkyl, —C(O)—(CH$_2$)$_{0-6}$-phenyl, —(CH$_2$)$_{0-6}$—C(O)-phenyl, —(CH)$_{0-6}$-het, —C(O)—(CH$_2$)$_{1-6}$-het, or R$_5$ is selected from a residue of an amino acid, wherein the alkyl, cycloalkyl, phenyl, and aryl substituents are unsubstituted or substituted;
Z$_1$ of Formula (VI) is, independently selected from —N(R$_{10}$)—C(O)—C$_{1-10}$-alkyl, —N(R$_{10}$)—C(O)—(CH$_2$)$_{0-6}$—C$_{3-7}$-cycloalkyl, —N(R$_{10}$)—C(O)—(CH$_2$)$_{0-6}$-phenyl, —N(R$_{10}$)—C(O)(CH$_2$)$_{1-6}$-het, —C(O)—N(R$_{11}$)(R$_{12}$), —C(O)—O—C$_{1-10}$-alkyl, —C(O)—O—(CH$_2$)$_{1-6}$—C$_{3-7}$-cycloalkyl, —C(O)—O—(CH$_2$)$_{0-6}$-phenyl, —C(O)—O—(CH$_2$)$_{1-6}$-het, —O—C(O)—C$_{1-10}$-alkyl, —O—C(O)—(CH$_2$)$_{1-6}$C$_{3-7}$-cycloalkyl, —O—C(O)—(CH$_2$)$_{0-6}$-phenyl, —O—C(O)—(CH$_2$)$_{1-6}$-het, wherein alkyl, cycloalkyl, and phenyl are unsubstituted or substituted;
het of Formula (VI) is, independently selected from a 5-7 member heterocyclic ring containing 1-4 heteroatoms selected from N, O, and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom;
R$_{10}$ of Formula (VI) is selected from H, —CH$_3$, CF$_3$, —CH$_2$OH, or —CH$_2$Cl;
R$_{11}$ and R$_{12}$ of Formula (VI) are independently selected from H, C$_{1-4}$-alkyl, C$_{3-7}$-cycloalkyl, —(CH$_2$)$_{1-6}$—C$_{3-7}$-cycloakyl, (CH$_2$)$_{0-6}$-phenyl, wherein alkyl, cycloalkyl, and phenyl are unsubstituted or substituted; or R$_{11}$ and R$_{12}$ together with the nitrogen form het, and
U of Formula (VI) is, independently, as shown in Formula (VII):

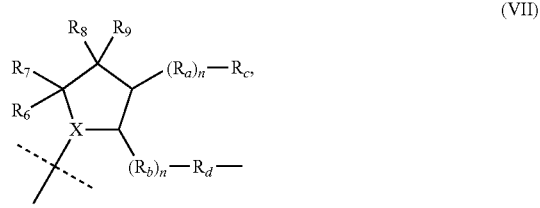

(VII)

wherein:
each n of Formula (VII) is, independently selected from 0 to 5;
X of Formula (VII) is selected from the group —CH and N;
R$_a$ and R$_b$, of Formula (VII) are independently selected from the group O, S, or N atom or C$_{0-8}$-alkyl wherein one or more of the carbon atoms in the alkyl chain are optionally replaced by a heteroatom selected from O, S, or N, and where each alkyl is, independently, either unsubstituted or substituted;
R$_d$ of Formula (VII) is selected from the group Re-Q-(R$_f$)$_p$(R$_g$)$_q$, and Ar$_1$-D-Ar$_2$;
R$_c$ of Formula (VII) is selected from the group H or any R$_c$ and R$_d$ together form a cycloalkyl or het; where if R$_c$ and R$_d$ form a cycloalkyl or het, R$_5$ is attached to the formed ring at a C or N atom;
p and q of Formula (VII) are independently selected from 0 or 1;
R$_e$ of Formula (VII) is selected from the group C$_{1-8}$-alkyl and alkylidene, and each Re is either unsubstituted or substituted;
Q is selected from the group N, O, S, S(O), and S(O)$_2$;
Ar$_1$ and Ar$_2$ of Formula (VII) are independently selected from the group of substituted or unsubstituted aryl and het;
R$_f$ and R$_g$ of Formula (VII) are independently selected from H, —C1-10-alkyl, C$_{1-10}$-alkylaryl, —OH, —O—C$_{1-10}$ alkyl, —(CH$_2$)$_{0-6}$—C$_{3-7}$-cycloalkyl, —O—(CH$_2$)$_{0-6}$-aryl, phenyl, aryl, phenyl-phenyl, —(CH$_2$)$_{1-6}$-het, —O—(CH$_2$)$_{1-6}$-het, —OR$_{13}$, —C(O)—R$_{13}$, —C(O)—N(R$_{13}$)(R$_{14}$), —N(R$_{13}$)(R$_{14}$), —S—R$_{13}$, —S(O)—R$_{13}$, —S(O)$_2$—R$_{13}$, —S(O)$_2$—NR$_{13}$R$_{14}$, —NR$_{13}$—S(O)$_2$—R$_{14}$, —S—C$_{1-10}$-alkyl, aryl-C$_{1-4}$-alkyl, or het-C$_{1-4}$-alkyl, wherein alkyl, cycloalkyl, het, and aryl are unsubstituted or substituted, —SO$_2$—C$_{1-2}$-alkyl, —SO$_2$—C$_{1-2}$-alkylphenyl, —O—C$_{1-4}$-alkyl, or any R$_g$ and R$_f$ together form a ring selected from het or aryl;
D of Formula (VII) is selected from the group —CO—, —C(O)—C$_{1-7}$-alkylene or arylene, —CF$_2$—, O—, —S(O)$_r$ where r is 0-2, 1,3-dioxalane, or C$_{1-7}$-alkyl-OH; where alkyl, alkylene, or arylene are unsubstituted or substituted with one or more halogens, OH, —O—C$_{1-6}$-alkyl, —S—C$_{1-6}$-alkyl, or —CF$_3$; or each D is, independently selected from N(R$_h$);
Rh is selected from the group H, unsubstituted or substituted C$_{1-7}$-alkyl, aryl, unsubstituted or substituted —O—(C$_{1-7}$-cycloalkyl), C(O)—C$_{1-10}$-alkyl, —C(O)—C$_{0-10}$-alkyl-aryl, —C—O—C$_{01-10}$-alkyl, —C—O—C$_{0-10}$-alkyl-aryl, —SO$_2$—C$_{1-10}$-alkyl, or —SO$_2$—(C$_{0-10}$-alkylaryl);
R$_6$, R$_7$, R$_8$, and R$_9$ of Formula (VII) are, independently, selected from the group H, —C$_{1-10}$-alkyl, —C$_{1-10}$-alkoxy, aryl-C$_{1-10}$-alkoxy, —OH, —O—C$_{1-10}$-alkyl, —(CH$_2$)$_{0-6}$—C$_{3-7}$-cycloalkyl, —O—(CH$_2$)$_{0-6}$-aryl, phenyl, —(CH$_2$)$_{1-6}$-het, —O—(CH$_2$)$_{1-6}$-het, —OR$_{13}$, —C(O)—R$_{13}$, —C(O)—N(R$_{13}$)(R$_{14}$), —N(R$_{13}$)(R$_{14}$), —S—R$_{13}$, —S(O)—R$_{13}$, —S(O)$_2$—R$_{13}$, —S(O)$_2$—NR$_{13}$R$_{14}$, or —NR$_{13}$—S(O)$_2$—R$_{14}$; wherein each alkyl, cycloalkyl, and aryl is unsubstituted or substituted; and any R$_6$, R$_7$, R$_8$, and R$_9$ optionally together form a ring system;
R$_{13}$ and R$_{14}$ of Formula (VII) are independently selected from the group H, C$_{1-10}$-alkyl, —(CH$_2$)$_{0-6}$—C$_{3-7}$-cycloalkyl, —(CH$_2$)$_{0-6}$—(CH)$_{0-1}$-(aryl)$_{1-2}$, —C(O)—C$_{1-10}$-alkyl, —C(O)—(CH$_2$)$_{1-6}$—C$_{3-7}$-cycloalkyl, —C(O)—O—(CH$_2$)$_{0-6}$-aryl, C(O)—(CH$_2$)$_{0-6}$—O-fluorenyl, —C(O)—NH—(CH$_2$)$_{0-6}$-aryl, —C(O)—(CH$_2$)$_{0-6}$-aryl, —C(O)—(CH$_2$)$_{0-6}$-het, —C(S)—C$_{1-10}$-alkyl, —C(S)—(CH$_2$)$_{1-6}$—C$_{3-7}$-cycloalkyl, —C(S)—O—(CH$_2$)$_{0-6}$-aryl, —C(S)—(CH$_2$)$_{0-6}$—O-fluorenyl, —C(S)—NH—(CH$_2$)$_{0-6}$-aryl, —C(S)—(CH$_2$)$_{0-6}$-aryl, or —C(S)—(CH$_2$)$_{1-6}$-het, wherein each alkyl, cycloalkyl, and aryl is unsubstituted or substituted: or any R$_{13}$ and R$_{14}$ together with a nitrogen atom form het;

wherein alkyl substituents of R$_{13}$ and R$_{14}$ of Formula (VII) are unsubstituted or substituted and when substituted, are substituted by one or more substituents selected from C$_{1-10}$-alkyl, halogen, OH, —O—C$_{1-6}$-alkyl, —S—C$_{1-6}$-alkyl, and —CF$_3$; and substituted phenyl or aryl of R$_{13}$ and R$_{14}$ are substituted by one or more substituents selected from halogen, hydroxyl. C$_{1-4}$-alkyl, C$_{1-4}$-alkoxy, nitro, —CN, —O—C(O)—C$_{1-4}$-alkyl, and —C(O)—O—C$_{1-4}$-aryl; or a pharmaceutically acceptable salt or hydrate thereof.

In certain embodiments, the compound further comprises an independently selected second ILM attached to the ILM of Formula (VI), or an unnatural mimetic thereof, by way of at least one additional independently selected linker group. In an embodiment, the second ILM is a derivative of Formula (VI), or an unnatural mimetic thereof. In a certain embodiment, the at least one additional independently selected linker group comprises two additional independently selected linker groups chemically linking the ILM and the second ILM. In an embodiment, the at least one additional linker group for an ILM of the Formula (VI), or an unnatural mimetic thereof, chemically links groups selected from R$_4$ and R$_5$. For example, an ILM of Formula (VI) and a second ILM of Formula (VI), or an unnatural mimetic thereof, can be linked as shown below:

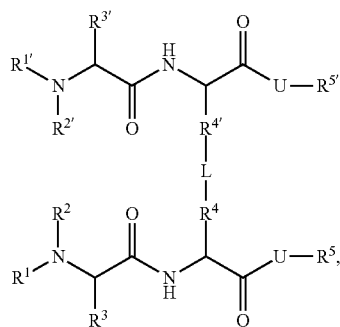
(A)

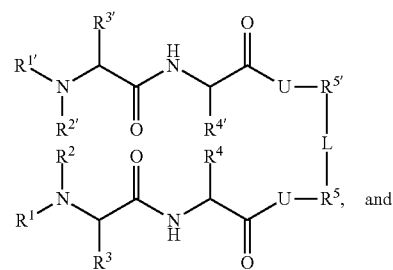
(B)

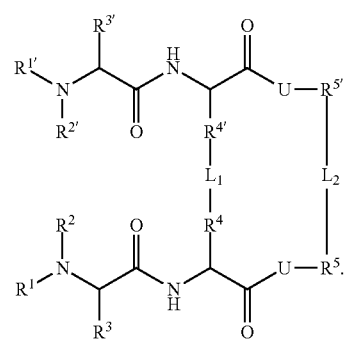
(C)

In certain embodiments, the ILM, the at least one additional independently selected linker group L, and the second ILM has a structure selected from the group consisting of:

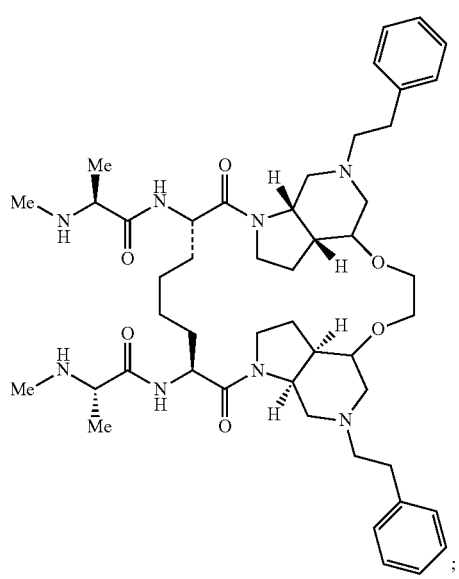
(A)

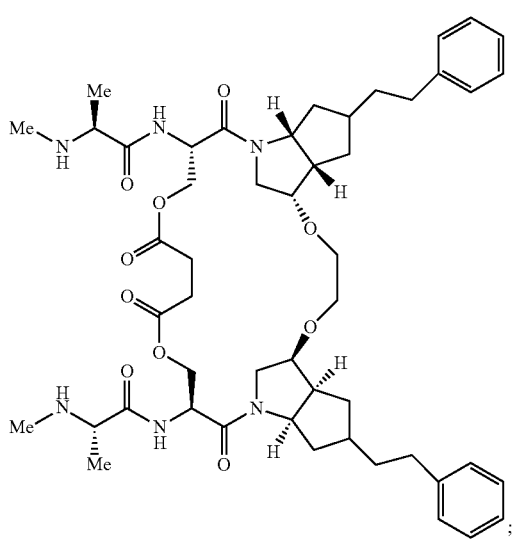
(B)

-continued
(C)
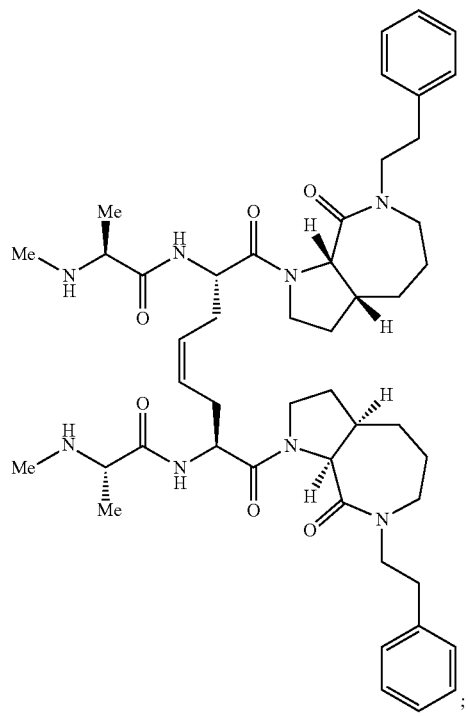
(D)
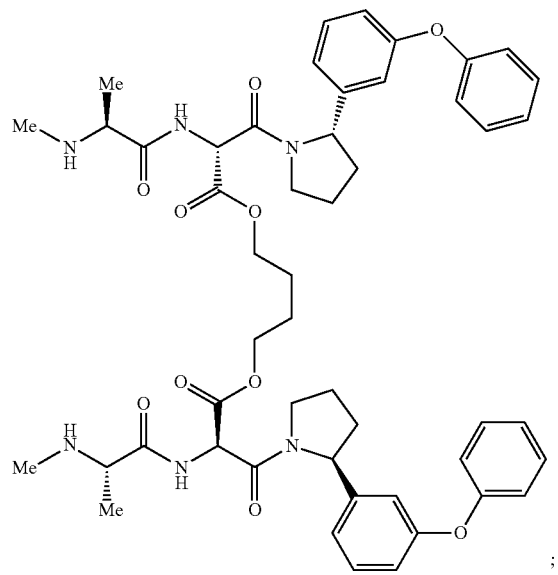
(E)
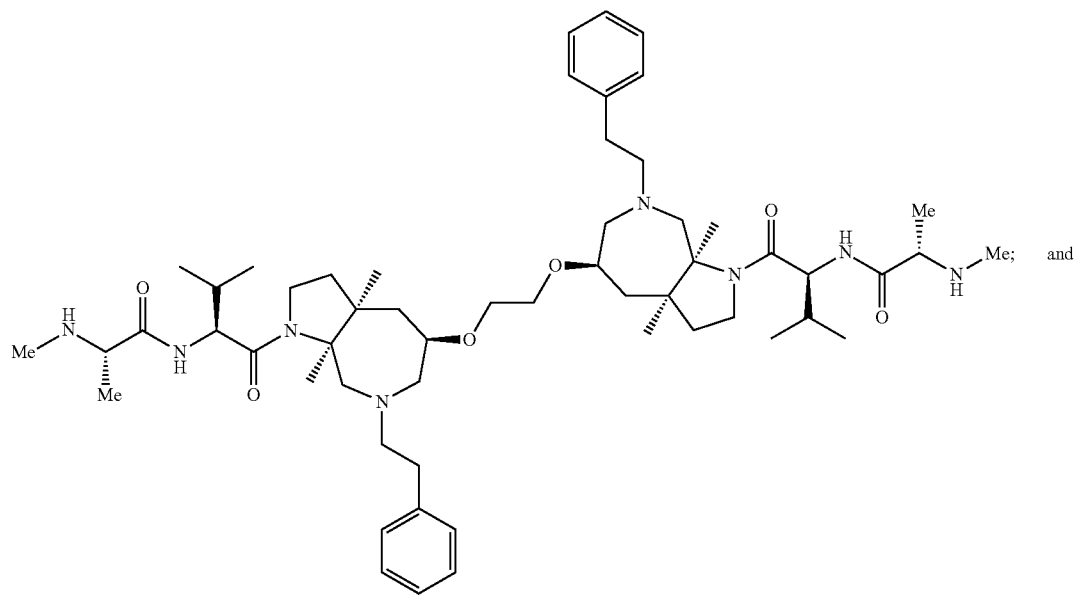
and

-continued (F)

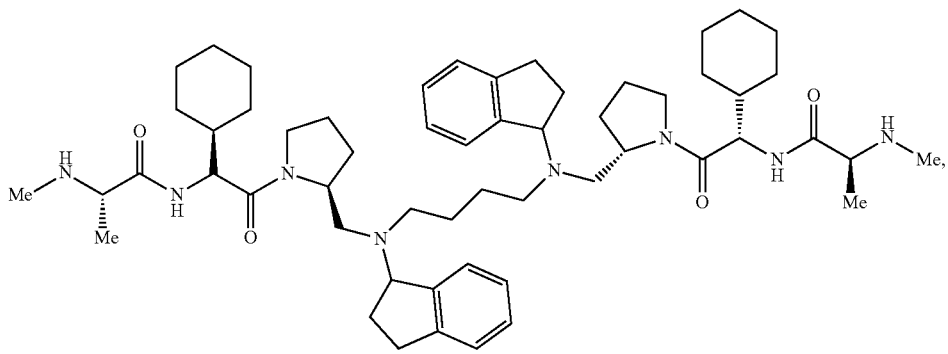

which are derivatives of IAP antagonists described in WO Pub. No. 2008/014236.

In any of the compounds described herein, the ILM can have the structure of Formula (VIII), which is based on the IAP ligands described in Ndubaku, C., et al. Antagonism of c-IAP and XIAP proteins is required for efficient induction of cell death by small-molecule IAP antagonists, *ACS Chem. Biol.*, 557-566, 4 (7) (2009), or an unnatural mimetic thereof:

(VIII)

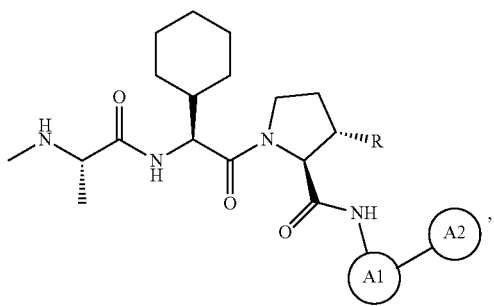

wherein each of A1 and A2 of Formula (VIII) is independently selected from optionally substituted monocyclic, fused rings, aryls and heteroaryls; and R of Formula (VIII) is selected from H or Me.

In a particular embodiment, the linker group L is attached to A1 of Formula (VIII). In another embodiment, the linker group L is attached to A2 of Formula (VIII).

In a particular embodiment, the ILM is selected from the group consisting of (A)

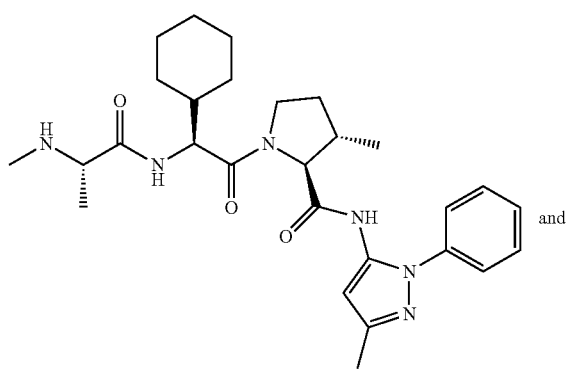 and

-continued (B)

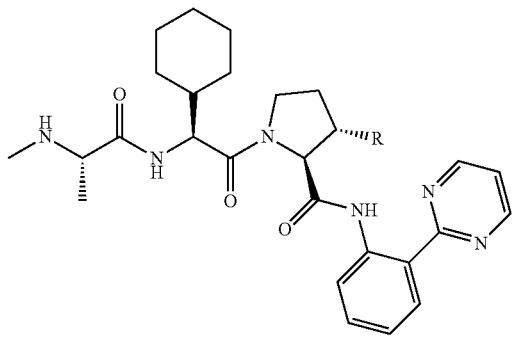

In any of the compounds described herein, the ILM can have the structure of Formula (IX), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

(IX)

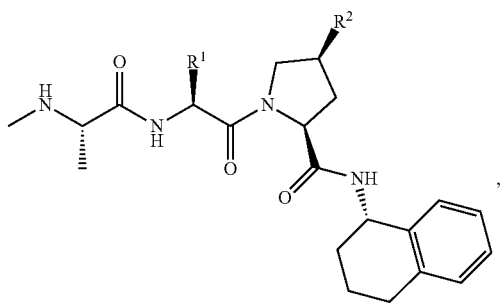

wherein $R^1$ is selected from alkyl, cycloalkyl and heterocycloalkyl and, most preferably, from isopropyl, tert-butyl, cyclohexyl and tetrahydropyranyl, and $R^2$ of Formula (IX) is selected from —OPh or H.

In any of the compounds described herein, the ILM can have the structure of Formula (X), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

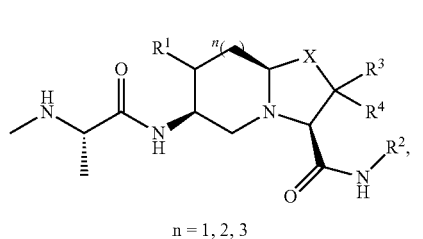

(X)

n = 1, 2, 3 wherein:

R¹ of Formula (X) is selected from H, —CH₂OH, —CH₂CH₂OH, —CH₂NH₂, —CH₂CH₂NH₂;

X of Formula (X) is selected from S or CH₂;

R² of Formula (X) is selected from:

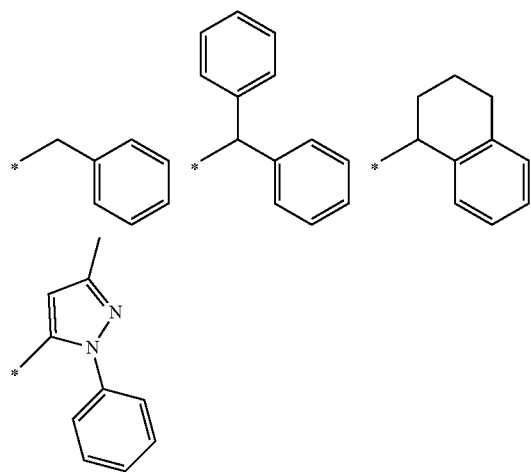

R³ and R⁴ of Formula (X) are independently selected from H or Me

In any of the compounds described herein, the ILM can have the structure of Formula (XI), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

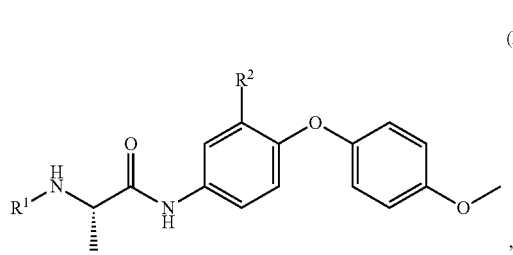

(XI)

wherein R¹ of Formula (XI) is selected from H or Me, and R² of Formula (XI) is selected from H or

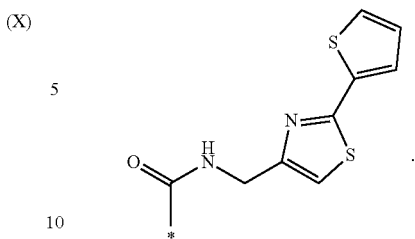

In any of the compounds described herein, the ILM can have the structure of Formula (XII), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

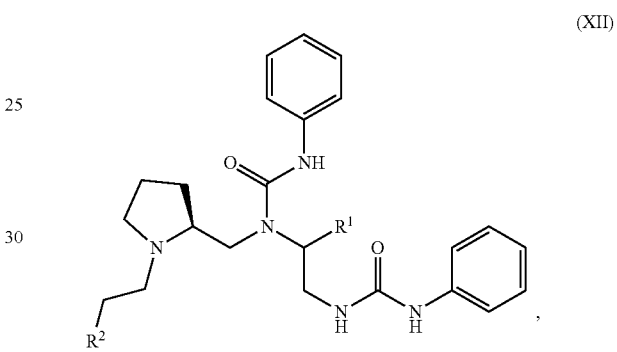

(XII)

wherein: R¹ of Formula (XII) is selected from:

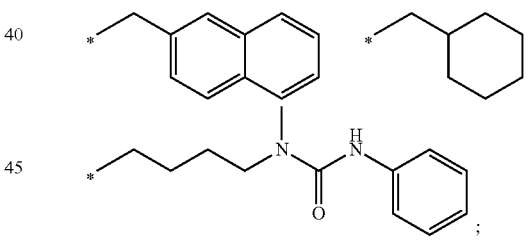

and

R² of Formula (XII) is selected from:

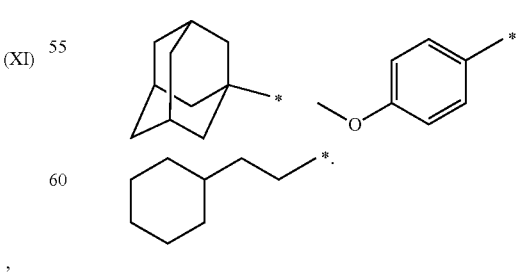

In any of the compounds described herein, the IAP E3 ubiquitin ligase binding moiety is selected from the group consisting of:

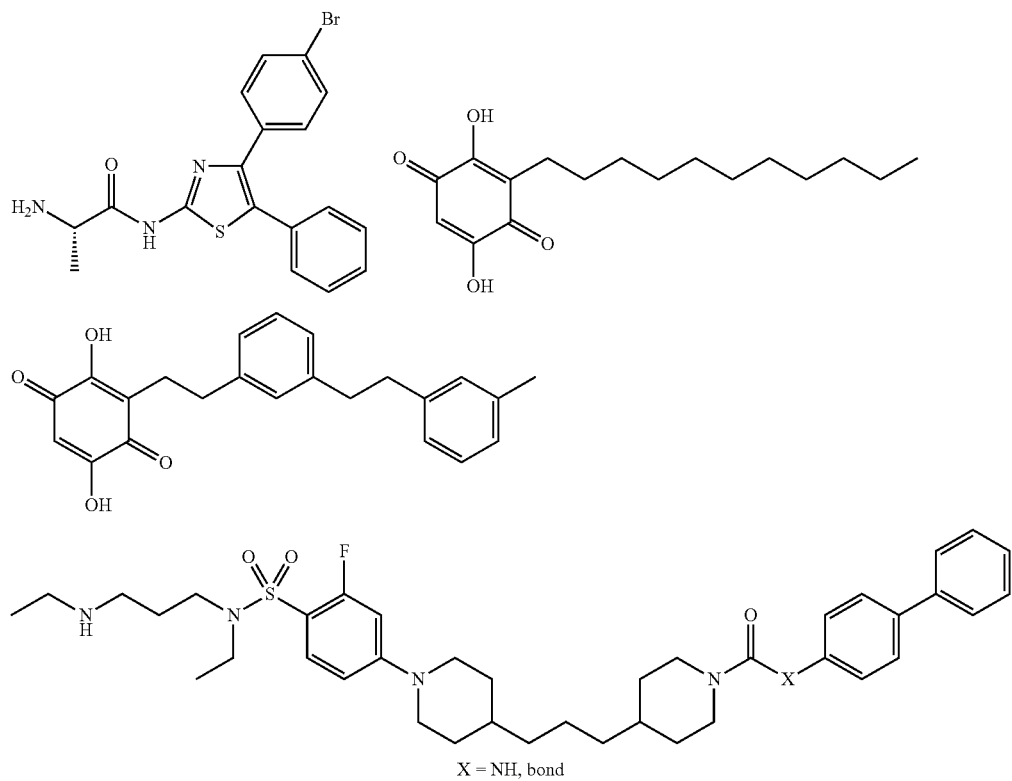
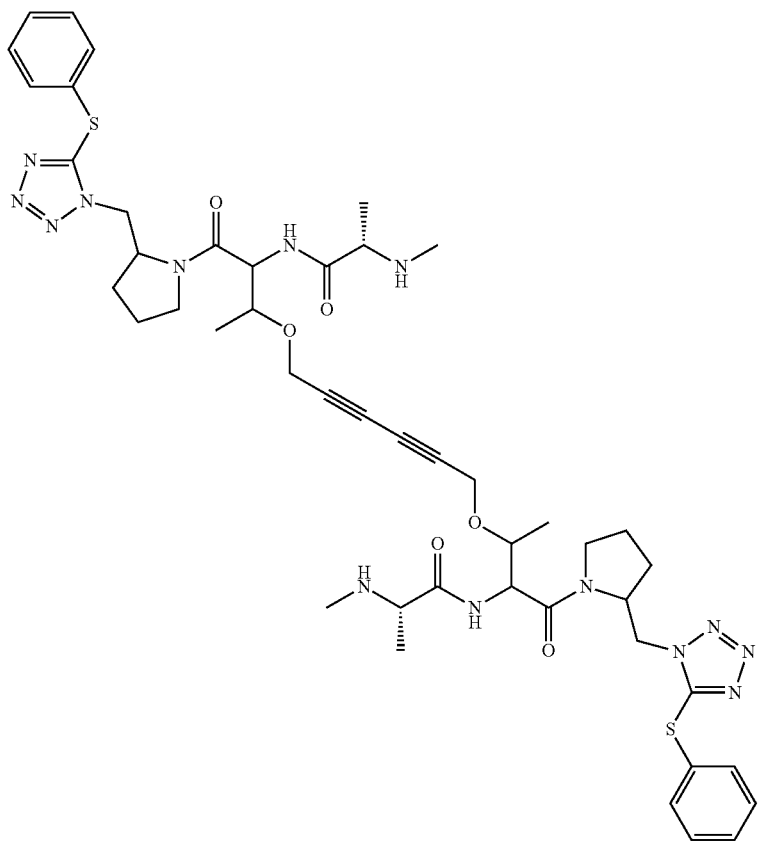

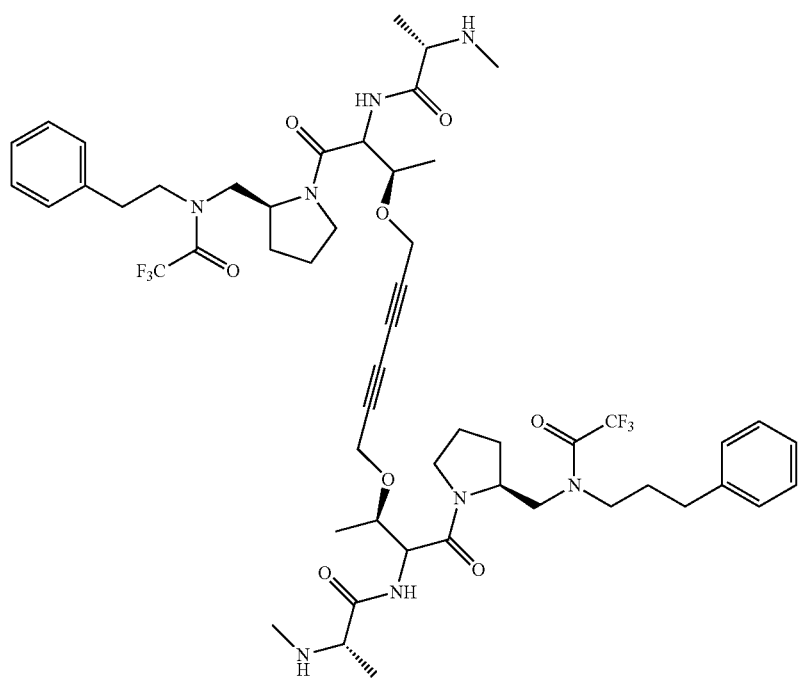
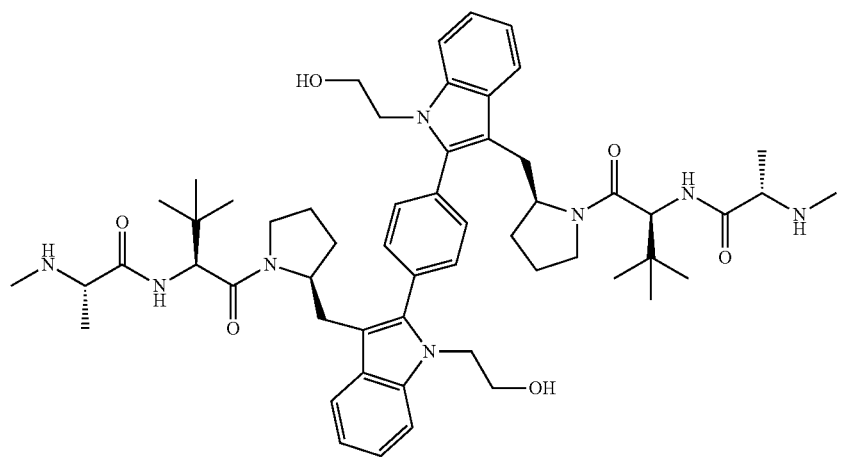
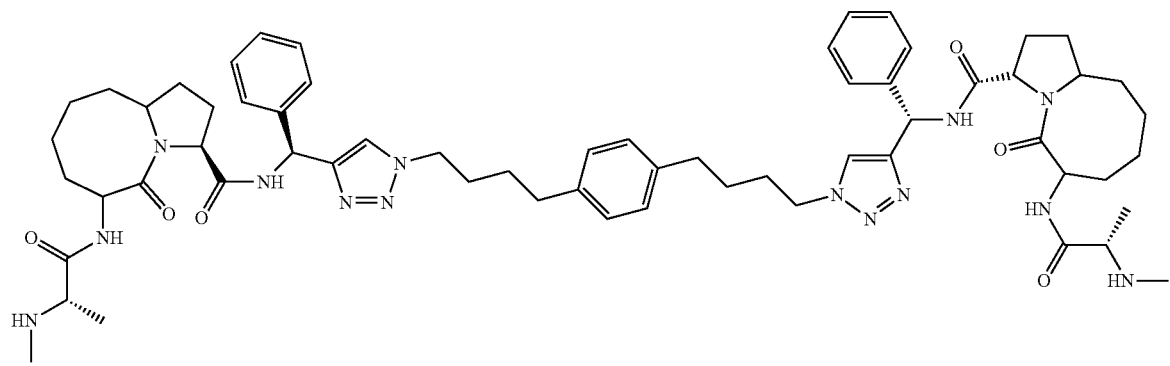

-continued
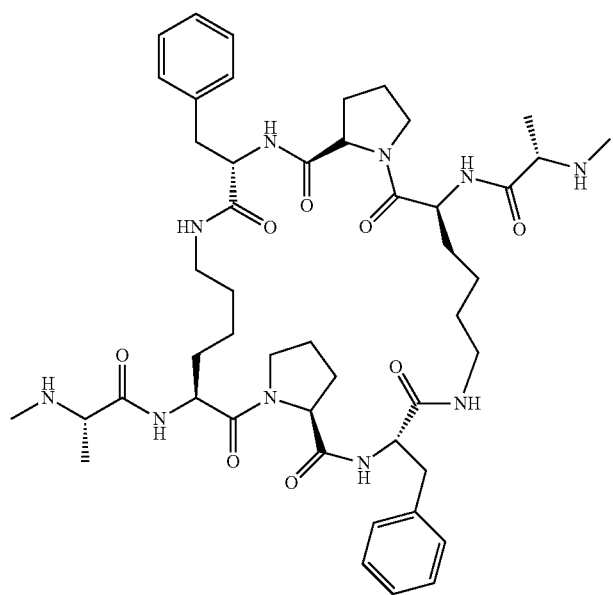
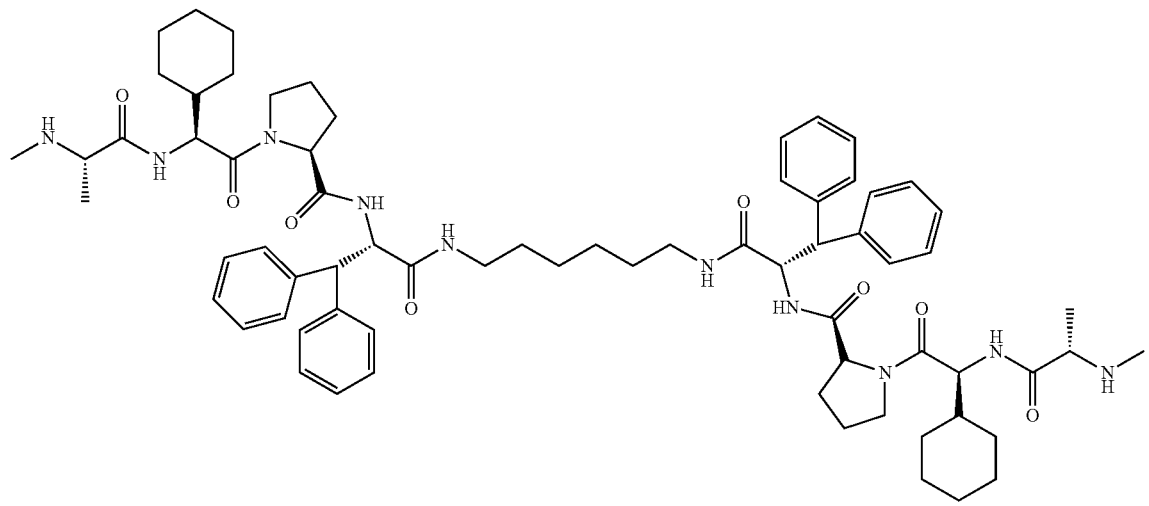
and
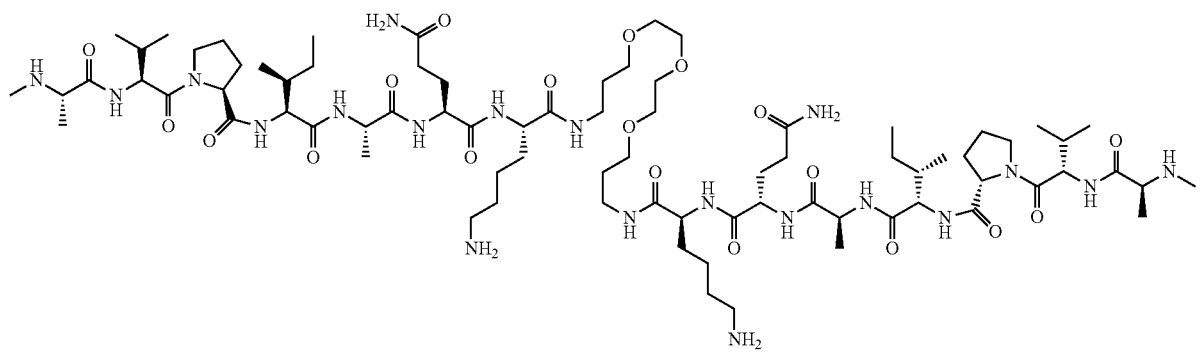

In any of the compounds described herein, the ILM can have the structure of Formula (XIII), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

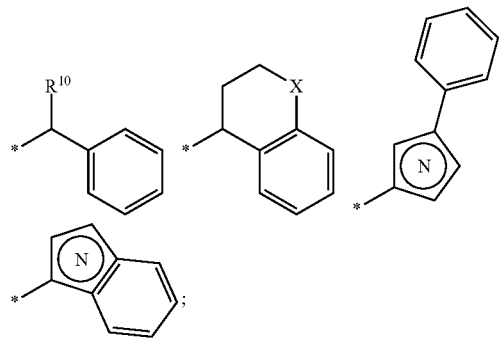

(XIII)

n = 0, 2 or, preferably, 1 wherein:

Z of Formula (XIII) is absent or O;

R¹ of Formula (XIII) is selected from:

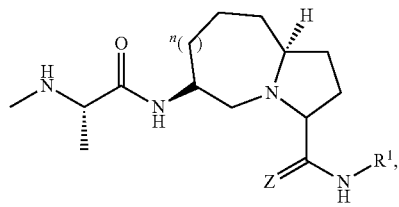

;

R¹⁰ of

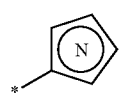

is selected from H, alkyl, or aryl;

X is selected from CH2 and O; and

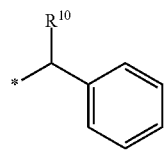

is a nitrogen-containing heteroaryl.

In any of the compounds described herein, the ILM can have the structure of Formula (XIV), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

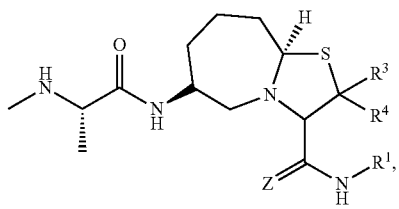

(XIV)

wherein:

Z of Formula (XIV) is absent or O;

R³ and R⁴ of Formula (XIV) are independently selected from H or Me;

R¹ of Formula (XIV) is selected from:

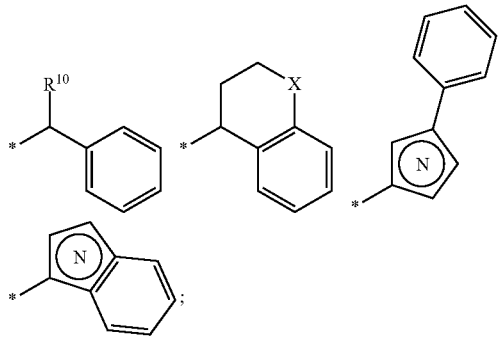

;

R¹⁰ of

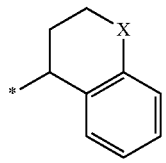

is selected from H, alkyl, or aryl;

X of

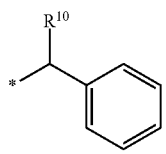

is selected from CH2 and O; and

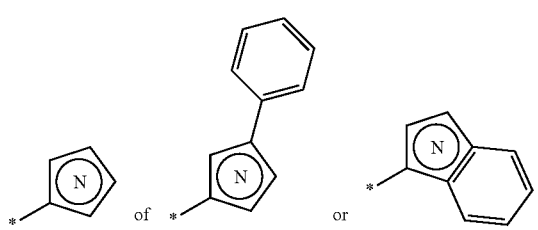

is a nitrogen-containing heteroaryl.

In any of the compounds described herein, the ILM is selected from the group consisting of:

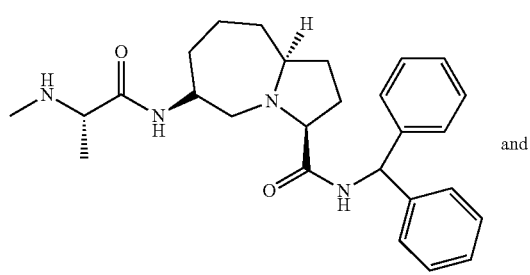

and

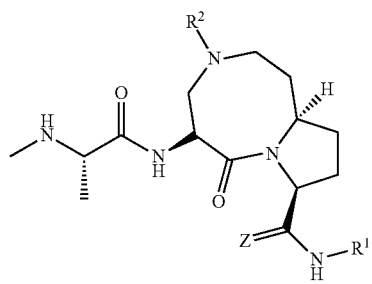

which are derivatives of ligands disclose in US Patent Pub. No. 2008/0269140 and U.S. Pat. No. 7,244,851.

In any of the compounds described herein, the ILM can have the structure of Formula (XV), which was a derivative of the IAP ligand described in WO Pub. No. 2008/128171, or an unnatural mimetic thereof:

(XV)

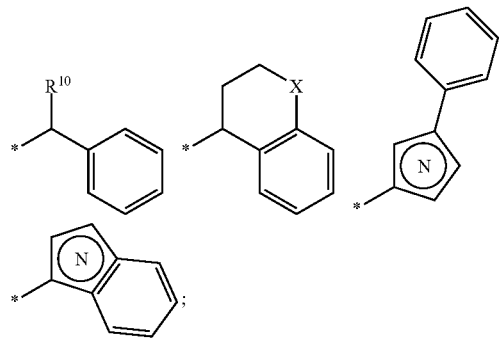

wherein:
Z of Formula (XV) is absent or O;
R$^1$ of Formula (XV) is selected from:

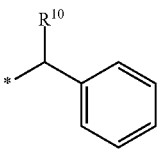

$R^{10}$ of

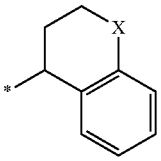

is selected from H, alkyl, or aryl;
X of

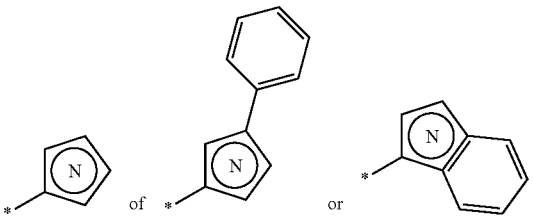

is selected from CH2 and O; and

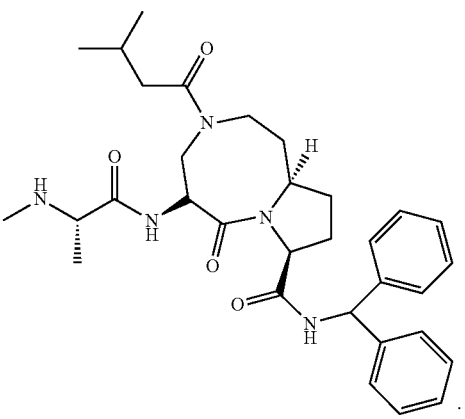

is a nitrogen-containing heteraryl; and
R$^2$ of Formula (XV) selected from H, alkyl, or acyl.

In a particular embodiment, the ILM has the following structure:

In any of the compounds described herein, the ILM can have the structure of Formula (XVI), which is based on the IAP ligand described in WO Pub. No. 2006/069063, or an unnatural mimetic thereof:

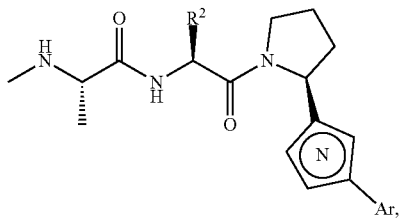

(XVI)

wherein:
R² of Formula (XVI) is selected from alkyl, cycloalkyl and heterocycloalkyl; more preferably, from isopropyl, tert-butyl, cyclohexyl and tetrahydropyranyl, most preferably from cyclohexyl;

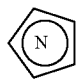

of Formula (XVI) is a 5- or 6-membered nitrogen-containing heteroaryl; more preferably, 5-membered nitrogen-containing heteroaryl, and most preferably thiazole; and Ar of Formula (XVI) is an aryl or a heteroaryl.

In any of the compounds described herein, the ILM can have the structure of Formula (XVII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

(XVII)

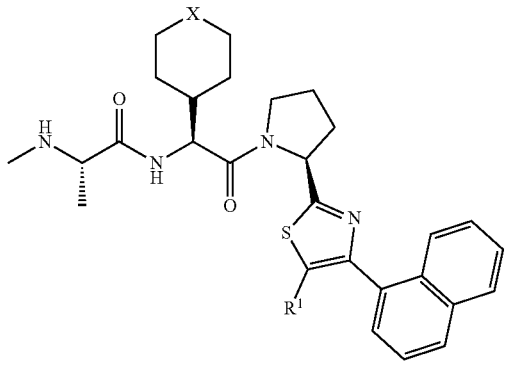

wherein:
R¹ of Formula (XVII) is selected from to group halogen (e.g. fluorine), cyano,

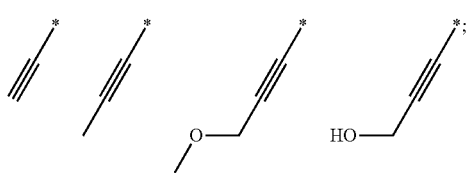

X of Formula (XVII) is selected from the group O or CH2.

In any of the compounds described herein, the ILM can have the structure of Formula (XVIII), which is based on the IAP ligands described in Cohen, F. et al., Antogonists of inhibitors of apoptosis proteins based on thiazole amide isosteres, Bioorg. Med. Chem. Lett., 20(7), 2229-33 (2010), or an unnatural mimetic thereof:

(XVIII)

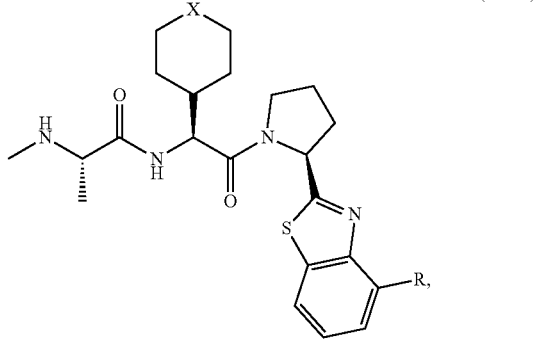

wherein R of Formula (XVIII) is selected from alkyl, aryl, heteroaryl, arylalkyl, heteroarylalkyl or halogen (in variable substitution position).

In any of the compounds described herein, the ILM can have the structure of Formula (XIX), which is based on the IAP ligands described in Cohen, F. et al., *Antogonists of inhibitors of apoptosis proteins based on thiazole amide isosteres*, Bioorg. Med. Chem. Lett., 20(7), 2229-33 (2010), or an unnatural mimetic thereof:

(XIX)

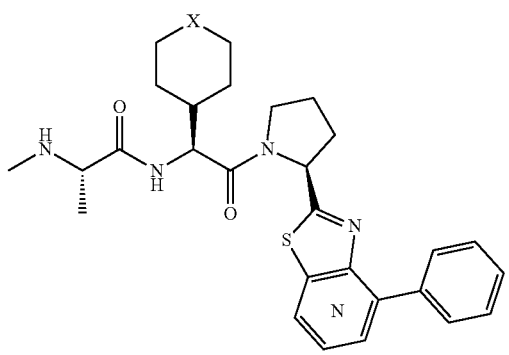

wherein

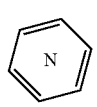

is a 6-member nitrogen heteroaryl.

In a certain embodiment, the ILM of the composition is selected from the group consisting of:

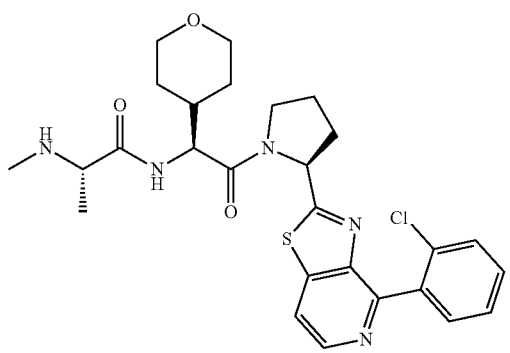

and

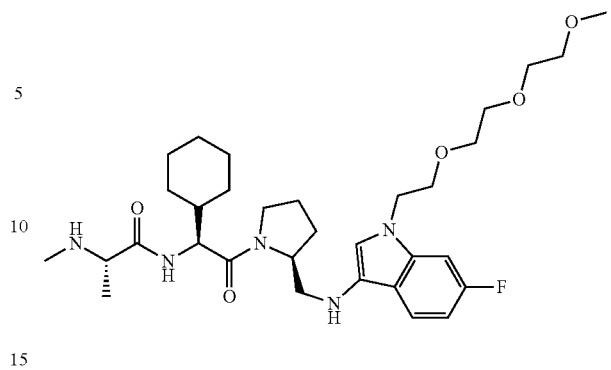

In any of the compounds described herein, the ILM can have the structure of Formula (XX), which is based on the IAP ligands described in WO Pub. No. 2007/101347, or an unnatural mimetic thereof:

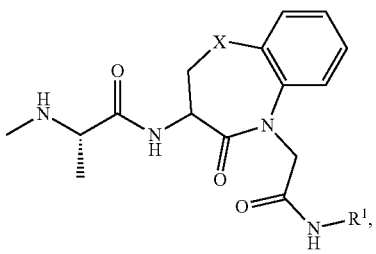 (XX)

wherein X of Formula (XX) is selected from $CH_2$, O, NH, or S.

In any of the compounds described herein, the ILM can have the structure of Formula (XXI), which is based on the IAP ligands described in U.S. Pat. Nos. 7,345,081 and 7,419,975, or an unnatural mimetic thereof:

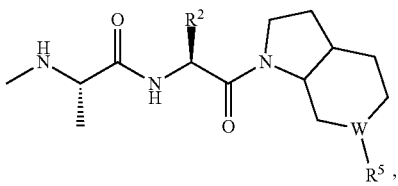 (XXI)

wherein:

$R^2$ of Formula (XXI) is selected from:

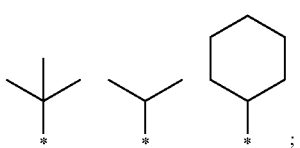

In certain embodiments, the ILM of the composition is selected from the group consisting of:

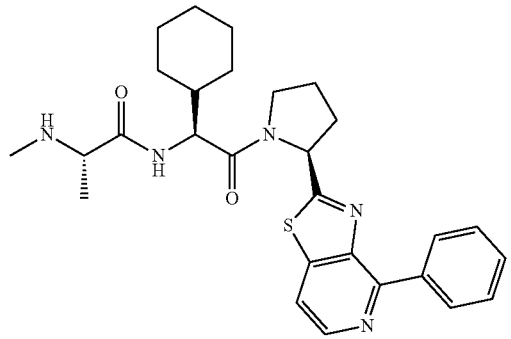

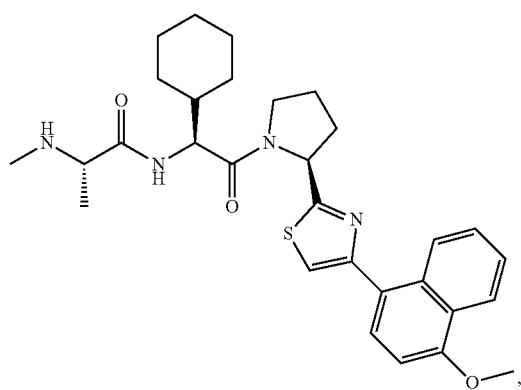

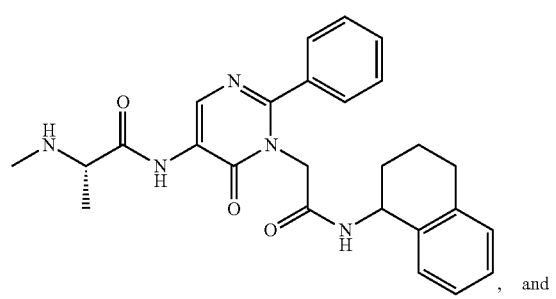

, and $R^5$ of Formula (XXI) is selected from:
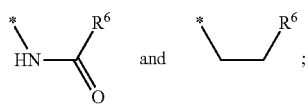
and
W of Formula (XXI) is selected from CH or N; and $R^6$ of
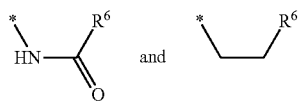
are independently a mono- or bicyclic fused aryl or heteroaryl.
In certain embodiments, the ILM of the compound is selected from the group consisting of:
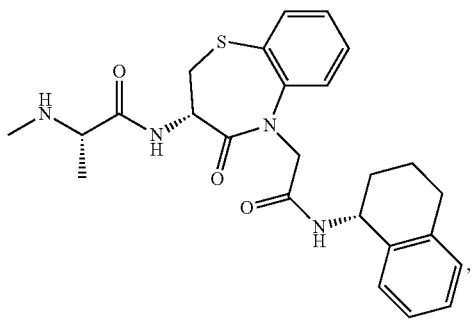
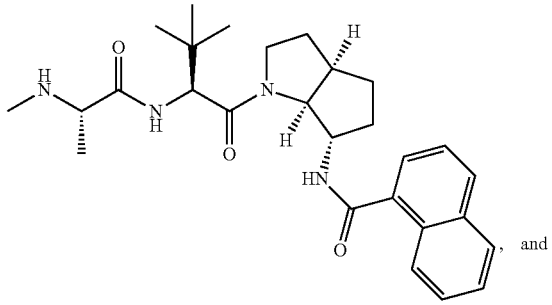
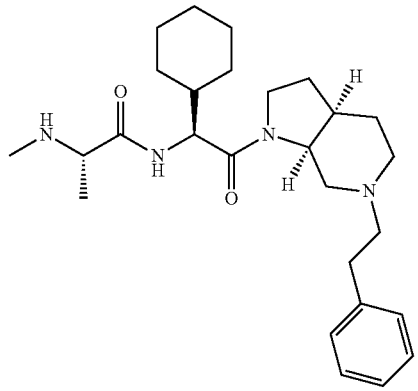
In certain embodiments, the ILM of the compound is selected from the group consisting of:
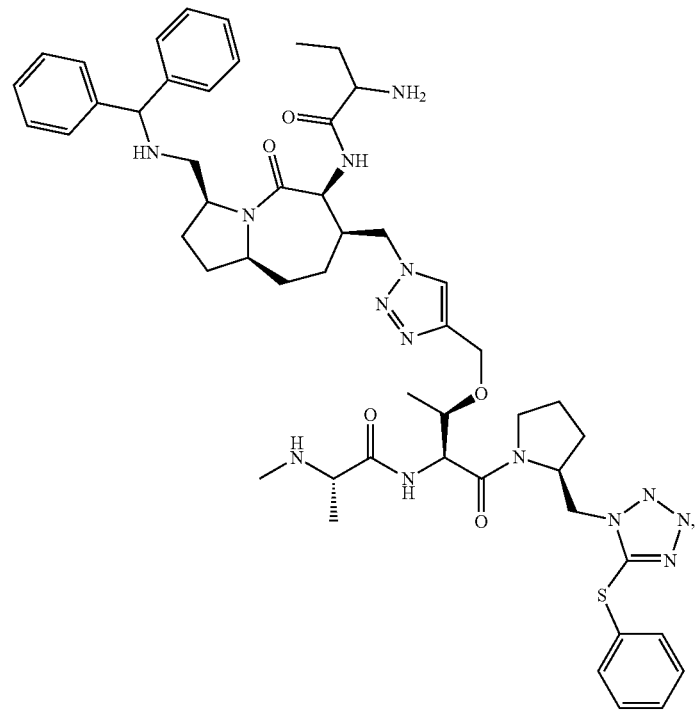

-continued
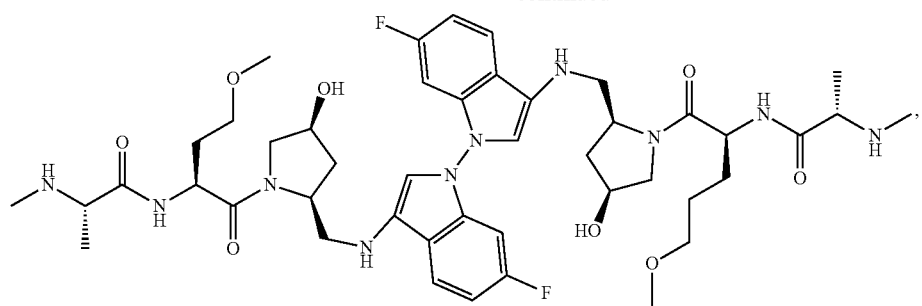
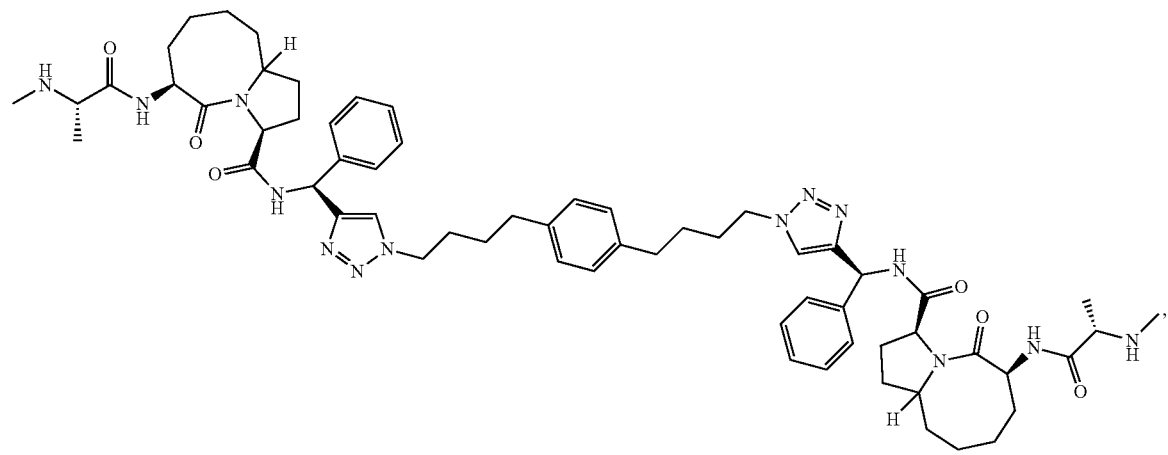

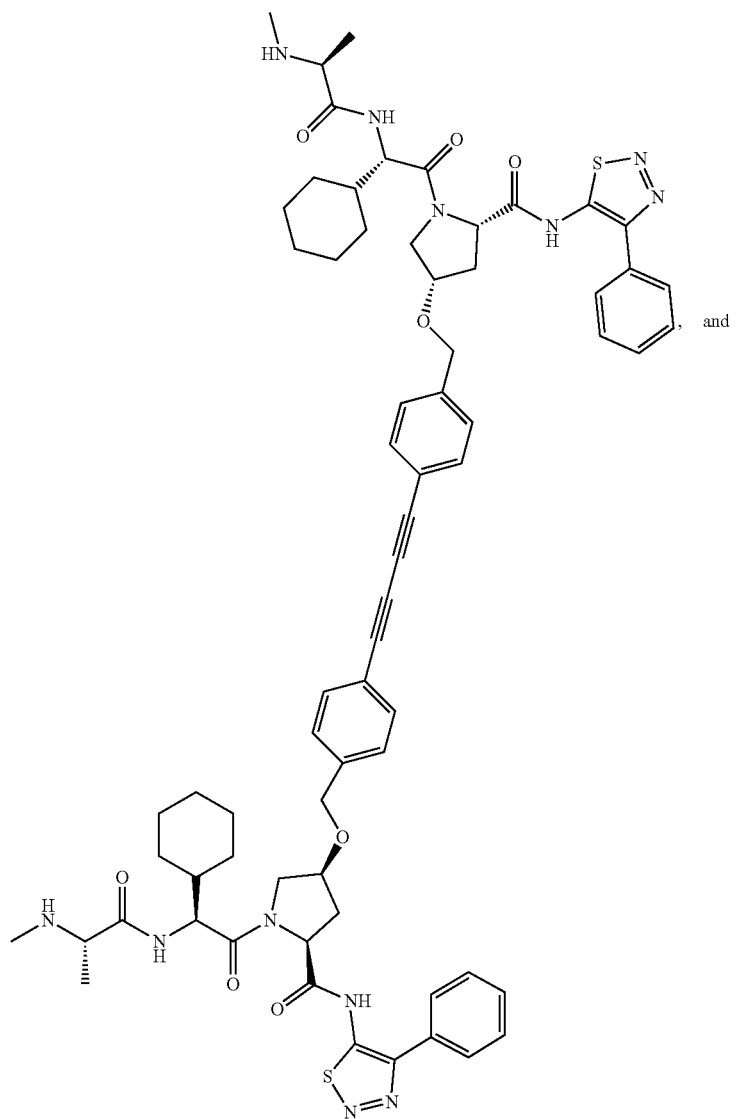, and

-continued

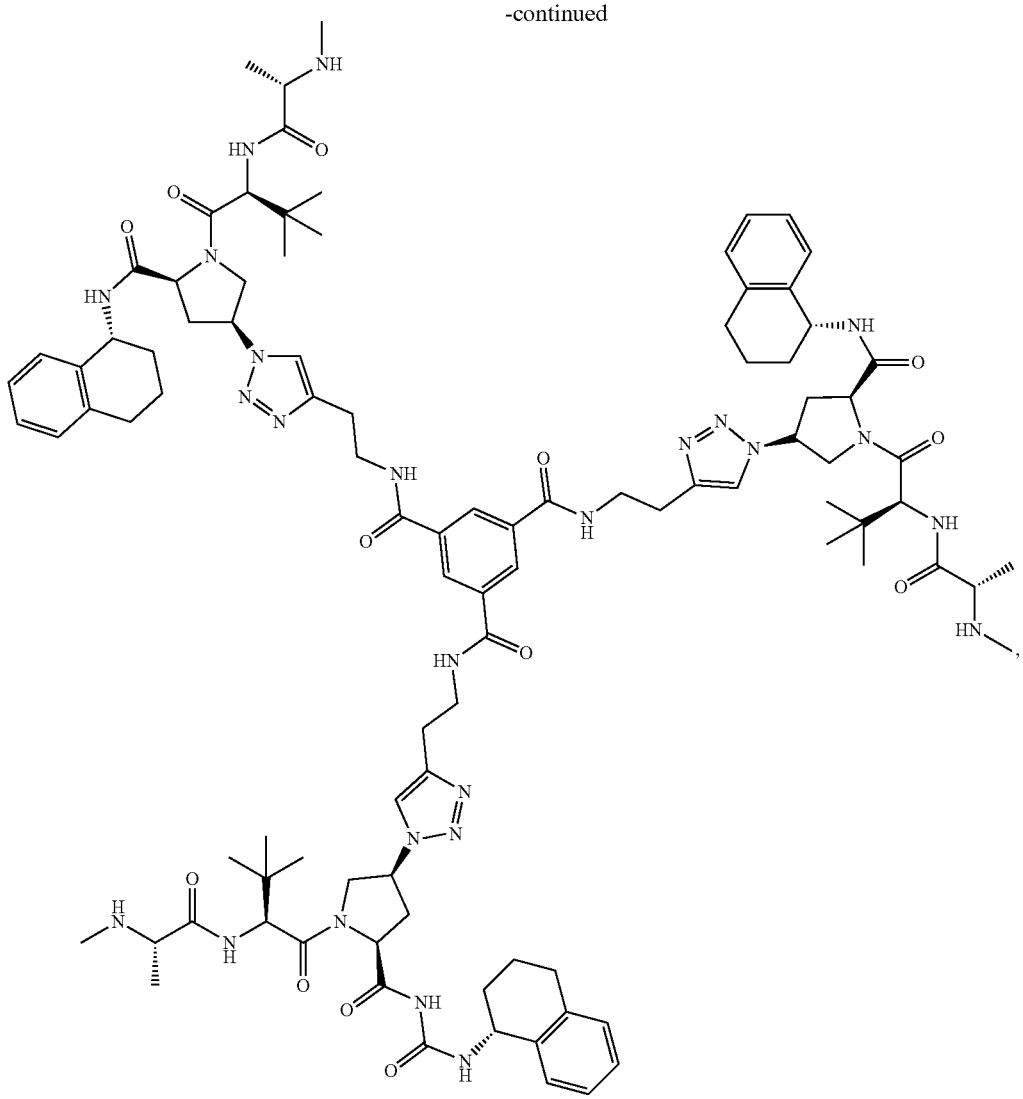

which are described in WO Pub. No. 2009/060292, U.S. Pat. No. 7,517,906, WO Pub. No. 2008/134679, WO Pub. No. 2007/130626, and WO Pub. No. 2008/128121.

In any of the compounds described herein, the ILM can have the structure of Formula (XXII) or (XXIII), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof:

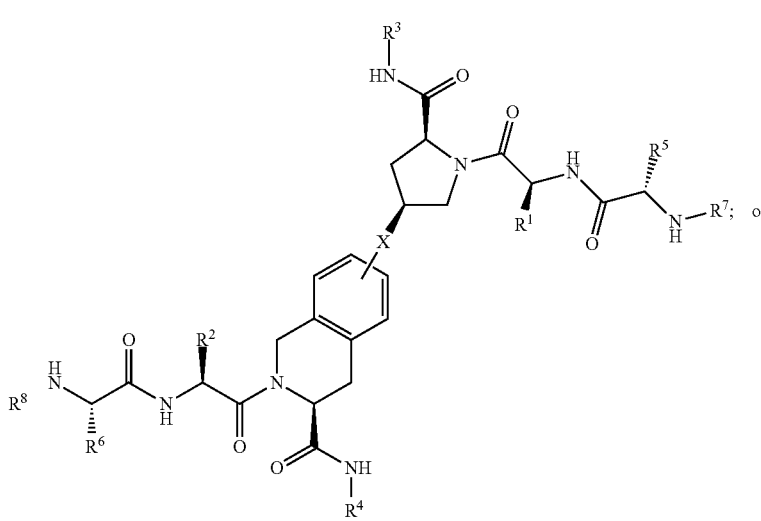

(XXII)

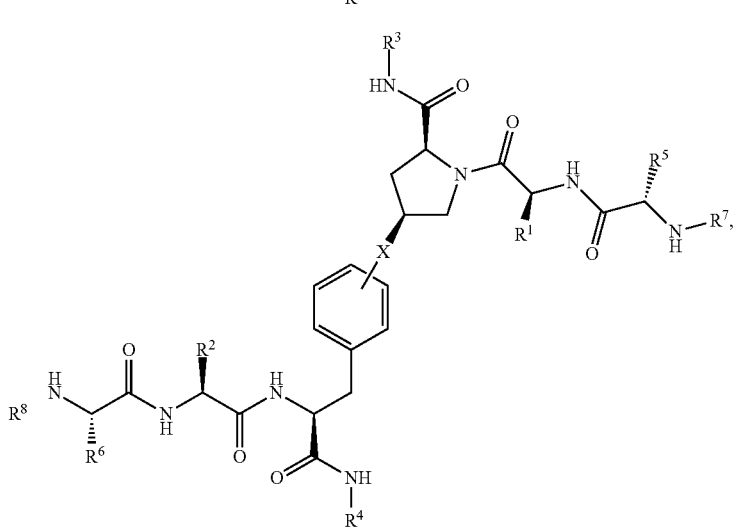

(XXIII)

wherein:
- $R^1$ of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;
- $R^2$ of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;
- or alternatively, $R^1$ and $R^2$ of Formula (XXII) or (XXIII) are independently optionally substituted thioalkyl wherein the substituents attached to the S atom of the thioalkyl are optionally substituted alkyl, optionally substituted branched alkyl, optionally substituted heterocyclyl, —$(CH_2)_v COR^{20}$, —$CH_2 CHR^{21} COR^{22}$ or —$CH_2 R^{23}$;

wherein:
- v is an integer from 1-3;
- $R^{20}$ and $R^{22}$ of —$(CH_2)_v COR^{20}$ and —$CH_2 R^{23}$ are independently selected from OH, $NR^{24}R^{25}$ or $OR^{26}$;
- $R^{21}$ of —$CH_2 CHR^{21} COR^2$ is selected from the group $NR^{24}R^{25}$;
- $R^{23}$ of —$CH_2 R^{23}$ is selected from optionally substituted aryl or optionally substituted heterocyclyl, where the optional substituents include alkyl and halogen;
- $R^{24}$ of $NR^{24}R^{25}$ is selected from hydrogen or optionally substituted alkyl;
- $R^{25}$ of $NR^{24}R^{25}$ is selected from hydrogen, optionally substituted alkyl, optionally substituted branched alkyl, optionally substituted arylalkyl, optionally substituted heterocyclyl, —$CH_2(OCH_2CH_2O)_m CH_3$, or a polyamine chain, such as spermine or spermidine;
- $R^{26}$ of $OR^{26}$ is selected from optionally substituted alkyl, wherein the optional substituents are OH, halogen or $NH_2$; and
- m is an integer from 1-8;
- $R^3$ and $R^4$ of Formula (XXII) or (XXIII) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXII) or (XXIII) are independently selected from hydrogen, optionally substituted alkyl or optionally substituted cycloalkyl; and X is selected from a bond or a chemical linker group, and/or a pharmaceutically acceptable salt, tautomer or stereoisomer thereof.

In certain embodiments, X is a bond or is selected from the group consisting of:

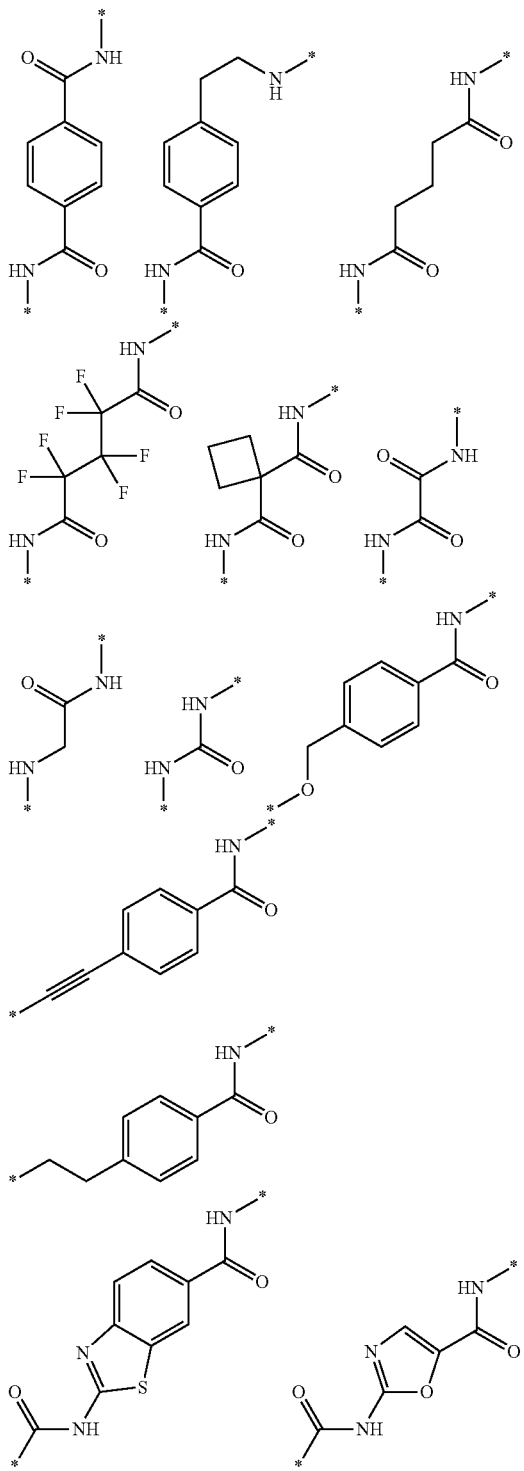

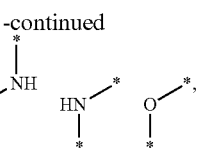

wherein "*" is the point of attachment of a PTM, L or ULM, e.g., an ILM.

In any of the compounds described herein, the ILM can have the structure of Formula (XXIV) or (XXVI), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof, and the chemical linker to linker group L as shown:

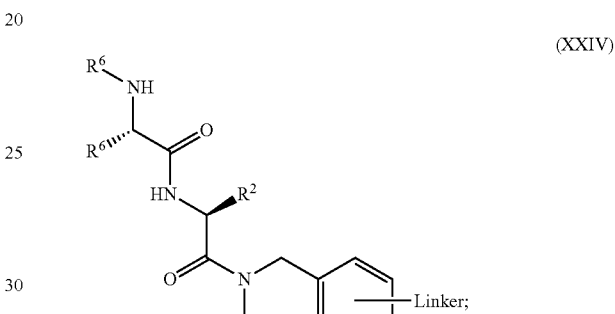

(XXIV)

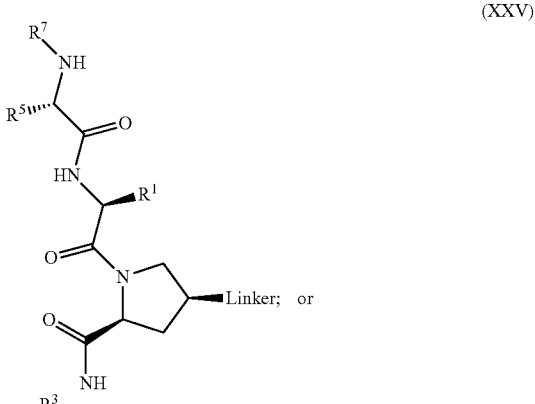

(XXV)

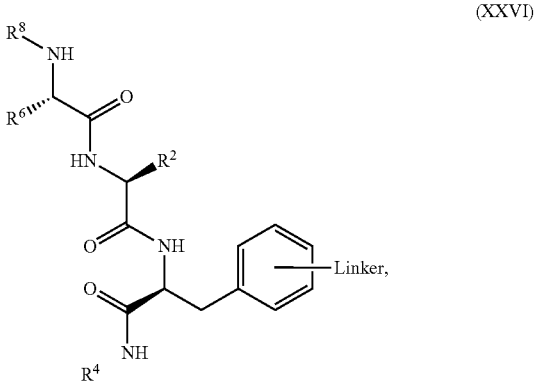

(XXVI)

wherein:
R¹ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

R² of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl; or alternatively, R¹ and R² of Formula (XXIV), (XXV) or (XXVI) are independently selected from optionally substituted thioalkyl wherein the substituents attached to the S atom of the thioalkyl are optionally substituted alkyl, optionally substituted branched alkyl, optionally substituted heterocyclyl, —(CH₂)ᵥCOR²⁰, —CH₂CHR²¹COR²² or —CH₂R²³, wherein:
v is an integer from 1-3;
R²⁰ and R²² of —(CH₂)ᵥCOR²⁰ and —CH₂R²³ are independently selected from OH, NR²⁴R²⁵ or OR²⁶;
R²¹ of —CH₂CHR²¹COR² is selected from NR²⁴R²⁵;
R²³ of —CH₂R²³ is selected from optionally substituted aryl or optionally substituted heterocyclyl, wherein the optional substituents include alkyl and halogen;
R²⁴ of NR²⁴R²⁵ is selected from hydrogen or optionally substituted alkyl;
R²⁵ of NR²⁴R²⁵ is selected from hydrogen, optionally substituted alkyl, optionally substituted branched alkyl, optionally substituted arylalkyl, optionally substituted heterocyclyl, —CH₂(OCH₂CH₂O)ₘCH₃, or a polyamine chain, such as spermine or spermidine;
R²⁶ of OR²⁶ is selected from optionally substituted alkyl, wherein the optional substituents are OH, halogen or NH₂; and
m is an integer from 1-8;

R³ and R⁴ of Formula (XXIV), (XXV) or (XXVI) are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R⁵, R⁶, R⁷ and R⁸ of Formula (XXIV), (XXV) or (XXVI) are independently hydrogen, optionally substituted alkyl or optionally substituted cycloalkyl; and/or a pharmaceutically acceptable salt, tautomer or stereoisomer thereof.

In a particular embodiment, the ILM according to Formulas (XXII) through (XXVI):
R⁷ and R⁸ are selected from the H or Me;
R⁵ and R⁶ are selected from the group comprising:

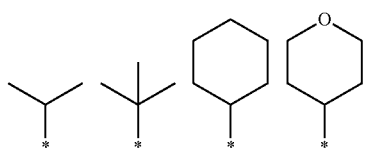

R³ and R⁴ are selected from the group comprising:

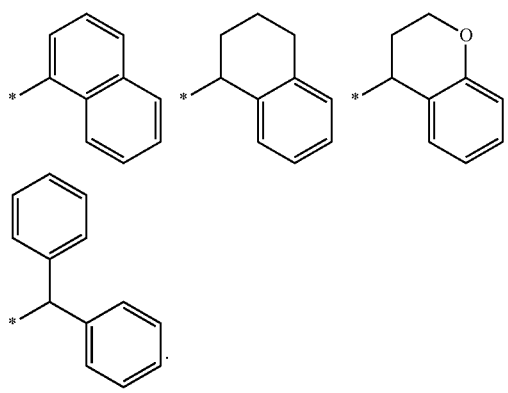

In any of the compounds described herein, the ILM can have the structure of Formula (XXVII) or (XXVII), which are derived from the IAP ligands described in WO Pub. No. 2014/055461 and Kim, K S, *Discovery of tetrahydroisoquinoline-based bivalent heterodimeric IAP antagonists.* Bioorg. Med. Chem. Lett. 24(21), 5022-9 (2014), or an unnatural mimetic thereof:

(XXVII)

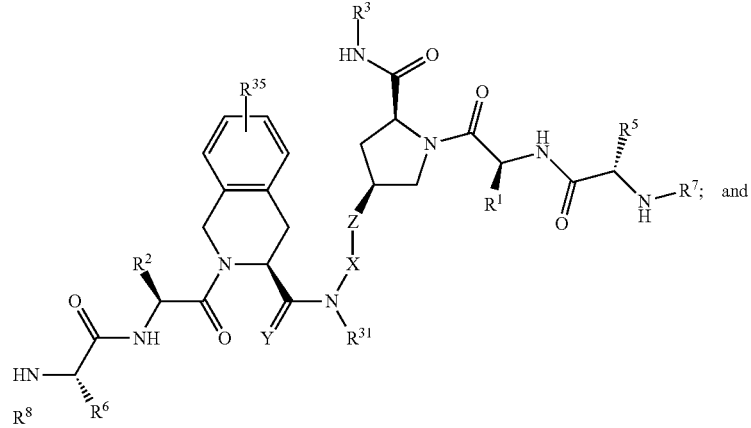

and (XXVIII)

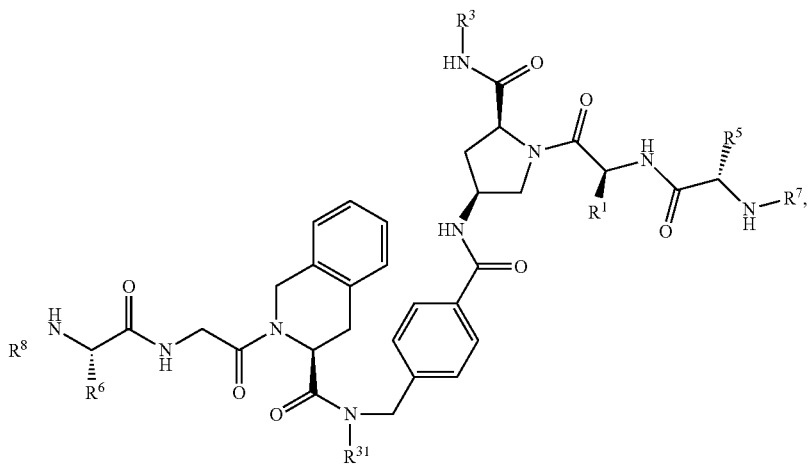

wherein:
- $R^{35}$ is 1-2 substituents selected from alkyl, halogen, alkoxy, cyano and haloalkoxy;
- $R^1$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;
- $R^2$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl; or alternatively,
- $R^1$ and $R^2$ of Formula (XXVII) and (XXVIII) are independently selected from an optionally substituted thioalkyl —$CR^{60}R^{61}SR^{70}$, wherein $R^{60}$ and $R^{61}$ are selected from H or methyl, and
- $R^{70}$ is selected from an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$, wherein:
- v is an integer from 1-3;
- $R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;
- $R^{21}$ of —$CH_2CHR^{21}COR^{22}$ is selected from $NR^{24}R^{25}$;
- $R^{23}$ of —$CH_2R^{23}$ is selected from an optionally substituted aryl or optionally substituted heterocyclyl, where the optional substituents include alkyl and halogen;
- $R^{24}$ of $NR^{24}R^{25}$ is selected from hydrogen or optionally substituted alkyl;
- $R^{25}$ of $NR^{24}R^{25}$ is selected from hydrogen, optionally substituted alkyl, optionally substituted branched alkyl, optionally substituted arylalkyl, optionally substituted heterocyclyl, —$CH_2CH_2(OCH_2CH_2)_mCH_3$, or a polyamine chain —$[CH_2CH_2(CH_2)_\delta NH]_\psi CH_2CH_2(CH_2)_{\bar\omega}NH_2$, such as spermine or spermidine;

wherein $\delta=0-2$, $\psi=1-3$, $\bar\omega=0-2$;
- $R^{26}$ of $OR^{26}$ is an optionally substituted alkyl, wherein the optional substituents are OH, halogen or $NH_2$; and
- m is an integer from 1-8,
- $R^3$ and $R^4$ of Formula (XXVII) and (XXVIII) are independently selected from an optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;
- $R^5$, $R^6$, $R^7$ and $R^8$ of Formula (XXVII) and (XXVIII) are independently selected from hydrogen, optionally substituted alkyl or optionally substituted cycloalkyl;
- $R^{31}$ of Formulas (XXVII) and (XXVIII) is selected from alkyl, aryl, arylalkyl, heteroaryl or heteroarylalkyl optionally further substituted, preferably selected form the group consisting of:

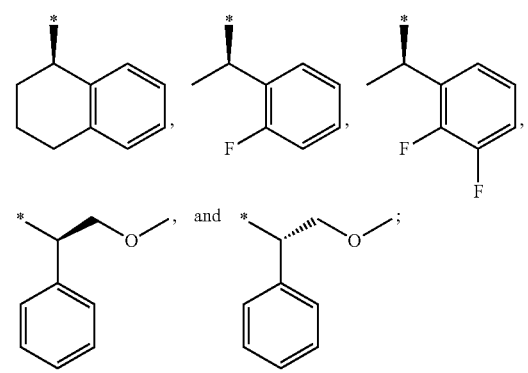

X of Formulas (XXVII) and (XXVIII) is selected from —$(CR^{81}R^{82})_m$—, optionally substituted heteroaryl or heterocyclyl,

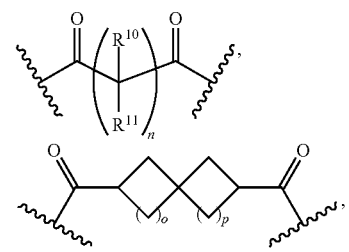

-continued

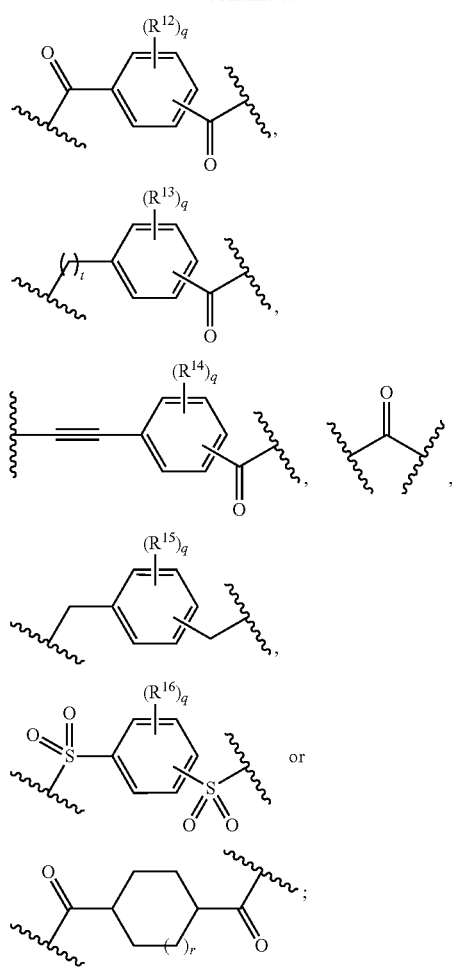

or

Z of Formulas (XXVII) is selected from C=O, —O—, —NR, —CONH—, —NHCO—, or may be absent;

$R^{81}$ and $R^{82}$ of —$(CR^{81}R^{82})_m$ are independently selected from hydrogen, halogen, alkyl or cycloalkyl, or $R^{81}$ and $R^{82}$ can be taken together to form a carbocyclic ring;

$R^{10}$ and $R^{11}$ of

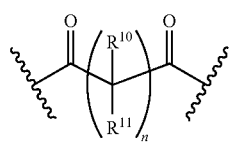

are independently selected from hydrogen, halogen or alkyl;

$R^{12}$, $R^{13}$, $R^{14}$, $R^{15}$ and $R^{16}$ of

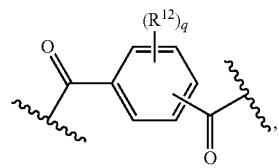

-continued

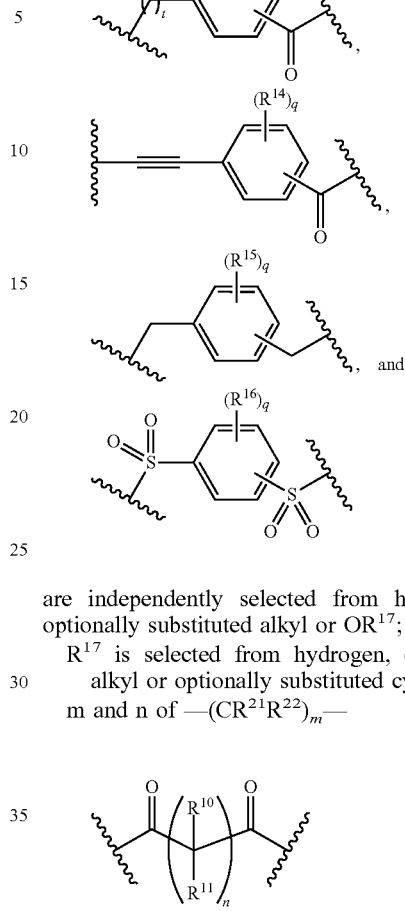

and are independently selected from hydrogen, halogen or optionally substituted alkyl or $OR^{17}$;

$R^{17}$ is selected from hydrogen, optionally substituted alkyl or optionally substituted cycloalkyl;

m and n of —$(CR^{21}R^{22})_m$—

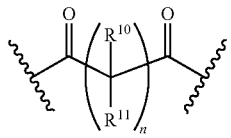

are independently 0, 1, 2, 3, or 4;

o and p of

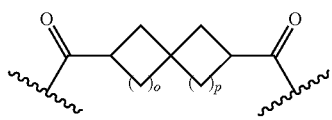

are independently 0, 1, 2 or 3;

q and t of

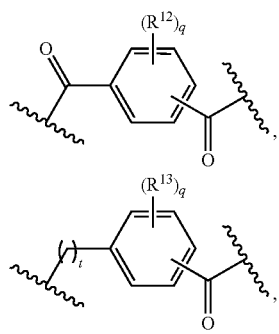

-continued

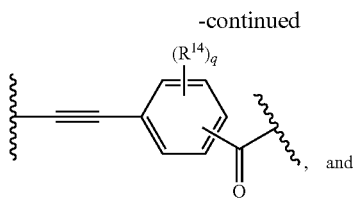, and

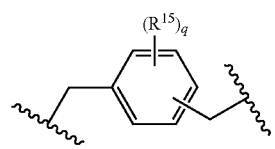

are independently 0, 1, 2, 3, or 4;

r of

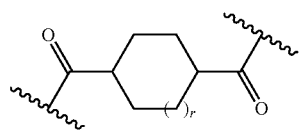

is 0 or 1;

and/or a pharmaceutically acceptable salt, tautomer or stereoisomer thereof.

In any of the compounds described herein, the ILM can have the structure of Formula (XXIX), (XXX), (XXXI), or (XXXII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof, and the chemical linker to linker group L as shown:

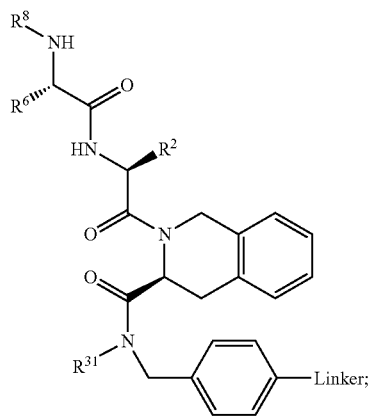
(XXIX)

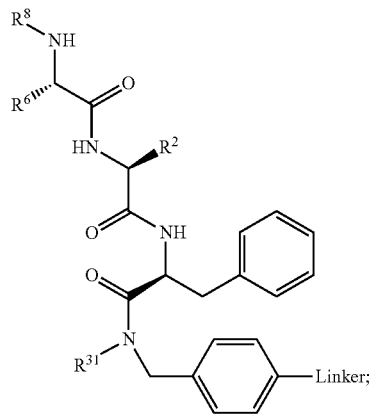
(XXX)

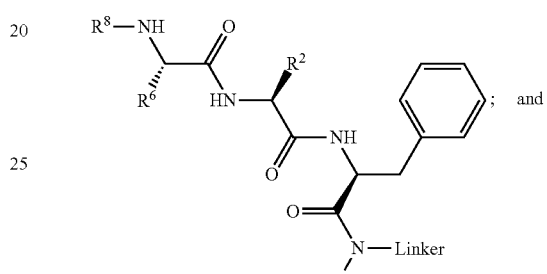
(XXXI)

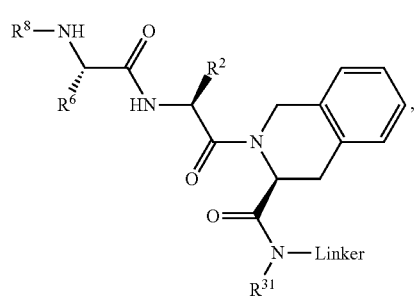
(XXXII)

wherein:
$R^2$ of Formula (XXIX) through (XXXII) is selected from H, an optionally substituted alkyl, optionally substituted cycloalkyl, optionally substituted cycloalkylalkyl, optionally substituted heterocyclyl, optionally substituted arylalkyl or optionally substituted aryl; or alternatively;

$R^1$ and $R^2$ of Formula (XXVII) and (XXVIII) are independently selected from H, an optionally substituted thioalkyl —$CR^{60}R^{61}SR^{70}$ wherein $R^{60}$ and $R^{61}$ are selected from H or methyl, and $R^{70}$ is an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$;

wherein:
v is an integer from 1-3;
$R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;
$R^{21}$ of —$CH_2CHR^{21}COR^{22}$ is selected from $NR^{24}R^{25}$;
$R^{23}$ of —$CH_2R^{23}$ is selected from an optionally substituted aryl or optionally substituted heterocyclyl, where the optional substituents include alkyl and halogen;
$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, —$CH_2CH_2(OCH_2CH_2)_mCH_3$, or a polyamine chain $[CH_2CH_2(CH_2)_\delta NH]_\psi CH_2CH_2(CH_2)_{\overline{\omega}}NH_2$, such as spermine or spermidine, wherein $\delta=0-2$, $\psi=1-3$, $\overline{\omega}=0-2$;

$R^{26}$ of $OR^{26}$ is an optionally substituted alkyl, wherein the optional substituents are OH, halogen or $NH_2$, m is an integer from 1-8;

$R^6$ and $R^8$ of Formula (XXIX) through (XXXII) are independently selected from hydrogen, optionally substituted alkyl or optionally substituted cycloalkyl; and $R^{31}$ of Formulas (XXIX) through (XXXII) is selected from alkyl, aryl, arylalkyl, heteroaryl or heteroarylalkyl optionally further substituted, preferably selected form the group consisting of:

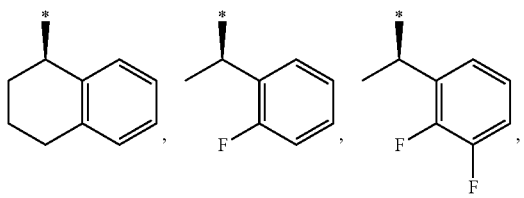

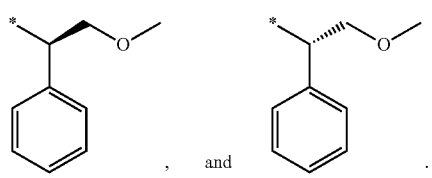

In certain embodiments, the ILM of the compound is:

In any of the compounds described herein, the ILM can have the structure of Formula (XXXIII), which are derived from the IAP ligands described in WO Pub. No. 2014/074658 and WO Pub. No. 2013/071035, or an unnatural mimetic thereof:

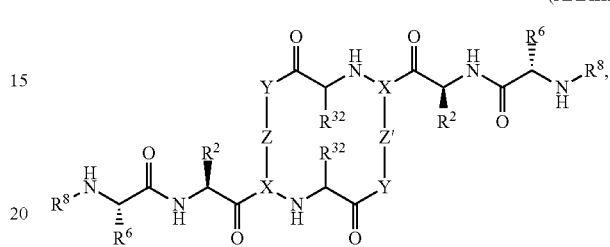

(XXXIII)

wherein:

$R^2$ of Formula (XXXIII) is selected from H, an optionally substituted alkyl, optionally substituted cycloalkyl, optionally substituted cycloalkylalkyl, optionally substituted heterocyclyl, optionally substituted arylalkyl or optionally substituted aryl;

$R^6$ and $R^8$ of Formula (XXXIII) are independently selected from hydrogen, optionally substituted alkyl or optionally substituted cycloalkyl;

$R^{32}$ of Formula (XXXIII) is selected from (C1-C4 alkylene)-$R^{33}$ wherein $R^{33}$ is selected from hydrogen, aryl, heteroaryl or cycloalkyl optionally further substituted;

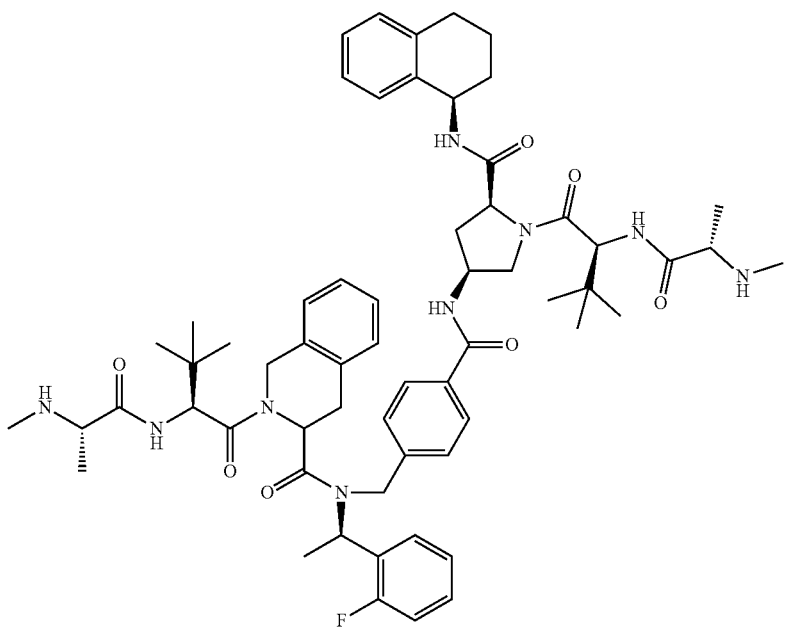

X of Formula (XXXIII) is selected from:
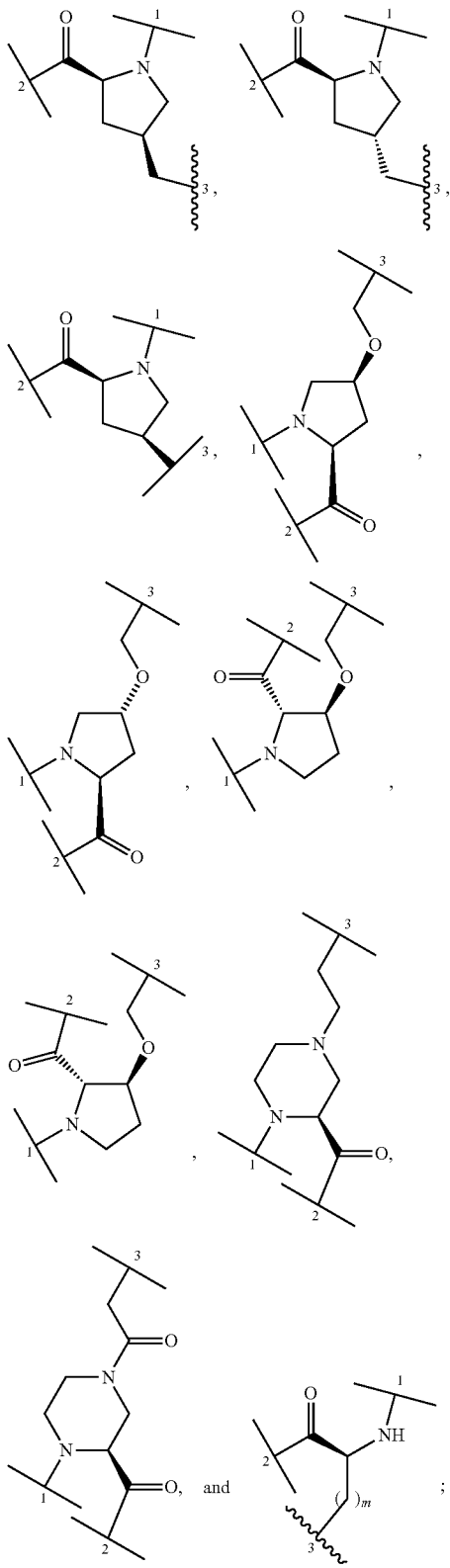
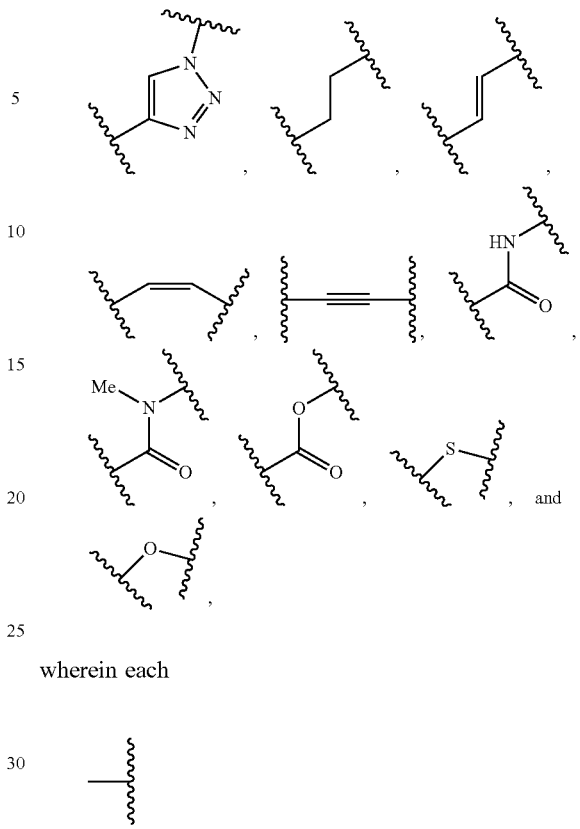
wherein each
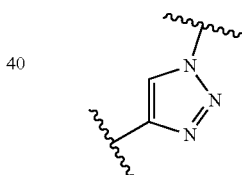
represents a point of attachment to the compound, and Z and Z' cannot both be
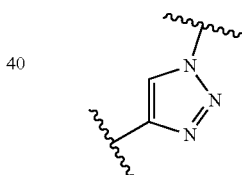
in any given compound;
Y of Formula (XXXIII) is selected from:
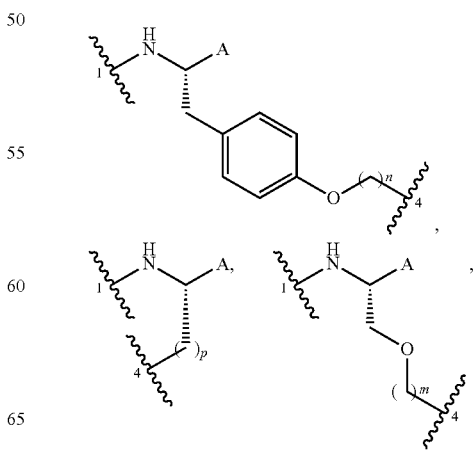
Z and Z' of Formula (XXXIII) are independently selected from:

-continued
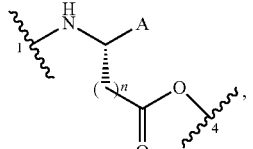
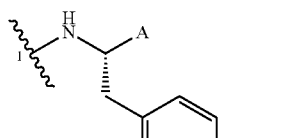
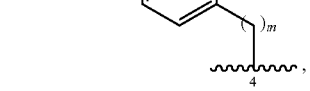
, and

wherein Z and Z' of Formula (XXXIII) are the same and Z is
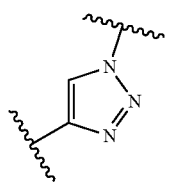
wherein each
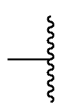
represents a point of attachment to the compound, X is selected from:
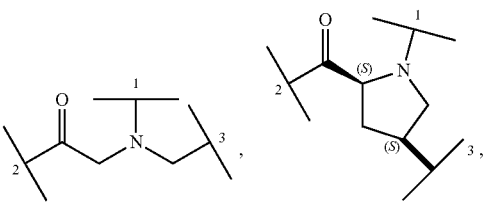
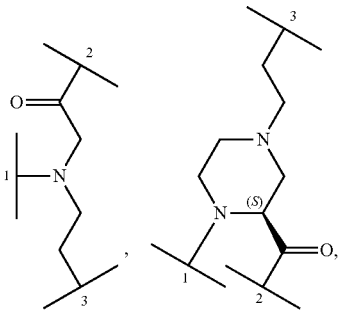
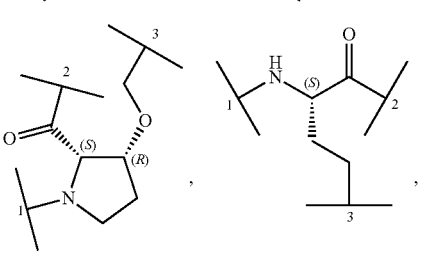
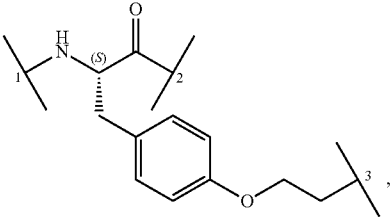
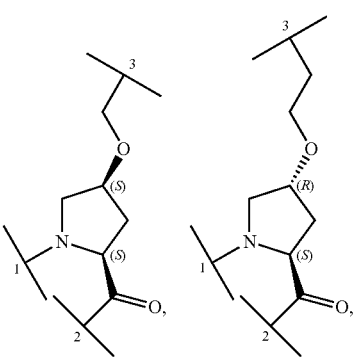
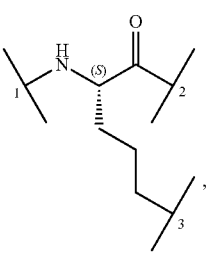

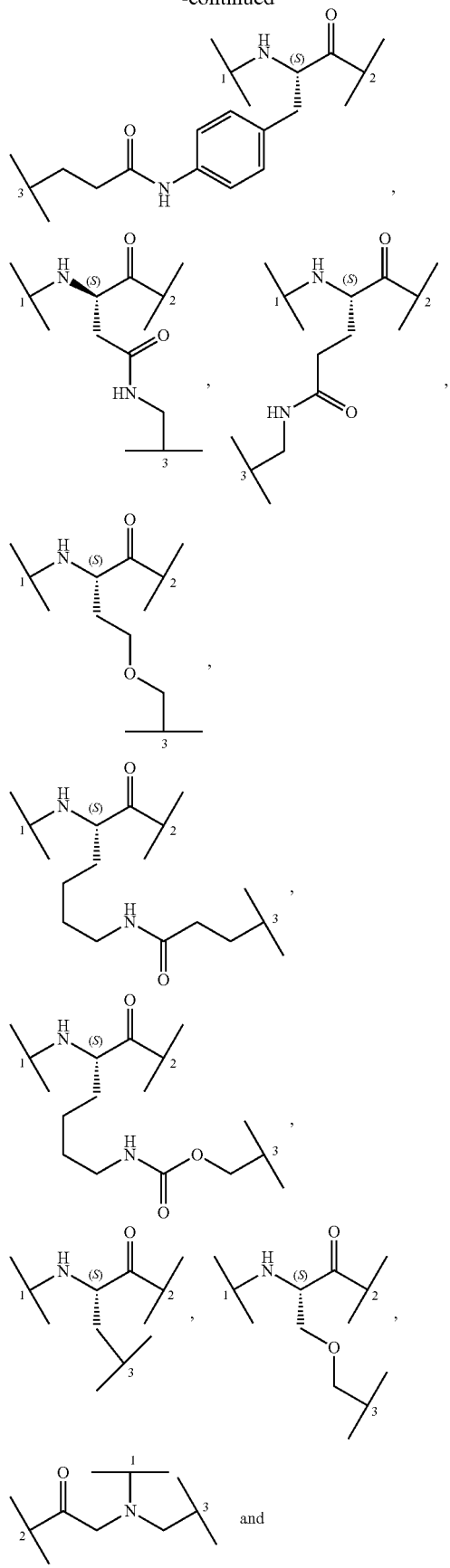
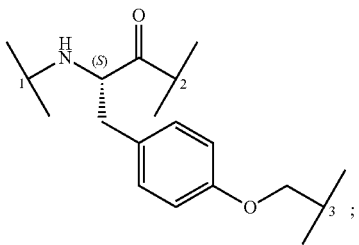
and
Y of Formula (XXXIII) is independently selected from:
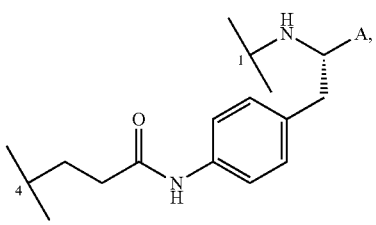
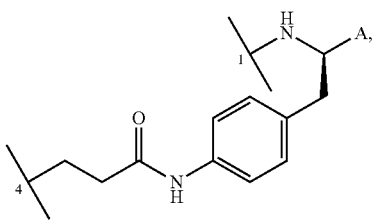
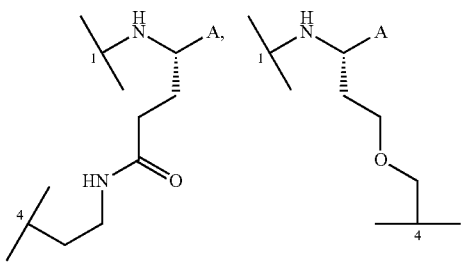
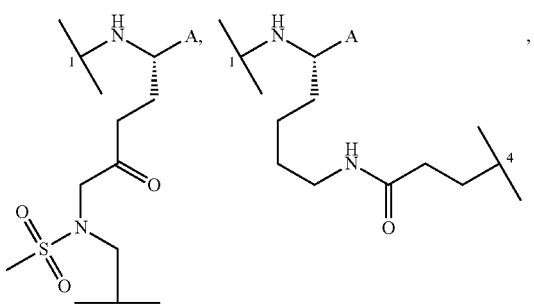
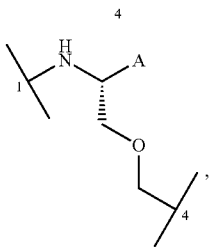

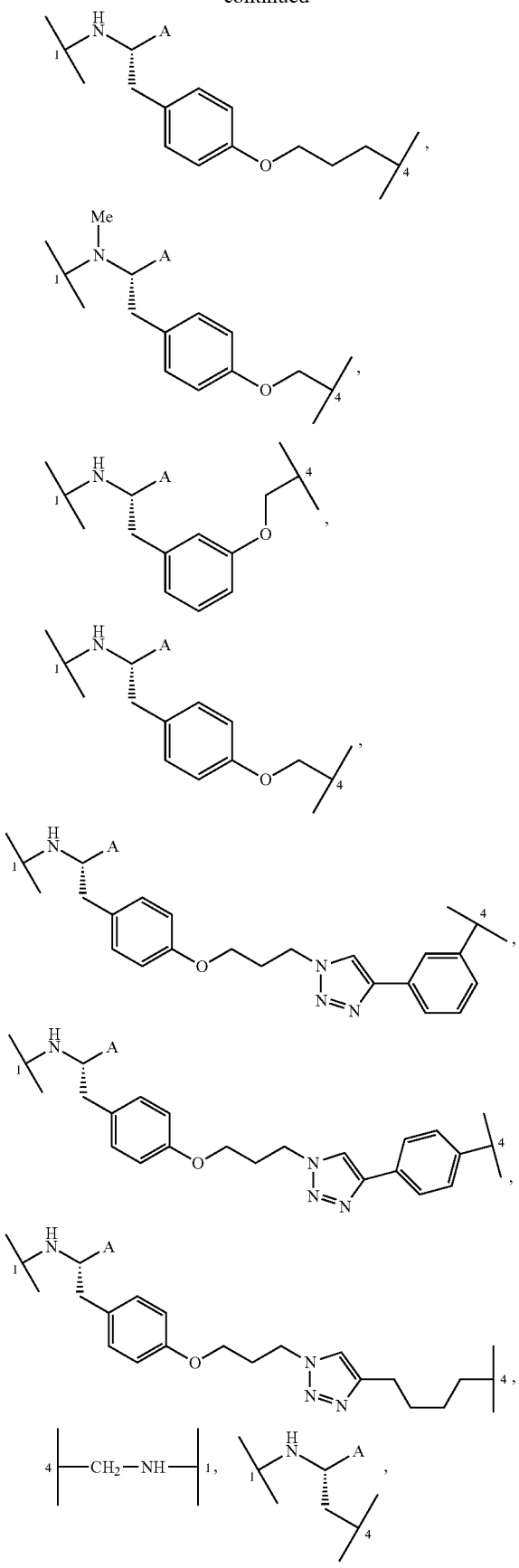
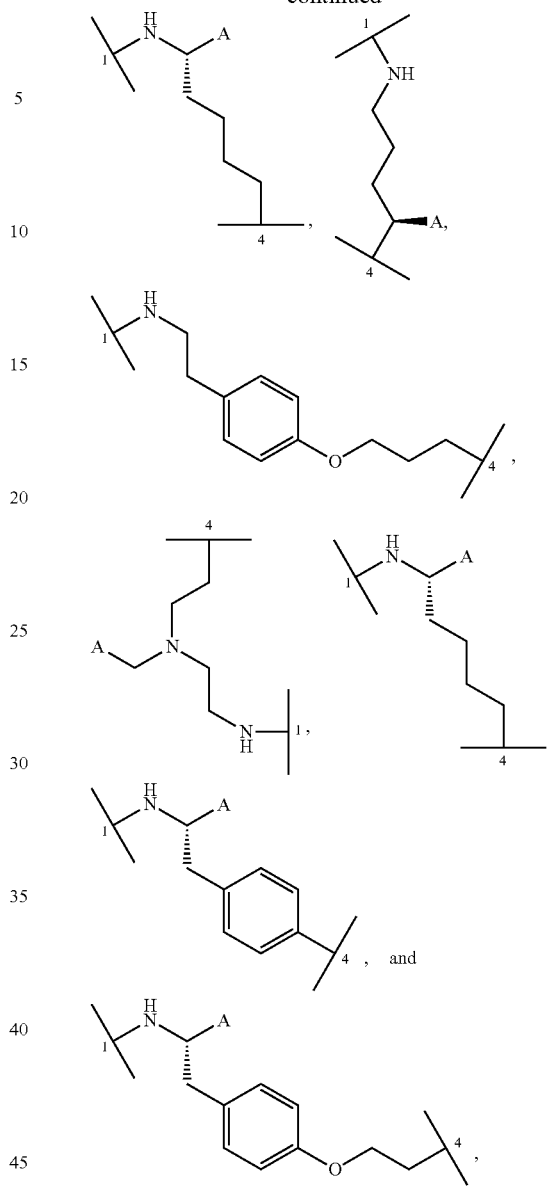
wherein:
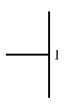
represents a point of attachment to a —C═O portion of the compound;
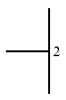
represents a point of attachment to a —NH portion of the compound;

represents a first point of attachment to Z;

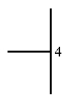

represents a second point of attachment to Z;

m is an integer from 0-3;

n is an integer from 1-3;

p is an integer from 0-4; and

A is —C(O)R³;

R³ is selected from —C(O)R³ is OH, NHCN, NHSO₂R¹⁰, NHOR¹¹ or N(R¹²)(R¹³);

R¹⁰ and F¹¹ of NHSO₂R¹⁰ and NHOR¹¹ are independently selected from hydrogen, optionally substituted —C₁-C₄ alkyl, cycloalkyl, aryl, heteroaryl, heterocyclyl or heterocycloalkyl;

R¹² and R¹³ of N(R¹²)(R¹³) are independently selected from hydrogen, —C₁-C₄ alkyl, —(C₁-C₄) alkylene)-NH—(C₁-C₄ alkyl), and —(C₁-C₄ alkylene)-O—(C₁-C₄ hydroxyalkyl), or R¹² and R¹³ taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XXXIV) or (XXXV), which are derived from the IAP ligands described in WO Pub. No. 2014/047024, or an unnatural mimetic thereof:

(XXXIV)

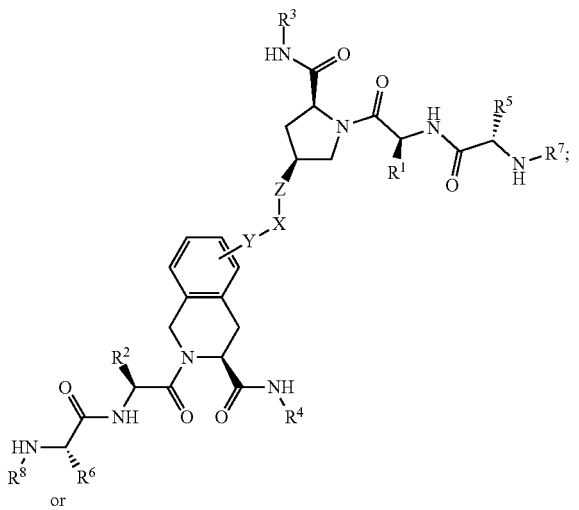

or (XXXV)

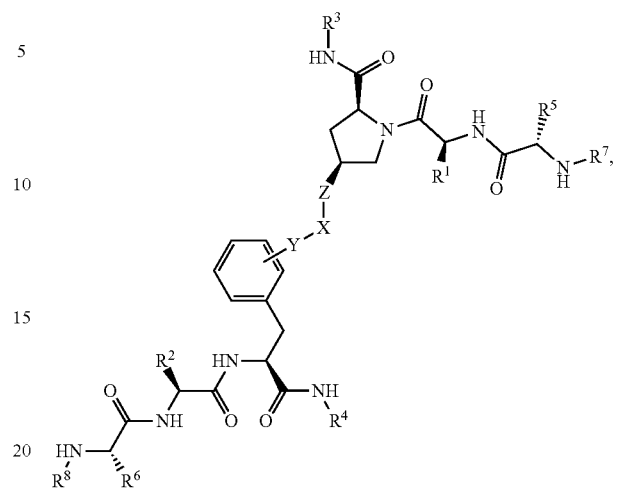

wherein:

X of Formula (XXXIV) or (XXXV) is absent or a group selected from —(CR¹⁰R¹¹)ₘ—, optionally substituted heteroaryl or optionally substituted heterocyclyl,

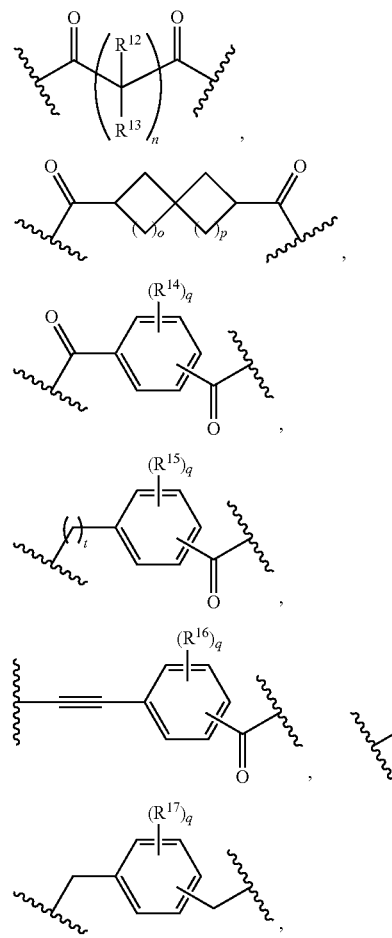

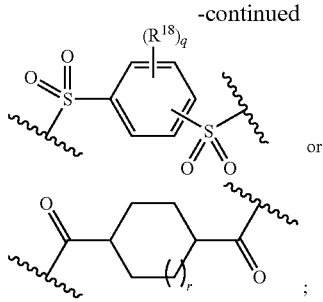

or

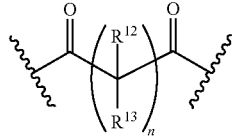

- Y and Z of Formula (XXXIV) or (XXXV) are independently selected from C=O, —O—, —NR$^9$—, —CONH—, —NHCO— or may be absent;
- R$^1$ and R$^2$ of Formula (XXXIV) or (XXXV) are independently selected from an optionally substituted alkyl, optionally substituted cycloalkyl, optionally substituted cycloalkylalkyl, optionally substituted arylalkyl, optionally substituted aryl, or
- R$^1$ and R$^2$ of Formula (XXXIV) or (XXXV) are independently selected from optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$; wherein
- v is an integer from 1-3;
- R$^{20}$ and R$^{22}$ of —(CH$_2$)$_v$COR$^{20}$ and —CH$_2$CHR$^{21}$COR$^{22}$ are independently selected from OH, NR$^{24}$R$^{25}$ or OR$^{26}$;
- R$^{21}$ of —CH$_2$CHR$^{21}$COR$^{22}$ is selected from NR$^{24}$R$^{25}$;
- R$^{23}$ of —CH$_2$R$^{23}$ are selected from an optionally substituted aryl or optionally substituted heterocyclyl, where the optional substituents include alkyl and halogen;
- R$^{24}$ of NR$^{24}$R$^{25}$ is selected from hydrogen or optionally substituted alkyl;
- R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$^{20}$)mCH3, or a polyamine chain;
- R$^{26}$ is an optionally substituted alkyl, wherein the optional substituents are OH, halogen or NH$_2$;
- m of —(CR$^{10}$R$^{11}$)$_m$— is an integer from 1-8;
- R$^3$ and R$^4$ of Formula (XXXIV) or (XXXV) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;
- R$^5$, R$^6$, R$^7$ and R$^8$ of Formula (XXXIV) or (XXXV) are independently selected from hydrogen, optionally substituted alkyl or optionally substituted cycloalkyl;
- R$^{10}$ and R$^{11}$ of —(CR$_{10}$R$^{11}$)$_m$— are independently selected from hydrogen, halogen or optionally substituted alkyl;

R$^{12}$ and R$^{13}$ of

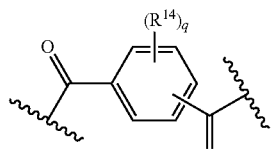

are independently selected from hydrogen, halogen or optionally substituted alkyl, or R$^{12}$ and R$^{13}$ can be taken together to form a carbocyclic ring;

R$^{14}$, R$^{15}$, R$^{16}$, R$^{17}$ and R$^{18}$ of

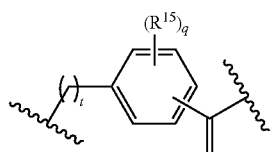

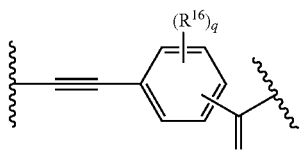

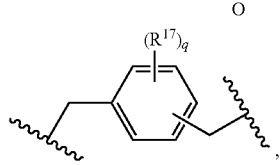

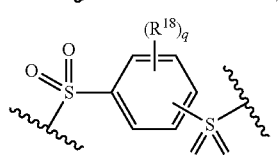, and

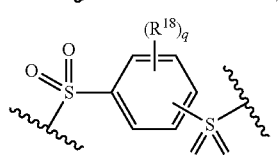

are independently selected from hydrogen, halogen, optionally substituted alkyl or OR$^{19}$;

- R$^{19}$ of OR$^{19}$ is selected from hydrogen, optionally substituted alkyl or optionally substituted cycloalkyl;
- m and n of —(CR$^{10}$R$^{11}$)$_m$— are independently 0, 1, 2, 3, or 4;
- o and p of —(CR$^{10}$R$^{11}$)$_m$— are independently 0, 1, 2 or 3;
- q of —(CR$^{10}$R$^{11}$)$_m$— is 0, 1, 2, 3, or 4; r is 0 or 1;
- t of —(CR$^{10}$R$^{11}$)$_m$— is 1, 2, or 3; and/or a pharmaceutically acceptable salt, tautomer or stereoisomer thereof.

In any of the compounds described herein, the ILM can have the structure of Formula (XXXVI), which are derived from the IAP ligands described in WO Pub. No. 2014/025759, or an unnatural mimetic thereof:

(XXXVI)

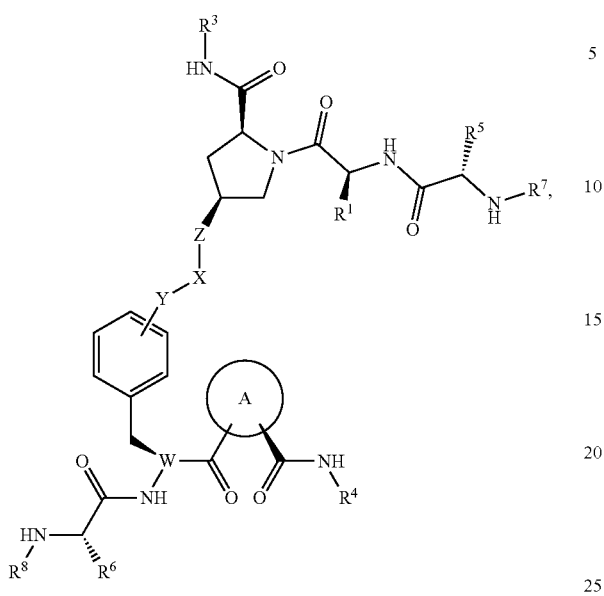

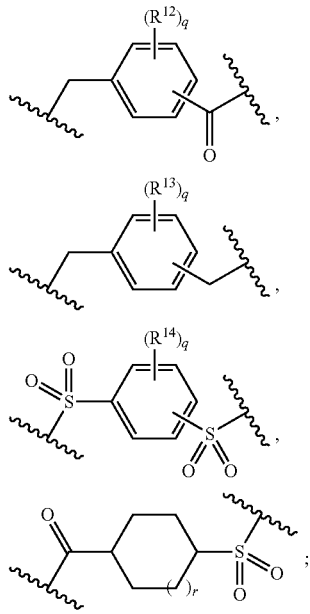

where:

A of Formula (XXXVI) is selected from:

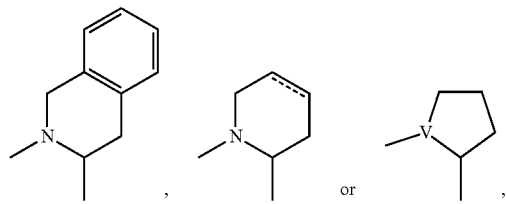

where the dotted line represents an optional double bond;

X of Formula (XXXVI) is selected from: —(CR$^{21}$R$^{22}$)$_m$—,

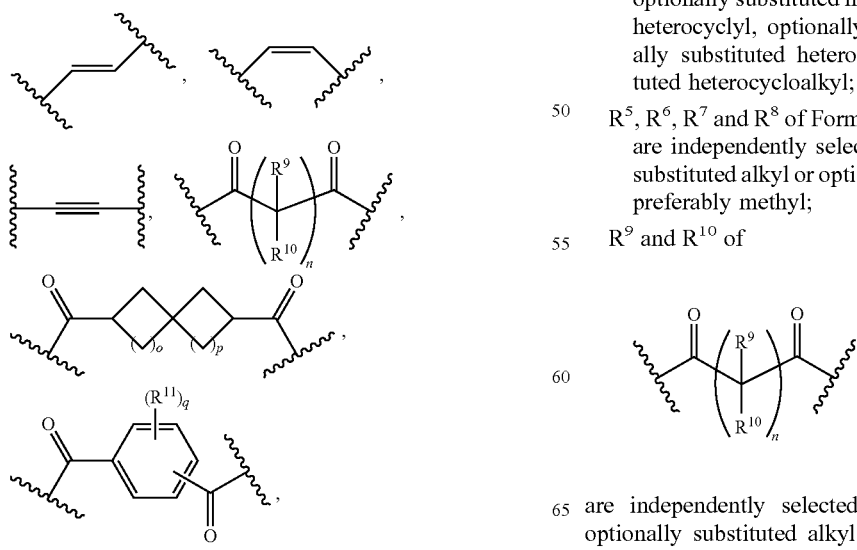

Y and Z of Formula (XXXVI) are independently selected from -O-, —NR$^6$— or are absent;

V of Formula (XXXVI) is selected from —N— or —CH—;

W of Formula (XXXVI) is selected from —CH— or —N—;

R$^1$ of Formula (XXXVI) is selected from an optionally substituted alkyl, optionally substituted cycloalkyl, optionally substituted cycloalkylalkyl, optionally substituted arylalkyl or optionally substituted aryl;

R$^3$ and R$^4$ of Formula (XXXVI) are independently selected from optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

R$^5$, R$^6$, R$^7$ and R$^8$ of Formula (XXIV), (XXV) or (XXVI) are independently selected from hydrogen, optionally substituted alkyl or optionally substituted cycloalkyl, or preferably methyl;

R$^9$ and R$^{10}$ of

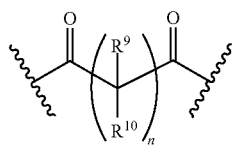

are independently selected from hydrogen, halogen or optionally substituted alkyl, or R$^9$ and R$^{10}$ can be taken together to form a ring;

$R^{11}$, $R^{12}$, $R^{13}$ and $R^{14}$ of

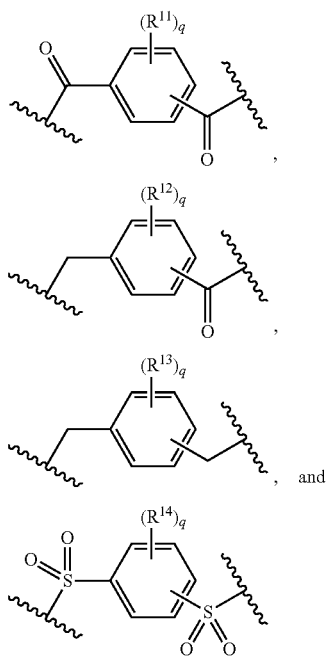

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

m and n of $-(CR^{21}R^{22})_m-$ and

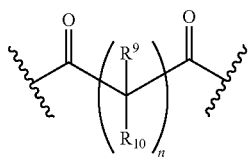

are independently selected from 0, 1, 2, 3, or 4;

o and p of

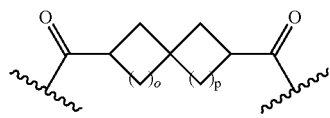

and are independently selected from 0, 1, 2 or 3;

q of is

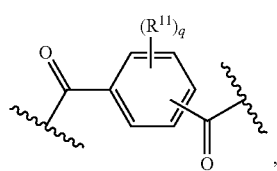

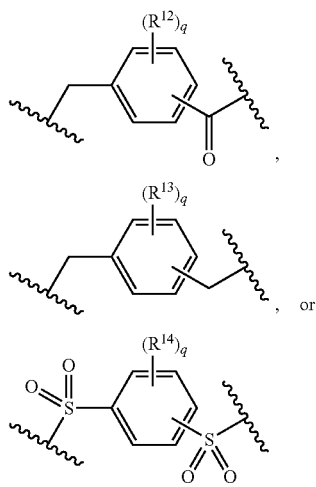

selected from 0, 1, 2, 3, or 4;

r of

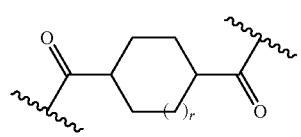

is selected from 0 or 1, and/or or a pharmaceutically acceptable salt, tautomer or stereoisomer thereof.

In any of the compounds described herein, the ILM can have the structure of Formula (XXXVII) or (XXXVIII), which are derived from the IAP ligands described in WO Pub. No. 2014/011712, or an unnatural mimetic thereof:

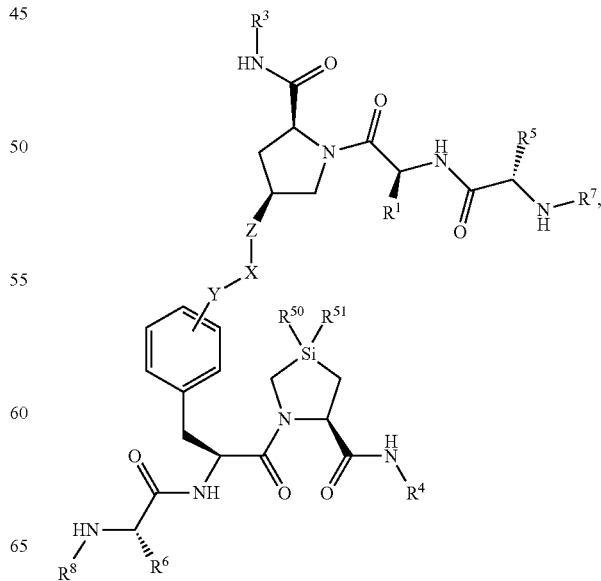

(XXXVII)

(XXXVIII)

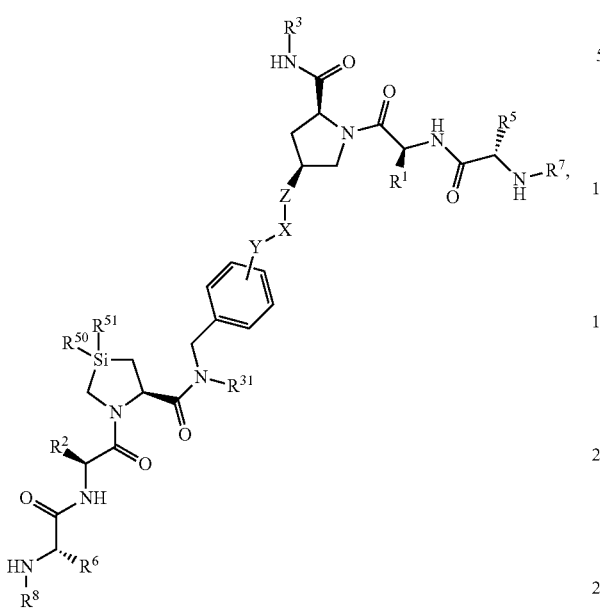

where:

X of Formulas (XXXVII) and (XXXVIII) is —(CR$^{16}$R$^{17}$)$_m$—,

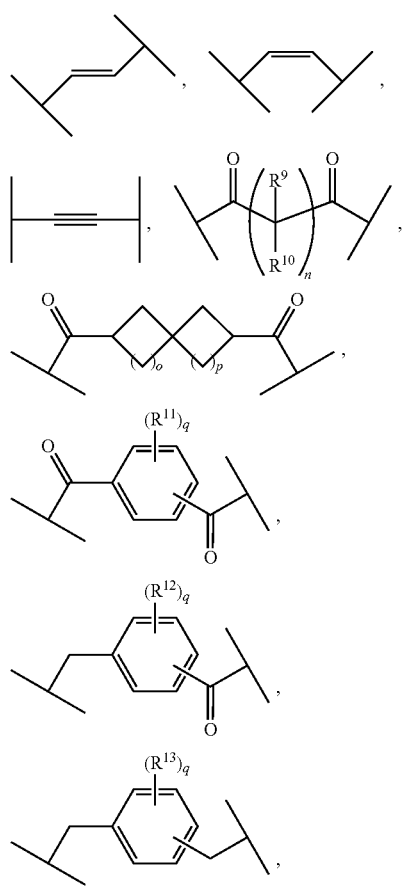

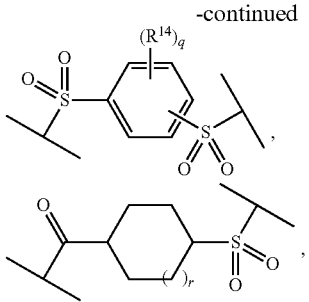

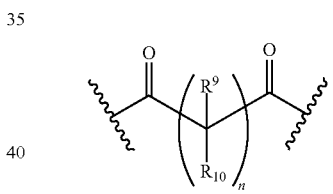

or absent;

Y and Z of Formula (XXXVII) and (XXXVIII) are independently selected from -O-, C=O, NR$^6$ or are absent;

R$^1$ and R$^2$ of Formula (XXXVII) and (XXXVIII) are selected from optionally substituted alkyl, optionally substituted cycloalkyl, optionally substituted alkylaryl or optionally substituted aryl;

R$^3$ and R$^4$ of Formula (XXXVII) and (XXXVIII) are independently selected from optionally substituted alkyl, optionally substituted cycloalkyl, optionally substituted cycloalkylalkyl, optionally substituted arylalkyl or optionally substituted aryl;

R$^5$ and R$^6$ of Formula (XXXVII) and (XXXVIII) are independently selected from optionally substituted alkyl or optionally substituted cycloalkyl;

R$^7$ and R$^8$ of Formula (XXXVII) and (XXXVIII) are independently selected from hydrogen, optionally substituted alkyl or optionally substituted cycloalkyl, or preferably methyl;

R$^9$ and R$^{10}$ of

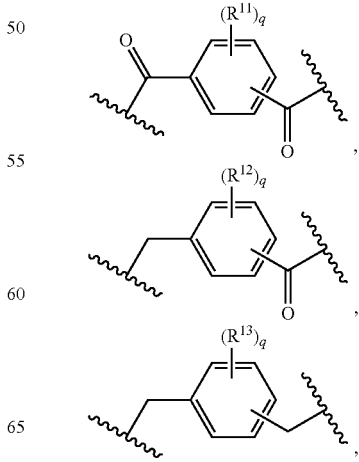

are independently selected from hydrogen, optionally substituted alkyl, or R$^9$ and R$^{10}$ may be taken together to form a ring;

R$^{11}$ to R$^{14}$ of

-continued

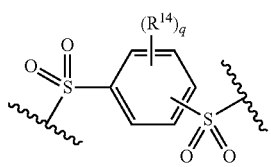

are independently selected from hydrogen, halogen, optionally substituted alkyl or $OR^{15}$;

$R^{15}$ of $OR^{15}$ is selected from hydrogen, optionally substituted alkyl or optionally substituted cycloalkyl;

$R^{16}$ and $R^{17}$ of $-(CR^{16}R^{17})_m-$ are independently selected from hydrogen, halogen or optionally substituted alkyl;

$R^{50}$ and $R^{51}$ of Formula (XXXVII) and (XXXVIII) are independently selected from optionally substituted alkyl, or $R^{50}$ and $R^{51}$ are taken together to form a ring;

m and n of $-(CR^{16}R^{17})_m-$ and

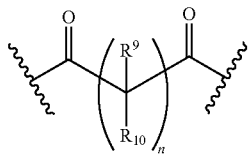

are independently an integer from 0-4;

o and p of

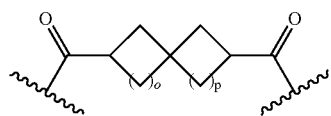

are independently an integer from 0-3;

q of

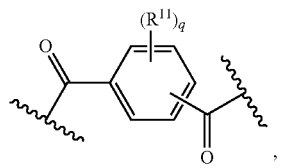

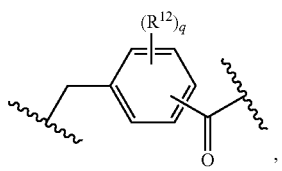

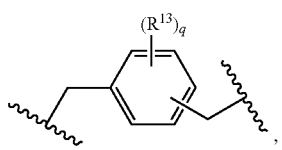

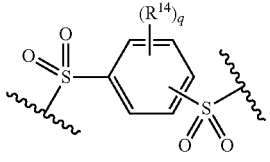

is an integer from 0-4; and r of

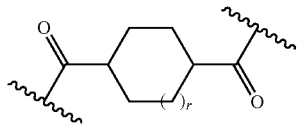

is an integer from 0-1;

or a pharmaceutically acceptable salt, tautomer or stereoisomer thereof.

In an embodiment, $R^1$ and $R^2$ of the ILM of Formula (XXXVII) or (XXXVIII) are t-butyl and $R^3$ and $R^4$ of the ILM of Formula (XXXVII) or (XXXVIII) are tetrahydronaphtalene.

In any of the compounds described herein, the ILM can have the structure of Formula (XXXIX) or (XL), which are derived from the IAP ligands described in WO Pub. No. 2013/071039, or an unnatural mimetic thereof:

(XXXIX)

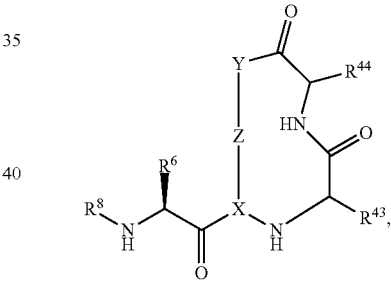

(XL)

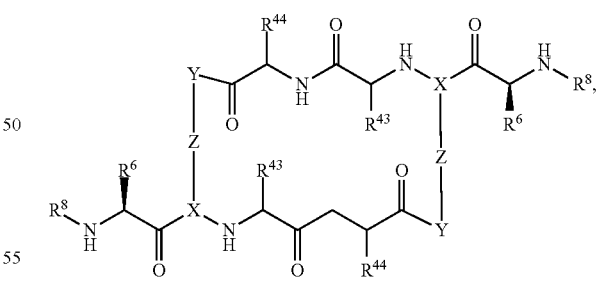

wherein:
$R^{43}$ and $R^{44}$ of Formulas (XXXIX) and (XL) are independently selected from hydrogen, alkyl, aryl, arylalkyl, heteroaryl, heteroarylalkyl, cycloalkyl, cycloalkylalkyl further optionally substituted, and $R^6$ and $R^8$ of Formula (XXXIX) and (XL) are independently selected from hydrogen, optionally substituted alkyl or optionally substituted cycloalkyl.

each X of Formulas (XXXIX) and (XL) is independently selected from:

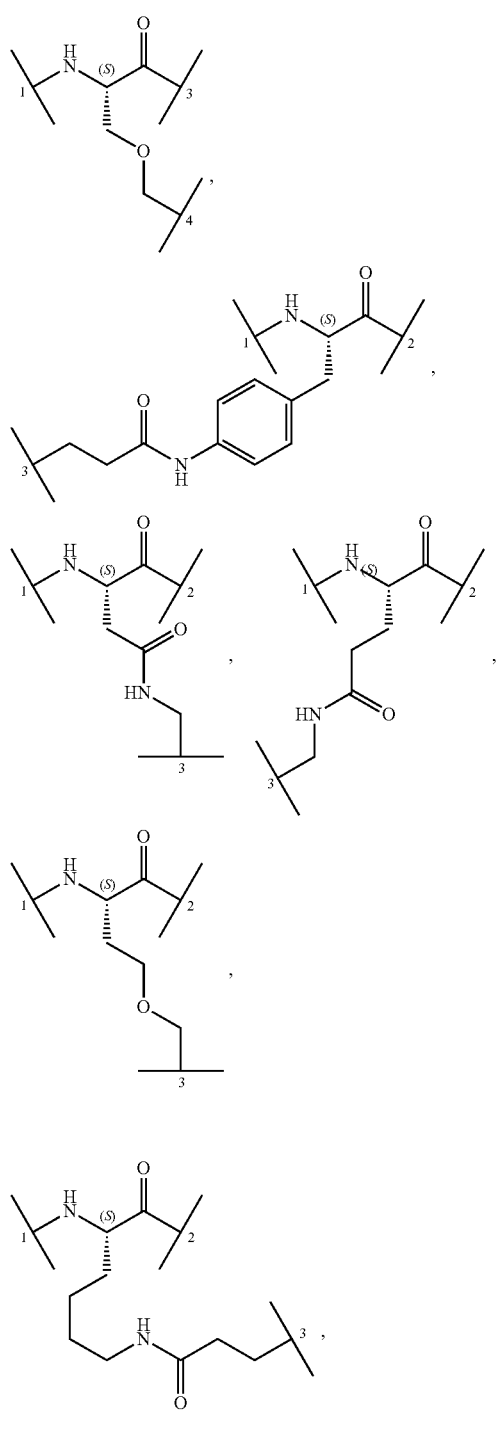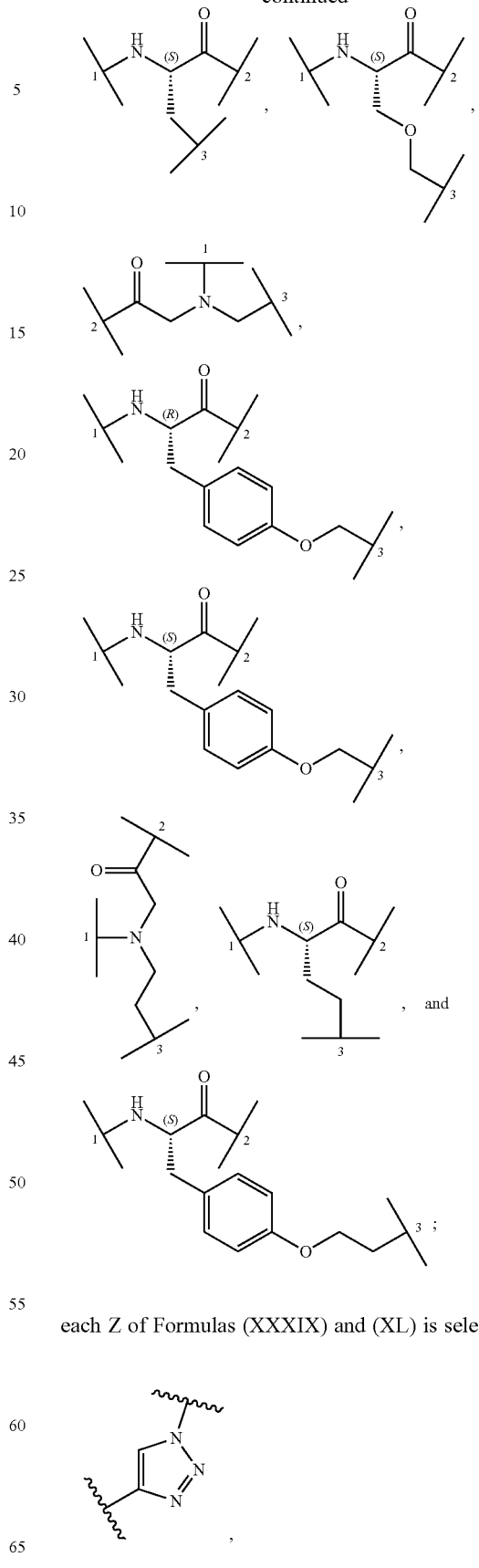
each Z of Formulas (XXXIX) and (XL) is selected from
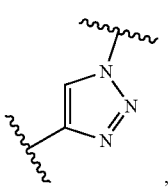 [SMILES: *c1cn(*)nn1]
, wherein each
represents a point of attachment to the compound; and each Y is selected from:
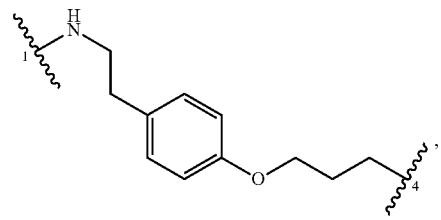
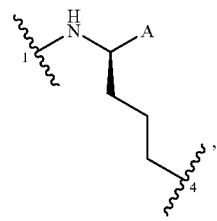
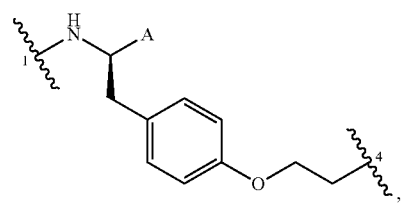
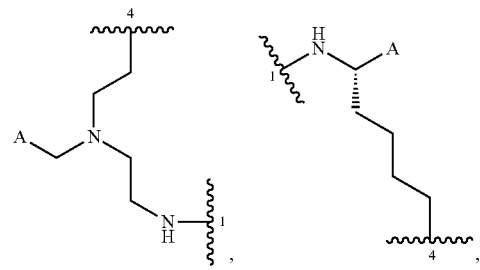
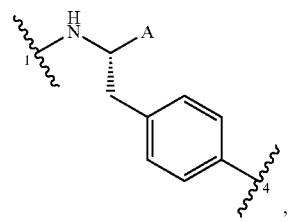
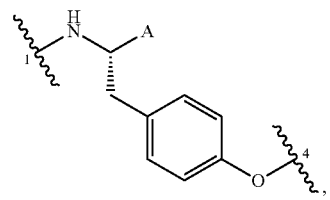
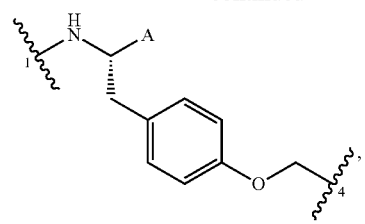
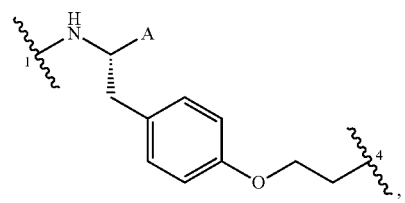
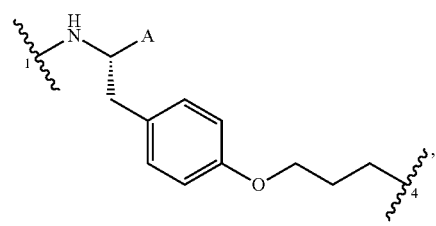
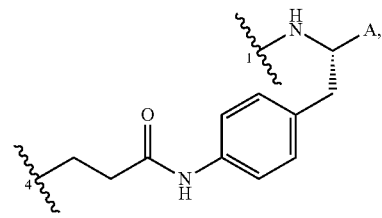
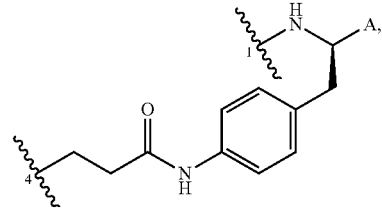
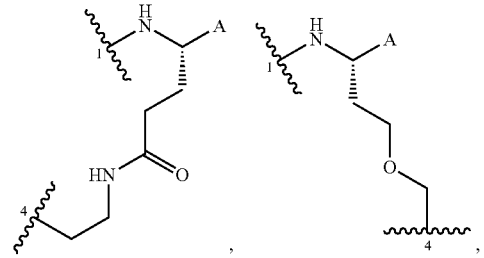
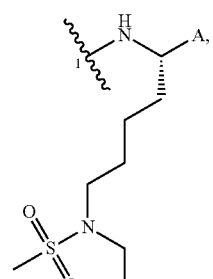

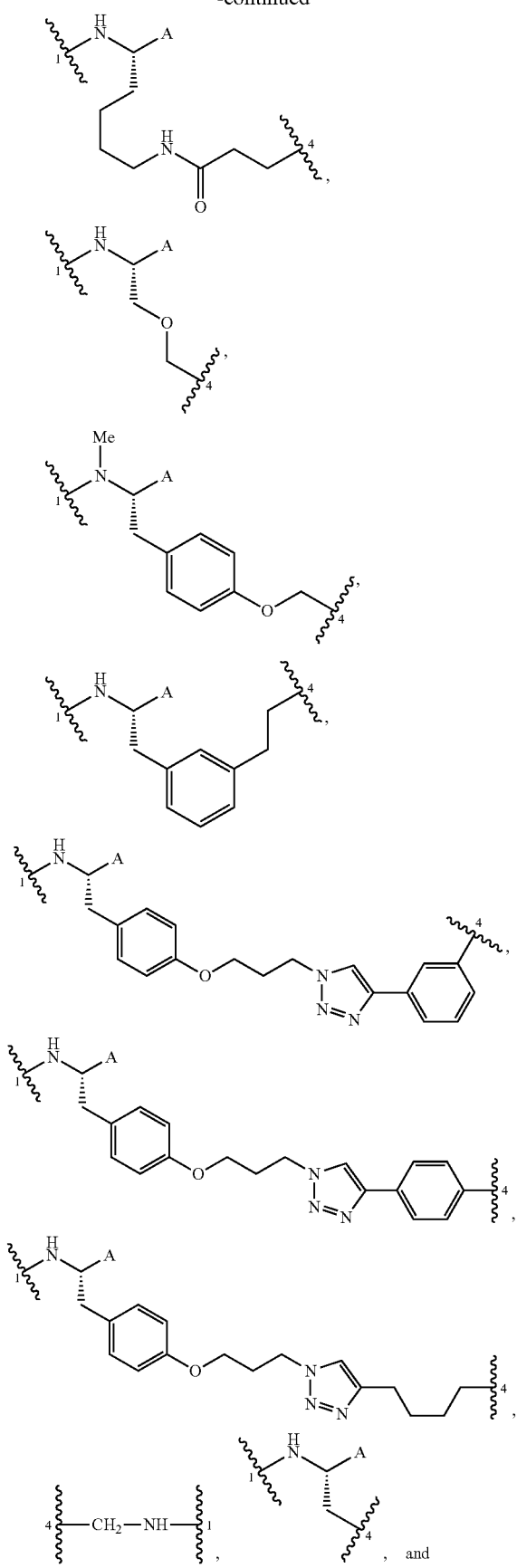
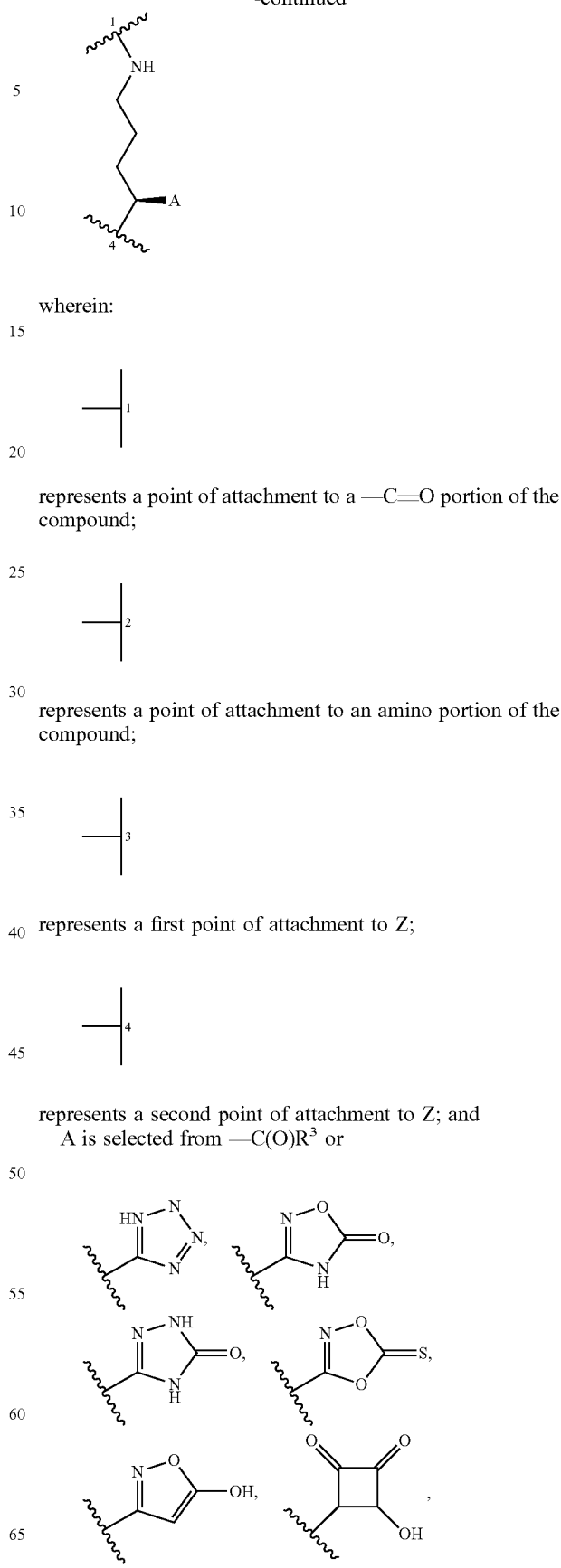
wherein:
represents a point of attachment to a —C=O portion of the compound;
represents a point of attachment to an amino portion of the compound;
represents a first point of attachment to Z;
represents a second point of attachment to Z; and
A is selected from —C(O)R³ or -continued

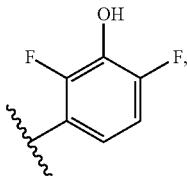

or a tautomeric form of any of the foregoing, wherein:
$R^3$ of —C(O)$R^3$ is selected from OH, NHCN, NHSO$_2$$R^{10}$, NHOR$^{11}$ or N($R^{12}$)($R^{13}$);
$R^{10}$ and $R^{11}$ of NHSO$_2$$R^{10}$ and NHOR$^{11}$ are independently selected from —$C_1$-$C_4$ alkyl, cycloalkyl, aryl, heteroaryl, or heterocycloalkyl, any of which are optionally substituted, and hydrogen;
each of $R^{12}$ and $R^{13}$ of N($R^{12}$)($R^{13}$) are independently selected from hydrogen, —$C_1$-$C_4$ alkyl, —($C_1$-$C_4$ alkylene)-NH—($C_1$-$C_4$ alkyl), benzyl, —($C_1$-$C_4$ alkylene)-C(O)OH, —($C_1$-$C_4$ alkylene)-C(O)CH$_3$, —CH(benzyl)-COOH, —$C_1$-$C_4$ alkoxy, and —($C_1$-$C_4$ alkylene)-O—($C_1$-$C_4$ hydroxyalkyl); or $R^{12}$ and $R^{13}$ of N($R^{12}$)($R^{13}$) are taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XLI), which are derived from the IAP ligands described in WO Pub. No. 2013/071039, or an unnatural mimetic thereof:

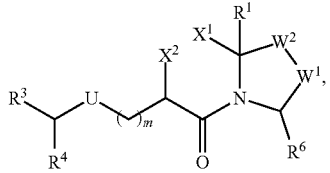

(XLI)

wherein:
$W^1$ of Formula (XLI) is selected from O, S, N—$R^A$, or C($R^{8a}$)($R^{8b}$);
$W^2$ of Formula (XLI) is selected from O, S, N—$R^A$, or C($R^{8c}$)($R^{8d}$); provided that $W^1$ and $W^2$ are not both O, or both S;
$R^1$ of Formula (XLI) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
when $X^1$ is selected from O, N—$R^A$, S, S(O), or S(O)$_2$, then $X^2$ is C($R^{2a}$$R^{2b}$);
or:
$X^1$ of Formula (XLI) is selected from CR$^{2c}$R$^{2d}$ and $X^2$ is CR$^{2a}$R$^{2b}$, and $R^{2c}$ and $R^{2a}$ together form a bond;
or:
$X^1$ and $X^2$ of Formula (XLI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;
or:
$X^1$ of Formula (XLI) is selected from CH$_2$ and $X^2$ is C=O, C=C($R^C$)$_2$, or C=NR$^C$; where each
$R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^A$ of N—$R^A$ is selected from H, $C_1$-$C_6$alkyl, —C(=O) $C_1$-$C_2$alkyl, substituted or unsubstituted aryl, or substituted or unsubstituted heteroaryl;
$R^{2a}$, $R^{2b}$, $R^{2c}$, $R^{2d}$ of CR$^{2c}$CR$^{2d}$ and CR$^{2a}$R$^{2b}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;
$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;
$R^D$ and $R^E$ of NR$^D$R$^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
m of Formula (XLI) is selected from 0, 1 or 2;
—U— of Formula (XLI) is selected from —NHC (=O)—, —C(=O)NH—, —NHS(=O)$_2$—, —S(=O)$_2$NH—, —NHC(=O)NH—, —NH(C=O) O—, —O(C=O)NH—, or —NHS(=O)$_2$NH—;
$R^3$ of Formula (XLI) is selected from $C_1$-$C_3$alkyl, or $C_1$-$C_3$fluoroalkyl;
$R^4$ of Formula (XLI) is selected from —NHR$^5$, —N($R^5$)2, —N+($R^5$)3 or —OR$^5$;
each $R^5$ of —NHR$^5$, —N($R^5$)2, —N+($R^5$)3 and —OR$^5$ is independently selected from H, $C_1$-$C_3$alkyl, $C_1$-$C_3$haloalkyl, $C_1$-$C_3$hetero alkyl and —$C_1$-$C_3$alkyl-($C_3$-$C_5$cycloalkyl);
or:
$R^3$ and $R^5$ of Formula (XLI) together with the atoms to which they are attached form a substituted or unsubstituted 5-7 membered ring;

or:
R³ of Formula (XLI) is bonded to a nitrogen atom of U to form a substituted or unsubstituted 5-7 membered ring;
R⁶ of Formula (XLI) is selected from —NHC(=O)R⁷, —C(=O)NHR⁷, —NHS(=O)2R⁷, —S(=O)₂NHR⁷; —NHC(=O)NHR⁷, —NHS(=O)₂NHR⁷, —(C₁-C₃alkyl)-NHC(=O)R⁷, —(C₁-C₃alkyl)-C(=O)NHR⁷, —(C₁-C₃alkyl)-NHS(=O)2R⁷, —(C₁-C₃alkyl)-S(=O)2NHR⁷; —(C₁-C₃alkyl)-NHC(=O)NHR⁷, —(C₁-C₃alkyl)-NHS(=O)2NHR⁷, substituted or unsubstituted C₂-C₁₀heterocycloalkyl, or substituted or unsubstituted heteroaryl;
each R⁷ of —NHC(=O)R⁷, —C(=O)NHR⁷, —NHS(=O)2R⁷, —S(=O)₂NHR⁷; —NHC(=O)NHR⁷, —NHS(=O)₂NHR⁷, —(C₁-C₃alkyl)-NHC(=O)R⁷, —(C₁-C₃alkyl)-C(=O)NHR⁷, —(C₁-C₃alkyl)-NHS(=O)2R⁷, —(C₁-C₃alkyl)-S(=O)2NHR⁷; —(C₁-C₃alkyl)-NHC(=O)NHR⁷, —(C₁-C₃alkyl)-NHS(=O)2NHR⁷ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH2)p-CH(substituted or unsubstituted aryl)2, —(CH₂)$_p$—CH(substituted or unsubstituted heteroaryl)2, —(CH₂)p-CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);
p of R⁷ is selected from 0, 1 or 2;
R⁸ᵃ, R⁸ᵇ, R⁸ᶜ, and R⁸ᵈ of C(R⁸ᵃ)(R⁸ᵇ) and C(R⁸ᶜ)(R⁸ᵈ) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;
or:
R⁸ᵃ and R⁸ᵈ are as defined above, and R⁸ᵇ and R⁸ᶜ together form a bond;
or:
R⁸ᵃ and R⁸ᵈ are as defined above, and R⁸ᵇ and R⁸ᶜ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;
or:
R⁸ᶜ and R⁸ᵈ are as defined above, and R⁸ᵃ and R⁸ᵇ together with the atoms to which they are attached form a substituted or unsubstituted saturated, or partially saturated 3-7 membered spirocycle or heterospirocycle comprising 1-3 heteroatoms selected from S, O and N;
or:
R⁸ᵃ and R⁸ᵇ are as defined above, and R⁸ᶜ and R⁸ᵈ together with the atoms to which they are attached form a substituted or unsubstituted saturated, or partially saturated 3-7 membered spirocycle or heterospirocycle comprising 1-3 heteroatoms selected from S, O and N; where each substituted alkyl, heteroalkyl, fused ring, spirocycle, heterospirocycle, cycloalkyl, heterocycloalkyl, aryl or heteroaryl is substituted with 1-3 R⁹; and
each R⁹ of R⁸ᵃ, R⁸ᵇ, R⁸ᶜ and R⁸ᵈ is independently selected from halogen, —OH, —SH, (C=O), CN, $C_1$-$C_4$alkyl, C1-C4fluoroalkyl, $C_1$-$C_4$ alkoxy, $C_1$-$C_4$ fluoroalkoxy, —NH₂, —NH($C_1$-$C_4$alkyl), —NH($C_1$-$C_4$alkyl)₂, —C(=O)OH, —C(=O)NH₂, —C(=O)$C_1$-$C_3$alkyl, —S(=O)₂CH₃, —NH($C_1$-$C_4$alkyl)-OH, —NH($C_1$-$C_4$alkyl)-O—($C_1$-$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)₂, or two R⁹ together with the atoms to which they are attached form a methylene dioxy or ethylene dioxy ring substituted or unsubstituted with halogen, —OH, or $C_1$-$C_3$alkyl. In any of the compounds described herein, the ILM can have the structure of Formula (XLII), which are derived from the IAP ligands described in WO Pub. No. 2013/071039, or an unnatural mimetic thereof:

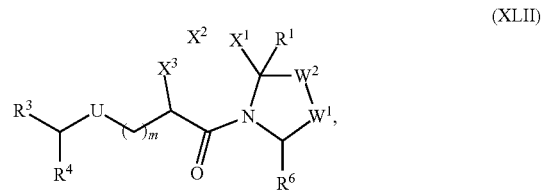

(XLII)

wherein:
W¹ of Formula (XLII) is O, S, N—R⁴, or C(R⁸ᵃ)(R⁸ᵇ);
W² of Formula (XLII) is O, S, N—R⁴, or C(R⁸ᶜ)(R⁸ᵈ); provided that W¹ and W² are not both O, or both S;
R¹ of Formula (XLII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
when X¹ of Formula (XLII) is N—R⁴, then X² is C=O, or CR$_{2c}$R²ᵈ, and X³ is CR²ᵃR²ᵇ;
or:
when X¹ of Formula (XLII) is selected from S, S(O), or S(O)₂, then X² is CR²ᶜR²ᵈ, and X³ is CR²ᵃR²ᵇ,
or:
when X¹ of Formula (XLII) is O, then X² is CR²ᶜR²ᵈ and N—R⁴ and X³ is CR²ᵃR²ᵇ;
or:
when X¹ of Formula (XLII) is CH₃, then X² is selected from O, N—R⁴, S, S(O), or S(O)₂, and X³ is CR²ᵃR²ᵇ;
when X¹ of Formula (XLII) is CR²ᵉR²ᶠ and X² is CR²ᶜR²ᵈ, and R²ᵉ and R²ᶜ together form a bond, and X³ of Formula (VLII) is CR²ᵃR²ᵇ;
or:
X¹ and X³ of Formula (XLII) are both CH₂ and X² of Formula (XLII) is C=0, C=C(R^C)2, or C=NR^C; where each R^C is independently selected from H, —CN, —OH, alkoxy, substituted or unsubstituted C1-C6alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

$X^1$ and $X^2$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ of Formula, (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLII) is $CR^{2e}R^{2f}$;

$R^A$ of N—$R^A$ is selected from H, $C_1$-$C_6$alkyl, —C(=O)$C_1$-$C_2$alkyl, substituted or unsubstituted aryl, or substituted or unsubstituted heteroaryl;

$R^2$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted C1-C6alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ of $NR^D R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLII) is selected from 0, 1 or 2;

—U— of Formula (XLII) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ of Formula (XLII) is selected from $C_1$-$C_3$alkyl, or $C_1$-$C_3$fluoroalkyl;

$R^4$ of Formula (XLII) is selected from —$NHR^5$, —$N(R^5)_2$, —$N+(R^5)_3$ or —$OR^5$;

each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$hetero alkyl and —$C_1$-$C_3$alkyl-($C_3$-$C_5$cycloalkyl);

or:

$R^3$ and $R^5$ of Formula (XLII) together with the atoms to which they are attached form a substituted or unsubstituted 5-7 membered ring;

or:

$R^3$ of Formula (XLII) is bonded to a nitrogen atom of U to form a substituted or unsubstituted 5-7 membered ring;

$R^6$ of Formula (XLII) is selected from —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)p-CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:
R$^{8c}$ and R$^{8d}$ are as defined above, and R$^{8a}$ and R$^{8b}$ together with the atoms to which they are attached form a substituted or unsubstituted saturated, or partially saturated 3-7 membered spirocycle or heterospirocycle comprising 1-3 heteroatoms selected from S, O and N;

or:
R$^{8a}$ and R$^{8b}$ are as defined above, and R$^{8c}$ and R$^{8d}$ together with the atoms to which they are attached form a substituted or unsubstituted saturated, or partially saturated 3-7 membered spirocycle or heterospirocycle comprising 1-3 heteroatoms selected from S, O and N; where each substituted alkyl, heteroalkyl, fused ring, spirocycle, heterospirocycle, cycloalkyl, heterocycloalkyl, aryl or heteroaryl is substituted with 1-3 R$^9$; and each R$^9$ of R$^{8a}$, R$^{8b}$, R$^{8c}$ and R$^{8d}$ is independently selected from halogen, —OH, —SH, (C=O), CN, C$_1$-C$_4$alkyl, C1-C4fluoroalkyl, C$_1$-C$_4$ alkoxy, C$_1$-C$_4$ fluoroalkoxy, —NH$_2$, —NH(C$_1$-C$_4$alkyl), —NH(C$_1$-C$_4$alkyl)$_2$, —C(=O)OH, —C(=O)NH$_2$, —C(=O)C$_1$-C$_3$alkyl, —S(=O)$_2$CH$_3$, —NH(C$_1$-C$_4$alkyl)-OH, —NH(C$_1$-C$_4$alkyl)-O—(C$_1$-C$_4$alkyl), —O(C$_1$-C$_4$alkyl)-NH2; —O(C$_1$-C$_4$alkyl)-NH—(C$_1$-C$_4$alkyl), and —O(C$_1$-C$_4$alkyl)-N—(C$_1$-C$_4$alkyl)$_2$, or two R$^9$ together with the atoms to which they are attached form a methylene dioxy or ethylene dioxy ring substituted or unsubstituted with halogen, —OH, or C$_1$-C$_3$alkyl.

In any of the compounds described herein, the ILM can have the structure of Formula (XLIII), which is derived from the IAP ligands described in WO Pub. No. 2013/071039, or an unnatural mimetic thereof:

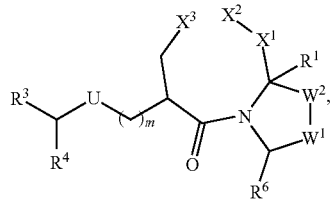

(XLIII)

wherein:
W$^1$ of Formula (XLIII) is selected from O, S, N—R$^A$, or C(R$^{8a}$)(R$^{8b}$);
W$^2$ of Formula (XLIII) is selected from O, S, N—R$^A$, or C(R$^{8c}$)(R$^{8d}$); provided that W$^1$ and W$^2$ are not both O, or both S;
R$^1$ of Formula (XLIII) is selected from H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl);
when X$^1$ of Formula (XLIII) is selected from N—R$^A$, S, S(O), or S(O)$_2$, then X$^2$ of Formula (XLIII) is CR$^{2c}$R$^{2d}$; and X$^3$ of Formula (XLIII) is CR$^{2a}$R$^{2b}$;
or:
when X$^1$ of Formula (XLIII) is O, then X$^2$ of Formula (XLIII) is selected from O, N—R$^A$, S, S(O), or S(O)$_2$, and X$^3$ of Formula (XLIII) is CR$^{2a}$R$^{2b}$;
or:
when X$^1$ of Formula (XLIII) is CR$^{2e}$R$^{2f}$ and X$^2$ of Formula (XLIII) is CR$^{2c}$R$^{2d}$, and R$^{2e}$ and R$^{2c}$ together form a bond, and X$^3$ of Formula (XLIII) is CR$^{2a}$R$^{2b}$;

or:
X$^1$ and X$^2$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^3$ of Formula (XLIII) is CR$^{2a}$R$^{2b}$;
or:
X$^2$ and X$^3$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^1$ of Formula (VLII) is CR$^{2e}$R$^{2f}$;
R$^A$ of N—R$^A$ is H, C$_1$-C$_6$alkyl, —C(=O)C$_1$-C$_2$alkyl, substituted or unsubstituted aryl, or substituted or unsubstituted heteroaryl;
R$^{2a}$, R$^{2b}$, R$^{2c}$, R$^{2d}$, R$^{2e}$, and R$^{2f}$ of CR$^{2c}$R$^{2d}$, CR$^{2a}$R$^{2b}$ and CR$^{2e}$R$^{2f}$ are independently selected from H, substituted or unsubstituted C$_1$-C$_6$alkyl, substituted or unsubstituted C$_1$-C$_6$heteroalkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl) and —C(=O)R$^B$;
R$^B$ of —C(=O)R$^B$ is substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl), or —NR$^D$R$^E$;
R$^D$ and R$^E$ of NR$^D$R$^E$ are independently selected from H, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);
m of Formula (XLIII) is 0, 1 or 2;
—U— of Formula (XLIII) is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
R$^3$ of Formula (XLIII) is C$_1$-C$_3$alkyl, or C$_1$-C$_3$fluoroalkyl;
R$^4$ of Formula (XLIII) is —NHR$^5$, —N(R$^5$)$_2$, —N+(R$^5$)$_3$ or —OR$^5$;
each R$^5$ of —NHR$^5$, —N(R$^5$)$_2$, —N+(R$^5$)$_3$ and —OR$^5$ is independently selected from H, C$_1$-C$_3$alkyl, C$_1$-C$_3$haloalkyl, C$_1$-C$_3$hetero alkyl and —C$_1$-C$_3$alkyl-(C$_3$-C$_5$cycloalkyl);

or:
R$^3$ and R$^5$ of Formula (XLIII) together with the atoms to which they are attached form a substituted or unsubstituted 5-7 membered ring;

or:
R$^3$ of Formula (XLIII) is bonded to a nitrogen atom of U to form a substituted or unsubstituted 5-7 membered ring;

R$^6$ of Formula (XLIII) is selected from —NHC(=O)R$^7$, —C(=O)NHR$^7$, —NHS(=O)2R$^7$, —S(=O)$_2$NHR$^7$; —NHC(=O)NHR$^7$, —NHS(=O)$_2$NHR$^7$, —(C$_1$-C$_3$alkyl)-NHC(=O)12$^7$, —(C$_1$-C$_3$alkyl)-C(=O)NHR$^7$, —(C$_1$-C$_3$alkyl)-NHS(=O)$_2$R$^7$, —(C$_1$-C$_3$alkyl)-S(=O)$_2$NHR$^7$; —(C$_1$-C$_3$alkyl)-NHC(=O)NHR$^7$, —(C$_1$-C$_3$alkyl)-NHS(=O)$_2$NHR$^7$, substituted or unsubstituted C$_2$-C$_{10}$heterocycloalkyl, or substituted or unsubstituted heteroaryl;

each R$^7$ of —NHC(=O)R$^7$, —C(=O)NHR$^7$, —NHS(=O)2R$^7$, —S(=O)$_2$NHR$^7$; —NHC(=O)NHR$^7$, —NHS(=O)$_2$NHR$^7$, —(C$_1$-C$_3$alkyl)-NHC(=O)R$^7$, —(C$_1$-C$_3$alkyl)-C(=O)NHR$^7$, —(C$_1$-C$_3$alkyl)-NHS(=O)$_2$R$^7$, —(C$_1$-C$_3$alkyl)-S(=O)2NHR$^7$; —(C$_1$-C$_3$alkyl)-NHC(=O)NHR$^7$, —(C$_1$-C$_3$alkyl)-NHS(=O)2NHR$^7$ is independently selected from C$_1$-C$_6$alkyl, C$_1$-C$_6$haloalkyl, C$_1$-C$_6$heteroalkyl, a substituted or unsubstituted C3-C10cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cycloalkyl), —C$_1$-C$_6$alkyl-(substituted or unsubstituted C2-C10heterocycloalkyl, —C1-C6alkyl-(substituted or unsubstituted aryl), —C$_1$-C$_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of R$^7$ is 0, 1 or 2;

R$^{8a}$, R$^{8b}$, R$^{8c}$, and R$^{8d}$ of C(R$^{8a}$)(R$^{8b}$) and C(R$^{8c}$)(R$^{8d}$) are independently selected from H, C$_1$-C$_6$alkyl, C$_1$-C$_6$fluoroalkyl, C$_1$-C$_6$ alkoxy, C$_1$-C$_6$heteroalkyl, and substituted or unsubstituted aryl;

or:
R$^{8a}$ and R$^{8d}$ are as defined above, and R$^{8b}$ and R$^{8c}$ together form a bond;

or:
R$^{8a}$ and R$^{8d}$ are as defined above, and R$^{8b}$ and R$^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:
R$^{8c}$ and R$^{8d}$ are as defined above, and R$^{8a}$ and R$^{8b}$ together with the atoms to which they are attached form a substituted or unsubstituted saturated, or partially saturated 3-7 membered spirocycle or heterospirocycle comprising 1-3 heteroatoms selected from S, O and N;

or:
R$^{8a}$ and R$^{8b}$ are as defined above, and R$^{8c}$ and R$^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 R$^9$; and each R$^9$ of R$^{8a}$, R$^{8b}$, R$^{8c}$ and R$^{8d}$ is independently selected from halogen, —OH, —SH, (C=O), CN, C$_1$-C$_4$alkyl, C1-C4fluoroalkyl, C$_1$-C$_4$ alkoxy, C$_1$-C$_4$ fluoroalkoxy, —NH$_2$, —NH(C$_1$-C$_4$alkyl), —NH(C$_1$-C$_4$alkyl)$_2$, —C(=O)OH, —C(=O)NH$_2$, —C(=O)C$_1$-C$_3$alkyl, —S(=O)$_2$CH$_3$, —NH(C$_1$-C$_4$alkyl)-OH, —NH(C$_1$-C$_4$alkyl)-O—(C$_1$-C$_4$alkyl), —O(C$_1$-C$_4$alkyl)-NH2; —O(C$_1$-C$_4$alkyl)-NH—(C$_1$-C$_4$alkyl), and —O(C$_1$-C$_4$alkyl)-N—(C$_1$-C$_4$alkyl)$_2$, or two R$^9$ together with the atoms to which they are attached form a methylene dioxy or ethylene dioxy ring substituted or unsubstituted with halogen, —OH, or C$_1$-C$_3$alkyl.

In any of the compounds described herein, the ILM can have the structure of Formula (XLIV), which is derived from the IAP ligands described in WO Pub. No. 2013/071039, or an unnatural mimetic thereof:

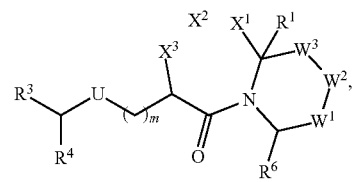

(XLIV)

wherein:
W$^1$ of Formula (XLIV) is selected from O, S, N—R$^A$, or C(R$^{8a}$)(R$^{8b}$);

W$^2$ of Formula (XLIV) is selected from O, S, N—R$^A$, or C(R$^{8c}$)(R$^{8d}$); provided that W$^1$ and W$^2$ are not both O, or both S;

W$^3$ of Formula (XLIV) is selected from O, S, N—R$^A$, or C(R$^{8e}$)(R$^{8f}$), providing that the ring comprising W$^1$, W$^2$, and W$^3$ does not comprise two adjacent oxygen atoms or sulfur atoms;

R$^1$ of Formula (XLIV) is selected from H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl);

when X$^1$ of Formula (XLIV) is O, then X$^2$ of Formula (XLIV) is selected from CR$^{2c}$R$^{2d}$ and N—R$^A$, and X$^3$ of Formula (XLIV) is CR$^{2a}$R$^{2b}$;

or:
when X$^1$ of Formula (XLIV) is CH$_2$, then X$^2$ of Formula (XLIV) is selected from O, N—R$^A$, S, S(O), or S(O)$_2$, and X$^3$ of Formula (XLIV) is CR$^{2a}$R$^{2b}$;

or:
when X$^1$ of Formula (XLIV) is CR$^{2e}$R$^{2f}$ and X$^2$ of Formula (XLIV) is CR$^{2c}$R$^{2d}$, and R$^{2e}$ and R$^{2c}$ together form a bond, and X$^3$ of Formula (VLIV) is CR$^{2a}$R$^{2b}$;

or:
X$^1$ and X$^3$ of Formula (XLIV) are both CH$_2$ and X$^2$ of Formula (XLII) is C=O, C=C(R$^c$)2, or C=NR$^C$;

where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

$X^1$ and $X^2$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIV) is $CR^{2a}R^{2b}$;

or:

$X^2$ and $X^3$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X of Formula (VLIV) is $CR^{2e}R^{2f}$;

$R^A$ of N—$R^A$ is selected from H, $C_1$-$C_6$alkyl, —C(=O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLIV) is selected from 0, 1 or 2;

—U— of Formula (XLIV) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ of Formula (XLIV) is selected from $C_1$-$C_3$alkyl, or $C_1$-$C_3$fluoroalkyl;

$R^4$ of Formula (XLIV) is selected from —$NHR^5$, —$N(R^5)_2$, —$N+(R^5)_3$ or —$OR^5$;

each $R^5$ of —$NHR^5$, —$N(R^5)_2$, —$N+(R^5)_3$ and —$OR^5$ is independently selected from H, $C_1$-$C_3$alkyl, $C_1$-$C_3$haloalkyl, $C_1$-$C_3$hetero alkyl and —$C_1$-$C_3$alkyl-($C_3$-$C_5$cycloalkyl);

or:

$R^3$ and $R^5$ of Formula (XLIV) together with the atoms to which they are attached form a substituted or unsubstituted 5-7 membered ring;

or:

$R^3$ of Formula (XLIII) is bonded to a nitrogen atom of U to form a substituted or unsubstituted 5-7 membered ring;

$R^6$ of Formula (XLIII) is selected from —NHC(=O)$R^7$, —C(=O)$NHR^7$, —NHS(=O)$2R^7$, —S(=O)$_2NHR^7$; —NHC(=O)$NHR^7$, —NHS(=O)$_2NHR^7$, —($C_1$-$C_3$alkyl)-NHC(=O)$R^7$, —($C_1$-$C_3$alkyl)-C(=O)$NHR^7$, —($C_1$-$C_3$alkyl)-NHS(=O)$_2R^7$, —($C_1$-$C_3$alkyl)-S(=O)$_2NHR^7$; —($C_1$-$C_3$alkyl)-NHC(=O)$NHR^7$, —($C_1$-$C_3$alkyl)-NHS(=O)$_2NHR^7$, substituted or unsubstituted $C_2$-$C_{10}$heterocycloalkyl, or substituted or unsubstituted heteroaryl;

each $R^7$ of —NHC(=O)$R^7$, —C(=O)$NHR^7$, —NHS(=O)$2R^7$, —S(=O)$_2NHR^7$; —NHC(=O)$NHR^7$, —NHS(=O)$_2NHR^7$, —($C_1$-$C_3$alkyl)-NHC(=O)$R^7$, —($C_1$-$C_3$alkyl)-C(=O)$NHR^7$, —($C_1$-$C_3$alkyl)-NHS(=O)$2R^7$, —($C_1$-$C_3$alkyl)-S(=O)$2NHR^7$; —($C_1$-$C_3$alkyl)-NHC(=O)$NHR^7$, —($C_1$-$C_3$alkyl)-NHS(=O)$2NHR^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)$_p$—CH(substituted or unsubstituted heteroaryl)2, —(CH$_2$)$_P$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, $R^{8d}$, $R^{8e}$, and $R^{8f}$ of $C(R^{8a})(R^{8b})$, $C(R^{8c})(R^{8d})$ and $C(R^{8e})(R^{8f})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$, and $R^{8f}$ of $C(R^{8a})(R_{8b})$, $C(R^{8c})(R^{8d})$ and $C(R^{8e})(R^{8f})$ are as defined above, and $R^{8b}$ and $R^{8c}$ together form a bond;

or:
$R^{8a}$, $R^{8b}$, $R^{8d}$, and $R^{8f}$ of $C(R^{8a})(R^{8b})$, $C(R^{8c})$, $C(R^{8d})$ and $C(R^{8e})(R^{8f})$ are as defined above, and $R^{8c}$ and $R^{8e}$ together form a bond;

or:
$R^{8a}$, $R^{8d}$, $R^{8e}$, and $R^{8f}$ of $C(R^{8a})(R^{8b})$, $C(R^{8c})(R^{8d})$ and $C(R^{8e})(R^{8f})$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:
$R^{8a}$, $R^{8b}$, $R^{8d}$, and $R^{8f}$ of $C(R^{8a})(R^{8b})$, $C(R^{8c})R^{8d})$, and $C(R^{8e})(R^{8f})$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:
$R^{8c}$, $R^{8d}$, $R^{8e}$, and $R^{8f}$ of $C(R^{8c})(R^{8d})$ and $C(R^{8e})(R^{8f})$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:
$R^{8a}$, $R^{8b}$, $R^{8e}$, and $R^{8f}$ of $C(R^{8a})(R^{8b})$ and $C(R^{8e})(R^{8f})$ are as defined above, and $R^{8e}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:
$R^{8a}$, $R^{8b}$, $R^{8e}$, and $R^{8d}$ of $C(R^{8a})(R^{8b})$ and $C(R^{8c})(R^{8d})$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

or:
where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8e}$, $R^{8d}$, $R^{8e}$, and $R^{8f}$ is independently selected from halogen, —OH, —SH, (C═O), CN, $C_1$-$C_4$alkyl, C1-C4fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(═O)OH, —C(═O)NH$_2$, —C(═O)$C_1$-$C_3$alkyl, —S(═O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLV), (XLVI) or (XLVII), which is derived from the IAP ligands described in Vamos, M., et al., *Expedient synthesis of highly potent antagonists of inhibitor of apoptosis proteins (IAPs) with unique selectivity for ML-IAP*, ACS Chem. Biol., 8(4), 725-32 (2013), or an unnatural mimetic thereof:

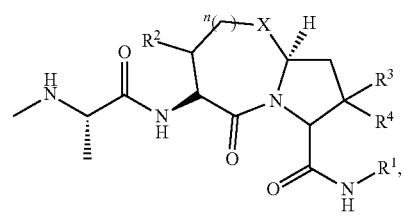

(XLV)

$n = 0, 1$

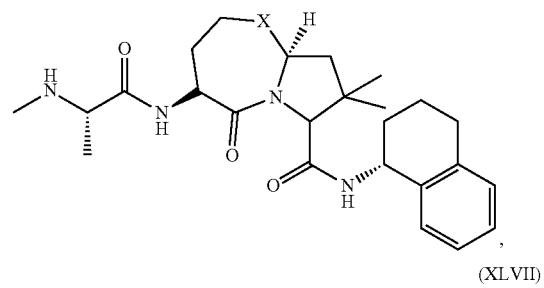

(XLVI)

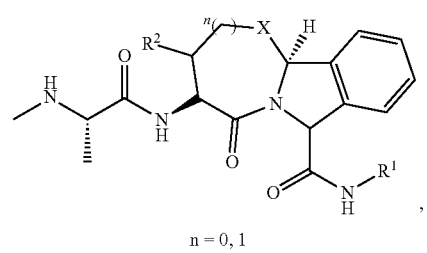

(XLVII)

$n = 0, 1$ wherein:
$R^2$, $R^3$ and $R^4$ of Formula (XLV) are independently selected from H or ME;

X of Formula (XLV) is independently selected from O or S; and $R^1$ of Formula (XLV) is selected from:

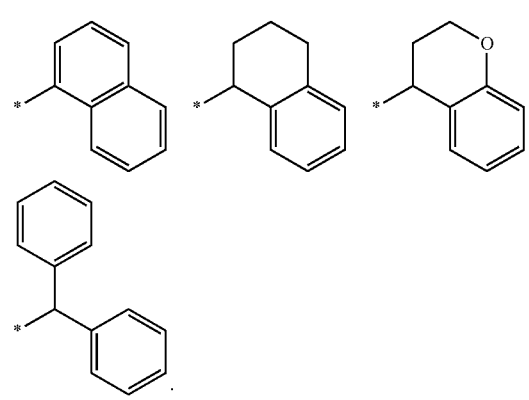

In a particular embodiment, the ILM has a structure according to Formula (XLVIII):

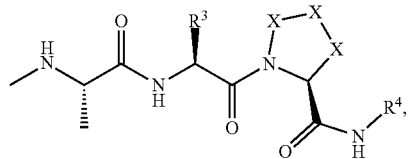

(XLVIII)

wherein $R^3$ and $R^4$ of Formula (XLVIII) are independently selected from H or ME;

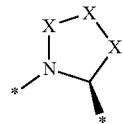

is a 5-member heterocycle selected from:

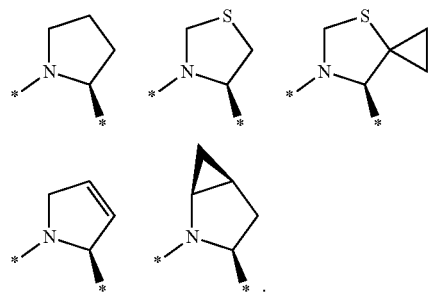

In a particular embodiment, the 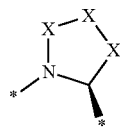 of Formula XLVIII) is

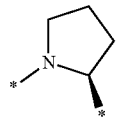 [SMILES: *[C@@H]1CCCN1*]

In a particular embodiment, the ILM has a structure and attached to a linker group L as shown below:

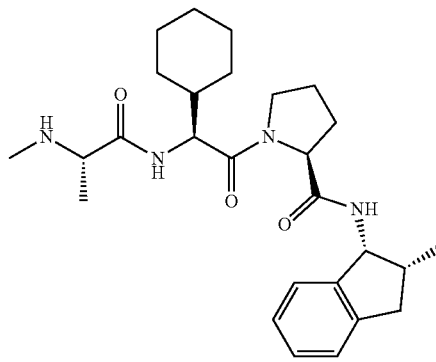

In a particular embodiment, the ILM has a structure according to Formula (XLIX), (L), or (LI):

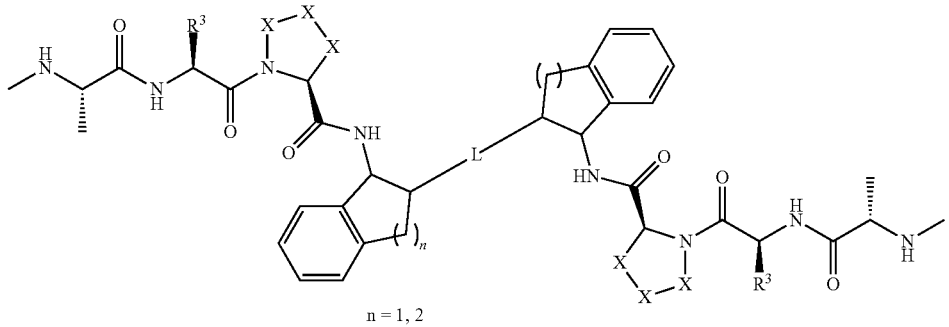
(XLIX)

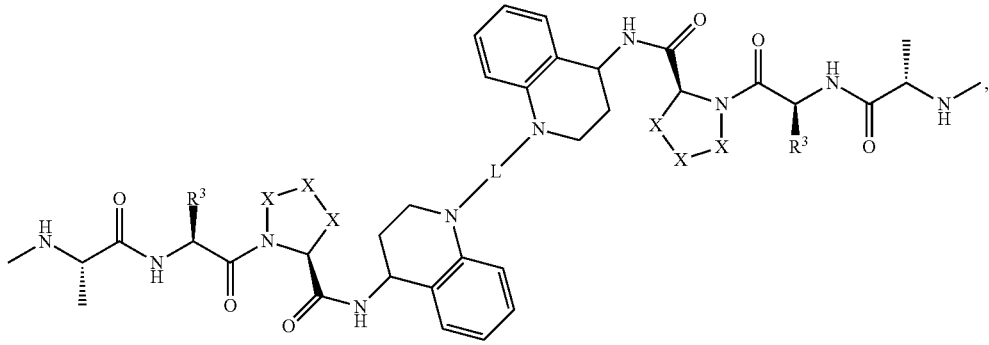
(L)

-continued
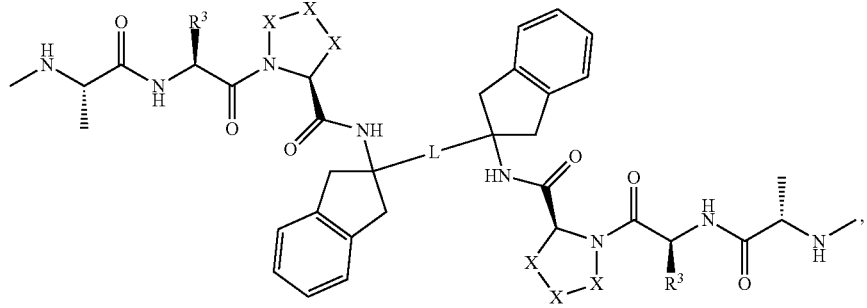
(LI)
wherein:
R³ of Formula (XLIX), (L) or (LI) are independently selected from H or ME;
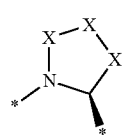
is a 5-member heterocycle selected from:
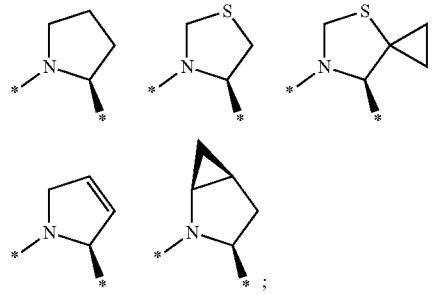
and
L of Formula (XLIX), (L) or (LI) is selected from:
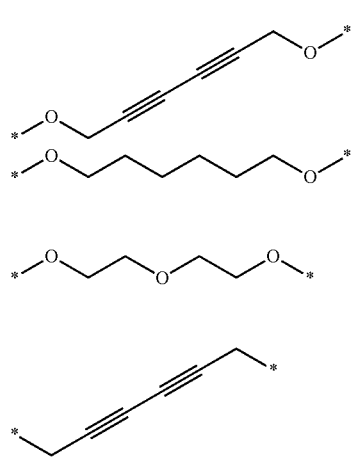
-continued
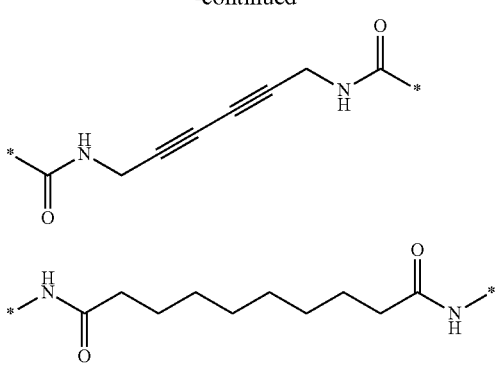
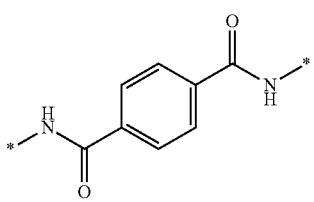
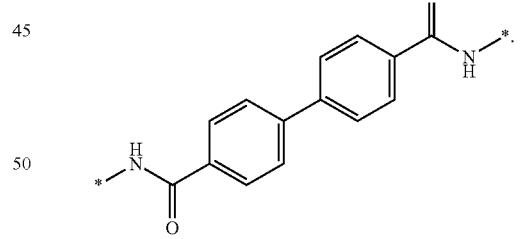
In a particular embodiment, L of Formula (XLIX), (L), or (LI)
In a particular embodiment, the ILM has a structure according to Formula (LII):

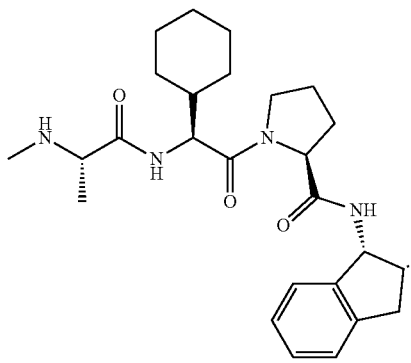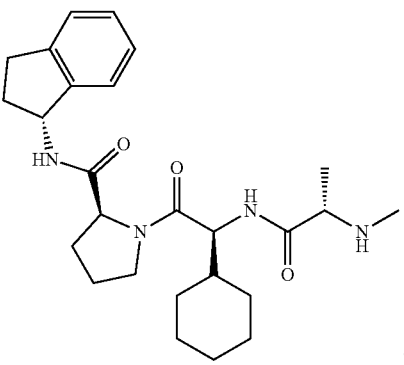

In a particular embodiment, the ILM according to Formula (LII) is chemically linked to the linker group L in the area denoted with

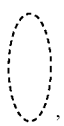, and as shown below:

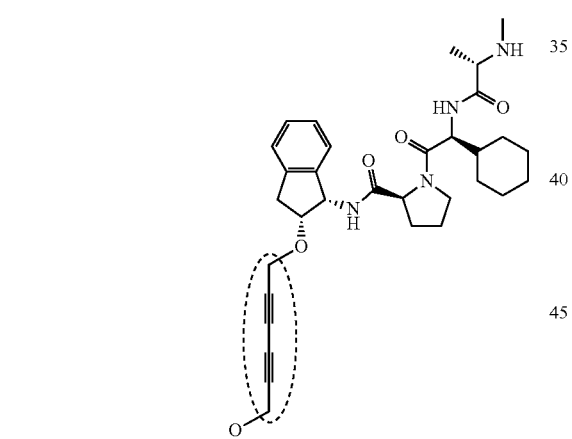

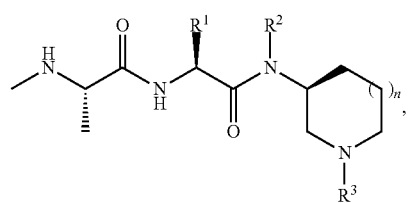 (LIII)

n = 0, 1, 2

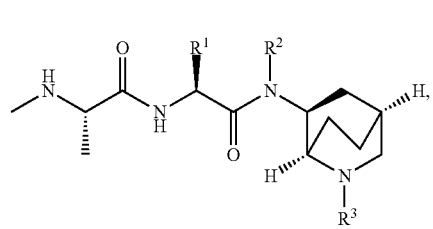 (LIV)

wherein:

$R^1$ of Formulas (LIII) and (LIV) is selected from:

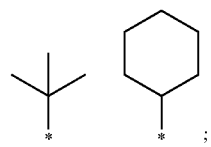;

$R^2$ of Formulas (LIII) and (LIV) is selected from H or Me;

$R^3$ of Formulas (LIII) and (LIV) is selected from:

In any of the compounds described herein, the ILM can have the structure of Formula (LIII) or (LIV), which is based on the IAP ligands described in Hennessy, E J, et al., *Discovery of aminopiperidine-based Smac mimetics as IAP antagonists*, Bioorg. Med. Chem. Lett., 22(4), 1960-4 (2012), or an unnatural mimetic thereof:

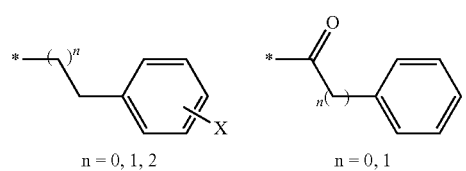

n = 0, 1, 2      n = 0, 1

-continued

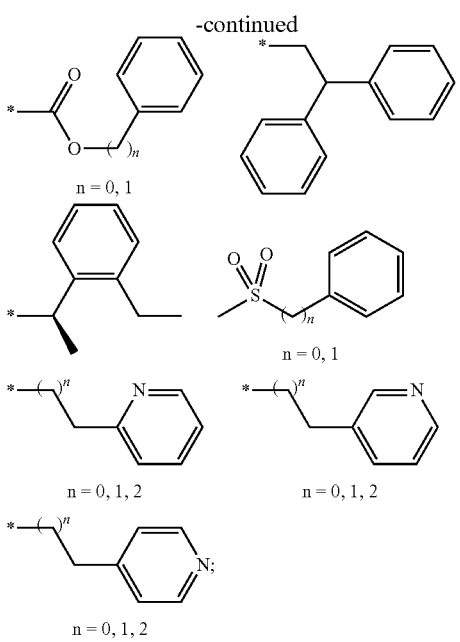

X of is selected from H, halogen, methyl, methoxy, hydroxy, nitro or trifluoromethyl.

In any of the compounds described herein, the ILM can have the structure of and be chemically linked to the linker as shown in Formula (LV) or (LVI), or an unnatural mimetic thereof:

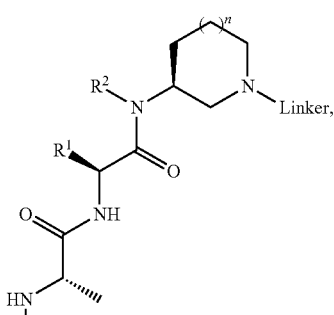

(LV)

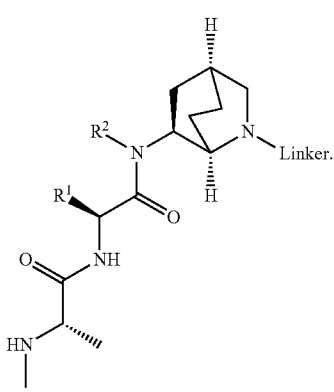

(LVI)

In any of the compounds described herein, the ILM can have the structure of Formula (LVII), which is based on the IAP ligands described in Cohen, F, et al., *Orally bioavailable antagonists of inhibitor of apoptosis proteins based on an azabicyclooctane scaffold*, J. Med. Chem., 52(6), 1723-30 (2009), or an unnatural mimetic thereof:

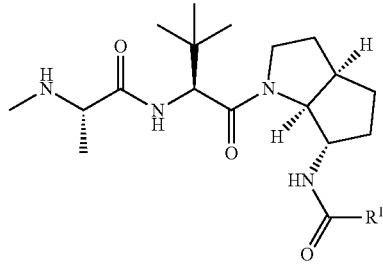

(LVII)

wherein:
R1 of Formulas (LVII) is selected from:

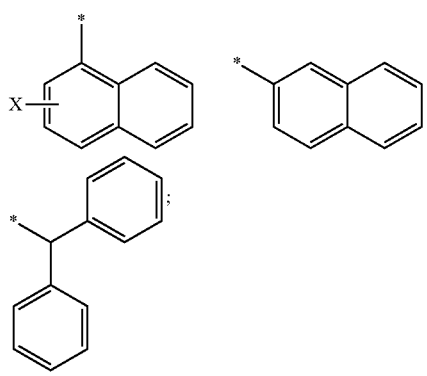

X of

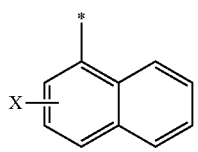

is selected from H, fluoro, methyl or methoxy.

In a particular embodiment, the ILM is represented by the following structure:

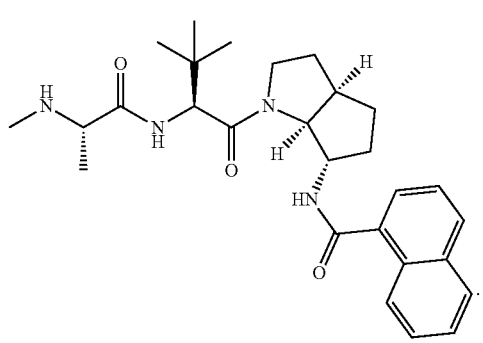 [SMILES: CN[C@@H](C)C(=O)N[C@H](C(=O)N1CC[C@H]2CC[C@H](NC(=O)c3cccc4ccccc34)[C@H]21)C(C)(C)C]

In a particular embodiment, the ILM is selected from the group consisting of, and which the chemical link between the ILM and linker group L is shown:

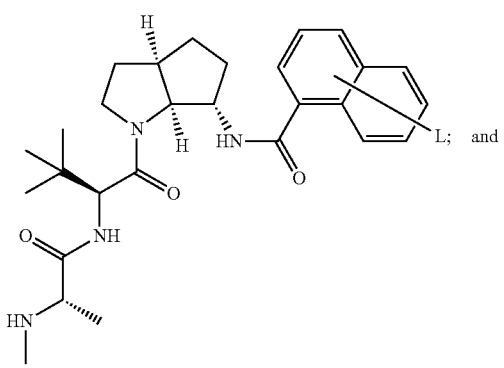

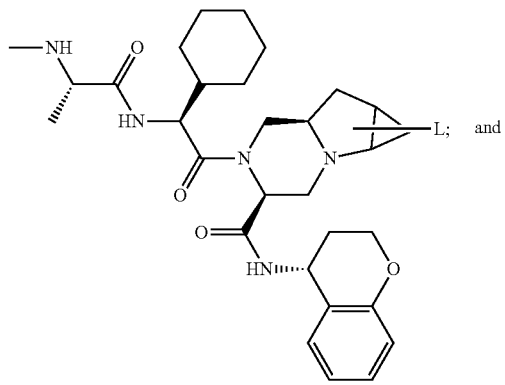

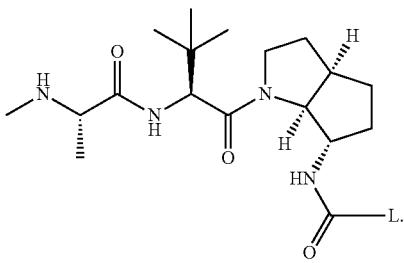

In any of the compounds described herein, the ILM is selected from the group consisting of the structures below, which are based on the IAP ligands described in Asano, M, et al., *Design, sterioselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

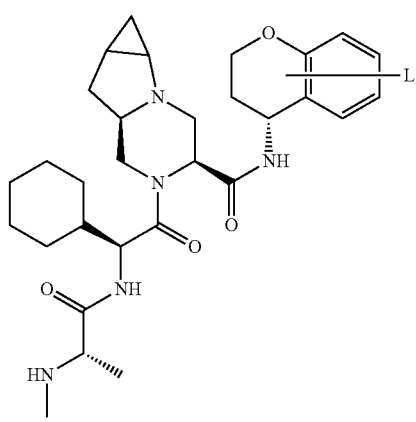

In any of the compounds described herein, the ILM can have the structure of Formula (LVIII), which is based on the IAP ligands described in Asano, M, et al., *Design, stereoselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:


or

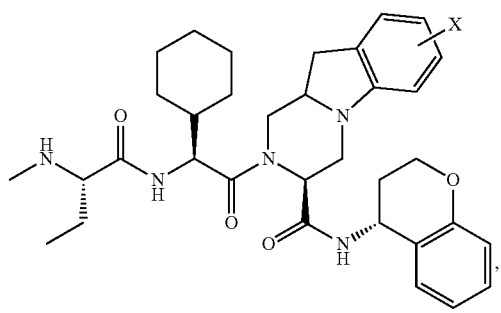

(LVIII)

wherein X of Formula (LVIII) is one or two substituents independently selected from H, halogen or cyano.

In any of the compounds described herein, the ILM can have the structure of and be chemically linked to the linker group L as shown in Formula (LIX) or (LX), or an unnatural mimetic thereof:


In a particular embodiment, the ILM is selected from the group consisting of, and which the chemical link between the ILM and linker group L is shown:

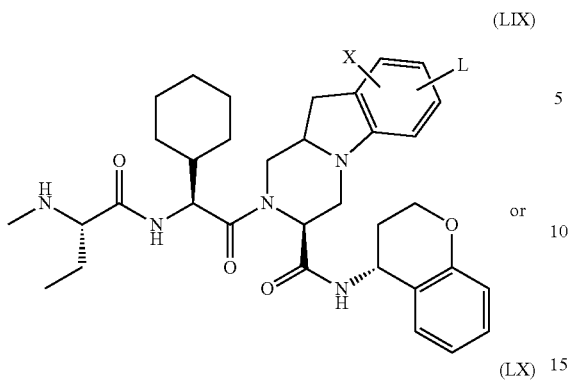
(LIX)

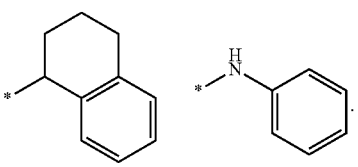

In any of the compounds described herein, the ILM can have the structure of and be chemically linked to the linker group L as shown in Formula (LXII) or (LLXIII), or an unnatural mimetic thereof:

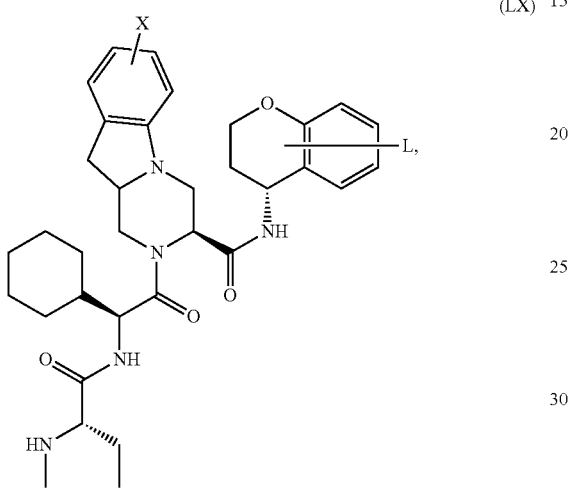
(LX)

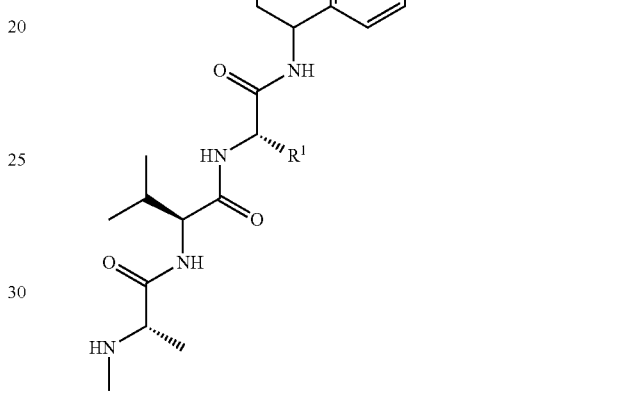
(LXII)

wherein X of Formula (LIX) and (LX) is one or two substituents independently selected from H, halogen or cyano, and; and L of Formulas (LIX) and (LX) is a linker group as described herein.

In any of the compounds described herein, the ILM can have the structure of Formula (LXI), which is based on the IAP ligands described in Ardecky, R J, et al., *Design, synthesis and evaluation of inhibitor of apoptosis (IAP) antagonists that are highly selective for the BIR2 domain of XIAP*, Bioorg. Med. Chem., 23(14): 4253-7 (2013), or an unnatural mimetic thereof:

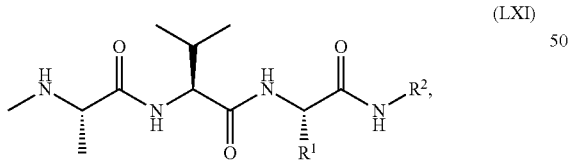
(LXI)

wherein:

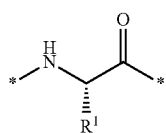

of Formula (LXI) is a natural or unnatural amino acid; and $R^2$ of Formula (LXI) is selected from:

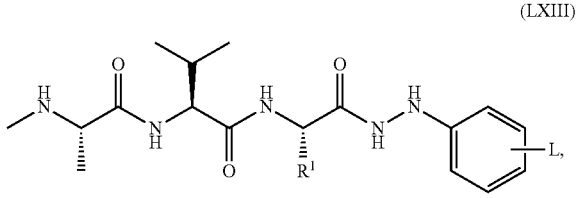
(LXIII)

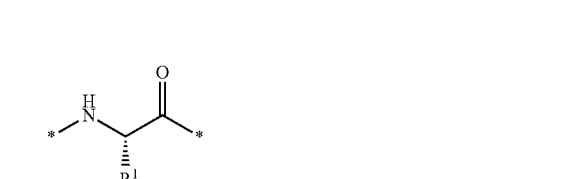

of Formula (LXI) is a natural or unnatural amino acid; and L of Formula (LXI) is a linker group as described herein.

In any of the compounds described herein, the ILM can have the structure selected from the group consisting of, which is based on the IAP ligands described in Wang, J, et al., *Discovery of novel second mitochondrial-derived activator of caspase mimetics as selective inhibitor or apoptosis protein inhibitors*, J. Pharmacol. Exp. Ther., 349(2): 319-29 (2014), or an unnatural mimetic thereof:

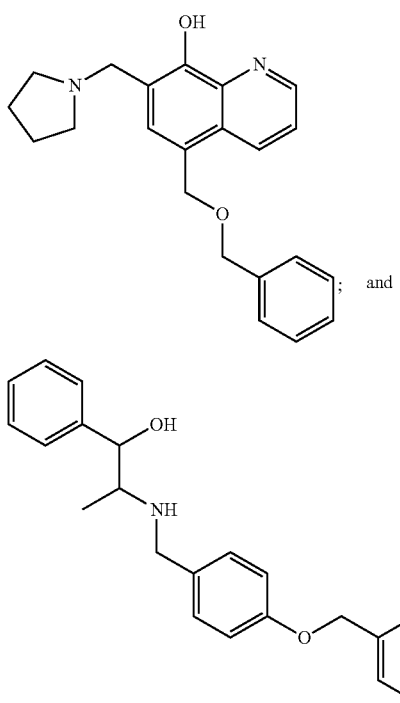

and

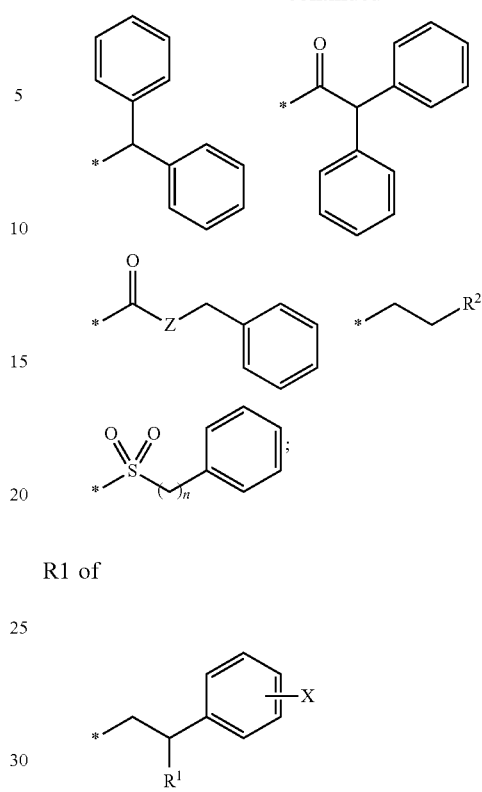

R1 of is selected from H or Me;

R2 of is selected from alkyl or cycloalkyl;

X of is 1-2 substitutents independently selected from halogen, hydroxy, methoxy, nitro and trifluoromethyl Z of is O or NH;

In any of the compounds described herein, the ILM has a structure according to Formula (LXIX), which is based on the IAP ligands described in Hird, A W, et al., Structure-based design and synthesis of tricyclic IAP (*Inhibitors of Apoptosis Proteins*) inhibitors, Bioorg. Med. Chem. Lett., 24(7): 1820-4 (2014), or an unnatural mimetic thereof:

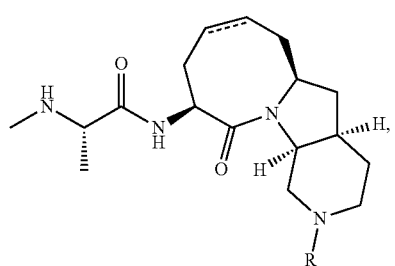

(LXIX)

wherein R of Formula LIX is selected from the group consisting of:

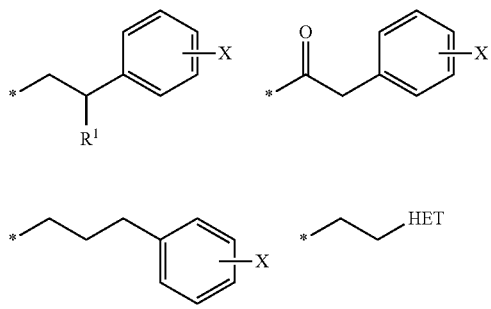

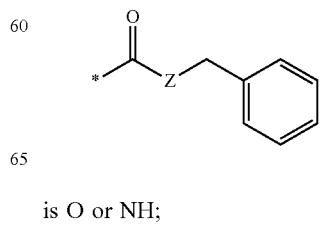

HET of
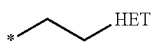
is mono- or fused bicyclic heteroaryl; and
--- of Formula (LIX) is an optional double bond.
In a particular embodiment, the ILM of the compound has a chemical structure as represented by:
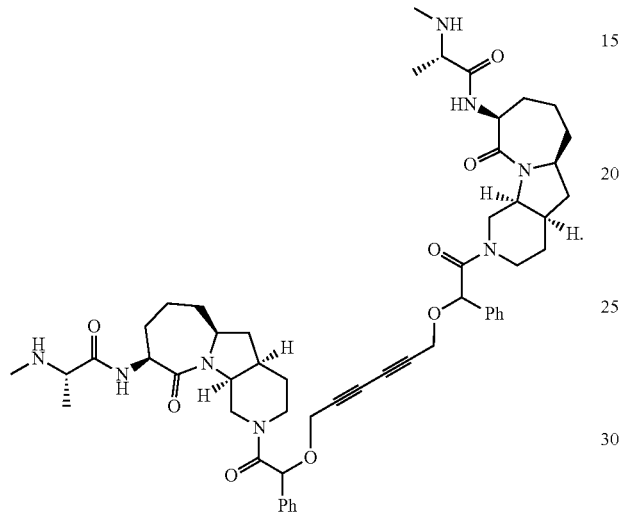
In a particular embodiment, the ILM of the compound has a chemical structure selected from the group consisting of:
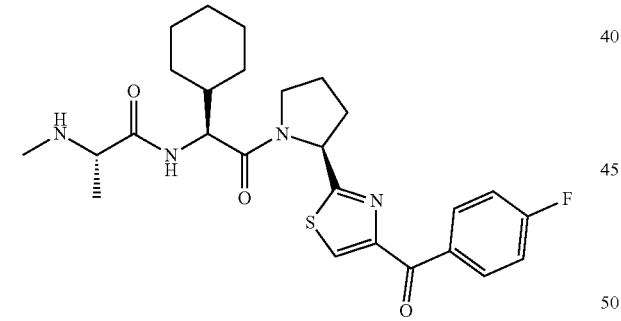
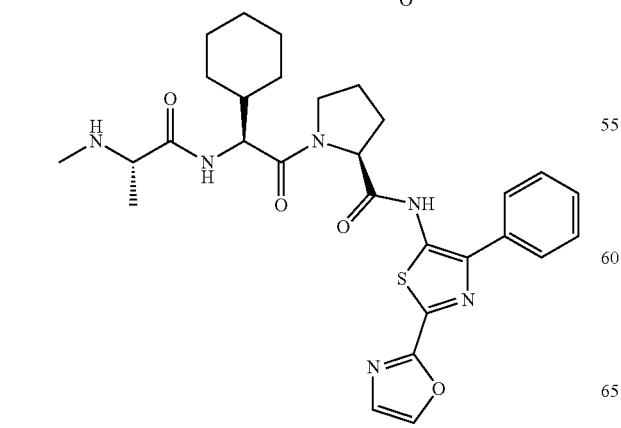
-continued
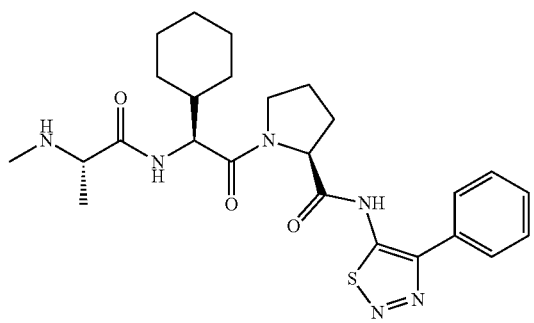
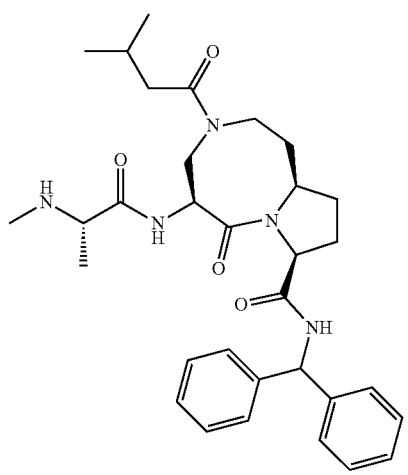
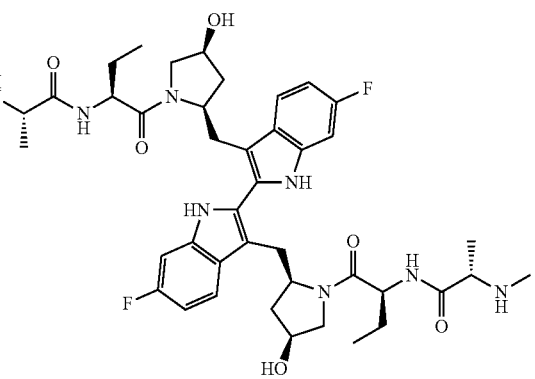
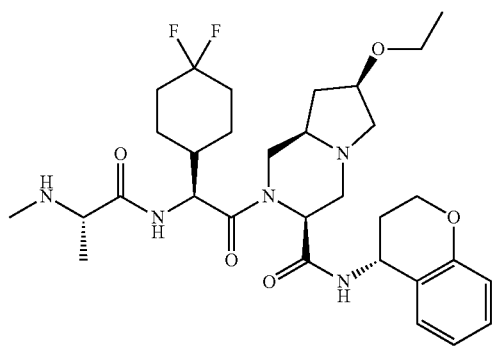

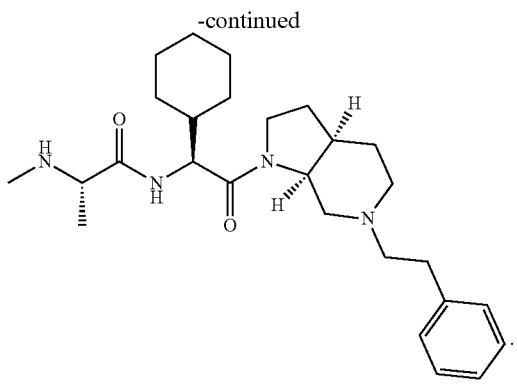

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopen-tylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{16}$ (preferably $C_2$-$C_{10}$ or $C_2$-$C_6$) hydrocarbon radicals containing at least one C=C bond.

The term "Alkynyl" refers to linear, branch-chained or cyclic hydrocarbon radicals (preferably $C_2$-$C_{10}$ or $C_2$-$C_6$) containing at least one CC bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substitutents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a side chain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—NR$_1$R$_2$ or —N(R$_1$)—C(O)—O—R$_1$, nitro, cyano and amine (especially including a $C_1$-$C_6$ alkylene-NR$_1$R$_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, $C_1$-$C_6$ alkyl, —(CH$_2$)$_n$O—(C$_1$-$C_6$ alkyl), —(CH$_2$)$_n$C(O)—(C$_1$-$C_6$ alkyl), —(CH$_2$)$_n$OC(O)—(C$_1$-$C_6$ alkyl), —(CH$_2$)$_n$C(O)O—(C$_1$-$C_6$ alkyl), —(CH$_2$)$_n$NHC(O)—R$_1$, —(CH$_2$)$_n$C(O)—NR$_1$R$_2$, —(OCH$_2$)$_n$OH, —(CH$_2$O)$_n$COOH, $C_1$-$C_6$ alkyl, —(OCH$_2$)$_n$O—(C$_1$-$C_6$ alkyl), —(CH$_2$O)$_n$C(O)—(C$_1$-$C_6$ alkyl), —(OCH$_2$)$_n$NHC(O)—R$_1$, —(CH$_2$O)$_n$C(O)—NR$_1$R$_2$, —S(O)$_2$—R$_S$, —S(O)—R$_S$ (R$_S$ is $C_1$-$C_6$ alkyl or a —(CH$_2$)$_m$—NR$_1$R$_2$ group), NO$_2$, CN or halogen (F, Cl, Br, I, preferably F or Cl), depending on the context of the use of the substituent. R$_1$ and R$_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—NR$_1$R$^2$ group where R$_1$ and R$_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "dihydrosulfonopyranyl" refers to the following radical:

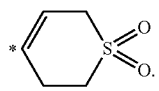

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heteroaromatic" or "heteroaryl" refers to 5- to 7-membered mono- or 8- to 10-membered bicyclic aromatic ring systems, any ring of which may consist of from one to four heteroatoms selected from N, O, or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —(CH$_2$)$_n$OH, —(CH$_2$)$_n$—O—(C$_1$-$C_6$)alkyl, —(CH$_2$)$_n$—O—(CH$_2$)$_n$—(C$_1$-$C_6$)alkyl, —(CH$_2$)$_n$—C(O)(C$_0$-$C_6$) alkyl, —(CH$_2$)$_n$—C(O)O(C$_0$-$C_6$) alkyl, —(CH$_2$)$_n$—OC(O)(C$_0$-$C_6$)alkyl, amine, mono- or di-(C$_1$-$C_6$ alkyl) amine wherein the alkyl group on the amine is optionally substituted with 1 or 2 hydroxyl groups or up to three halo (preferably F, CO groups, OH, COOH, $C_1$-$C_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is preferably substituted with a linker group attached to a PTM group, including a ULM group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

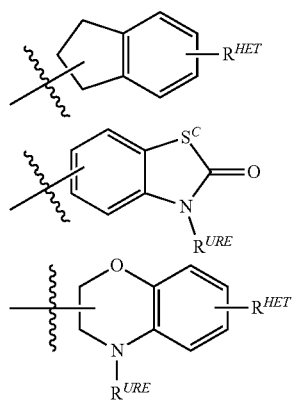

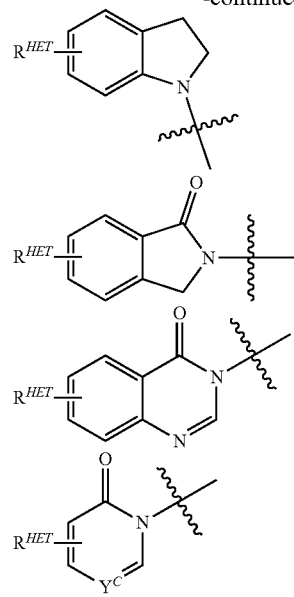

wherein
$S^c$ is $CHR^{SS}$, $NR^{URE}$; or O;
$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);
$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);
$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
$Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO— heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "carboxyalkyl" refers to an alkylated carboxy group such as tert-butoxycarbonyl, in which the point of attachment to the rest of the molecule is the carbonyl group.

The term "cyclic heterodionyl" refers to a heterocyclic compound bearing two carbonyl substituents. Examples include thiazolidine dionyls, oxazolidine dionyls and pyrrolidine dionyls.

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopen-tylethyl, cyclohexylethyl and cyclohexyl, among others. In certain embodiments, the alkyl group is end-capped with a halogen group (Br, Cl, F, or I).

The term "alkylamino" refers to a radical formed by the removal of one hydrogen atom from the nitrogen of an alkylamine, such as butylamine, and the term "dialkylamino" refers to a radical formed by the removal of one hydrogen atom from the nitrogen of a secondary amine, such as dibutylamine. In both cases it is expected that the point of attachment to the rest of the molecule is the nitrogen atom.

The term "lower alkyl" alone or in combination means an alkane-derived radical containing from 1 to 6 carbon atoms (unless specifically defined) that includes a straight chain alkyl or branched alkyl. The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like.

The term "lower alkoxy" refers to methoxy, ethoxy or propoxy.

"Lower alkylene" refers to a divalent alkane-derived radical containing 1-6 carbon atoms, straight chain or branched, from which two hydrogen atoms are taken from the same carbon atom or from different carbon atoms. Examples of lower alkylene include, but are not limited to, methylene —$CH_2$—, ethylene —$CH_2CH_2$—, propylene —$CH_2CH_2CH_2$—, isopropylene —$CH(CH_3)CH$—, and the like.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. Examples of lower alkenyl groups include ethenyl, propenyl, isopropenyl, butenyl, and the like.

"Lower alkynyl" alone or in combination means a straight or branched hydrocarbon containing 2-6 carbon atoms (unless specifically defined) containing at least one, preferably one, carbon to carbon triple bond. Examples of alkynyl groups include ethynyl, propynyl, butynyl, and the like.

The term "alkoxy" refers to a saturated or partially unsaturated branched or straight chain monovalent hydrocarbon alcohol radical derived by the removal of the hydrogen atom from the hydroxide oxygen substituent on a parent alkane, alkene or alkyne. Where specific levels of saturation are intended, the nomenclature "alkoxy", "alkenyloxy" and "alkynyloxy" are used consistent with the definitions of alkyl, alkenyl and alkynyl. Examples include $C_{1-8}$alkoxy or $C_{1-4}$alkoxy groups The term "alkoxyether" refers to a saturated branched or straight chain monovalent hydrocarbon alcohol radical derived by the removal of the hydrogen atom from the hydroxide oxygen substituent on a hydroxyether. Examples include 1-hydroxyl-2-methoxy-ethane and 1-(2-hydroxylethoxy)-2-methoxy-ethane groups.

The term "benzo-fused cycloalkyl" refers to a bicyclic fused ring system radical wherein one of the rings is phenyl and the other is a cycloalkyl or cycloalkenyl ring. Typical benzo-fused cycloalkyl radicals include indanyl, 1,2,3,4-tetrahydro-naphthalenyl, 6,7,8,9,-tetrahydro-5H-benzocycloheptenyl, 5,6,7,8,9,10-hexahydro-benzocyclooctenyl and the like. A benzo-fused cycloalkyl ring system is a subset of the aryl group.

The term "cycloalkenyl" refers to a partially unsaturated cycloalkyl radical derived by the removal of one hydrogen atom from a hydrocarbon ring system that contains at least one carbon-carbon double bond. Examples include cyclohexenyl, cyclopentenyl and 1,2,5,6-cyclooctadienyl.

The term "benzo-fused heteroaryl" refers to a bicyclic fused ring system radical wherein one of the rings is phenyl and the other is a heteroaryl ring. Typical benzo-fused heteroaryl radicals include indolyl, indolinyl, isoindolyl, benzo[b]furyl, benzo[b]thienyl, indazolyl, benzthiazolyl, quinolinyl, isoquinolinyl, cinnolinyl, phthalazinyl, quinazolinyl, and the like. A benzo-fused heteroaryl ring is a subset of the heteroaryl group.

The term "benzo-fused heterocyclyl" refers to a bicyclic fused ring system radical wherein one of the rings is phenyl and the other is a heterocyclyl ring. Typical benzo-fused heterocyclyl radicals include 1,3-benzodioxolyl (also known as 1,3-methylenedioxyphenyl), 2,3-dihydro-1,4-benzodioxinyl (also known as 1,4-ethylenedioxyphenyl), benzo-dihydro-furyl, benzo-tetrahydro-pyranyl, benzo-dihydro-thienyl and the like.

The term "heterocyclyl" refers to a saturated or partially unsaturated monocyclic ring radical derived by the removal of one hydrogen atom from a single carbon or nitrogen ring atom. Typical heterocyclyl radicals include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like, pyrrolinyl.

The term "fused ring system" refers to a bicyclic molecule in which two adjacent atoms are present in each of the two cyclic moieties. Heteroatoms may optionally be present. Examples include benzothiazole, 1,3-benzodioxole and decahydronaphthalene.

The term "hetero" used as a prefix for a ring system refers to the replacement of at least one ring carbon atom with one or more atoms independently selected from N, S, o or P. Examples include rings wherein 1, 2, 3 or 4 ring members are a nitrogen atom; or, 0, 1, 2 or 3 ring members are nitrogen atoms and 1 member is an oxygen or sulfur atom.

The term "heteroaralkyl" refers to a C.sub.16 alkyl group containing a heteroaryl substituent. Examples include furylmethyl and pyridylpropyl. It is intended that the point of attachment to the rest of the molecule be the alkyl group.

The term "hydroxyalkyl" refers to both linear and branched chain radicals of up to 6 carbon atoms, in which one hydrogen atom has been replaced with an OH group.

The term "hydroxyalkylamino" refers to an hydroxyalkyl group in which one hydrogen atom from the carbon chain has been replaced with an amino group, wherein the nitrogen is the point of attachment to the rest of the molecule.

The term "sulfonyl" refers to the group —$S(O)_2R_a$, where $R_a$ is hydrogen, alkyl, cycloalkyl, haloalkyl, aryl, aralkyl, heteroaryl and heteroaralkyl. A "sulfonylating agent" adds the —$S(O)_2R_a$ group to a molecule.

In any of the embodiments described herein, the W, X, Y, Z, G, G', R, R', R'', Q1-Q4, A, and Rn can independently be covalently coupled to a linker and/or a linker to which is attached one or more PTM, ULM, ILM or ILM' groups.

Exemplary MLMs

In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain preferred embodiments, MLM is a derivative of substituted imidazoline represented as Formula (A-1), or thiazoloimidazoline represented as Formula (A-2), or spiro indolinone represented as Formula (A-3), or pyrollidine represented as Formula (A-4), or piperidinone/morphlinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

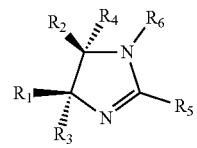

Formula (A-1)

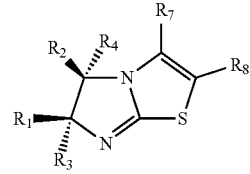

Formula (A-2)

-continued

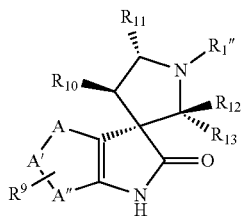
Formula (A-3)

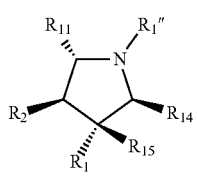
Formula (A-4)

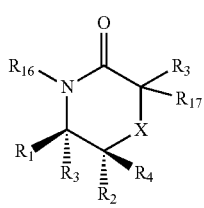
Formula (A-5)

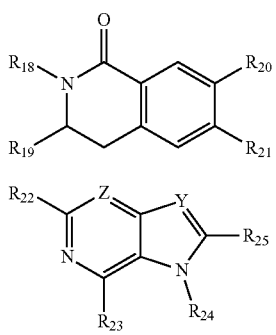
Formula (A-6)

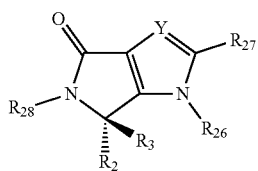
Formula (A-7)

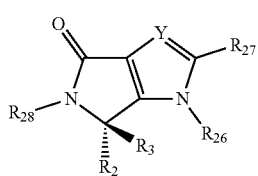
Formula (A-8)

wherein in Formula (A-1) through Formula (A-8),

X of Formula (A-1) through Formula (A-8) is selected from the group consisting of carbon, oxygen, sulfur, sulfoxide, sulfone, and N—$R^a$;

$R^a$ is independently H or an alkyl group with carbon number 1 to 6;

Y and Z of Formula (A-1) through Formula (A-8) are independently carbon or nitrogen;

A, A' and A" of Formula (A-1) through Formula (A-8) are independently selected from C, N, O or S, can also be one or two atoms forming a fused bicyclic ring, or a 6,5- and 5,5-fused aromatic bicyclic group;

$R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;

$R_3$, $R_4$ of Formula (A-1) through Formula (A-8) are independently selected from the group consisting of H, methyl and C1 to C6 alkyl;

$R_5$ of Formula (A-1) through Formula (A-8) is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:

halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);

$R_6$ of Formula (A-1) through Formula (A-8) is H or —C(=O)$R^b$, wherein $R^b$ of Formula (A-1) through Formula (A-8) is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-1-piperidinyl, and 3-$R^c$-1-piperidinyl, wherein $R^c$ of Formula (A-1) through Formula (A-8) is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein $R^d$ of Formula (A-1) through Formula (A-8) is selected from the group consisting of alkoxy, alkyl sulfone, alkyl sulfoxide, N-substituted carboxamide, —NHC(O)-alkyl, —NH—SO$_2$-alkyl, aryl, substituted aryl, heteroaryl, substituted heteroaryl;

$R_7$ of Formula (A-1) through Formula (A-8) is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;

$R_8$ of Formula (A-1) through Formula (A-8) is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:

$R^e$ of Formula (A-1) through Formula (A-8) is an alkylene with 1 to 6 carbons, or a bond;

$R^f$ of Formula (A-1) through Formula (A-8) is a substituted 4- to 7-membered heterocycle;

$R^g$ of Formula (A-1) through Formula (A-8) is selected from the group consisting of aryl, hetero aryl, substituted aryl or heteroaryl, and 4- to 7-membered heterocycle;

$R_9$ of Formula (A-1) through Formula (A-8) is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

$R_{10}$ of Formula (A-1) through Formula (A-8) is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

$R_{11}$ of Formula (A-1) through Formula (A-8) is —C(O)—N($R^h$)($R^i$), wherein $R^h$ and $R^i$ are selected from groups consisting of the following:
- H, C1 to C6 alkyl, alkoxy substituted alkyl, sulfone substituted alkyl, aryl, heterol aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ of Formula (A-1) through Formula (A-8) are independently selected from the group consisting of H, connected to form a ring, 4-hydroxycyclohehexane; mono- and dihydroxy substituted alkyl (C3 to C6); 3-hydroxycyclobutane; phenyl-4-carboxylic acid, and substituted phenyl-4-carboxylic acid;

$R_{12}$ and $R_{13}$ of Formula (A-1) through Formula (A-8) are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, R12 and R13 can be connected to form a 5- and 6-membered ring with or without substitution on the ring;

$R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ of Formula (A-1) through Formula (A-8) is CN;

$R_{16}$ of Formula (A-1) through Formula (A-8) is selected from the group consisting of C1-6 alkyl, C1-6 cycloalkyl, C2-6 alkenyl, C1-6 alkyl or C3-6 cycloalkyl with one or multiple hydrogens replaced by fluorine, alkyl or cycloalkyl with one $CH_2$ replaced by S(=O), —S, or —S(=O)$_2$, alkyl or cycloalkyl with terminal $CH_3$ replaced by S(=O)$_2$N(alkyl)(alkyl), —C(=O)N(alkyl)(alkyl), —N(alkyl)S(=O)$_2$(alkyl), —C(=O)2(alkyl), —O(alkyl), C1-6 alkyl or alkylcycloalkyl with hydron replaced by hydroxyl group, a 3 to 7 membered cycloalkyl or heterocycloalkyl, optionally containing a —(C=0)- group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ of Formula (A-1) through Formula (A-8) is selected from the group consisting of $(CH_2)nC(O)NR^kR^i$, wherein $R^k$ and $R^l$ are independently selected from H, C1-6 alkyl, hydroxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, alkyl aryl with alkyl group containing 1-6 carbons, and alkyl heteroaryl with alkyl group containing 1-6 carbons, wherein the aryl or heteroaryl group can be further substituted;

$R_{18}$ of Formula (A-1) through Formula (A-8) is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[alkyl]-(heterocycle-substituted)-cycloalkyl];

$R_{19}$ of Formula (A-1) through Formula (A-8) is selected from the group consisting of aryl, heteroaryl, bicyclic heteroaryl, and these aryl or heteroaryl groups can be substituted with halogen, C1-6 alkyl, C1-6 cycloalkyl, $CF_3$, F, CN, alkyne, alkyl sulfone, the halogen substitution can be mono- bis- or tri-substituted;

$R_{20}$ and $R_{21}$ of Formula (A-1) through Formula (A-8) are independently selected from C1-6 alkyl, C1-6 cycloalkyl, C1-6 alkoxy, hydroxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

$R_{22}$ of Formula (A-1) through Formula (A-8) is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ of Formula (A-1) through Formula (A-8) is selected from aryl, heteroaryl, —O-aryl, —O— heteroaryl, —O-alkyl, —O-alkyl-cycloalkyl, —NH-alkyl, —NH-alkyl-cycloalkyl, —N(H)-aryl, —N(H)— heteroaryl, —N(alkyl)-aryl, —N(alkyl)-heteroaryl, the aryl or heteroaryl groups can be substituted with halogen, C1-6 alkyl, hydroxylated C1-6 alkyl, cycloalkyl, fluorine-substituted C1-6 alkyl, CN, alkoxy, alkyl sulfone, amide and sulfonamide;

$R_{24}$ of Formula (A-1) through Formula (A-8) is selected from the group consisting of —CH2-(C1-6 alkyl), —CH2-cycloalkyl, —CH2-aryl, CH2-heteroaryl, where alkyl, cycloalkyl, aryl and heteroaryl can be substituted with halogen, alkoxy, hydoxylated alkyl, cyano-substituted alkyl, cycloalyl and substituted cycloalkyl;

$R_{25}$ of Formula (A-1) through Formula (A-8) is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5,6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ of Formula (A-1) through Formula (A-8) is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —NH$_2$, —NH-alkyl, NH—C(O)alkyl, —NH—S(O)$_2$-alkyl, and —S(O)$_2$-alkyl;

$R_{27}$ of Formula (A-1) through Formula (A-8) is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution;

$R_{28}$ of Formula (A-1) through Formula (A-8) is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_{1'''}$ of Formula (A-1) through Formula (A-8) is selected from the group consisting of alkyl, aryl substituted alkyl, alkoxy substituted alkyl, cycloalkyl, aryl-substituted cycloalkyl, and alkoxy substituted cycloalkyl.

In certain embodiments, the heterocycles in $R^f$ and $R^g$ of Formula (A-1) through Formula (A-8) are substituted pyrrolidine, substituted piperidine, substituted piperizine.

More specifically, non-limiting examples of MLMs include those shown below as well as those 'hybrid' molecules that arise from the combination of 1 or more of the different features shown in the molecules below.

Using MLM in Formula A-1 through A-8, the following PROTACs can be prepared to target a particular protein for degradation, where 'L" is a connector (i.e. a linker group), and "PTM" is a ligand binding to a target protein.

In certain embodiments, the description provides a bifunctional molecule comprising a structure selected from the group consisting of:

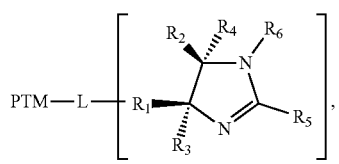
Formula (A-9)

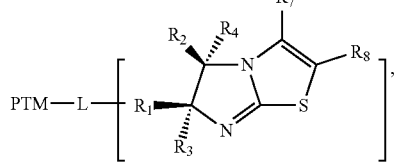
Formula (A-10)

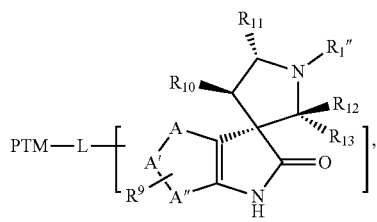
Formula (A-11)

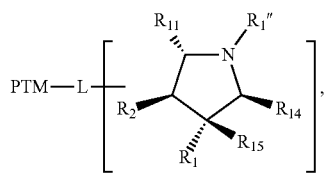
Formula (A-12)

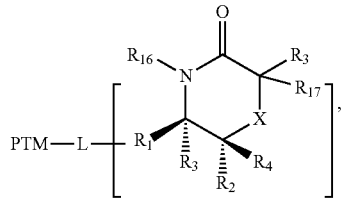
Formula (A-13)

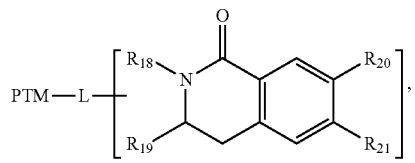
Formula (A-14)

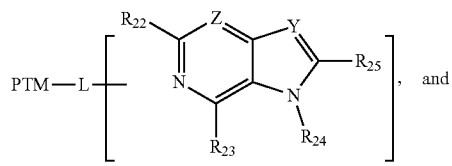
Formula (A-15)

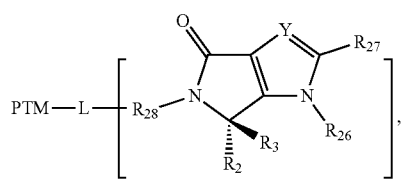
Formula (A-16)

wherein X, $R^a$, Y, Z, A, A', A", $R_1$, $R_2$, $R_3$, $R_4$, $R_5$, $R_6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{1'''}$ are as defined herein with regard to Formulas (A-1) through (A-8).

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

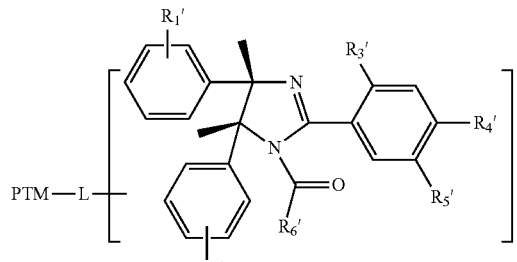
A-1-1

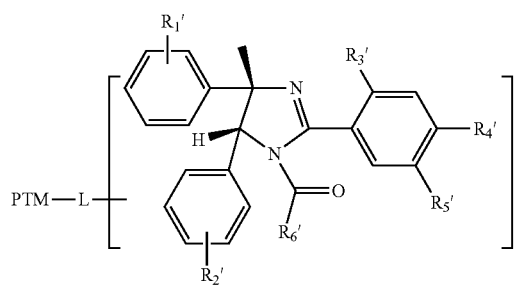
A-1-2

-continued

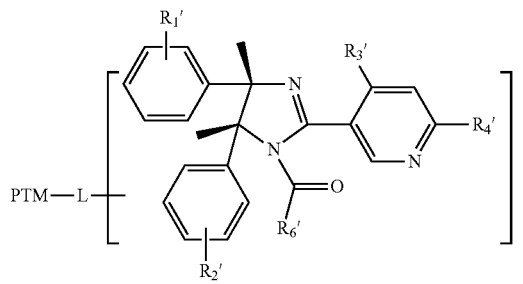

A-1-3

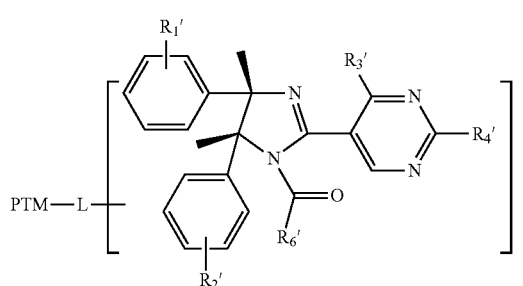

A-1-4 wherein:

R1' and R2' of Formulas A-1-1 through A-1-4 (i.e., A-1-1, A-1-2, A-1-3, and A-1-4) are independently selected from the group consisting of F, Cl, Br, I, acetylene, CN, CF$_3$ and NO$_2$;

R3' is selected from the group consisting of —OCH$_3$, —OCH$_2$CH$_3$, —OCH$_2$CH$_2$F, —OCH$_2$CH$_2$OCH$_3$, and —OCH(CH$_3$)$_2$;

R4' of Formulas A-1-1 through A-1-4 is selected from the group consisting of H, halogen, —CH$_3$, —CF$_3$, —OCH$_3$, —C(CH$_3$)$_3$, —CH(CH$_3$)$_2$, -cyclopropyl, —CN, —C(CH$_3$)$_2$OH, —C(CH$_3$)$_2$OCH$_2$CH$_3$, —C(CH$_3$)$_2$CH$_2$OH, —C(CH$_3$)$_2$CH$_2$OCH$_2$CH$_3$, —C(CH$_3$)$_2$CH$_2$OCH$_2$CH$_2$OH, —C(CH$_3$)$_2$CH$_2$OCH$_2$CH$_3$, —C(CH$_3$)$_2$CN, —C(CH$_3$)$_2$C(O)CH$_3$, —C(CH$_3$)$_2$C(O)NHCH$_3$, —C(CH$_3$)$_2$C(O)N(CH$_3$)$_2$, —SCH$_3$, —SCH$_2$CH$_3$, —S(O)$_2$CH$_3$, —S(O$_2$)CH$_2$CH$_3$, —NHC(CH$_3$)$_3$, —N(CH$_3$)$_2$, pyrrolidinyl, and 4-morpholinyl;

R5' of Formulas A-1-1 through A-1-4 is selected from the group consisting of halogen, -cyclopropyl, —S(O)$_2$CH$_3$, —S(O)$_2$CH$_2$CH$_3$, 1-pyrrolidinyl, —NH$_2$, —N(CH$_3$)$_2$, and —NHC(CH$_3$)$_3$; and R6' of Formulas A-1-1 through A-1-4 is selected from the structures presented below where the linker connection point is indicated as "*".

Beside R6' as the point for linker attachment, R4' can also serve as the linker attachment position. In the case that R4' is the linker connection site, linker will be connected to the terminal atom of R4' groups shown above.

In certain embodiments, the linker connection position of Formulas A-1-1 through A-1-4 is at least one of R4' or R6' or both.

In certain embodiments, R6' of Formulas A-1-1 through A-1-4 is independently selected from the group consisting of H,

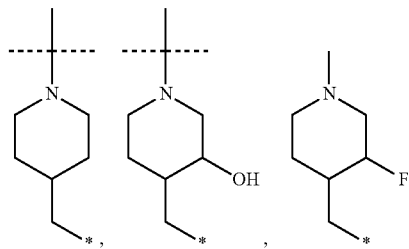

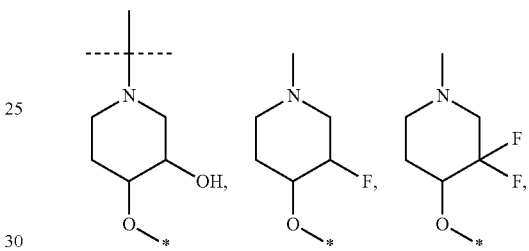

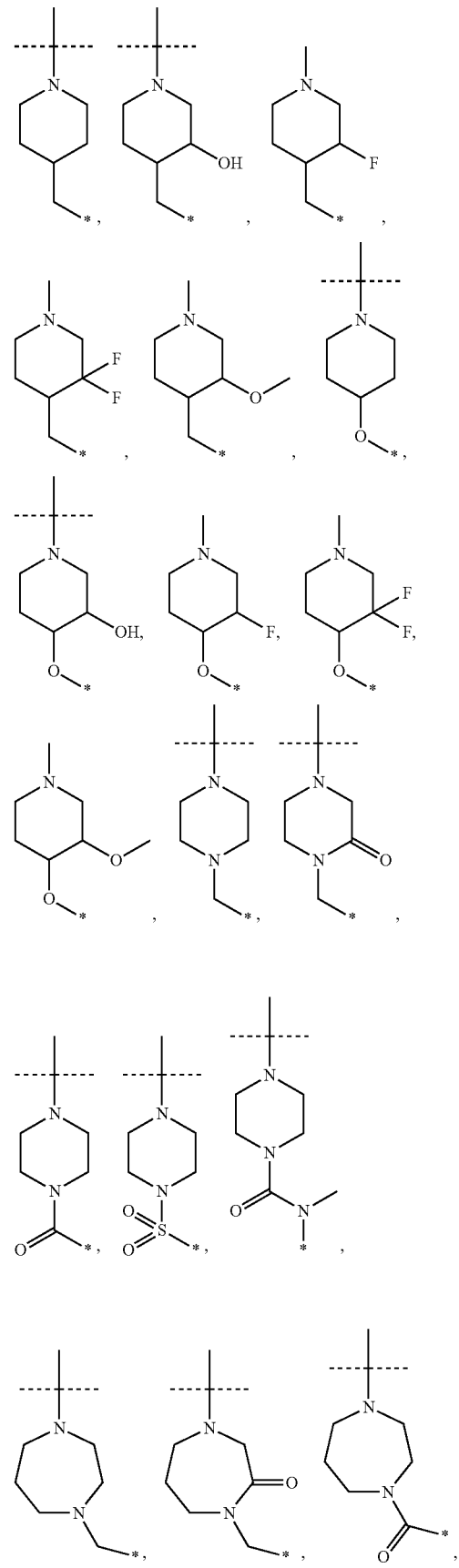

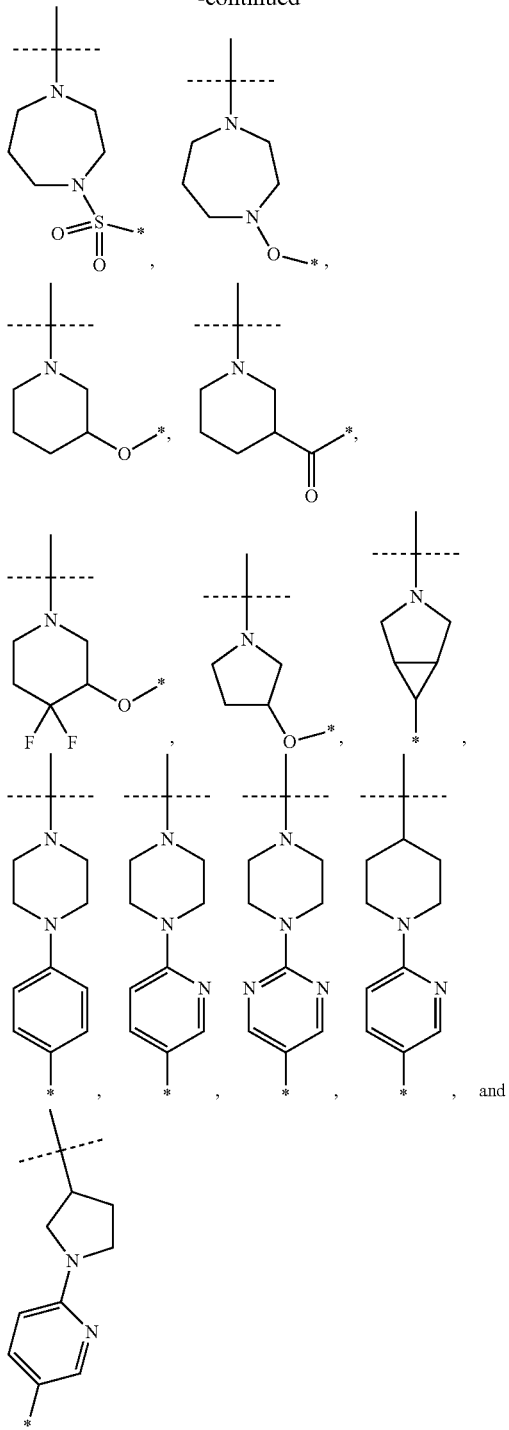

wherein "*" indicates the point of attachment of the linker.

In certain embodiments, the linker of Formula A-4-1 through A-4-6 is attached to at least one of $R_1'$, $R_2'$, $R_3'$, $R_4'$, $R_5'$, $R_6'$, or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-1, A-4-2, A-4-3, A-4-4, A-4-5, and A-4-6:

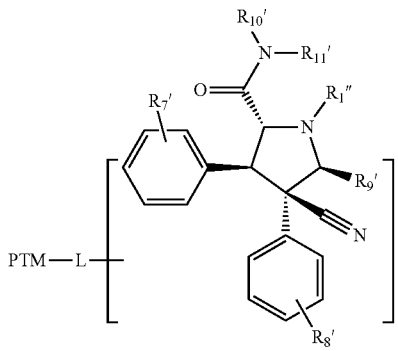

A-4-1

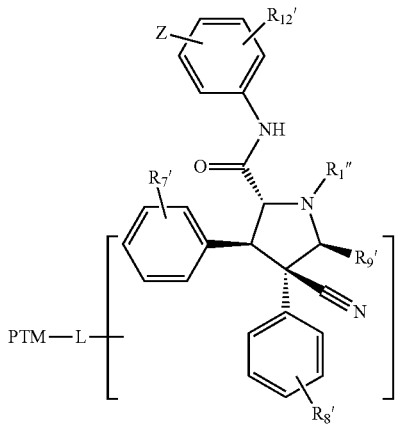

A-4-2

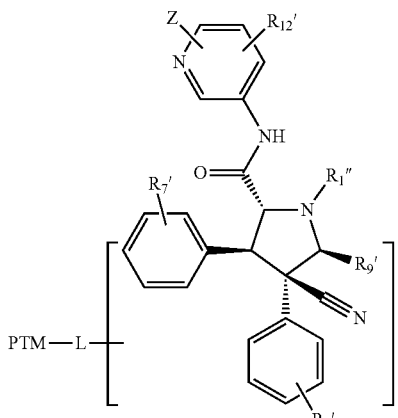

A-4-3

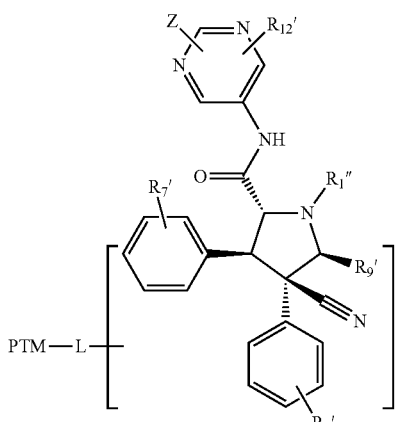

A-4-4

A-4-5

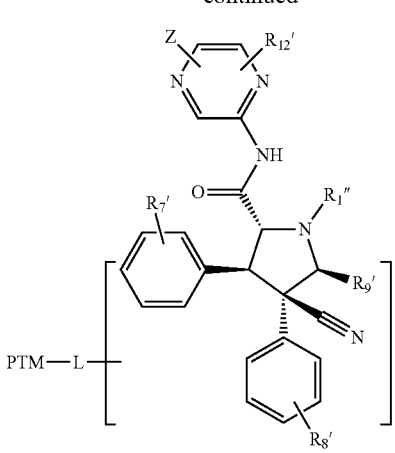

A-4-6

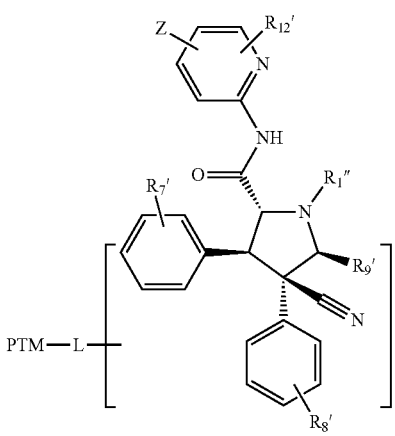

wherein:
R7' of Formula A-4-1 through A-4-6 (i.e., A-4-1, A-4-2, A-4-3, A-4-4, A-4-5, and A-4-6) is a member selected from the group consisting of halogen, mono-, and di- or tri-substituted halogen;
R8' of Formula A-4-1 through A-4-6 is selected from the group consisting of H, —F, —Cl, —Br, —I, —CN, —NO$_2$, ethylnyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted;
R9' of Formula A-4-1 through A-4-6 is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;
Z of Formula A-4-1 through A-4-6 is selected from the group consisting of H, —OCH$_3$, —OCH$_2$CH$_3$, and halogen;
R10' and R11' of Formula A-4-1 through A-4-6 are each independently selected from the group consisting of H, (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COOH, (CH$_2$)$_n$—COOR', (CH$_2$)$_n$—CONR'R", (CH$_2$)$_n$—OR', (CH$_2$)$_n$—SR', (CH$_2$)$_n$—SOR', (CH$_2$)$_n$—CH(OH)—R', (CH$_2$)$_n$—COR', (CH$_2$)$_n$—SO$_2$R', (CH$_2$)$_n$—SONR'R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)$_m$—(CH$_2$)$_n$—NR'COR", (CH$_2$CH$_2$O)$_m$(CH$_2$)$_n$—NR'SO$_2$R", (CH$_2$CH$_2$O)$_n$(CH$_2$)$_n$—COOH, (CH$_2$CH$_2$O)$_m$(CH$_2$)$_n$—COOR', (CH$_2$CH$_2$O)$_m$—(CH2)$_n$—CONR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—(CH$_2$)$_n$—SONR'R", (CH$_2$CH$_2$O)$_m$—(CH$_2$)$_n$—SO$_2$NR'R", (CH$_2$)$_p$—(CH$_2$CH$_2$O)$_m$—(CH$_2$)$_n$R', (CH$_2$)$_p$—(CH$_2$CH$_2$O)$_m$—(CH$_2$)$_n$—OH, (CH$_2$)$_p$—(CH$_2$CH$_2$O)$_m$—(CH$_2$)n-OR', (CH$_2$)$_p$—(CH$_2$CH$_2$O)$_m$—(CH$_2$)$_n$—NR'R", (CH$_2$)$_p$—(CH$_2$CH$_2$O)$_m$—(CH$_2$)$_n$—NR'COR", (CH$_2$)$_p$—(CH$_2$CH$_2$O)$_m$—(CH$_2$)$_n$—NR'SO$_2$R", (CH$_2$)$_p$—(CH$_2$CH$_2$O)$_m$—(CH$_2$)$_n$—COOH, (CH$_2$)$_p$—(CH$_2$CH$_2$O)$_m$—(CH$_2$)$_n$—COOR', (CH$_2$)$_p$—(CH$_2$CH$_2$O)$_m$—(CH$_2$)$_n$—CONR'R", (CH$_2$)$_p$—(CH$_2$CH$_2$O)$_m$—(CH$_2$)$_n$—SO$_2$R', (CH2)$_p$—(CH$_2$CH$_2$O)$_m$—(CH$_2$)$_n$—COR', (CH$_2$)$_p$—(CH$_2$CH$_2$O)$_m$—(CH$_2$)$_n$—SONR'R", (CH$_2$)$_p$—(CH$_2$CH$_2$O)$_m$—(CH$_2$)$_n$—SO$_2$NR'R", Aryl-(CH$_2$)$_n$—COOH, and heteroaryl-alkyl-CO-alkyl-NR'R"m, wherein the alkyl may be substituted with OR', and heteroaryl-(CH$_2$)$_n$-heterocycle wherein the heterocycle may optionally be substituted with alkyl, hydroxyl, COOR' and COR'; wherein R' and R" are selected from H, alkyl, alkyl substituted with halogen, hydroxyl, NH2, NH(alkyl), N(alkyl)$_2$, oxo, carboxy, cycloalkyl and heteroaryl;

m, n, and p are independently 0 to 6;

R12' of Formula A-4-1 through A-4-6 is selected from the group consisting of —O-(alkyl), —O-(alkyl)-alkoxy, —C(O)-(alkyl), —C(OH)-alkyl-alkoxy, —C(O)—NH-(alkyl), —C(O)—N-(alkyl)$_2$, —S(O)-(alkyl), S(O)$_2$-(alkyl), —C(O)-(cyclic amine), and —O-aryl-(alkyl), —O-aryl-(alkoxy);

R1" of Formula A-4-1 through A-4-6 is selected from the group consisting of alkyl, aryl substituted alkyl, alkoxy substituted alkyl, cycloalkyl, ary-substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position of Formula A-4-1 through A-4-6 is at least one of Z, R8', R9', R10', R11", R12", or R1".

The method used to design chimeric molecules as presented in A-1-1 through A-1-4, A-4-1 through A-4-6 can be applied to MLM with formula A-2, A-3, A-5, A-6, A-7 and A-8, wherein the solvent exposed area in the MLM can be connected to linker "L" which will be attached to target protein ligand "PTM", to construct PROTACs.

Exemplary MDM2 binding moieties include, but not limited, the following:

The HDM2/MDM2 inhibitors identified in Vassilev, et al., In vivo activation of the p53 pathway by small-molecule antagonists of MDM2, SCIENCE vol: 303, pag: 844-848 (2004), and Schneekloth, et al., Targeted intracellular protein degradation induced by a small molecule: En route to chemical proteomics, Bioorg. Med. Chem. Lett. 18 (2008) 5904-5908, including (or additionally) the compounds nutlin-3, nutlin-2, and nutlin-1 (derivatized) as described below, as well as all derivatives and analogs thereof:

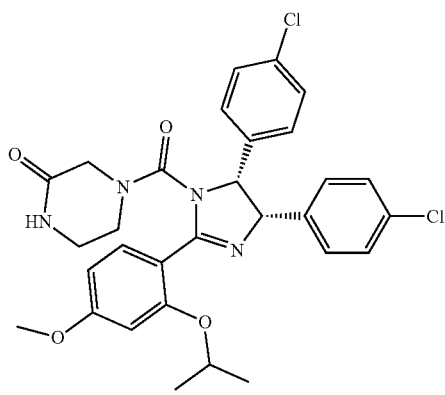 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM) group is attached, for example, at the methoxy group or as a hydroxyl group);

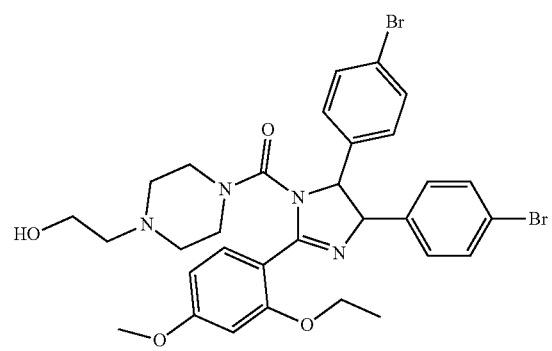 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group); and

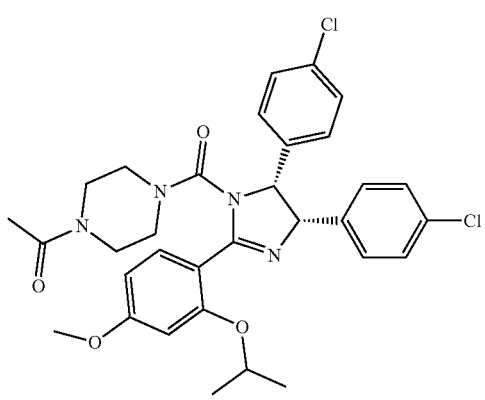 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -(L-MLM) group is attached, for example, via the methoxy group or as a hydroxyl group).

Exemplary CLMs

Neo-Imide Compounds

In one aspect the description provides compounds useful for binding and/or inhibiting cereblon. In certain embodiments, the compound is selected from the group consisting of chemical structures:

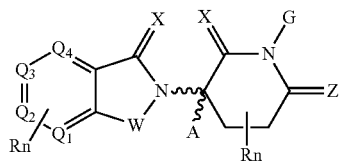  (a)

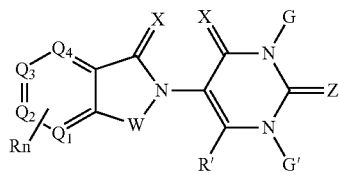  (b)

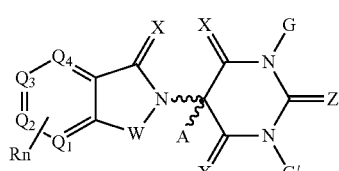  (c)

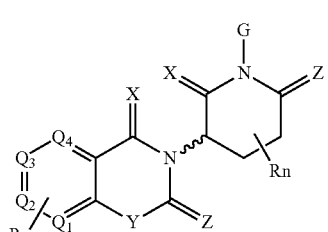  (d)

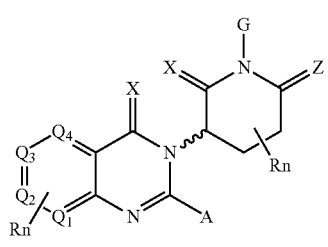  (e)

and

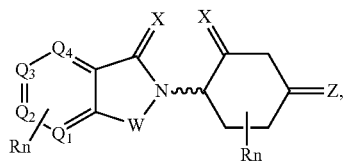  (f)

wherein:

W of Formulas (a) through (e) is independently selected from the group $CH_2$, CHR, C=O, $SO_2$, NH, and N-alkyl;

X of Formulas (a) through (e) is independently selected from the group O, S and $H_2$, Y of Formulas (a) through (e) is independently selected from the group $CH_2$, —C=CR', NH, N-alkyl, N-aryl, N-hetaryl, N-cycloalkyl, N-heterocyclyl, O, and S; Z of Formulas (a) through (e) is independently selected from the group O, and S or $H_2$ except that both X and Z cannot be $H_2$, G and G' of Formulas (a) through (e) are independently selected from the group H, alkyl (linear, branched, optionally substituted), OH, R' OCOOR, R'OCONRR", $CH_2$-heterocyclyl optionally substituted with R', and benzyl optionally substituted with R';

Q1-Q4 of Formulas (a) through (e) represent a carbon C substituted with a group independently selected from R', N or N-oxide;

A of Formulas (a) through (e) is independently selected from the group alkyl (linear, branched, optionally substituted), cycloalkyl, Cl and F;

R of Formulas (a) through (e) comprises, but is not limited to: —CONR'R", —OR', —NR'R", —SR', —SO$_2$R', —SO$_2$NR' R", —CR' R"—, —CR' NR' R"—, (—CR'O)$_n$R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF$_5$ and —OCF$_3$ R' and R" of Formulas (a) through (e) are independently selected from a bond, H, alkyl, cycloalkyl, aryl, heteroaryl, heterocyclic, —C(=O)R, heterocyclyl, each of which is optionally substituted;

n of Formulas (a) through (e) is an integer from 1-10 (e.g., 1-4);

⁓ of Formulas (a) through (e) represents a bond that may be stereospecific ((R) or (S)) or non-stereospecific; and R$_n$ of Formulas (a) through (e) comprises 1-4 independent functional groups or atoms.

Exemplary CLMs

In any of the compounds described herein, the CLM comprises a chemical structure selected from the group:

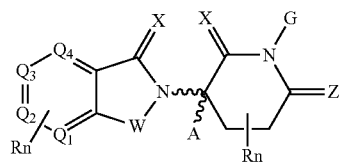

(a)

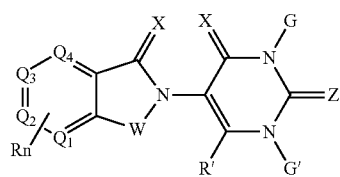

(b)

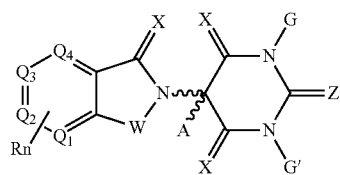

(c)

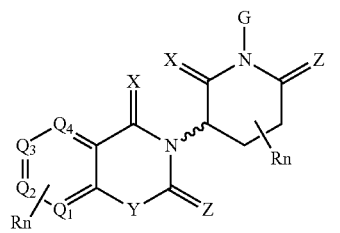

(d)

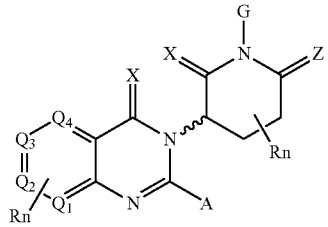

(e)

and

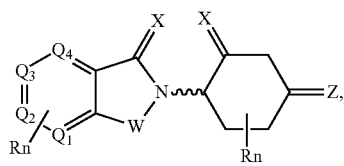

(f)

wherein:

W of Formulas (a) through (e) is independently selected from the group CH$_2$, CHR, C=O, SO$_2$, NH, and N-alkyl;

X of Formulas (a) through (e) is independently selected from the group O, S and H2;

Y of Formulas (a) through (e) is independently selected from the group CH$_2$, —C=CR', NH, N-alkyl, N-aryl, N-hetaryl, N-cycloalkyl, N-heterocyclyl, O, and S;

Z of Formulas (a) through (e) is independently selected from the group O, and S or H2 except that both X and Z cannot be H2;

G and G' of Formulas (a) through (e) are independently selected from the group H, alkyl (linear, branched, optionally substituted), OH, R'OCOOR, R'OCONRR", CH$_2$-heterocyclyl optionally substituted with R', and benzyl optionally substituted with R';

Q1-Q4 of Formulas (a) through (e) represent a carbon C substituted with a group independently selected from R', N or N-oxide;

A of Formulas (a) through (e) is independently selected from the group H, alkyl (linear, branched, optionally substituted), cycloalkyl, Cl and F;

R of Formulas (a) through (e) comprises, but is not limited to: —CONR'R", —OR', —NR'R", —SR', —SO2R', —SO2NR'R", —CR'R"—, —CR'NR'R"—, (—CR'O)$_n$R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF3, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R')R", —SF5 and —OCF3

R' and R" of Formulas (a) through (e) are independently selected from a bond, H, alkyl, cycloalkyl, aryl, heteroaryl, heterocyclic, —C(=O)R, heterocyclyl, each of which is optionally substituted;

n of Formulas (a) through (e) is an integer from 1-10 (e.g., 1-4);

⁓ of Formulas (a) through (e) represents a bond that may be stereospecific ((R) or (S)) or non-stereospecific; and Rn of Formulas (a) through (e) comprises 1-4 independent functional groups or atoms, and optionally, one of which is modified to be covalently joined to a PTM, a chemical linker group (L), a ULM, CLM (or CLM') or combination thereof.

In certain embodiments described herein, the CLM or ULM comprises a chemical structure selected from the group:

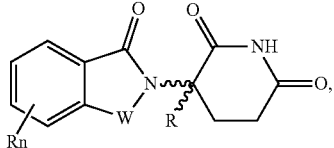

Formula (g)

wherein:
- W of Formula (g) is independently selected from the group CH$_2$, C=O, NH, and N-alkyl;
- R of Formula (g) is independently selected from a H, methyl, alkyl (e.g., a C1-C6 alkyl (linear, branched, optionally substituted));
- ⁓ of Formula (g) represents a bond that may be stereo-specific ((R) or (S)) or non-stereospecific; and
- Rn of Formula (g) comprises 1-4 independently selected functional groups or atoms, and optionally, one of which is modified to be covalently joined to a PTM, a chemical linker group (L), a ULM, CLM (or CLM') or combination thereof.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

More specifically, non-limiting examples of CLMs include those shown below as well as those "hybrid" molecules that arise from the combination of 1 or more of the different features shown in the molecules below.

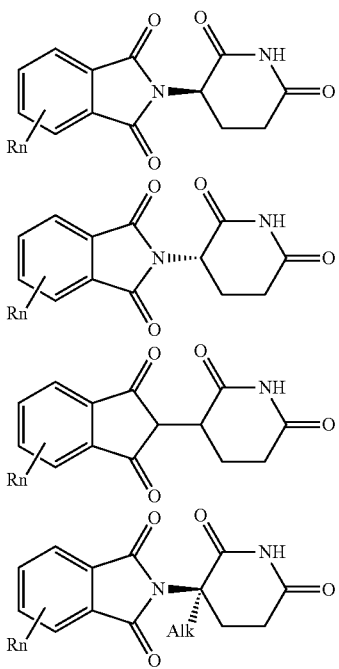

-continued

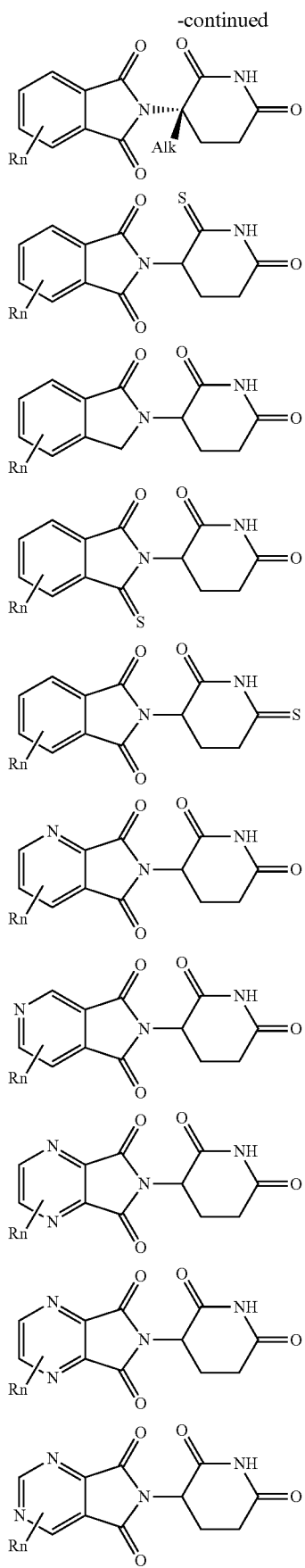

145
-continued
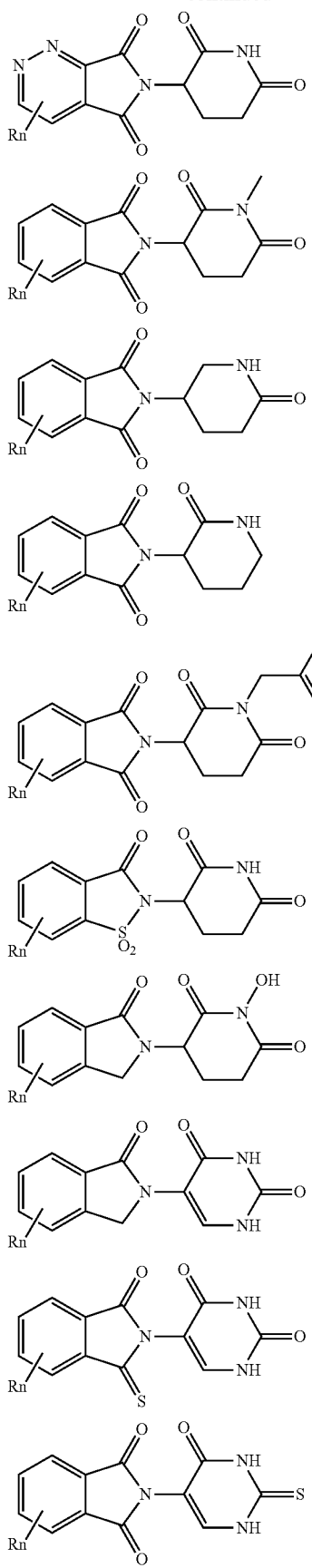
146
-continued
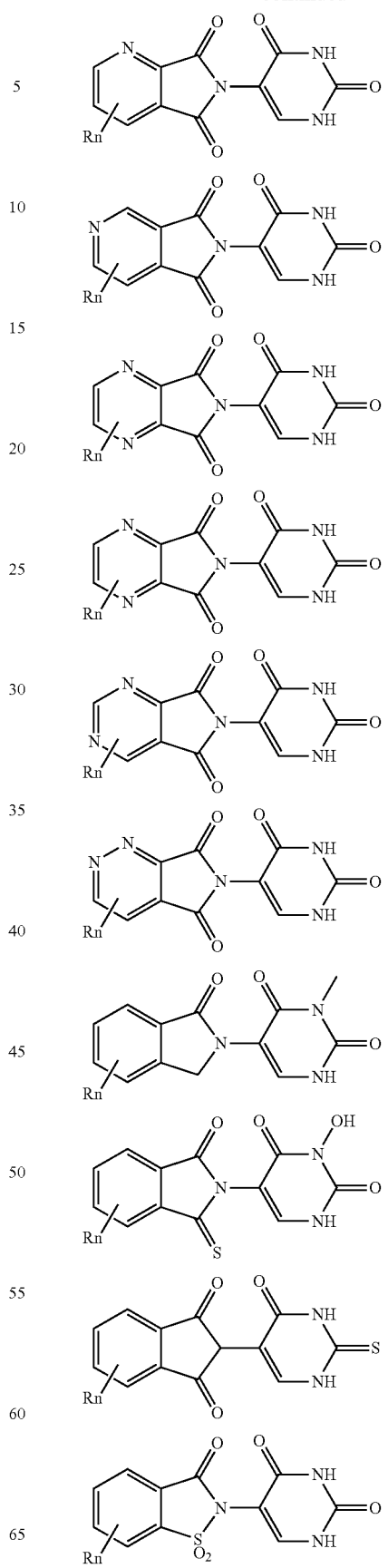

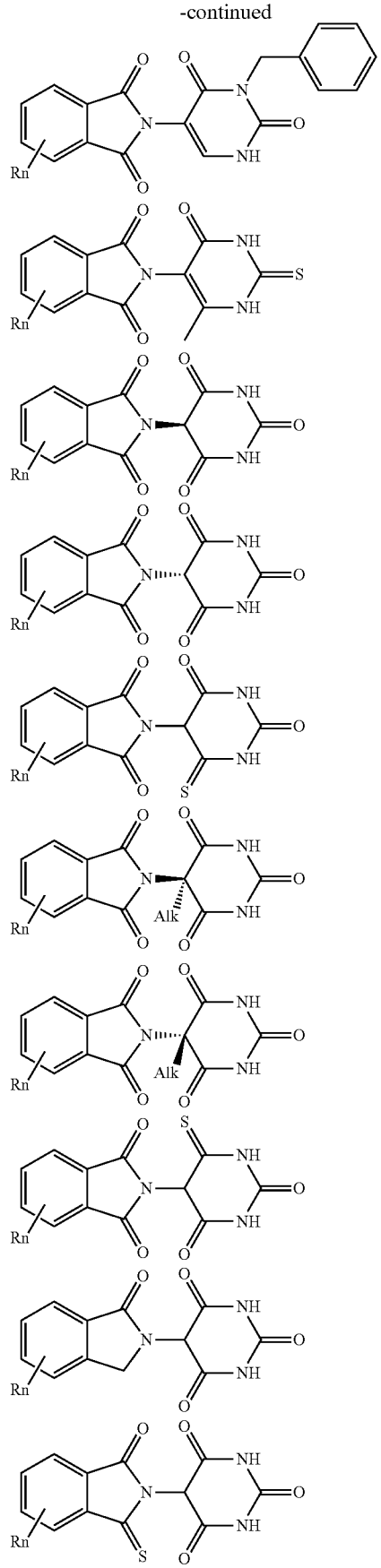
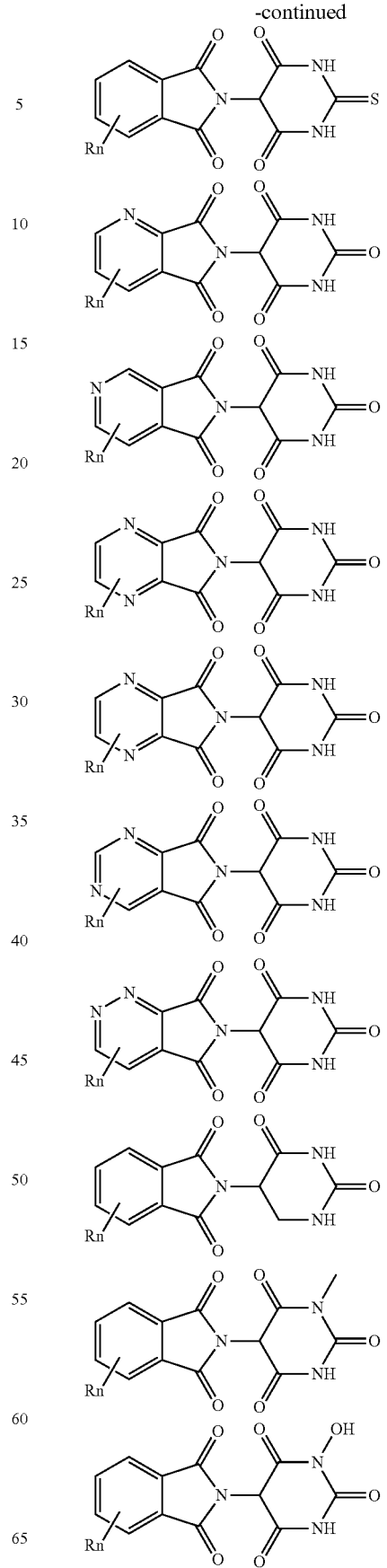

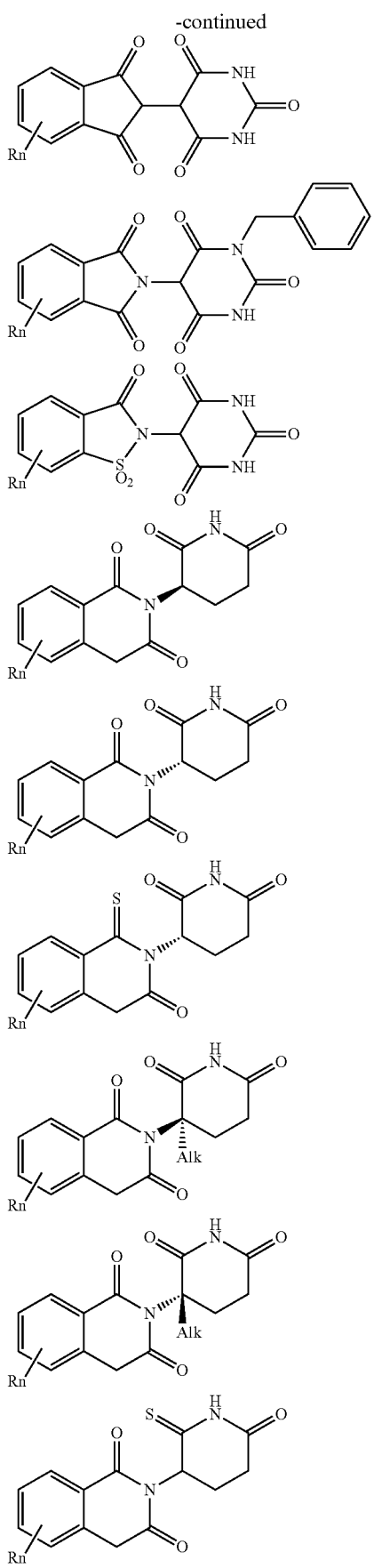
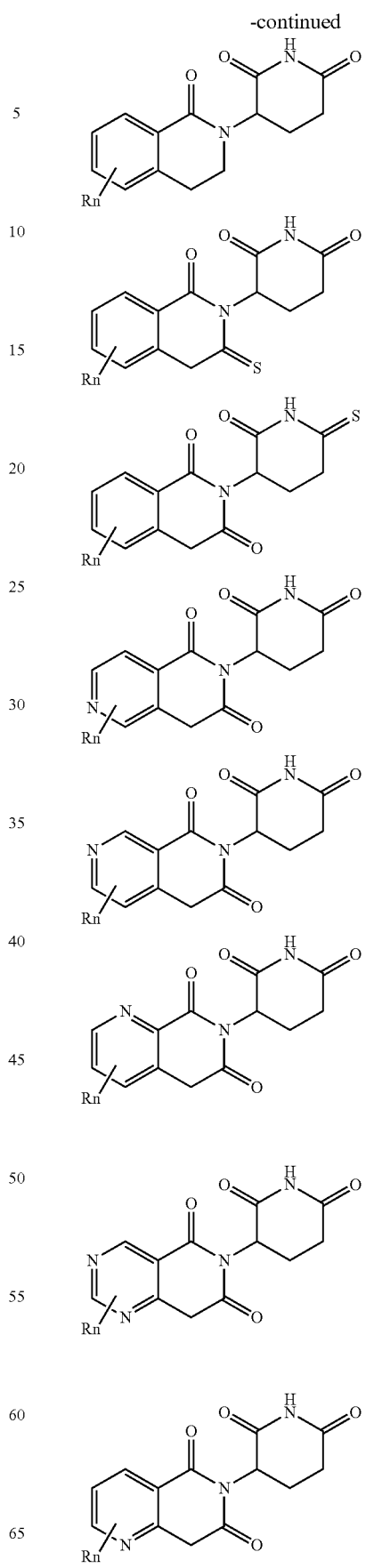

151
-continued
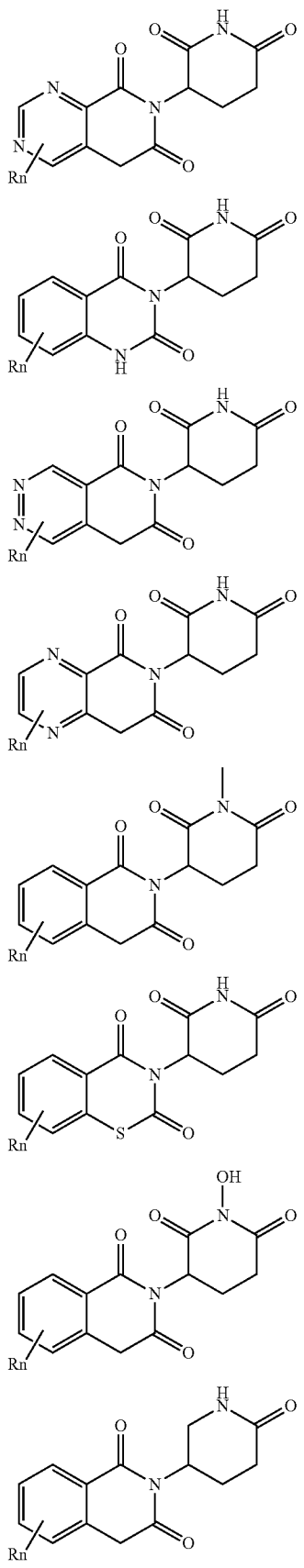
152
-continued
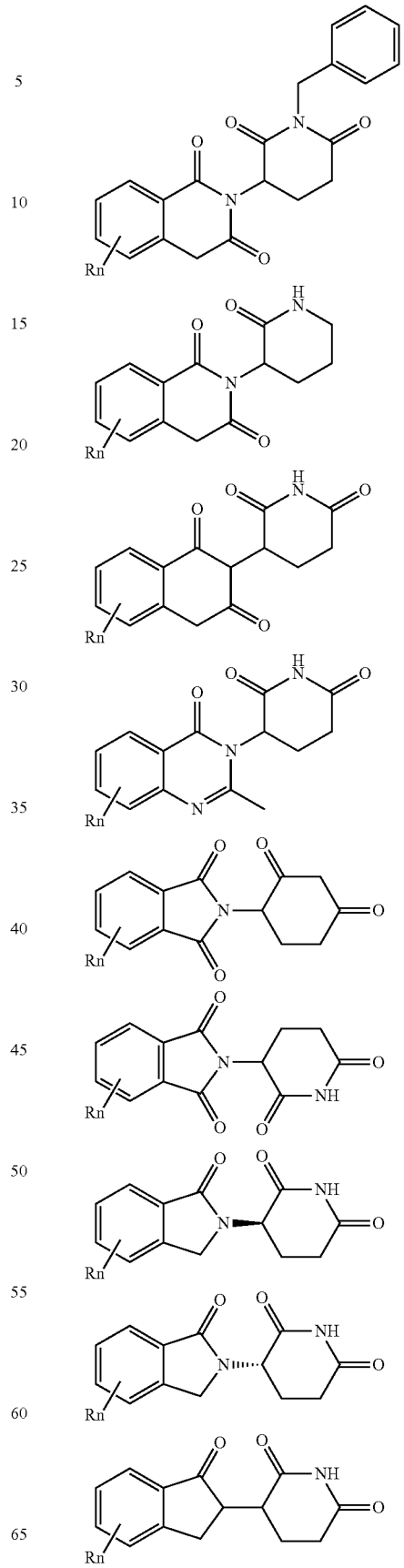

153
-continued
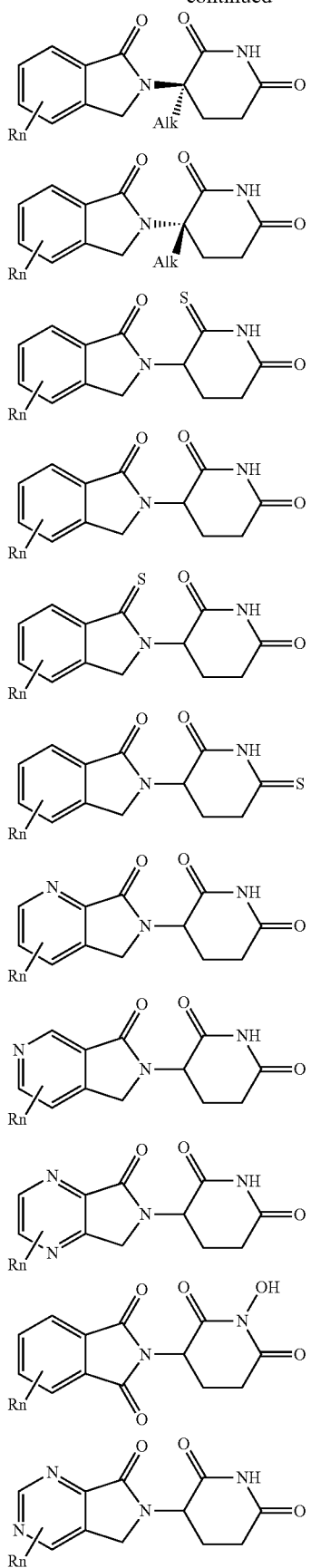
154
-continued
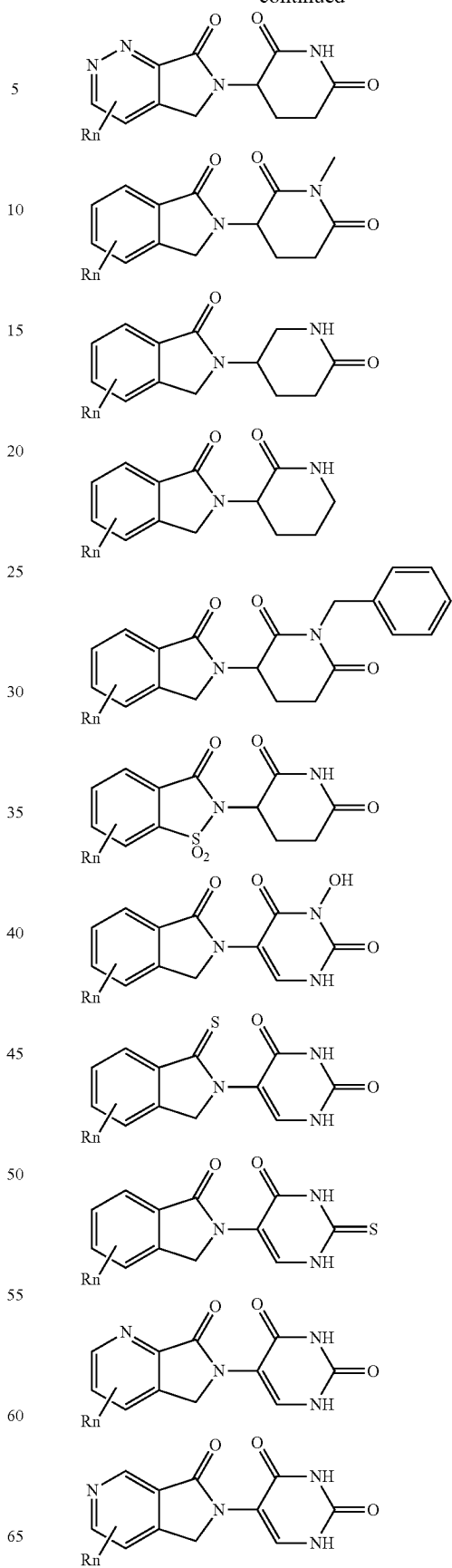

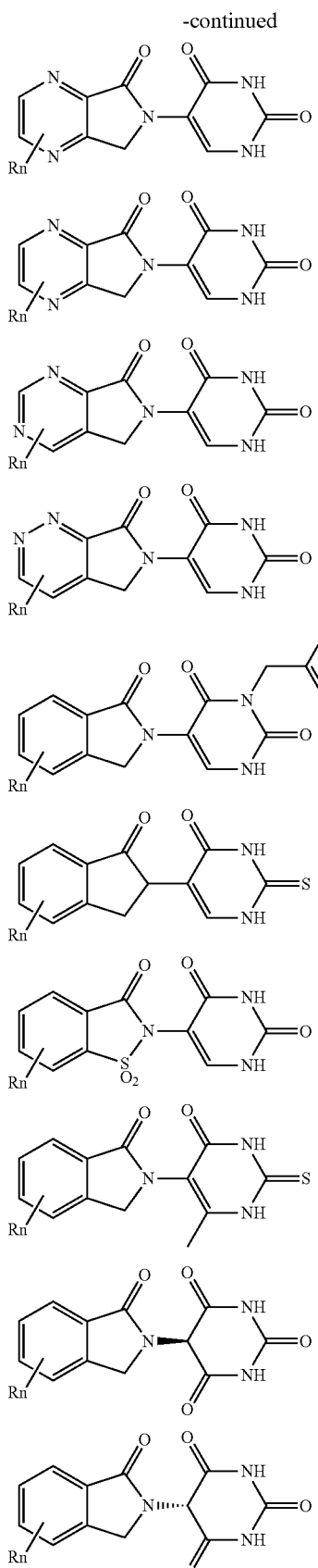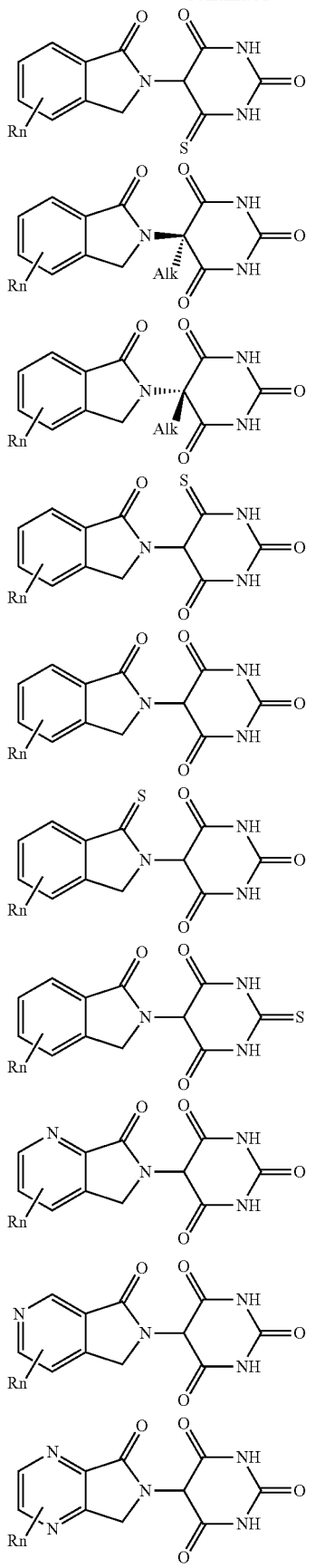

157
-continued
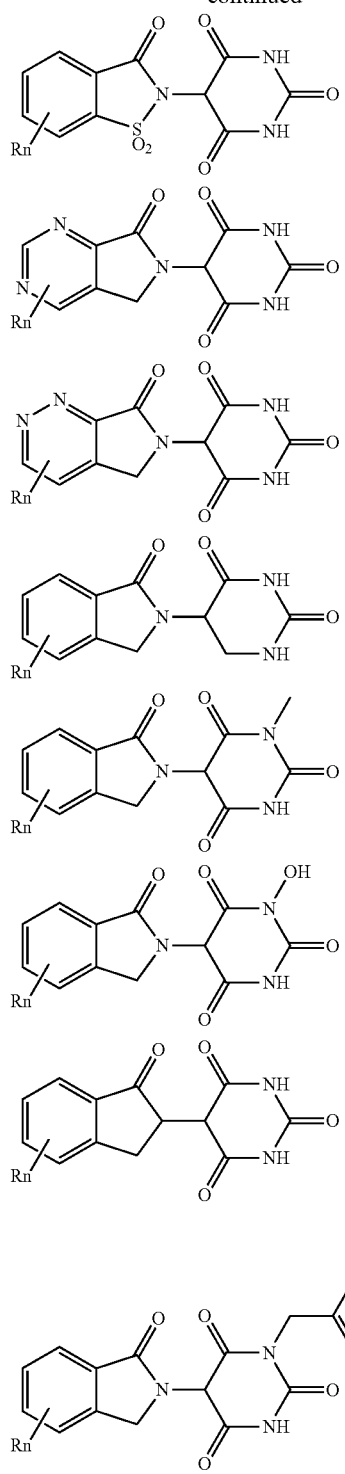
158
-continued
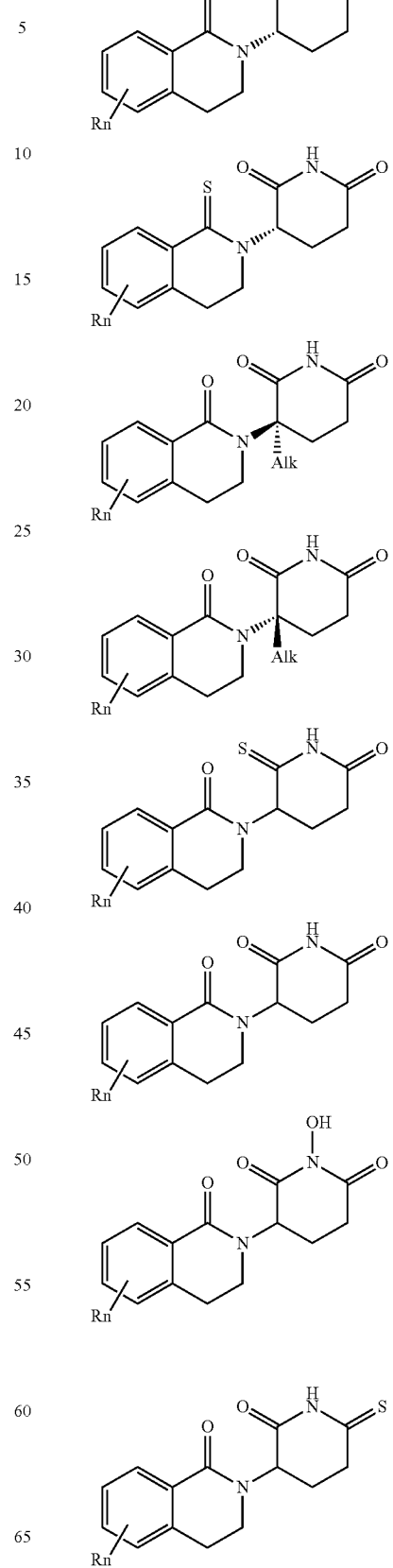

159
-continued
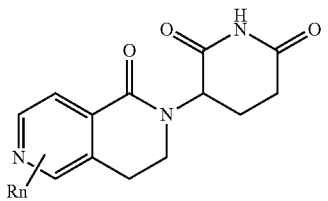
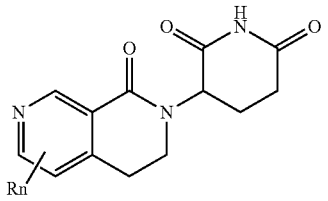
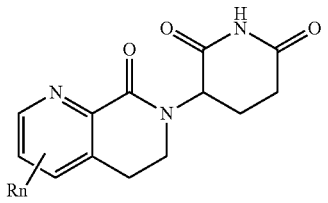
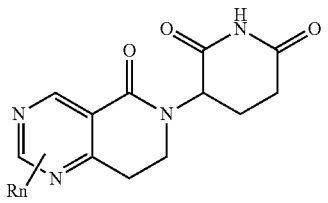
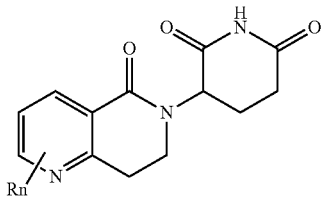
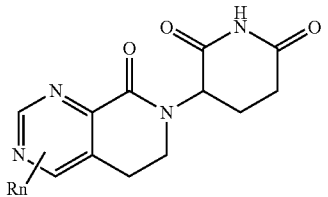
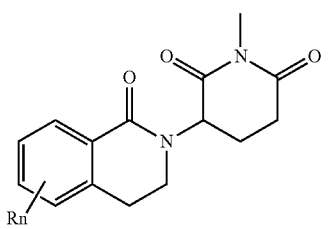
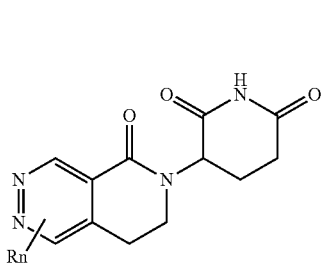
160
-continued
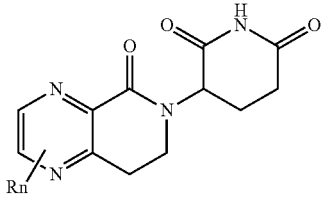
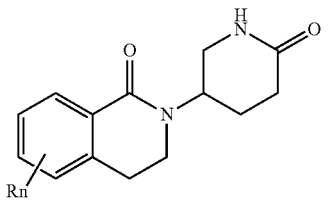
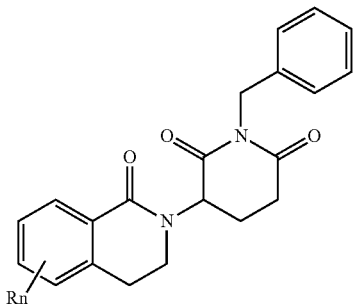
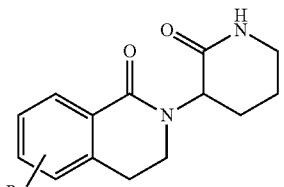
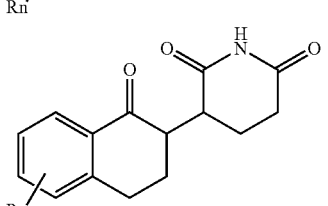
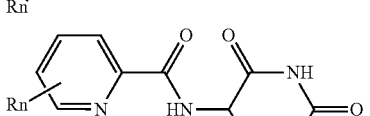
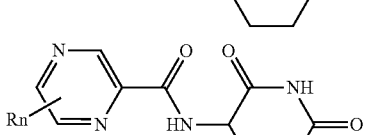
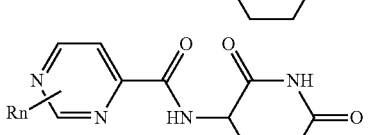
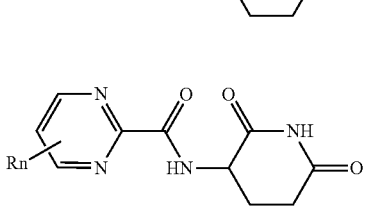

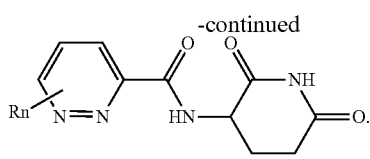
In any of the compounds described herein, the CLM comprises a chemical structure selected from the group:
(h)
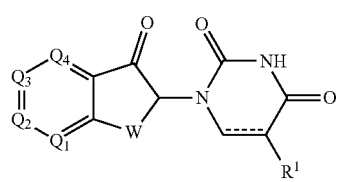
(i)
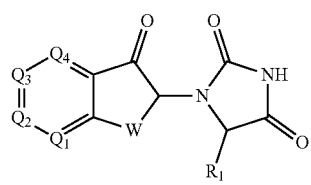
(j)
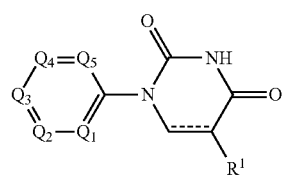
(k)
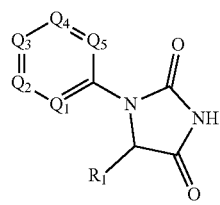
(l)
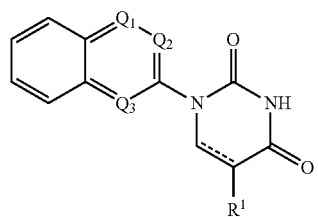
(m)
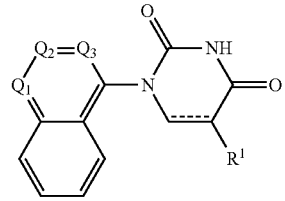
(n)
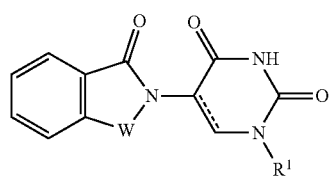
(o)
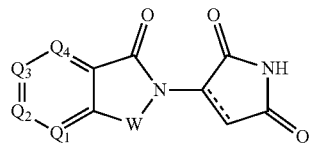
(p)
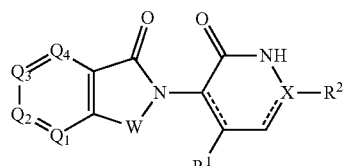
(q)
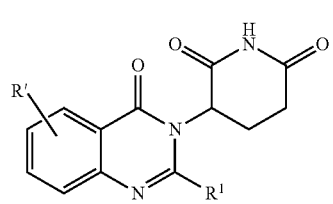
(r)
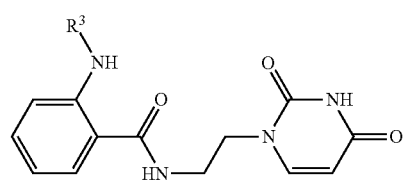
(s)
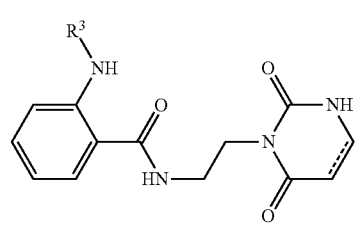
(t)
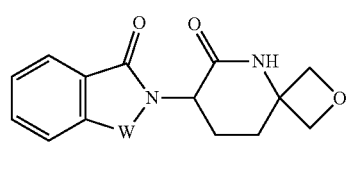
(u)
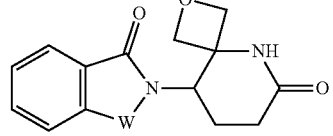
(v)
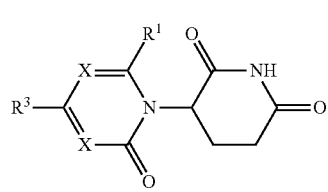
(w)
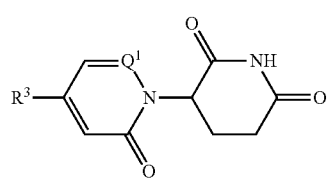

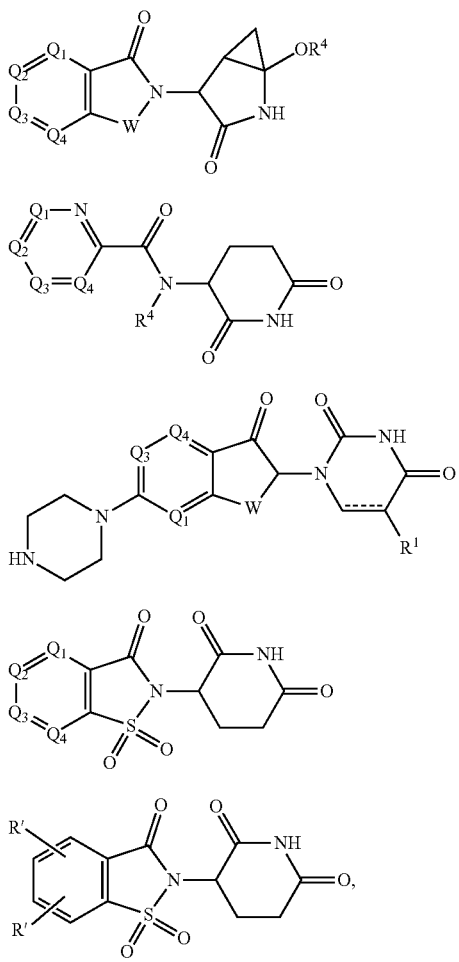

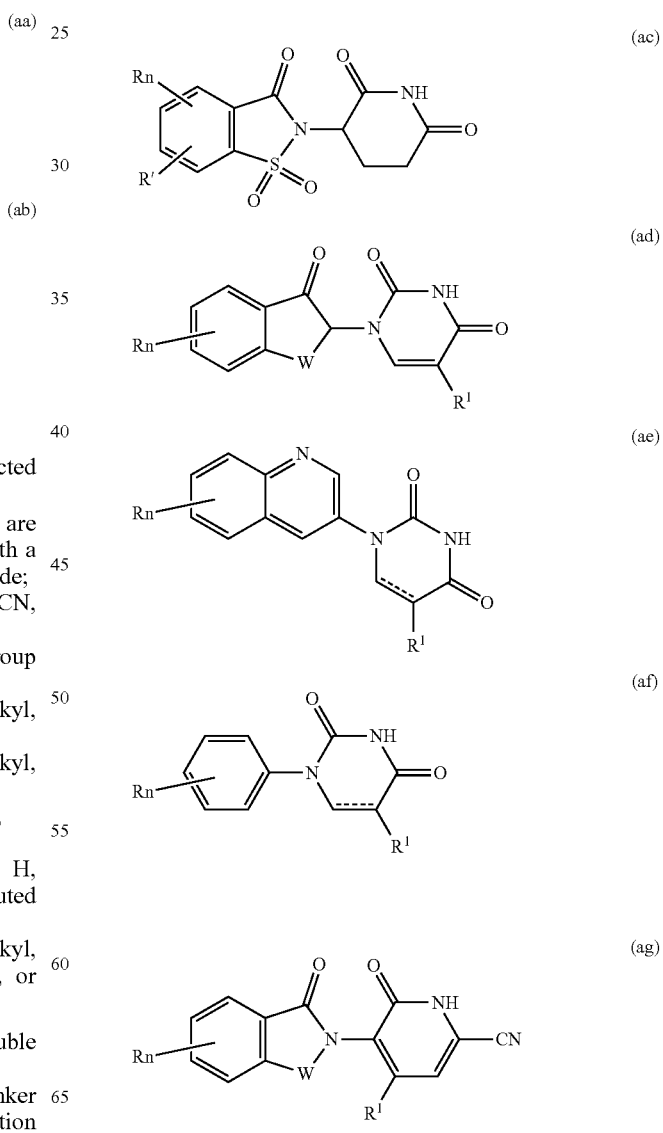

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$) of Formulas (h) through (ab).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$ of Formulas (h) through (ab).

In any of the embodiments described herein, the W, X, $R^1$, $R^2$, $R^3$, $R^4$, R', $Q_1$, $Q_2$, $Q_3$, $Q_4$, and $Q_5$ of Formulas (h) through (ab) can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

wherein:
W of Formulas (h) through (ab) is independently selected from $CH_2$, CHR, C=O, $SO_2$, NH, and N-alkyl;
$Q_1$, $Q_2$, $Q_3$, $Q_4$, $Q_5$ of Formulas (h) through (ab) are independently represent a carbon C substituted with a group independently selected from R', N or N-oxide;
$R^1$ of Formulas (h) through (ab) is selected from H, CN, C1-C3 alkyl;
$R^2$ of Formulas (h) through (ab) is selected from the group H, CN, C1-C3 alkyl, $CHF_2$, $CF_3$, CHO;
$R^3$ of Formulas (h) through (ab) is selected from H, alkyl, substituted alkyl, alkoxy, substituted alkoxy;
$R^4$ of Formulas (h) through (ab) is selected from H, alkyl, substituted alkyl;
$R^5$ of Formulas (h) through (ab) is H or lower alkyl;
X of Formulas (h) through (ab) is C, CH or N;
R' of Formulas (h) through (ab) is selected from H, halogen, alkyl, substituted alkyl, alkoxy, substituted alkoxy;
R of Formulas (h) through (ab) is H, OH, lower alkyl, lower alkoxy, cyano, halogenated lower alkoxy, or halogenated lower alkyl
⫽ of Formulas (h) through (ab) is a single or double bond; and
the CLM is covalently joined to a PTM, a chemical linker group (L), a ULM, CLM (or CLM') or combination thereof.

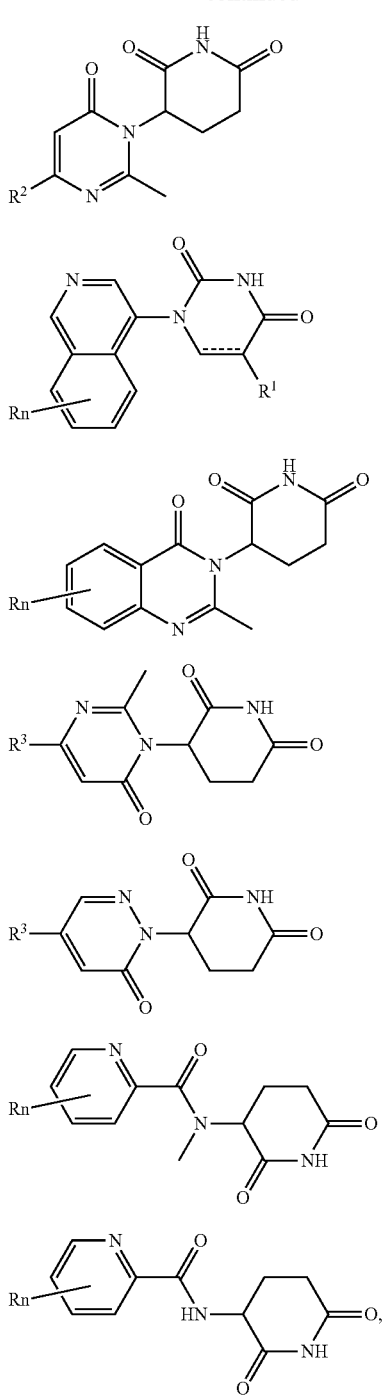

wherein:
W of Formulas (ac) through (an) is independently selected from the group $CH_2$, CHR, C=O, $SO_2$, NH, and N-alkyl;
$R^1$ of Formulas (ac) through (an) is selected from the group H, CN, C1-C3 alkyl;
$R^3$ of Formulas (ac) through (an) is selected from H, alkyl, substituted alkyl, alkoxy, substituted alkoxy;
R of Formulas (ac) through (an) is H;
⫶⫶ is a single or double bond; and
Rn of Formulas (ac) through (an) comprises a functional group or an atom.

In any of the embodiments described herein, the W, $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any aspect or embodiment described herein, $R_n$ of Formulas (ac) through (an) is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

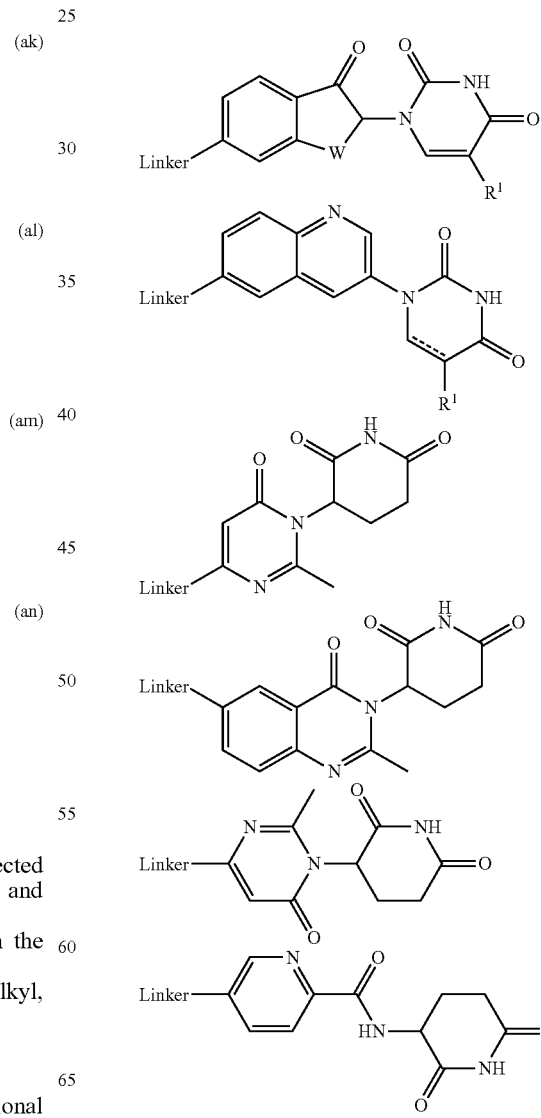

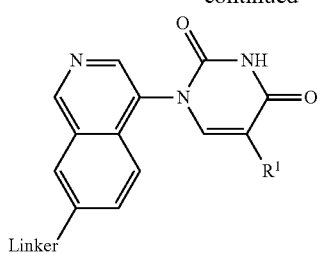
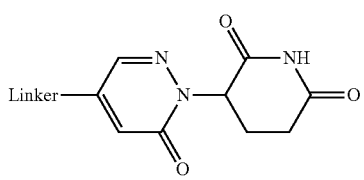
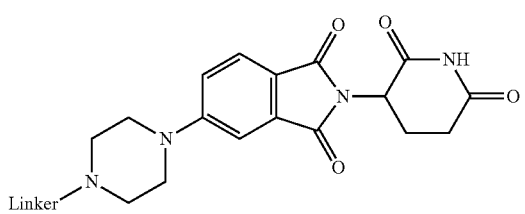
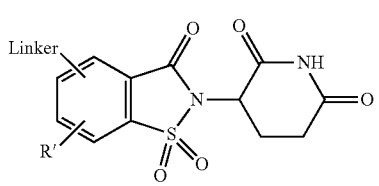
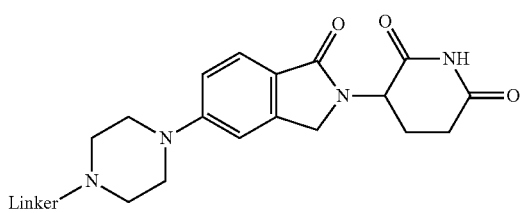
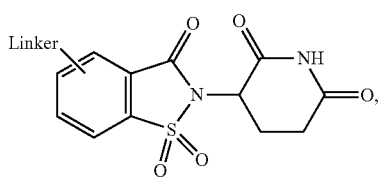
wherein R' is a halogen and R¹ is as described above with regard to Formulas (h) through (ab) or (ac) through (an).
In certain cases, the CLM can be imides that bind to cereblon E3 ligase. These imides and linker attachment point can be but not limited to the following structures:
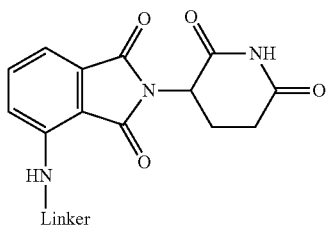
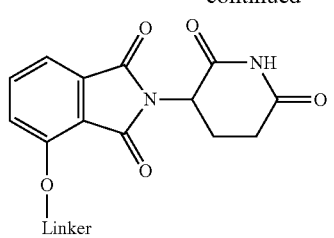
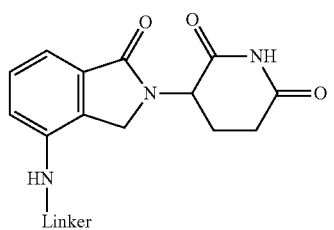
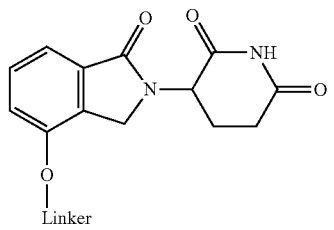
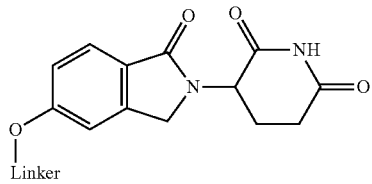
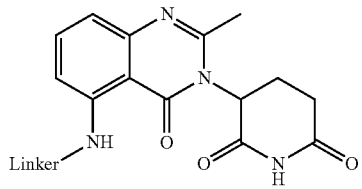
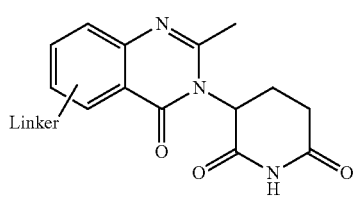
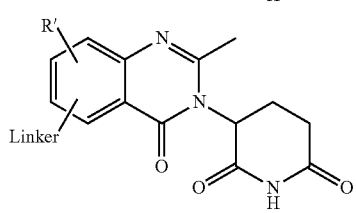
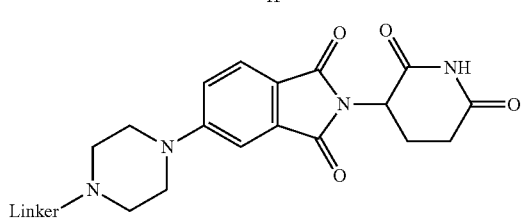

-continued

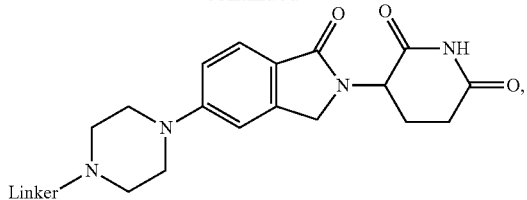

wherein
R' is a halogen.

Exemplary VLMs

In certain embodiments of the compounds as described herein, ULM is VLM and comprises a chemical structure selected from the group ULM-a:

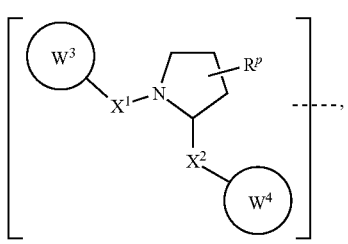

ULM-a wherein:
- where a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;
- $X^1$, $X^2$ of Formula ULM-a are each independently selected from the group of a bond, O, $NR^{Y3}$, $CR^{Y3}R^{Y4}$, C=O, C=S, SO, and $SO_2$;
- $R^{Y3}$, $R^{Y4}$ of Formula ULM-a are each independently selected from the group of H, linear or branched $C_{1-6}$ alkyl, optionally substituted by 1 or more halo, $C_{1-6}$ alkoxyl (optionally substituted by 0-3 $R^P$ groups);
- $R^P$ of Formula ULM-a is 0, 1, 2, or 3 groups independently selected from the group H, halo, —OH, $C_{1-3}$ alkyl, C=O;
- $W^3$ of Formula ULM-a is selected from the group of an optionally substituted -T-N($R^{1a}R^{1b}$)$X^3$, an optionally substituted -T-N($R^{1a}R^{1b}$), an optionally substituted -T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle;
- $X^3$ of Formula ULM-a is C=O, $R^1$, $R^{1a}$, $R^{1b}$;
- each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;
- T of Formula ULM-a is covalently bonded to $X^1$; and
- $W^4$ of Formula ULM-a is an optionally substituted —NR1-T-Aryl, an optionally substituted —NR1-T-Heteroaryl group or an optionally substituted —NR1-T-Heterocycle, where —NR1 is covalently bonded to $X^2$ and R1 is H or CH3, preferably H.

In any of the embodiments described herein, T is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, often 0, 1, 2, or 3, preferably 0 or 1.

In certain embodiments, $W^4$ of Formula ULM-a is

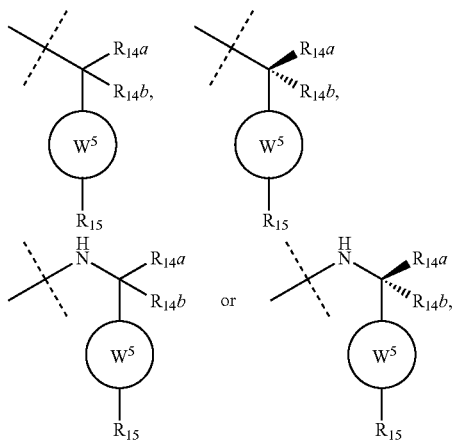

wherein
$R_{14a}$, $R_{14b}$, are each independently selected from the group of H, haloalkyl, or optionally substituted alkyl;

In any of the embodiments, $W^5$ of Formula ULM-a is selected from the group of a phenyl or a 5-10 membered heteroaryl, and $R_{15}$ of Formula ULM-a is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl;

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 0-3 $R^P$ groups in the pyrrolidine moiety. Each $R^P$ is independently H, halo, —OH, C1-3alkyl, C=O.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

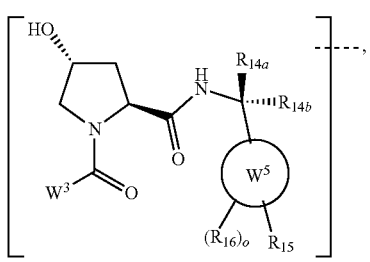

wherein:
W³ of Formula ULM-b is selected from the group of an optionally substituted aryl, optionally substituted heteroaryl, or

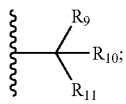

R₉ and R₁₀ of Formula ULM-b are independently hydrogen, optionally substituted alkyl, optionally substituted cycloalkyl, optionally substituted hydroxyalkyl, optionally substituted heteroaryl, or haloalkyl, or R₉, R₁₀, and the carbon atom to which they are attached form an optionally substituted cycloalkyl;

R₁₁ of Formula ULM-b is selected from the group of an optionally substituted heterocyclic, optionally substituted alkoxy, optionally substituted heteroaryl, optionally substituted aryl,

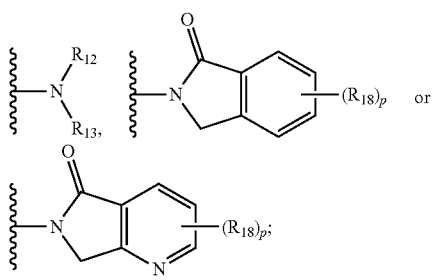

R₁₂ of Formula ULM-b is selected from the group of H or optionally substituted alkyl;

R₁₃ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

R₁₄ₐ, R₁₄ᵦ of Formula ULM-b, are each independently selected from the group of H, haloalkyl, or optionally substituted alkyl;

W⁵ of Formula ULM-b is selected from the group of a phenyl or a 5-10 membered heteroaryl, R₁₅ of Formula ULM-b is selected from the group of H, halogen, CN, OH, NO₂, N R₁₄ₐR₁₄ᵦ, OR₁₄ₐ, CONR₁₄ₐR₁₄ᵦ, NR₁₄ₐCOR₁₄ᵦ, SO₂NR₁₄ₐR₁₄ᵦ, NR₁₄ₐSO₂R₁₄ᵦ, optionally substituted alkyl, optionally substituted haloalkyl, optionally substituted haloalkoxy; aryl, heteroaryl, cycloalkyl, or cycloheteroalkyl (each optionally substituted);

R₁₆ of Formula ULM-b is independently selected from the group of H, halo, optionally substituted alkyl, optionally substituted haloalkyl, hydroxy, or optionally substituted haloalkoxy;

o of Formula ULM-b is 0, 1, 2, 3, or 4;

R₁₈ of Formula ULM-b is independently selected from the group of halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, R₁₅ of Formula ULM-b is

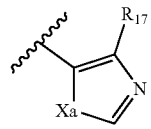

wherein R₁₇ is H, halo, optionally substituted C₃₋₆cycloalkyl, optionally substituted C₁₋₆alkyl, optionally substituted C₁₋₆alkenyl, and C₁₋₆haloalkyl; and Xa is S or O.

In certain embodiments, R₁₇ of Formula ULM-b is selected from the group methyl, ethyl, isopropyl, and cyclopropyl.

In certain additional embodiments, R₁₅ of Formula ULM-b is selected from the group consisting of:

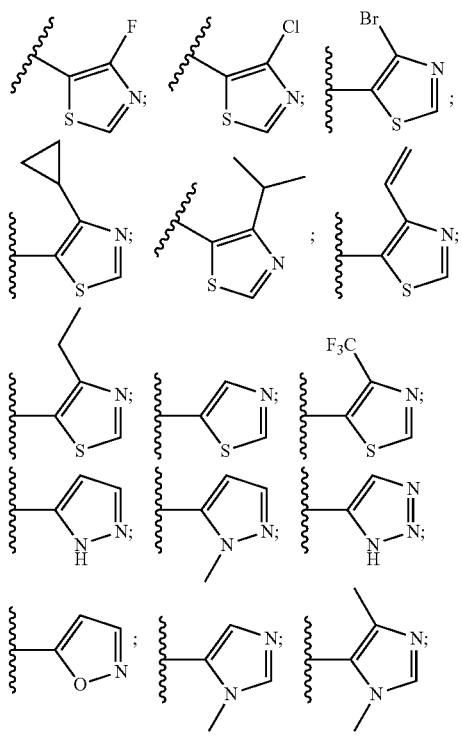

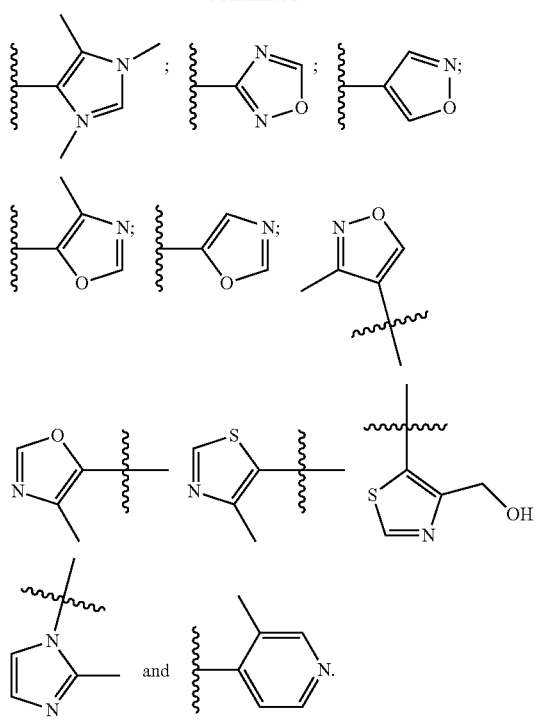
In certain embodiments, $R_{11}$ of Formula ULM-b is selected from the group consisting of:
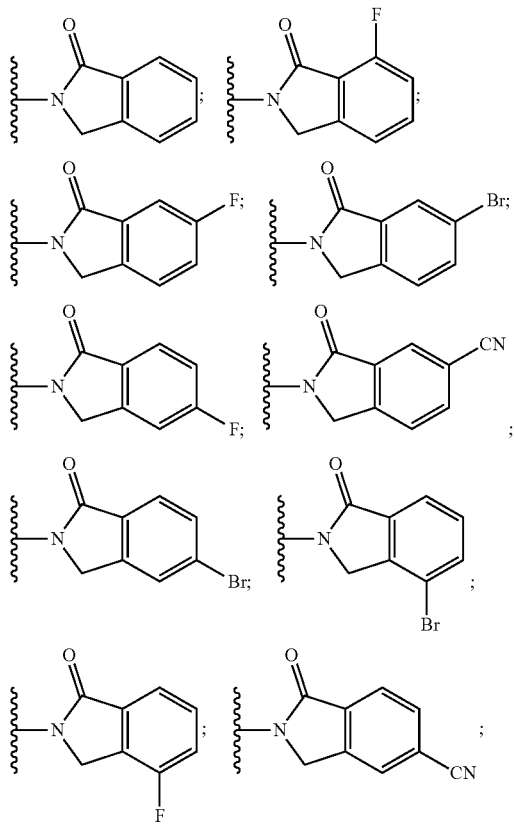
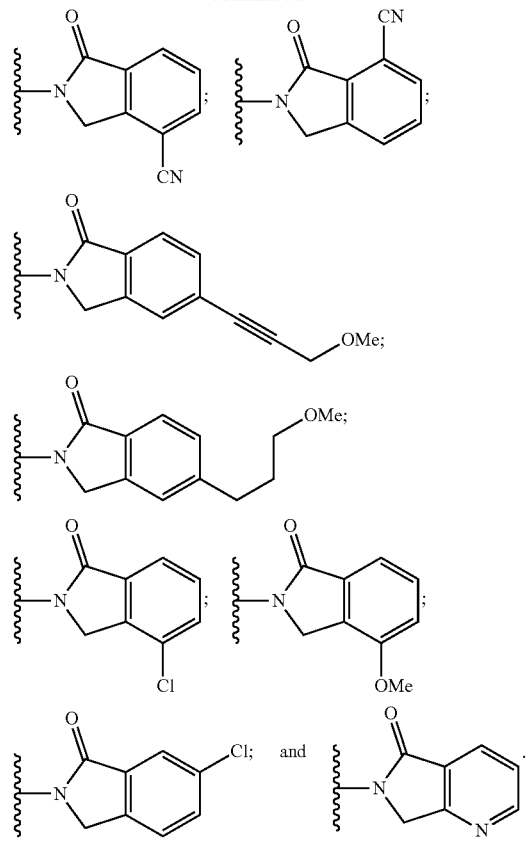
In certain embodiments, ULM has a chemical structure selected from the group of:
ULM-c
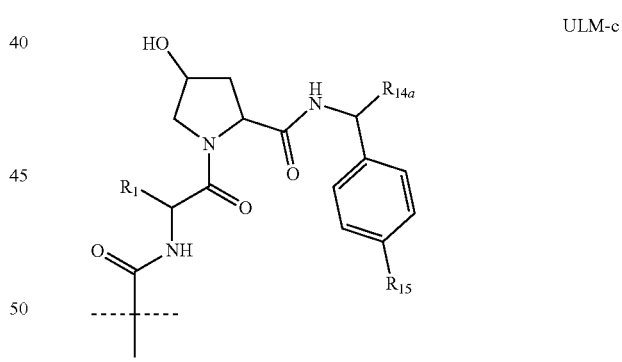
ULM-d
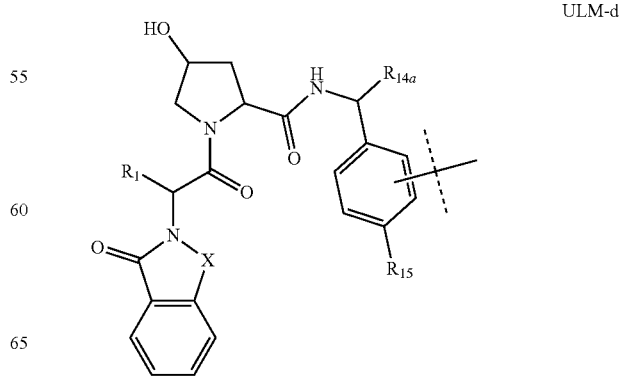

-continued

ULM-e

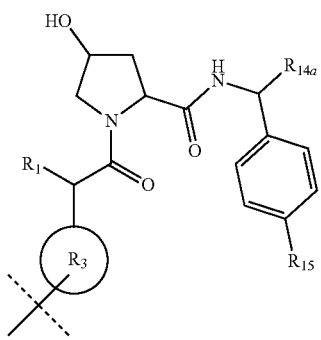

wherein:
R₁ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

R₁₄ₐ of Formulas ULM-c, ULM-d, and ULM-e is H, haloalkyl, optionally substituted alkyl, methyl, fluoromethyl, hydroxymethyl, ethyl, isopropyl, or cyclopropyl;

R₁₅ of Formulas ULM-c, ULM-d, and ULM-e is selected from the group consisting of H, halogen, CN, OH, NO₂, optionally substituted heteroaryl, optionally substituted aryl; optionally substituted alkyl, optionally substituted haloalkyl, optionally substituted haloalkoxy, cycloalkyl, or cycloheteroalkyl;

X of Formulas ULM-c, ULM-d, and ULM-e is C, CH₂, or C=O

R₃ of Formulas ULM-c, ULM-d, and ULM-e is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

ULM-f

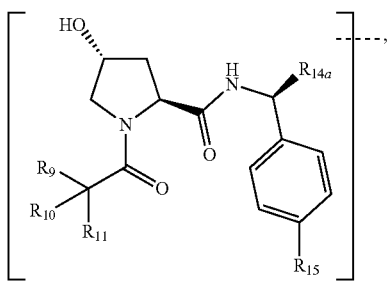

wherein:
R₁₄ₐ of Formula ULM-f is H, haloalkyl, optionally substituted alkyl, methyl, fluoromethyl, hydroxymethyl, ethyl, isopropyl, or cyclopropyl;
R₉ of Formula ULM-f is H;
R₁₀ of Formula ULM-f is H, ethyl, isopropyl, tert-butyl, sec-butyl, cyclopropyl, cyclobutyl, cyclopentyl, or cyclohexyl;

R₁₁ of Formula ULM-f is

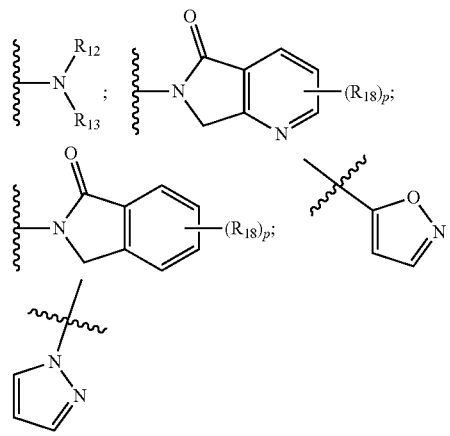

or optionally substituted heteroaryl;
p of Formula ULM-f is 0, 1, 2, 3, or 4;
each R₁₈ of Formula ULM-f is independently halo, optionally substituted alkoxy, cyano, optionally substituted alkyl, haloalkyl, haloalkoxy or a linker;
R₁₂ of Formula ULM-f is H, C=O;
R₁₃ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl,
R₁₅ of Formula ULM-f is selected from the group consisting of H, halogen, Cl, CN, OH, NO₂, optionally substituted heteroaryl, optionally substituted aryl;

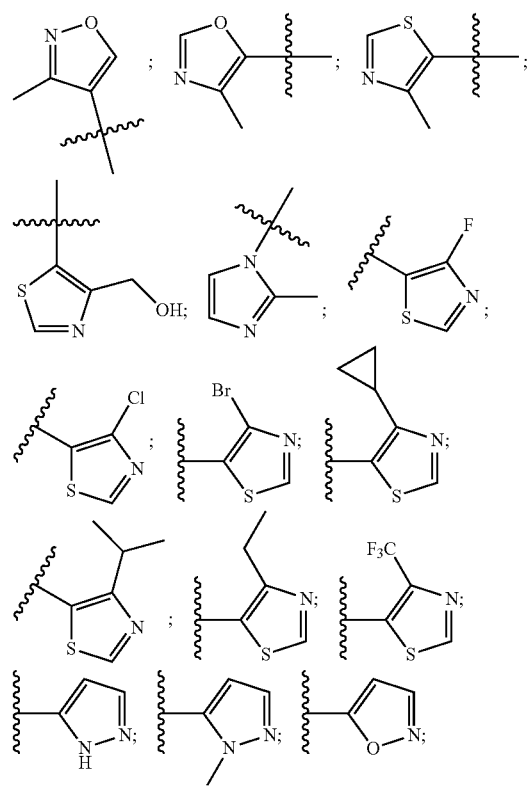

-continued
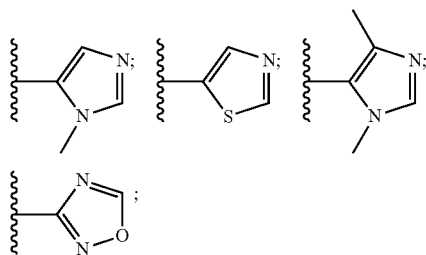
and
the dashed line of Formula ULM-f indicates the site of attachment of at least one PTM, another ULM (ULM') or a chemical linker moiety coupling at least one PTM or a ULM' or both to ULM.
In certain embodiments, the ULM is selected from the following structures:
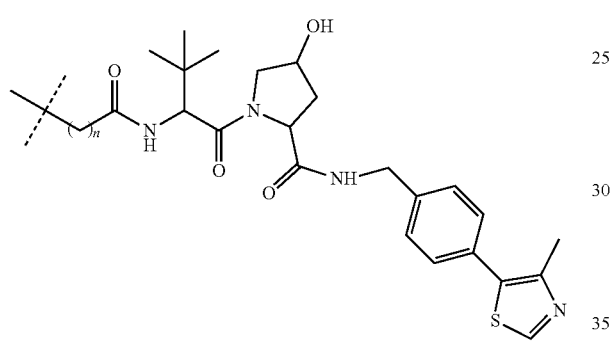
ULM-a2
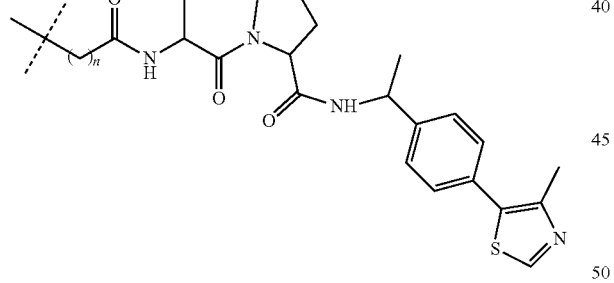
ULM-a3
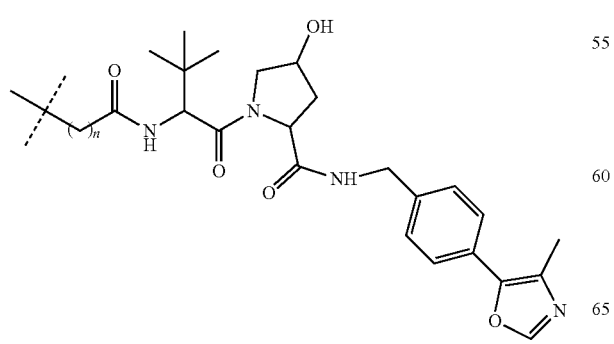
ULM-a4
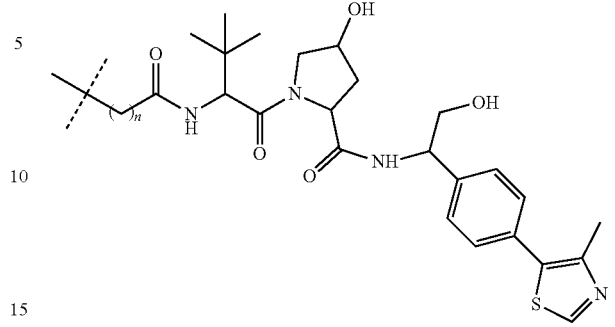
ULM-a5
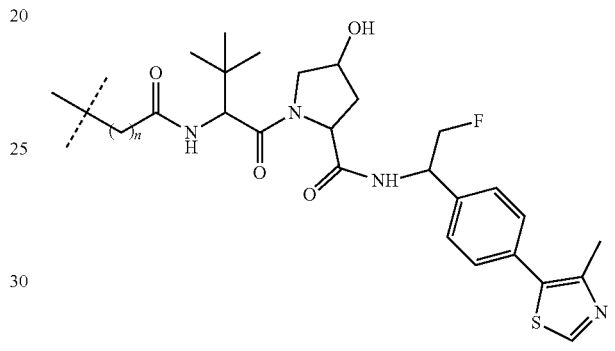
ULM-a6
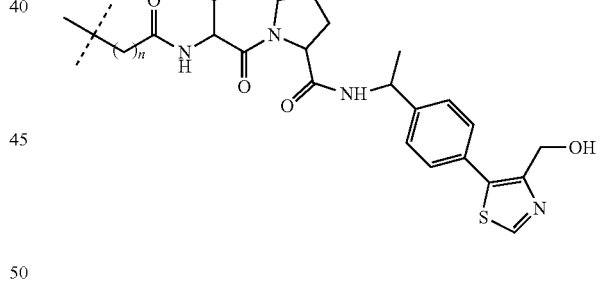
ULM-a7
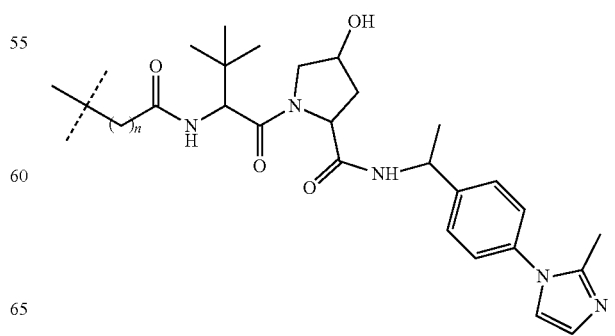

ULM-a8
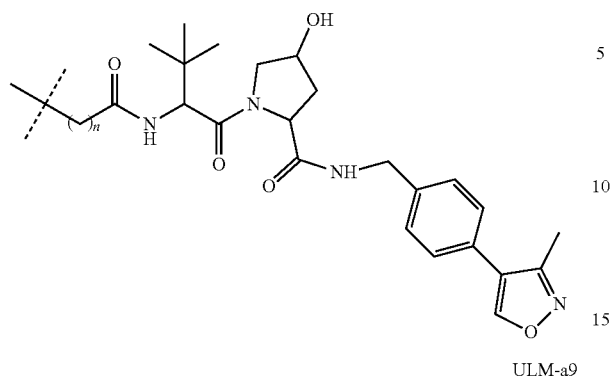
ULM-a9
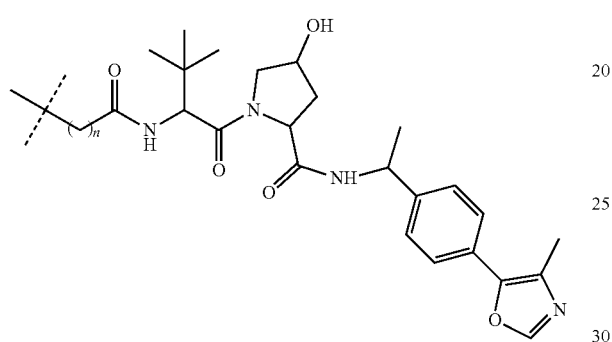
ULM-a10
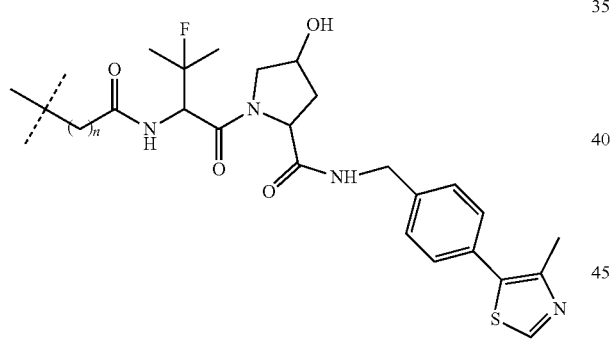
ULM-a11
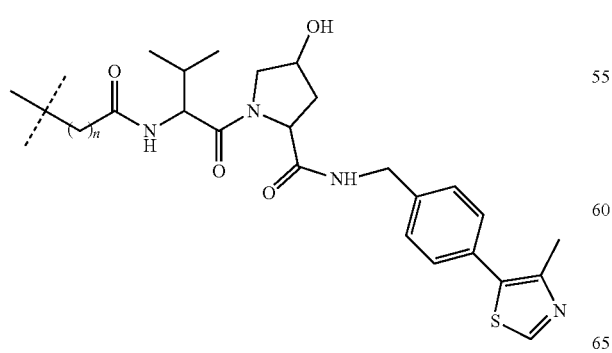
ULM-a12
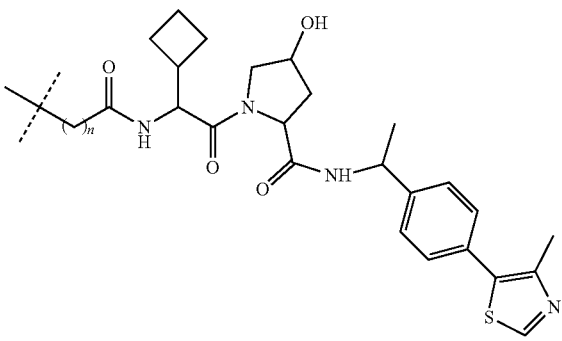
ULM-a13
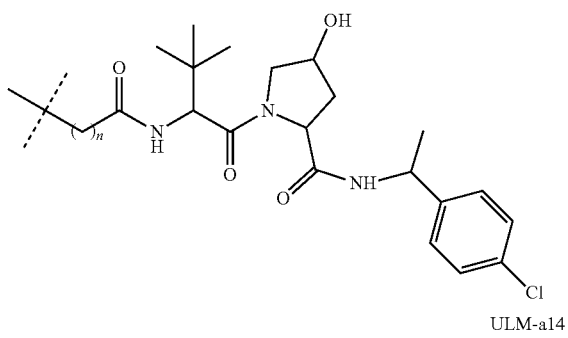
ULM-a14
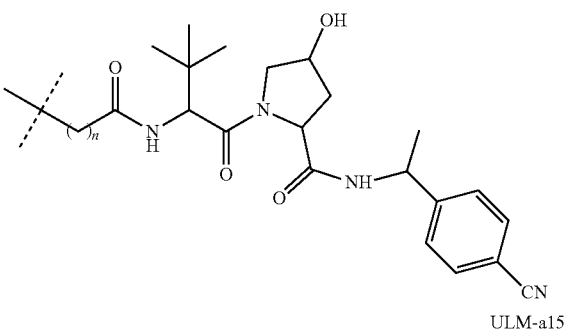
ULM-a15
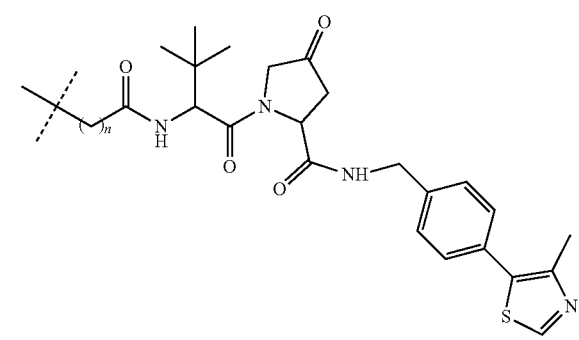
wherein n is 0 or 1.
In certain embodiments, the ULM is selected from the following structures:

ULM-b1
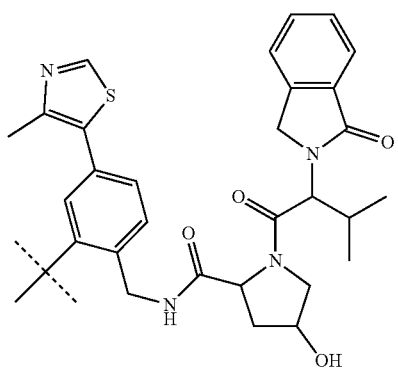
ULM-b2
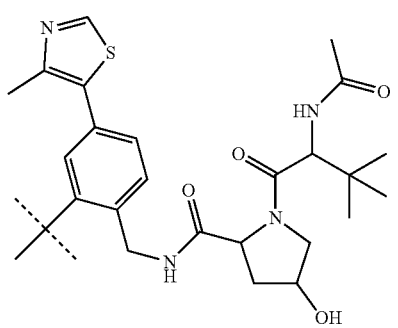
ULM-b3
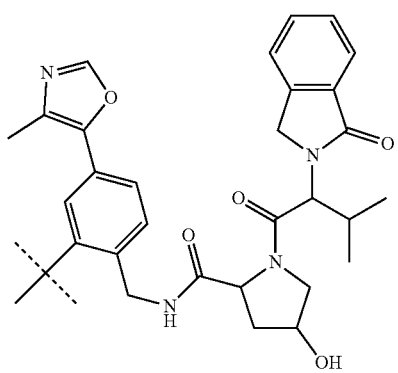
ULM-b4
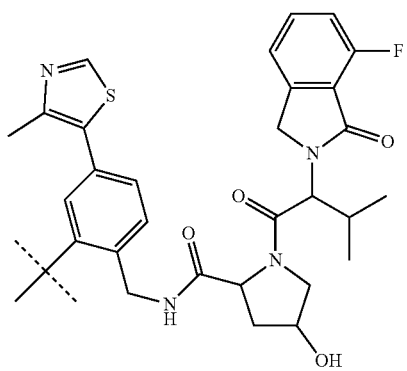
ULM-b5
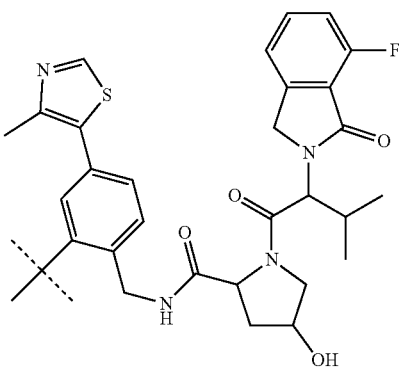
ULM-b6
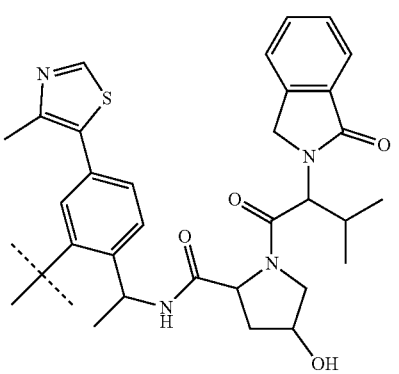
ULM-b7
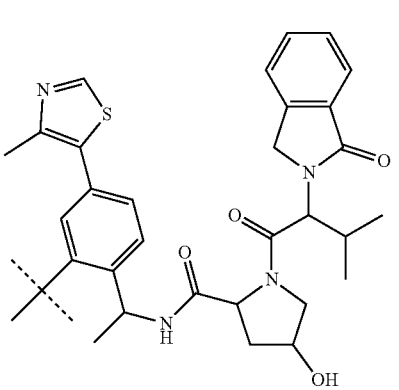
ULM-b8
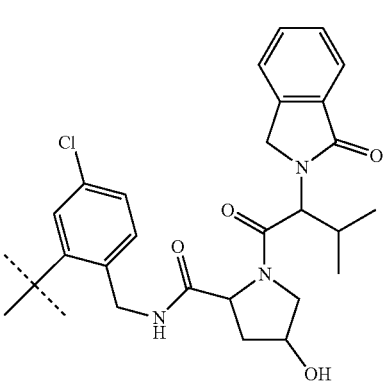

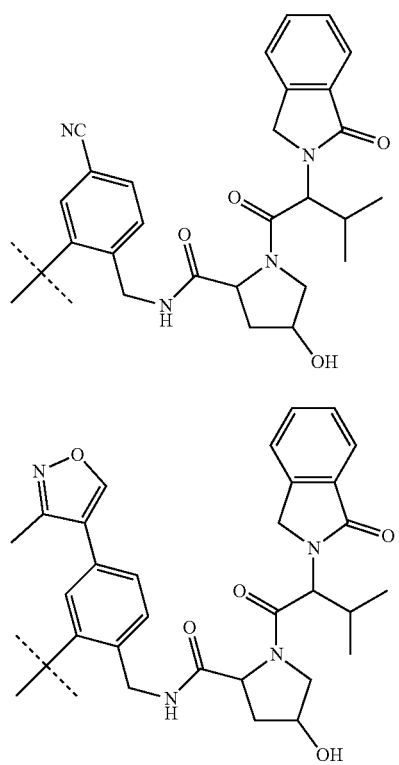
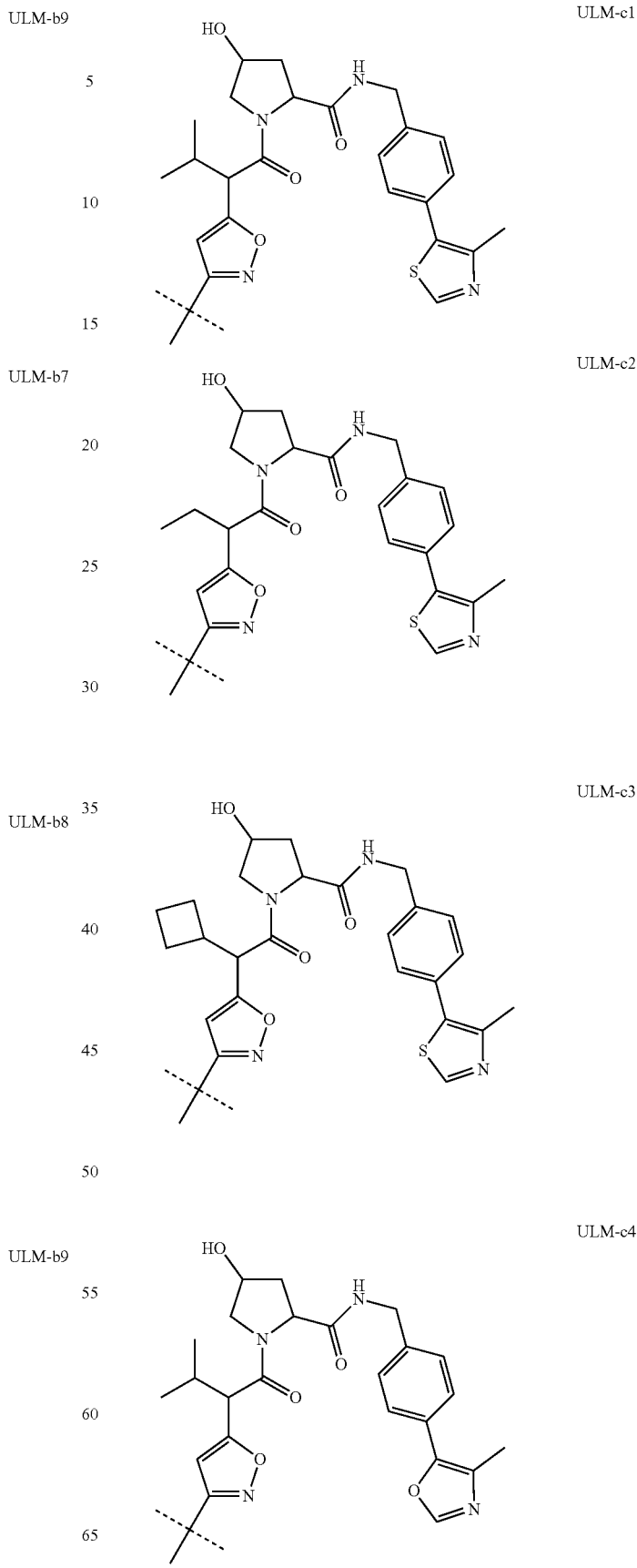

ULM-c5
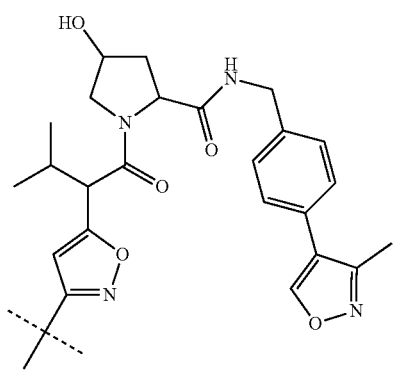
ULM-c6
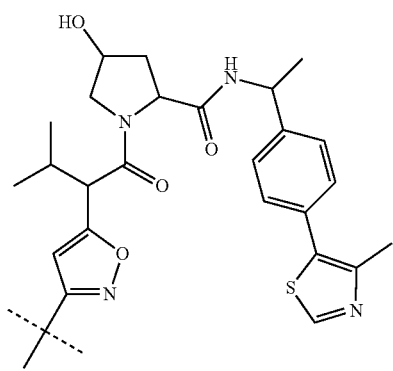
ULM-c7
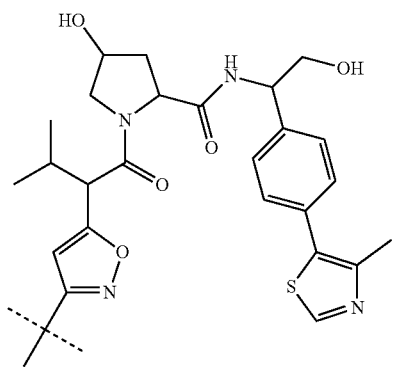
ULM-c8
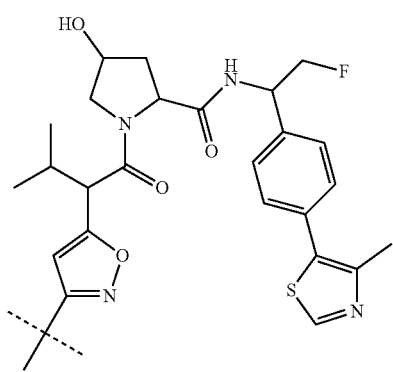
ULM-c9
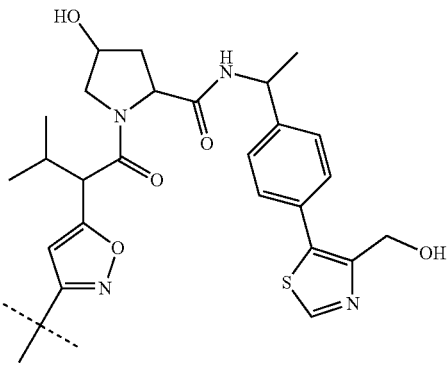
ULM-c10
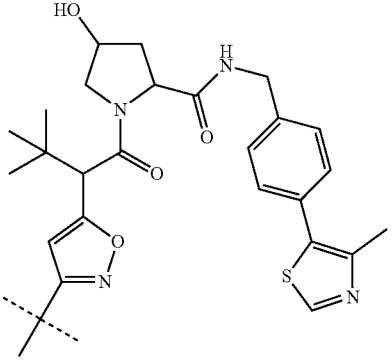
ULM-c11
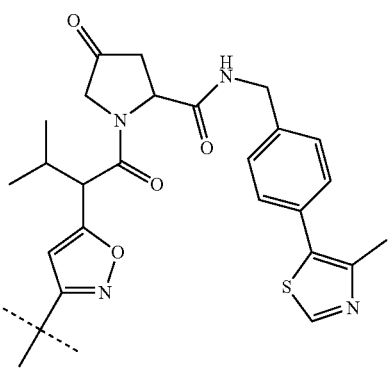
ULM-c12
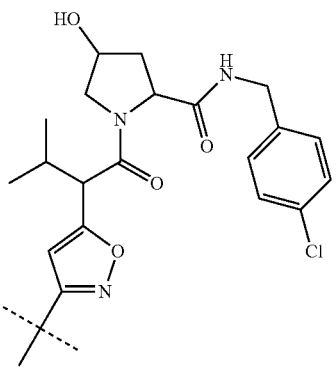

ULM-c13
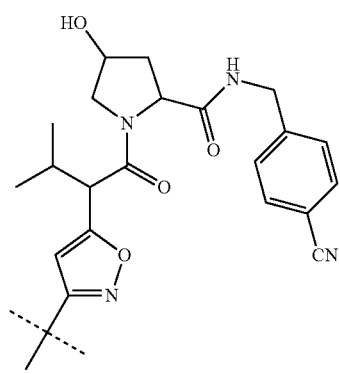
ULM-c14
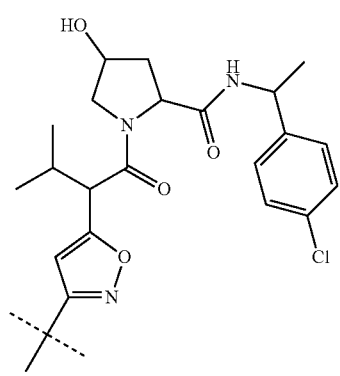
ULM-c15
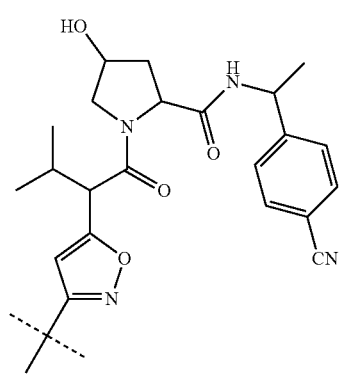
ULM-d1
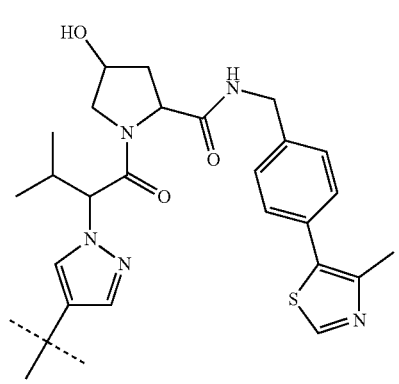
ULM-d2
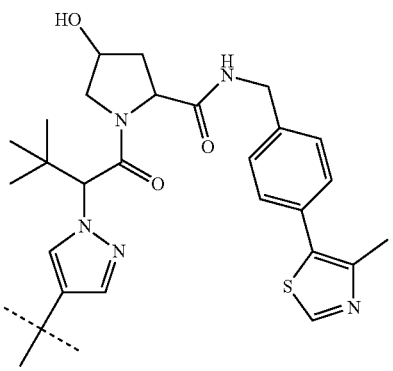
ULM-d3
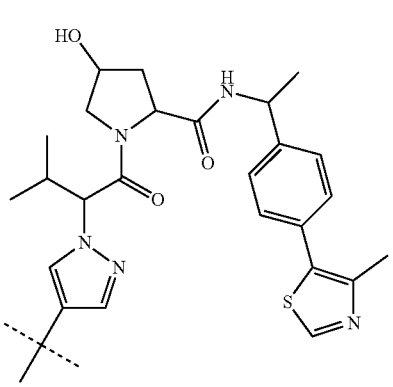
ULM-d4
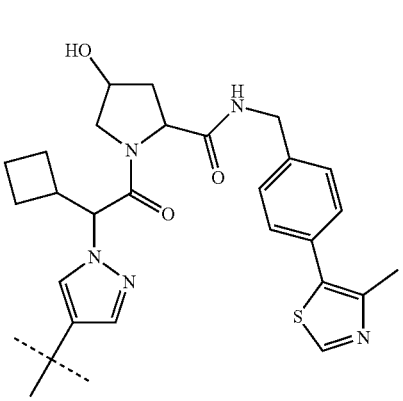
ULM-d5
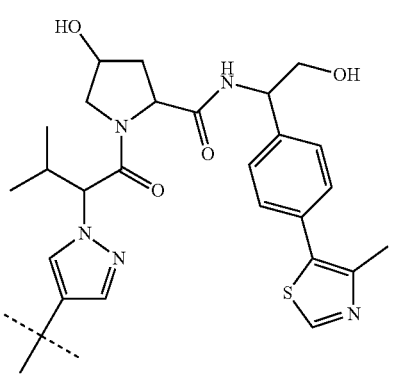

-continued

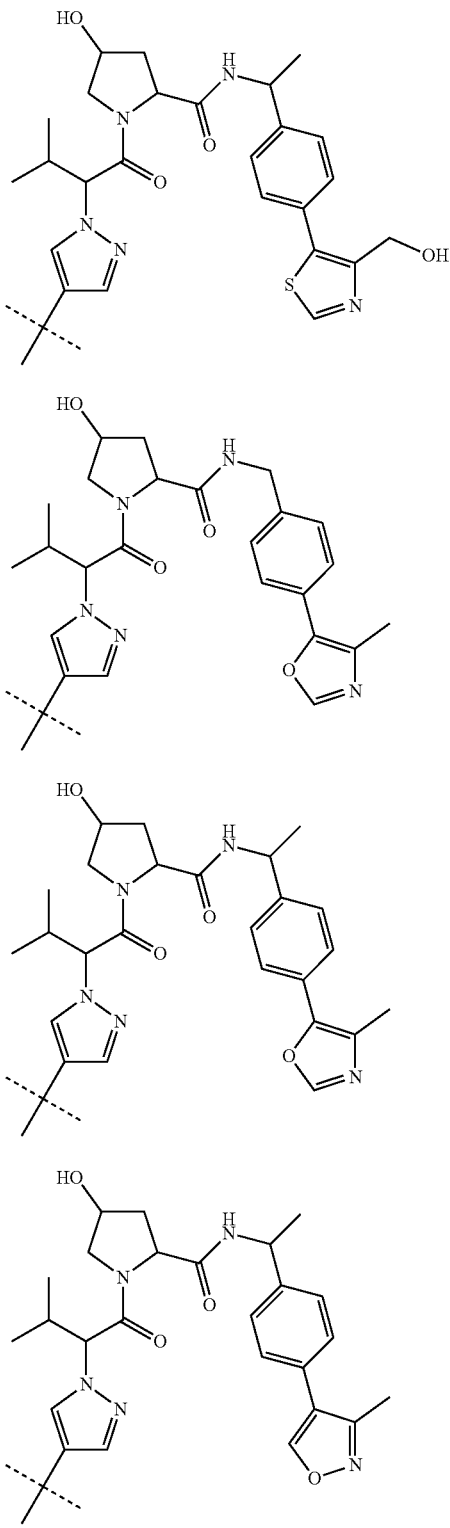

ULM-d6

ULM-d7

ULM-d8

ULM-d9 wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

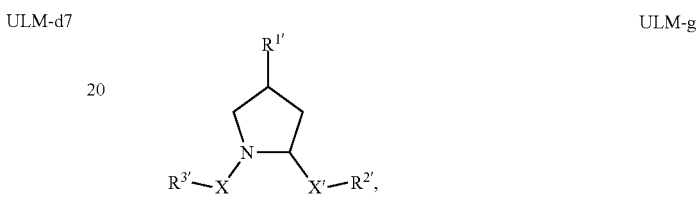

ULM-g wherein:
$R^{1'}$ of ULM-g is an optionally substituted $C_1$-$C_6$ alkyl group, an optionally substituted —$(CH_2)_n$OH, an optionally substituted —$(CH_2)_n$SH, an optionally substituted $(CH_2)_n$—O—$(C_1$-$C_6)$alkyl group, an optionally substituted $(CH_2)_n$—WCOCW—$(C_0$-$C_6)$alkyl group containing an epoxide moiety WCOCW where each W is independently H or a $C_1$-$C_3$ alkyl group, an optionally substituted —$(CH_2)_n$COOH, an optionally substituted —$(CH_2)_n$C(O)—$(C_1$-$C_6$alkyl), an optionally substituted —$(CH_2)_n$NHC(O)—$R_1$, an optionally substituted —$(CH_2)_n$C(O)—$NR_1R_2$, an optionally substituted —$(CH_2)_n$OC(O)—$NR_1R_2$, —$(CH_2O)_n$H, an optionally substituted —$(CH_2)_n$OC(O)—$(C_1$-$C_6$ alkyl), an optionally substituted —$(CH_2)_n$C(O)—O—$(C_1$-$C_6$ alkyl), an optionally substituted —$(CH_2O)_n$COOH, an optionally substituted —$(OCH_2)_n$O—$(C_1$-$C_6$ alkyl), an optionally substituted —$(CH_2O)_n$C(O)—$(C_1$-$C_6$ alkyl), an optionally substituted —$(OCH_2)_n$NHC(O)—$R_1$, an optionally substituted —$(CH_2O)_n$C(O)—$NR_1R_2$, —$(CH_2CH_2O)_n$H, an optionally substituted —$(CH_2CH_2O)_n$COOH, an optionally substituted —$(OCH_2CH_2)_n$O—$(C_1$-$C_6$alkyl), an optionally substituted —$(CH_2CH_2O)_n$C(O)—$(C_1$-$C_6$ alkyl), an optionally substituted —$(OCH_2CH_2)_n$NHC(O)—$R_1$, an optionally substituted —$(CH_2CH_2O)_n$C(O)—$NR_1R_2$, an optionally substituted —$SO_2R_S$, an optionally substituted $S(O)R_S$, $NO_2$, CN or halogen (F, Cl, Br, I, preferably F or Cl);
$R_1$ and $R_2$ of ULM-g are each independently H or a $C_1$-$C_6$ alkyl group which may be optionally substituted with one or two hydroxyl groups or up to three halogen groups (preferably fluorine);
$R_S$ of ULM-g is a $C_1$-$C_6$ alkyl group, an optionally substituted aryl, heteroaryl or heterocycle group or a —$(CH_2)_m NR_1R_2$ group;
X and X' of ULM-g are each independently C=O, C=S, —S(O), $S(O)_2$, (preferably X and X' are both C=O);
$R^{2'}$ of ULM-g is an optionally substituted —$(CH_2)_n$—$(C=O)_u(NR_1)_v(SO_2)_w$alkyl group, an optionally substituted —$(CH_2)_n$—$(C=O)_u(NR_1)_v$ $(SO_2)_w NR_{1N}R_{2N}$ group, an optionally substituted —$(CH_2)_n$—$(C=O)_u$ (NR₁)ᵥ(SO₂)ᵥᵥ-Aryl, an optionally substituted —(CH₂)ₙ—(C═O)ᵤ(NR₁)ᵥ(SO₂)ᵥᵥ-Heteroaryl, an optionally substituted —(CH₂)ₙ—(C═O)ᵥNR₁(SO₂)ᵥᵥ-Heterocycle, an optionally substituted —NR¹—(CH₂)ₙ—C(O)ᵤ(NR₁)ᵥ(SO₂)ᵥᵥ-alkyl, an optionally substituted —NR¹—(CH₂)ₙ—C(O)ᵤ(NR₁)ᵥ(SO₂)ᵥᵥ—NR₁ₙR₂ₙ, an optionally substituted —NR¹—(CH₂)ₙ—C(O)ᵤ(NR₁)ᵥ(SO₂)ᵥᵥ—NR₁C(O)R₁ₙ, an optionally substituted —NR¹—(CH₂)ₙ—(C═O)ᵤ(NR₁)ᵥ(SO₂)ᵥᵥ-Aryl, an optionally substituted —NR¹—(CH₂)ₙ—(C═O)ᵤ(NR₁)ᵥ(SO₂)ᵥᵥ-Heteroaryl or an optionally substituted —NR¹—(CH₂)ₙ—(C═O)ᵥNR₁(SO₂)ᵥᵥ-Heterocycle, an optionally substituted —X^{R2'}-alkyl group; an optionally substituted —X^{R2'}— Aryl group; an optionally substituted —X^{R2'}— Heteroaryl group; an optionally substituted —X^{R2'}— Heterocycle group; an optionally substituted;

R³' of ULM-g is an optionally substituted alkyl, an optionally substituted —(CH₂)ₙ—(O)ᵤ(NR₁)ᵥ(SO₂)ᵥᵥ-alkyl, an optionally substituted —(CH₂)ₙ—C(O)ᵤ(NR₁)ᵥ(SO₂)ᵥᵥ—NR₁ₙR₂ₙ, an optionally substituted —(CH₂)ₙ—C(O)ᵤ(NR₁)ᵥ(SO₂)ᵥᵥ—NR₁C(O)R₁ₙ, an optionally substituted —(CH₂)ₙ—C(O)ᵤ(NR₁)ᵥ(SO₂)ᵥᵥ—C(O)NR₁R₂, an optionally substituted —(CH₂)ₙ—C(O)ᵤ(NR₁)ᵥ(SO₂)ᵥᵥ-Aryl, an optionally substituted —(CH₂)ₙ—C(O)ᵤ(NR₁)(SO₂)ᵥᵥ-Heteroaryl, an optionally substituted —(CH₂)ₙ—C(O)ᵤ(NR₁)(SO₂)ᵥᵥ-Heterocycle, an optionally substituted —NR¹—(CH₂)ₙ—C(O)ᵤ(NR₁)ᵥ(SO₂)ᵥᵥ-alkyl, an optionally substituted —NR¹—(CH₂)ₙ—C(O)ᵤ(NR₁)ᵥ(SO₂)ᵥᵥ—NR₁ₙR₂ₙ, an optionally substituted —NR¹—(CH₂)ₙ—C(O)ᵤ(NR₁)ᵥ(SO₂)ᵥᵥ—NR₁C(O)R₁ₙ, an optionally substituted —NR¹—(CH₂)ₙ—C(O)ᵤ(NR₁)ᵥ(SO₂)ᵥᵥ-Aryl, an optionally substituted —NR¹—(CH₂)ₙ—C(O)ᵤ(Nᵣ)(SO₂)ᵥᵥ-Heteroaryl, an optionally substituted —NR¹—(CH₂)ₙ—C(O)ᵤ(NR₁)ᵥ(SO₂)ᵥᵥ-Heterocycle, an optionally substituted —O—(CH₂)n-(C═O)ᵤ(NR₁)ᵥ(SO₂)ᵥᵥ-alkyl, an optionally substituted —O—(CH₂)n-(C═O)ᵤ(NR)ᵥ(SO₂)ᵥᵥ—NR₁ₙR₂ₙ, an optionally substituted —O—(CH₂)n-(C═O)ᵤ(NR₁)ᵥ(SO₂)ᵥᵥ—NR₁C(O)R₁ₙ, an optionally substituted —O—(CH₂)n-(C═O)ᵤ(NR₁)ᵥ(SO₂)ᵥᵥ-Aryl, an optionally substituted —O—(CH₂)ₙ—(C═O)(NR₁)(SO²)ᵥᵥ-Heteroaryl or an optionally substituted —O—(CH₂)ₙ—(C═O)ᵤ(NR₁)ᵥ(SO₂)ᵥᵥ-Heterocycle; —(CH₂)ₙ—(V)ₙ'—(CH₂)ₙ—(V)ₙ'-alkyl group, an optionally substituted —(CH₂)ₙ—(V)ₙ'—(CH₂)ₙ—(V)ₙ'-Aryl group, an optionally substituted —(CH₂)ₙ—(V)ₙ'—(CH₂)ₙ—(V)ₙ'-Heteroaryl group, an optionally substituted —(CH₂)ₙ—(V)ₙ'—(CH₂)ₙ—(V)ₙ'-Heterocycle group, an optionally substituted —(CH₂)ₙ—N(R₁')(C═O)ₘ'—(V)ₙ'-alkyl group, an optionally substituted —(CH₂)ₙ—N(R₁')(C═O)ₘ'—(V)ₙ'-Aryl group, an optionally substituted —(CH₂)ₙ—N(R₁')(C═O)ₘ'—(V)ₙ'-Heteroaryl group, an optionally substituted —(CH₂)ₙ—N(R₁')(C═O)ₘ'—(V)ₙ'-Heterocycle group, an optionally substituted —X^{R3'}— alkyl group; an optionally substituted —X^{R3'}— Aryl group; an optionally substituted —X^{R3'}-Heteroaryl group; an optionally substituted —X^{R3'}-Heterocycle group; an optionally substituted;

$R_{1N}$ and $R_{2N}$ of ULM-g are each independently H, $C_1$-$C_6$ alkyl which is optionally substituted with one or two hydroxyl groups and up to three halogen groups or an optionally substituted —(CH₂)ₙ-Aryl, —(CH₂)ₙ-Heteroaryl or —(CH₂)ₙ-Heterocycle group;

V of ULM-g is O, S or NR₁;

$R_1$ of ULM-g is the same as above;
$R^1$ and $R_1$, of ULM-g are each independently H or a $C_1$-$C_3$ alkyl group;
$X^{R2'}$ and $X^{R3'}$ of ULM-g are each independently an optionally substituted —CH₂)ₙ—, —CH₂)ₙ—CH(Xᵥ)═CH(Xᵥ)— (cis or trans), —CH₂)ₙ—CH═CH—, —(CH₂CH₂O)ₙ— or a $C_3$-$C_6$ cycloalkyl group, where $X_v$ is H, a halo or a $C_1$-$C_3$ alkyl group which is optionally substituted; each m of ULM-g is independently 0, 1, 2, 3, 4, 5, 6;
each m' of ULM-g is independently 0 or 1;
each n of ULM-g is independently 0, 1, 2, 3, 4, 5, 6;
each n' of ULM-g is independently 0 or 1;
each u of ULM-g is independently 0 or 1;
each v of ULM-g is independently 0 or 1;
each w of ULM-g is independently 0 or 1; and
any one or more of R¹', R²', R³', X and X' of ULM-g is optionally modified to be covalently bonded to the PTM group through a linker group when PTM is not ULM', or when PTM is ULM', any one or more of R¹', R²', R³', X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

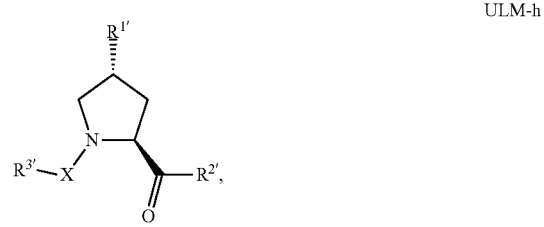

ULM-h wherein:
each of R¹', R² and R³ of ULM-h are the same as above and X is C═O, C═S, —S(O) group or a S(O)₂ group, more preferably a C═O group, and
any one or more of R¹', R²' and R³' of ULM-h are optionally modified to bind a linker group to which is further covalently bonded to the PTM group when PTM is not ULM', or when PTM is ULM', any one or more of R¹, R², R³ of each of ULM and ULM' are optionally modified to be covalently bonded to each other directly or through a linker group, or
a pharmaceutically acceptable salt, enantiomer, diastereomer, solvate or polymorph thereof.

In any of the aspects or embodiments described herein, the ULM, and when present, ULM', are each independently according to the chemical structure:

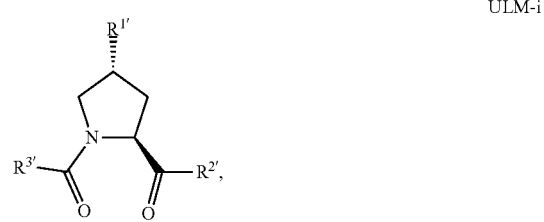

ULM-i wherein:
any one or more of R¹', R²' and R³' of ULM-I are optionally modified to bind a linker group to which is further covalently bonded to the PTM group when PTM is not ULM', or when PTM is ULM', any one or more of R¹, R², R³ of each of ULM and ULM' are optionally modified to be covalently bonded to each other directly or through a linker group, or
a pharmaceutically acceptable salt, enantiomer, diastereomer, solvate or polymorph thereof.

In further preferred aspects of the invention, $R^{1'}$ of ULM-g through ULM-i is preferably a hydroxyl group or a group which may be metabolized to a hydroxyl or carboxylic group, such that the compound represents a prodrug form of an active compound. Exemplary preferred $R^{1'}$ groups include, for example, —$(CH_2)_n$OH, $(CH_2)_n$—O—$(C_1$-$C_6)$alkyl group, —$(CH_2)_n$COOH, —$(CH_2O)_n$H, an optionally substituted —$(CH_2)_n$OC(O)—$(C_1$-$C_6$ alkyl), or an optionally substituted —$(CH_2)_n$C(O)—O—$(C_1$-$C_6$ alkyl), wherein n is 0 or 1. Where $R^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C=O, C=S, —S(O) group or a S(O)₂ group, more preferably a C=O group;

R² of ULM-g through ULM-i is preferably an optionally substituted —NR¹-T-Aryl, an optionally substituted —NR¹-T-Heteroaryl group or an optionally substituted —NR¹-T-Heterocycle, where R¹ is H or CH₃, preferably H and T is an optionally substituted —(CH₂)ₙ— group, wherein each one of the methylene groups may be optionally substituted with one or two substituents, preferably selected from halogen, an amino acid sidechain as otherwise described herein or a C₁-C₃ alkyl group, preferably one or two methyl groups, which may be optionally substituted; and n is 0 to 6, often 0, 1, 2 or 3, preferably 0 or 1. Alternatively, T may also be a —(CH₂O)ₙ— group, a (OCH₂)ₙ— group, a —(CH₂CH₂O)ₙ— group, a —(OCH₂CH₂)ₙ— group, all of which groups are optionally substituted.

Preferred Aryl groups for R²' of ULM-g through ULM-i include optionally substituted phenyl or naphthyl groups, preferably phenyl groups, wherein the phenyl or naphthyl group is connected to a PTM (including a ULM' group) with a linker group and/or optionally substituted with a halogen (preferably F or Cl), an amine, monoalkyl- or dialkyl amine (preferably, dimethylamine), F, Cl, OH, COOH, C₁-C₆ alkyl, preferably CH₃, CF₃, OMe, OCF₃, NO₂, or CN group (each of which may be substituted in ortho-, meta- and/or para-positions of the phenyl ring, preferably para-), an optionally substituted phenyl group (the phenyl group itself is optionally connected to a PTM group, including a ULM', with a linker group), and/or optionally substituted with at least one of F, Cl, OH, COOH, CH₃, CF₃, OMe, OCF₃, NO₂, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

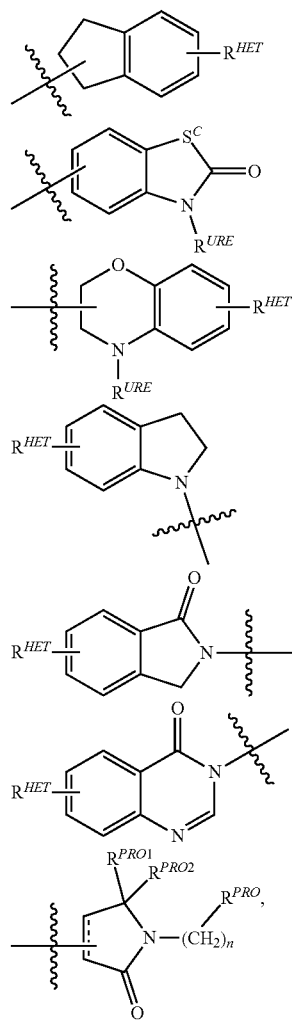

wherein:
$S^c$ of ULM-g through ULM-i is CHR$^{SS}$, NR$^{URE}$, or O;
$R^{HET}$ of ULM-g through ULM-i is H, CN, NO₂, halo (preferably Cl or F), optionally substituted C₁-C₆ alkyl (preferably substituted with one or two hydroxyl groups or up to three halo groups (e.g. CF₃), optionally substituted O(C₁-C₆ alkyl) (preferably substituted with one or two hydroxyl groups or up to three halo groups) or an optionally substituted acetylenic group —C≡C—R$_a$ where R$_a$ is H or a C₁-C₆ alkyl group (preferably C₁-C₃ alkyl);

$R^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

$R^{UBE}$ of ULM g through ULM-i is H, a C$_1$-C$_6$ alkyl (preferably H or C$_1$-C$_3$ alkyl) or a —C(O)(C$_1$-C$_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ of ULM-g through ULM-i is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted C$_1$-C$_3$ alkyl group or together form a keto group; and each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally attached to a PTM group (including a ULM' group) via a linker group.

In certain preferred aspects,

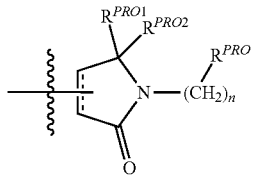

of ULM-g through ULM-i is a

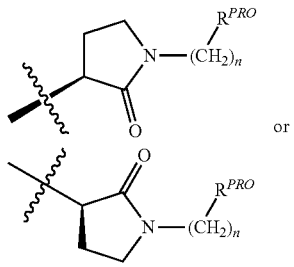

group,
where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3-, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

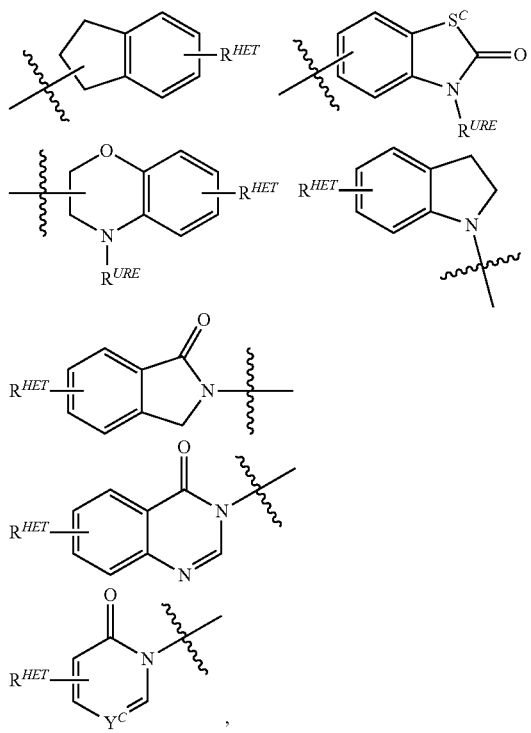

wherein:
$S^c$ of ULM-g through ULM-i is CHR$^{SS}$, NR$^{URE}$, or O;
$R^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C— R$_a$ where R$_a$ of ULM-g through ULM-i is H or a C$_1$-C$_6$ alkyl group (preferably C$_1$-C$_3$ alkyl);
$R^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected to a PTM group (including a ULM' group) via a linker group.

Preferred heterocycle groups for $R^2$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

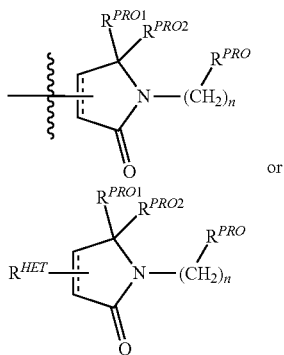

preferably, a

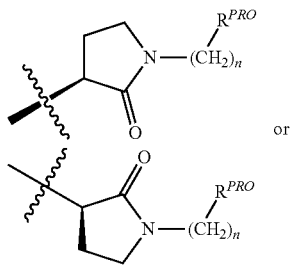

group,
wherein:
 $R^{PRO}$ of ULM-g through ULM-i is H, optionally substituted $C_1$-$C_6$ alkyl or an optionally substituted aryl, heteroaryl or heterocyclic group;
 $R^{PRO1}$ and $R^{PRO2}$ of ULM-g through ULM-i are each independently H, an optionally substituted $C_1$-$C_3$ alkyl group or together form a keto group and
 each n of ULM-g through ULM-i is independently 0, 1, 2, 3, 4, 5, or 6 (often 0 or 1), each of which groups may be optionally connected to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^3$ of ULM-g through ULM-i is preferably an optionally substituted -T-Aryl, an optionally substituted -T-Heteroaryl, an optionally substituted -T-Heterocycle, an optionally substituted-$NR^1$-T-Aryl, an optionally substituted —$NR^1$-T-Heteroaryl or an optionally substituted-$NR^1$-T-Heterocycle, where $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected to a PTM group (including a ULM' group) via a linker group and/or optionally substituted with a halogen (preferably F or Cl), an amine, monoalkyl- or dialkyl amine (preferably, dimethylamine), an amido group (preferably a —$(CH_2)_m$—$NR_1C(O)R_2$ group where m, $R_1$ and $R_2$ are the same as above), a halo (often F or Cl), OH, $CH_3$, $CF_3$, OMe, $OCF_3$, $NO_2$, CN or a $S(O)_2R_S$ group ($R_S$ is a a $C_1$-$C_6$ alkyl group, an optionally substituted aryl, heteroaryl or heterocycle group or a —$(CH_2)_mNR_1R_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

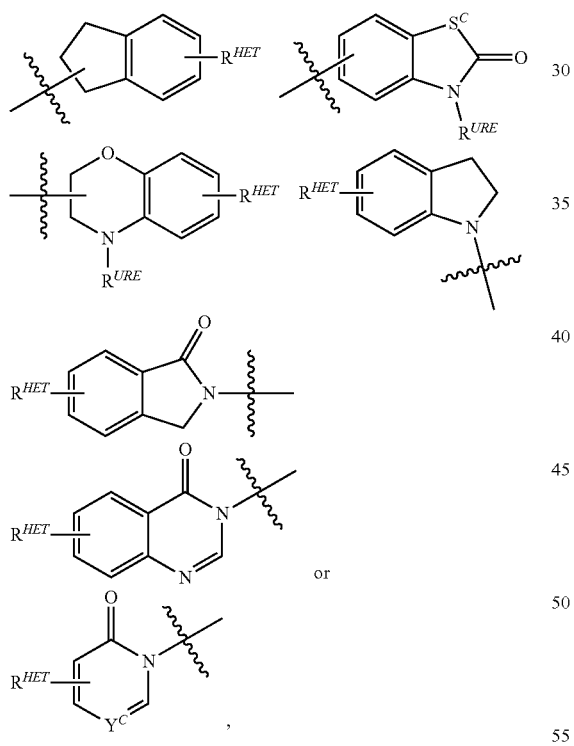

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C— $R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected to a PTM group (including a ULM' group) via a linker group.

Preferred heterocycle groups for $R^{3'}$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

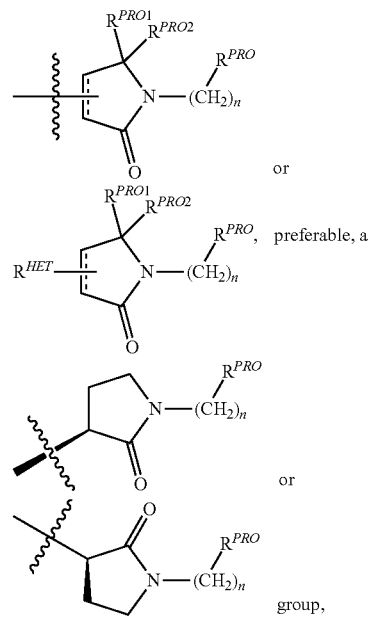

group, wherein:
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is 0, 1, 2, 3, 4, 5, or 6 (preferably 0 or 1), wherein each of said Heterocycle groups may be optionally connected to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl, wherein:
$R_1$ of ULM-g through ULM-i is H or a $C_1$-$C_3$ alkyl group (preferably H);
$X^{R2'}$ of ULM-g through ULM-i is an optionally substituted —$(CH_2)_n$—, —$(CH_2)_n$—$CH(X_v)$=$CH(X_v)$— (cis or trans), —$(CH_2)_n$—$CH \equiv CH$—, —$(CH_2CH_2O)_n$— or a $C_3$-$C_6$ cycloalkyl group; and
$X_v$ of ULM-g through ULM-i is H, a halo or a $C_1$-$C_3$ alkyl group which is optionally substituted with one or two hydroxyl groups or up to three halogen groups;
Alkyl of ULM-g through ULM-i is an optionally substituted $C1$-$C_{10}$ alkyl (preferably a $C_1$-$C_6$ alkyl) group (in certain preferred embodiments, the alkyl group is end-capped with a halo group, often a Cl or Br);
Aryl of ULM-g through ULM-i is an optionally substituted phenyl or naphthyl group (preferably, a phenyl group); and
HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

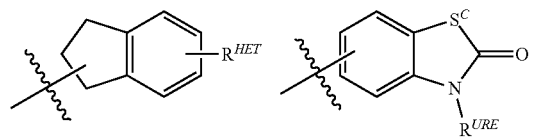

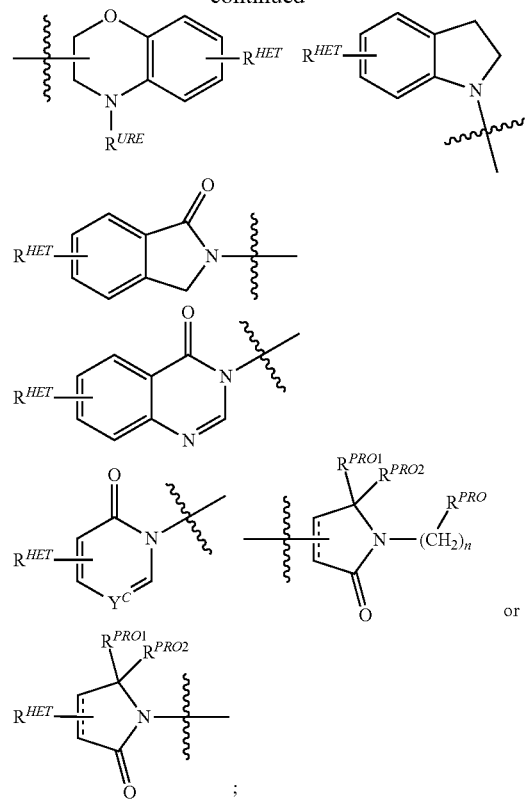

$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —$C \equiv C$—$R_a$ where $R_a$ is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—$(C_1$-$C_6$ alkyl) (preferably substituted with one or two hydroxyl groups or up to three halo groups) or an optionally substituted —$C(O)(C_1$-$C_6$ alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —$C(O)(C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;
$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{PRO}$ of ULM-g through ULM-i is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ of ULM-g through ULM-i are each independently H, an optionally substituted C$_1$-C$_3$ alkyl group or together form a keto group, and each n of ULM-g through ULM-i is independently 0, 1, 2, 3, 4, 5, or 6 (preferably 0 or 1).

Each of said groups may be optionally connected to a PTM group (including a ULM' group) via a linker group.

In certain alternative preferred embodiments of the present invention, R$^{3'}$ of ULM-g through ULM-i is an optionally substituted —(CH$_2$)$_n$—(V)$_{n'}$—(CH$_2$)$_n$—(V)$_{n'}$—R$^{S3'}$ group, an optionally substituted —(CH$_2$)$_n$—N(R$^{1'}$)(C═O)$_m$—(V)$_n$—R$^{S3'}$ group, an optionally substituted —X$^{R3'}$-alkyl group, an optionally substituted —X$^{R3'}$-Aryl group; an optionally substituted —X$^{R3'}$-HET group, an optionally substituted —X$^{R3'}$-Aryl-HET group or an optionally substituted —X$^{R3'}$-HET-Aryl group, wherein:

R$^{S3'}$ is an optionally substituted alkyl group (C$_1$-C$_{10}$, preferably C$_1$-C$_6$ alkyl), an optionally substituted Aryl group or a HET group;

R$_{1'}$ is H or a C$_1$-C$_3$ alkyl group (preferably H);

V is O, S or NR$_1$;

X$^{R3'}$ is —(CH$_2$)$_n$—, —(CH$_2$CH$_2$O)$_n$—, —CH$_2$)$_n$—CH(X$_v$)═CH(X$_v$)— (cis or trans), —CH$_2$)$_n$—CH═CH—, or a C$_3$-C$_6$ cycloalkyl group, all optionally substituted;

X$_v$ is H, a halo or a C$_1$-C$_3$ alkyl group which is optionally substituted with one or two hydroxyl groups or up to three halogen groups;

Alkyl is an optionally substituted C$_1$-C$_{10}$ alkyl (preferably a C$_1$-C$_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a C$_1$-C$_3$ alkyl group, preferably methyl or a halo group, preferably F or Cl), or a group according to the chemical structure:

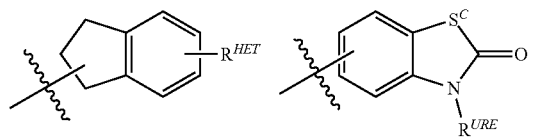

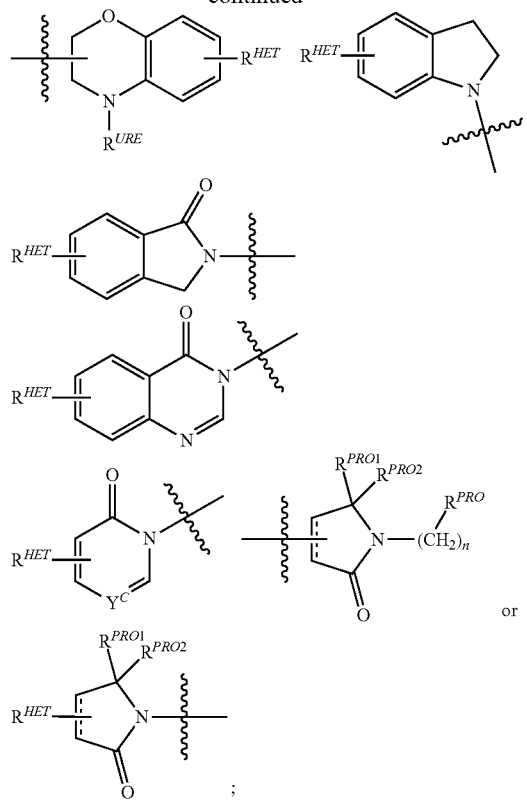

S$^c$ of ULM-g through ULM-i is CHR$^{SS}$, NR$^{URE}$, or O;

R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ of ULM-g through ULM-i is H, a C$_1$-C$_6$ alkyl (preferably H or C$_1$-C$_3$ alkyl) or a —C(O)(C$_0$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

Y$^C$ of ULM-g through ULM-i is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or CO, benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected to a PTM group (including a ULM' group) via a linker.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$—HET, wherein:

said Aryl of ULM-g through ULM-i is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_nO(C_1$-$C_6)$alkyl, amine, mono- or di-$(C_1$-$C_6$ alkyl) amine wherein the alkyl group on the amine is optionally substituted with 1 or 2 hydroxyl groups or up to three halo (preferably F, Cl) groups, or said Aryl group of ULM-g through ULM-i is substituted with —$(CH_2)_n$OH, —$(CH_2)_n$—O—$(C_1$-$C_6)$alkyl, —$(CH_2)_n$—O—$(CH_2)_n$—$(C_1$-$C_6)$alkyl, —$(CH_2)_n$—C(O)($C_0$-$C_6$) alkyl, —$(CH_2)_n$—C(O)O($C_0$-$C_6)$alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, CN, $NO_2$, an optionally substituted —$(CH_2)_n$—$(V)_{m'}$—$CH_2)_n$—$(V)_{m'}$—$(C_1$-$C_6)$alkyl group, a —$(V)_{m'}$—$(CH_2CH_2O)_n$—$R^{PEG}$ group where V is O, S or $NR_1$, $R_1$ is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

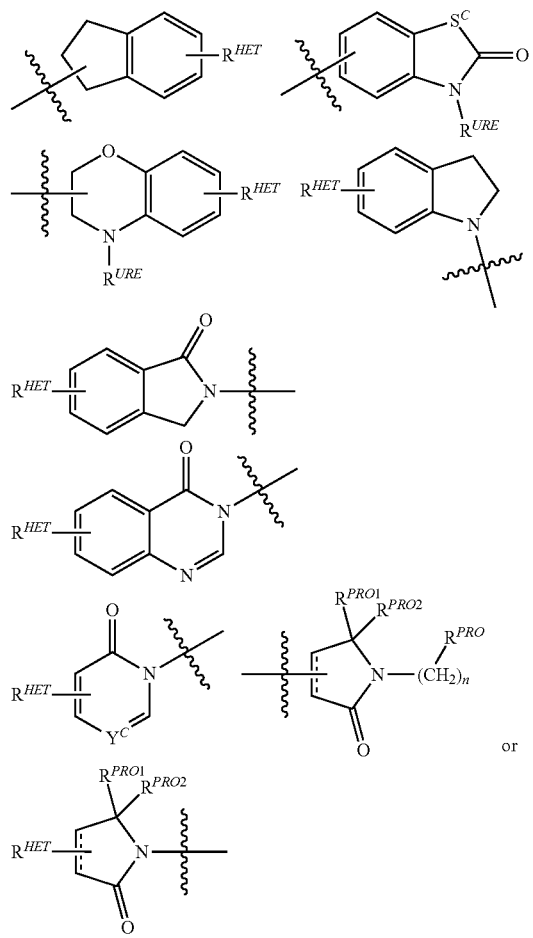

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted O($C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group; HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine, or a group according to the chemical structure:

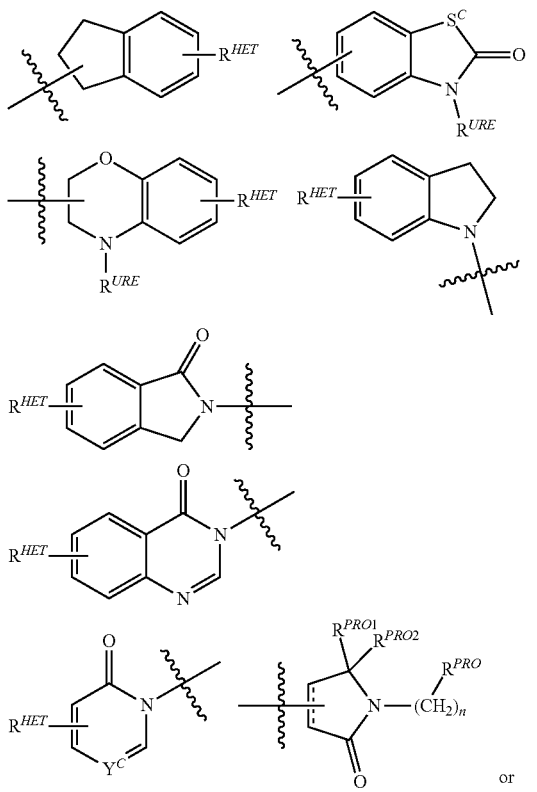

-continued

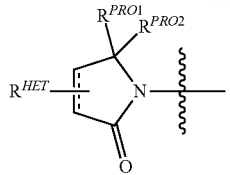

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or CO, optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected to a PTM group (including a ULM' group) via a linker group.

In still additional embodiments, preferred compounds include those according to the chemical structure:

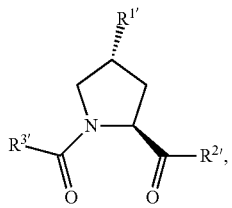

wherein:
$R^{1'}$ of ULM-i is OH or a group which is metabolized in a patient or subject to OH;

$R^{2'}$ of ULM-i is a —NH—$CH_2$-Aryl-HET (preferably, a phenyl linked directly to a methyl substituted thiazole);

$R^3$ of ULM-i is a —$CHR^{CR3'}$—NH—C(O)—$R^{3P1}$ group or a —$CHR^{CR3'}$—$R^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —($CH_2$)—$OCH_3$ group where n is 1 or 2 (preferably 2), or a

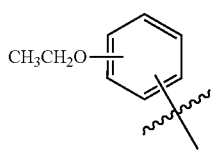

group (the ethyl ether group is preferably meta-substituted on the phenyl moiety), a morpholino group (linked to the carbonyl at the 2- or 3-position;

$R^{3P2}$ of ULM-i is a

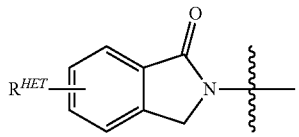

group;

Aryl of ULM-i is phenyl;

HET of ULM-i is an optionally substituted thiazole or isothiazole; and $R^{HET}$ of ULM-i is H or a halo group (preferably H);

or a pharmaceutically acceptable salt, stereoisomer, solvate or polymorph thereof, wherein each of said compounds is optionally connected to a PTM group (including a ULM' group) via a linker group.

In certain aspects, bifunctional compounds comprising a ubiquitin E3 ligase binding moiety (ULM), wherein ULM is a group according to the chemical structure:

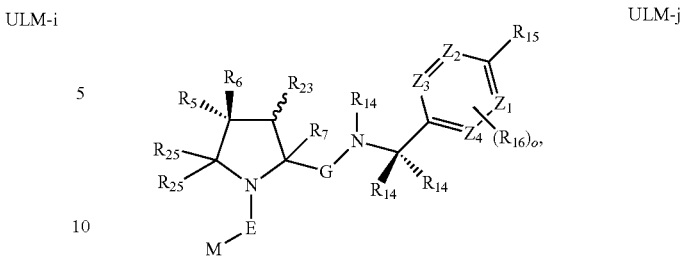

wherein:
each $R_5$ and $R_6$ of ULM-j is independently OH, SH, or optionally substituted alkyl or $R_5$, $R_6$, and the carbon atom to which they are attached form a carbonyl;

$R_7$ of ULM-j is H or optionally substituted alkyl;

E of ULM-j is a bond, C=O, or C=S;

G of ULM-j is a bond, optionally substituted alkyl, —COOH or C=J;

J of ULM-j is O or N—$R_8$;

$R_8$ of ULM-j is H, CN, optionally substituted alkyl or optionally substituted alkoxy;

M of ULM-j is optionally substituted aryl, optionally substituted heteroaryl, optionally substituted heterocyclic or

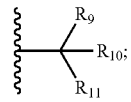

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;

$R_{11}$ of ULM-j is optionally substituted heterocyclic, optionally substituted alkoxy, optionally substituted heteroaryl, optionally substituted aryl, or

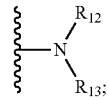

$R_{12}$ of ULM-j is H or optionally substituted alkyl;

$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate, each $R_{14}$ of ULM-j is independently H, haloalkyl, optionally substituted cycloalkyl, optionally substituted alkyl or optionally substituted heterocycloalkyl;

$R_{15}$ of ULM-j is H, optionally substituted heteroaryl, haloalkyl, optionally substituted aryl, optionally substituted alkoxy, or optionally substituted heterocyclyl;

each $R_{16}$ of ULM-j is independently halo, optionally substituted alkyl, optionally substituted haloalkyl, CN, or optionally substituted haloalkoxy;

each $R_{25}$ of ULM-j is independently H or optionally substituted alkyl; or both $R_{25}$ groups can be taken together to form an oxo or optionally substituted cycloalkyl group;

$R_{23}$ of ULM-j is H or OH;

$Z_1$, $Z_2$, $Z_3$, and $Z_4$ of ULM-j are independently C or N; and o of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C=O and M is

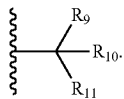

In certain embodiments, wherein E of ULM-j is C=O, $R_{11}$ is optionally substituted heterocyclic or

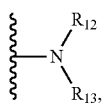

and M is

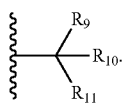

In certain embodiments, wherein E of ULM-j is C=O, M is

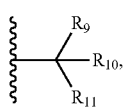

and $R_{11}$ is

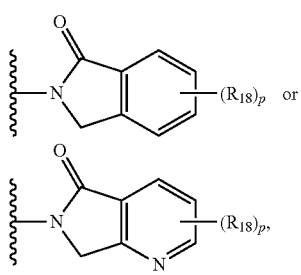

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

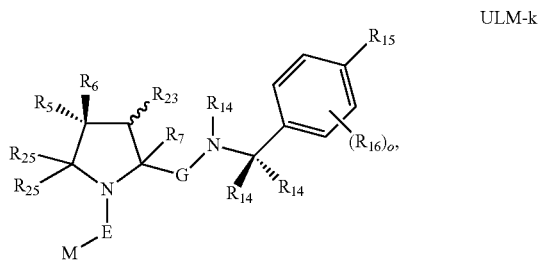

wherein:
G of ULM-k is C=J, J is O;
$R_7$ of ULM-k is H;
each $R_{14}$ of ULM-k is H;
o of ULM-k is 0;
$R_{15}$ of ULM-k is

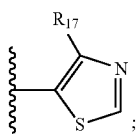

and $R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

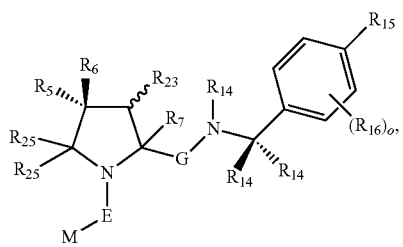

wherein:
G of ULM-k is C=J, J is O;
$R_7$ of ULM-k is H;
each $R_{14}$ of ULM-k is H;
o of ULM-k is 0; and
$R_{15}$ of ULM-k is selected from the group consisting of:

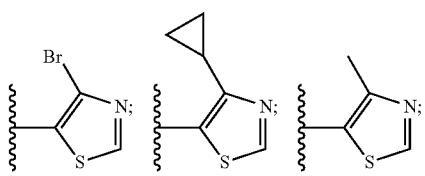

-continued
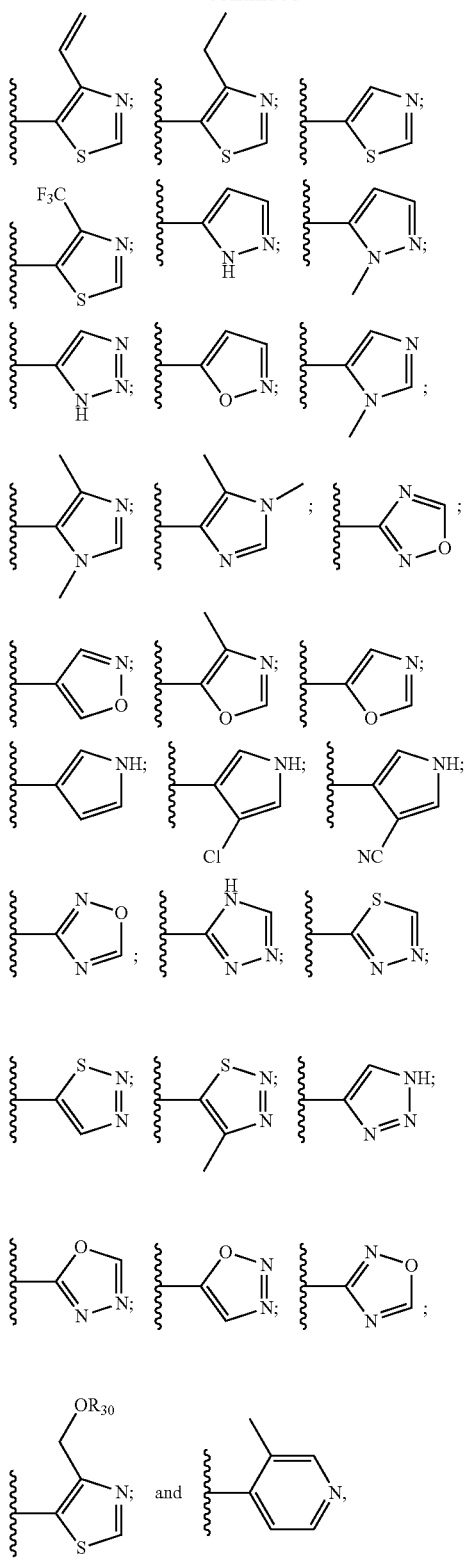
wherein $R_{30}$ of ULM-k is H or an optionally substituted alkyl.
In other embodiments, ULM and where present, ULM', are each independently a group according to the chemical structure:
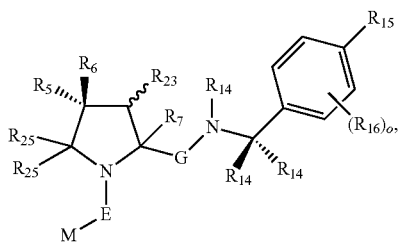
wherein:
E of ULM-k is C=O;
M of ULM-k is
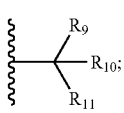
and
$R_{11}$ of ULM-k is selected from the group consisting of:
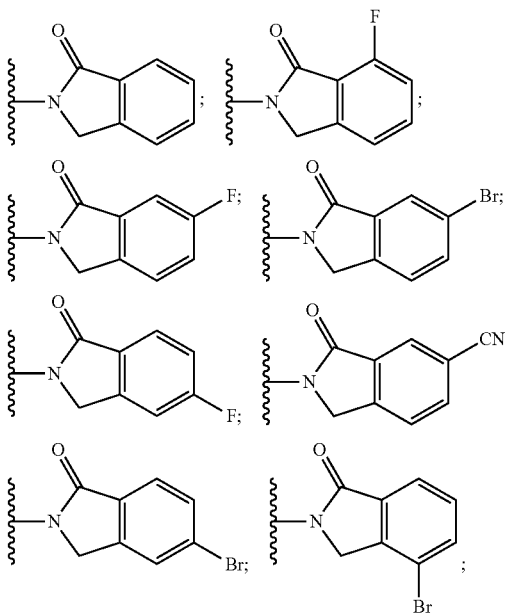
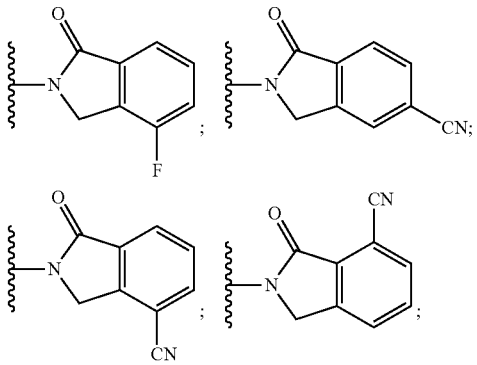

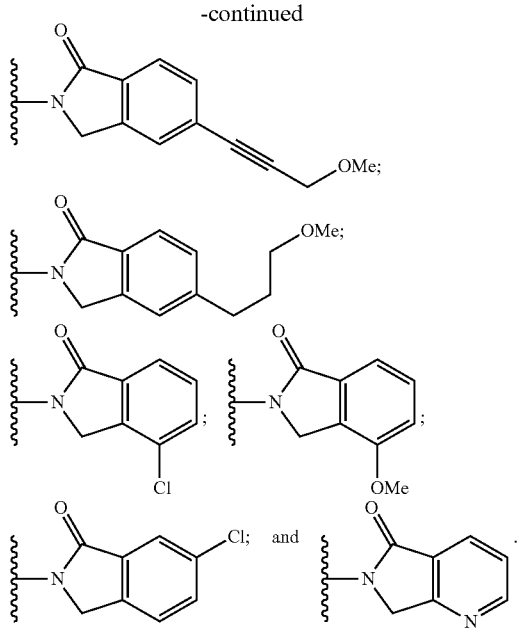

In still other embodiments, a compound of the chemical structure,

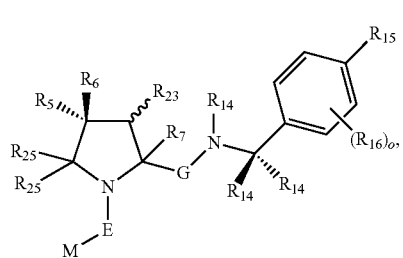
ULM-k wherein:
E of ULM-k is C=O;
$R_{11}$ of ULM-k is

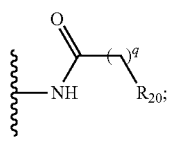

and
M of ULM-k is

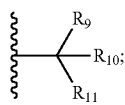

q of ULM-k is 1 or 2;
$R_{20}$ of ULM-k is H, optionally substituted alkyl, optionally substituted cycloalkyl, optionally substituted aryl, or

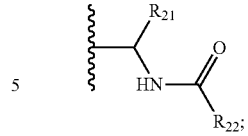

$R_{21}$ of ULM-k is H or optionally substituted alkyl; and
$R_{22}$ of ULM-k is H, optionally substituted alkyl, optionally substituted alkoxy, or haloalkyl.

In any embodiment described herein, $R_{11}$ of ULM-j or ULM-k is selected from the group consisting of:

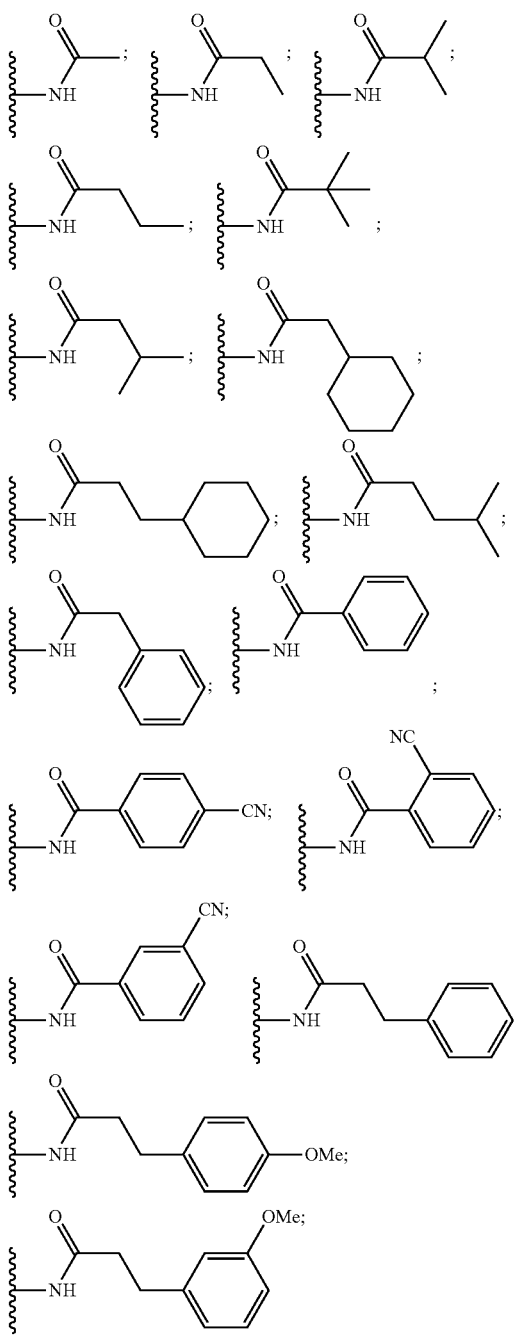

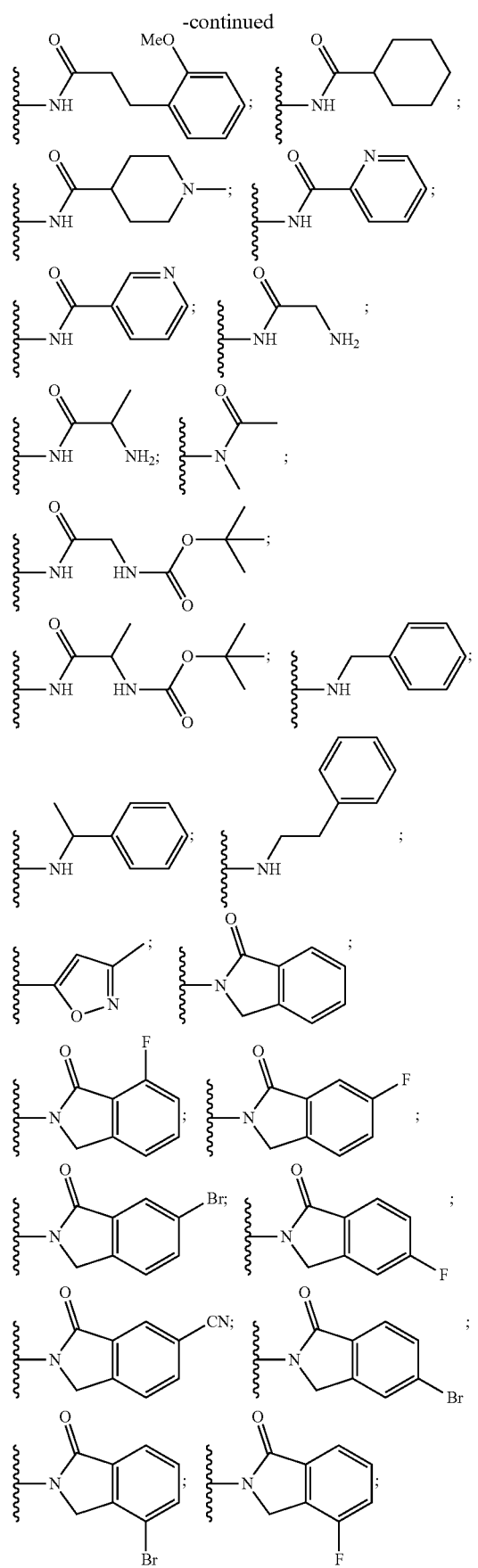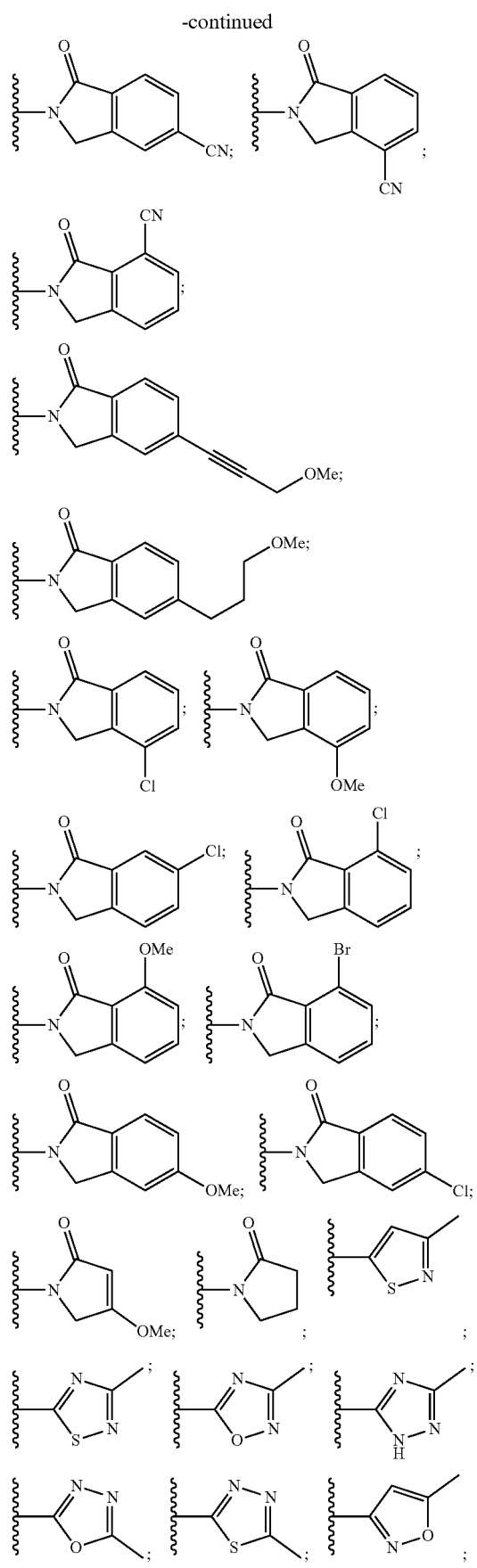

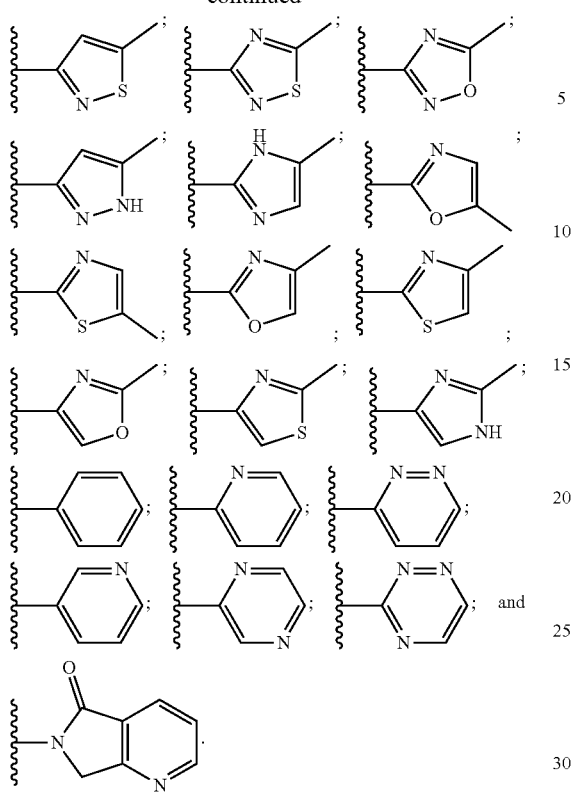
In certain embodiments, $R_{11}$ of ULM-j or ULM-k is selected from the group consisting of:
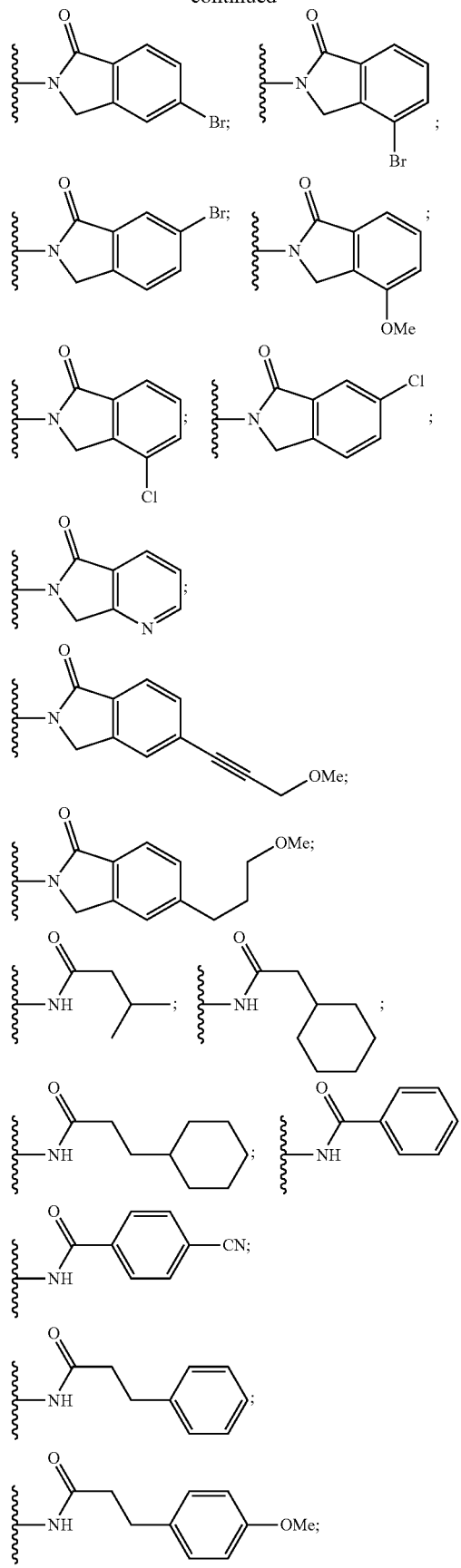

In certain embodiments, ULM (or when present ULM') is a group according to the chemical structure:

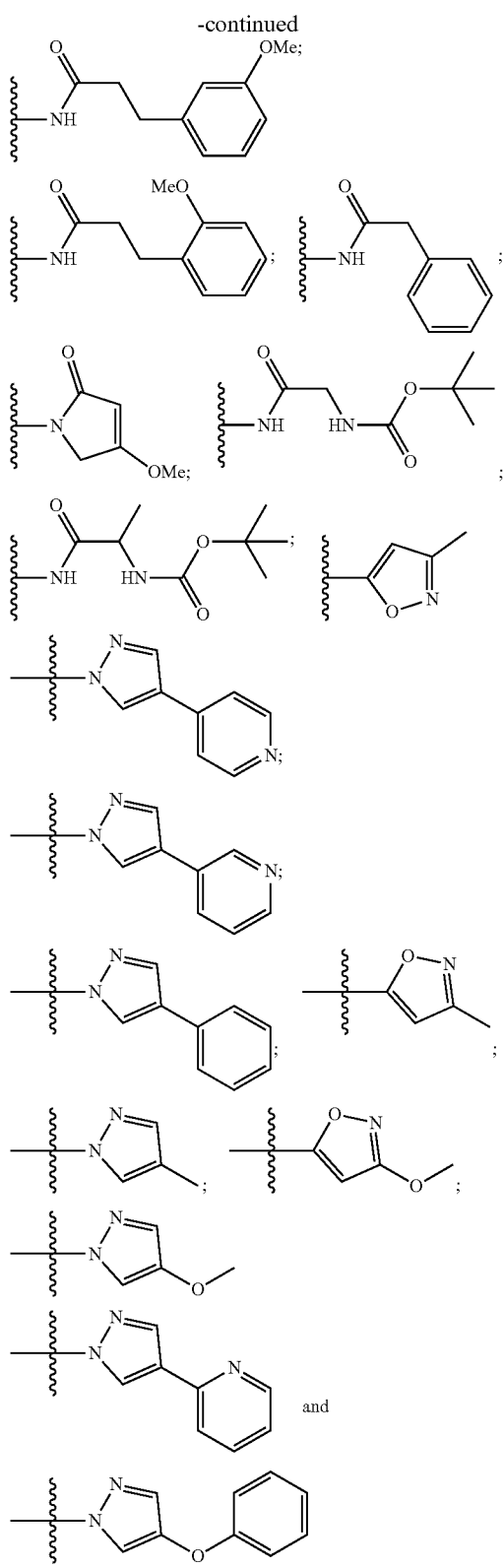

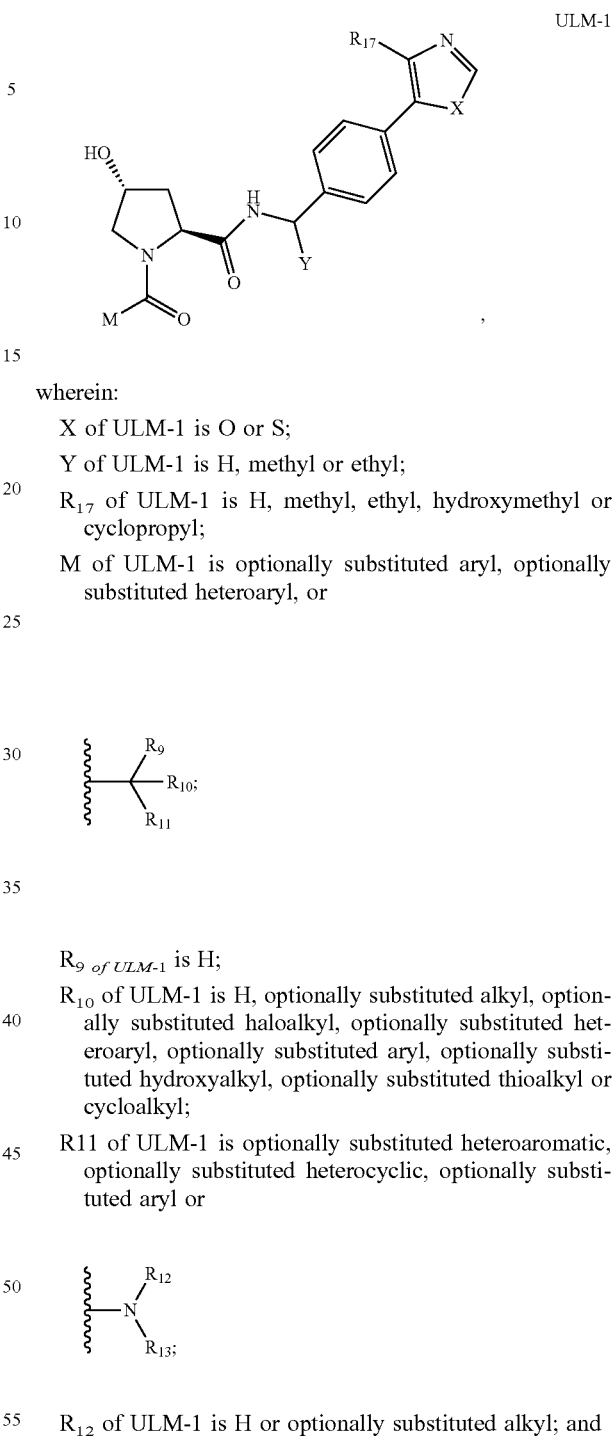

wherein:
X of ULM-1 is O or S;
Y of ULM-1 is H, methyl or ethyl;
$R_{17}$ of ULM-1 is H, methyl, ethyl, hydroxymethyl or cyclopropyl;
M of ULM-1 is optionally substituted aryl, optionally substituted heteroaryl, or $R_9$ of ULM-1 is H;
$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;
R11 of ULM-1 is optionally substituted heteroaromatic, optionally substituted heterocyclic, optionally substituted aryl or $R_{12}$ of ULM-1 is H or optionally substituted alkyl; and
$R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

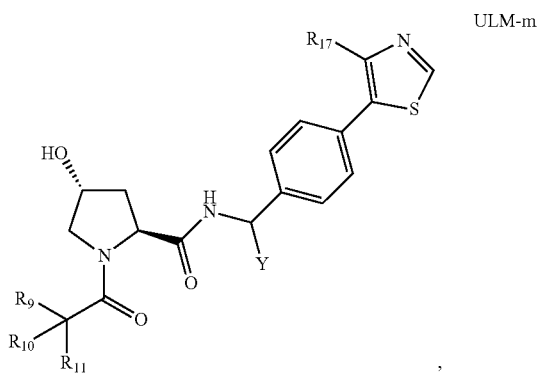

ULM-m

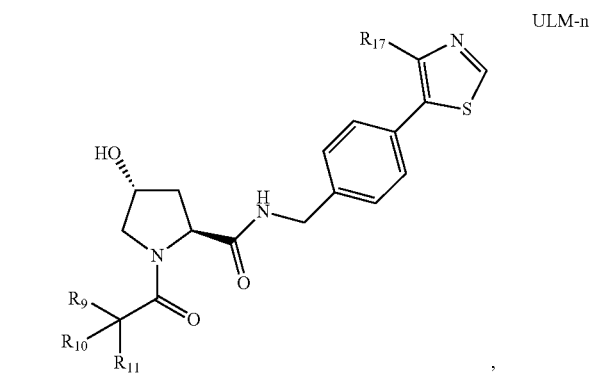

ULM-n wherein:
Y of ULM-m is H, methyol or ethyl
R₉ of ULM-m is H;
R₁₀ is isopropyl, tert-butyl, sec-butyl, cyclopentyl, or cyclohexyl;
R₁₁ of ULM-m is optionally substituted amide, optionally substituted isoindolinone, optionally substituted isooxazole, optionally substituted heterocycles.

In other preferred embodiments of the invention, ULM and where present, ULM', are each independently a group according to the chemical structure:

wherein:
R₁₇ of ULM-n is methyl, ethyl, or cyclopropyl; and
R₉, R₁₀, and R₁₁ of ULM-n are as defined above. In other instances, R₉ is H; and
R₁₀ of ULM-n is H, alkyl, or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the invention, the ULM moiety is selected from the group consisting of:

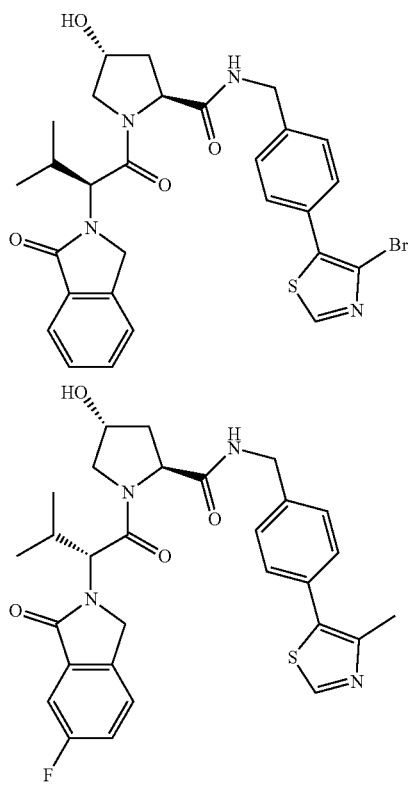

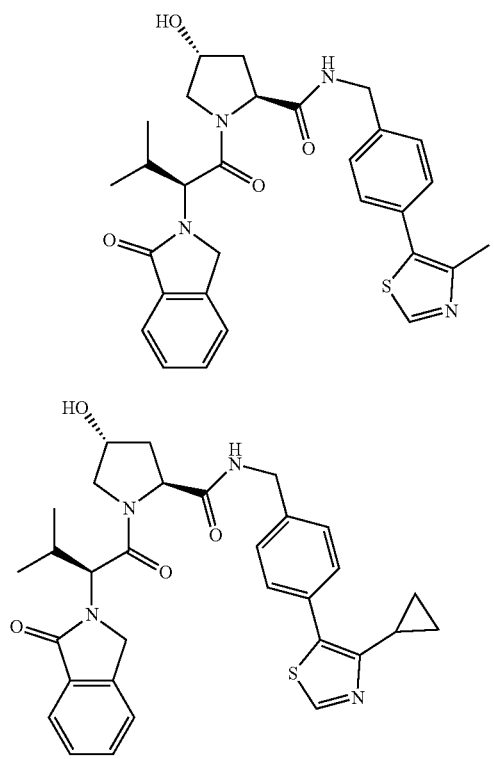

-continued
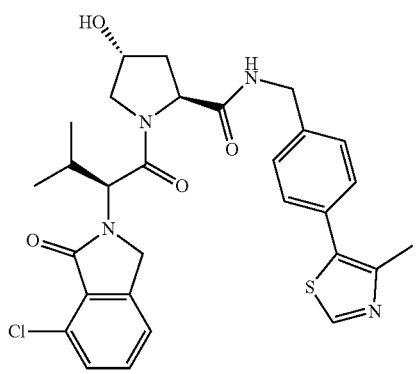
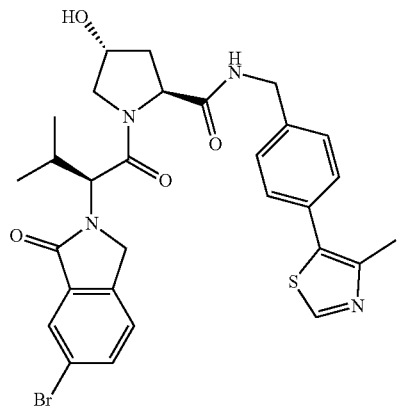
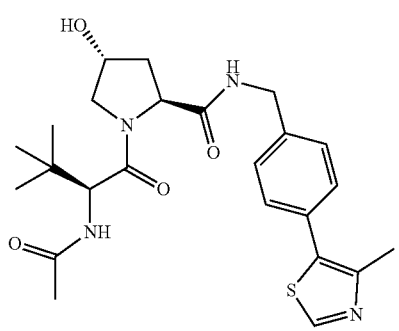
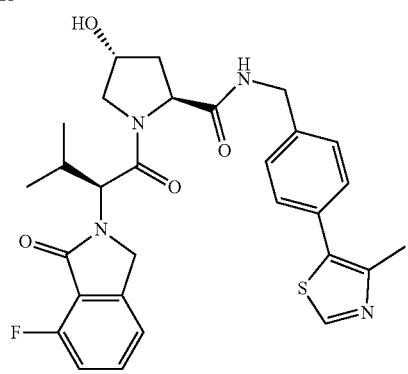
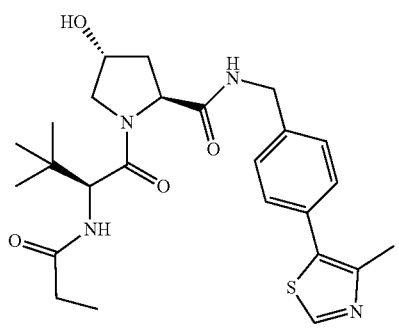
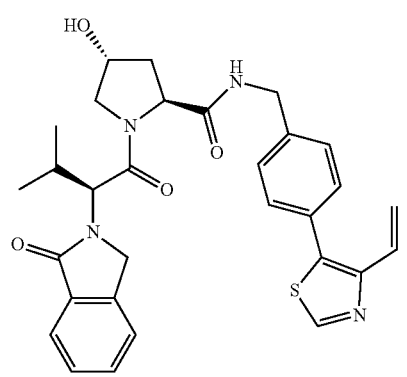
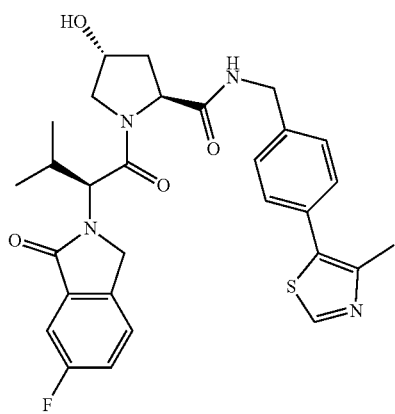
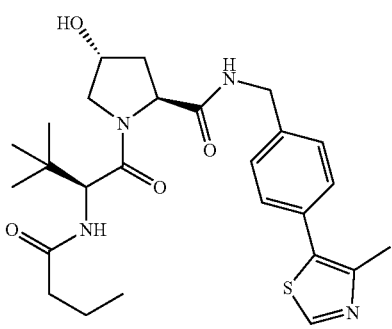

-continued
227
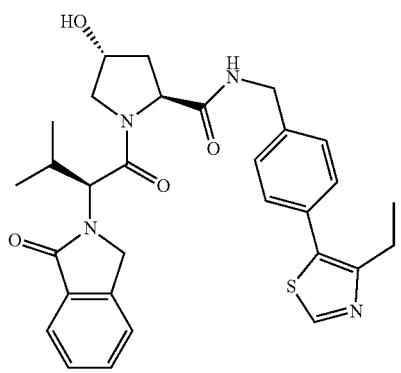
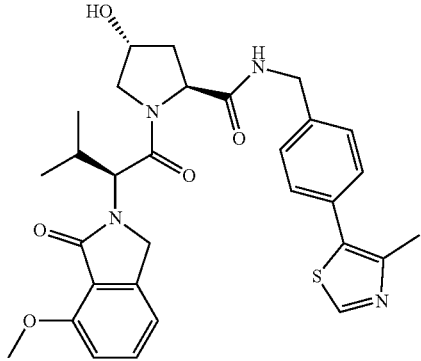
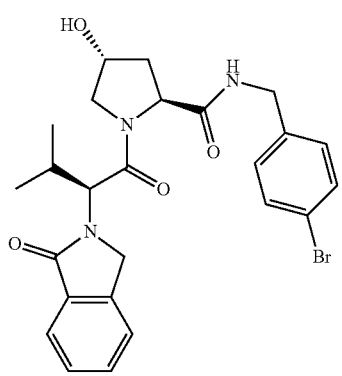
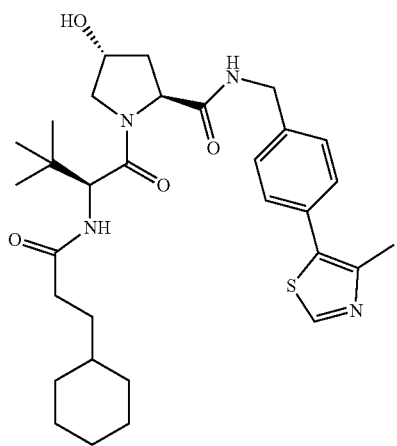
228
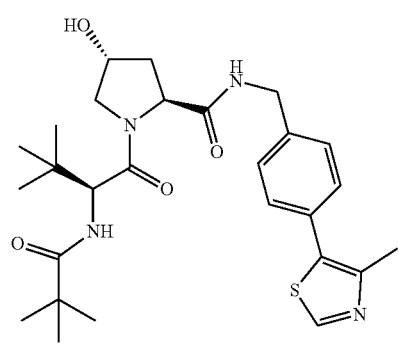
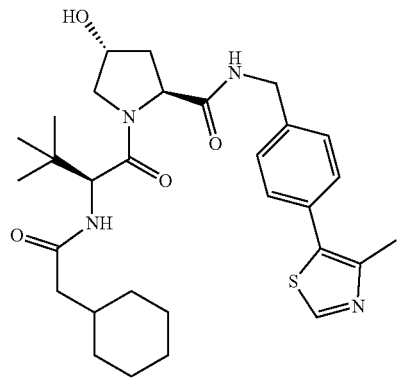
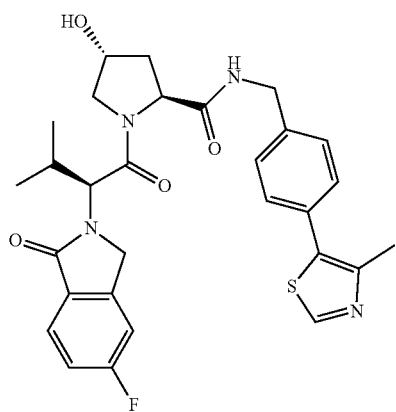
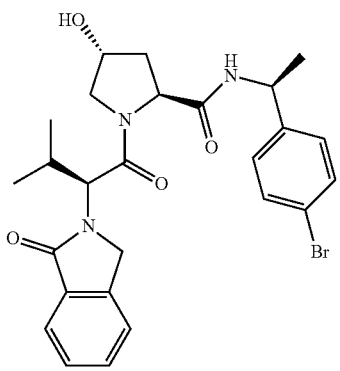

229
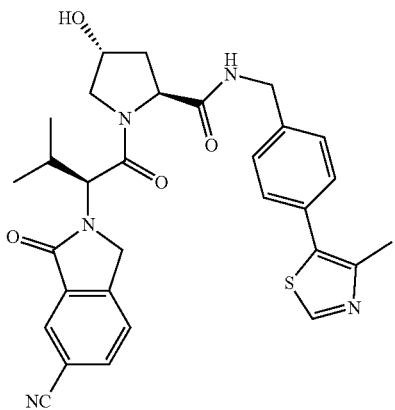
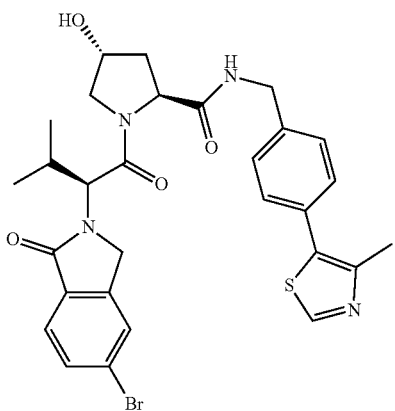
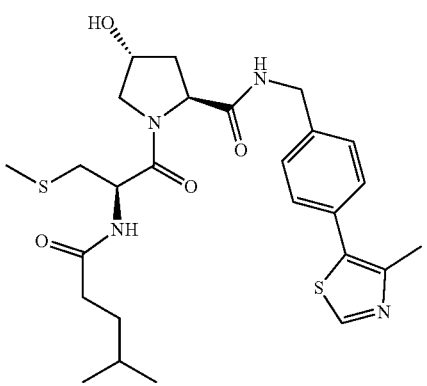
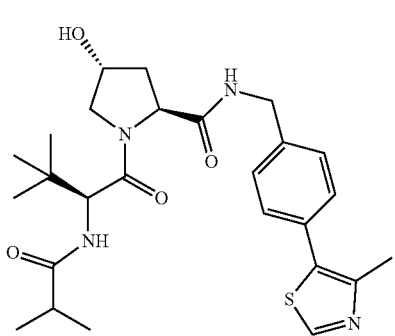
230
-continued
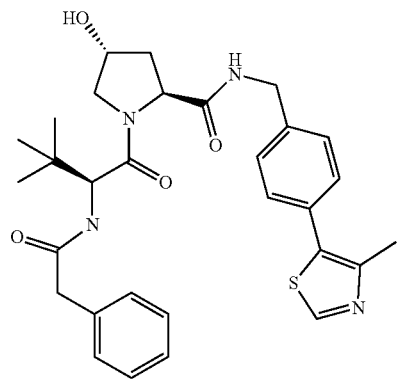
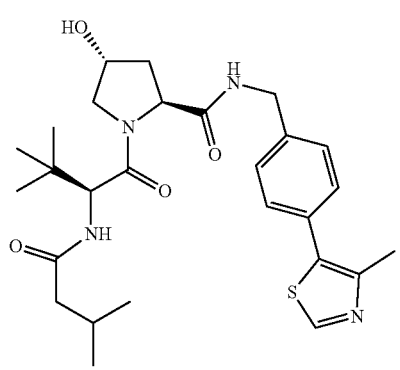
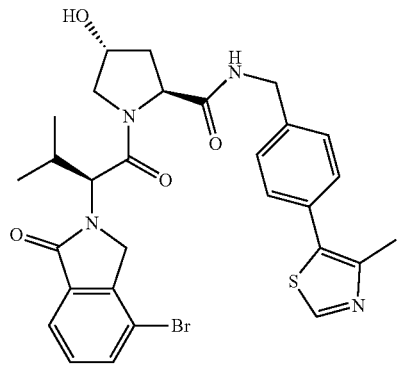
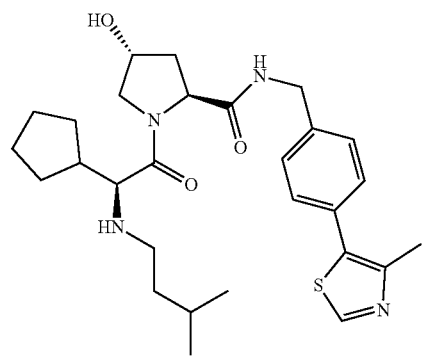

-continued
231
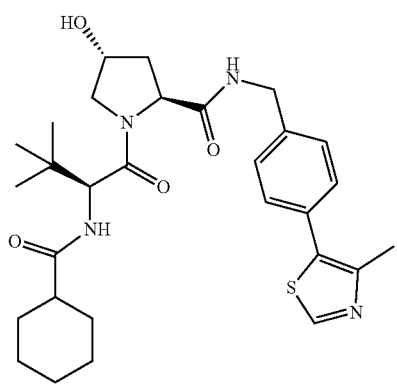
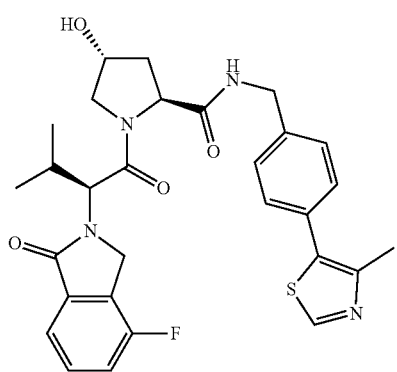
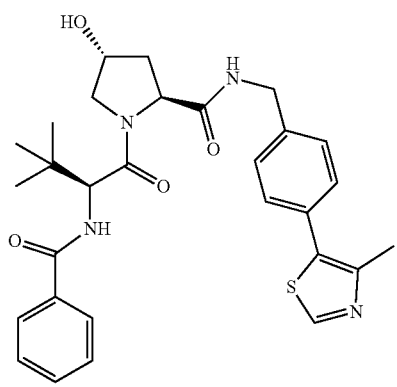
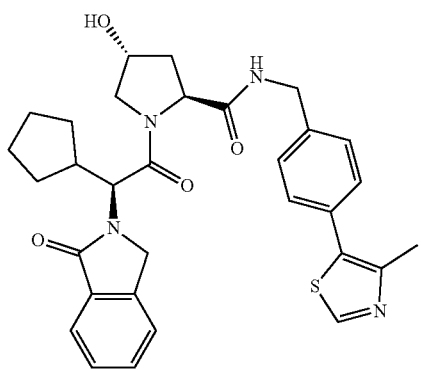
232
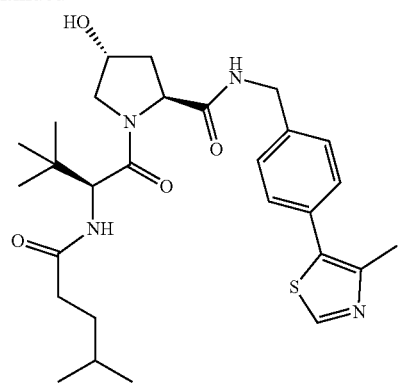
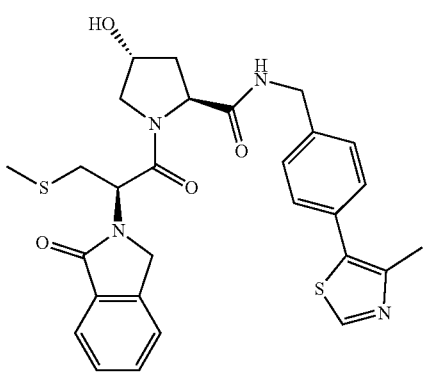
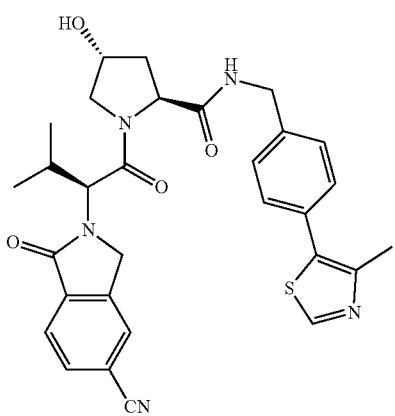
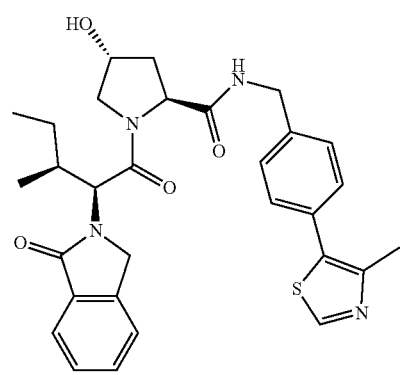

-continued
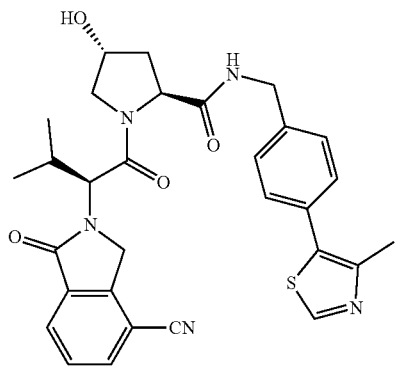
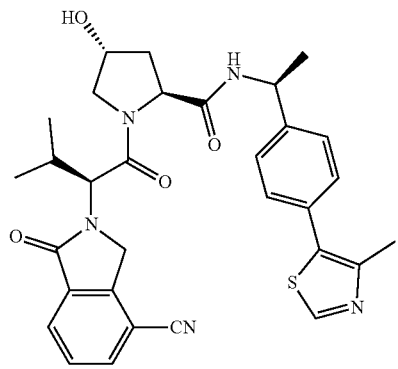
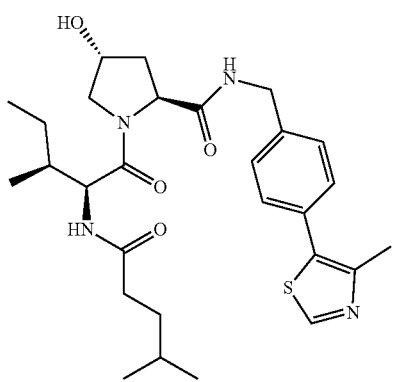
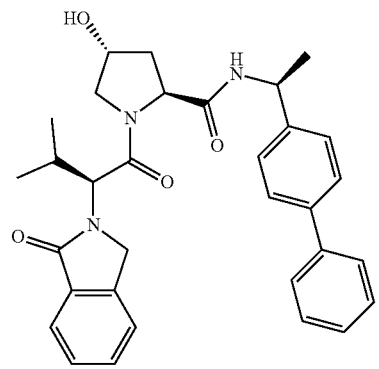
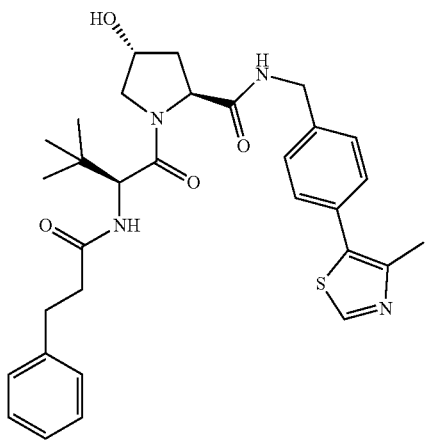
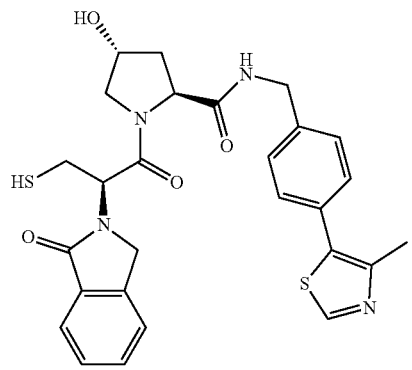
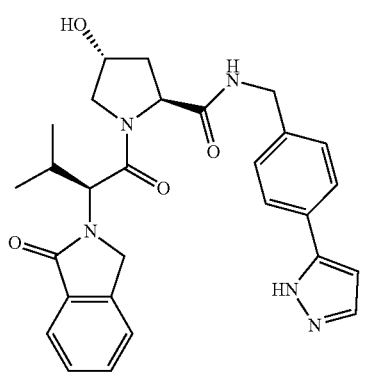
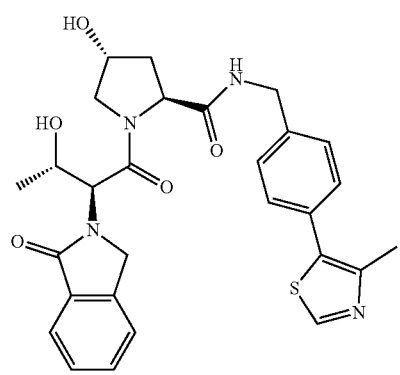

235
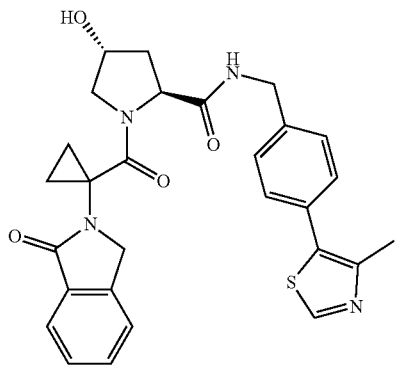
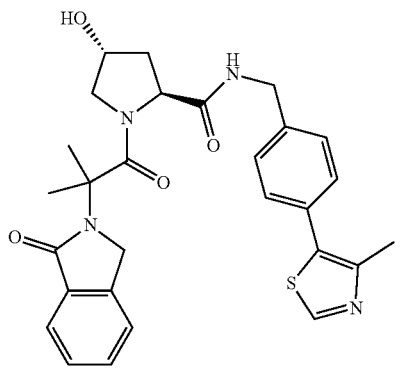
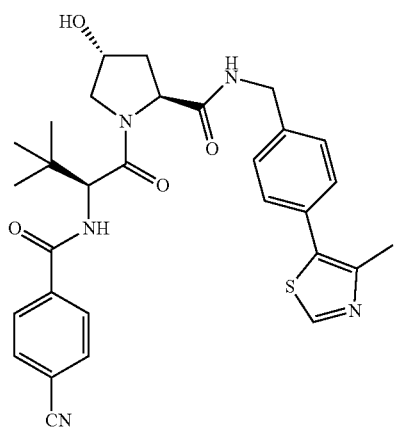
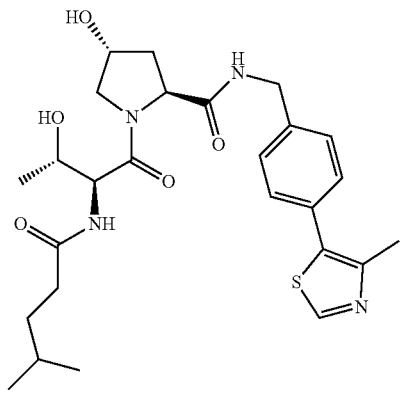
236
-continued
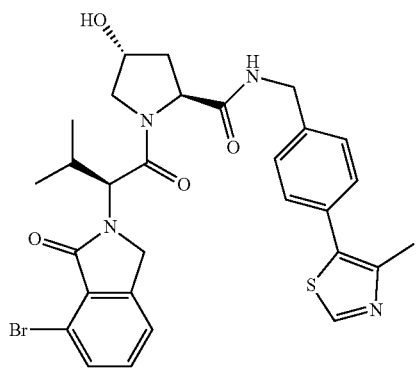
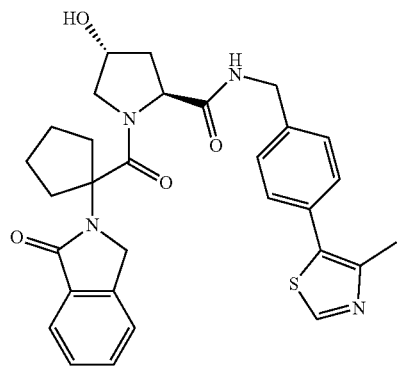
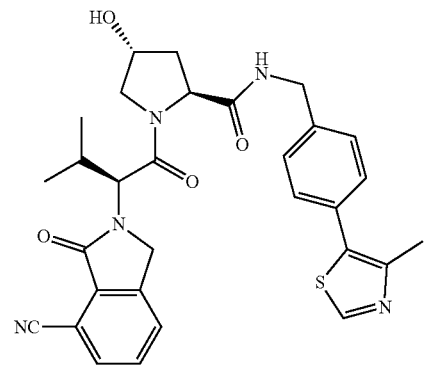
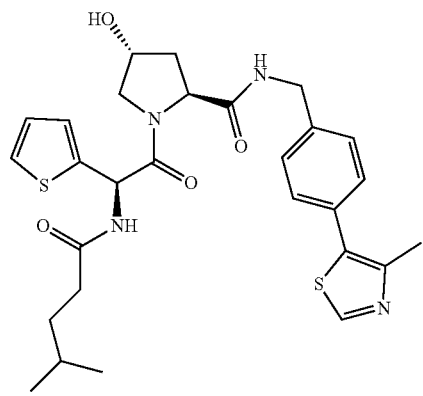

-continued
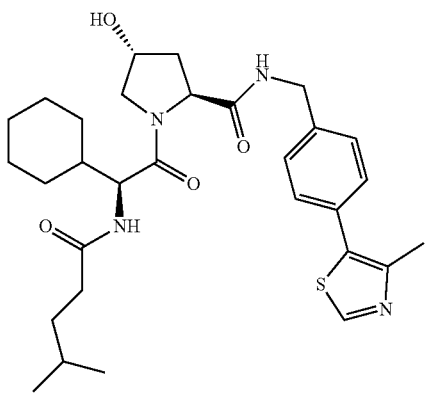
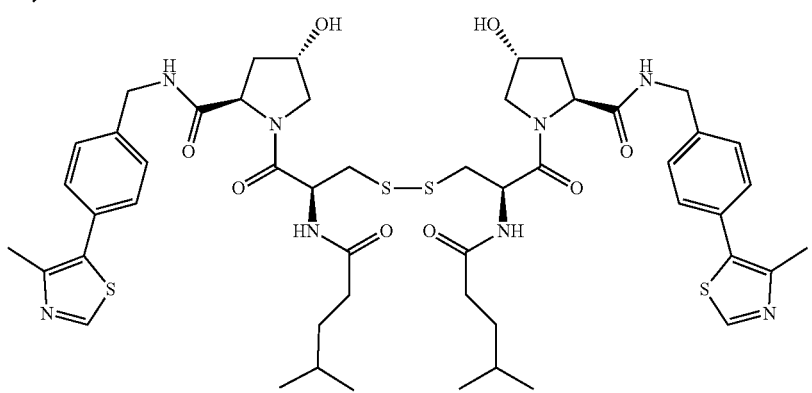
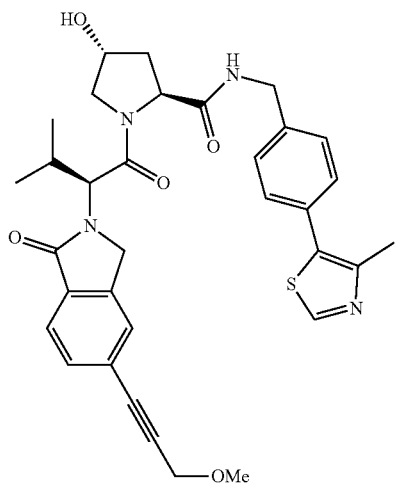
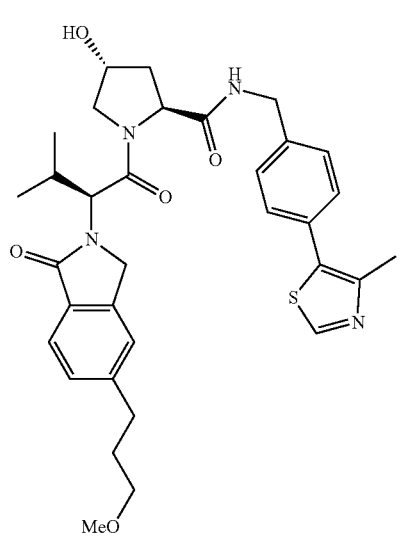
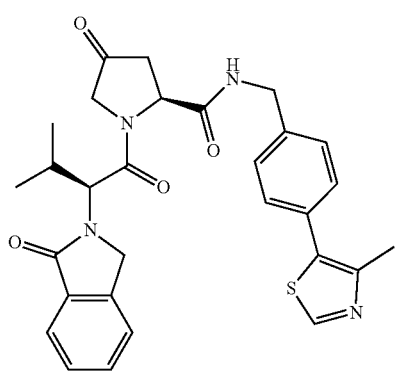
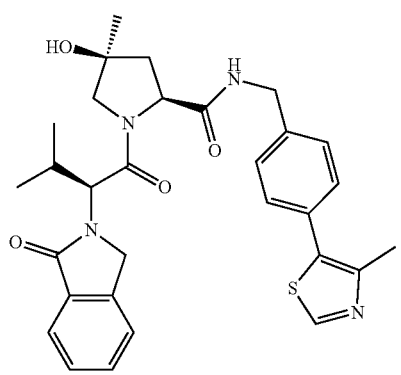

-continued
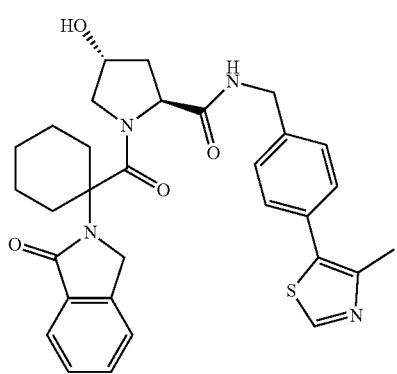
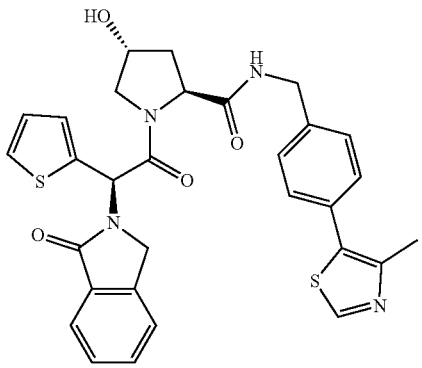
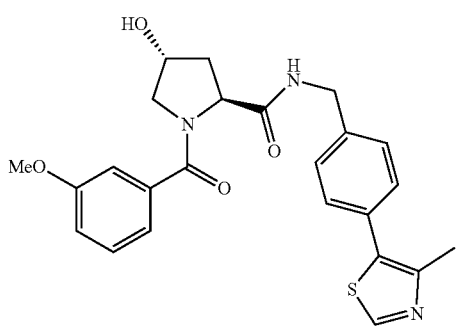
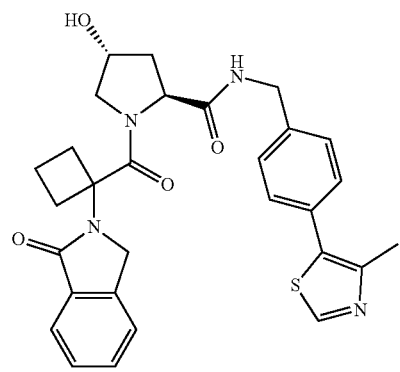
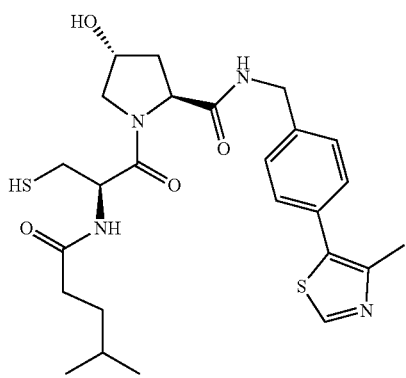
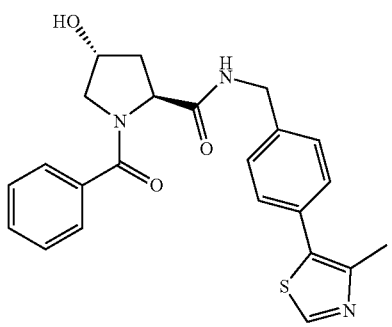
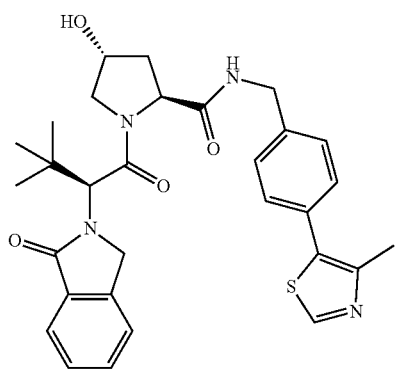
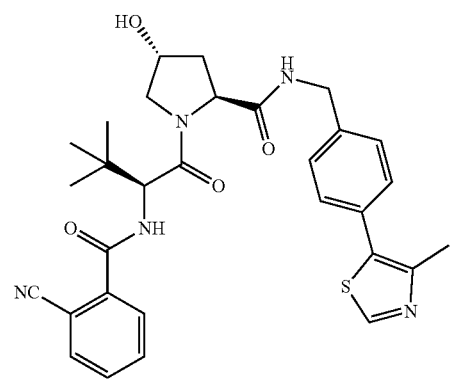

-continued
241
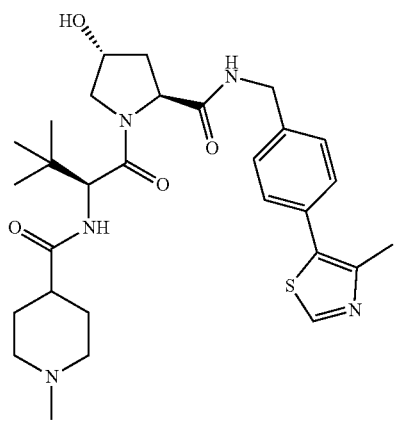
242
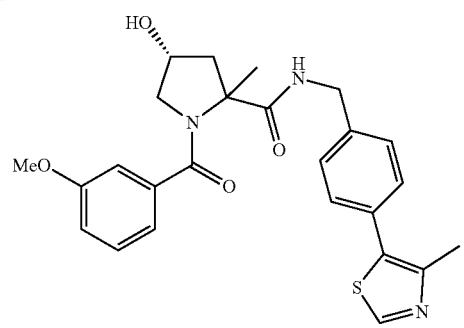
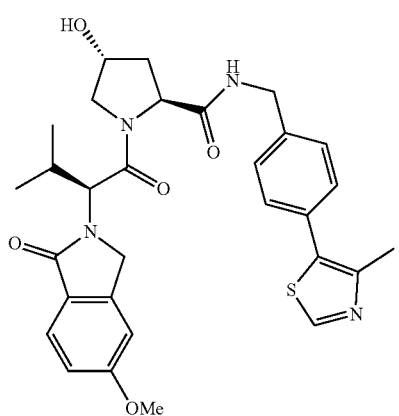
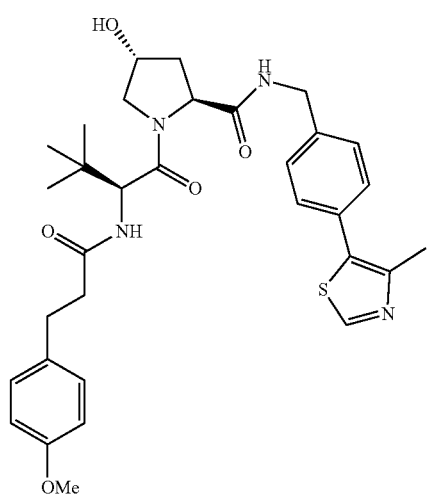
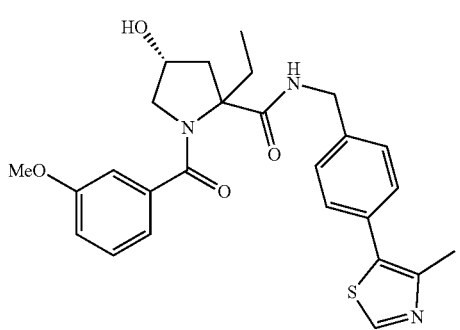
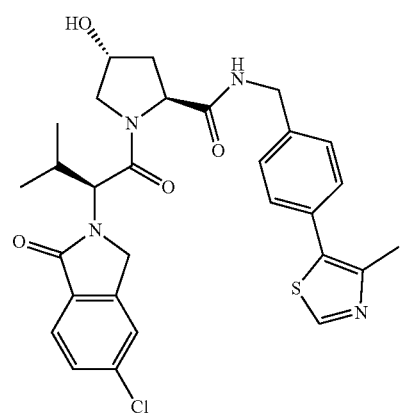

243
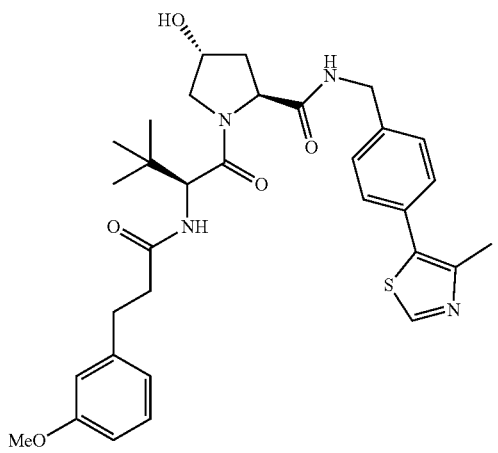
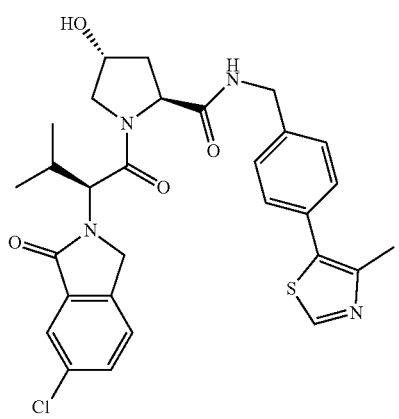
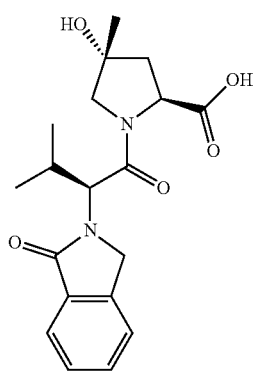
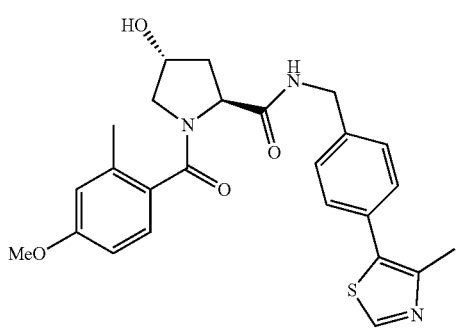
244
-continued
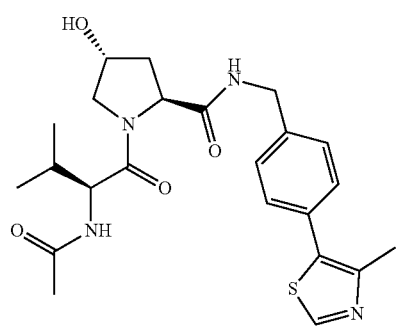
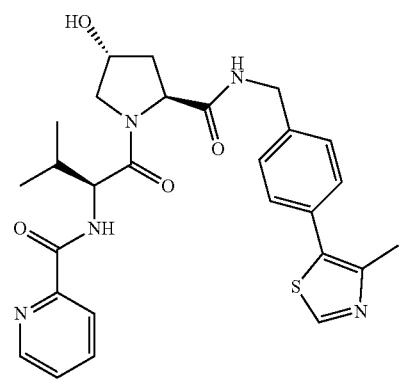
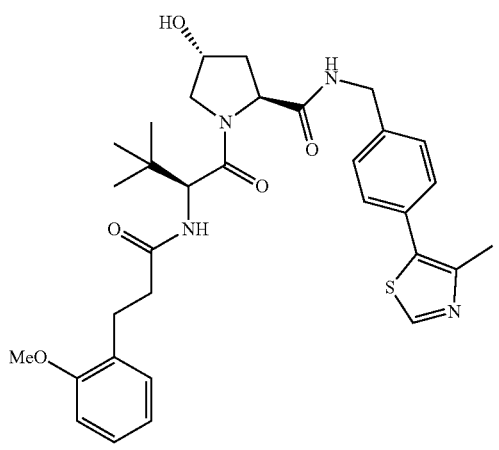
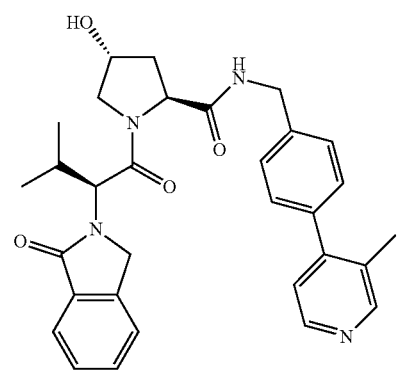

-continued
| 245 | 246 |
|---|---|
| 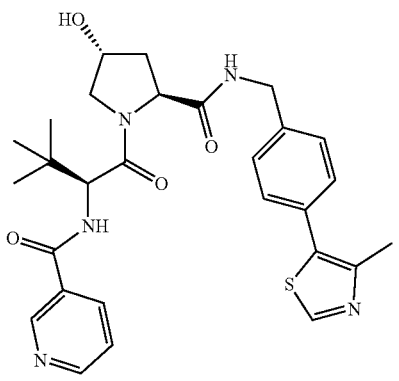 | 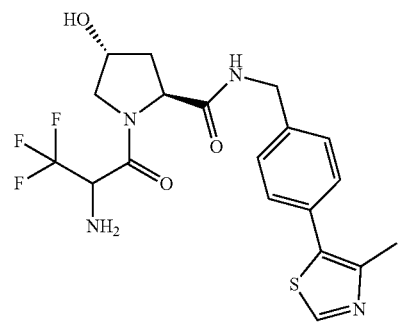 |
| 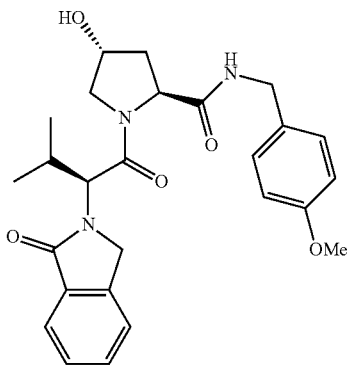 | 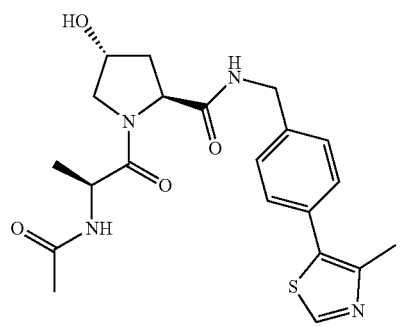 |
| 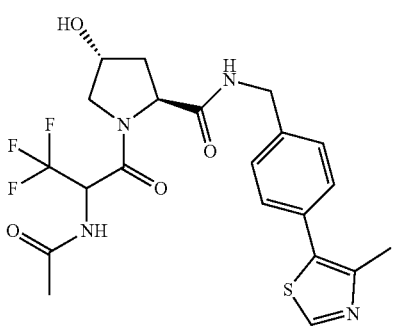 | 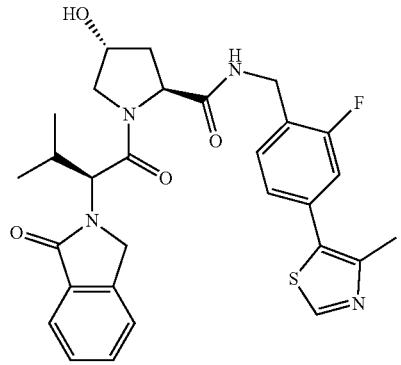 |
| 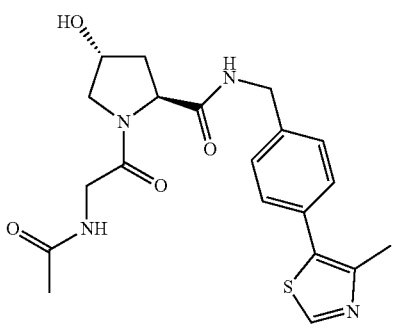 | 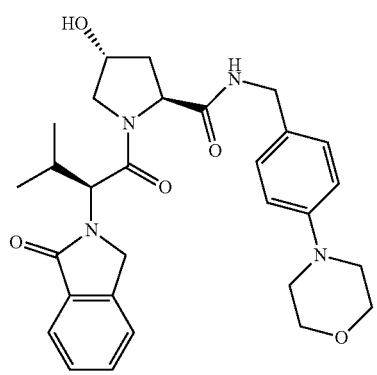 |

247
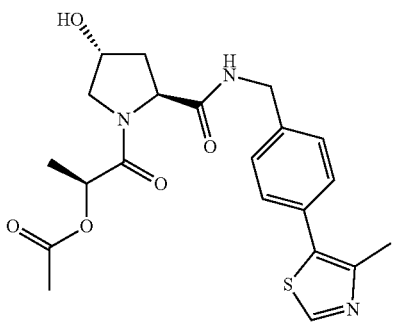
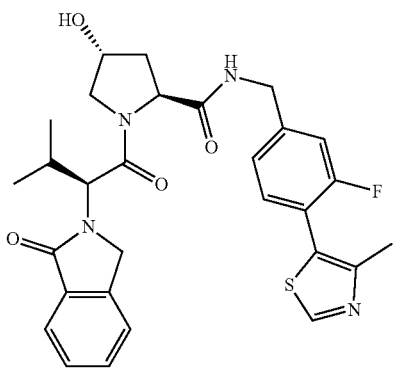
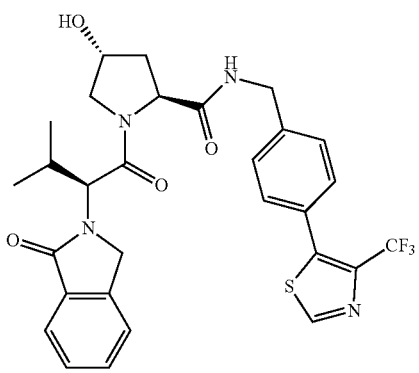
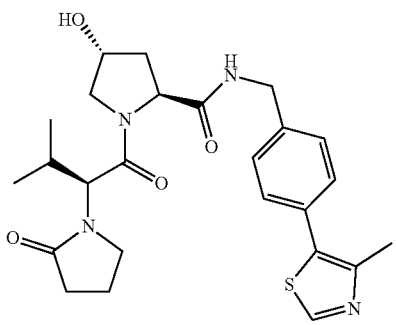
248
-continued
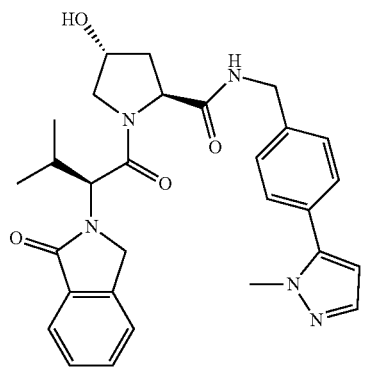
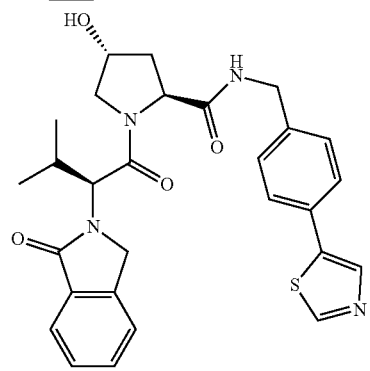
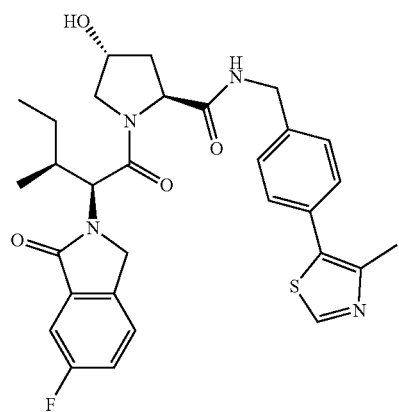
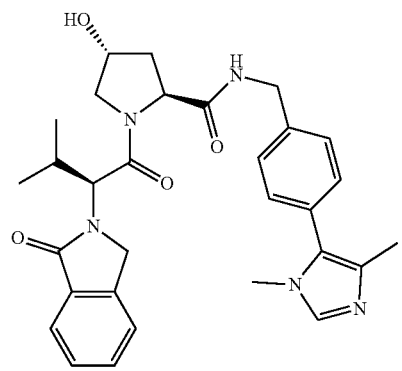

249
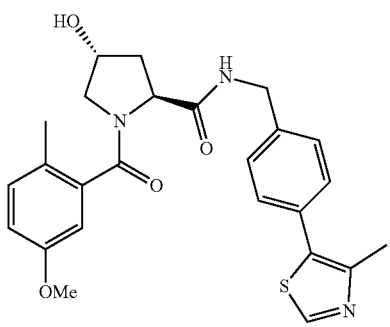
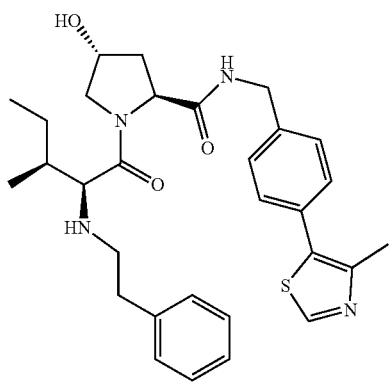
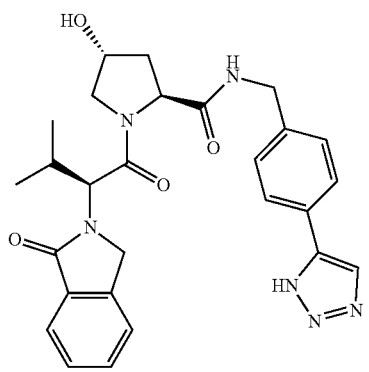
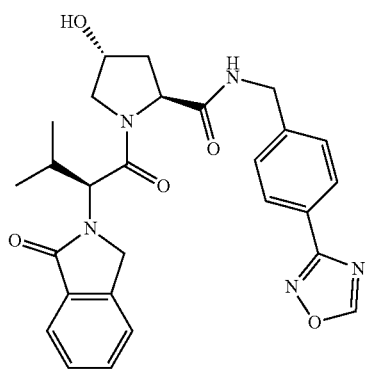
250
-continued
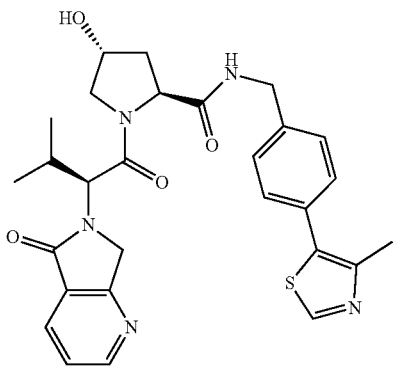
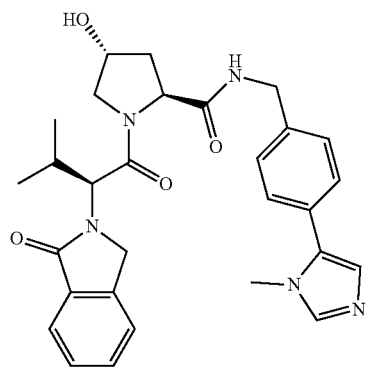
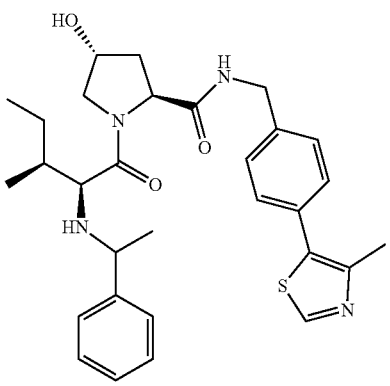

251 252
-continued
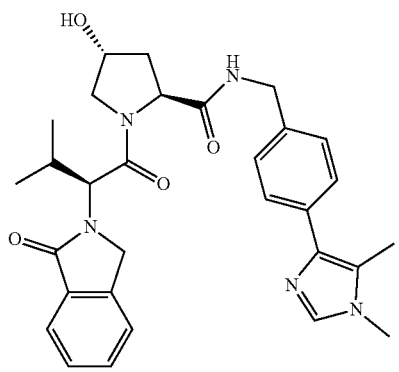
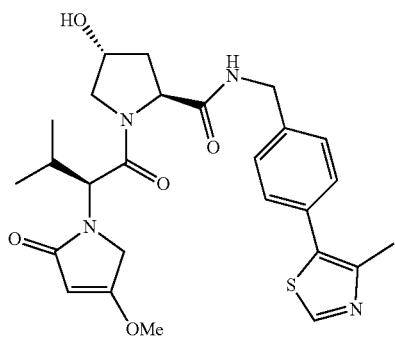
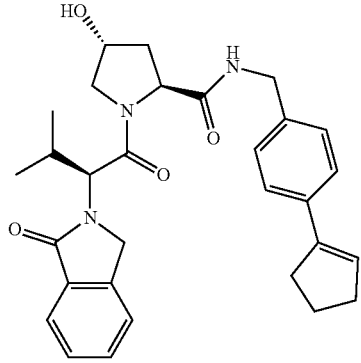
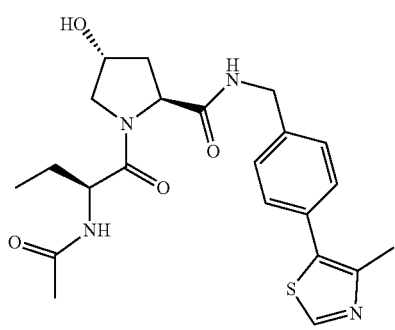
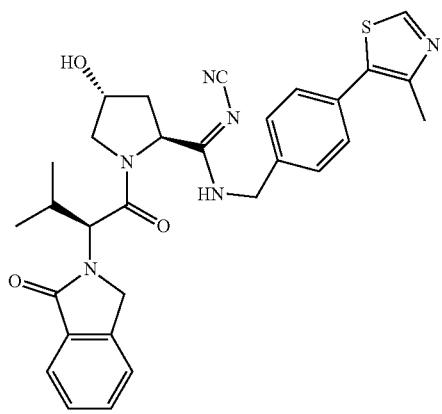
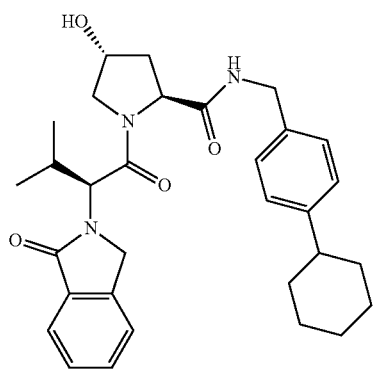
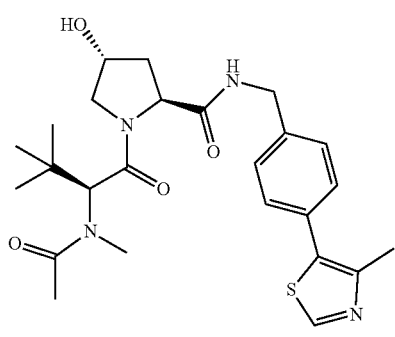
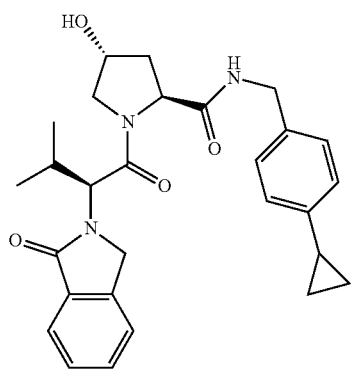

-continued
| 253 | 254 |
|---|---|
| 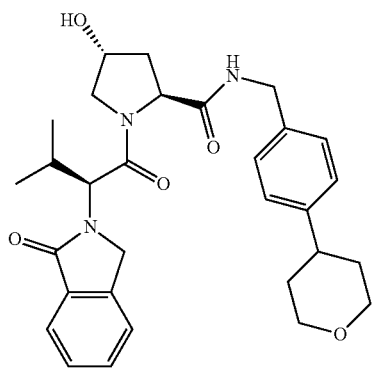 | 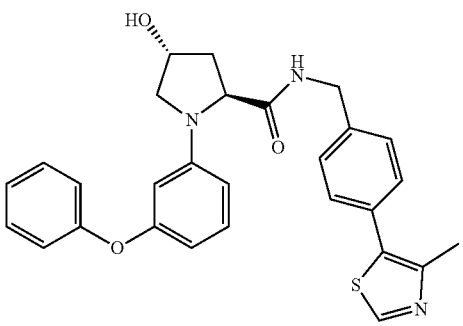 |
| 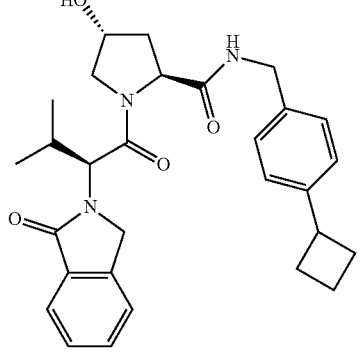 | 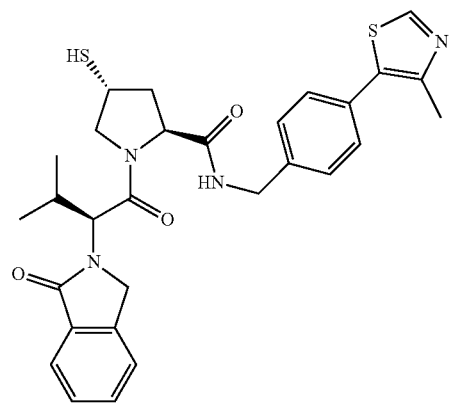 |
| 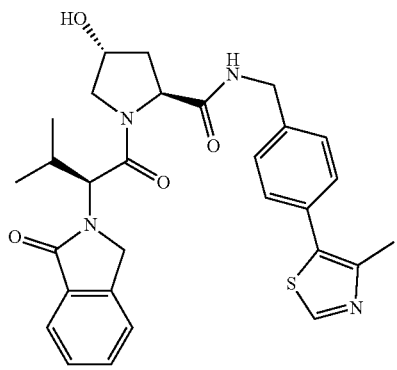 | 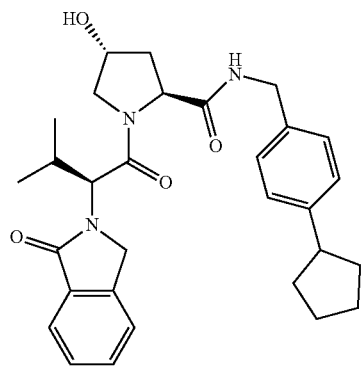 |
| 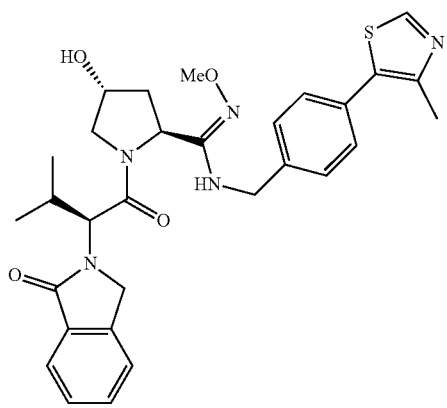 | 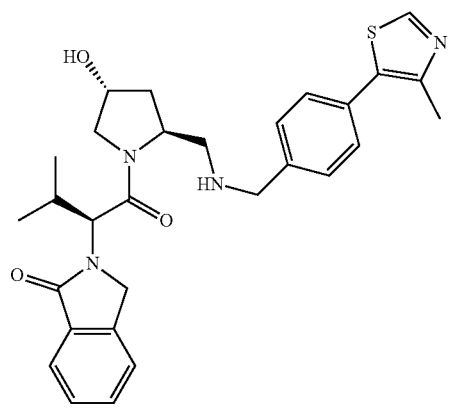 |

255
256
-continued
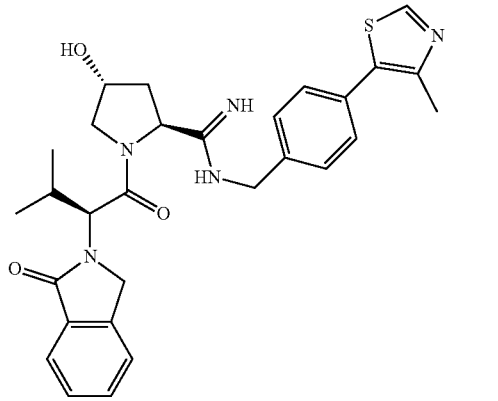
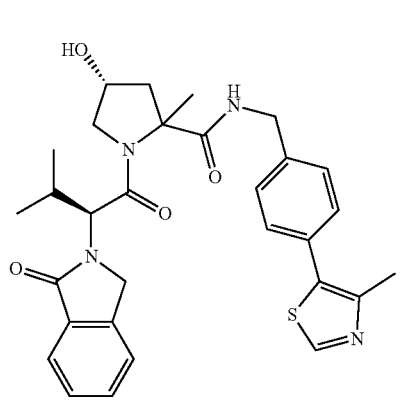
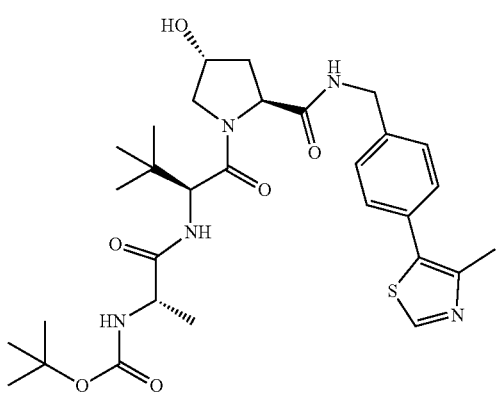
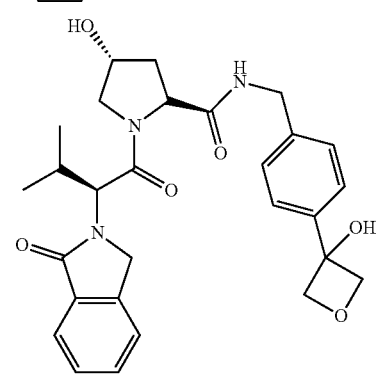
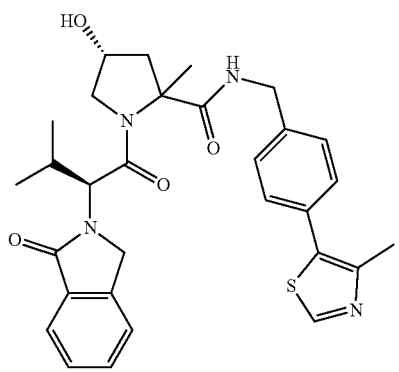
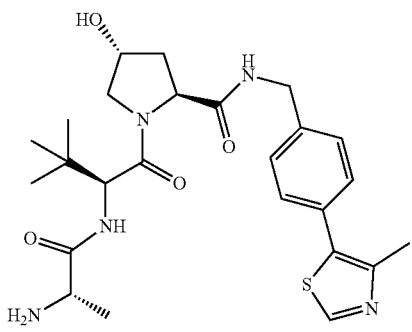
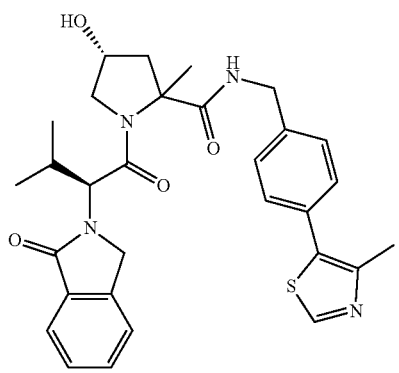
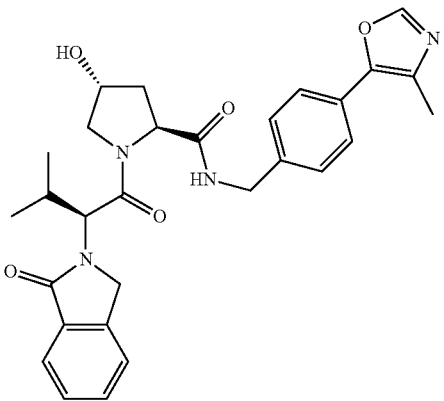

257 258
-continued
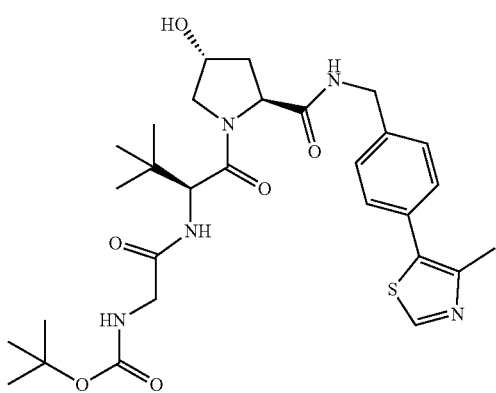
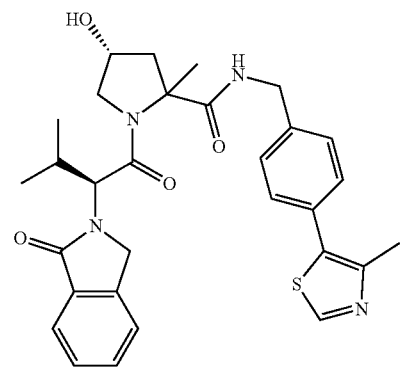
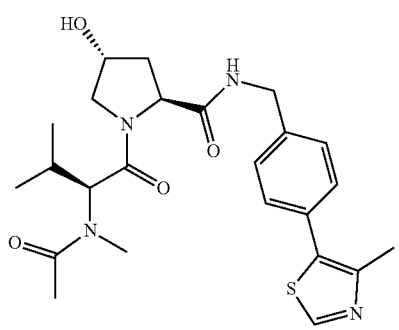
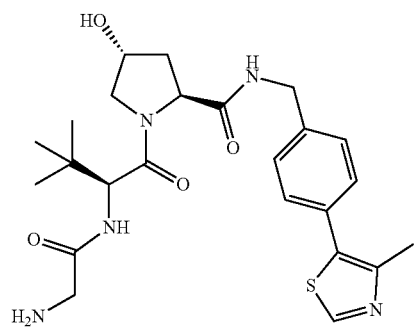
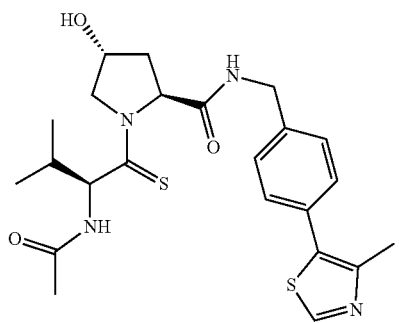
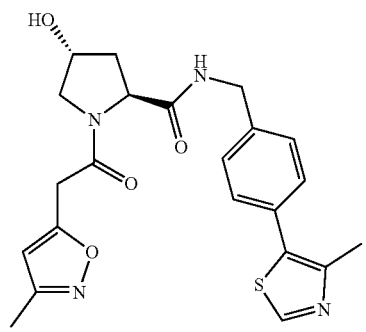
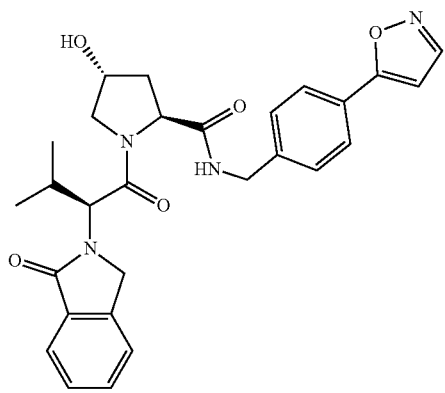
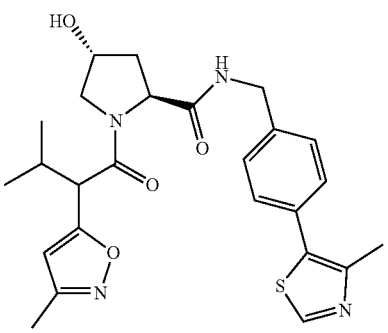

-continued
| 259 | 260 |
|---|---|
| 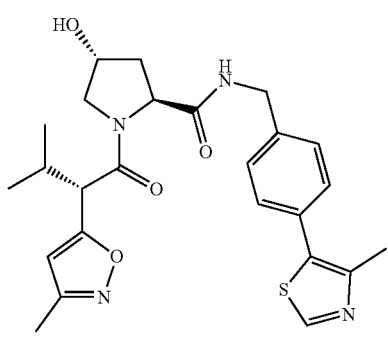 | 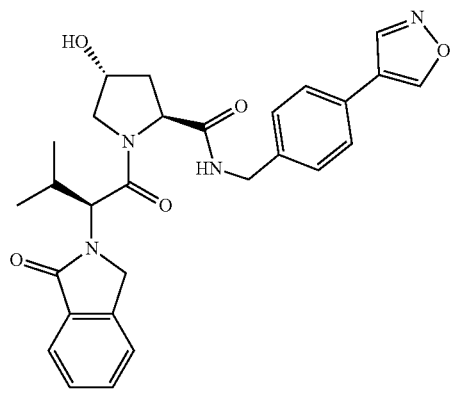 |
| 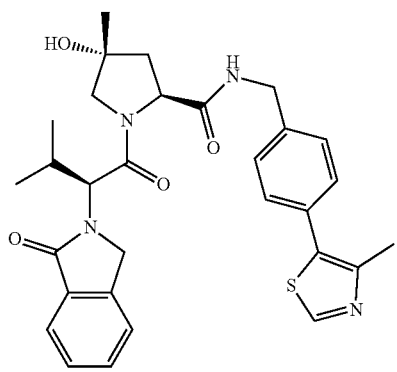 | 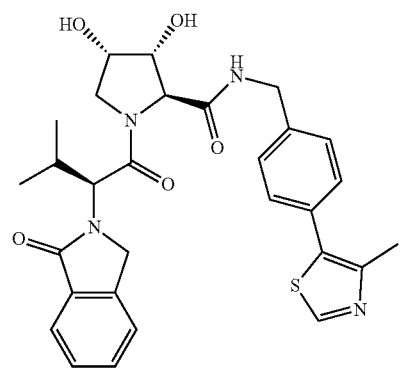 |
| 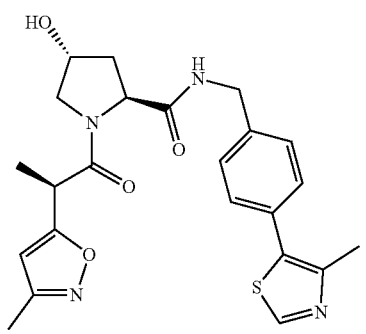 | 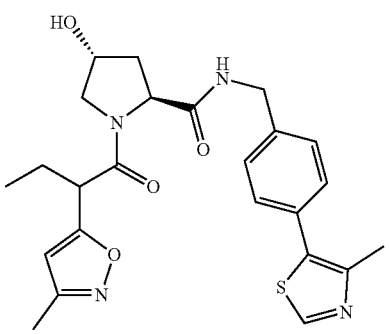 |
| 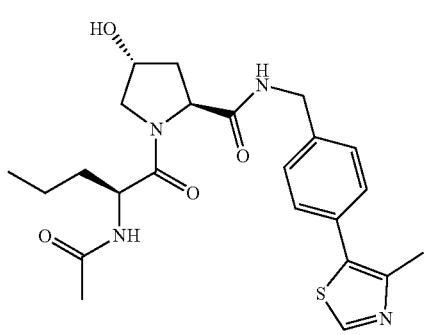 | 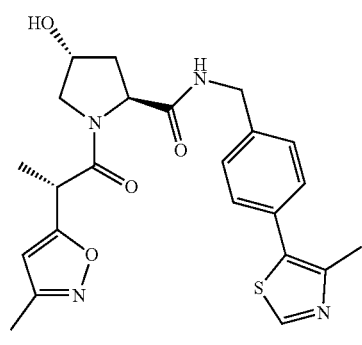 |

261
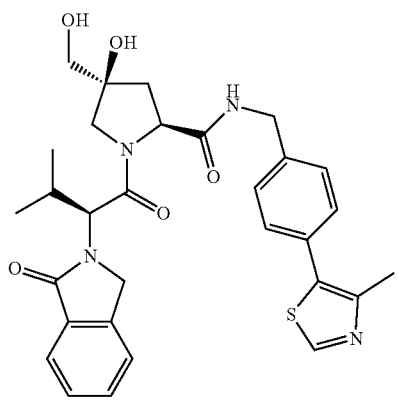
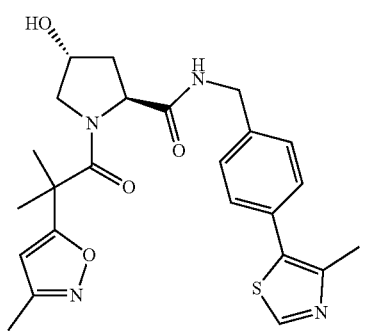
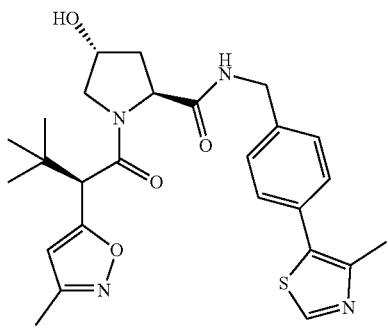
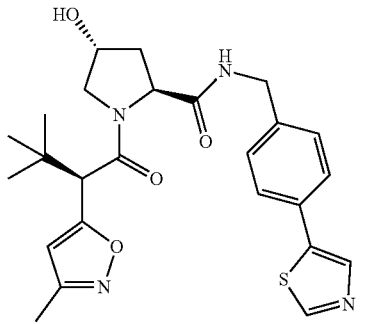
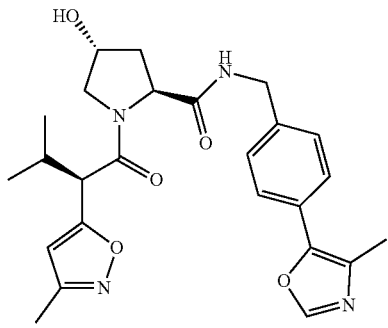
262
-continued
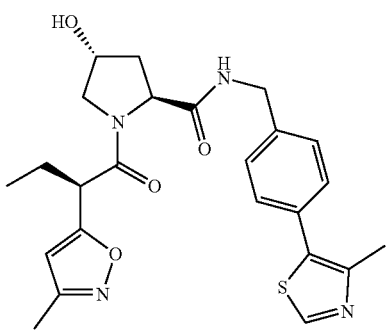
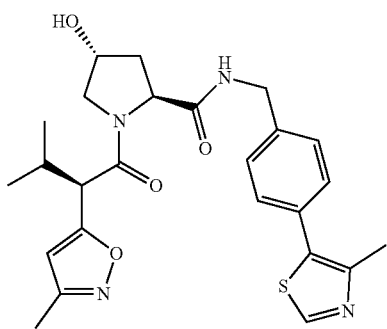
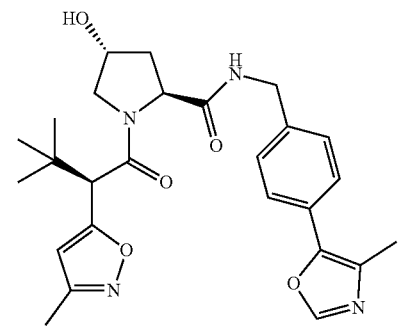
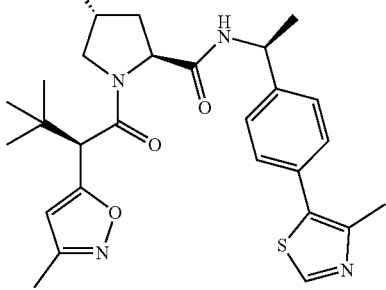
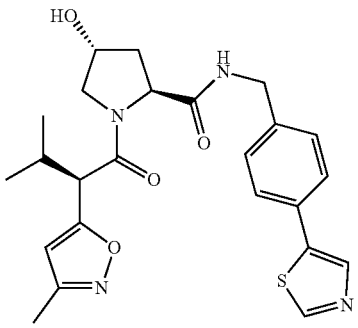

263
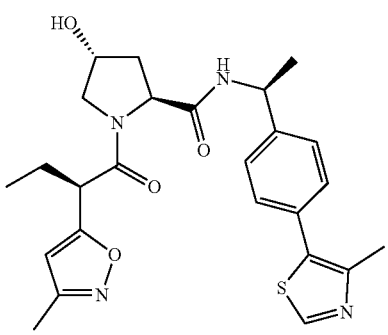
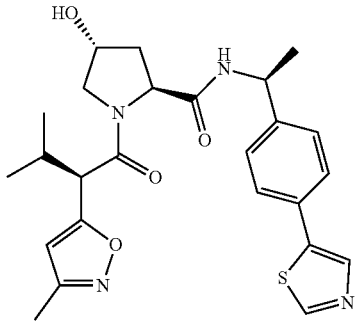
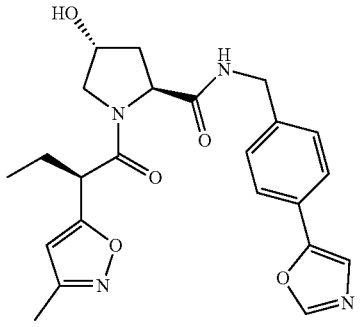
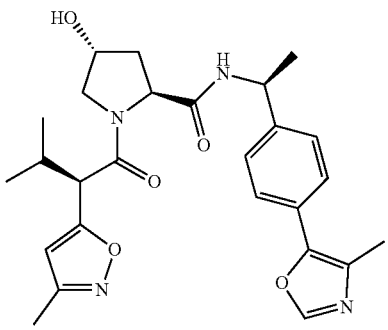
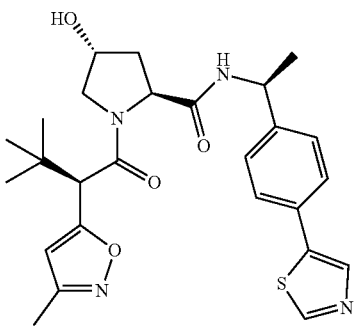
264
-continued
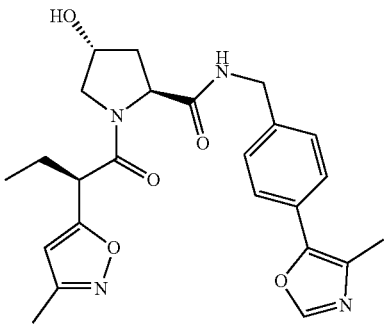
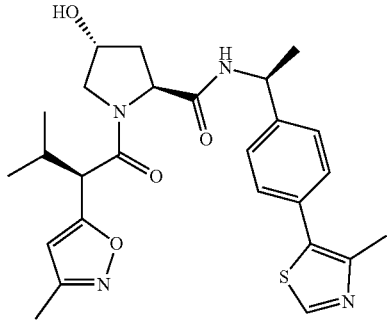
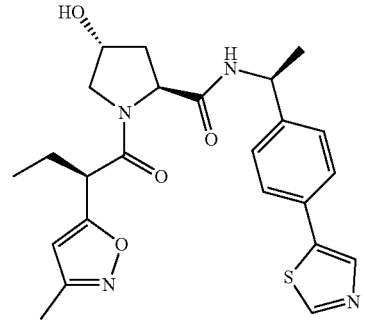
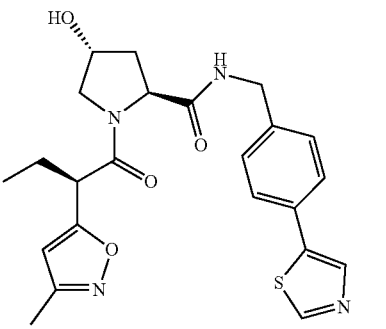
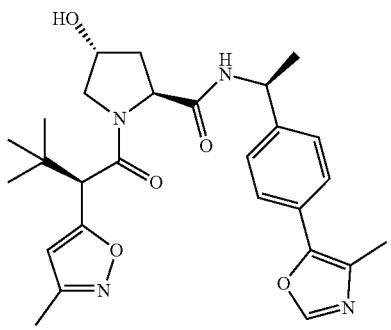

265
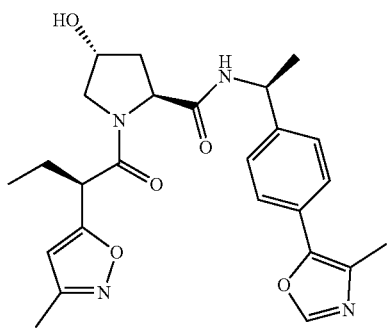
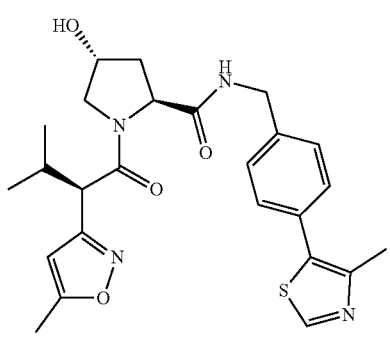
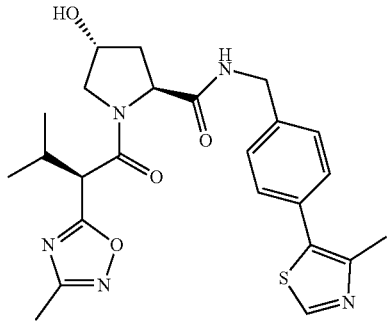
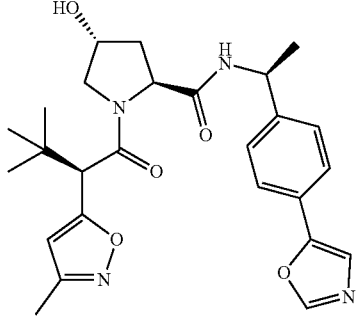
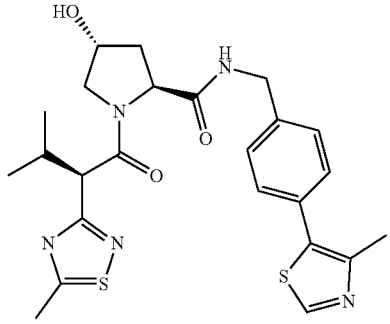
-continued
266
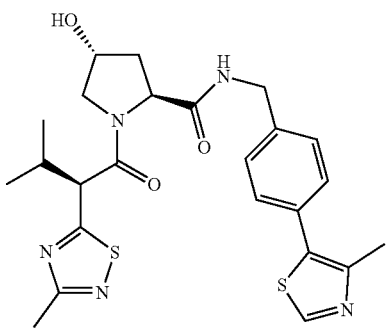
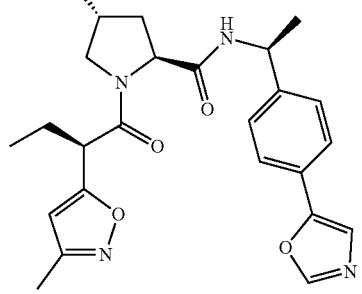
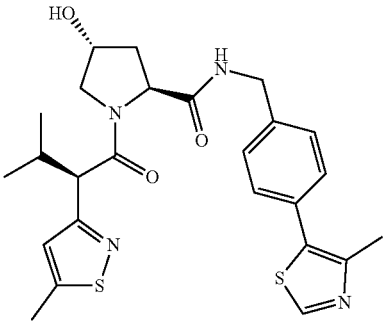
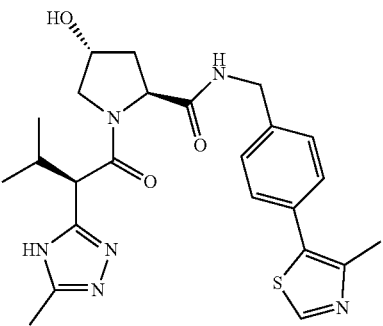
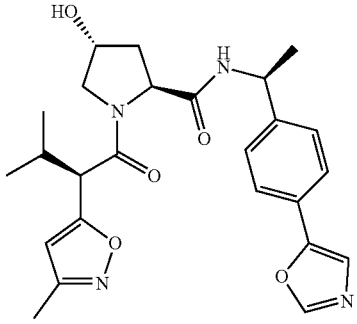

-continued
267
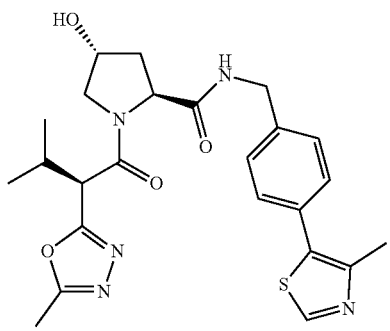
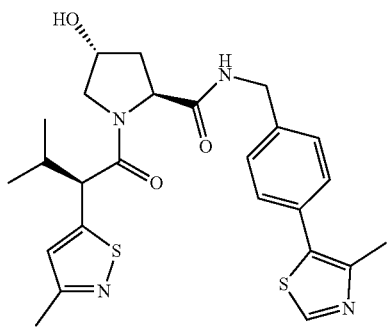
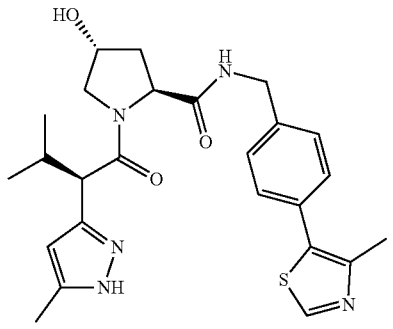
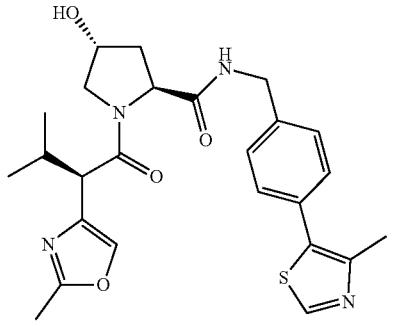
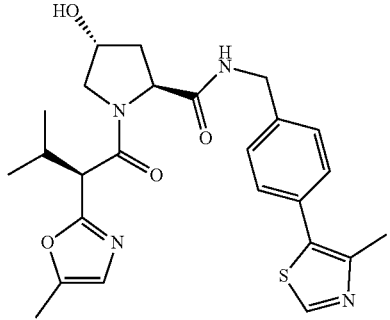
268
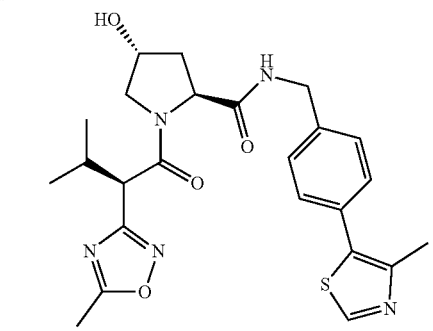
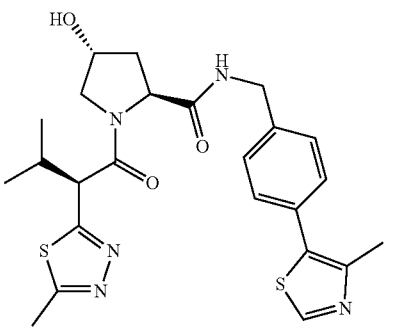
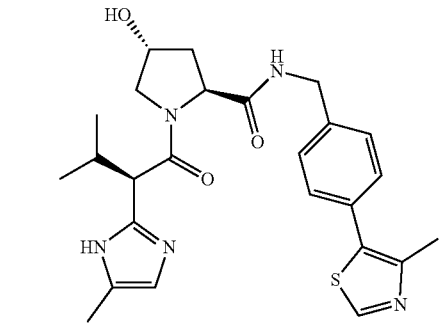
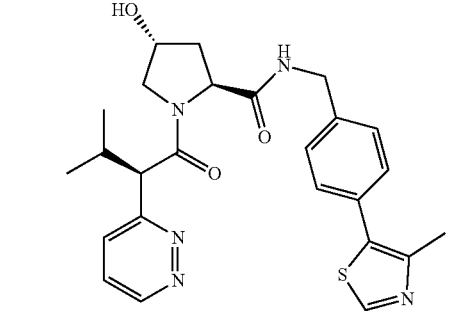
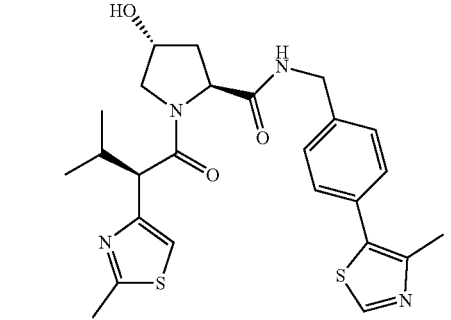

269
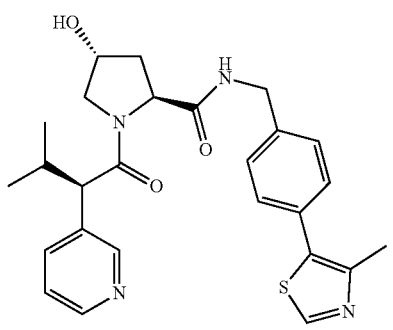
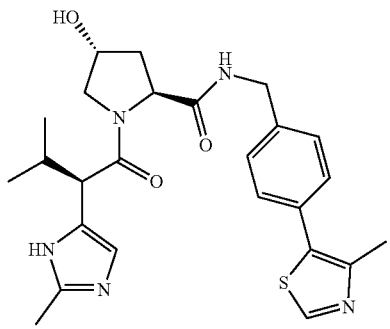
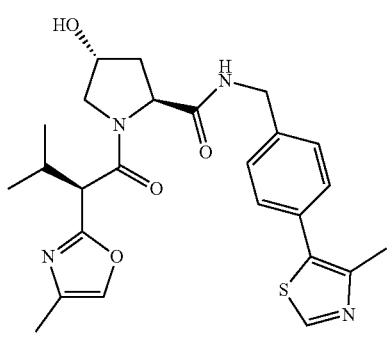
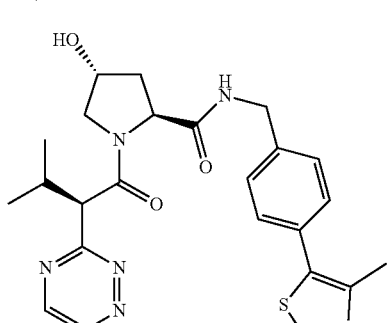
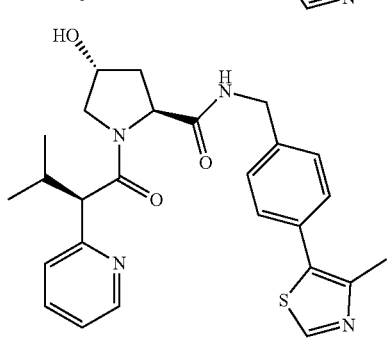
270
-continued
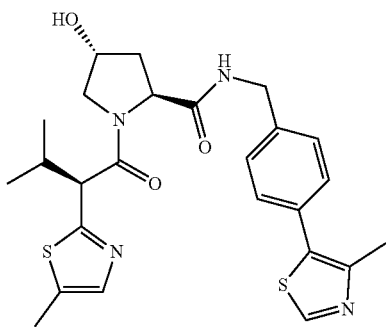
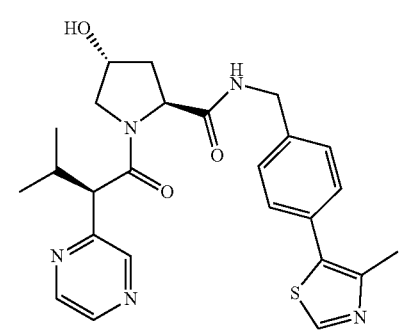
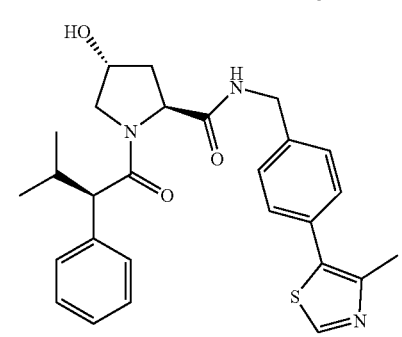
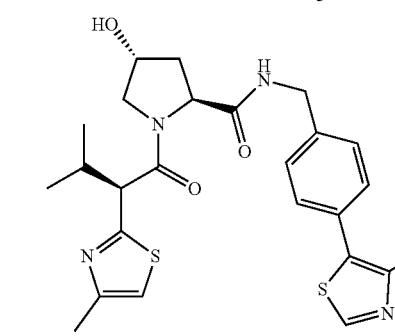
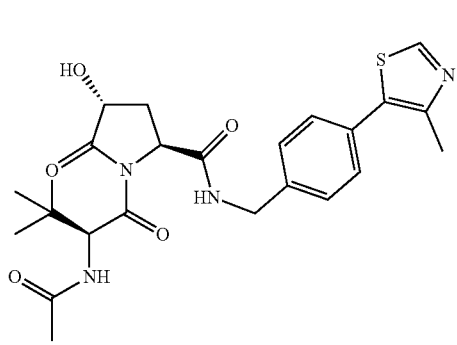

271
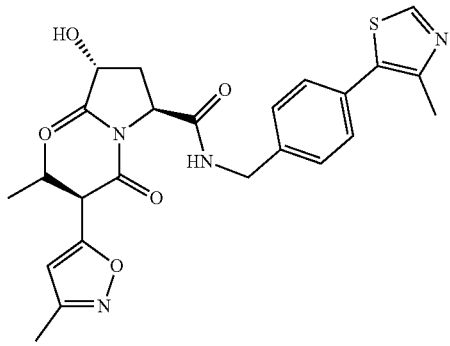
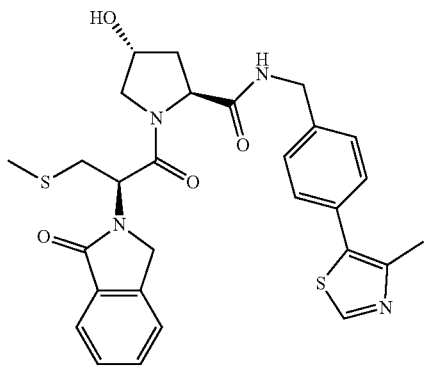
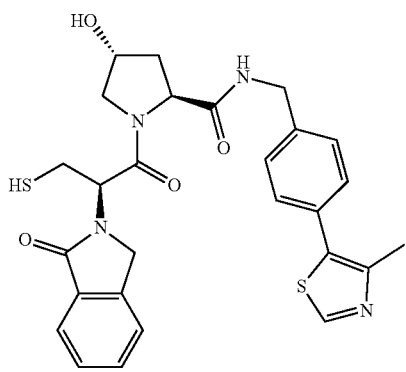
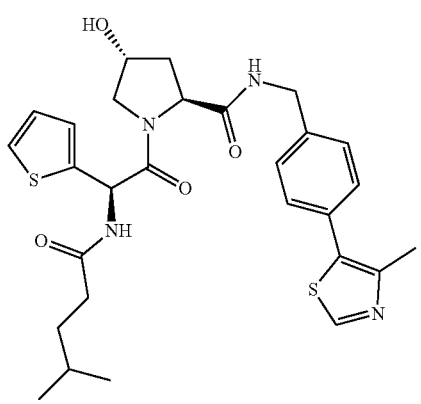
272
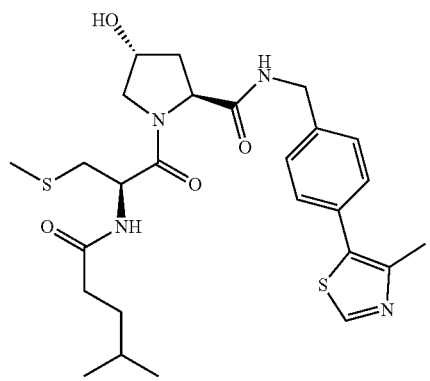
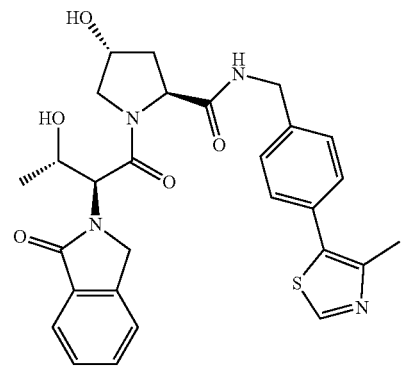
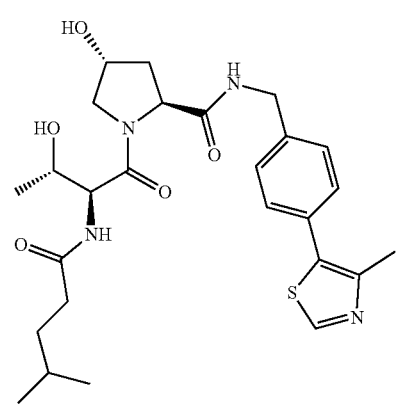
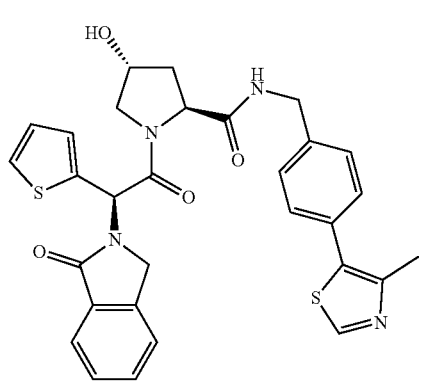

273
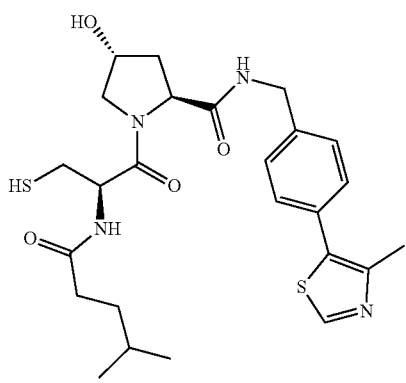
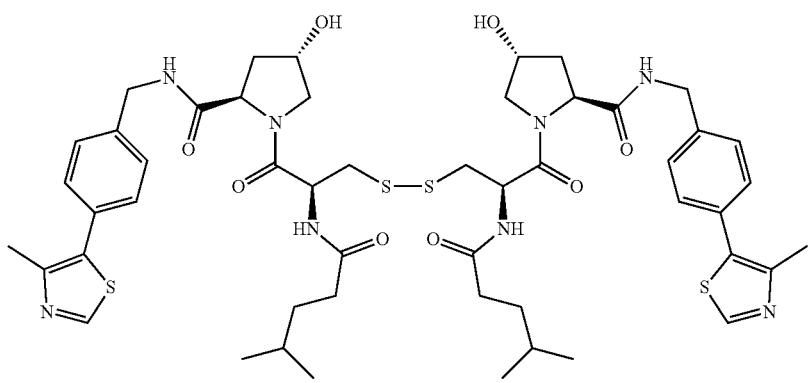
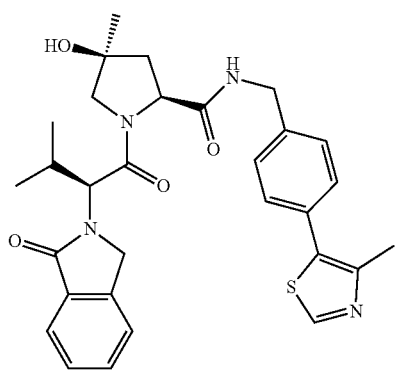
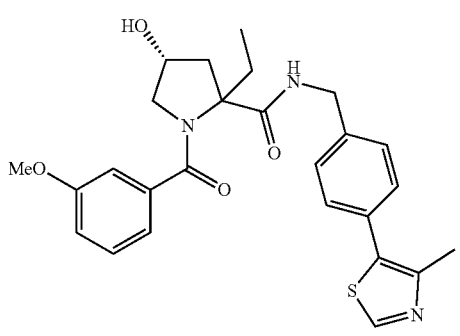
-continued
274
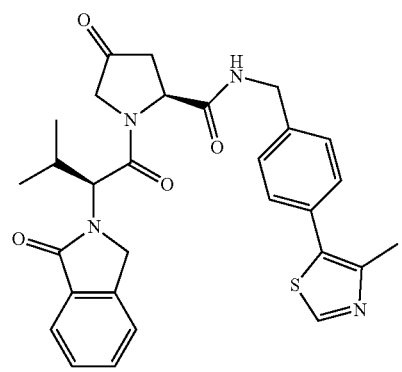
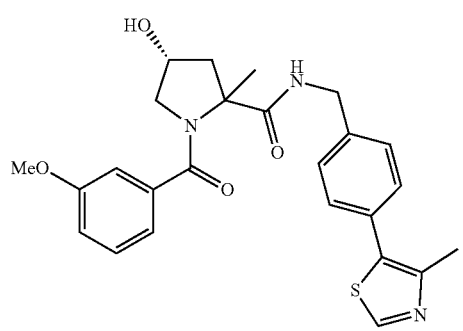
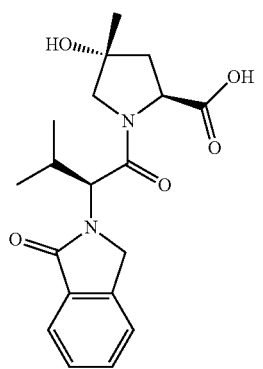

275
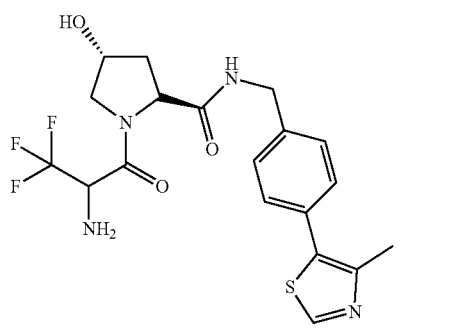
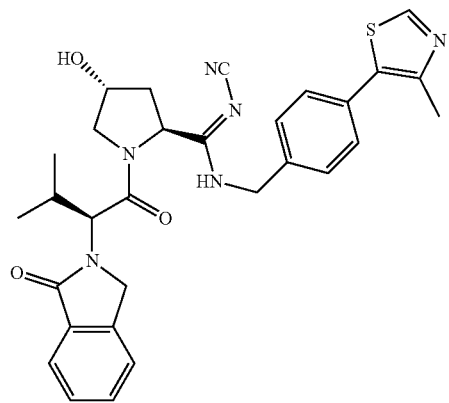
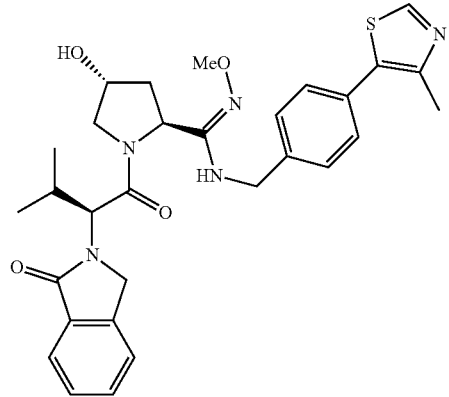
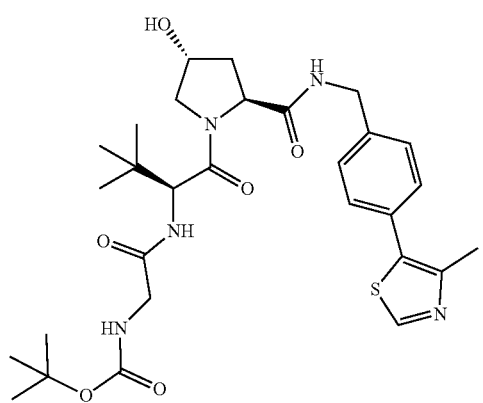
276
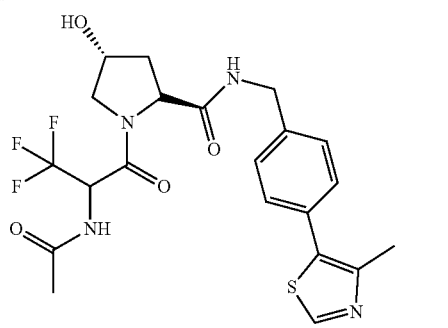
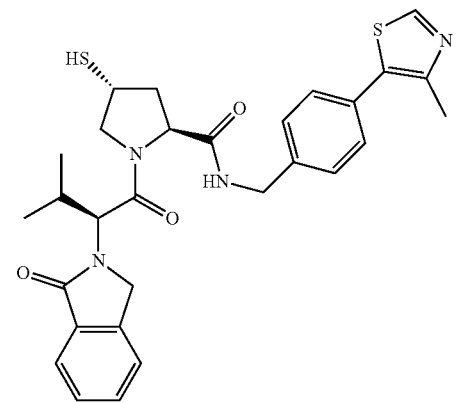
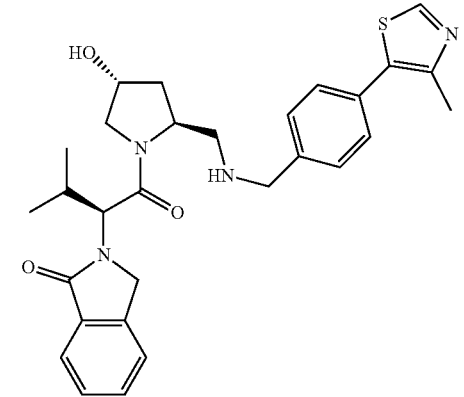
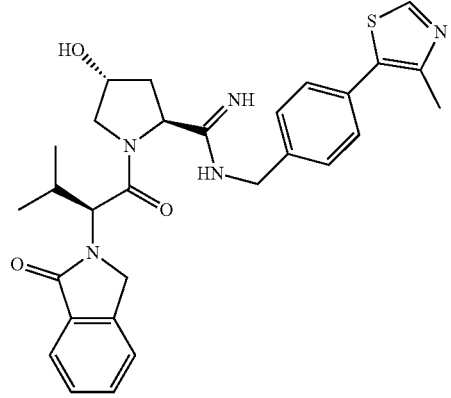

-continued
277
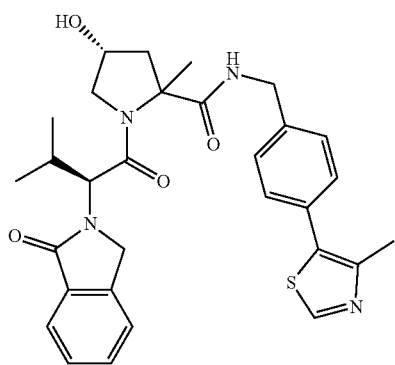
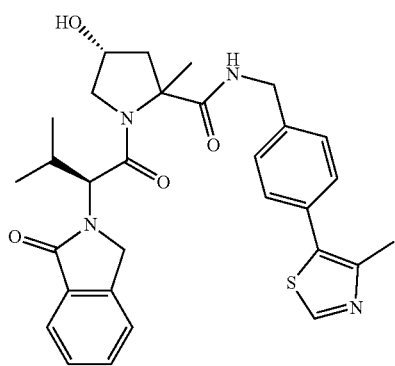
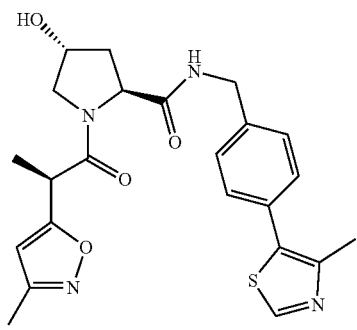
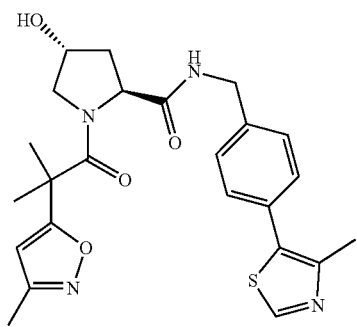
278
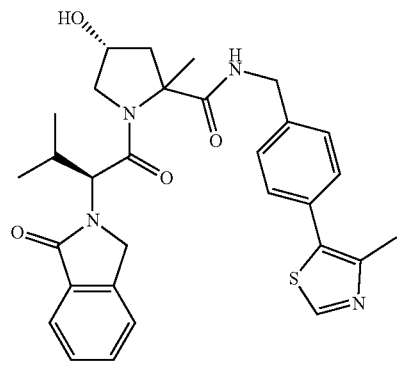
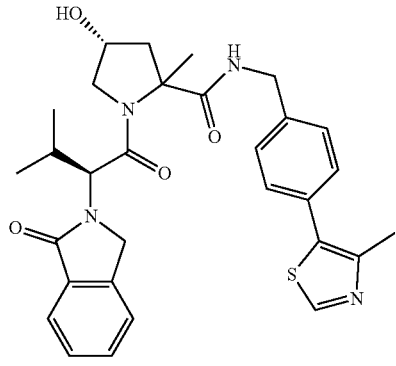
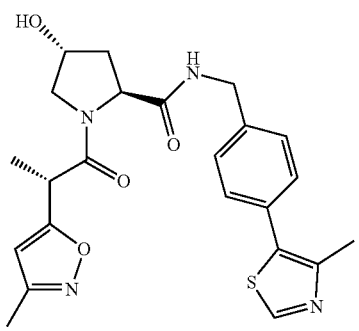
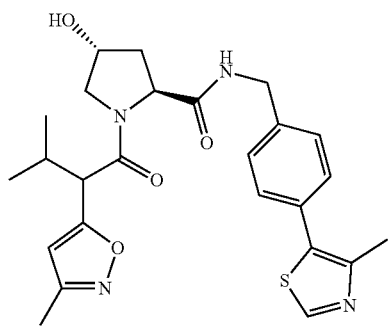

279                                                     280
-continued
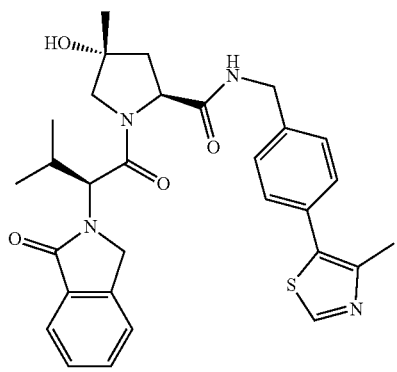
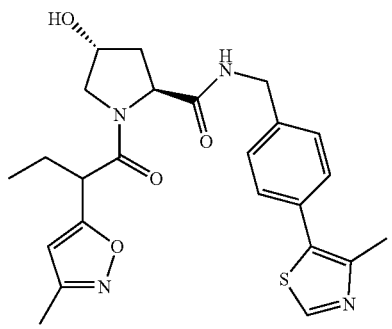
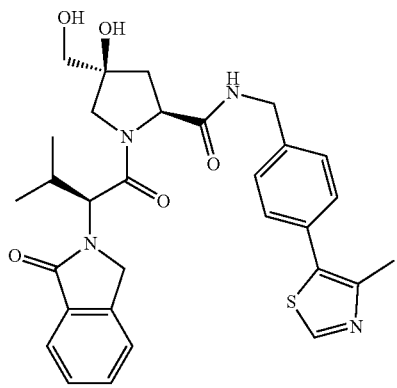
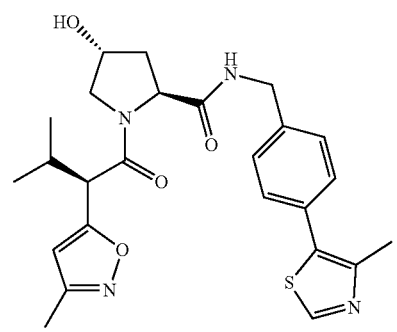
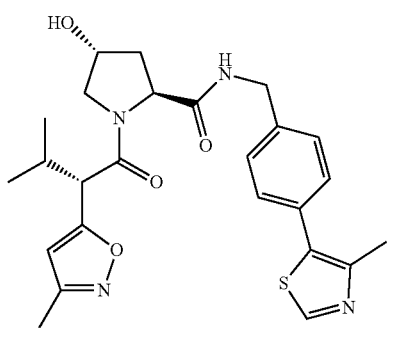
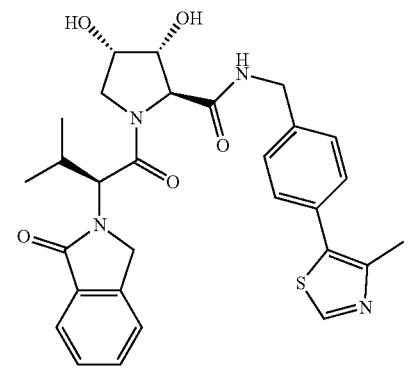
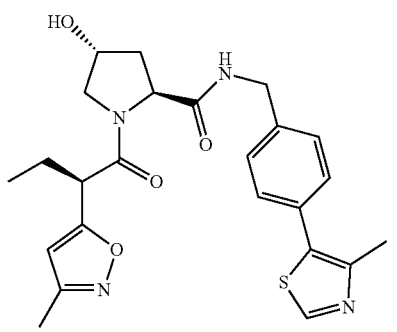
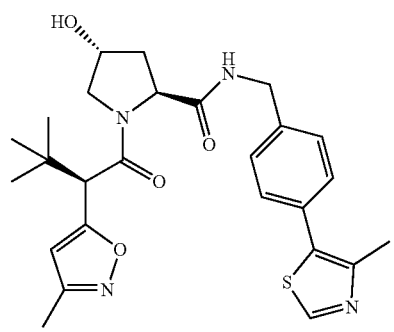

281
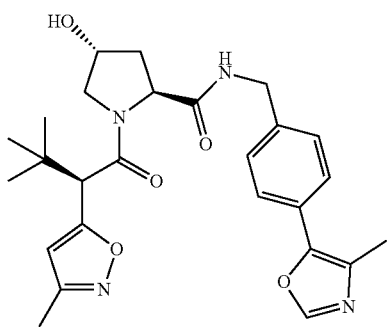
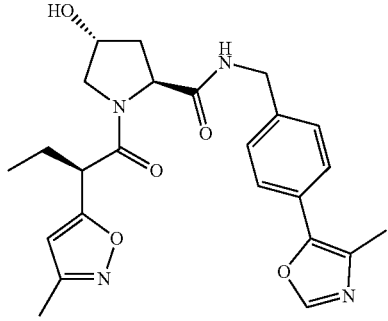
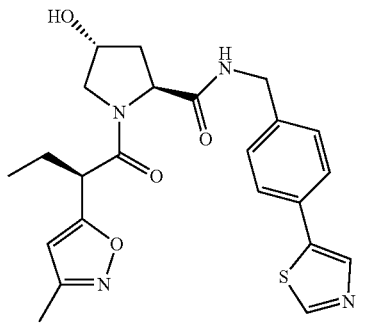
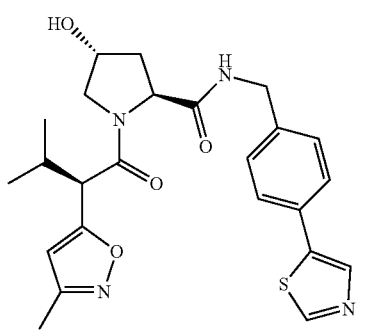
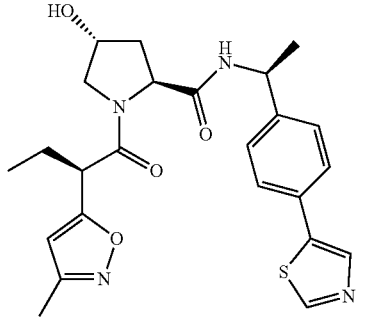
282
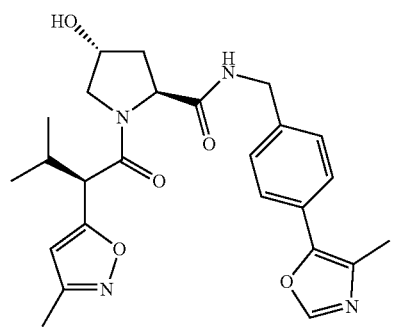
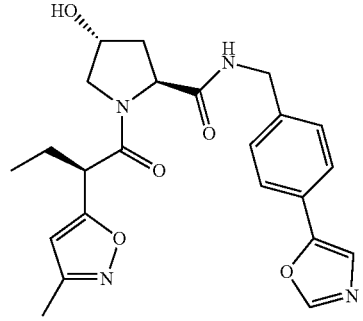
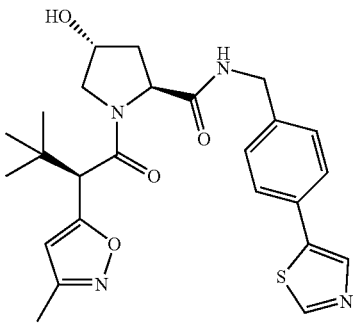
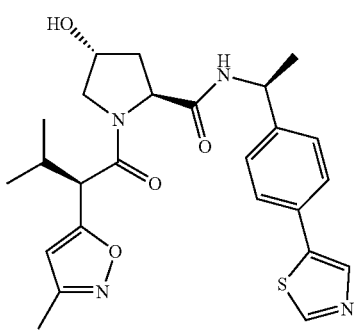
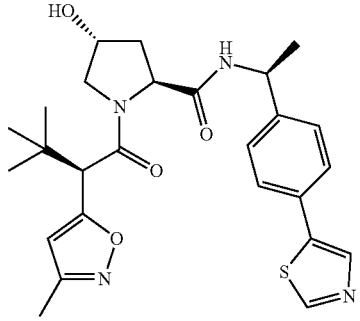

283
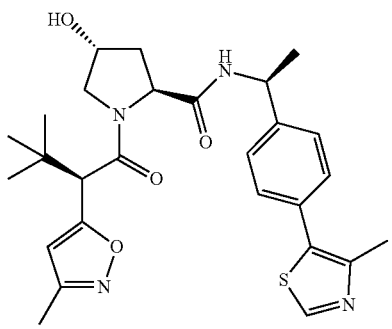
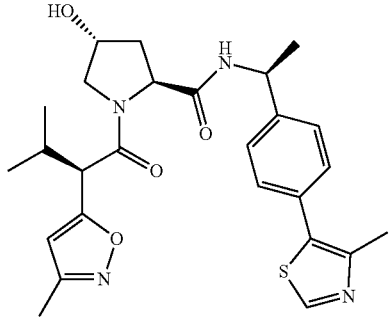
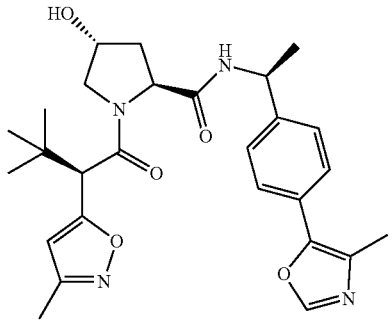
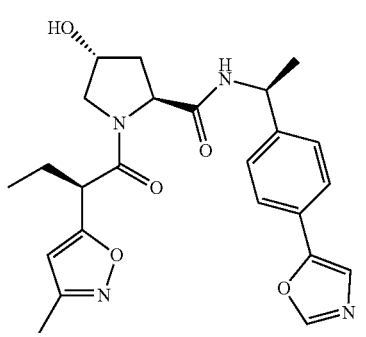
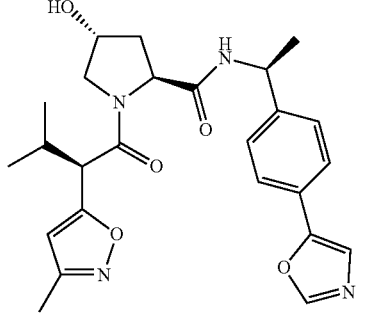
284
-continued
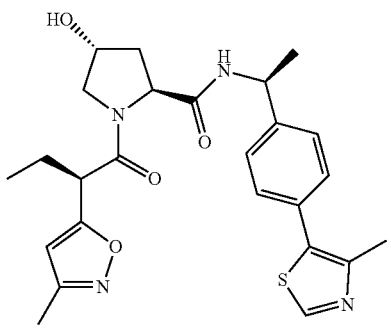
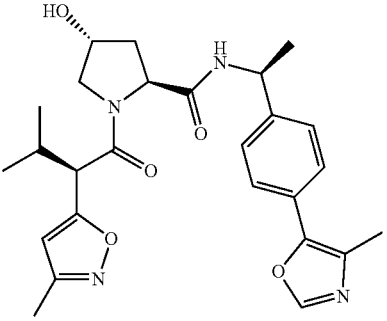
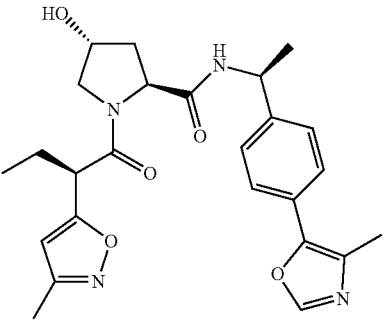
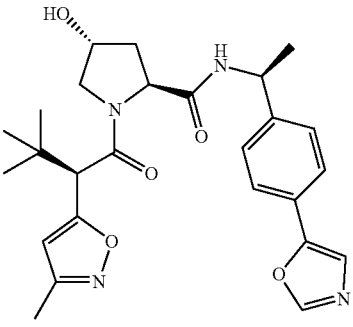
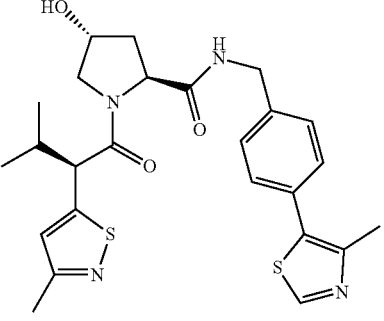

285 286
-continued
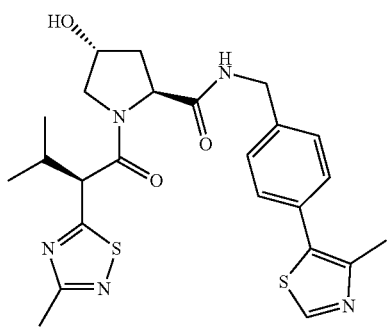
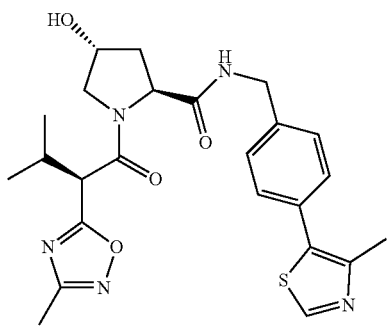
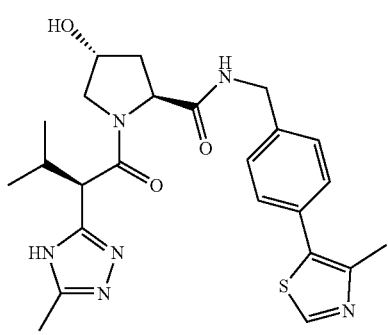
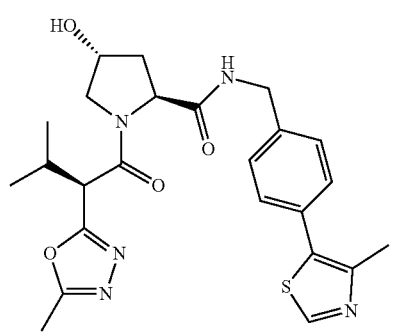
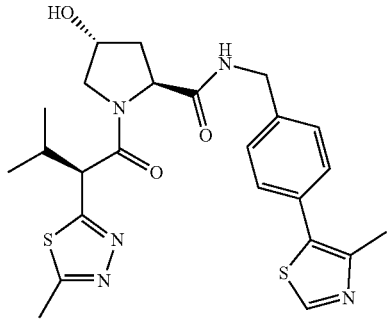
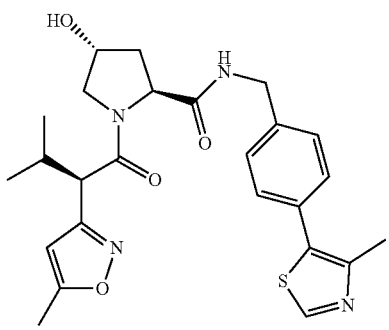
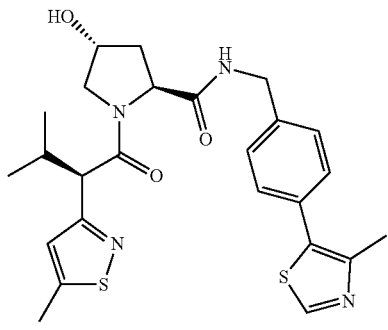
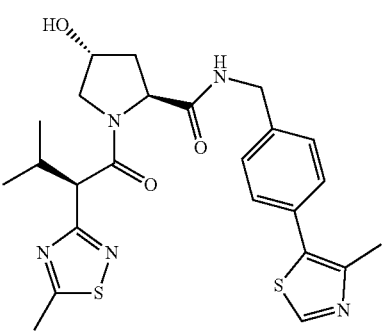
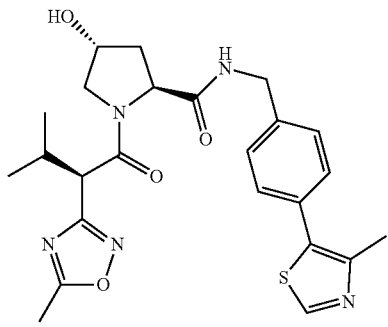
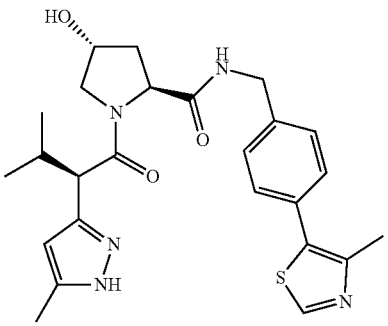

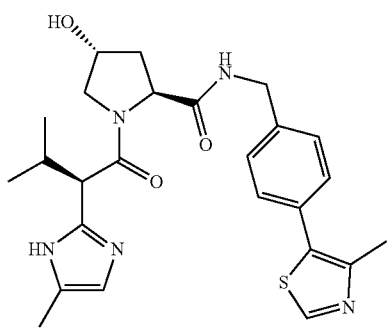
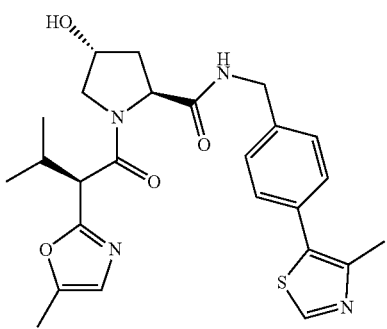
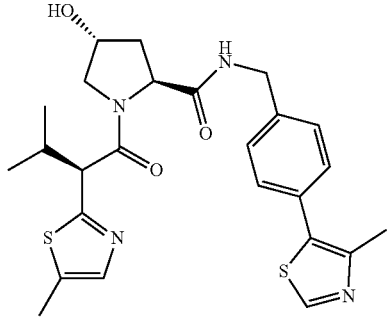
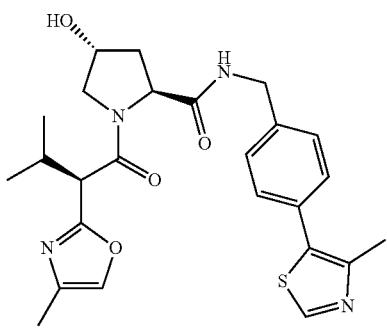
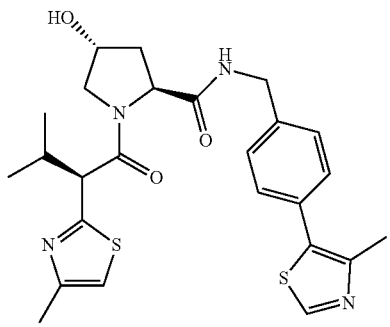
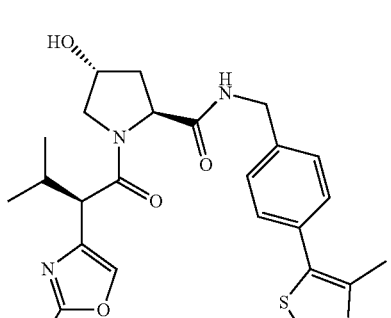
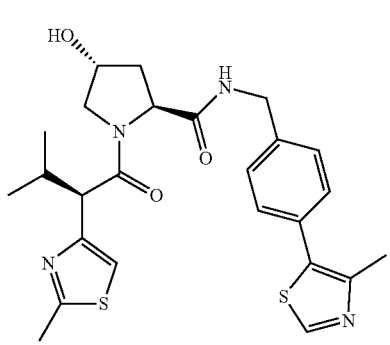
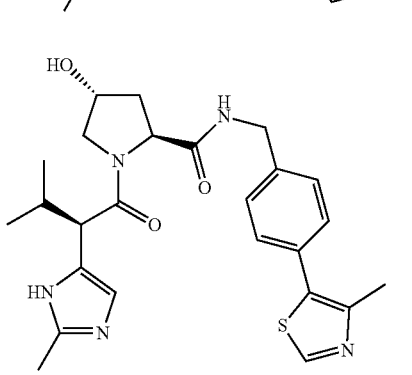
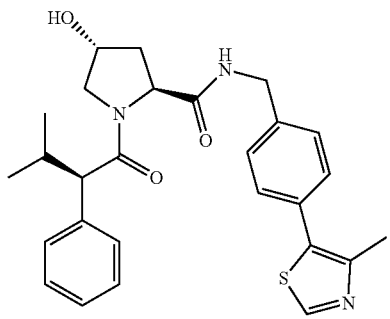
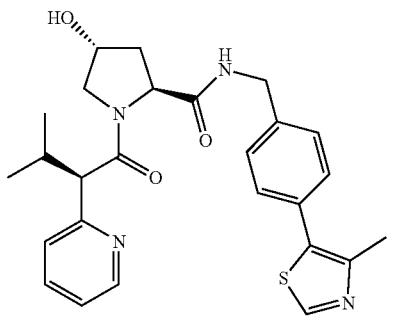

-continued
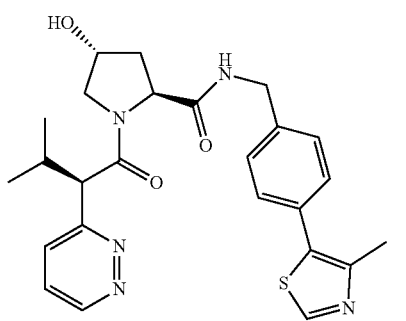
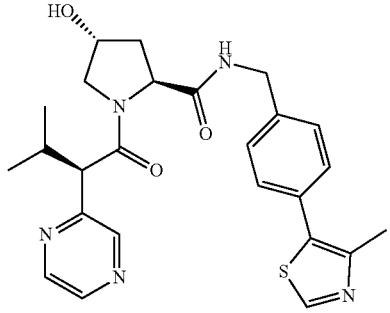
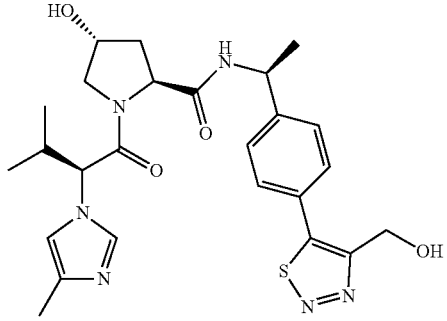
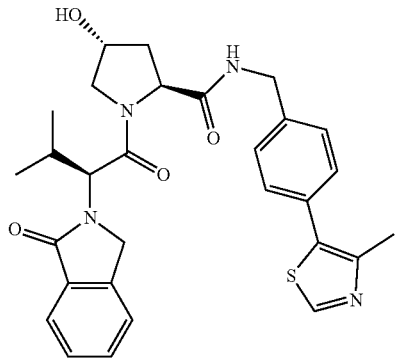
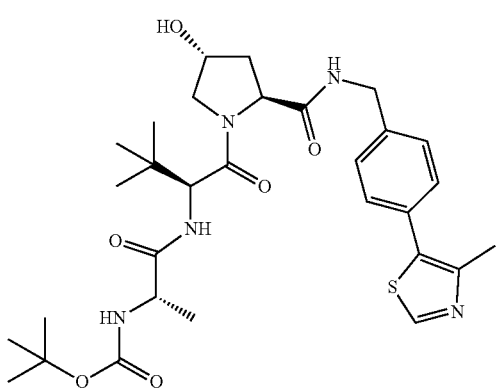
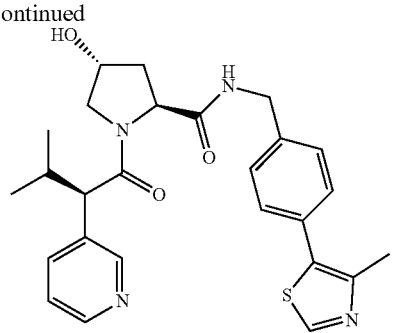
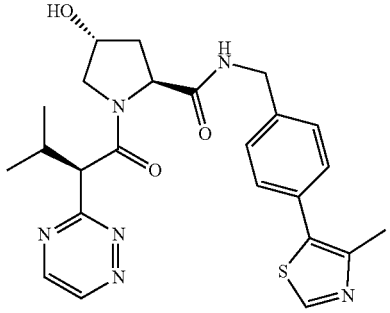
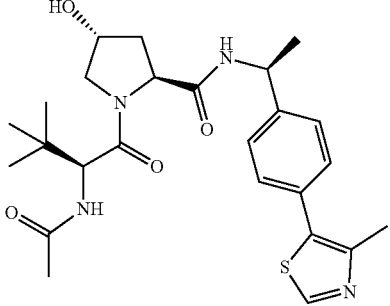
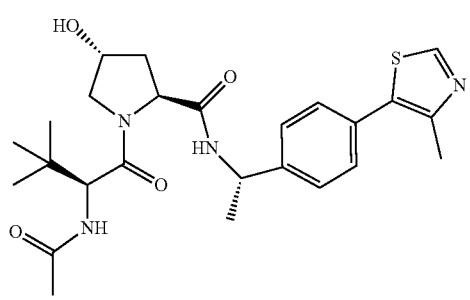
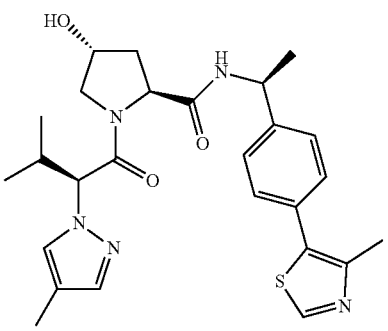

291
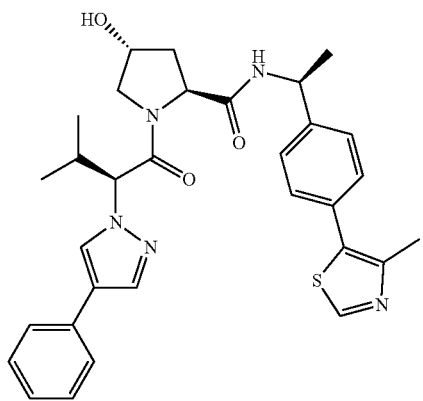
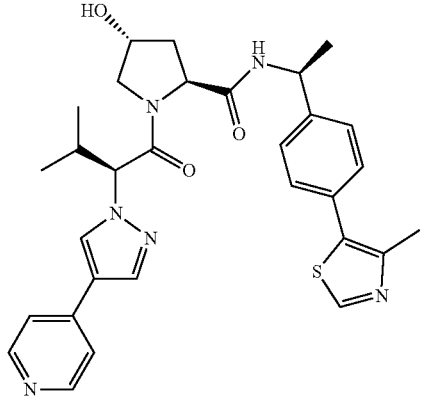
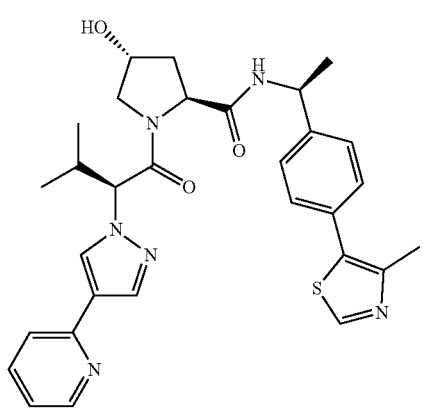
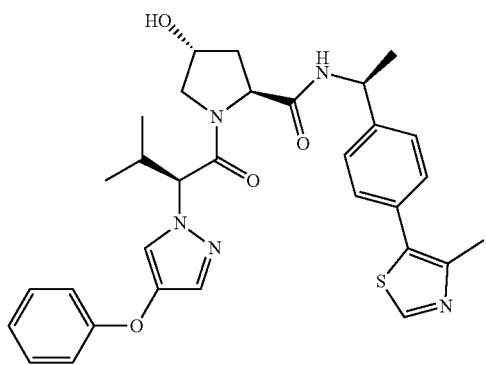
292
-continued
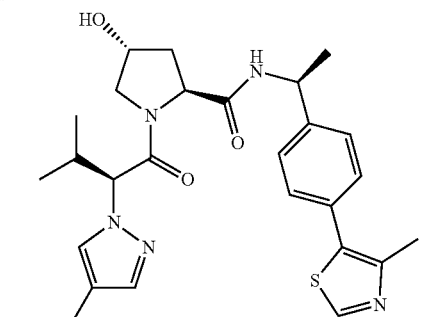
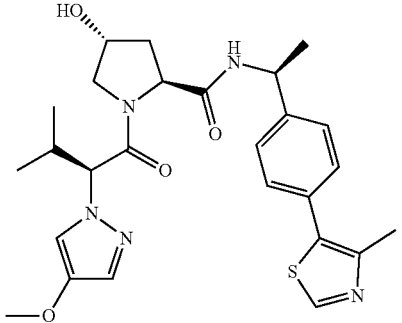
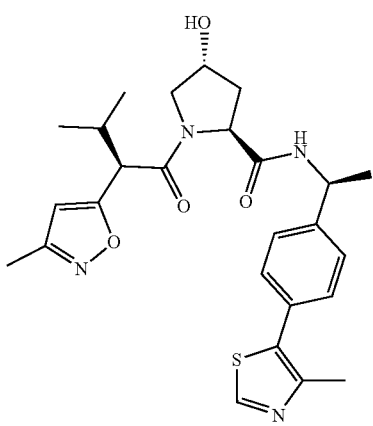
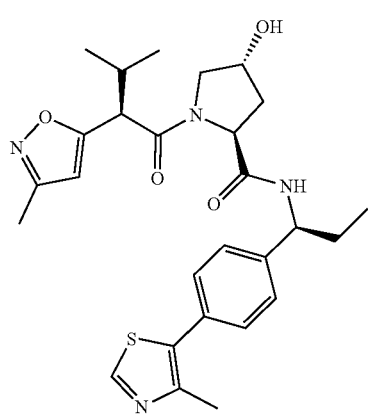
and -continued

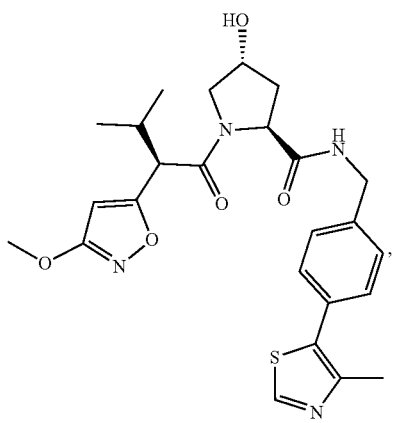

wherein the VLM may be connected to a PTM via a linker, as described herein, at any appropriate location, including, e.g., an aryl, heteroaryl, phenyl, or phenyl of an indole group, optionally via any appropriate functional group, such as an amine, ester, ether, alkyl, or alkoxy.

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., $-A^L_1 \ldots (A^L)_q$- or $-(A^L)_q$-), wherein $A^L_1$ is a group coupled to PTM, and $(A^L)_q$ is a group coupled to ULM.

In certain embodiments, the linker group L has the chemical structure $-(A^L)_q$-:

$(A^L)_q$ is a group that is connected to at least one of a ULM moiety, a PTM moiety, or a combination thereof;

q of the linker is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $CC-C_{1-8}$alkyl, CCH, $CH=CH(C_{1-8}alkyl)$, $C(C_{1-8}alkyl)=CH(C_{1-8}alkyl)$, $C(C_{1-8}alkyl)=C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)$ $SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$.

In certain embodiments, q of the linker is an integer greater than or equal to 0. In certain embodiments, q is an integer greater than or equal to 1.

In certain embodiments, e.g., where q of the linker is greater than 2, $(A^L)_q$ is a group which is connected to ULM, and $A^L_1$ and $(A^L)_q$ are connected via structural units of the linker (L).

In certain embodiments, e.g., where q of the linker is 2, $(A^L)_q$ is a group which is connected to $A^L_1$ and to a ULM.

In certain embodiments, e.g., where q of the linker is 1, the structure of the linker group L is $-A^L_1$-, and $A^L_1$ is a group which is connected to a ULM moiety and a PTM moiety.

In certain embodiments, the linker (L) comprises a group represented by a general structure selected from the group consisting of:

—$NR(CH_2)_n$-(lower alkyl)-, —$NR(CH_2)_n$-(lower alkoxyl)-, —$NR(CH_2)_n$-(lower alkoxyl)-$OCH_2$—, —$NR(CH_2)_n$-(lower alkoxyl)-(lower alkyl)-$OCH_2$—, —$NR(CH_2)_n$-(cycloalkyl)-(lower alkyl)-$OCH_2$—, —$NR(CH_2)_n$-(hetero cycloalkyl)-, —$NR(CH_2CH_2O)_n$-(lower alkyl)-O—$CH_2$—, —$NR(CH_2CH_2O)_n$-(hetero cycloalkyl)-O—$CH_2$—, —$NR(CH_2CH_2O)_n$-Aryl-O—$CH_2$—, —$NR(CH_2CH_2O)_n$-(hetero aryl)-O—$CH_2$—, —$NR(CH_2CH_2O)_n$-(cycloalkyl)-O-(hetero aryl)-O—$CH_2$—, —$NR(CH_2CH_2O)_n$-(cycloalkyl)-O-Aryl-O—$CH_2$—, —$NR(CH_2CH_2O)_n$-(lower alkyl)-NH-Aryl-O—$CH_2$—, —$NR(CH_2CH_2O)_n$-(lower alkyl)-O-Aryl-$CH_2$, —$NR(CH_2CH_2O)_n$-cycloalkyl-O-Aryl-, —$NR(CH_2CH_2O)_n$-cycloalkyl-O-(hetero aryl)1-, —$NR(CH_2CH_2)n$-(cycloalkyl)-O-(heterocycle)-$CH_2$, —$NR(CH_2CH_2)n$-(heterocycle)-(heterocycle)-$CH_2$, —$N(R_1R_2)$-(heterocycle)-$CH_2$; where n of the linker can be 0 to 10;

R of the linker can be H, lower alkyl;

R1 and R2 of the linker can form a ring with the connecting N.

In certain embodiments, the linker (L) comprises a group represented by a general structure selected from the group consisting of:

—N(R)—(CH2)$_m$—O(CH2)$_n$—O(CH2)$_o$—O(CH2)$_p$—O(CH2)$_q$—O(CH2)$_r$—OCH2-, —O—(CH2)$_m$—O(CH2)$_n$—O(CH2)$_o$—O(CH2)$_p$—O(CH2)$_q$—O(CH2)$_r$-OCH2-, —O—(CH2)$_m$—O(CH2)$_n$—O(CH2)$_o$—O(CH2)$_p$—O(CH2)$_q$—O(CH2)$_r$—O—; —N(R)—(CH2)$_m$—O(CH2)$_n$—O(CH2)$_o$—O(CH2)$_p$—O(CH2)$_q$—O(CH2)$_r$—O—; —(CH2)$_m$—O(CH2)$_n$—O(CH2)$_o$—O(CH2)$_p$—O(CH2)$_q$—O(CH2)$_r$—O—; —(CH2)$_m$—O(CH2)$_n$—O(CH2)$_o$—O(CH2)$_p$—O(CH2)$_q$—O(CH2)$_r$-OCH2-;

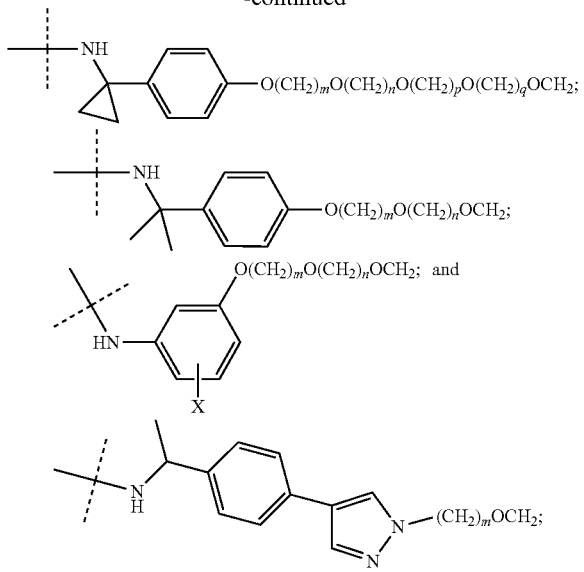
wherein
m, n, o, p, q, and r of the linker are independently 0, 1, 2, 3, 4, 5, 6;
when the number is zero, there is no N—O or O—O bond
R of the linker is H, methyl and ethyl;
X of the linker is H and F
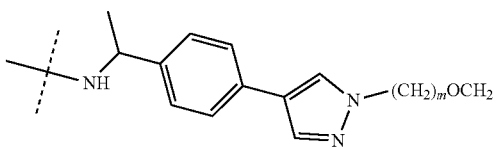
where m of the linker can be 2, 3, 4, 5
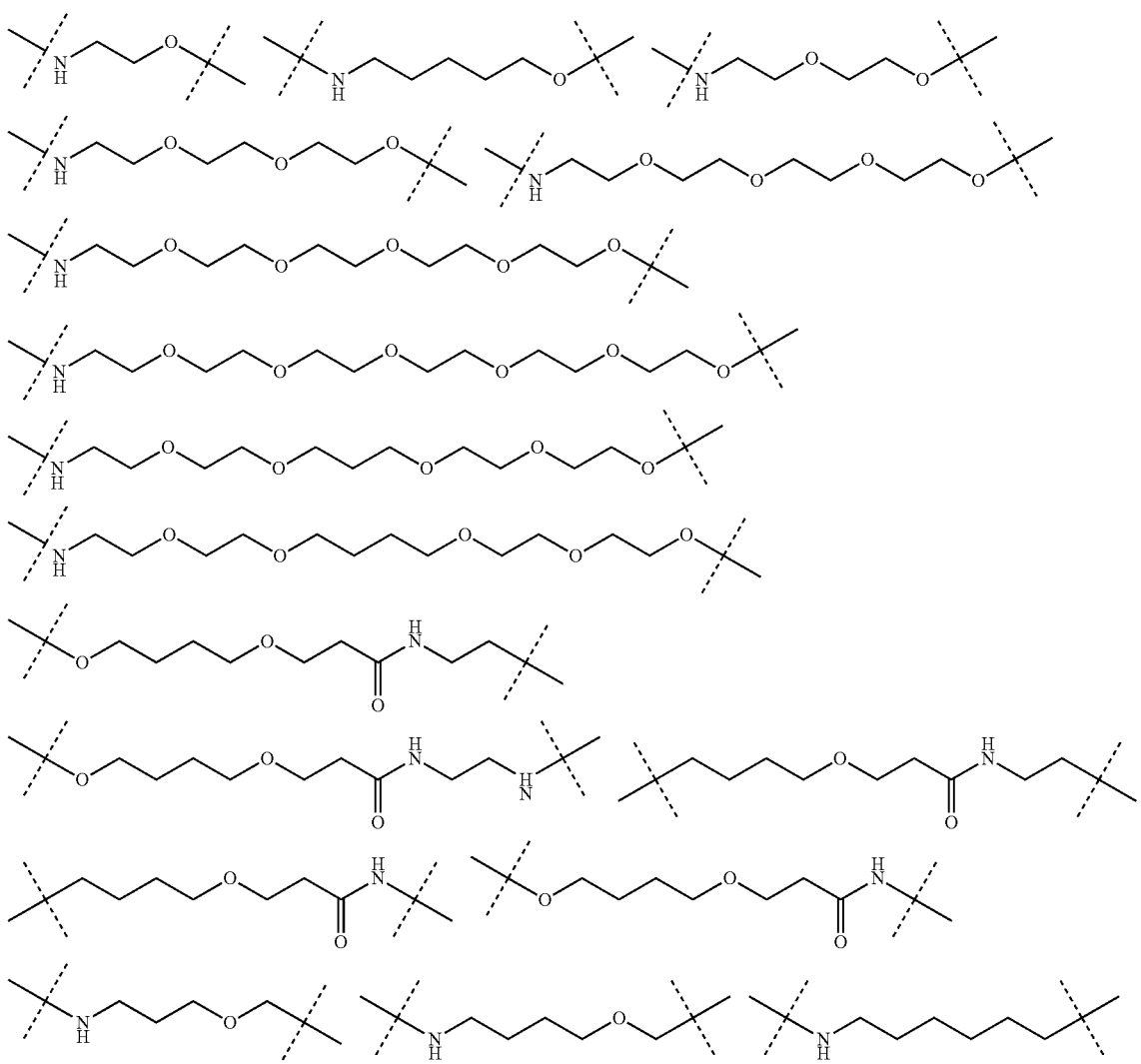

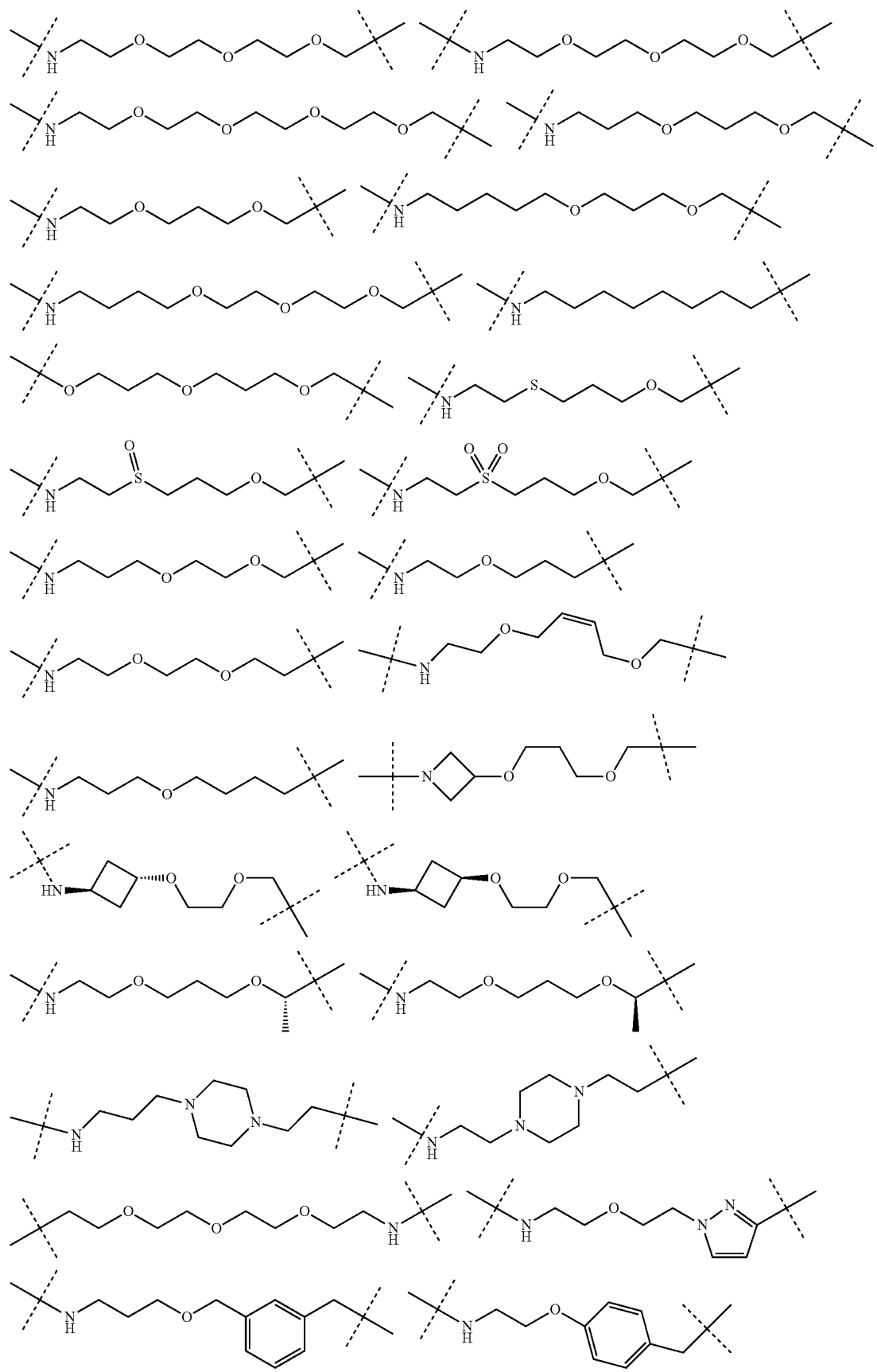

-continued
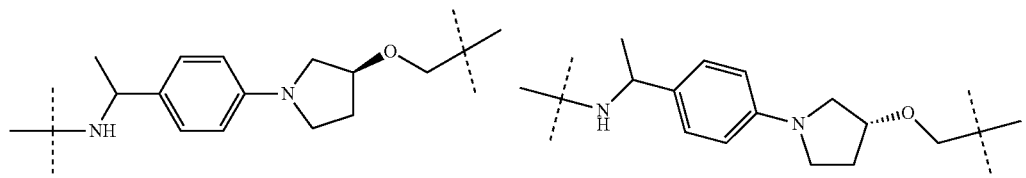
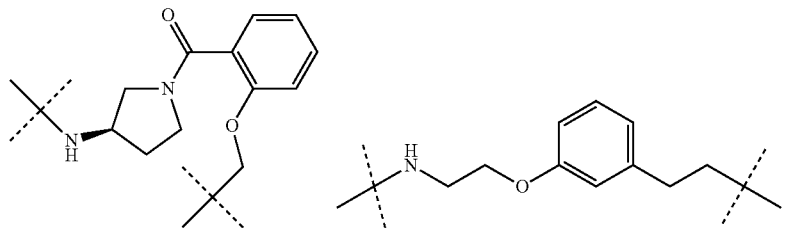
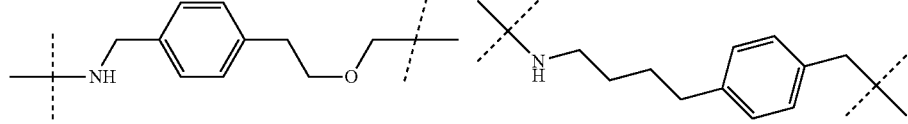
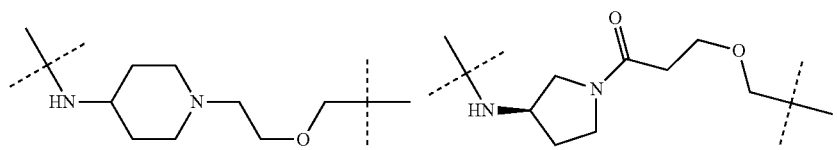
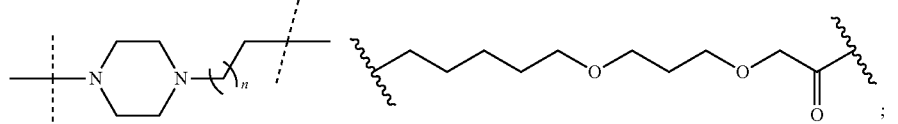
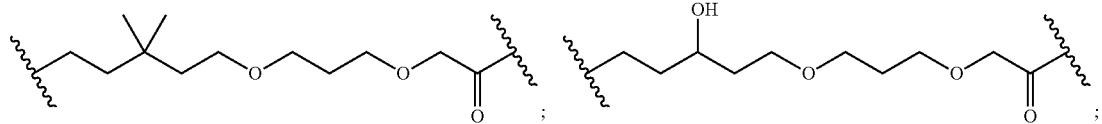
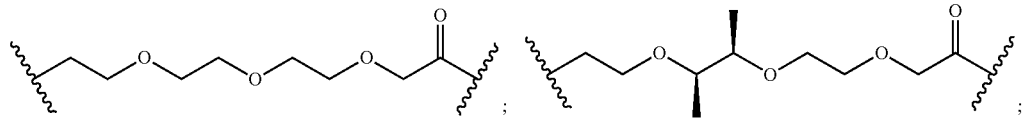
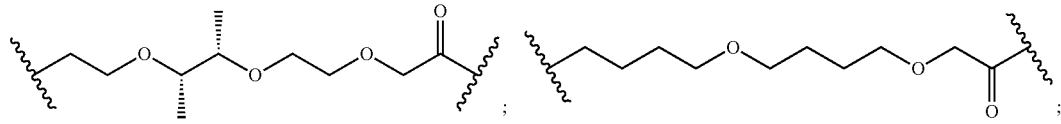
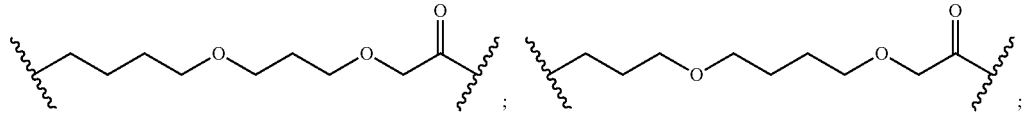
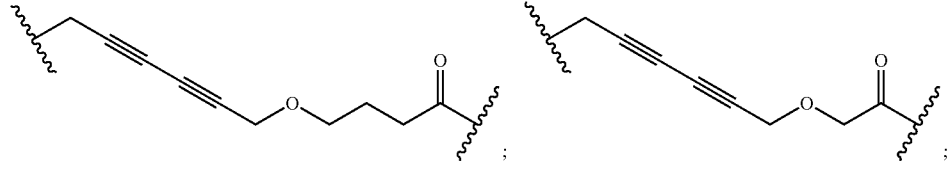
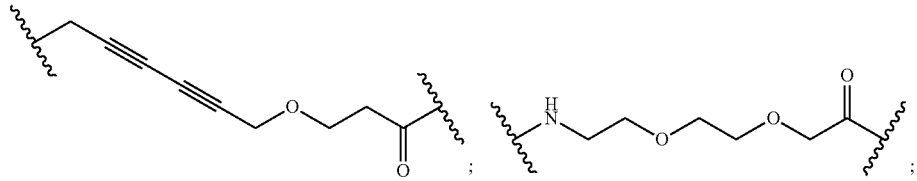

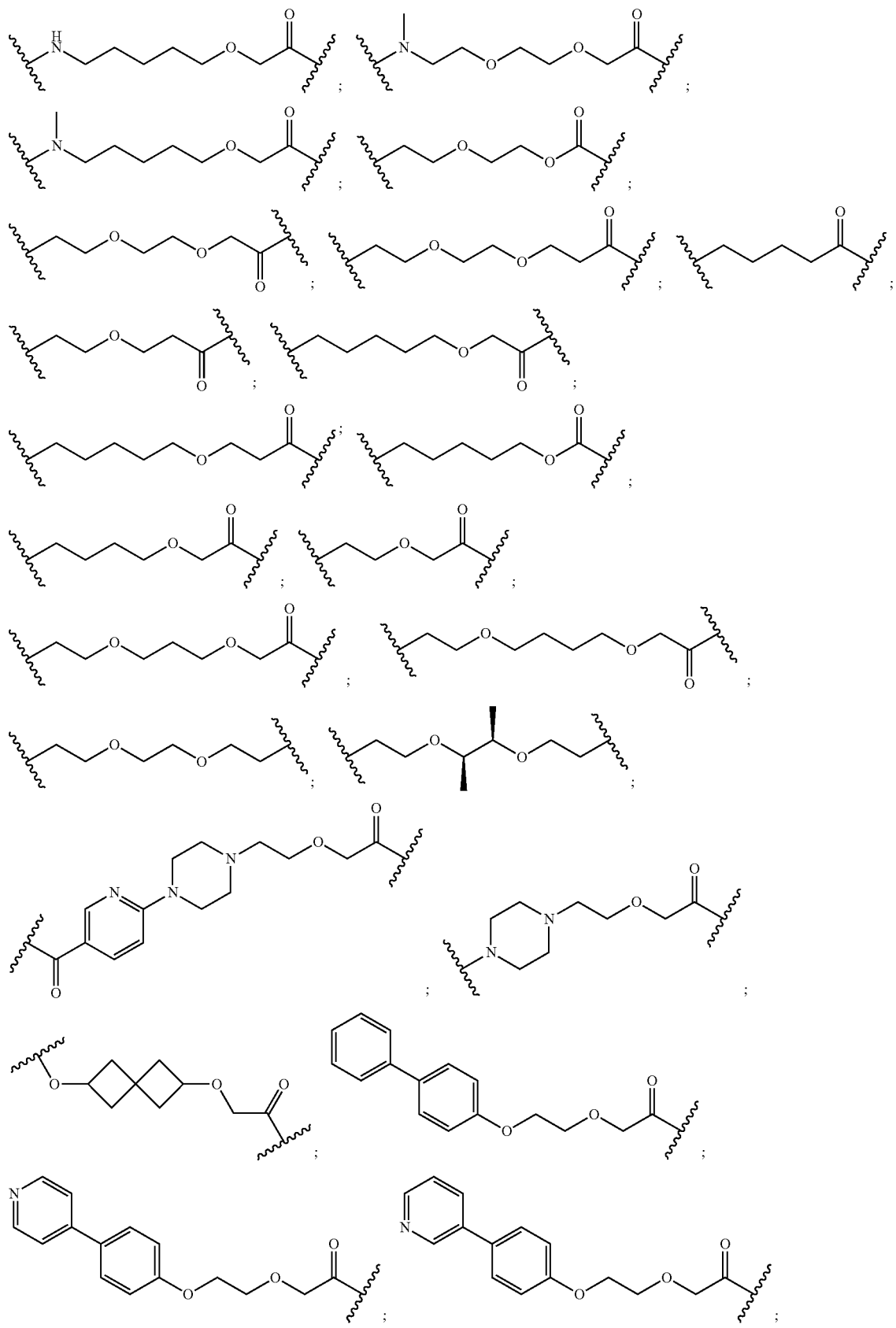

305
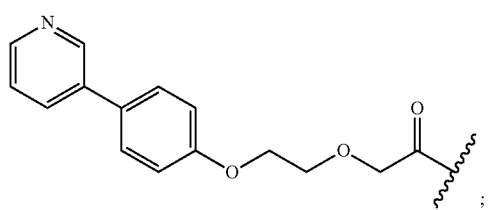
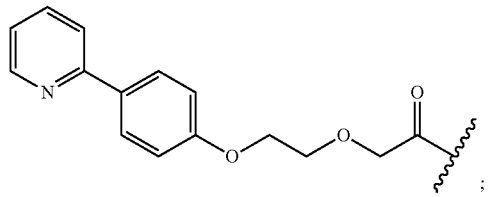
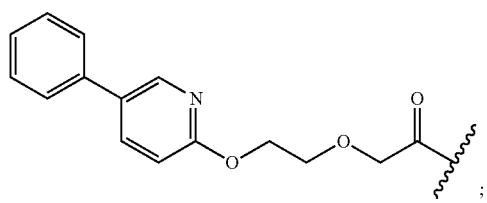
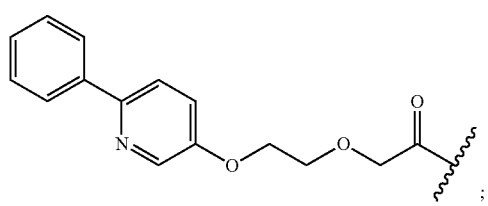
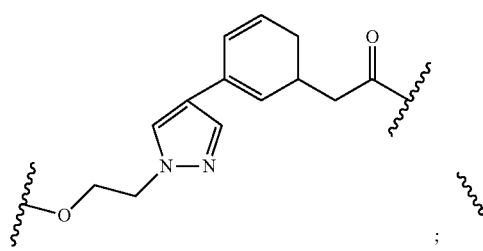
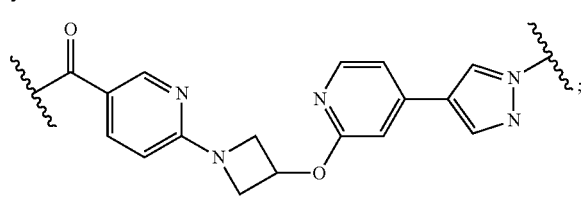
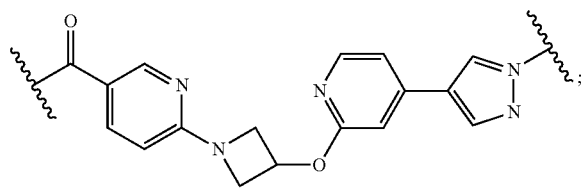
306
-continued
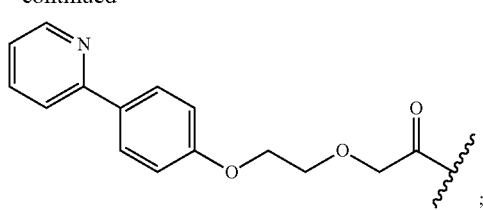
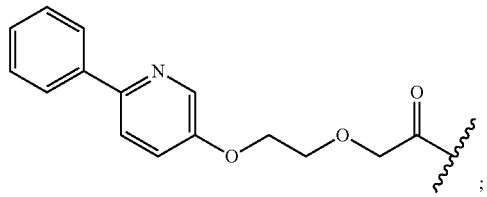
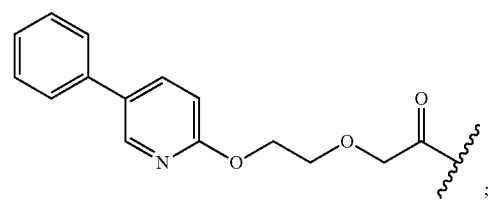
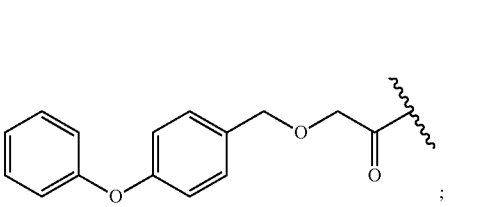
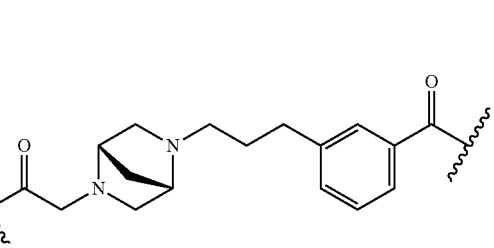
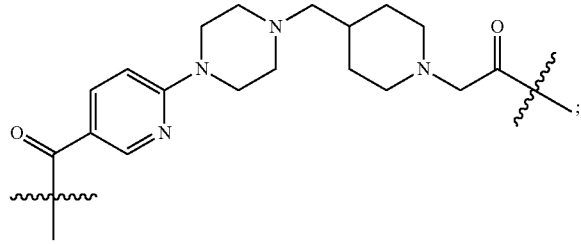

-continued
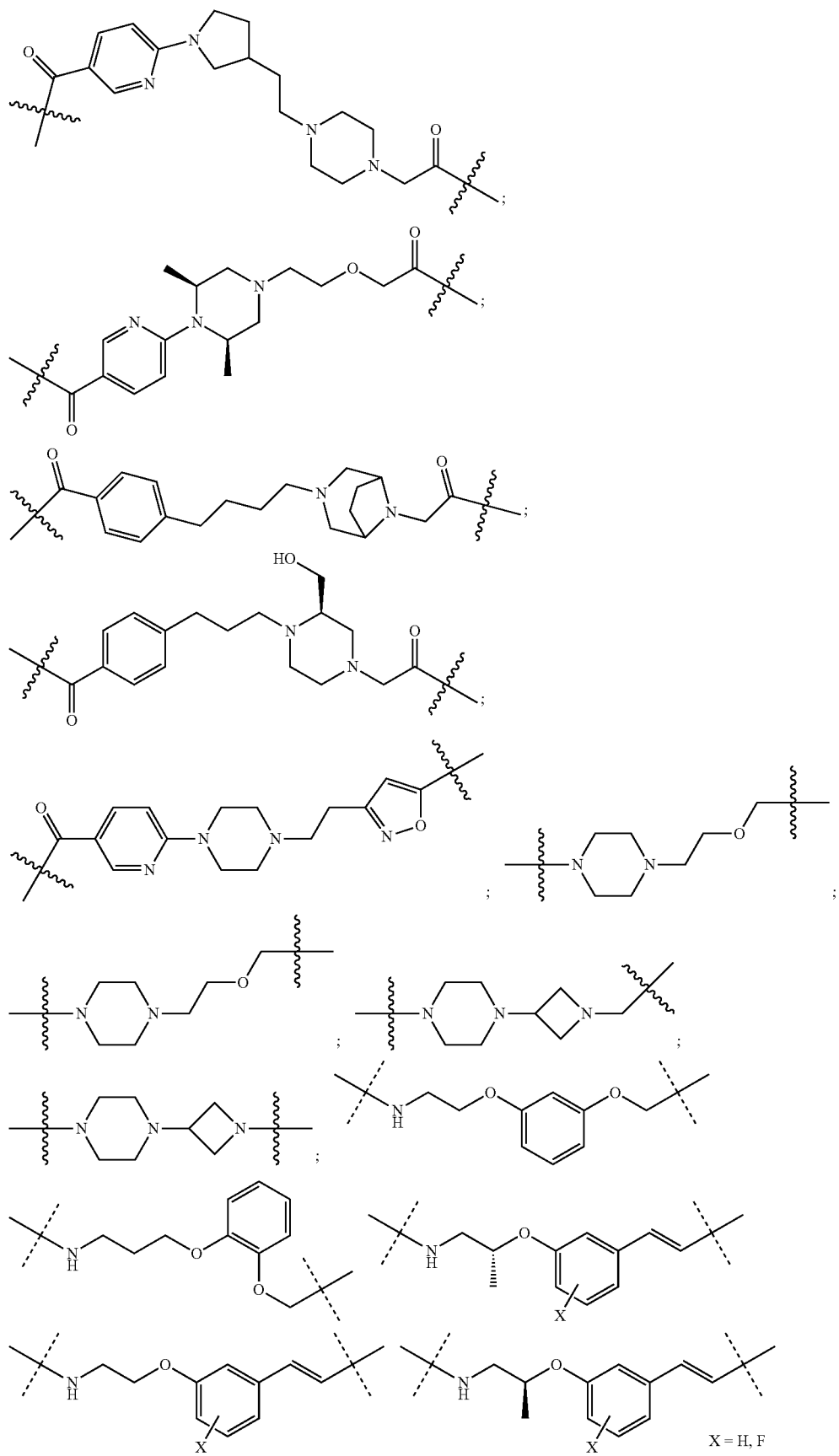

-continued
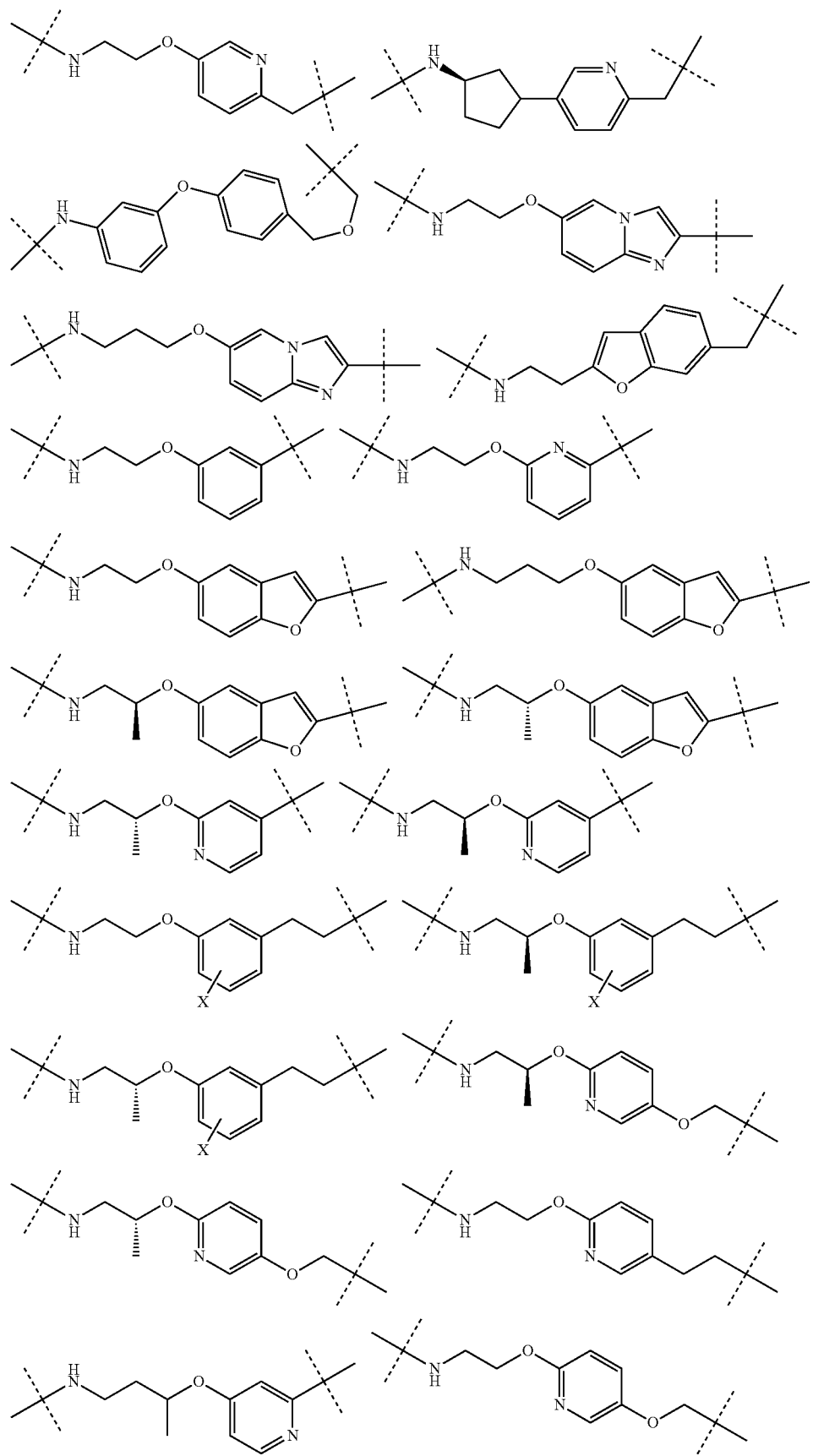

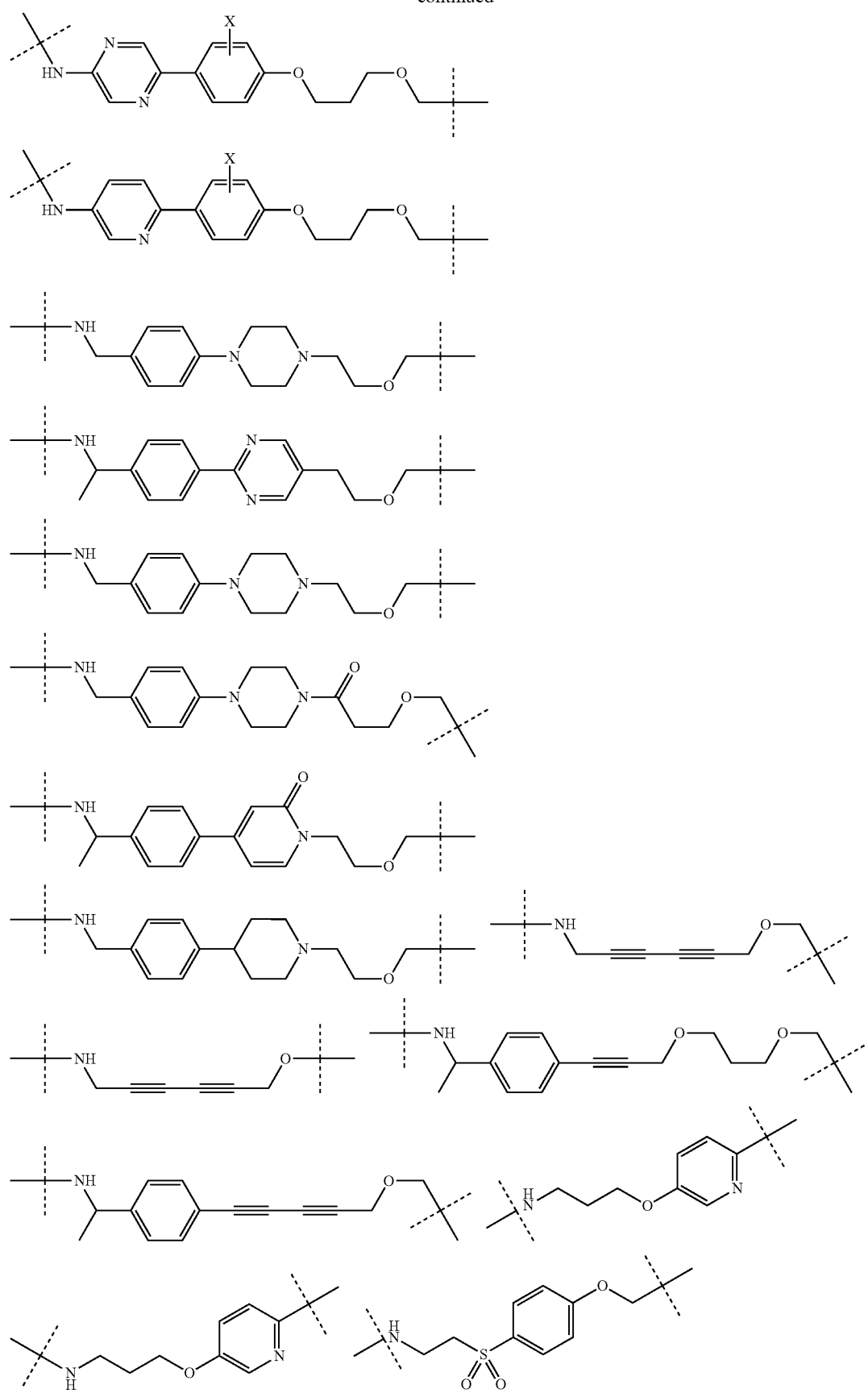

-continued
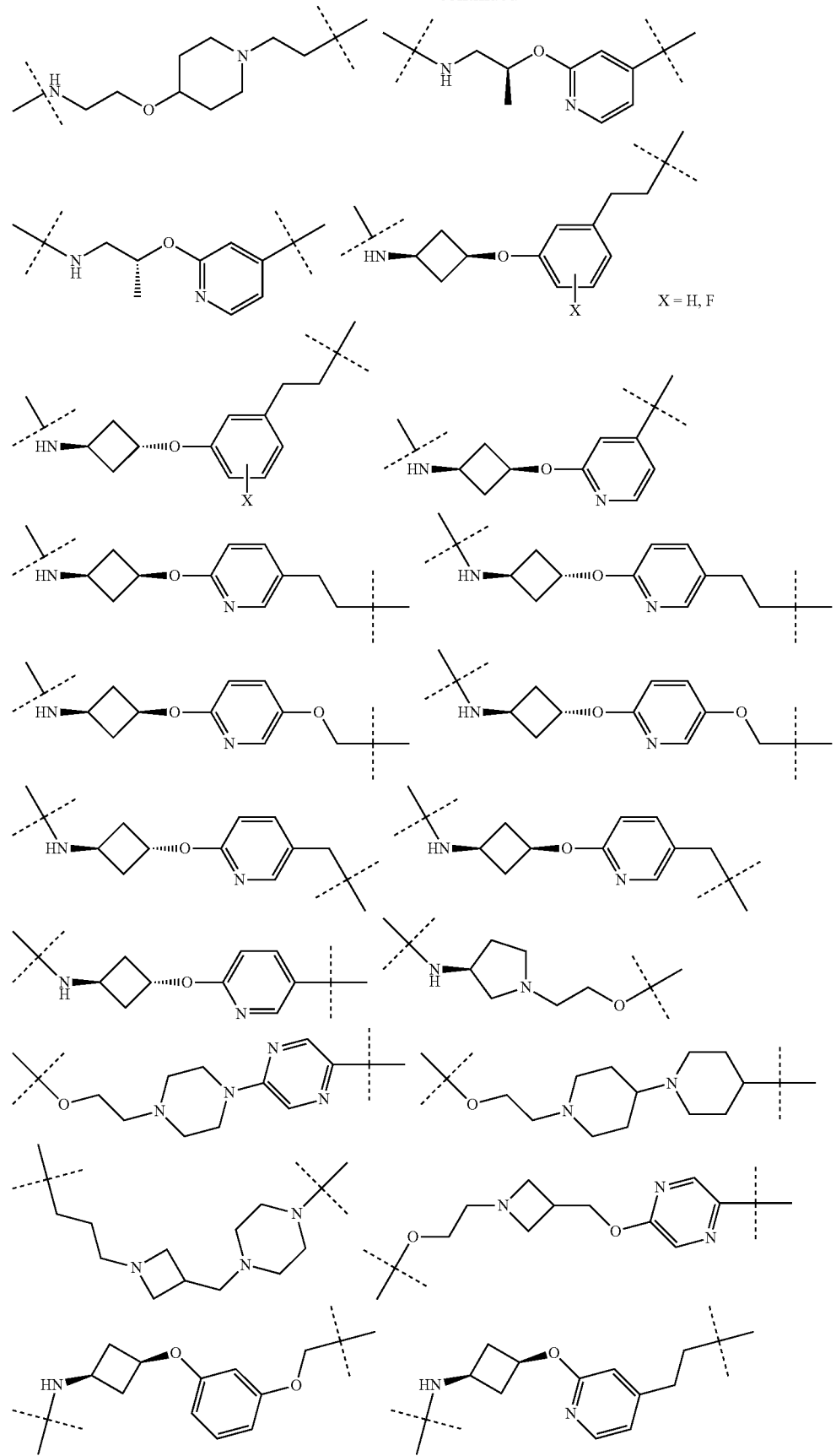
X = H, F

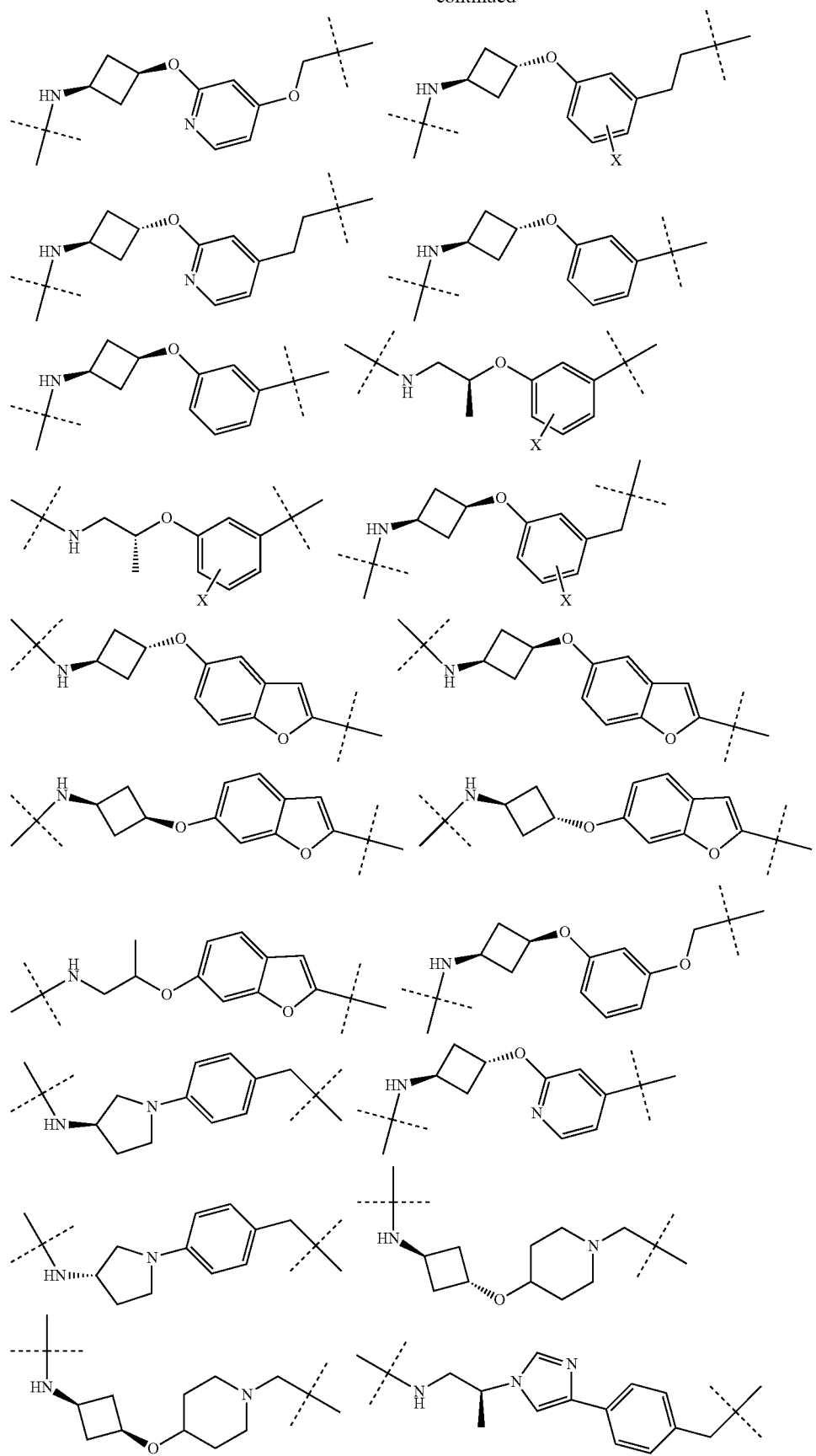

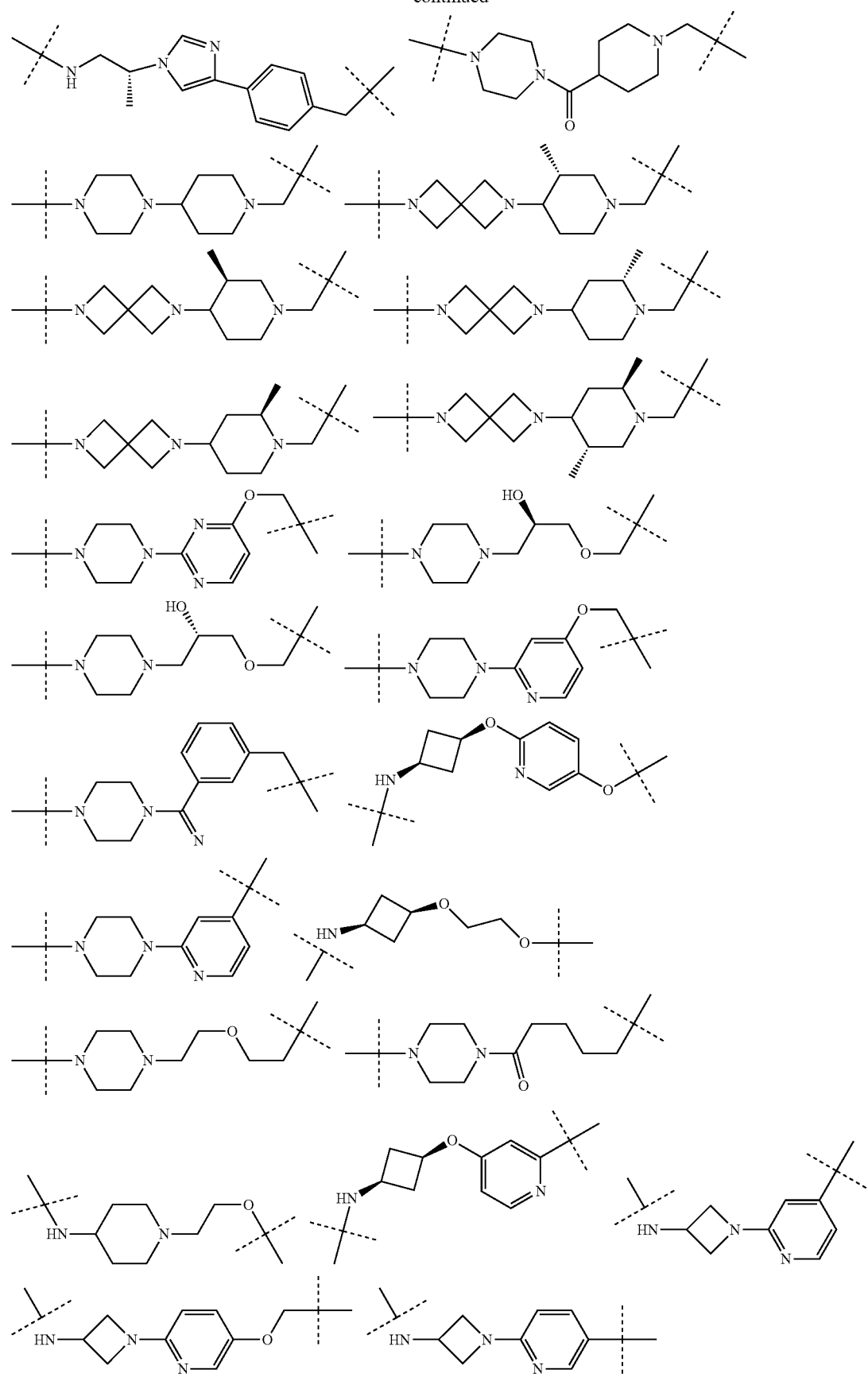

-continued
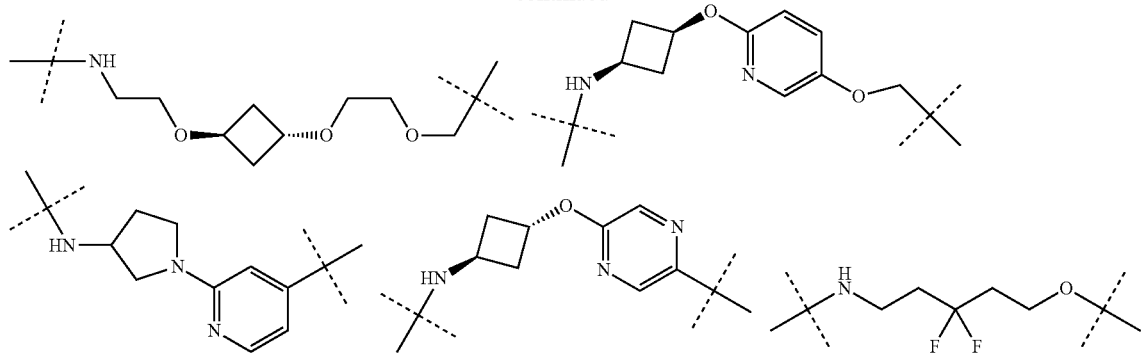
wherein each n and m of the linker can independently be 0, 1, 2, 3, 4, 5, 6.
In any aspect or embodiment described herein, the linker (L) is selected from the group consisting of:
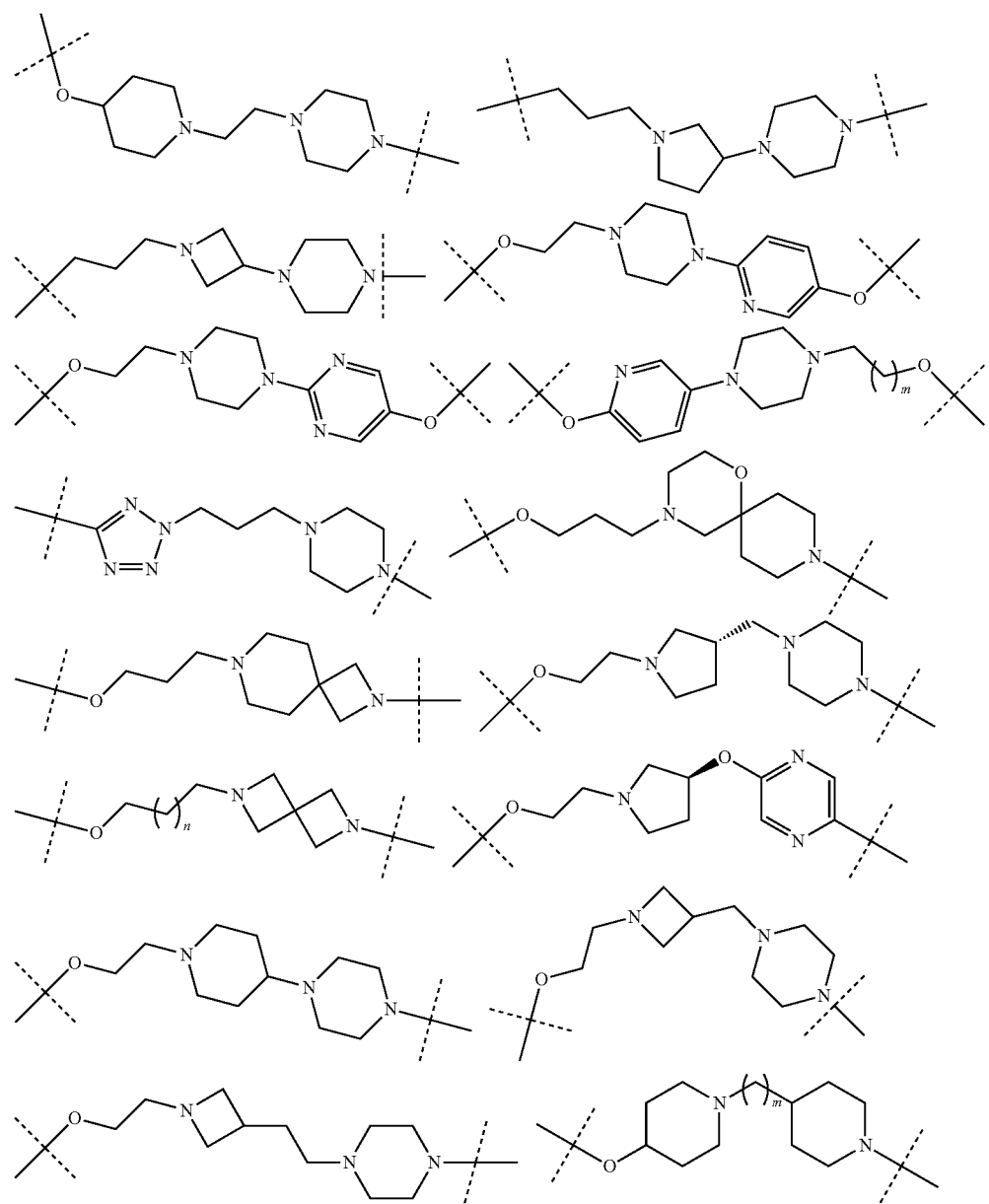

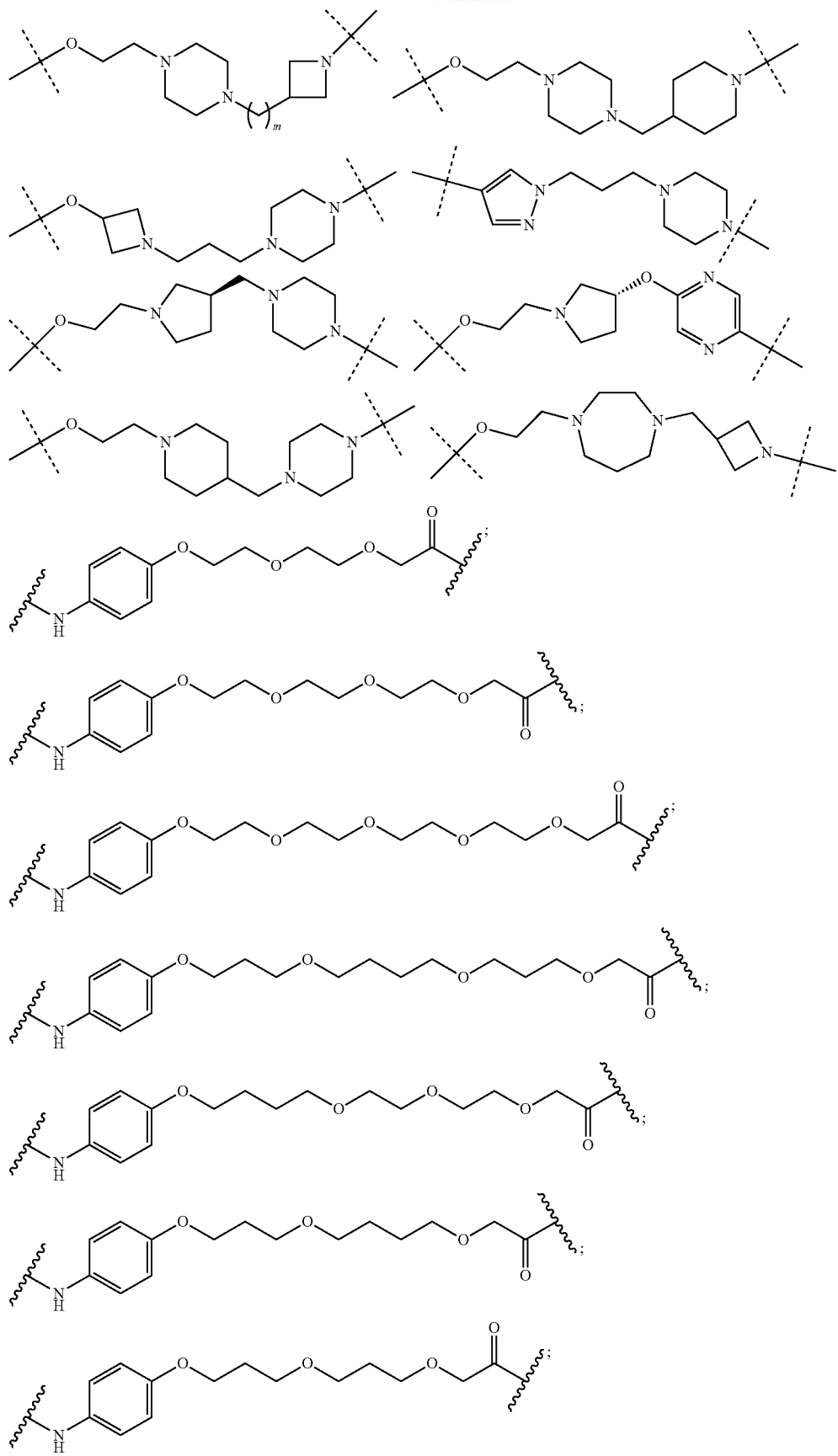

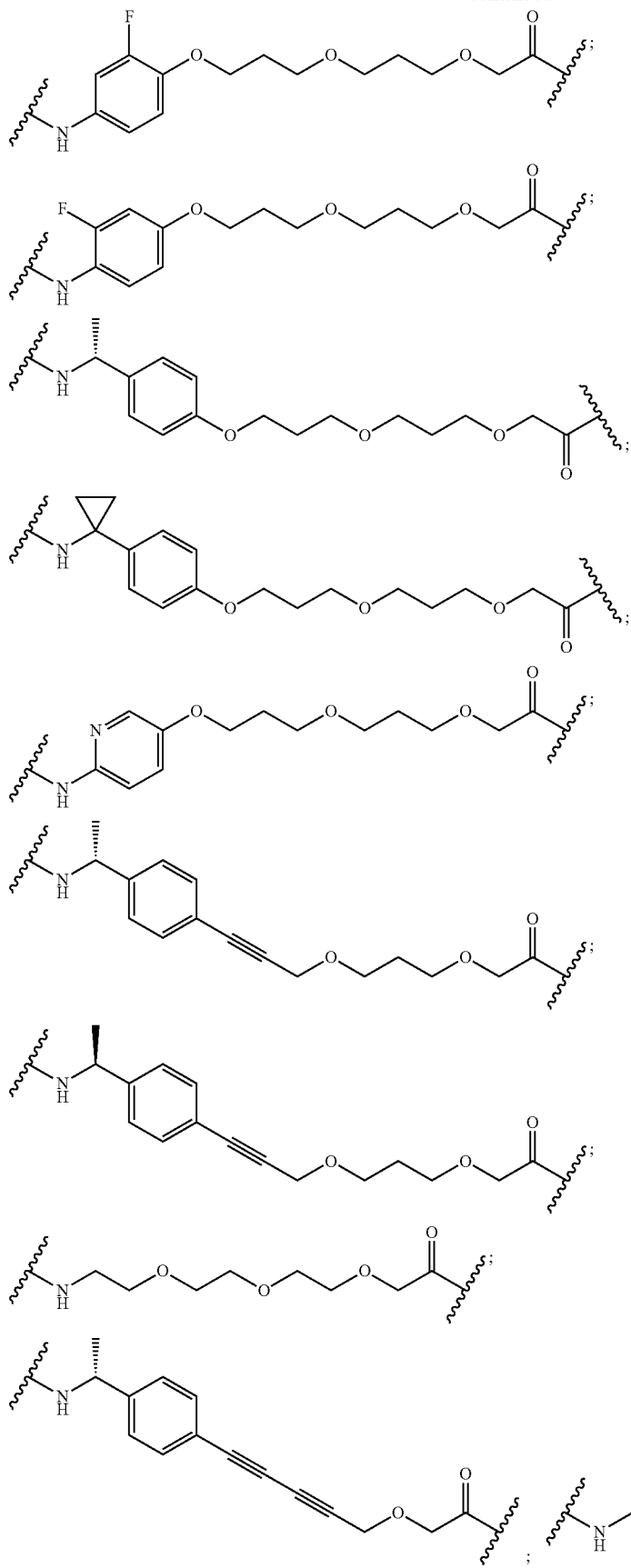

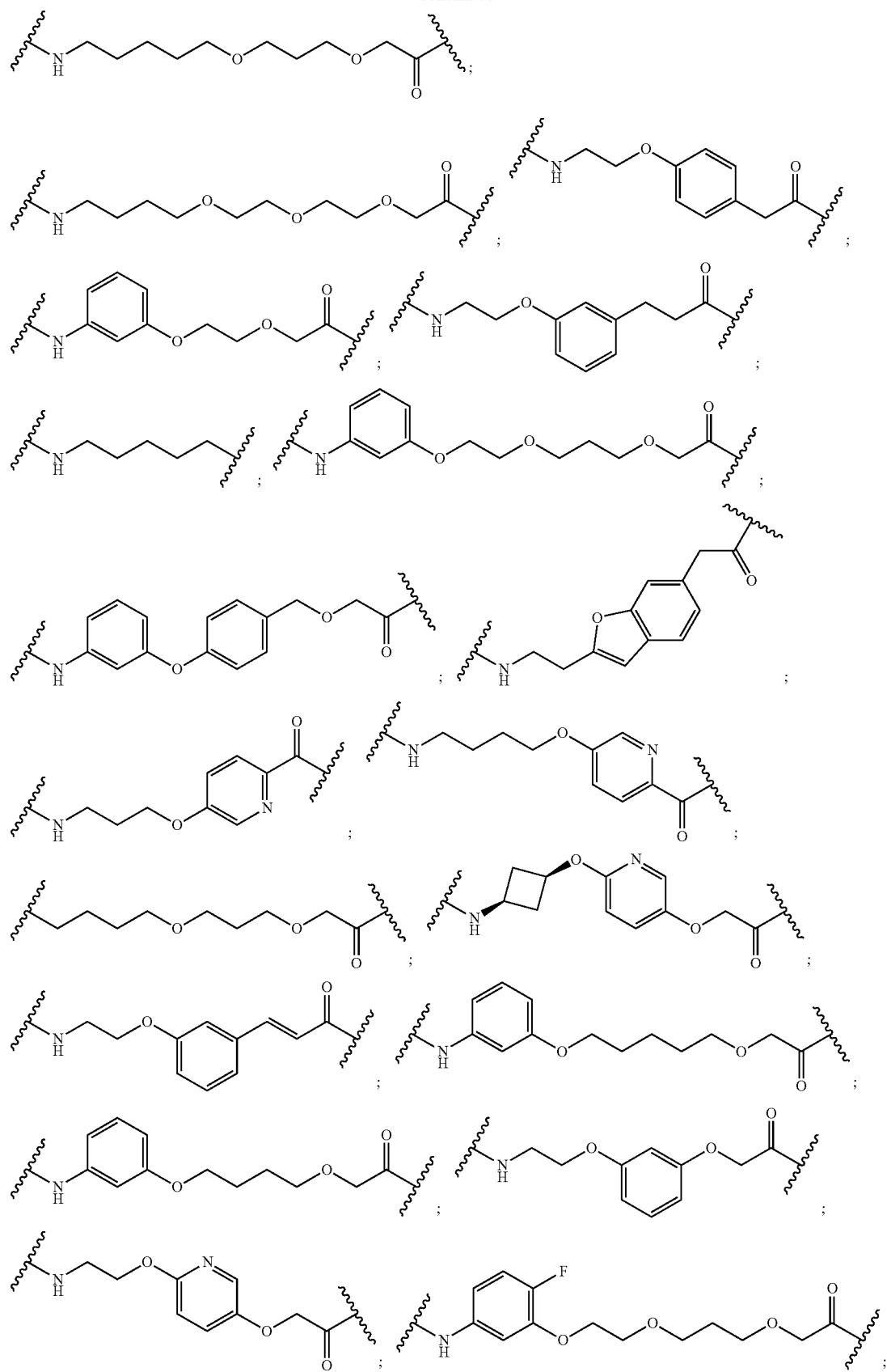

-continued
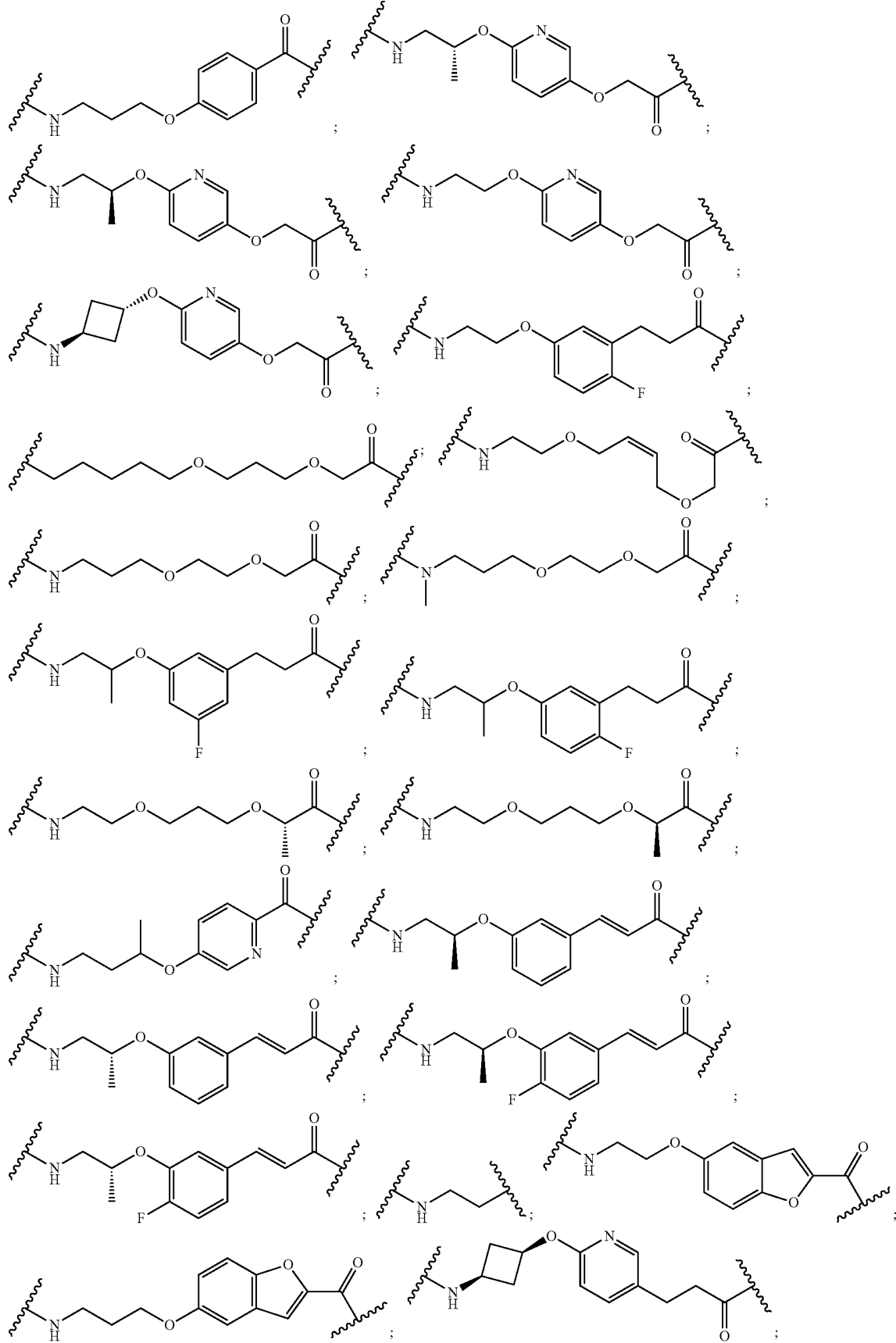

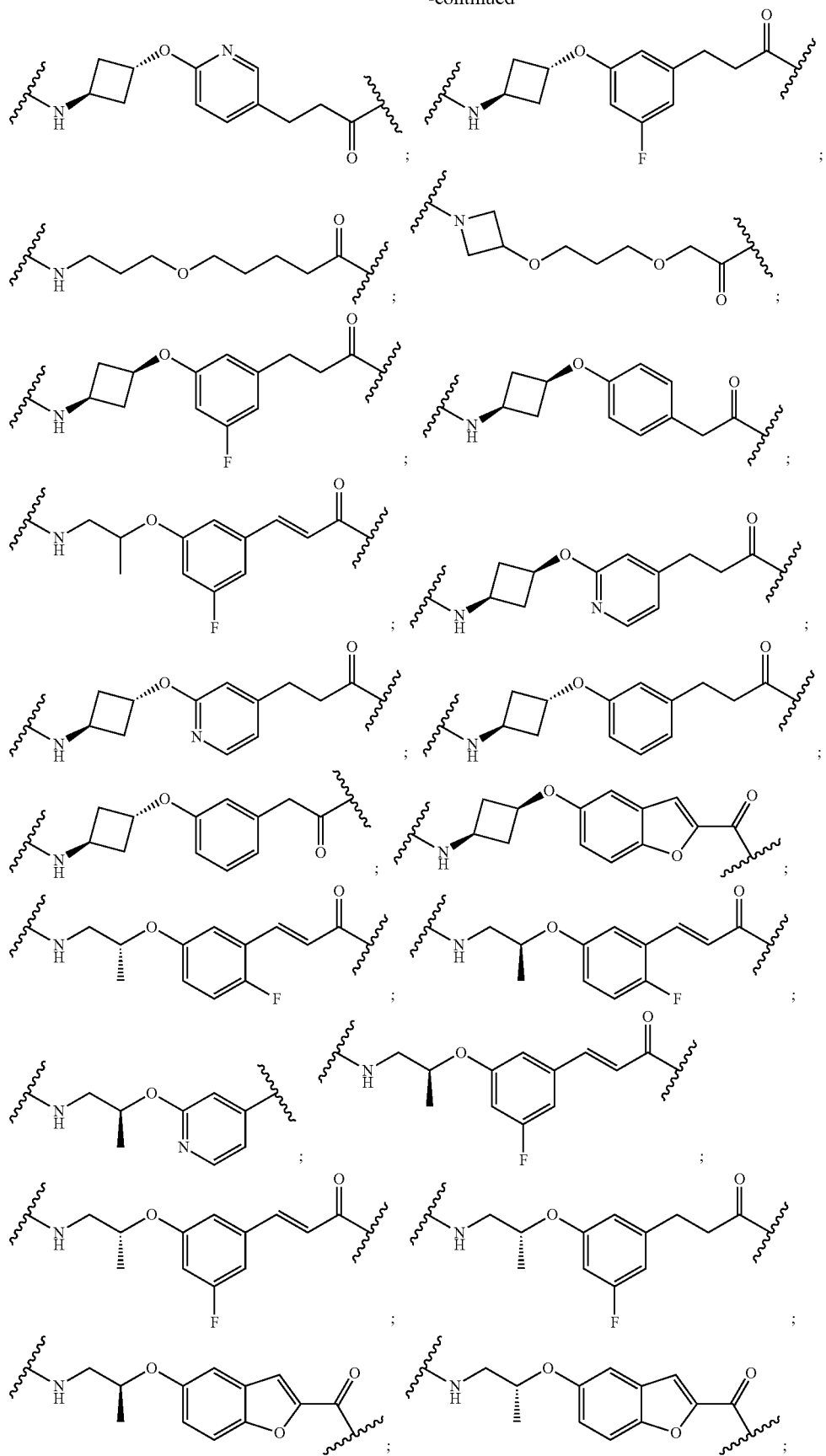

-continued
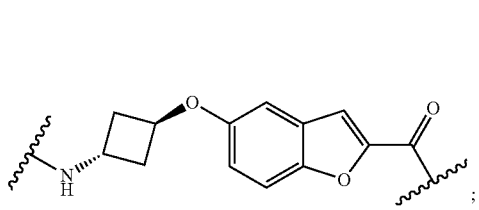
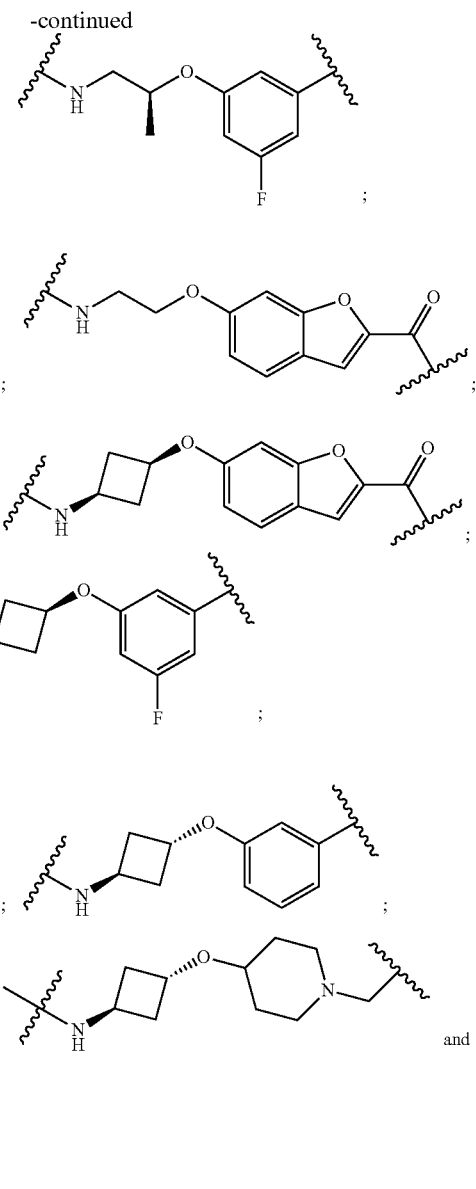
wherein each m and n is independently selected from 0, 1, 2, 3, 4, 5, or 6.
In any aspect or embodiment described herein, the linker (L) is selected from the group consisting of:
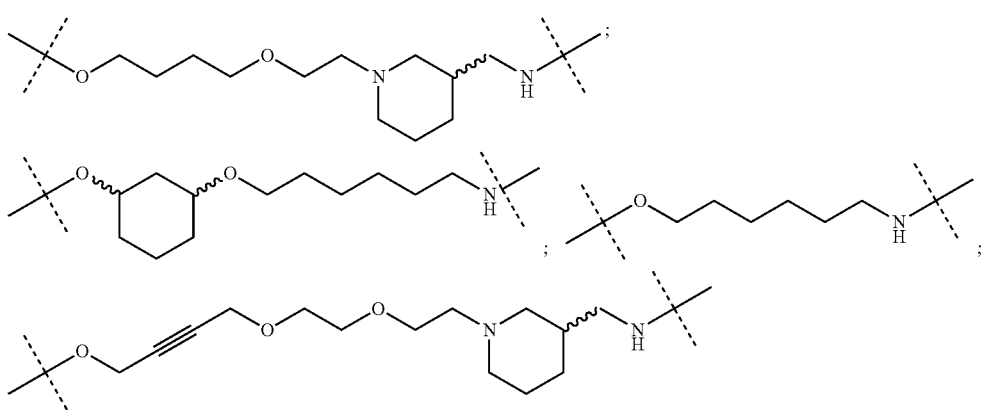

-continued
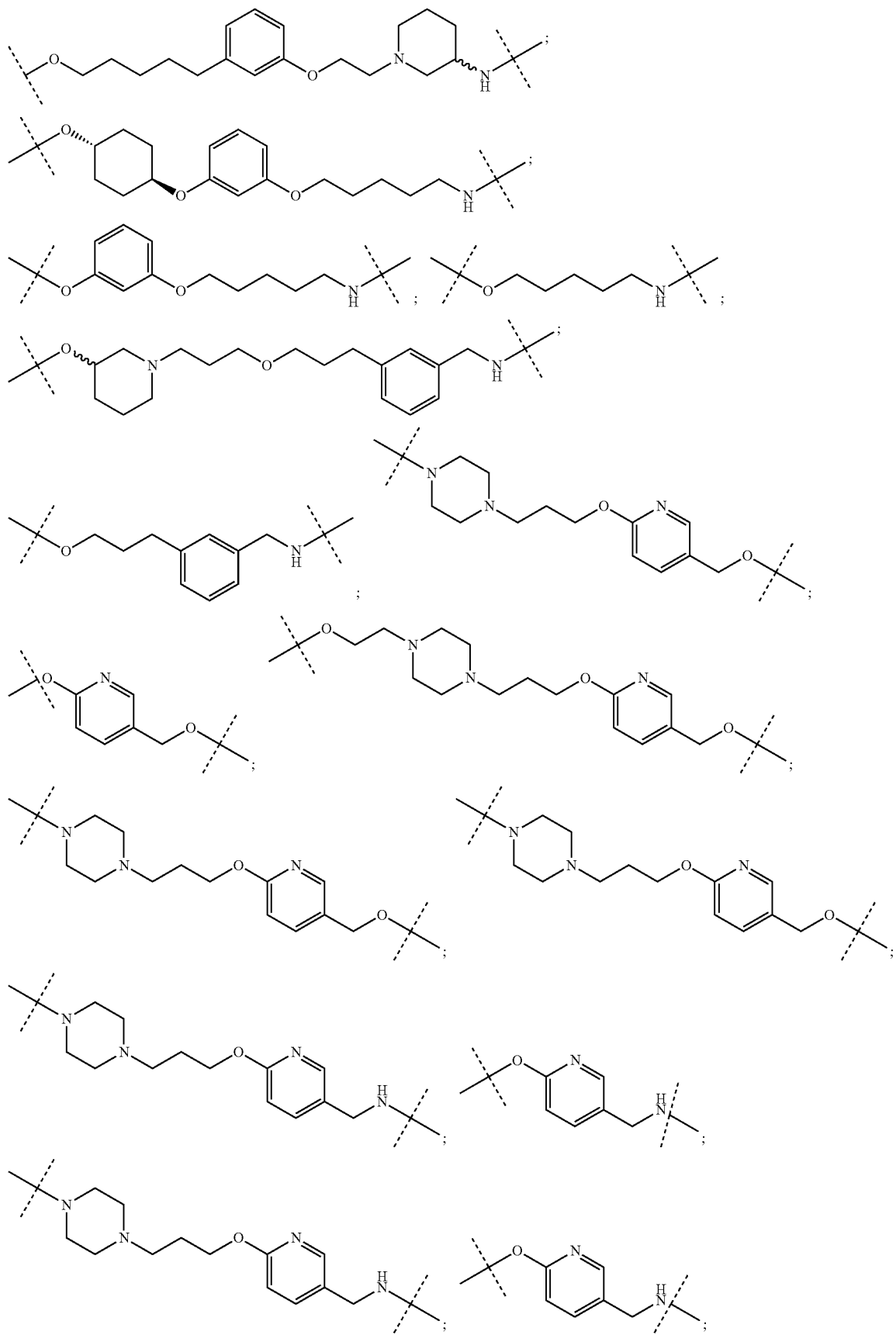

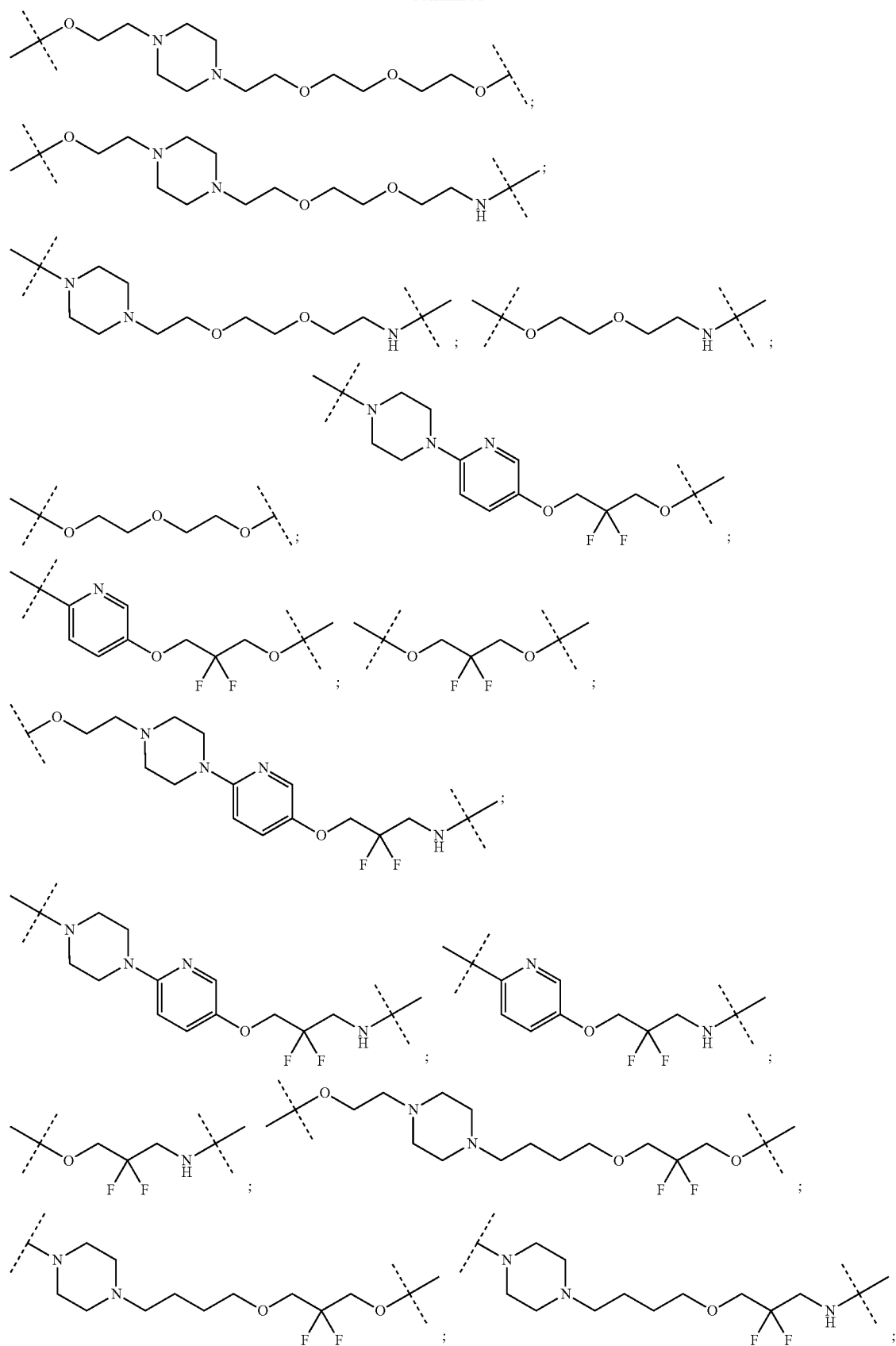

-continued
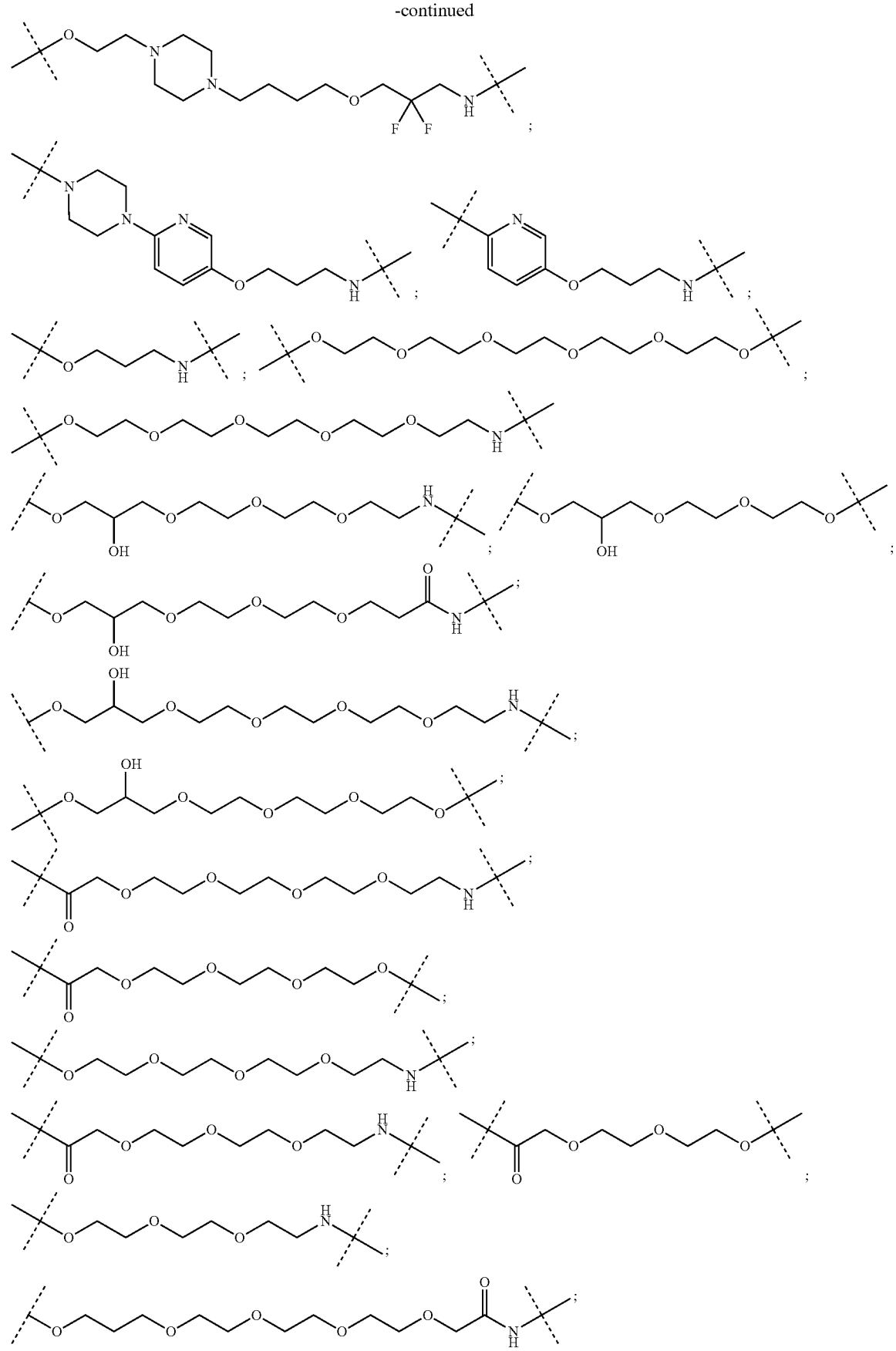

-continued
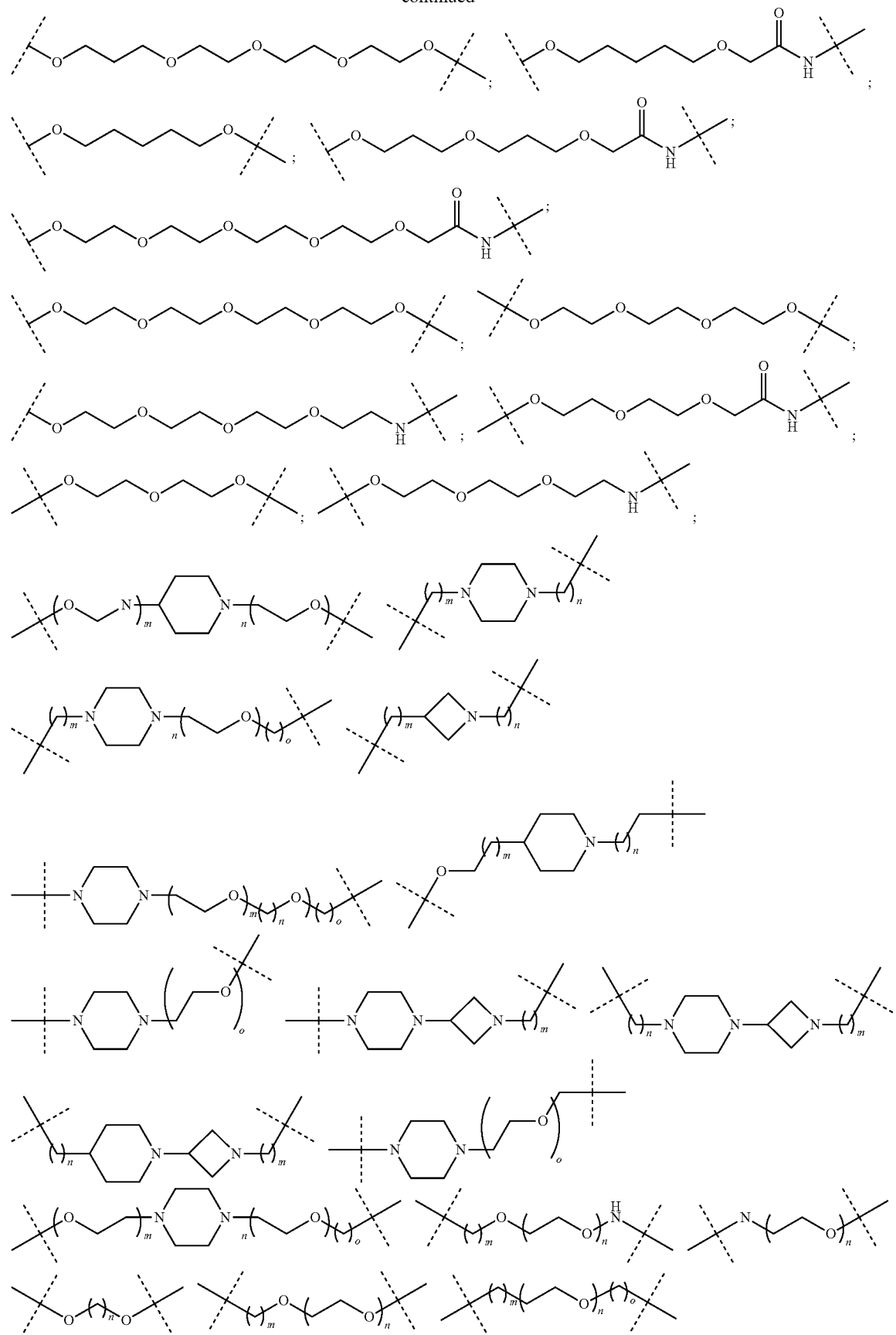

-continued
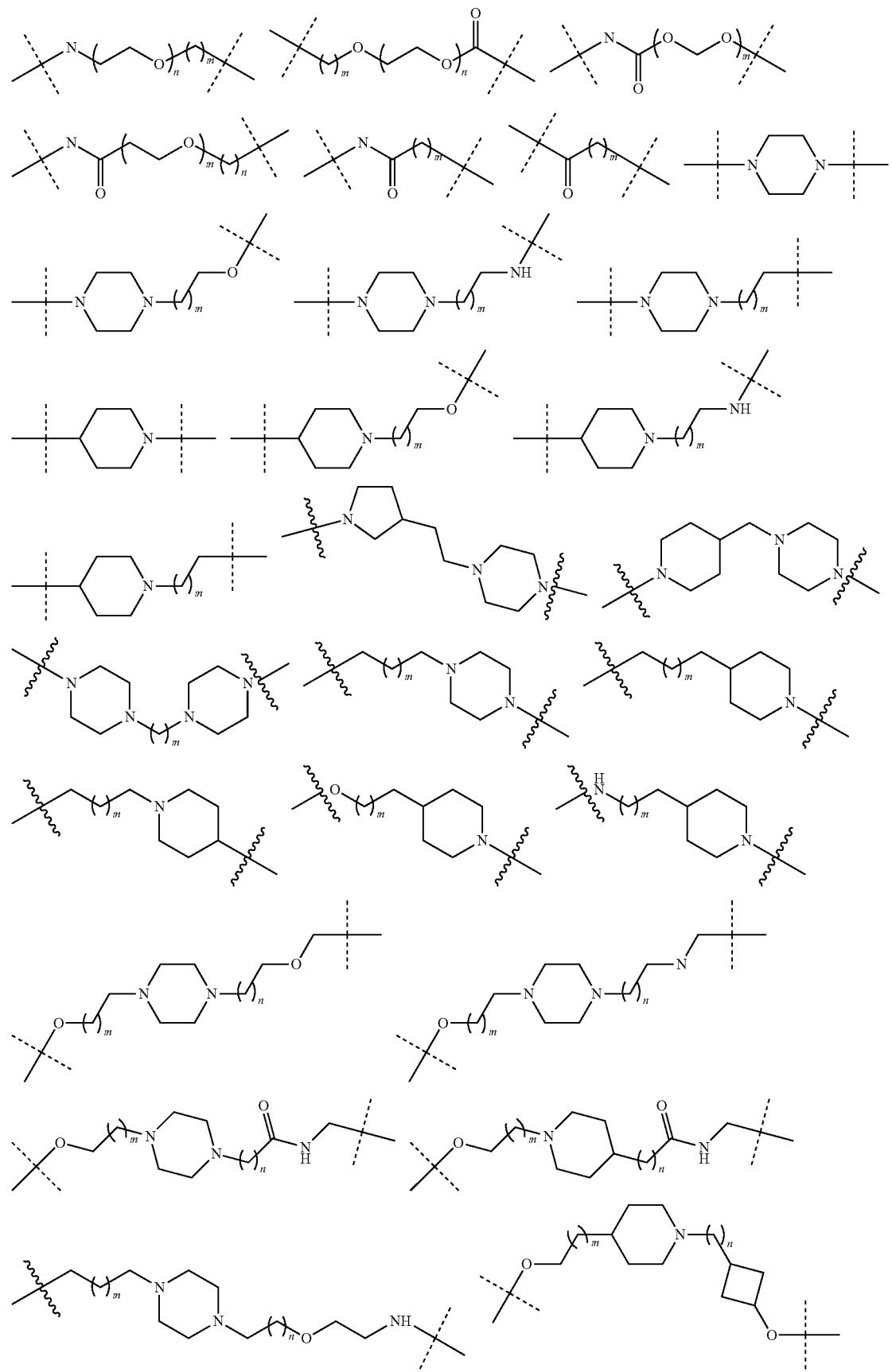

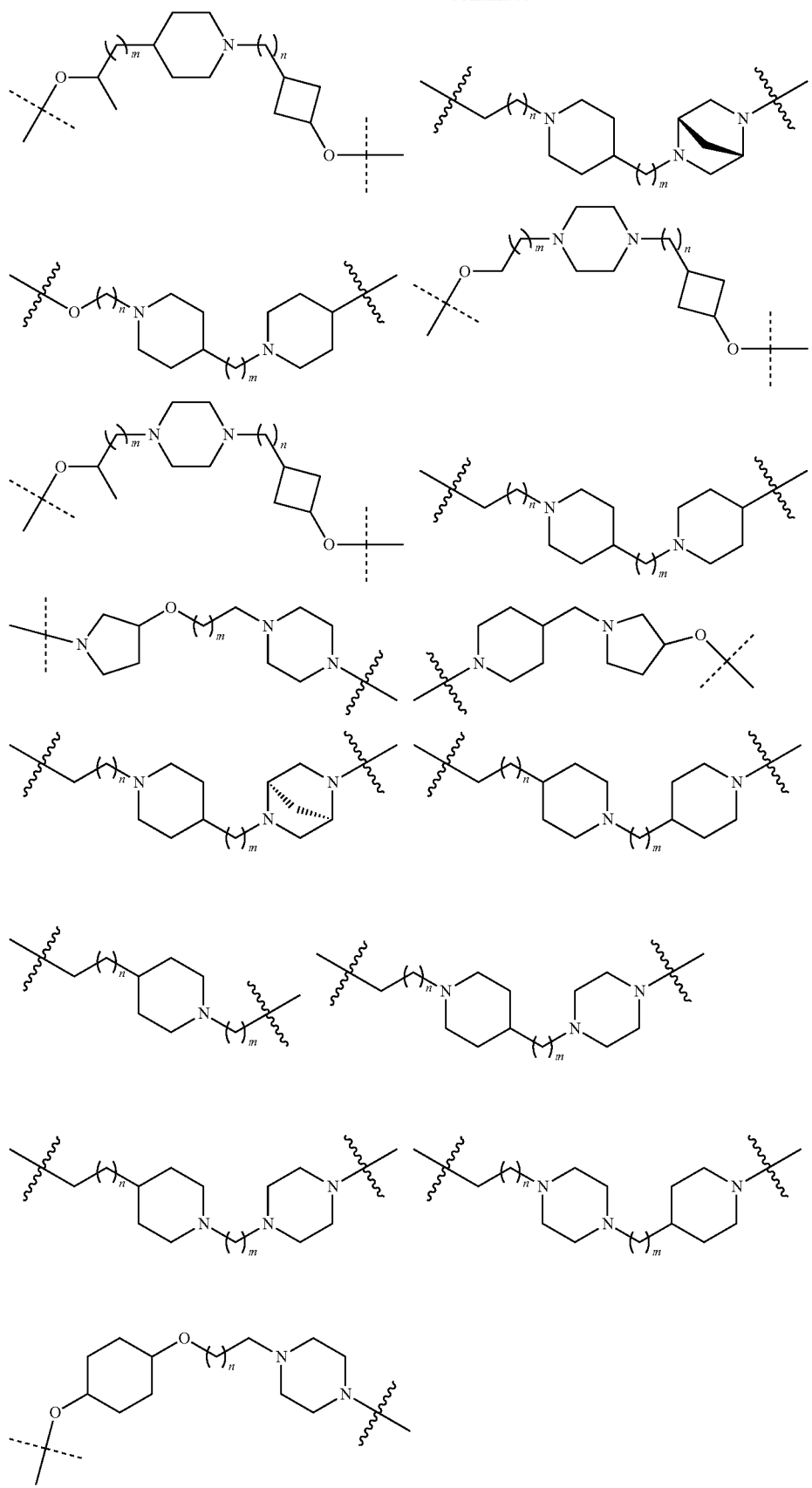

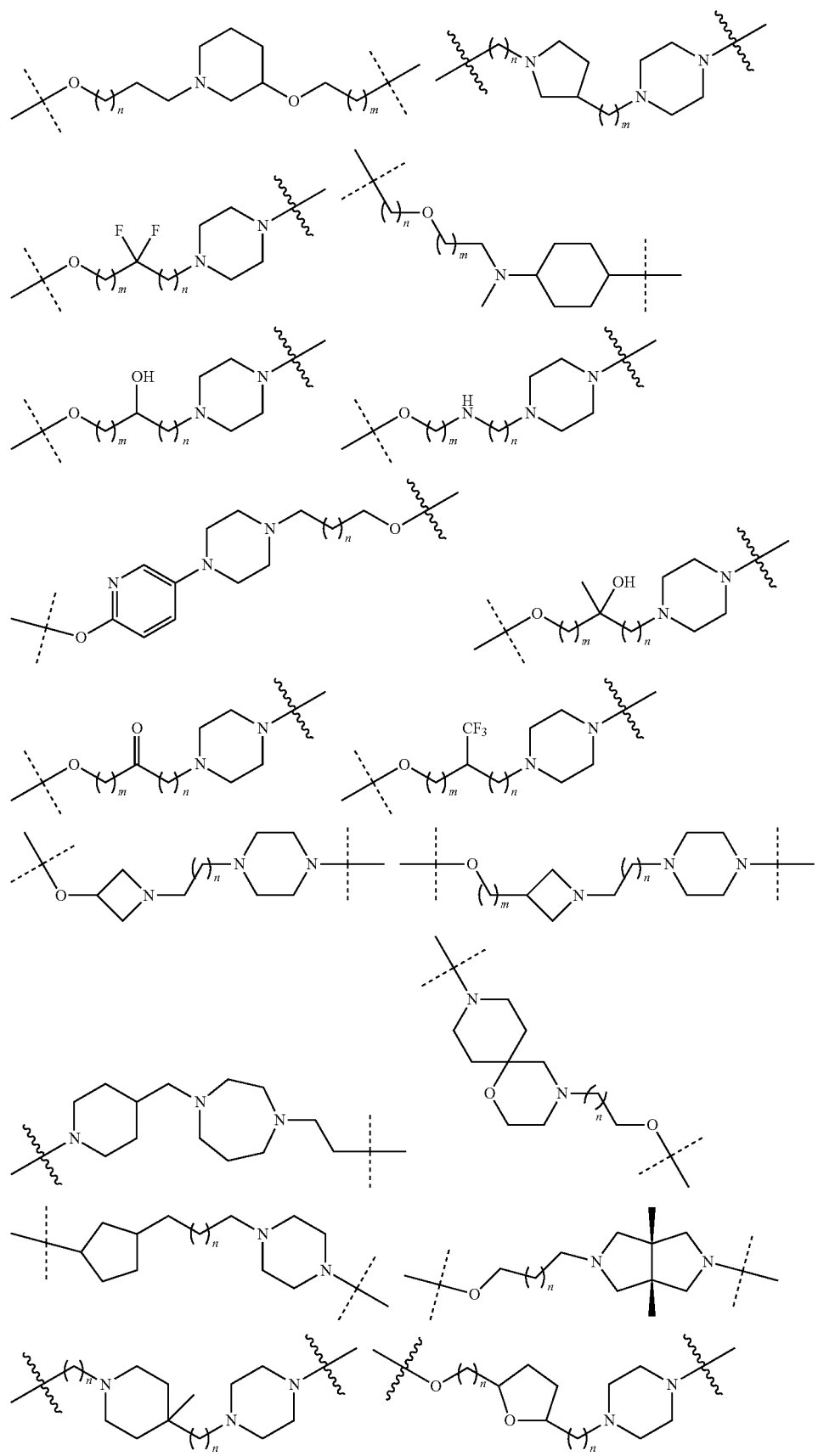

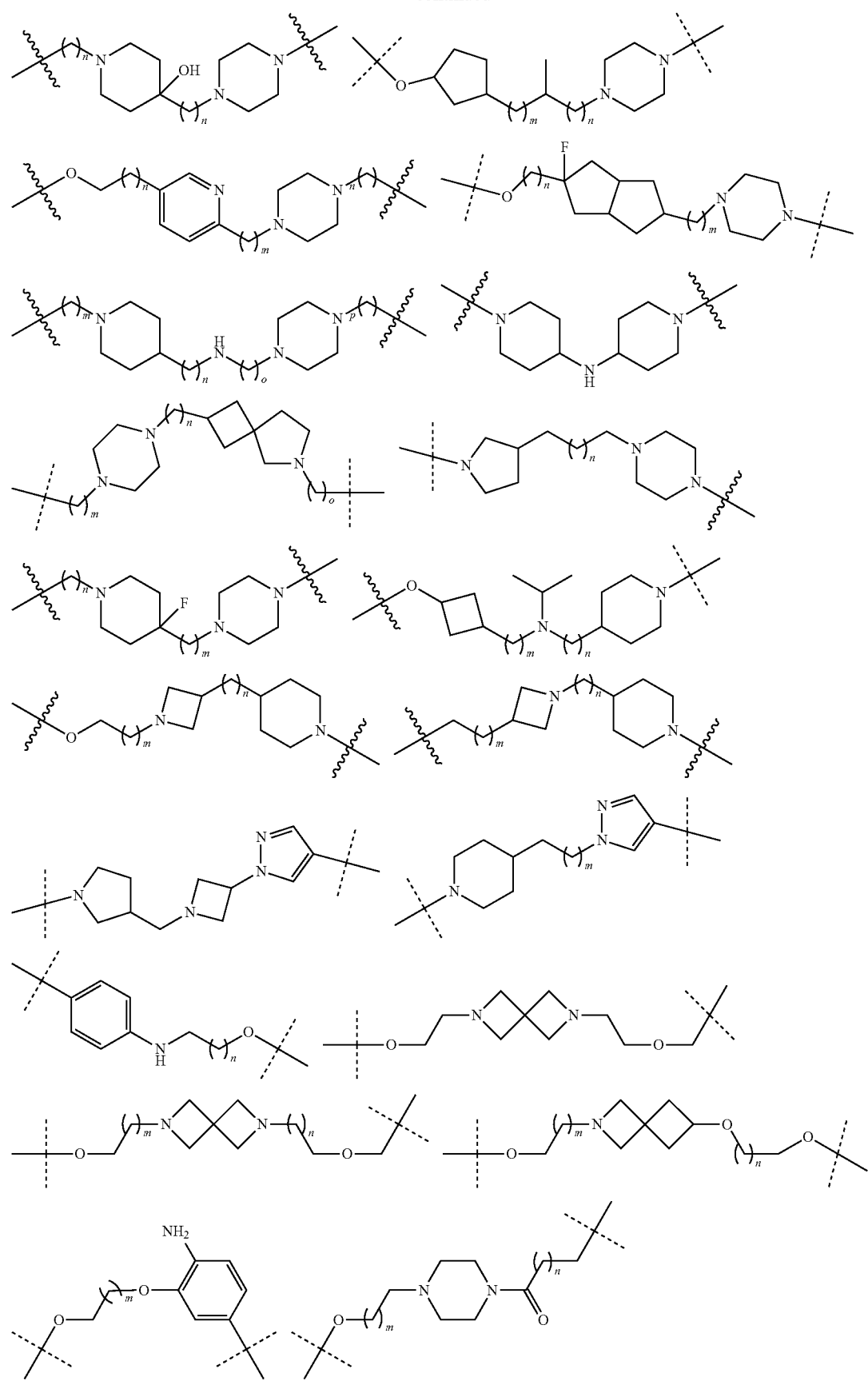

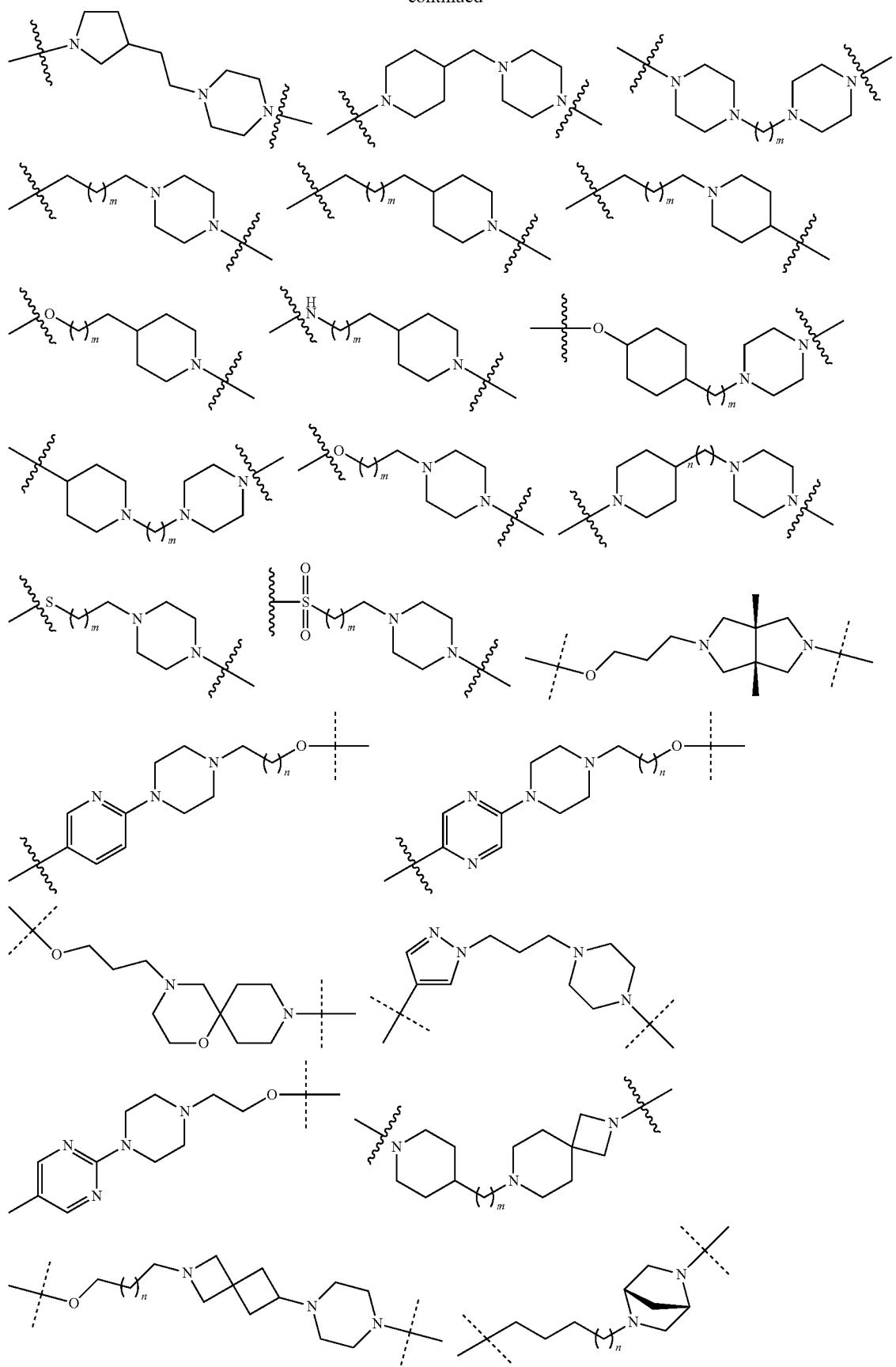

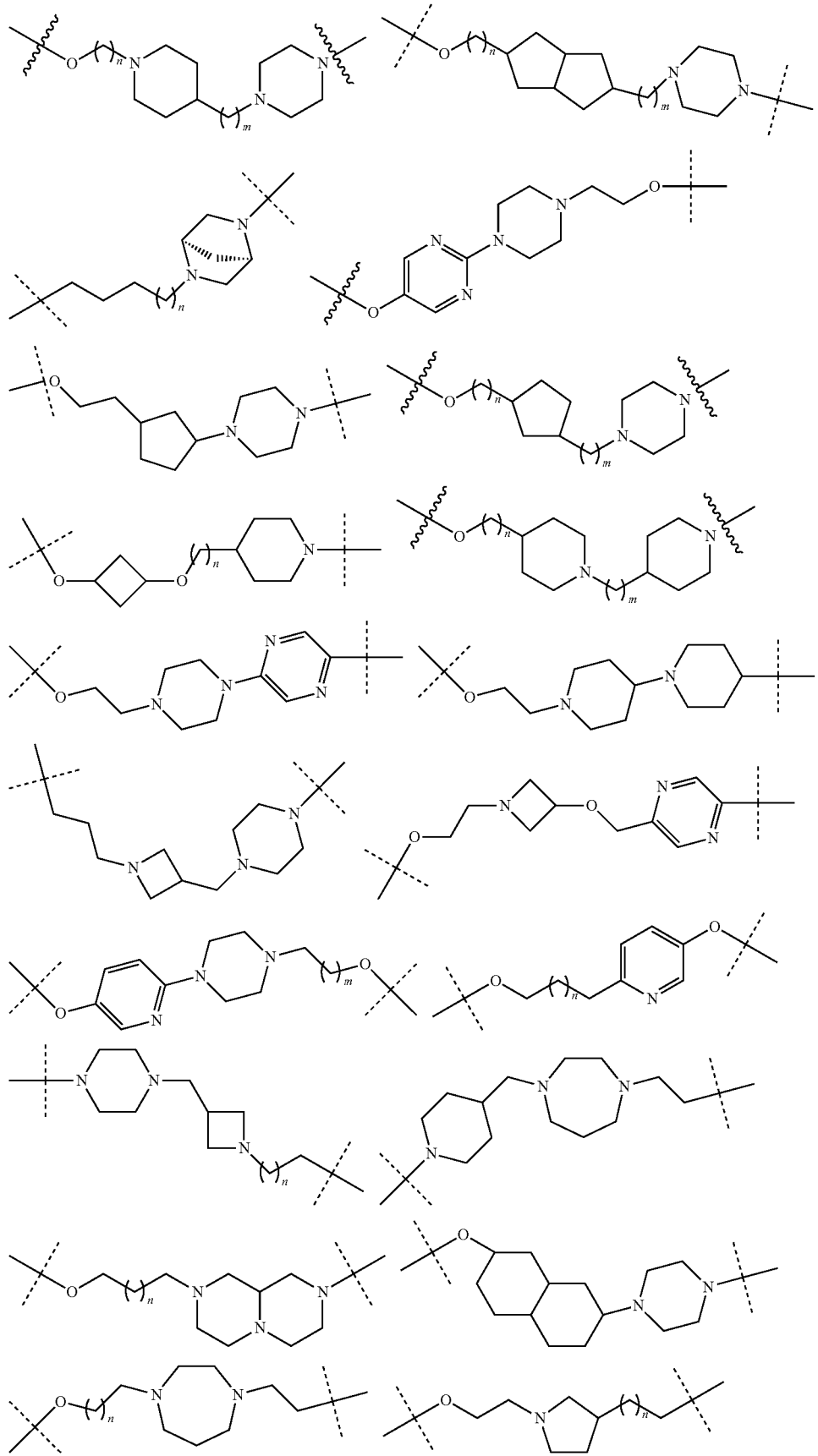

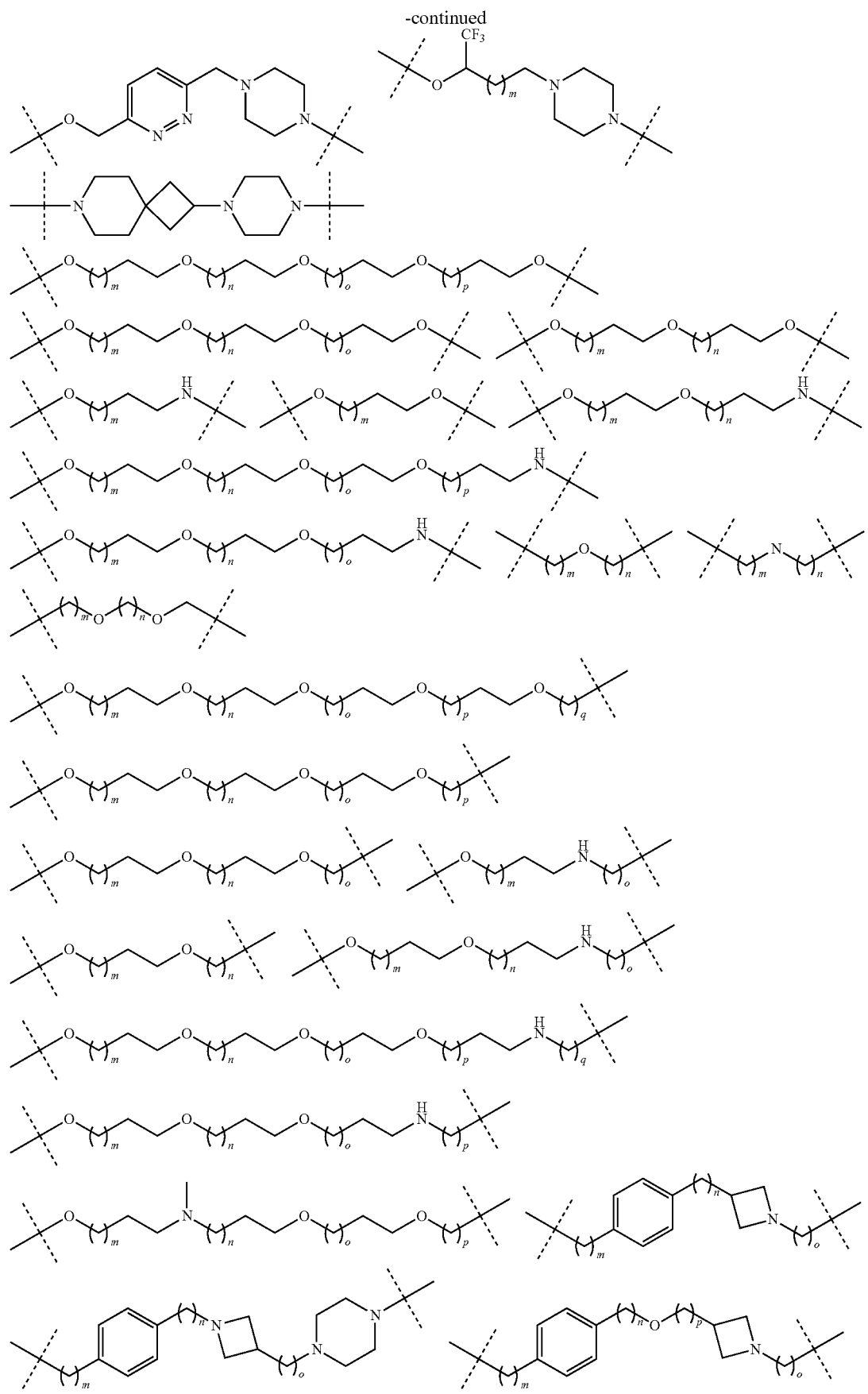

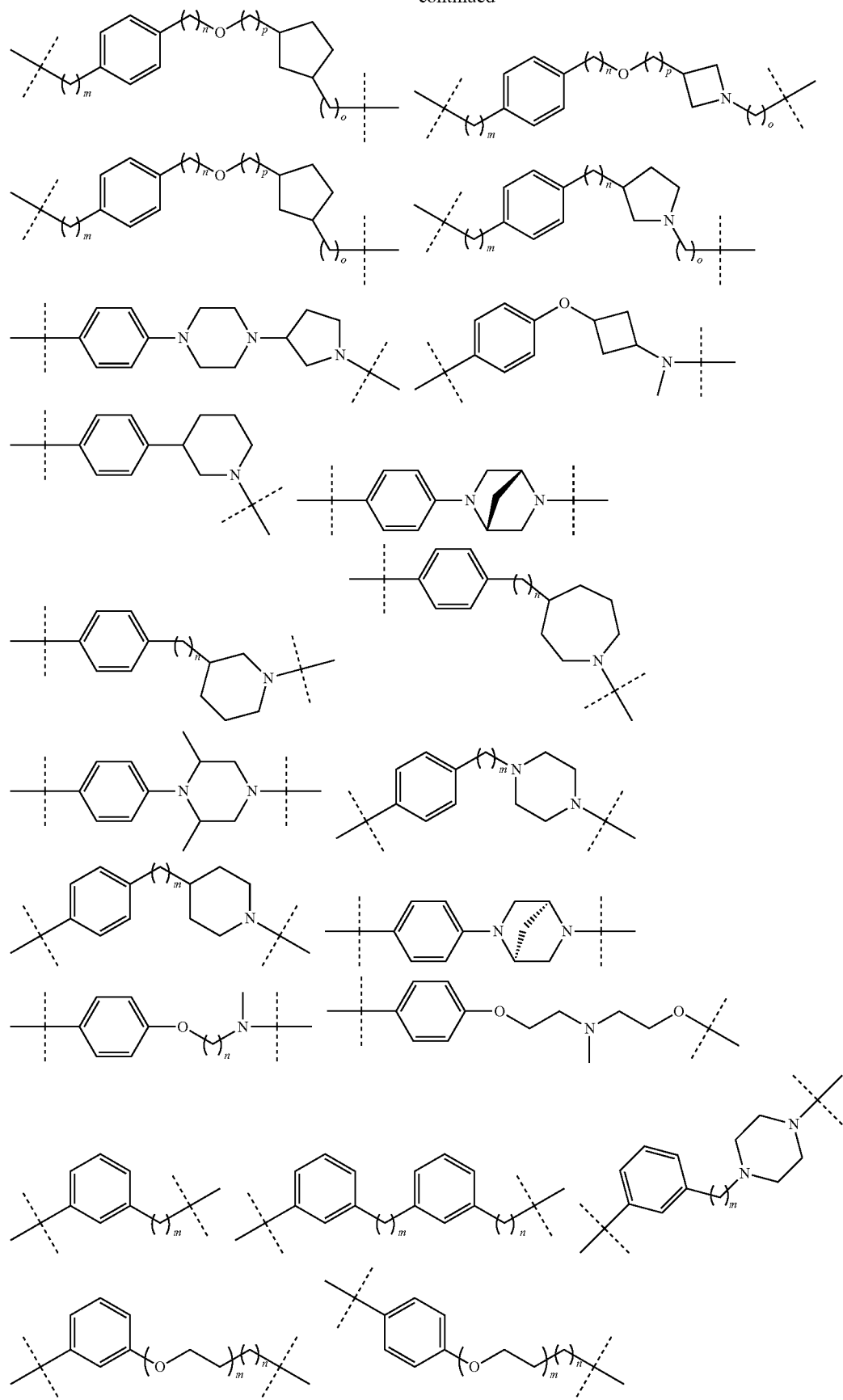

-continued
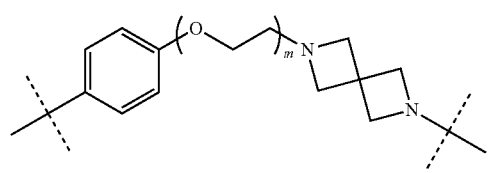
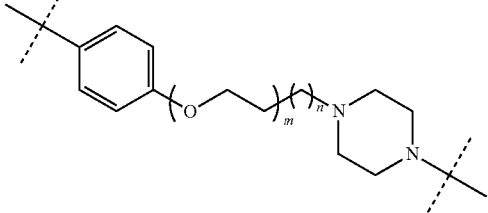
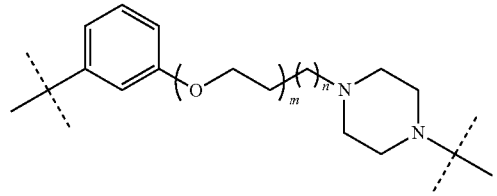
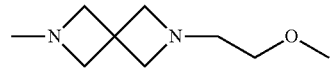
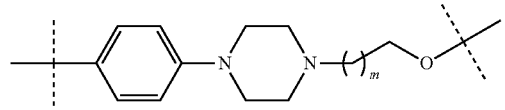
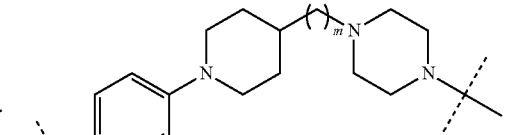
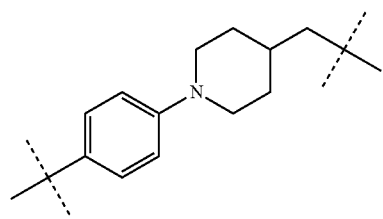
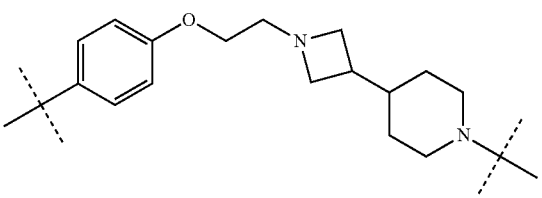
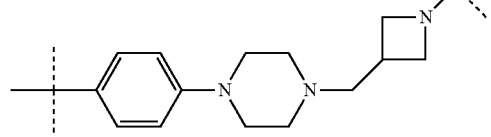
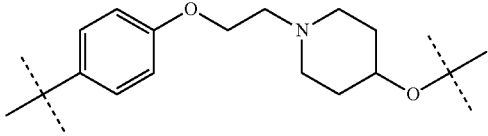
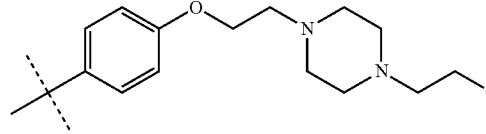
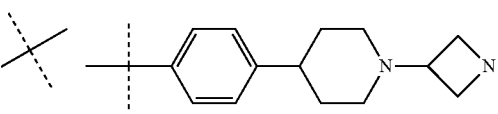
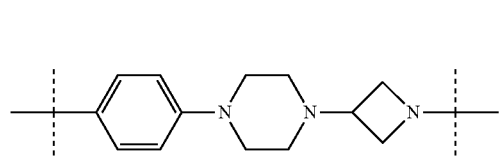
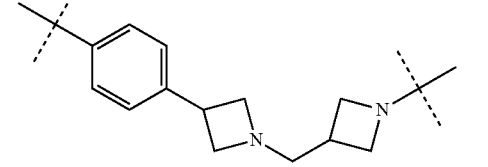
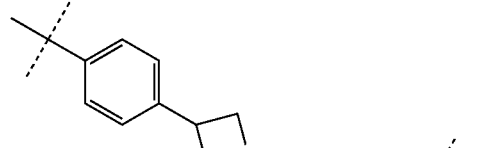
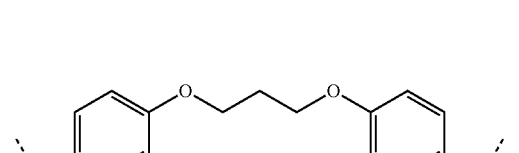
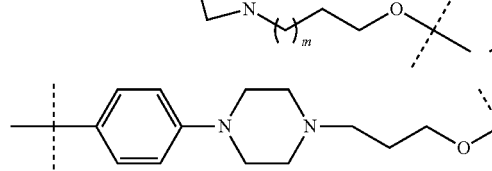

359 360
-continued
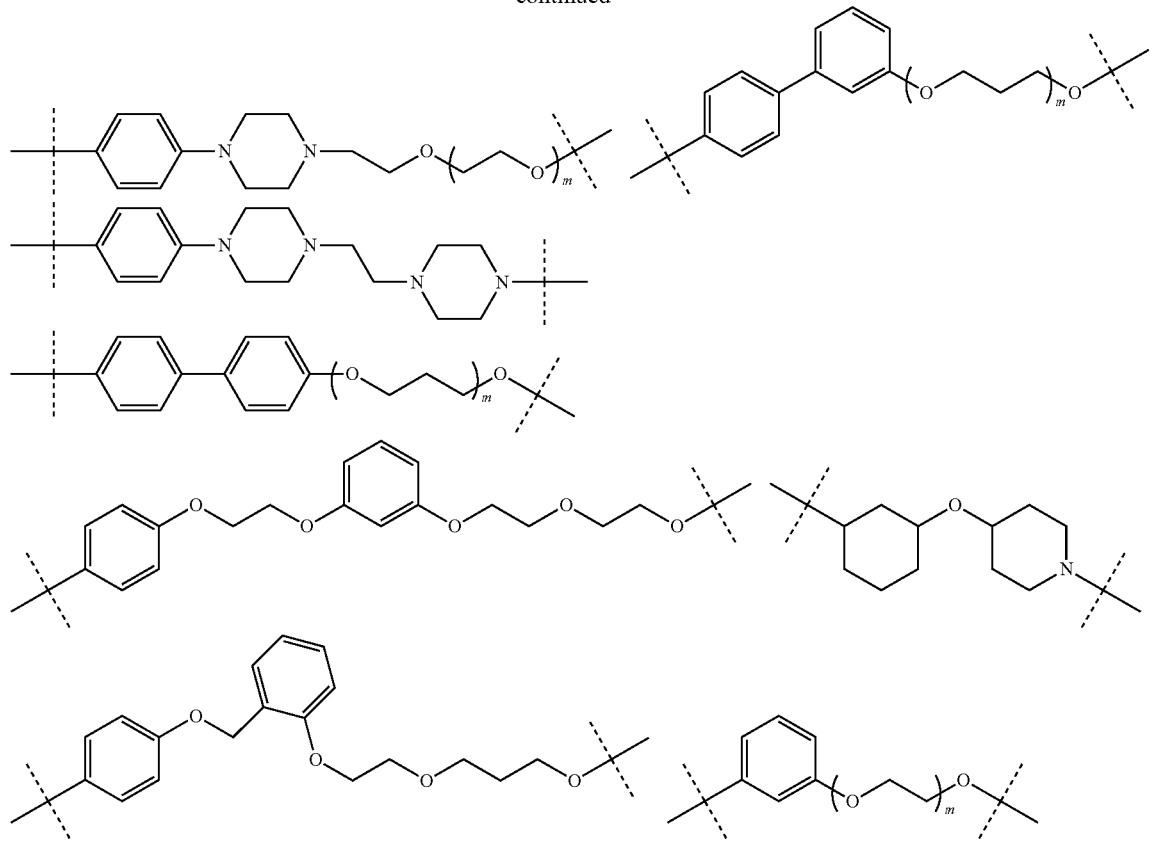
35
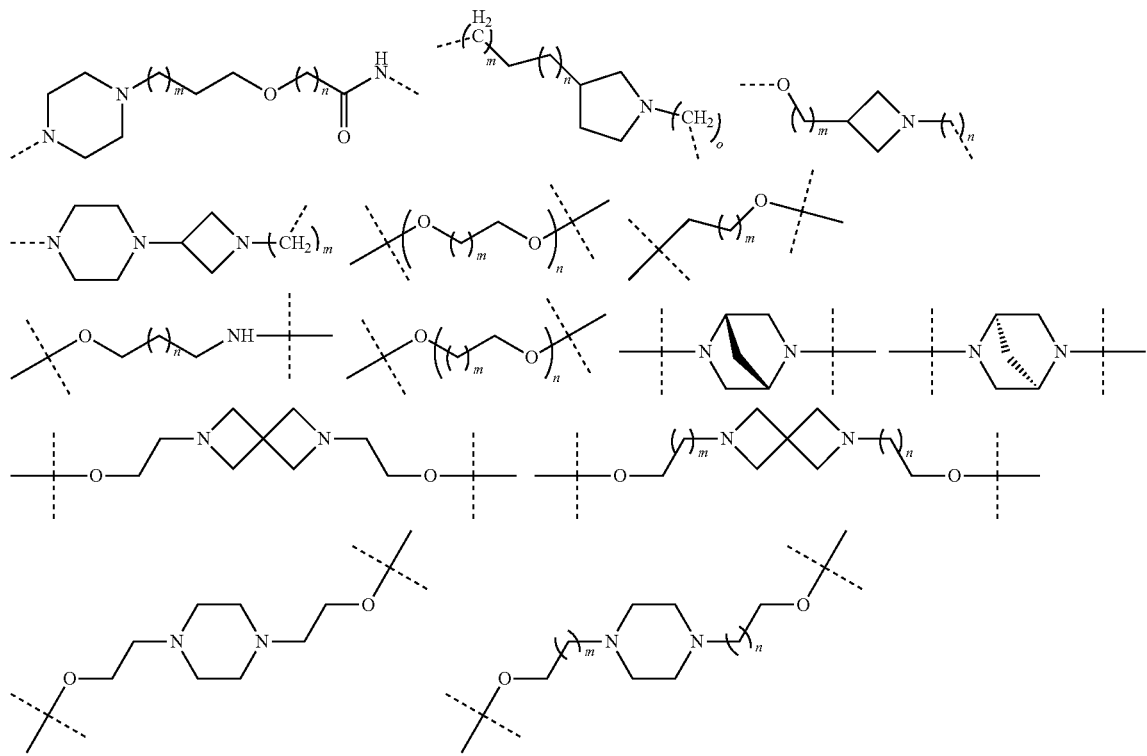

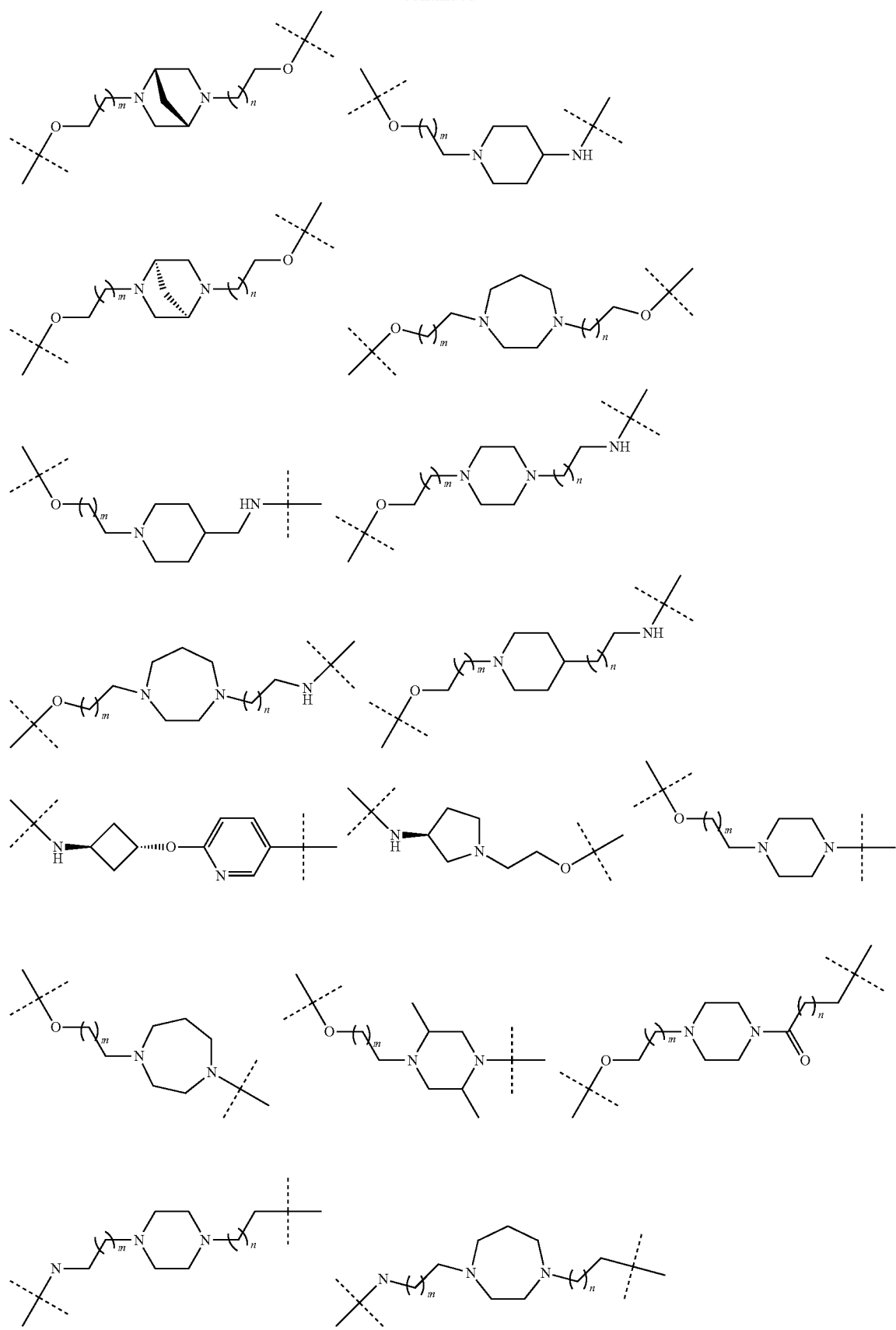

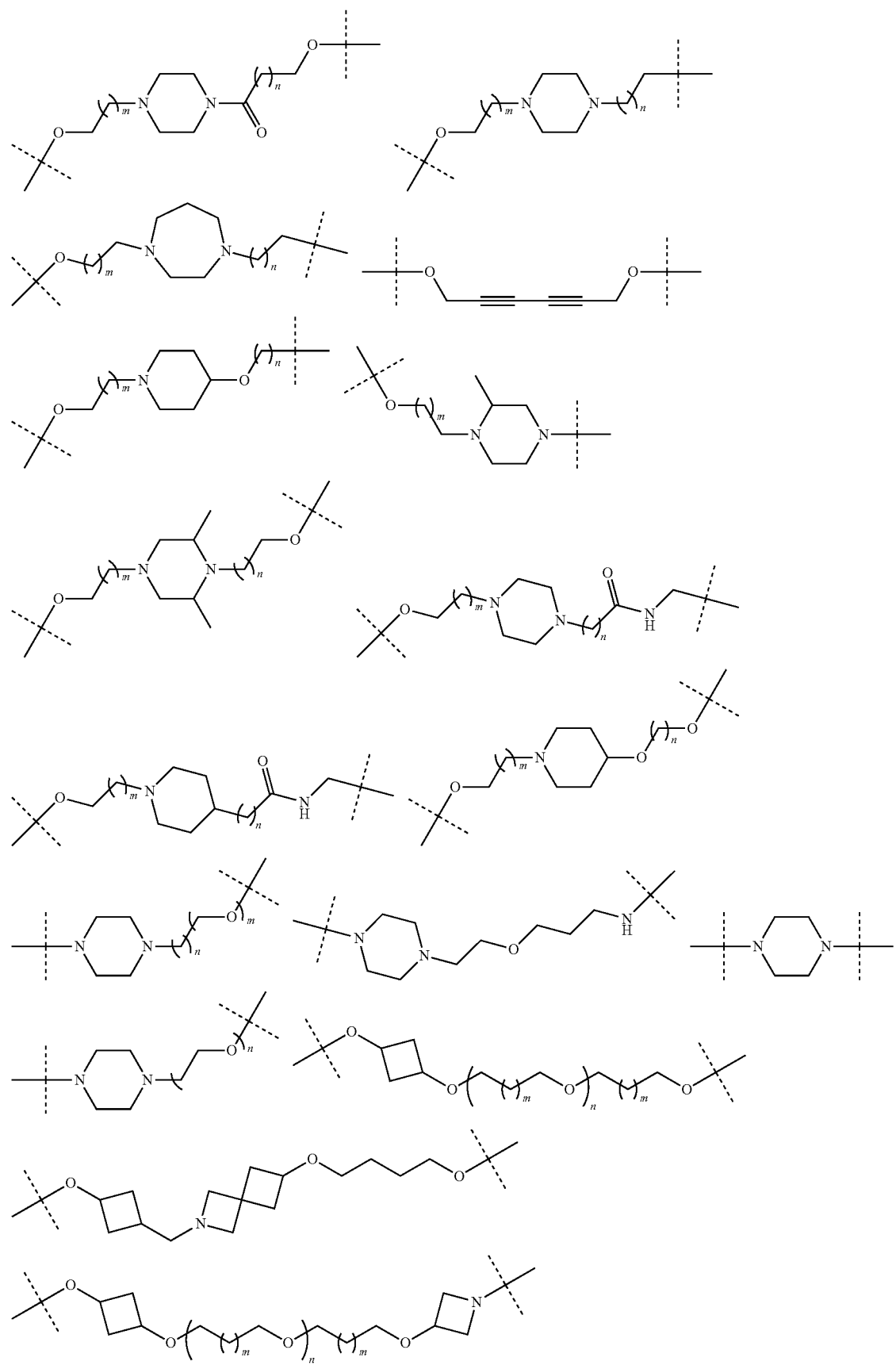

-continued
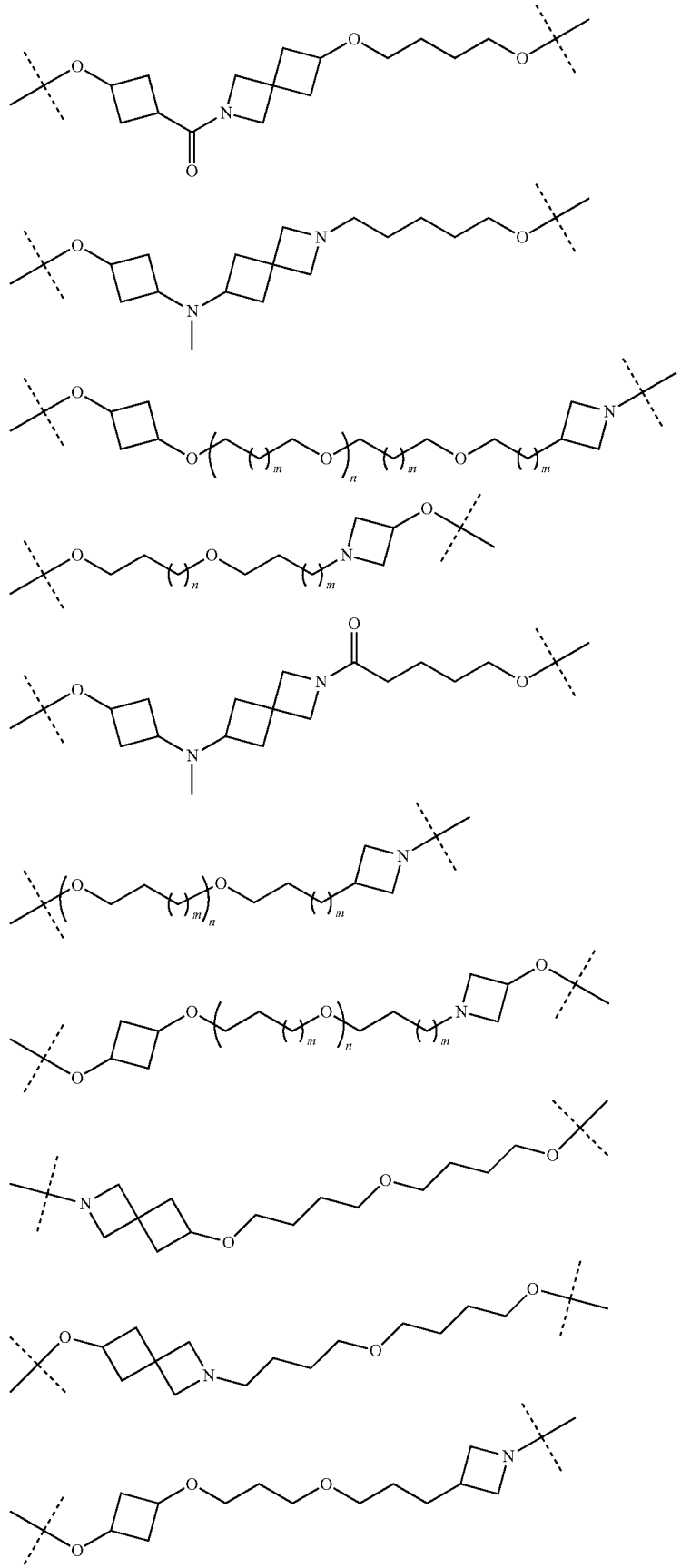

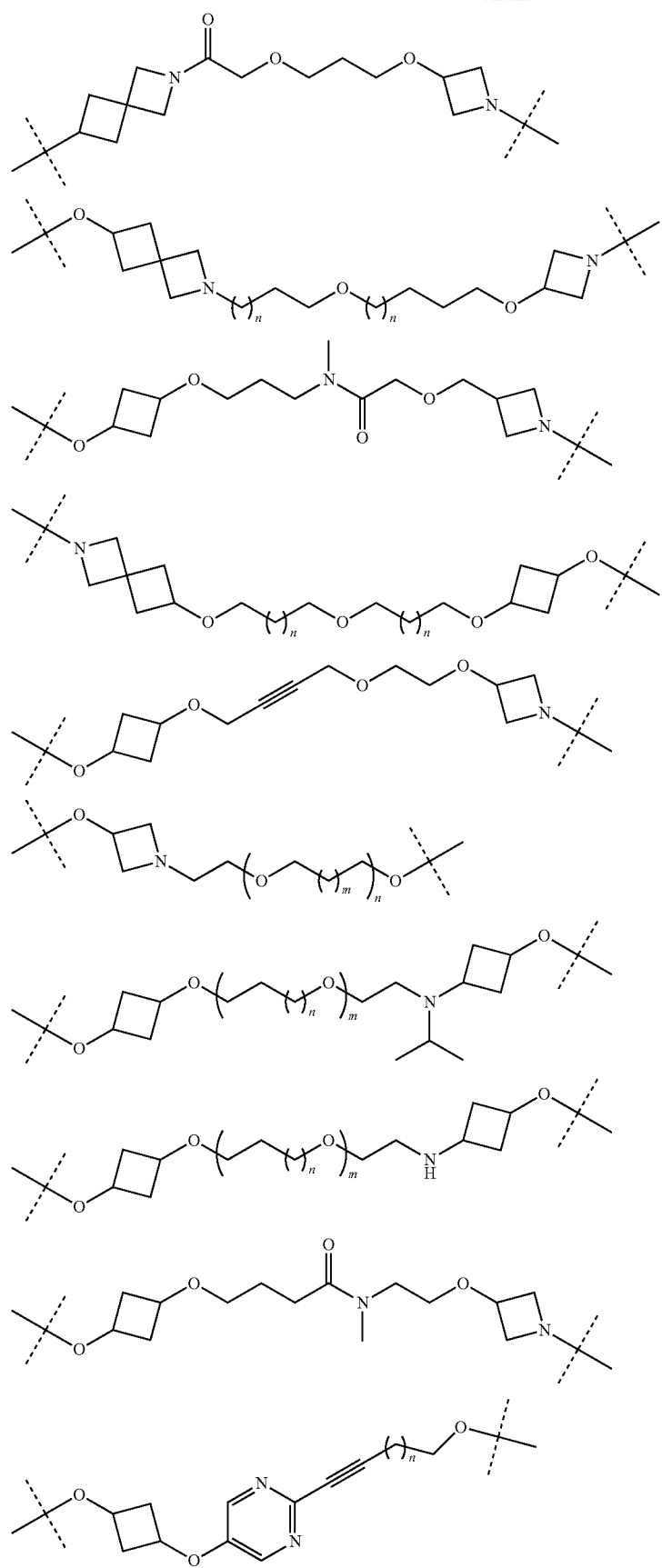

-continued
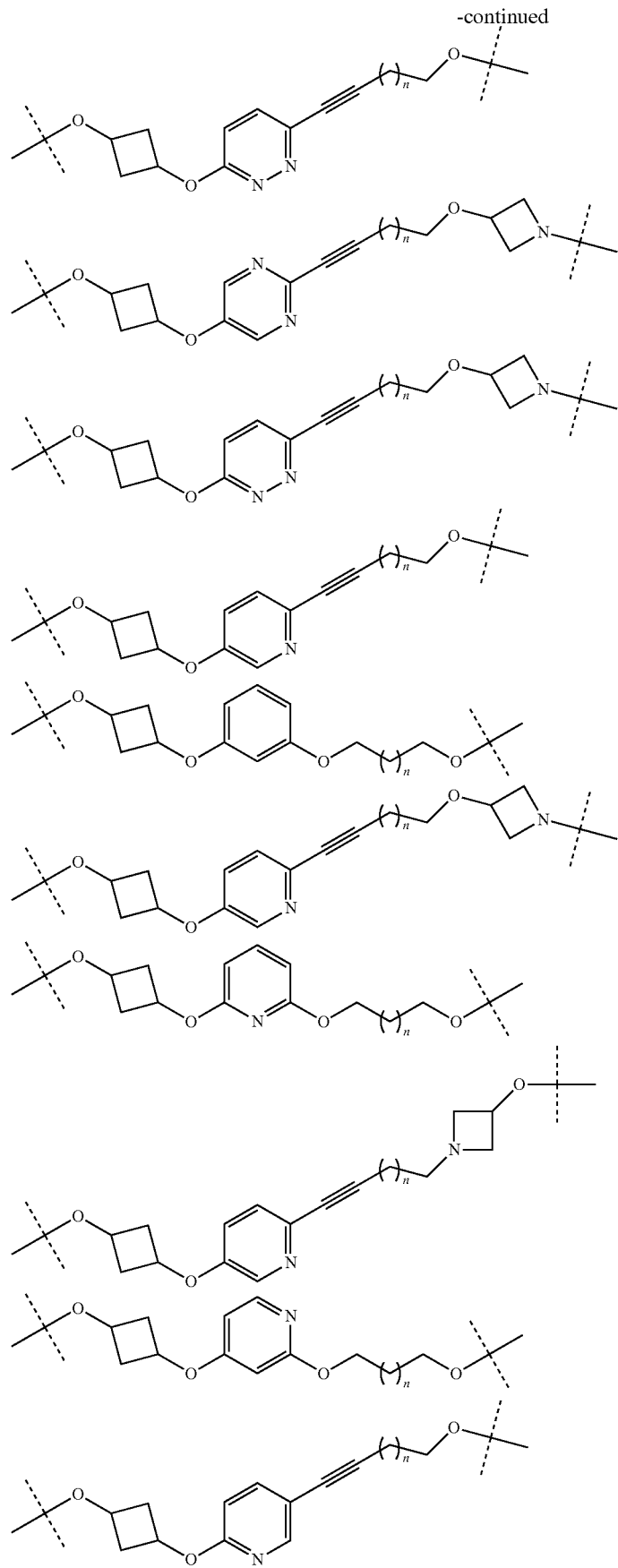

-continued
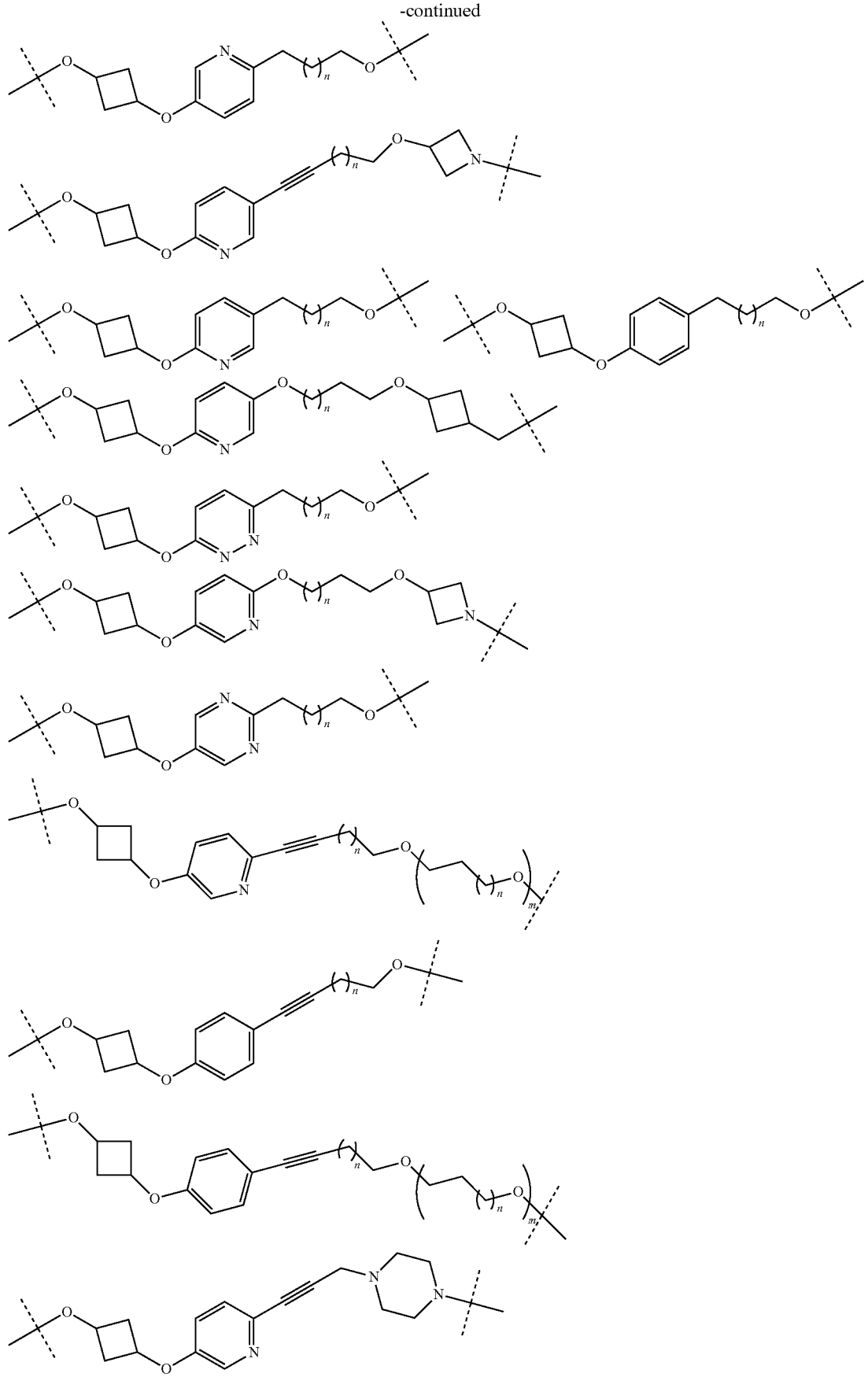

-continued
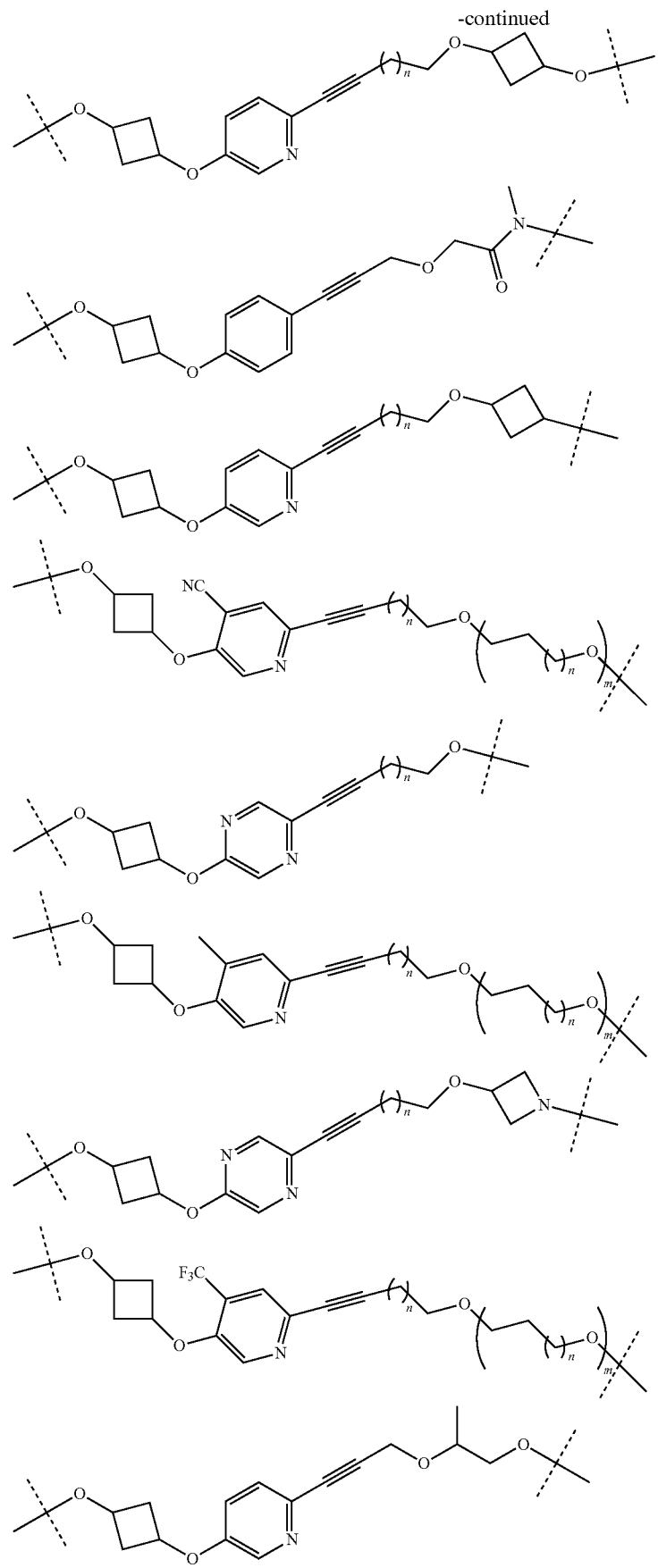

-continued
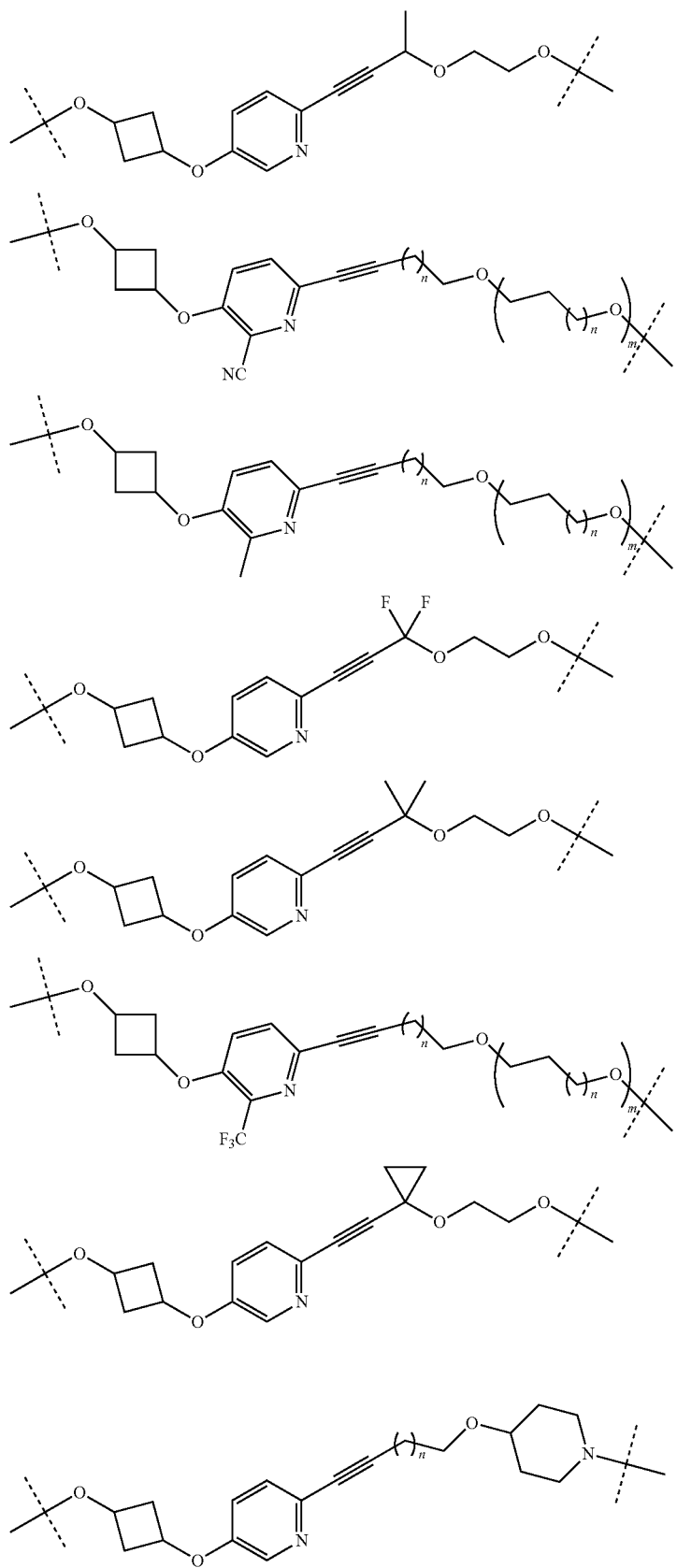

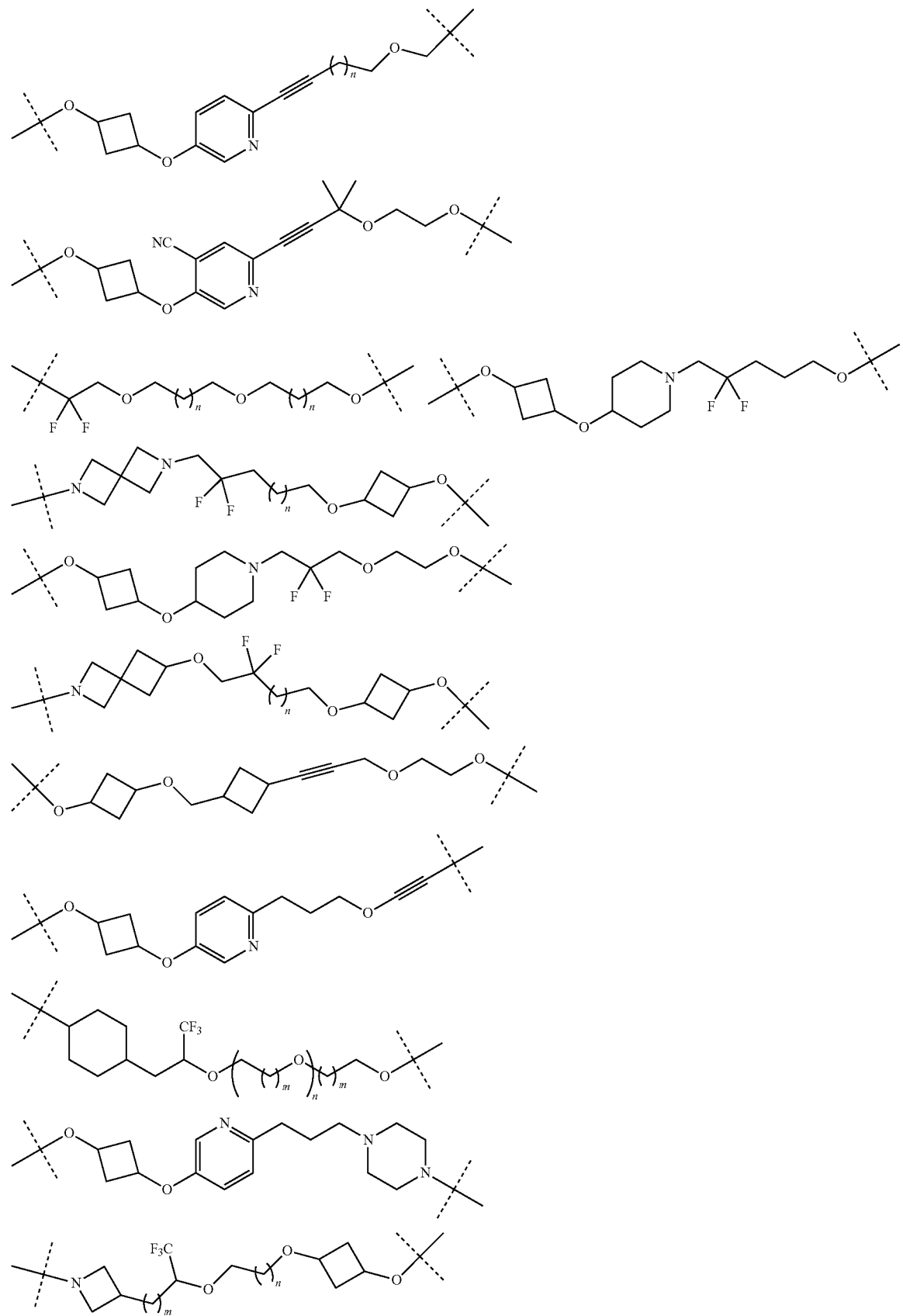

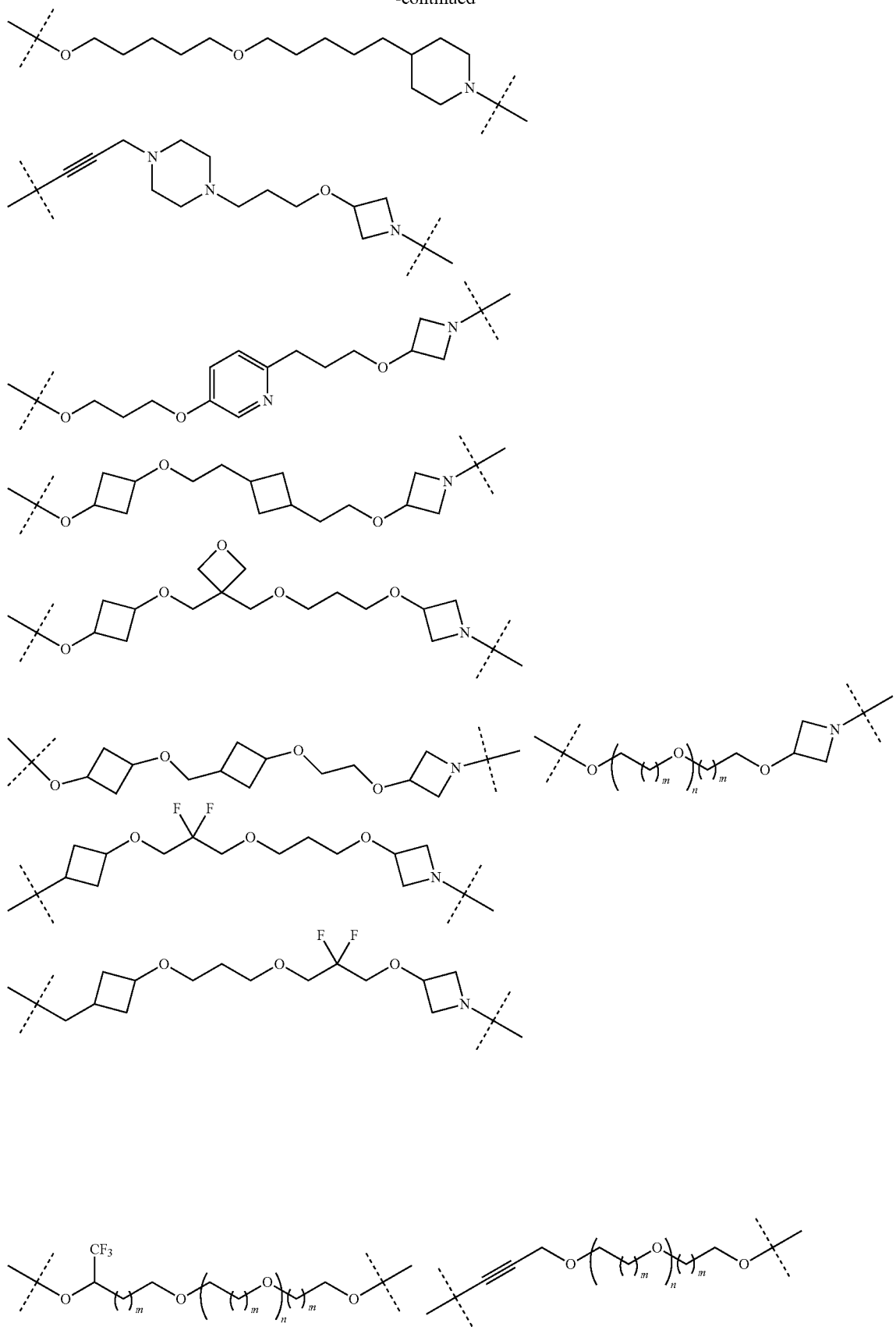

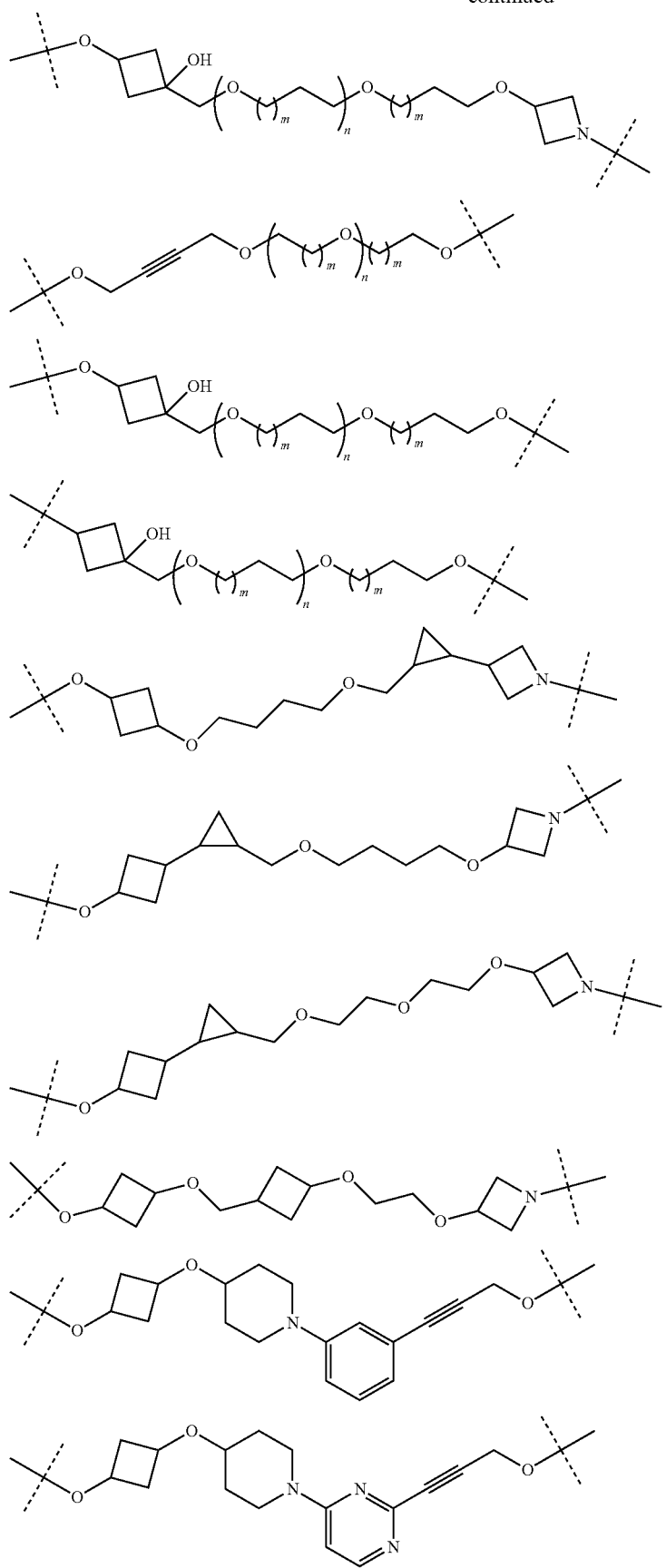

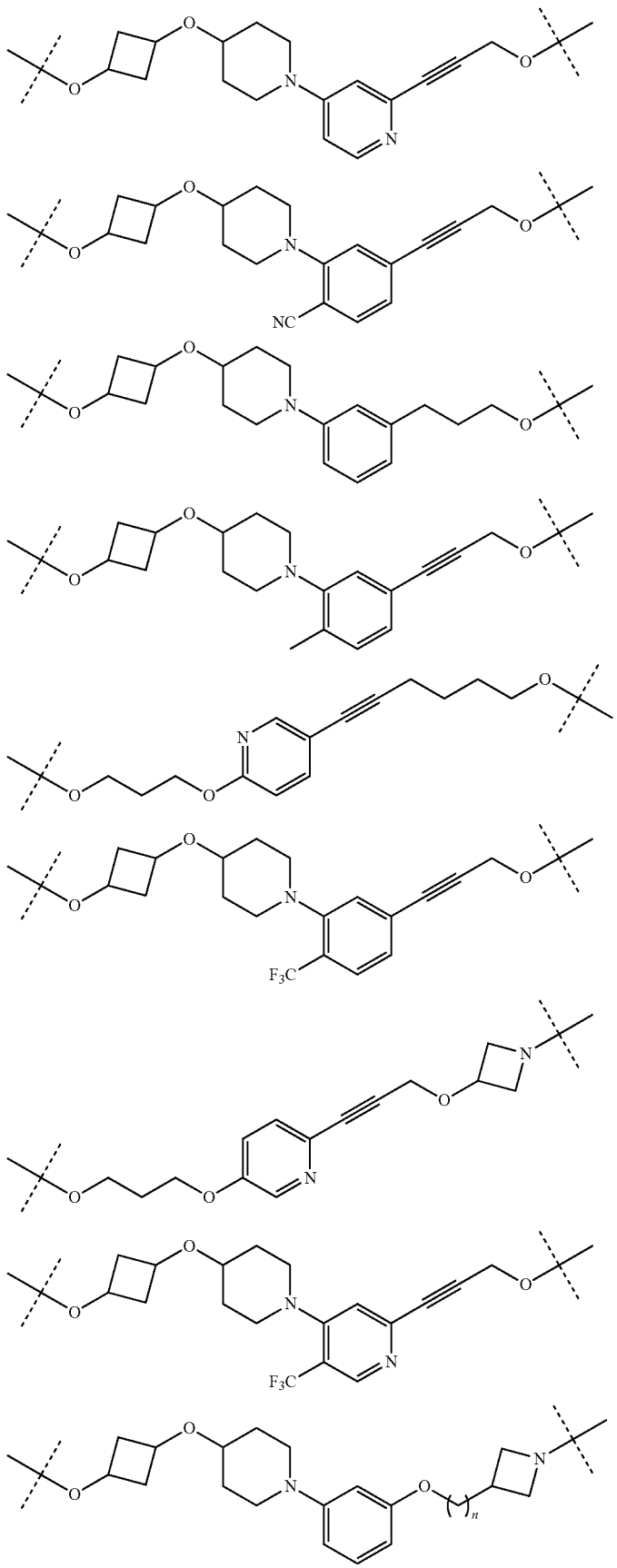

-continued
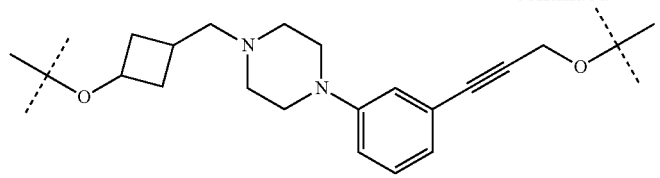
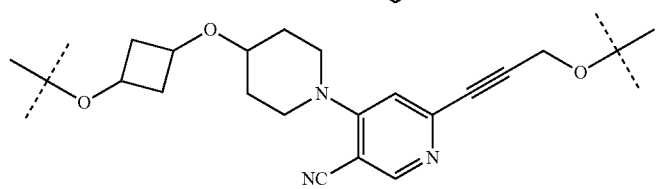
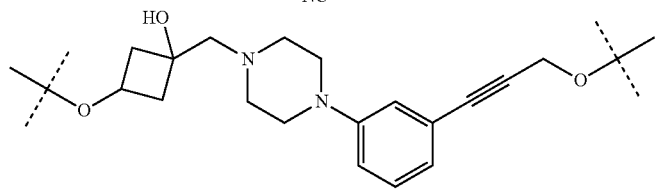
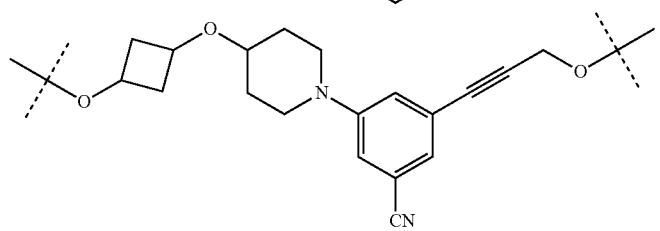
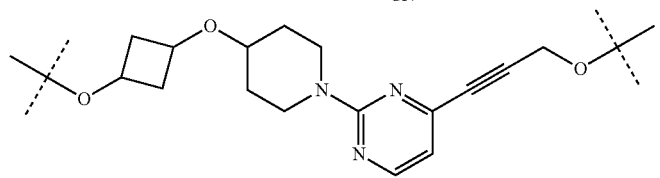
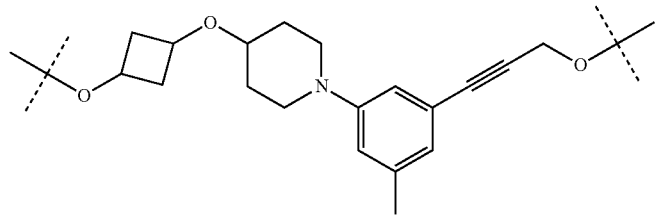
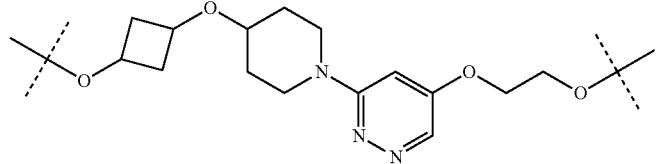
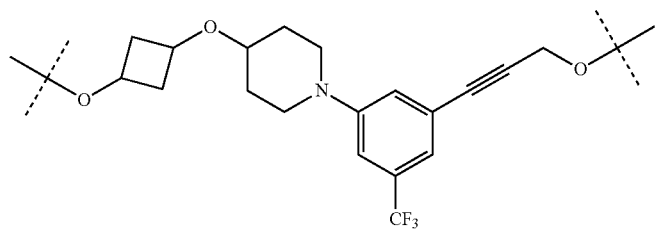
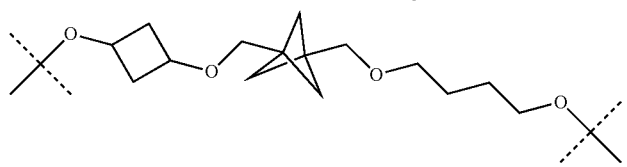

-continued
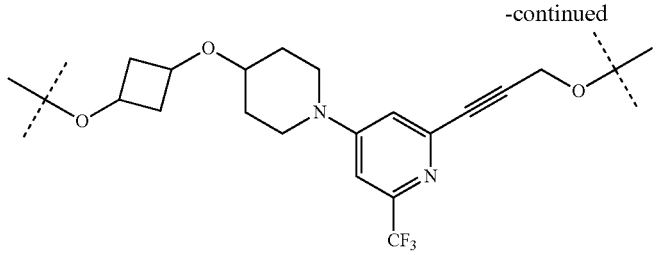
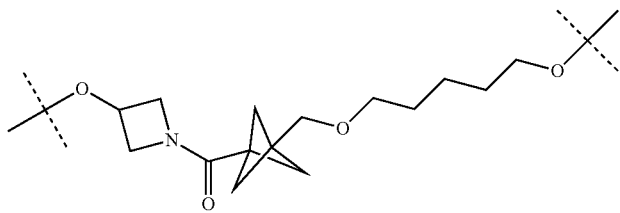
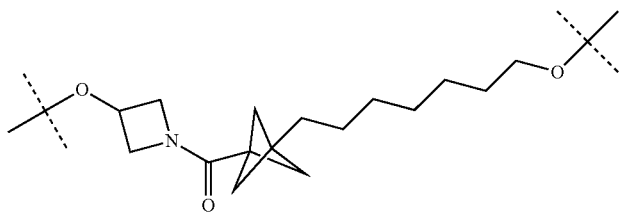
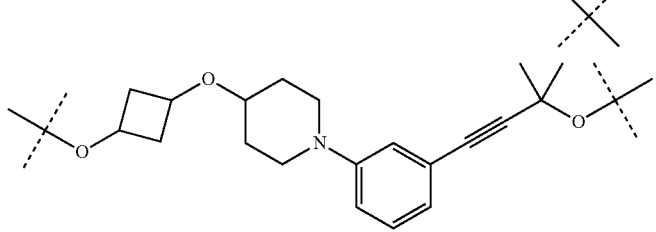
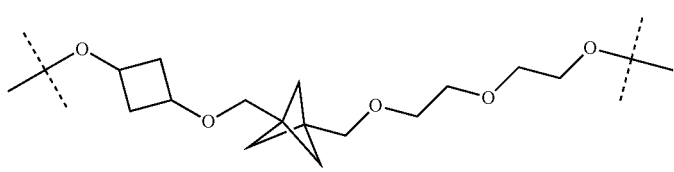
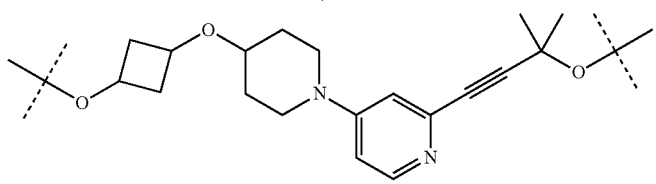

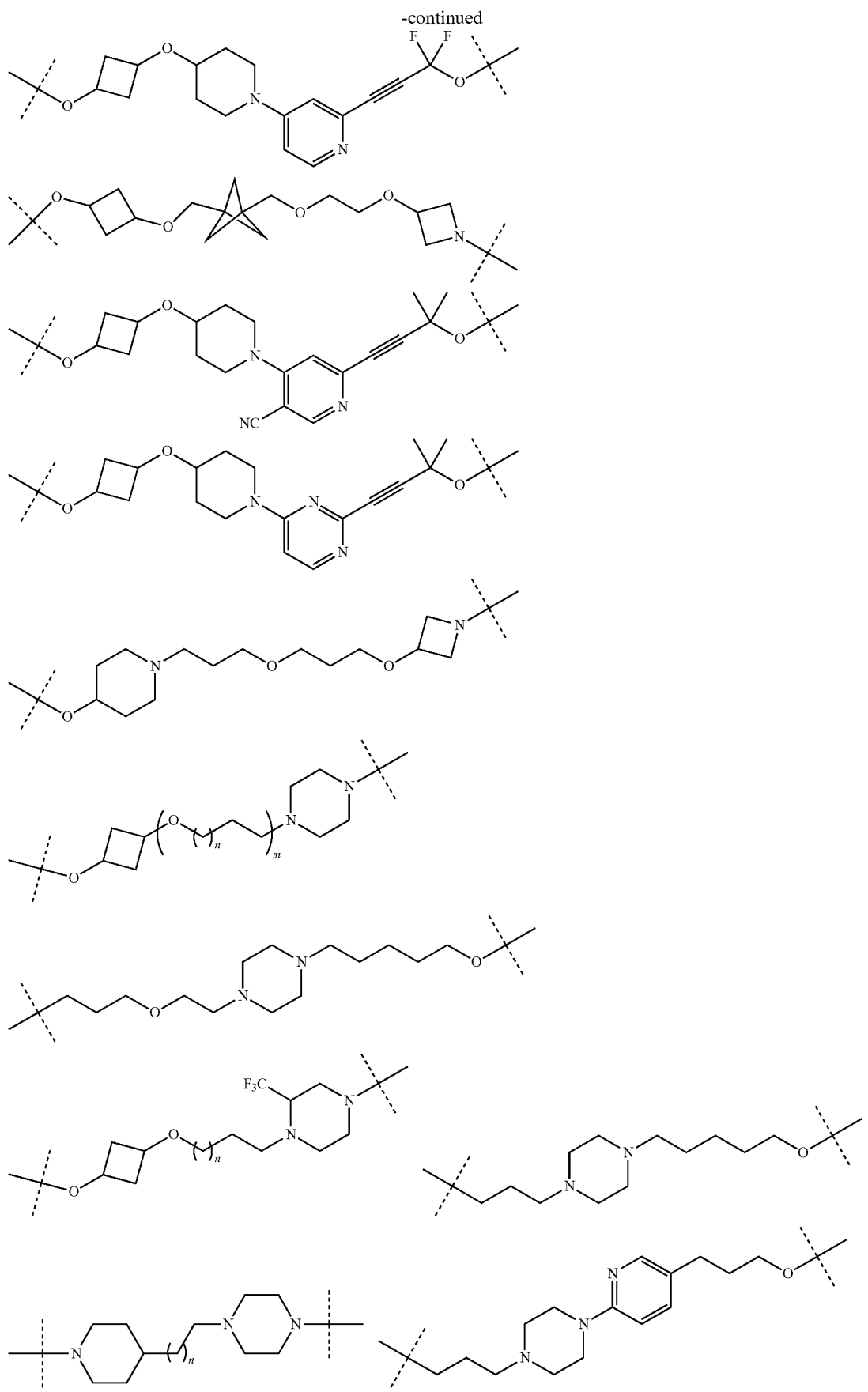

-continued
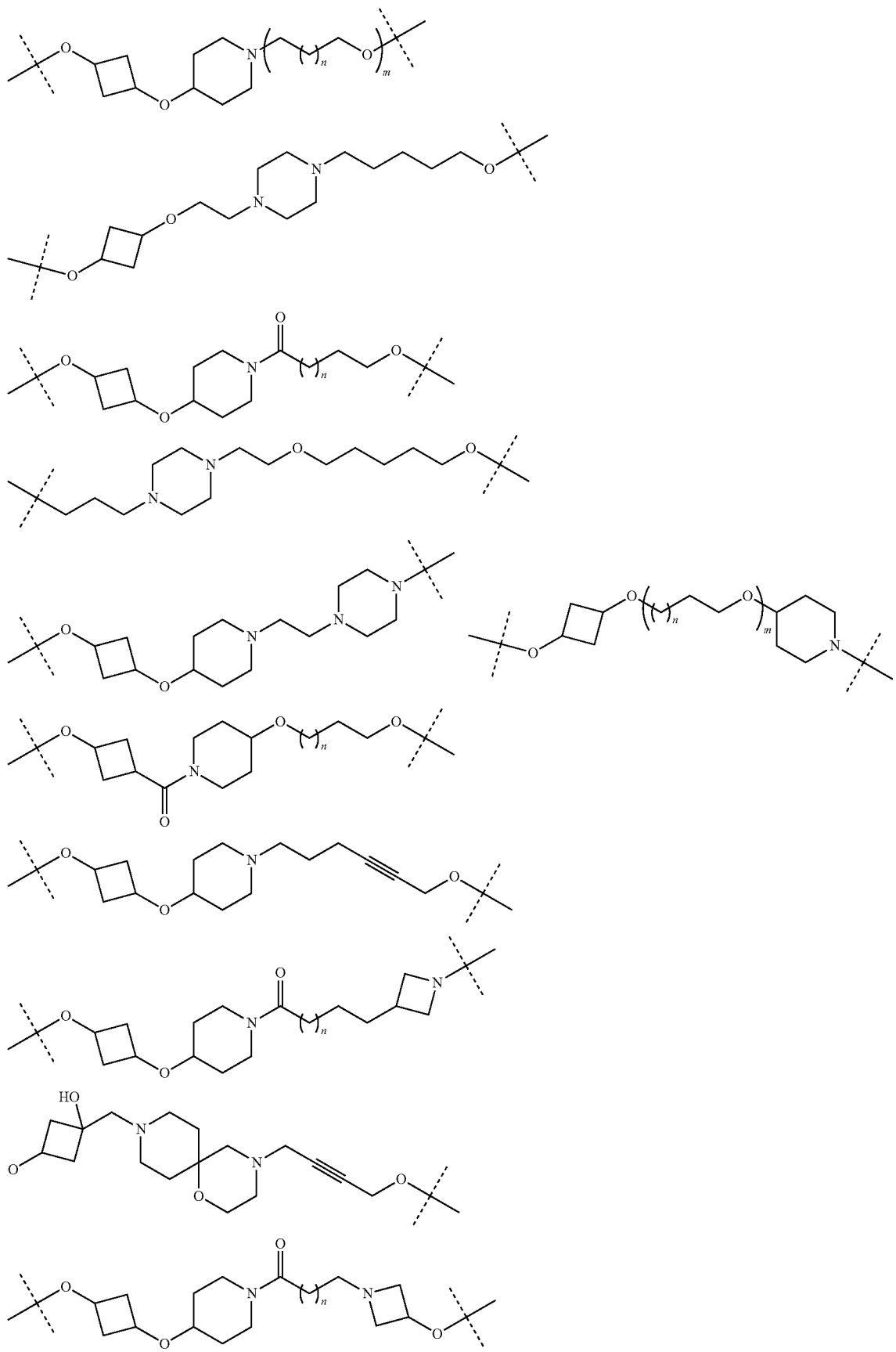

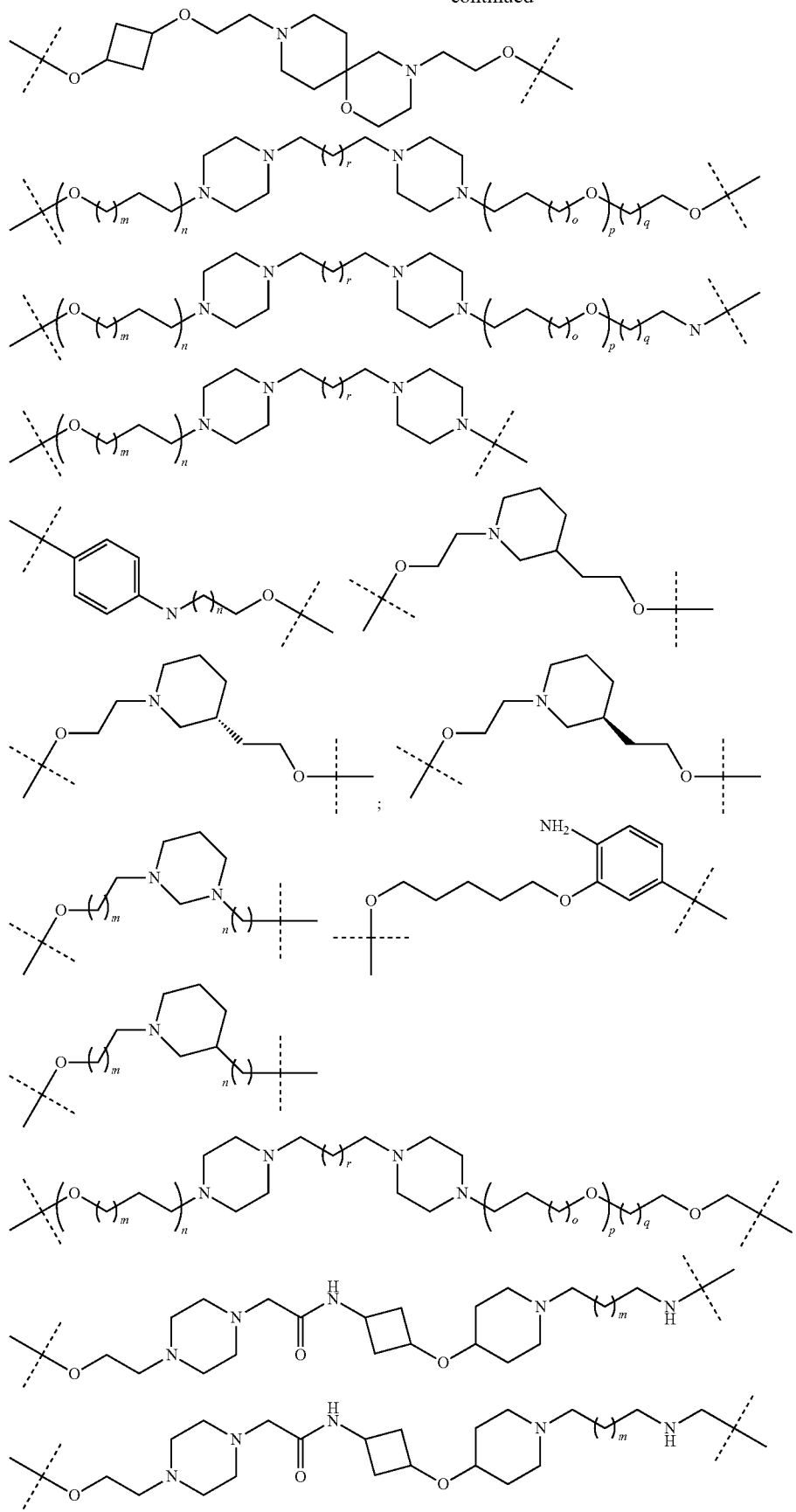

-continued
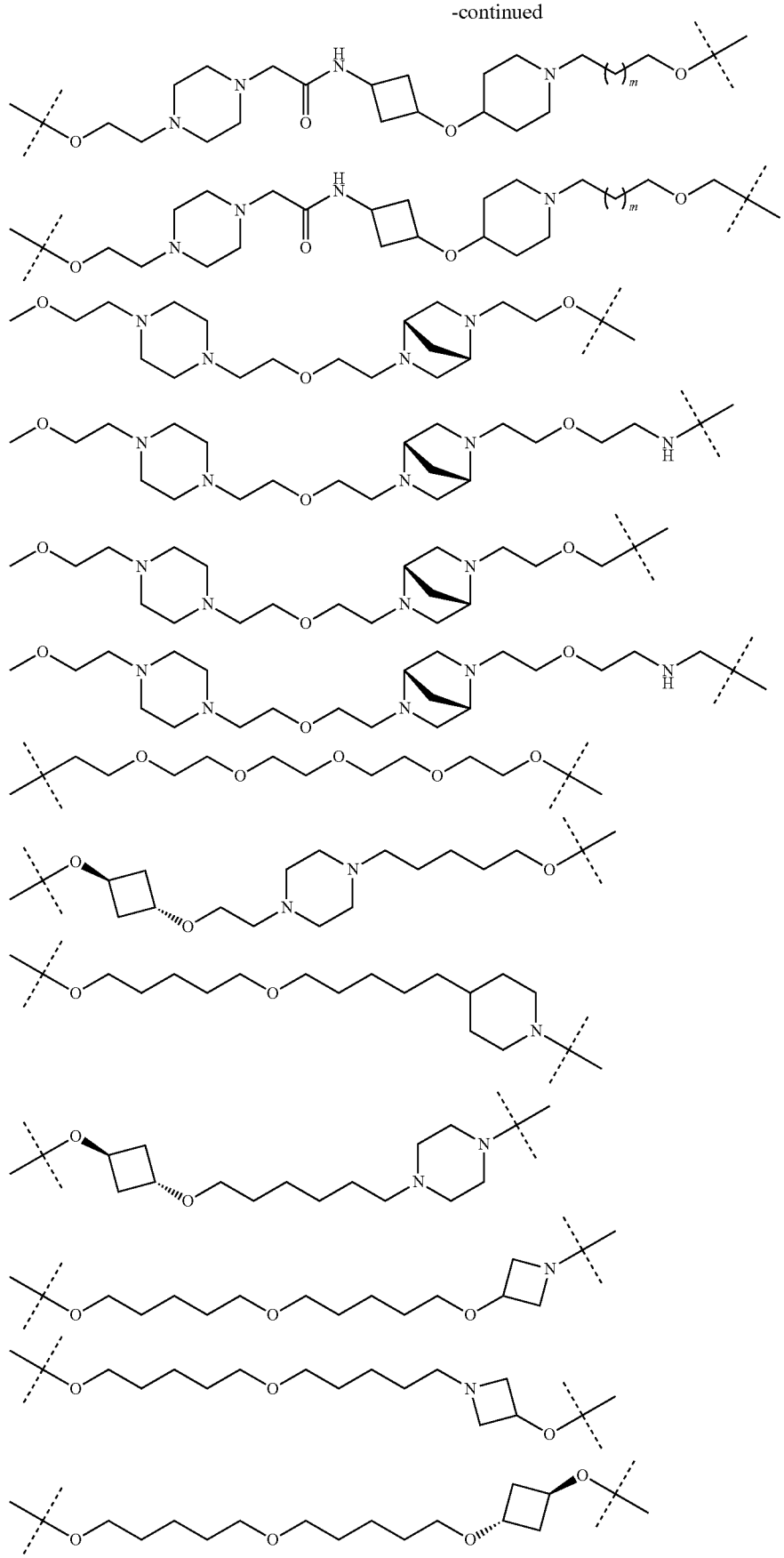

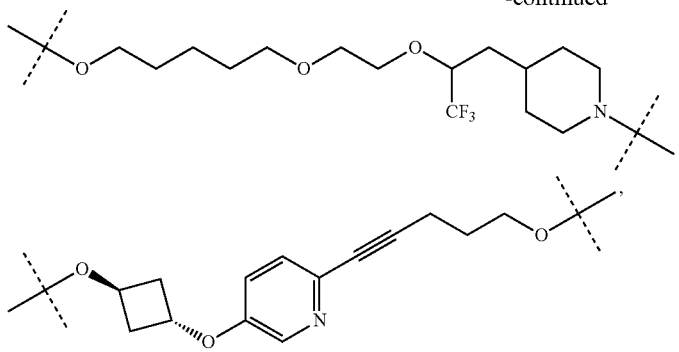
wherein each m, n, o, p, q, and r is independently 0, 1, 2, 3, 4, 5, 6, or 7.
In any aspect or embodiment described herein, L is selected from the group consisting of:
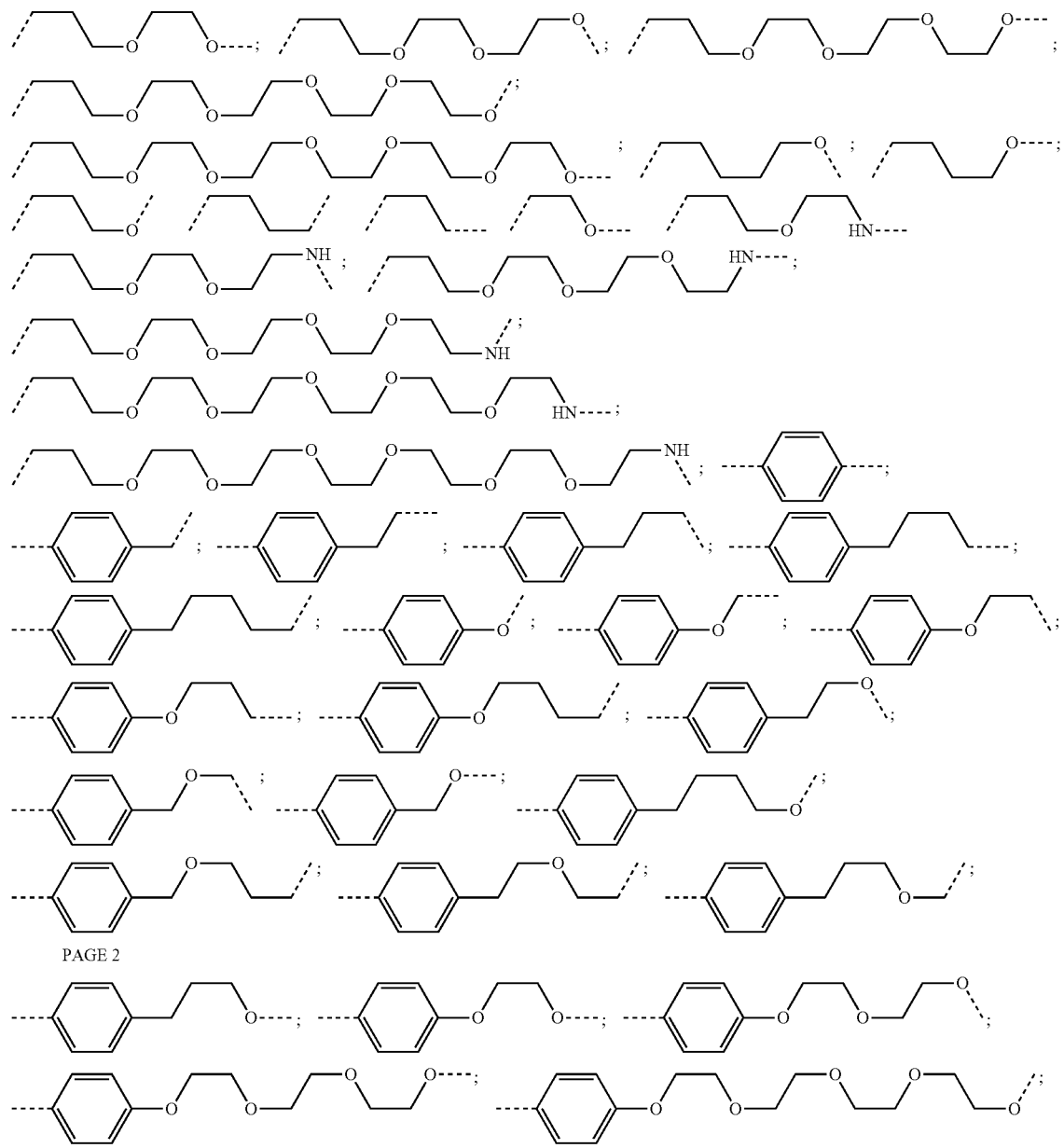

-continued
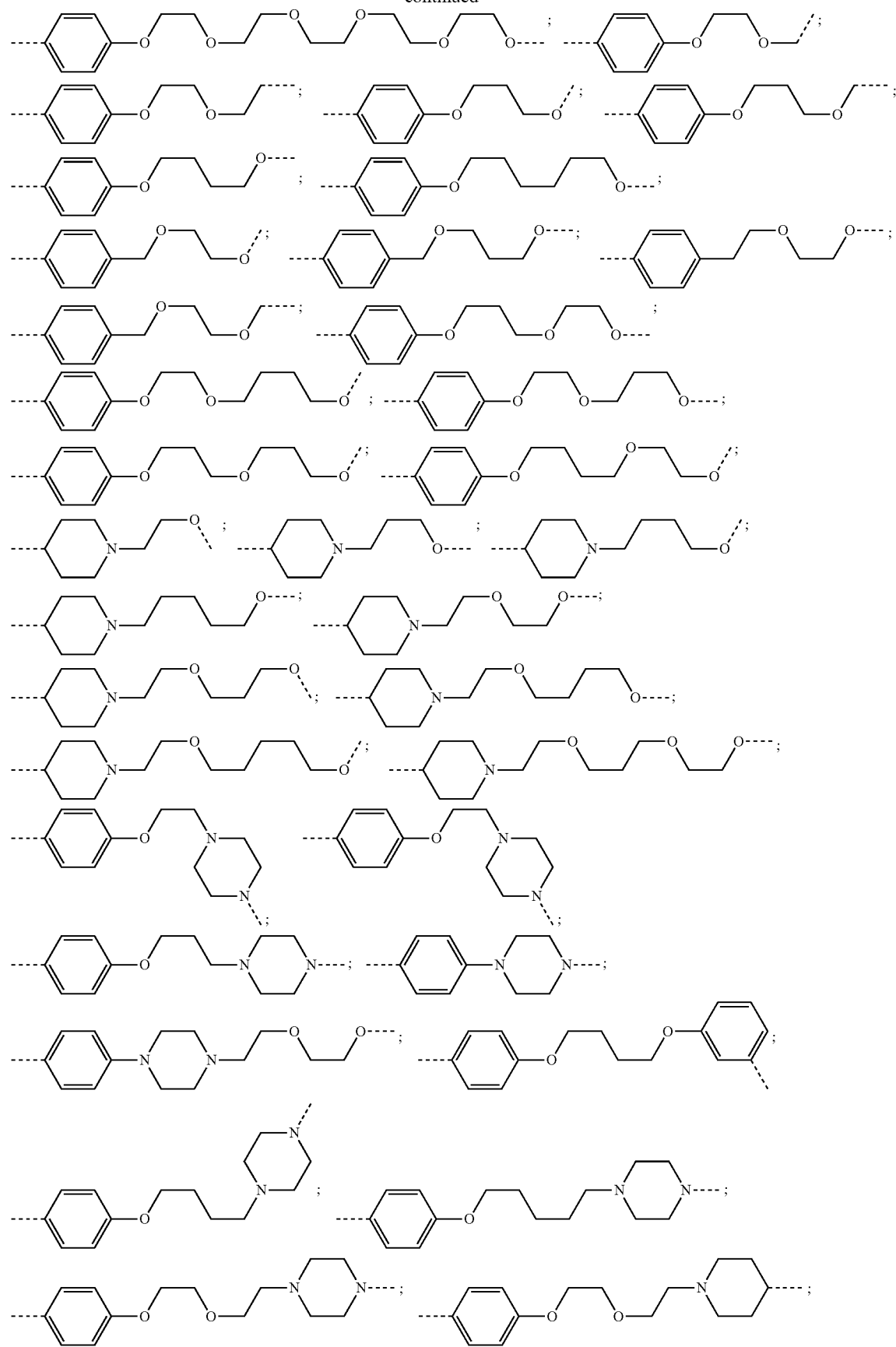

-continued
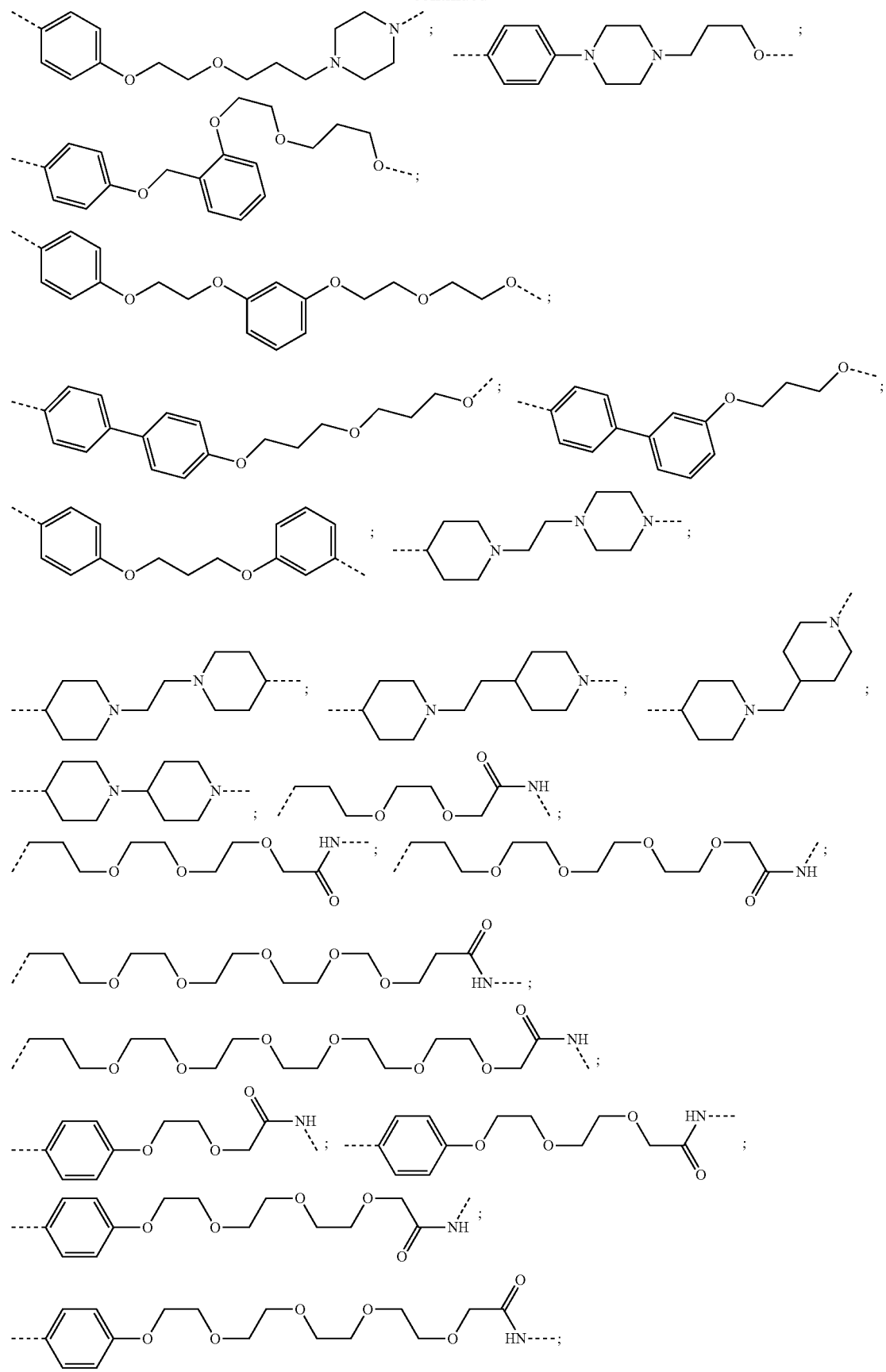

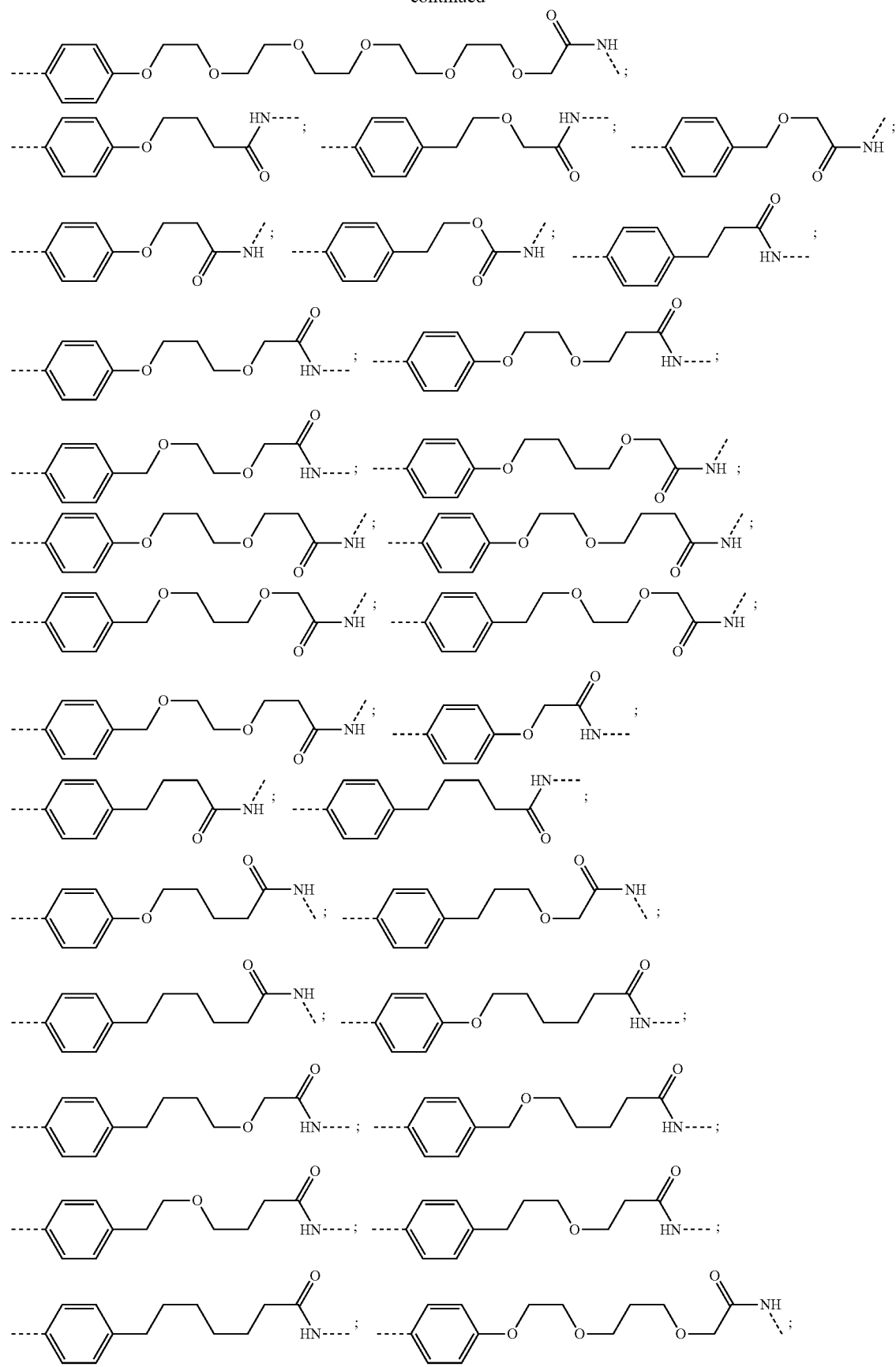

405 406
-continued
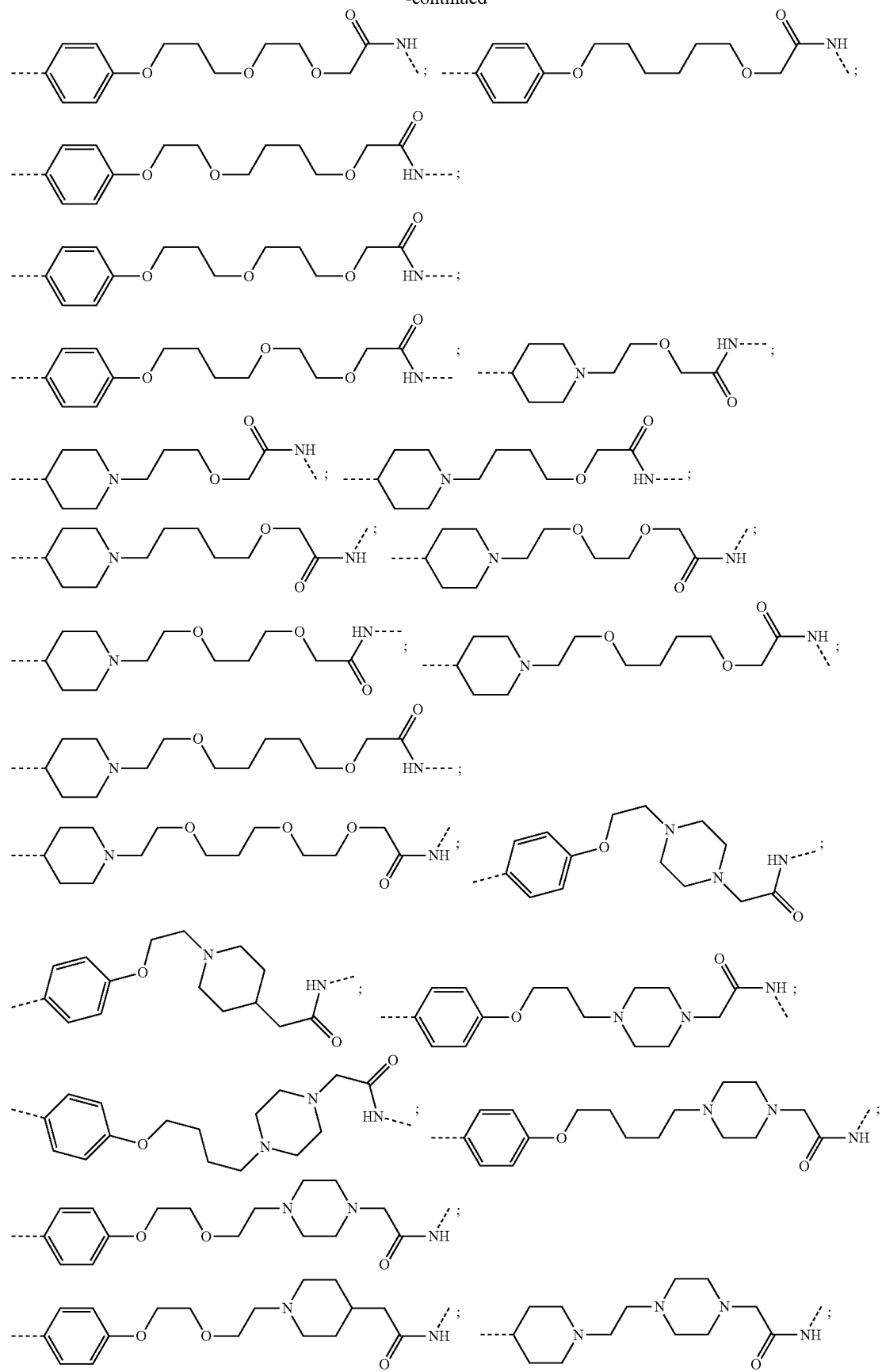

407 408
-continued
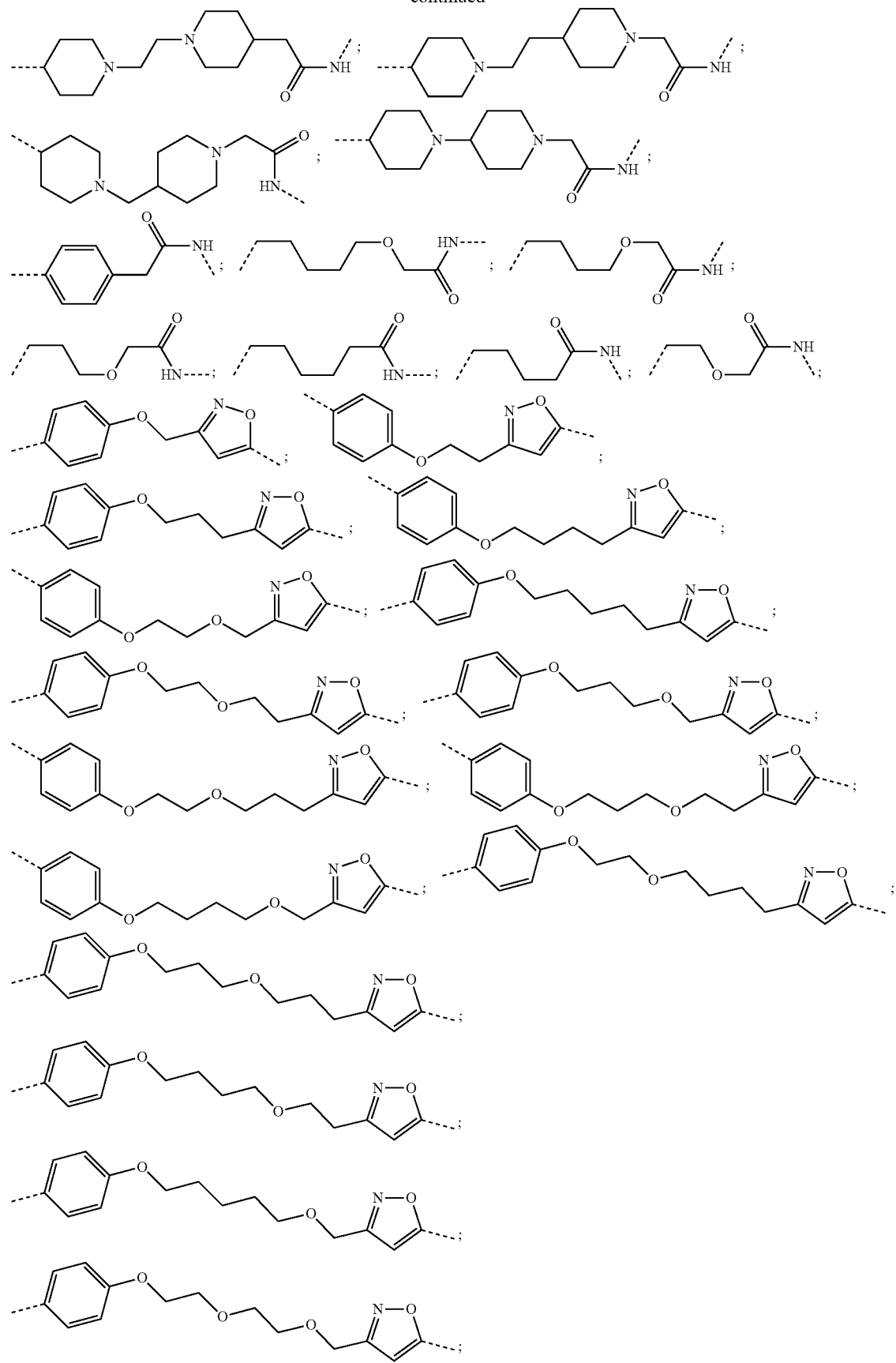

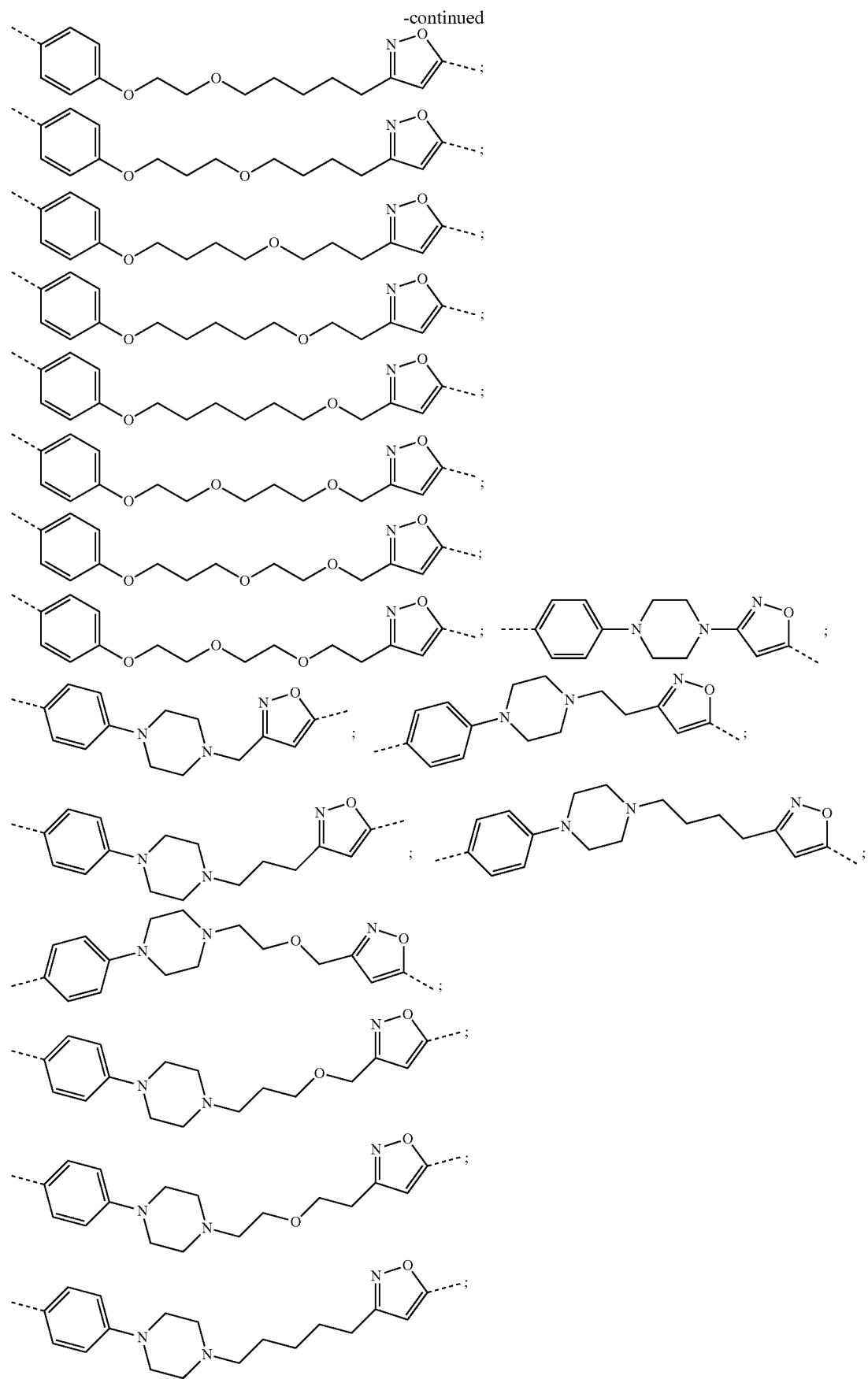

-continued
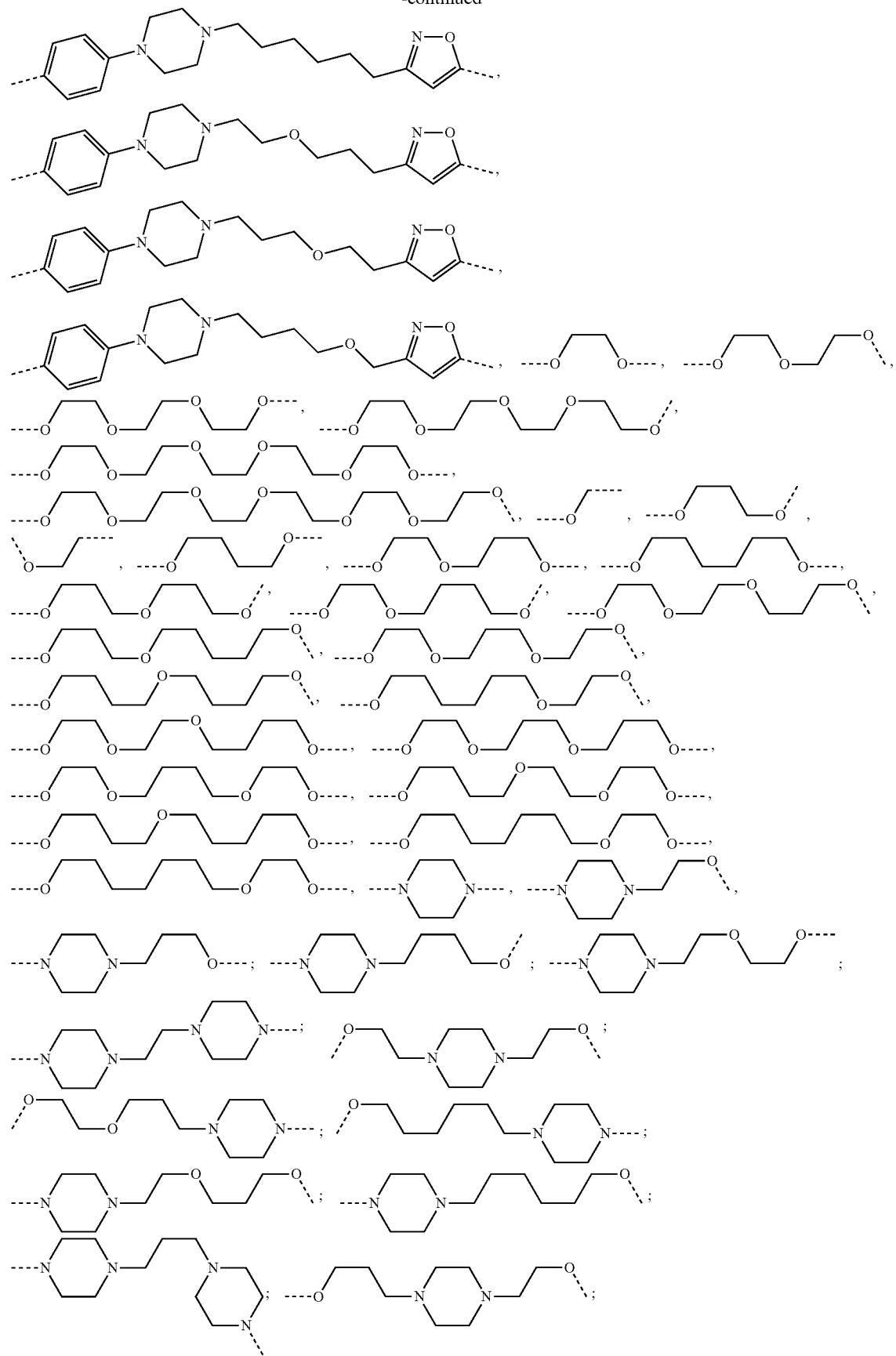

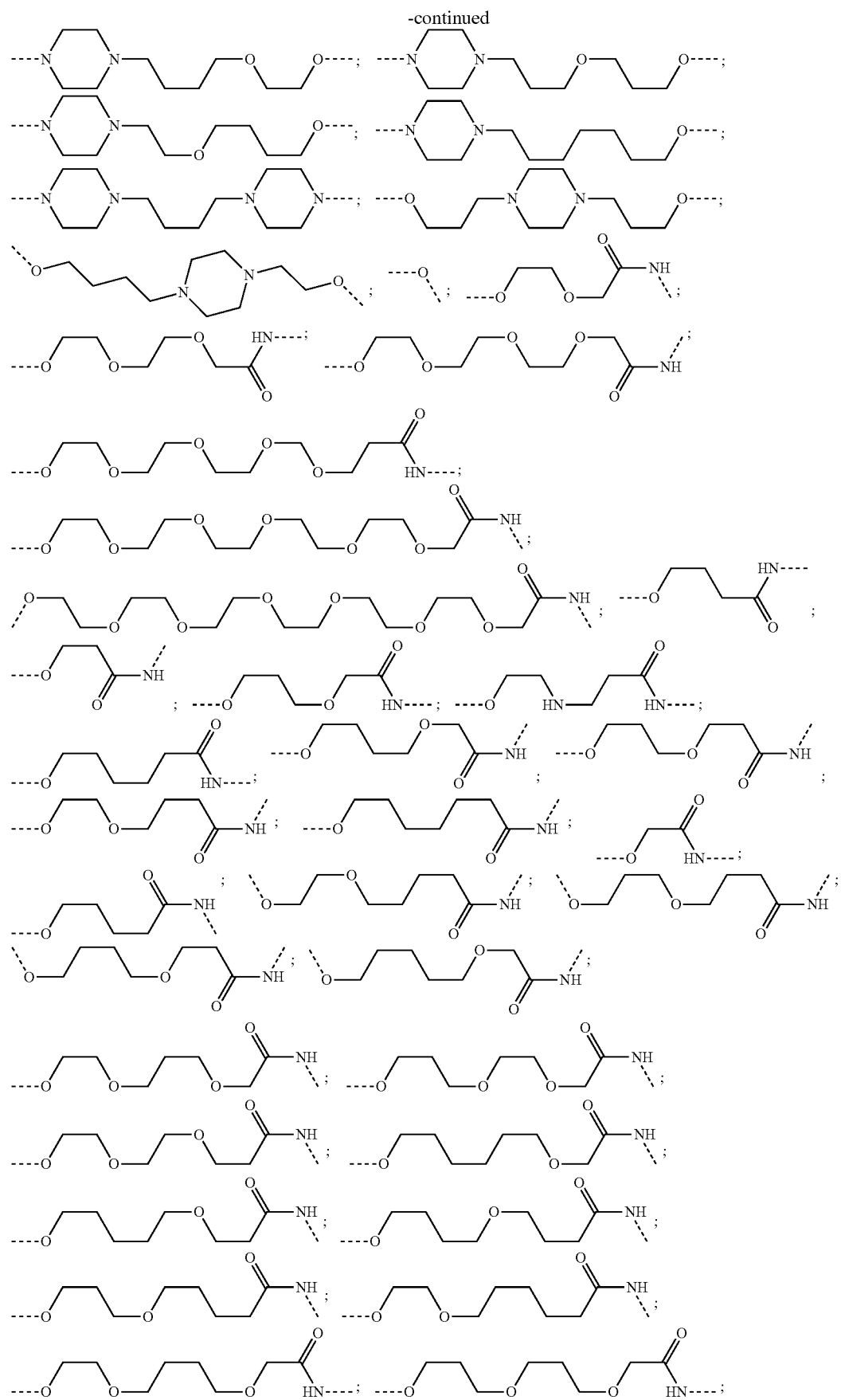

-continued
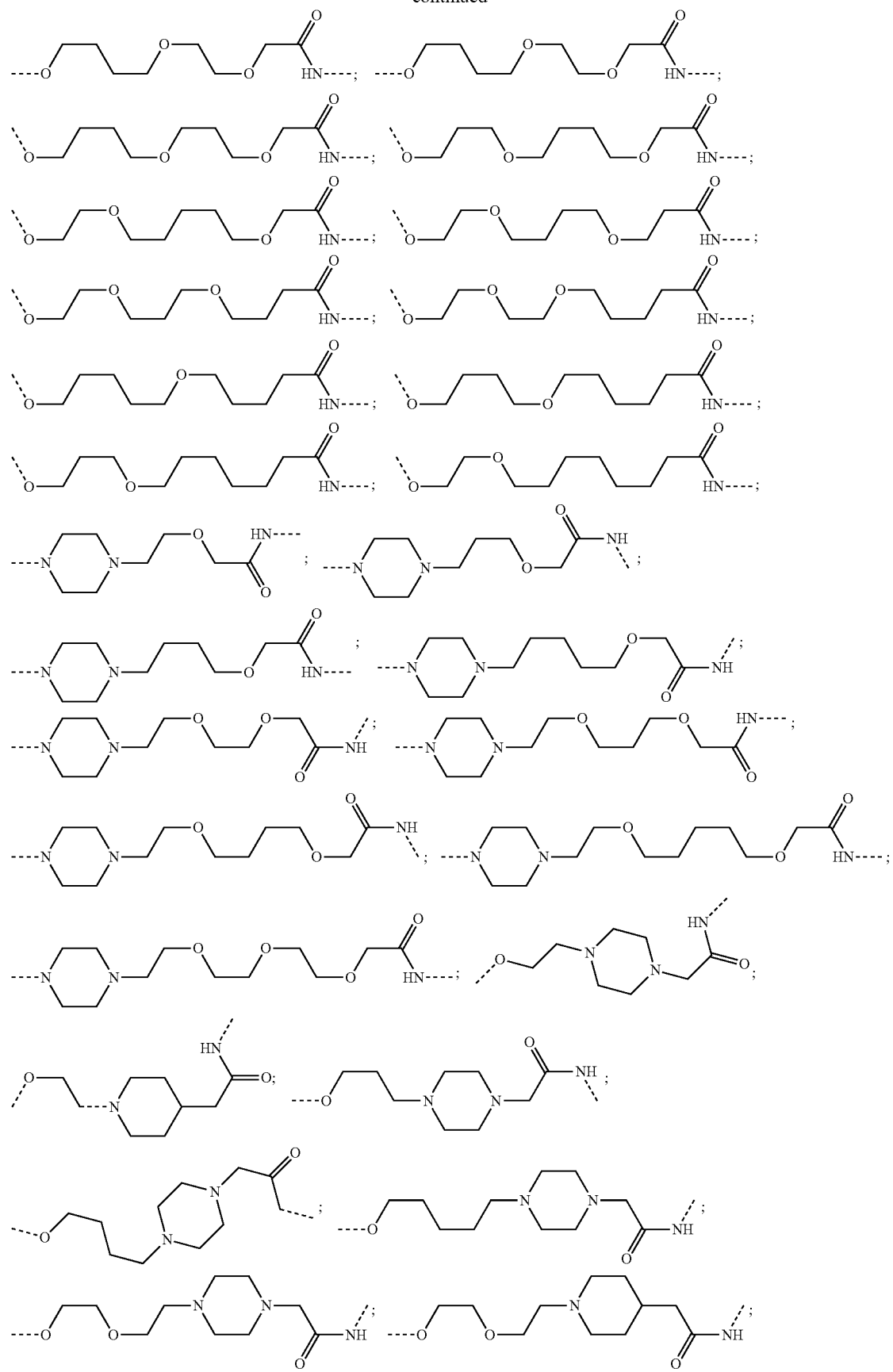

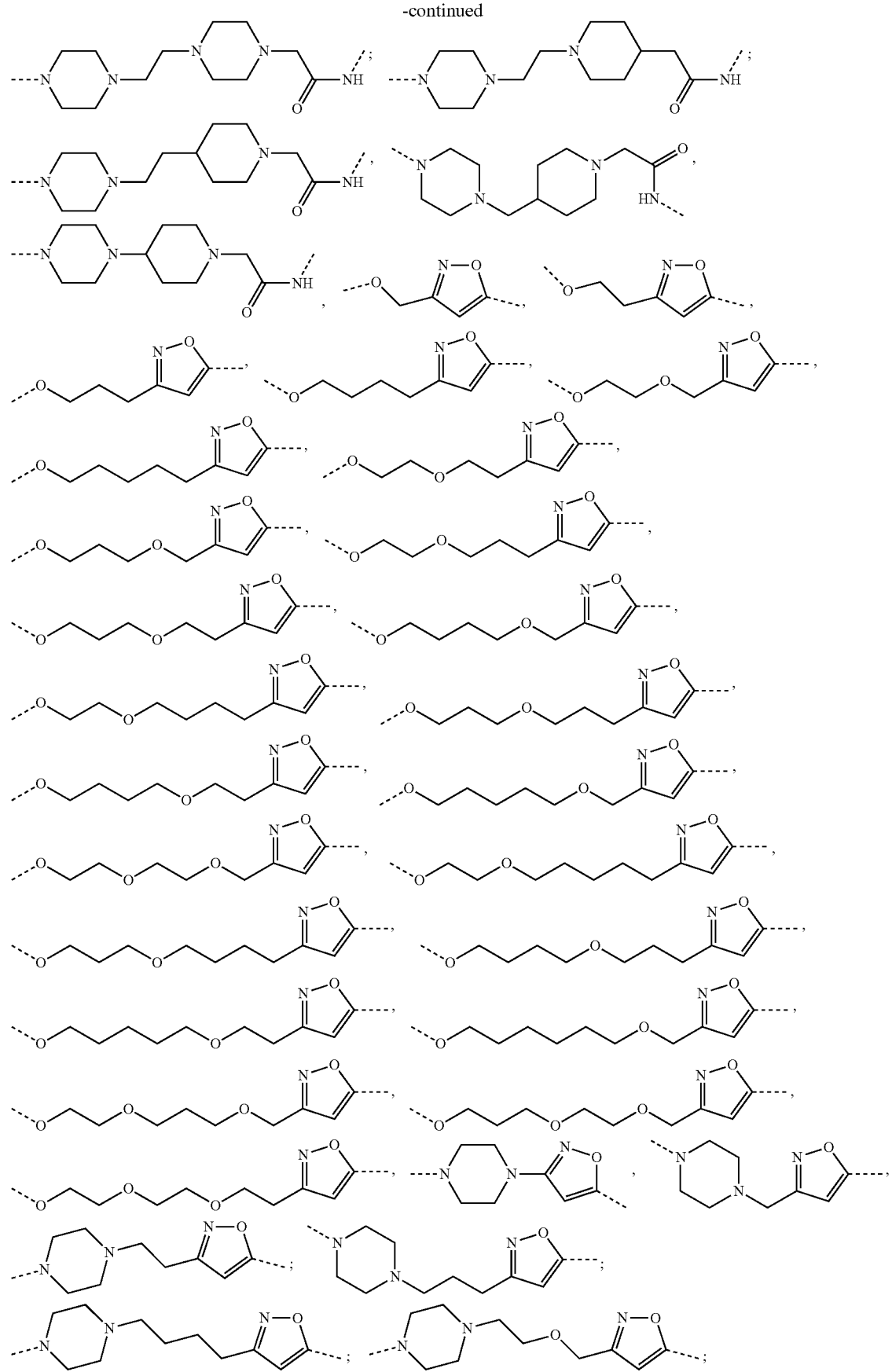

-continued

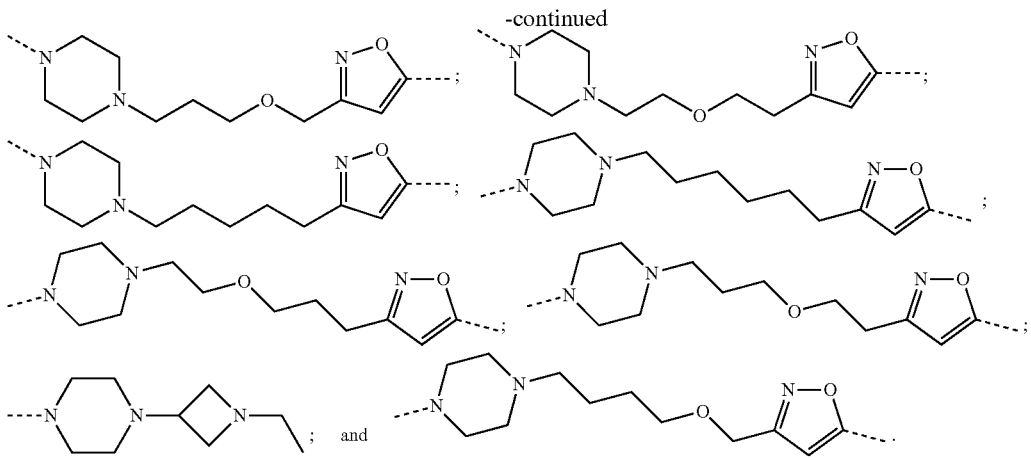

In additional embodiments, the linker (L) comprises a structure selected from, but not limited to the structure shown below, where a dashed line indicates the attachment point to the PTM or ULM moieties.

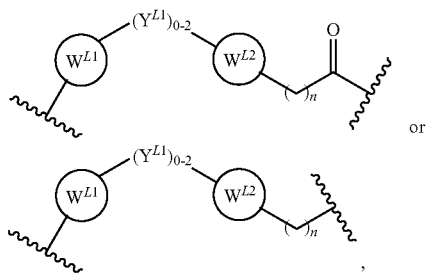

wherein:
W$^{L1}$ and W$^{L2}$ are each independently a 4-8 membered ring with 0-4 heteroatoms, optionally substituted with R$^Q$, each R$^Q$ is independently a H, halo, OH, CN, CF$_3$, C$_1$-C$_6$ alkyl (linear, branched, optionally substituted), C$_1$-C$_6$ alkoxy (linear, branched, optionally substituted), or 2 R$^Q$ groups taken together with the atom they are attached to, form a 4-8 membered ring system containing 0-4 heteroatoms;
Y$^{L1}$ is each independently a bond, C$_1$-C$_6$ alkyl (linear, branched, optionally substituted) and optionally one or more C atoms are replaced with 0; or C$_1$-C$_6$ alkoxy (linear, branched, optionally substituted);
n is 0-10; and
a dashed line indicates the attachment point to the PTM or ULM moieties.

In additional embodiments, the linker (L) comprises a structure selected from, but not limited to the structure shown below, where a dashed line indicates the attachment point to the PTM or ULM moieties.

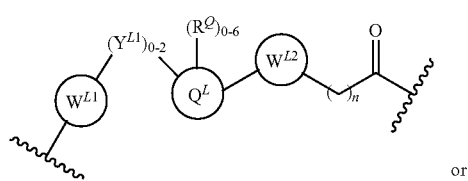

or

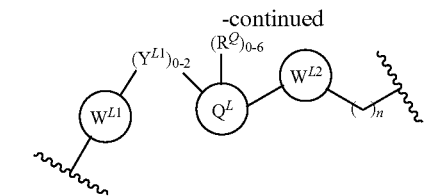

wherein:
W$^{L1}$ and W$^{L2}$ are each independently aryl, heteroaryl, cyclic, heterocyclic, C$_{1-6}$ alkyl, bicyclic, biaryl, biheteroaryl, or biheterocyclic, each optionally substituted with R$^Q$, each R$^Q$ is independently a H, halo, OH, CN, CF$_3$, hydroxyl, nitro, C≡CH, C$_{2-6}$ alkenyl, C$_{2-6}$ alkynyl, C$_1$-C$_6$ alkyl (linear, branched, optionally substituted), C$_1$-C$_6$ alkoxy (linear, branched, optionally substituted), OC$_{1-3}$alkyl (optionally substituted by 1 or more —F), OH, NH$_2$, NR$^{Y1}$R$^{Y2}$, CN, or 2 R$^Q$ groups taken together with the atom they are attached to, form a 4-8 membered ring system containing 0-4 heteroatoms;
Y$^{L1}$ is each independently a bond, NR$^{YL1}$, O, S, NR$^{YL2}$, CR$^{YL1}$R$^{YL2}$, C=O, C=S, SO, SO$_2$, C$_1$-C$_6$ alkyl (linear, branched, optionally substituted) and optionally one or more C atoms are replaced with O; C$_1$-C$_6$ alkoxy (linear, branched, optionally substituted);
Q$^L$ is a 3-6 membered alicyclic or aromatic ring with 0-4 heteroatoms, optionally bridged, optionally substituted with 0-6 R$^Q$, each 0 is independently H, C$_{1-6}$ alkyl (linear, branched, optionally substituted by 1 or more halo, C$_{1-6}$ alkoxyl), or 2 R$^Q$ groups taken together with the atom they are attached to, form a 3-8 membered ring system containing 0-2 heteroatoms);
R$^{YL1}$, R$^{YL2}$ are each independently H, OH, C$_{1-6}$ alkyl (linear, branched, optionally substituted by 1 or more halo, C$_{1-6}$ alkoxyl), or R$^1$, R$^2$ together with the atom they are attached to, form a 3-8 membered ring system containing 0-2 heteroatoms);
n is 0-10; and
a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described above, which binds to a target protein (e.g., FLT3) or polypeptide, which is ubiquitinated by an ubiquitin ligase and is chemically linked directly to the ULM group or through a linker moiety L, or PTM is alternatively a ULM' group which is also an ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

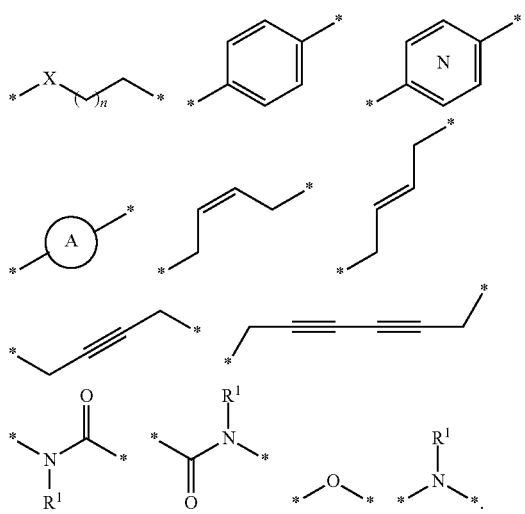

The X is selected from the group consisting of O, N, S, S(O) and SO$_2$; n is integer from 1-5, 5; R$^{L1}$ is hydrogen or alkyl,

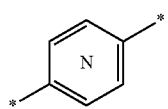

is a mono- or bicyclic aryl or heteroaryl optionally substituted with 1-3 substituents selected from alkyl, halogen, haloalkyl, hydroxy, alkoxy or cyano;

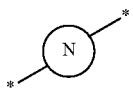

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is FLT3 or mutants thereof.

PTM groups according to the present disclosure include, for example, any moiety which binds to FLT3. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by an ubiquitin ligase is a target protein according to the present disclosure. In general, target proteins may include, for example, tyrosine kinases. Proteins of interest can include proteins from eurkaryotes including humans as targets for drug therapy, and other animals, including domesticated animals, among numerous others. The present disclosure may be used to treat a number of disease states and/or conditions, including any disease state and/or condition in which FLT3 is dysregulated and where a patient would benefit from the degradation of FLT3.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In certain additional embodiments, the disease is acute myeloid leukemia (AML), acute promelocytic leukemia (APL), B and T cell acute lymphoblastic leukemia (ALL), chronic melogenous leukemia (CML), and myelodysplasia (MDS).

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer or other neoplasias, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM, CLM, ILM, and/or MLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including receptors, such as cytokine receptors such as FLT3. The target proteins may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include FLT3, among numerous others. The compositions described below exemplify some of the members of the small molecule target proteins. An exemplary protein target moiety according to the present disclosure includes FLT3.

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In an embodiment, the PTM is represented by Formula PTM-I or Formula PTM-II (which correspond to Formula I and Formula II from U.S. Patent Application Publication No. 2006/0281768 A1, which is incorporated herein in its entirety for all purposes):

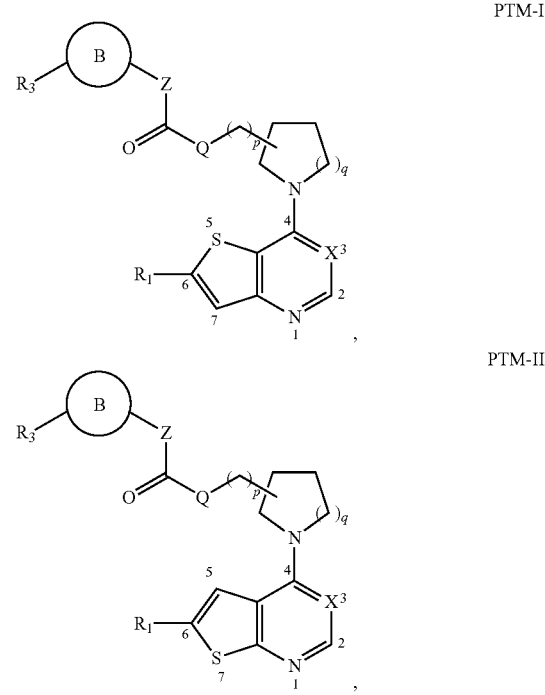

or N-oxides thereof, wherein:
q of PTM-I or PTM-II is 0, 1 or 2;
p of PTM-I or PTM-II is 0 or 1;
Q of PTM-I or PTM-II is NH, N(alkyl), O, 1 or a direct bond;
X of PTM-I or PTM-II is N or CH;
Z of PTM-I or PTM-II is NH, N(alkyl), or CH2;
B of PTM-I or PTM-II is aryl (wherein said aryl is preferably phenyl), cyclopentadienyl, cycloalkyl (wherein said cycloalkyl is preferably cyclopentanyl, cyclohexanyl, cyclopentenyl or cyclohexenyl), heteroaryl (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or a nine to ten membered benzo-fused heteroaryl (wherein said nine to ten membered benzo-fused heteroaryl is preferably benzothiazolyl, benzooxazolyl, benzoimidazolyl, benzofuranyl, indolyl, quinolinyl, isoquinolinyl, or benzo [b]thiophenyl);

$R_1$ is H,

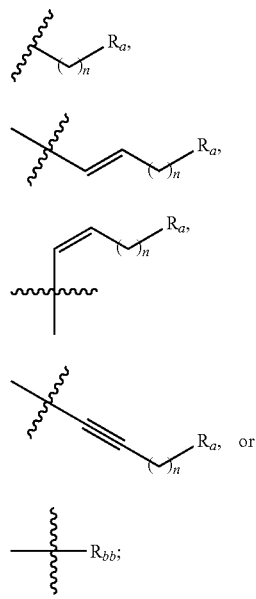

wherein n is 1, 2, 3 or 4;

$R_a$ of PTM-I or PTM-II is hydrogen, heteroaryl optionally substituted with $R_5$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, triazolyl, or pyrazinyl), hydroxyl, alkylamino, dialkylamino, oxazolidinonyl optionally substituted with $R_5$, pyrrolidinonyl optionally substituted with $R_5$, piperidinonyl optionally substituted with $R_5$, cyclic heterodionyl optionally substituted with $R_5$, heterocyclyl optionally substituted with $R_5$ (wherein said heterocyclyl is preferably pyrrolidinyl, tetrahydrofuranyl, tetrahydrothiophenyl, imidazolidinyl, thiazolidinyl, oxazolidinyl, tetrahydropyranyl, tetrahydrothiopyranyl, thiomorphlinyl, thiomorpholinyl-1, 1-dioxide, piperidinyl, morpholinyl or piperazinyl), —COOR$_y$, —CONR$_w$R$_x$, —N(R$_y$)CON(R$_w$)(R$_x$), N(R$_w$)C(O)OR$_x$, —N(R$_w$)COR$_y$, —SR$_y$, —SOR$_y$, —SO$_2$R$_y$, —NR$_w$SO$_2$R$_y$, —NR$_w$SO$_2$R$_x$, SO$_3$R$_y$, or —OSO$_2$NR$_w$R$_x$;

$R_{bb}$ of PTM-I or PTM-II is hydrogen, halogen, aryl, heteroaryl, or heterocyclyl;

$R_5$ of PTM-I or PTM-II is one, two, or three substituents independently selected from: halogen, cyano, trifluoromethyl, amino, hydroxyl, alkoxy, —C(O)alkyl, —SO$_2$alkyl, C(O)N(alkyl)$_2$, alkyl, —C$_{(1-4)}$alkyl-OH, or alkylamino;

$R_w$ and $R_x$ of PTM-I or PTM-II are independently selected from: hydrogen, alkyl, alkenyl, aralkyl (wherein the aryl portion of said aralkyl is preferrably phenyl), or heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or $R_w$ and $R_x$ may optionally be taken together to form a 5 to 7 membered ring, optionally containing a heteromoiety selected from: O, NH, N(alkyl), SO$_2$, SO, or S, preferably selected from the group consisting of:

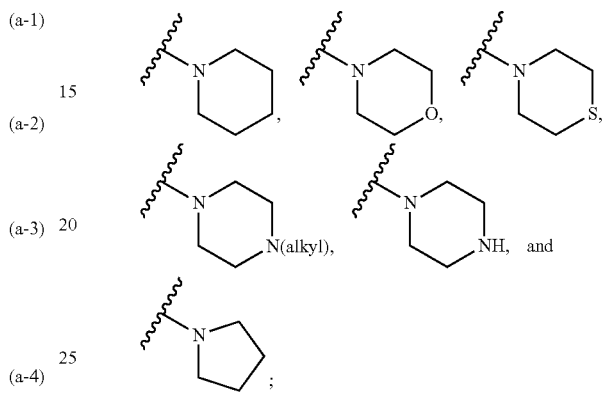

$R_y$ of PTM-I or PTM-II is selected from: hydrogen, alkyl, alkenyl, cycloalkyl (wherein said cycloalkyl is preferably cyclopentanyl or cyclohexanyl), aryl (wherein said aryl is preferably phenyl), aralkyl (wherein the aryl portion of said aralkyl is preferably phenyl), heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or heteroaryl (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl);

$R_3$ of PTM-I or PTM-II is one or more substituents, optionally present, and independently selected from: alkyl, alkoxy, halogen, alkoxyether, hydroxyl, thio, nitro, cycloalkyl optionally substituted with R4 (wherein said cycloalkyl is preferably cyclopentanyl or cyclohexanyl), heteroaryl optionally substituted with R4 (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide; and most preferably pyrrolyl, furanyl, thiophenyl, imidazolyl, thiazolyl, oxazolyl, pyridinyl, pyrimidinyl, or pyrazinyl), alkylamino, heterocyclyl optionally substituted with R4 (wherein said heterocyclyl is preferably azapenyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, morpholinyl, or piperazinyl), partially unsaturated heterocyclyl optionally substituted with $R_4$, (wherein said partially unsaturated heterocyclyl is preferably tetrahydropyridinyl, tetrahydropyrazinyl, dihydrofuranyl, dihydrooxazinyl, dihydropyrrolyl, or dihydroimidazolyl), —O(cycloalkyl), pyrrolidinone optionally substituted with $R_4$, phenoxy optionally substituted with $R_4$, —CN, —OCHF$_2$, OCF$_3$, —CF$_3$, halogenated alkyl, heteroaryloxy optionally substituted with R$_4$, dialkylamino, NHSO$_2$alkyl, thioalkyl, or —SO$_2$alkyl; wherein R4 is independently selected from: halogen, cyano, trifluoromethyl, amino, hydroxyl, alkoxy, —C(O)alkyl, —CO$_2$alkyl, —SO$_2$alkyl, C(O)N(alkyl)$_2$, alkyl, or alkylamino; and the PTM-I or PTM-II is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-I or PTM-II is covalently joined to a ULM, a chemical linker group (L), a CLM, an ILM, a VLM, MLM, a ULM', a CLM', a ILM', a VLM', a MLM', or combination thereof via an R group (e.g., R$^1$, R$^3$, R$^4$, R$^5$, R$^a$, R$^{bb}$, R$^w$, R$^x$, or R$^y$).

In certain embodiments, the N-oxides of PTM-I and PTM-II are present on one or more of: N-1 or N-3 (when X-3 is N).

In other preferred embodiments, the PTM of Formula PTM-I and Formula PTM-II include at least one of the following:
q of PTM-I or PTM-II is 1 or 2;
p of PTM-I or PTM-II is 0 or 1;
Q of PTM-I or PTM-II is NH, N(alkyl), 0, or a direct bond;
X of PTM-I or PTM-II is N;
Z of PTM-I or PTM-II is NH, N(alkyl), or CH$_2$;
B of PTM-I or PTM-II is aryl or heteroaryl;
R$_1$ of PTM-I or PTM-II is:

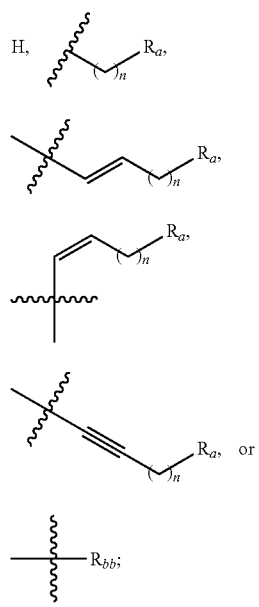

wherein n of PTM-I or PTM-II is 1, 2, 3 or 4;
R$_a$ of PTM-I or PTM-II is hydrogen, heteroaryl optionally substituted with R$_5$, hydroxyl, alkylamino, dialkylamino, oxazolidinonyl optionally substituted with R$_5$, pyrrolidinonyl optionally substituted with R$_5$, piperidinonyl optionally substituted with R$_5$, cyclic heterodionyl optionally substituted with R$_5$, heterocyclyl optionally substituted with R$_5$, COOR$_y$, —CONR$_w$R$_x$, —N(R$_y$)CON(R$_w$)(R$_x$), —N(R$_w$)C(O)OR$_x$, —N(R$_w$)COR$_y$, —SR$_y$, SOR$_y$, —SO$_2$R$_y$, —NR$_w$SO$_2$R$_y$, —NR$_w$SO$_2$R$_x$, —SO$_3$R$_y$, or —OSO$_2$NR$_w$R$_x$;

R$_{bb}$ of PTM-I or PTM-II is hydrogen, halogen, aryl, heteroaryl, or heterocyclyl;

R$_5$ of PTM-I or PTM-II is one, two, or three substituents independently selected from: halogen, cyano, trifluoromethyl, amino, hydroxyl, alkoxy, —C(O)alkyl, —SO$_2$alkyl, C(O)N(alkyl)$_2$, alkyl, —C$_{(1-4)}$alkyl-OH, or alkylamino;

R$_w$ and R$_x$ of PTM-I or PTM-II are independently selected from: hydrogen, alkyl, alkenyl, aralkyl, or heteroaralkyl, or R$_w$ and R$_x$ may optionally be taken together to form a 5 to 7 membered ring, optionally containing a heteromoiety selected from O, NH, N(alkyl), SO$_2$, SO, or S;

R$_y$ of PTM-I or PTM-II is selected from: hydrogen, alkyl, alkenyl, cycloalkyl, aryl, aralkyl, heteroaralkyl, or heteroaryl; and R$_3$ of PTM-I or PTM-II is one or more substituents, optionally present, and independently selected from: alkyl, alkoxy, halogen, alkoxyether, hydroxyl, thio, nitro, cycloalkyl optionally substituted with R$_4$, heteroaryl optionally substituted with R$_4$, alkylamino, heterocyclyl optionally substituted with R$_4$, partially unsaturated heterocyclyl optionally substituted with R$_4$, —O(cycloalkyl), pyrrolidinone optionally substituted with R$_4$, phenoxy optionally substituted with R$_4$, —CN, —OCHF$_2$, —OCF$_3$, —CF$_3$, halogenated alkyl, heteroaryloxy optionally substituted with R$_4$, dialkylamino, —NHSO$_2$alkyl, thioalkyl, or SO$_2$alkyl; wherein R4 is independently selected from: halogen, cyano, trifluoromethyl, amino, hydroxyl, alkoxy, —C(O)alkyl, —CO$_2$alkyl, —SO$_2$alkyl, —C(O)N(alkyl)$_2$, alkyl, or alkylamino.

In additional embodiments, the PTM of Formula PTM-I and PTM-II comprise:
q of PTM-I or PTM-II is 1 or 2;
p of PTM-I or PTM-II is 0 or 1;
Q of PTM-I or PTM-II is NH, 0, or a direct bond;
X of PTM-I or PTM-II is N;
Z of PTM-I or PTM-II is NH or CH$_2$;
B of PTM-I or PTM-II is aryl or heteroaryl;
R$_1$ of PTM-I or PTM-II is:

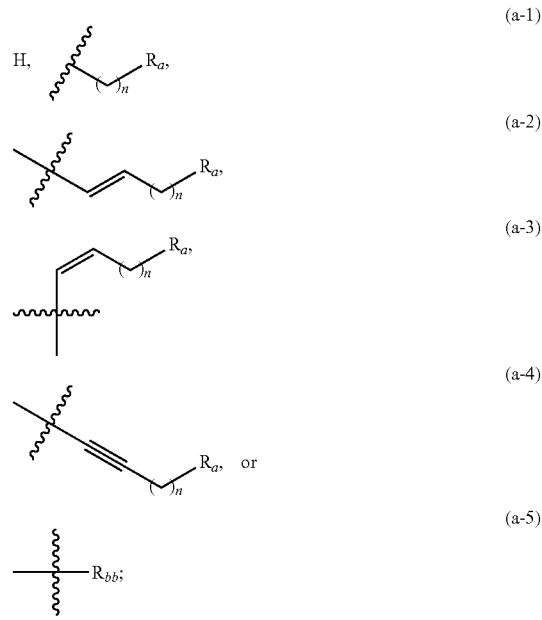

wherein n of PTM-I or PTM-II is 1, 2, 3 or 4;

$R_a$ of PTM-I or PTM-II is hydrogen, heteroaryl optionally substituted with $R_5$, hydroxyl, alkylamino, dialkylamino, oxazolidinonyl optionally substituted with $R_5$, pyrrolidinonyl optionally substituted with $R_5$, piperidinonyl optionally substituted with $R_5$, cyclic heterodionyl optionally substituted with $R_5$, heterocyclyl optionally substituted with $R_5$, $COOR_y$, —$CONR_wR_x$, —$N(R_y)CON(R_w)(R_x)$, —$N(R_w)C(O)OR_x$, —$N(R_w)COR_y$, —$SR_y$, $SOR_y$, —$SO_2R_y$, —$NR_wSO_2R_y$, —$NR_wSO_2R_x$, —$SO_3R_y$, or —$OSO_2NRR_x$;

$R_{bb}$ of PTM-I or PTM-II is hydrogen, halogen, aryl, heteroaryl, or heterocyclyl;

$R_5$ of PTM-I or PTM-II is one, two, or three substituents independently selected from: halogen, cyano, trifluoromethyl, amino, hydroxyl, alkoxy, —C(O)alkyl, —$SO_2$alkyl, $C(O)N(alkyl)_2$, alkyl, —$C_{(1-4)}$alkyl-OH, or alkylamino;

$R_w$ and $R_x$ of PTM-I or PTM-II are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), $SO_2$, SO, or S;

$R_y$ of PTM-I or PTM-II is selected from: hydrogen, alkyl, alkenyl, cycloalkyl, aryl, aralkyl, heteroaralkyl, or heteroaryl; and $R_3$ of PTM-I or PTM-II is one or more substituents, optionally present, and independently selected from: alkyl, alkoxy, halogen, alkoxyether, cycloalkyl optionally substituted with $R_4$, alkylamino, heterocyclyl optionally substituted with $R_4$, —O(cycloalkyl), phenoxy optionally substituted with $R_4$, dialkylamino, or —$SO_2$alkyl; wherein $R_4$ is independently selected from: halogen, cyano, trifluoromethyl, amino, hydroxyl, alkoxy, C(O)alkyl, —$CO_2$alkyl, —$SO_2$alkyl, —$C(O)N(alkyl)_2$, alkyl, or alkylamino.

In yet further embodiments, the PTM of Formula PTM-I and PTM-II comprises:
q of PTM-I or PTM-II is 1 or 2;
p of PTM-I or PTM-II is 0 or 1;
Q of PTM-I or PTM-II is NH, 0, or a direct bond;
Z of PTM-I or PTM-II is NH or $CH_2$;
B of PTM-I or PTM-II is aryl or heteroaryl;
X of PTM-I or PTM-II is N;
$R_1$ of PTM-I or PTM-II is:

(a-1)

H, ⋯$(\quad)_a$—$R_a$, or (a-5)

⋯—$R_{bb}$;

wherein n of PTM-I or PTM-II is 1, 2, 3 or 4;

$R_a$ of PTM-I or PTM-II is hydrogen, hydroxyl, alkylamino, dialkylamino, heterocyclyl optionally substituted with $R_5$, —$CONR_wR_x$, —$N(R_y)CON(R_w)(R_x)$, $N(R_w)C(O)OR_x$, —$N(R_w)COR_y$, —$SO_2R_y$, —$NR_wSO_2R_y$, or —$NR_wSO_2R_x$;

$R_{bb}$ of PTM-I or PTM-II is hydrogen, halogen, aryl, heteroaryl, or heterocyclyl;

$R_5$ of PTM-I or PTM-II is one, two, or three substituents independently selected from: halogen, cyano, trifluoromethyl, amino, hydroxyl, alkoxy, —C(O)alkyl, —$SO_2$alkyl, $C(O)N(alkyl)_2$, alkyl, —$C_{(14)}$alkyl-OH, or alkylamino;

$R_w$ and $R_x$ of PTM-I or PTM-II are independently selected from: hydrogen, alkyl, alkenyl, aralkyl, or heteroaralkyl, or $R_w$ and $R_x$ may optionally be taken together to form a 5 to 7 membered ring, optionally containing a heteromoiety selected from O, NH, N(alkyl), $SO_2$, SO, or S;

$R_y$ of PTM-I or PTM-II is selected from: hydrogen, alkyl, alkenyl, cycloalkyl, aryl, aralkyl, heteroaralkyl, or heteroaryl; and $R_3$ of PTM-I or PTM-II is one substituentselected from: alkyl, alkoxy, halogen, alkoxyether, cycloalkyl optionally substituted with $R_4$, alkylamino, heterocyclyl optionally substituted with $R_4$, —O(cycloalkyl), phenoxy optionally substituted with $R_4$, dialkylamino, or $SO_2$alkyl; wherein $R_4$ is independently selected from: halogen, cyano, trifluoromethyl, amino, hydroxyl, alkoxy, —C(O)alkyl, —$CO_2$alkyl, —$SO_2$alkyl, —$C(O)N(alkyl)_2$, alkyl, or alkylamino.

In certain embodiments, the PTM of Formula PTM-I or PTM-II comprises:
q of PTM-I or PTM-II is 1 or 2;
p of PTM-I or PTM-II is 0 or 1;
Q of PTM-I or PTM-II is NH, 0, or a direct bond;
Z of PTM-I or PTM-II is NH or $CH_2$;
B of PTM-I or PTM-II is phenyl or pyridyl;
X of PTM-I or PTM-II is N;
$R_1$ of PTM-I or PTM-II is:

(a-5)

⋯—$R_{bb}$;

wherein $R_{bb}$ of PTM-I or PTM-II is hydrogen, halogen, aryl, or heteroaryl;

$R_3$ of PTM-I or PTM-II is one substituent selected from: alkyl, alkoxy, heterocyclyl, —O(cycloalkyl), phenoxy, or dialkylamino.

In a particular embodiment, the PTM of Formula PTM-I or PTM-II comprises:
q of PTM-I or PTM-II is 1 or 2;
p of PTM-I or PTM-II is 0;
Q i of PTM-I or PTM-II s NH or O;
Z of PTM-I or PTM-II is NH;
B of PTM-I or PTM-II is phenyl or pyridyl;
X of PTM-I or PTM-II is N;
$R_1$ of PTM-I or PTM-II is:

(a-5)

⋯—$R_{bb}$;

wherein $R_{bb}$ of PTM-I or PTM-II is hydrogen;

$R_3$ of PTM-I or PTM-II is one substituent selected from: alkyl, —O(cycloalkyl), phenoxy, or dialkylamino.

The compounds of Formula PTM-I and Formula PTM-II may be converted to the corresponding N-oxide forms following art-known procedures for converting a trivalent nitrogen into its N-oxide form. For example, the N-oxidation reaction may be carried out by reacting the starting material of Formula PTM-I or Formula PTM-II with an appropriate organic or inorganic peroxide (for example, hydrogen peroxide, alkali metal or earth alkaline metal peroxides, such as sodium peroxide, potassium peroxide; appropriate organic peroxides may comprise peroxy acids such as, benzenecarboperoxoic acid or halo substituted benzenecarboperoxoic acid [such as 3-chlorobenzenecarboperoxoic acid], peroxoalkanoic acids [such as peroxoacetic acid], alkylhydroperoxides [such as tbutyl hydro-peroxide]). Suitable solvents include, for example, water, lower alcohols (such as ethanol and the like), hydrocarbons (such as toluene), ketones (such as 2-butanone), halogenated hydrocarbons [such as dichloromethane], and mixtures of such solvents.

In certain embodiments, the PTM is selected from;

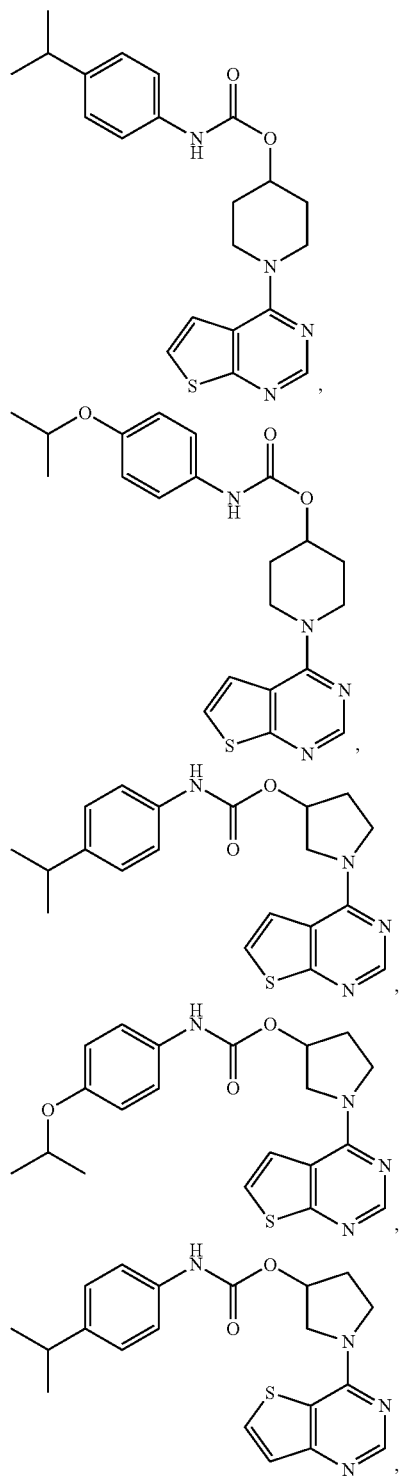

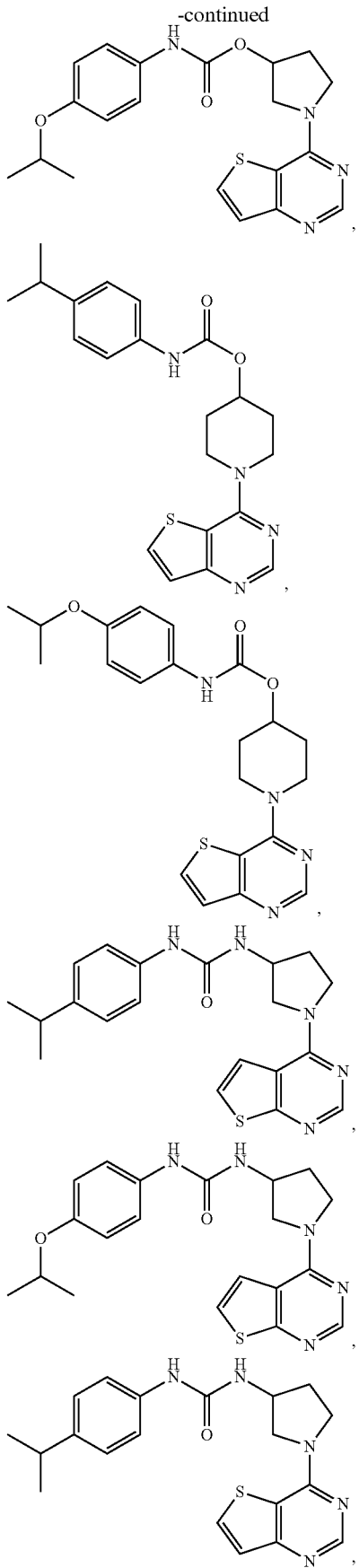

433
-continued
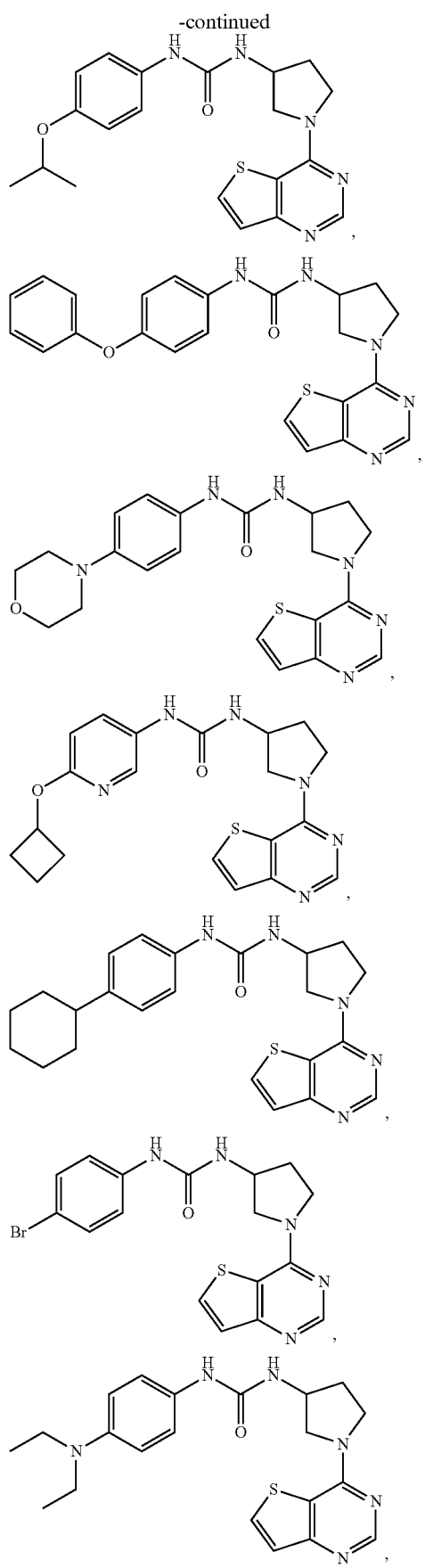
434
-continued
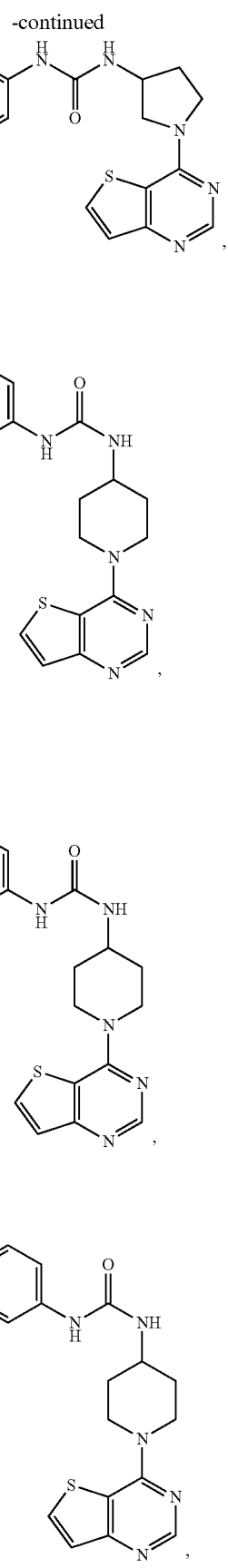

435
-continued

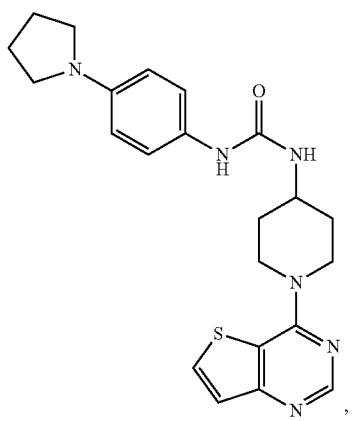

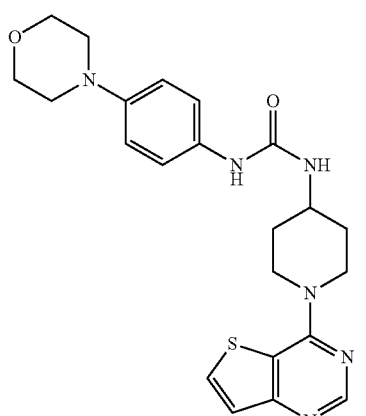

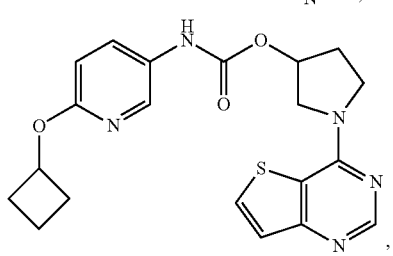

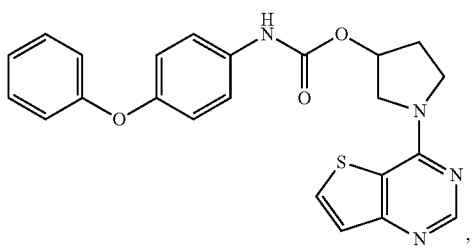

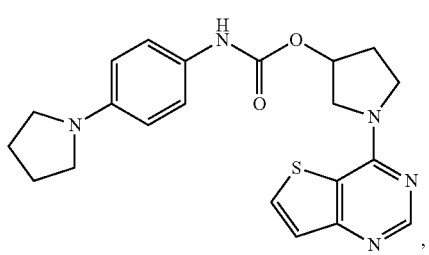

436
-continued

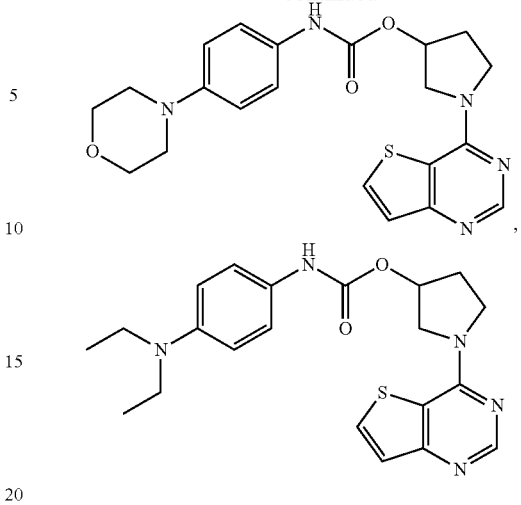

In an embodiment, the PTM is represented by Formula PTM-III (which correspond to Formula I from U.S. Patent Application Publication No. 2007/0149572 A1, which is incorporated herein in its entirety for all purposes):

PTM-III

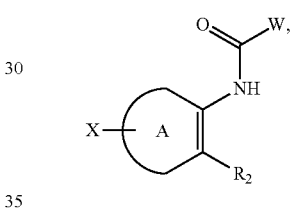

wherein:

A of PTM-III is selected from phenyl or pyridyl, either of which may be substituted with one of chloro, fluoro, methyl, —$N_3$, —$NH_2$, NH(alkyl), —N(alkyl)$_2$, S(alkyl), —O(alkyl), or 4-aminophenyl;

W of PTM-III is selected from pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —Cl, —CN, —$NO_2$, —OMe, or —$CF_3$ substitution, connected to any other carbon;

$R^2$ of PTM-III is selected from cycloalkyl (including cyclohexenyl, cyclopentenyl), thiophenyl, dihydrosulfonopyranyl, phenyl, furanyl, tetrahydropyridyl, or dihydropyranyl, any of which may be independently substituted with one or two of each of the following: chloro, fluoro, and $C_{(1-3)}$alkyl (including 4,4-dimethyl cyclohexenyl, 4-methyl cyclohexenyl, 2-methyl thiophenyl, 3-methyl thiophenyl), with the proviso that tetrahydropyridyl is connected to the ring A through a carbon-carbon bond;

X of PTM-III is selected from:

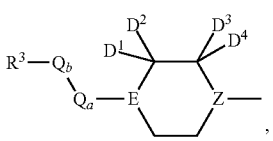

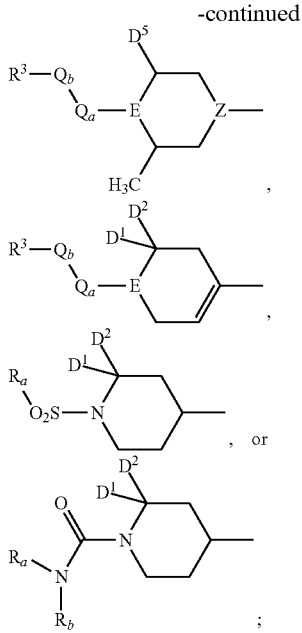

Z of PTM-III is CH or N;

$D^1$ and $D^2$ of PTM-III are each hydrogen or taken together form a double bond to an oxygen;

$D^3$ and $D^4$ of PTM-III are each hydrogen or taken together form a double bond to an oxygen;

$D^5$ of PTM-III is selected from hydrogen or —$CH_3$, wherein said —$CH_3$ may be relatively oriented syn or anti;

$R_a$ and $R_b$ of PTM-III are independently selected from hydrogen, cycloalkyl, haloalkyl, aryl, aralkyl, heteroaryl, or heteroaralkyl;

E of PTM-III is selected from N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;

$Q_a$ of PTM-III is selected from being absent, —$CH_2$—, —$CH_2CH_2$—, or C(O);

$Q_b$ of PTM-III is selected from being absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;

$R^3$ of PTM-III is selected from hydrogen, phenyl, hydroxyalkylamino (including 2-hydroxy ethylamino), (hydroxyalkyl)$_2$amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxyeth-2-yl), —COOH, —$CONH_2$, —CN, —$SO_2$-alkyl-$R^4$ (including —$SO_2CH_3$), $NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); $R^3$ may also be absent, with the proviso that $R^3$ is not absent when E is nitrogen;

$R^4$ of PTM-III is selected from hydrogen, —OH, alkoxy, carboxy, carboxamido, or carbamoyl; and the PTM-III is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-I is covalently joined to a ULM, a chemical linker group (L), a CLM, an ILM, a VLM, MLM, a ULM', a CLM', a ILM', a VLM', a MLM', or combination thereof via an R group or a D group (e.g., $R^2$, $R^3$, $D^2$, $D^3$, $D^4$, or $D^5$).

In any aspect or embodiment described herein, A of PTM-III is phenyl.

In any aspect or embodiments describe herein, W of PTM-III is furan-2-yl, 1H-pyrrol-2-yl, or 1H-imidazol-2-yl, any of which may be substituted at the 4 or 5 carbons with CN.

In any aspect or embodiment described herein, W of PTM-III is 3H-2-imidazolyl-4-carbonitrile or 5-cyano-1H-pyrrol-2-yl.

In any aspect or embodiment described herein, W of PTM-III is 3H-2-imidazolyl-4-carbonitrile.

In any aspect or embodiment described herein, $R^2$ of PTM-III is cycloalkyl (including cyclohexenyl, cyclopentenyl), which may substituted with one or two $C_{(1-3)}$alkyl (including 4,4-dimethyl cyclohexenyl, 4-methyl cyclohexenyl);

In any aspect or embodiment described herein, $R^2$ of PTM-III is cyclohexenyl, which may substituted with one or two $C_{(1-3)}$alkyl.

In any aspect or embodiment described herein, $R^2$ of PTM-III is cyclohexenyl, 4,4-dimethyl cyclohexenyl, or 4-methyl cyclohexenyl.

In any aspect or embodiment described herein, $R^2$ of PTM-III is cyclohexenyl.

In any aspect or embodiment described herein, X of PTM-III is

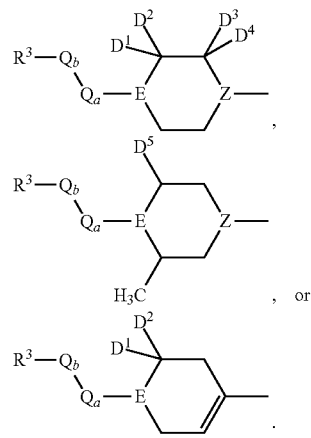

In any aspect or embodiment described herein, X of PTM-III is

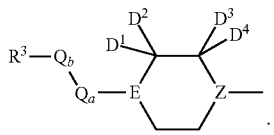

In any aspect or embodiment described herein, Z of PTM-III is CH.

In any aspect or embodiment described herein, $D^1$ and $D^2$ of PTM-III are each hydrogen.

In any aspect or embodiment described herein, $D^3$ and $D^4$ of PTM-III are each hydrogen.

In any aspect or embodiment described herein, E of PTM-III is N, with the proviso that E may not be N if the following three conditions are simultaneously met: $Q_a$ is absent, $Q_b$ is absent, and $R^3$ is an amino group or cyclic amino radical wherein the point of attachment to E is N.

In any aspect or embodiment described herein, $Q_a$ of PTM-III is absent, $CH_2CH_2$—, or C(O).

In any aspect or embodiment described herein, $Q_a$ of PTM-III is absent or C(O).

In any aspect or embodiment described herein, $Q_a$ of PTM-III is C(O).

In any aspect or embodiment described herein, $Q_b$ of PTM-III is absent, $CH_2CH_2$—, or C(O), with the proviso that $Q_b$ may not be C(O) if $Q_a$ is C(O).

In any aspect or embodiment described herein, $Q_b$ of PTM-III is absent or C(O), with the proviso that $Q_b$ may not be C(O) if $Q_a$ is C(O).

In any aspect or embodiment described herein, $R^3$ of PTM-III is hydrogen, phenyl, 2-hydroxy ethylamino, 1-hydroxyeth-2-yl(methyl)amino, methylamino, 2-amino isopropyl, 1,3-dihydroxy isopropyl, 1,2-dihydroxy ethyl, methoxy, dimethylamino, 1-hydroxyeth-2-yl, COOH, —$CONH_2$, —CN, —$SO_2$—, —$SO_2CH_3$), —$NH_2$, piperidinyl, morpholinyl, imidazolyl, pyridyl, pyridyl N-oxide), or 1 methyl imidazolyl.

In any aspect or embodiment described herein, $R^3$ of PTM-III is alkylamino (including methylamino), dialkylamino (including dimethylamino), or —$SO_2$-alkyl-$R^4$ (including —$SO_2CH_3$).

In any aspect or embodiment described herein, $R^3$ of PTM-III is methylamino, dimethylamino, or —$SO_2CH_3$.

In any aspect or embodiment described herein, $R^3$ of PTM-III is dimethylamino.

In any aspect or embodiment described herein, $R^4$ of PTM-III is hydrogen.

In other preferred embodiments, the PTM of Formula PTM-III comprises:

A of PTM-III is phenyl which may be substituted with one of chloro, fluoro, and methyl;

W of PTM-III is pyrrolyl, imidazolyl, isoxazolyl, oxazolyl, 1,2,4 triazolyl, or furanyl any of which may be connected through any carbon atom, wherein the pyrrolyl, imidazolyl, isoxazolyl, oxazolyl, 1,2,4 triazolyl, or furanyl may contain one —Cl, —CN, —$NO_2$, —OMe, or —$CF_3$ substitution, connected to any other carbon;

$R^2$ of PTM-III is cycloalkyl, thiophenyl, dihydrosulfonopyranyl, phenyl, furanyl, tetrahydropyridyl, or dihydropyranyl, any of which may be independently substituted with one or two of each of the following: chloro, fluoro, and $C_{(1-3)}$alkyl, with the proviso that tetrahydropyridyl is connected to the ring A through a carbon-carbon bond;

X of PTM-III is

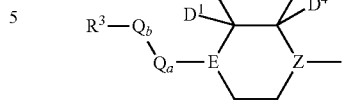

and is attached to the phenyl A ring para to the nitrogen substituent, as depicted in

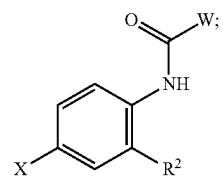

Z of PTM-III is CH or N;

$D^1$ and $D^2$ of PTM-III are each hydrogen or taken together form a double bond to an oxygen;

$D^3$ and $D^4$ of PTM-III are hydrogen;

E of PTM-III is N or $SO_2$; with the proviso that E may not be N if the following three conditions are simultaneously met: $Q_a$ is absent, $Q_b$ is absent, and $R^3$ is an amino group or cyclic amino radical wherein the point of attachment to E is N;

$Q_a$ of PTM-III is absent, —$CH_2$—, —$CH_2CH_2$—, or C(O);

$Q_b$ of PTM-III is absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N; and $R^3$ of PTM-III is hydrogen, piperidinyl, alkylamino, dialkylamino, hydroxyalkylamino, (hydroxyalkyl)$_2$amino, imidazolyl, 1-methyl imidazolyl, pyridyl, pyridyl N-oxide, hydroxyalkyl, —COOH, —$CONH_2$, —CN, —$SO_2CH_3$, —$NH_2$, morpholinyl; $R^3$ may also be absent, with the proviso that $R^3$ is not absent when E is nitrogen.

In other preferred embodiment, the PTM of Formula PTM-III comprises:

A of PTM-III is phenyl;

W of PTM-III is pyrrolyl, imidazolyl, isoxazolyl, oxazolyl, or 1,2,4 triazolyl, any of which may be connected through any carbon atom, wherein the pyrrolyl, imidazolyl, isoxazolyl, oxazolyl, or 1,2,4 triazolyl, may contain one —Cl, —CN, —$NO_2$, —OMe, or —$CF_3$ substitution, connected to any other carbon;

$R^2$ of PTM-III is cycloalkyl, furanyl, or tetrahydropyridyl, any of which may be independently substituted with one or two of each of the substituents selected from the group consisting of chloro, fluoro, and $C_{(1-3)}$alkyl, with the proviso that tetrahydropyridyl must be connected to the ring A through a carbon-carbon bond.

X of PTM-III is

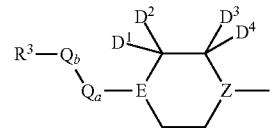

and is attached to the phenyl A ring para to the nitrogen substituent, as depicted in

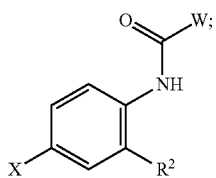

Z of PTM-III is CH or N;

D¹ and D² of PTM-III are each hydrogen or taken together form a double bond to an oxygen;

D³ and D⁴ of PTM-III are hydrogen;

E of PTM-III is N or SO₂; with the proviso that E may not be N if the following three conditions are simultaneously met: $Q_a$ is absent, $Q_b$ is absent, and R³ is an amino group or cyclic amino radical wherein the point of attachment to E is N;

$Q_a$ of PTM-III is absent, —CH₂—, —CH₂CH₂—, or C(O);

$Q_b$ of PTM-III is absent, —NH—, —CH₂—, —CH₂CH₂—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if R³ is an amino group or cyclic amino radical wherein the point of attachment to $Q_b$ is N; and R³ of PTM-III is hydrogen, piperidinyl, alkylamino, dialkylamino, hydroxyalkylamino, (hydroxyalkyl)₂amino, imidazolyl, 1-methyl imidazolyl, pyridyl, pyridyl N-oxide, hydroxyalkyl, —COOH, —CONH₂, —CN, —SO₂CH₃, —NH₂, morpholinyl; R³ may also be absent, with the proviso that R³ is not absent when E is nitrogen.

In other preferred embodiments, the PTM of Formula PTM-III comprises:

A of PTM-III is phenyl;

W of PTM-III is pyrrolyl, imidazolyl, isoxazolyl, oxazolyl, or 1,2,4 triazolyl, any of which may be connected through any carbon atom, wherein the pyrrolyl, imidazolyl, isoxazolyl, oxazolyl, or 1,2,4 triazolyl, may contain one —Cl, —CN, —NO₂, —OMe, or —CF₃ substitution, connected to any other carbon;

R² of PTM-III is cycloalkyl, furanyl, or tetrahydropyridyl, any of which may be independently substituted with one or two of each of the substituents selected from the group consisting of chloro, fluoro, and $C_{(1-3)}$alkyl, with the proviso that tetrahydropyridyl must be connected to the ring A through a carbon-carbon bond;

X of PTM-III is

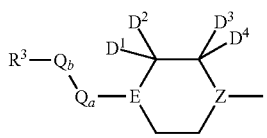

and is attached to the phenyl A ring para to the nitrogen substituent, as depicted in

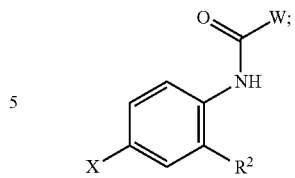

Z of PTM-III is CH or N;

D¹ and D² of PTM-III are each hydrogen or taken together form a double bond to an oxygen;

D³ and D⁴ of PTM-III are hydrogen;

E of PTM-III is N; with the proviso that E may not be N if the following three conditions are simultaneously met: $Q_a$ is absent, $Q_b$ is absent, and R³ is an amino group or cyclic amino radical wherein the point of attachment to E is N;

Qa of PTM-III is absent, —CH₂—, —CH₂CH₂—, or C(O);

$Q_b$ of PTM-III is absent, —NH—, —CH₂—, —CH₂CH₂—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if R³ is an amino group or cyclic amino radical wherein the point of attachment to $Q_b$ is N; and R³ of PTM-III is hydrogen, piperidinyl, alkylamino, dialkylamino, hydroxyalkylamino, (hydroxyalkyl)₂amino, imidazolyl, 1-methyl imidazolyl, hydroxyalkyl, COOH, —CONH₂, —CN, —SO₂CH₃, —NH₂, or morpholinyl.

In yet a further preferred embodiment, the PTM of Formula PTM-III comprises:

A of PTM-III is phenyl;

W of PTM-III is pyrrolyl, or imidazolyl, wherein the pyrrolyl, or imidazolyl, may contain one —Cl, —CN, —NO₂, —OMe, or —CF₃ substitution, connected to any other carbon;

R² of PTM-III is cycloalkyl, furanyl, or tetrahydropyridyl, any of which may be independently substituted with one or two of each of the substituents selected from the group consisting of chloro, fluoro, and $C_{(1-3)}$alkyl, with the proviso that tetrahydropyridyl must be connected to the ring A through a carbon-carbon bond;

X of PTM-III is

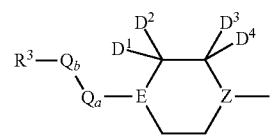

and is attached to the phenyl A ring para to the nitrogen substituent, as depicted in

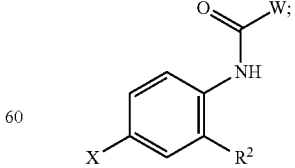

Z of PTM-III is CH or N;

D¹ and D² of PTM-III are each hydrogen or taken together form a double bond to an oxygen;

D³ and D⁴ of PTM-III are hydrogen;

E of PTM-III is N; with the proviso that E may not be N if the following three conditions are simultaneously met: $Q_a$ is absent, $Q_b$ is absent, and $R^3$ is an amino group or cyclic amino radical wherein the point of attachment to E is N;

$Q_a$ of PTM-III is C(O);

$Q_b$ of PTM-III is absent, —NH—, —CH$_2$—, —CH$_2$CH$_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N; and $R^3$ of PTM-III is hydrogen, piperidinyl, hydroxyalkylamino, (hydroxyalkyl)$_2$amino, alkylamino, dialkylamino, imidazolyl, 1-methyl imidazolyl, pyridyl, pyridyl N-oxide, hydroxyalkyl, —COOH, —CONH$_2$, —CN, —SO$_2$CH$_3$, —NH$_2$, or morpholinyl.

In some embodiments, the PTM of PTM-III is selected from the group consisting of: (PTM-III-1) 5-cyano-furan-2-carboxylic acid [4-(4-methyl-piperazin-1-yl)-2-(3-methyl-thiophen-2-yl)-phenyl]-amide, (PTM-III-2) 5-cyano-furan-2-carboxylic acid [4-(4-methyl-piperazin-1-yl)-2-(2-methyl-thiophen-3-yl)-phenyl]-amide, (PTM-III-3) 4-cyano-1H-imidazole-2-carboxylic acid [4-(1-acetyl-piperidin-4-yl)-2-(1,2,5,6-tetrahydro-pyridin-3-yl)-phenyl]-amide, (PTM-III-4) 4-cyano-1H-imidazole-2-carboxylic acid [2-cyclohex-1-enyl-4-(1,1-dioxo-hexahydro-1$\lambda^6$-thiopyran-4-yl)-phenyl]-amide, (PTM-III-5) 5-cyano-furan-2-carboxylic acid [2-cyclohex-1-enyl-4-(4-methyl-piperazin-1-yl)-phenyl]-amide, (PTM-III-6) 5-cyano-furan-2-carboxylic acid [2-(3,6-dihydro-2H-pyran-4-yl)-4-(4-methyl-piperazin-1-yl)-phenyl]-amide, (PTM-III-7) 4-cyano-1H-imidazole-2-carboxylic acid [2-(1,1-dioxo-1,2,3,6-tetrahydro-1$\lambda^6$-thiopyran-4-yl)-4-piperidin-4-yl-phenyl]-amide, (PTM-III-8) 4-cyano-1H-imidazole-2-carboxylic acid [4-(1-acetyl-piperidin-4-yl)-2-(1,1-dioxo-1,2,3,6-tetrahydro-1$\lambda^6$-thiopyran-4-yl)-phenyl]-amide, (PTM-III-9) 5-cyano-furan-2-carboxylic acid [2'-methyl-5-(4-methyl-piperazin-1-yl)-biphenyl-2-yl]-amide, (PTM-III-10) 5-cyano-furan-2-carboxylic acid [2'-fluoro-5-(4-methyl-piperazin-1-yl)-biphenyl-2-yl]-amide, (PTM-III-11) (4-{4-[(4-cyano-1H-imidazole-2-carbonyl)-amino]-3-cyclohex-1-enyl-phenyl}-piperidin-1-yl)-acetic acid, (PTM-III-12) 4-cyano-1H-imidazole-2-carboxylic acid [4-(1-carbamoylmethyl-piperidin-4-yl)-2-cyclohex-1-enyl-phenyl]-amide, (PTM-III-13) 4-cyano-1H-imidazole-2-carboxylic acid [2-(4-methyl-cyclohex-1-enyl)-4-piperidin-4-yl-phenyl]-amide, (PTM-III-14) 4-cyano-1H-imidazole-2-carboxylic acid {2-cyclohex-1-enyl-4-[1-(2-hydroxy-ethyl)-piperidin-4-yl]-phenyl}-amide, (PTM-III-15) 4-cyano-1H-imidazole-2-carboxylic acid [2-(4-methyl-cyclohex-1-enyl)-4-(1-pyridin-2-ylmethyl-piperidin-4-yl)-phenyl]-amide, (PTM-III-16) 4-cyano-1H-imidazole-2-carboxylic acid {2-cyclohex-1-enyl-4-[1-(2-hydroxy-1-hydroxymethyl-ethyl)-piperidin-4-yl]-phenyl}-amide, (PTM-III-17) 4-cyano-1H-imidazole-2-carboxylic acid {4-[11-(2-cyano-ethyl)-piperidin-4-yl]-2-cyclohex-1-enyl-phenyl}-amide, (PTM-III-18) 4-cyano-1H-imidazole-2-carboxylic acid {2-cyclohex-1-enyl-4-[1-(2-morpholin-4-yl-ethyl)-piperidin-4-yl]-phenyl}-amide, (PTM-III-19) 4-cyano-1H-imidazole-2-carboxylic acid (2-cyclohex-1-enyl-4-piperidin-4-yl-phenyl)-amide, (PTM-III-20) 4-cyano-1H-imidazole-2-carboxylic acid {2-cyclohex-1-enyl-4-[1-(2-methanesulfonyl-ethyl)-piperidin-4-yl]-phenyl}-amide, (PTM-III-21) 4-cyano-1H-imidazole-2-carboxylic acid [2-cyclohex-1-enyl-4-(1-pyridin-2-ylmethyl-piperidin-4-yl)-phenyl]-amide, (PTM-III-22) 4-cyano-1H-imidazole-2-carboxylic acid {2-cyclopent-1-enyl-4-[1-(1-methyl-1H-imidazol-2-ylmethyl)-piperidin-4-yl]-phenyl}-amide, (PTM-III-23) 4-cyano-1H-imidazole-2-carboxylic acid (2-cyclopent-1-enyl-4-piperidin-4-yl-phenyl)-amide, (PTM-III-24) 4-cyano-1H-pyrrole-2-carboxylic acid (2-cyclohex-1-enyl-4-piperidin-4-yl-phenyl)-amide, (PTM-III-25) 4-cyano-1H-imidazole-2-carboxylic acid [2-cyclohex-1-enyl-4-(3,4,5,6-tetrahydro-2H-[1,2']bipyridinyl-4-yl)-phenyl]-amide, (PTM-III-26) 4-cyano-1H-pyrrole-2-carboxylic acid [4-(1-acetyl-piperidin-4-yl)-2-cyclohex-1-enyl-phenyl]-amide, (PTM-III-27) 4-cyano-1H-imidazole-2-carboxylic acid {2-cyclohex-1-enyl-4-[1-(1-oxy-pyridine-3-carbonyl)-piperidin-4-yl]-phenyl}-amide, (PTM-III-28) 4-cyano-1H-imidazole-2-carboxylic acid {2-cyclohex-1-enyl-4-[1-(1-oxy-pyridine-4-carbonyl)-piperidin-4-yl]-phenyl}-amide, (PTM-III-29) 4-cyano-1H-imidazole-2-carboxylic acid {2-cyclohex-1-enyl-4-[1-(3-morpholin-4-yl-propionyl)-piperidin-4-yl]-phenyl}-amide, (PTM-III-30) 4-{4-[(4-cyano-1H-imidazole-2-carbonyl)-amino]-3-cyclohex-1-enyl-phenyl}-piperidine-1-carboxylic acid amide, (PTM-III-31) 4-cyano-1H-imidazole-2-carboxylic acid {2-cyclohex-1-enyl-4-[1-(pyridine-3-carbonyl)-piperidin-4-yl]-phenyl}-amide, (PTM-III-32) 4-{4-[(4-cyano-1H-imidazole-2-carbonyl)-amino]-3-cyclohex-1-enyl-phenyl}-piperidine-1-carboxylic acid (2-hydroxy-ethyl)-amide, (PTM-III-33) 4-cyano-1H-imidazole-2-carboxylic acid {2-cyclohex-1-enyl-4-[1-(2-3H-imidazol-4-yl-acetyl)-piperidin-4-yl]-phenyl}-amide, (PTM-III-34) 4-cyano-1H-imidazole-2-carboxylic acid {2-cyclohex-1-enyl-4-[1-(2-pyridin-4-yl-acetyl)-piperidin-4-yl]-phenyl}-amide, (PTM-III-35) 4-cyano-1H-imidazole-2-carboxylic acid (2-cyclohex-1-enyl-4-{1-[2-(1-methyl-1H-imidazol-4-yl)-acetyl]-piperidin-4-yl}-phenyl)-amide, (PTM-III-36) 4-cyano-1H-imidazole-2-carboxylic acid {2-cyclohex-1-enyl-4-[1-(2-pyridin-3-yl-acetyl)-piperidin-4-yl]-phenyl}-amide, (PTM-III-37) 4-cyano-1H-imidazole-2-carboxylic acid {2-cyclohex-1-enyl-4-[1-(2-methanesulfonyl-acetyl)-piperidin-4-yl]-phenyl}-amide, (PTM-III-38) 4-cyano-1H-imidazole-2-carboxylic acid {2-cyclohex-1-enyl-4-[1-(2-pyridin-2-yl-acetyl)-piperidin-4-yl]-phenyl}-amide, (PTM-III-39) 4-cyano-1H-imidazole-2-carboxylic acid [4-(1-acetyl-piperidin-4-yl)-2-cyclohex-1-enyl-phenyl]-amide, (PTM-III-40) 4-cyano-1H-imidazole-2-carboxylic acid [2-cyclohex-1-enyl-4-(1-{2-[(2-hydroxy-ethyl)-methylamino]-acetyl}-piperidin-4-yl)-phenyl]-amide, (PTM-III-41) 4-cyano-1H-imidazole-2-carboxylic acid {2-cyclohex-1-enyl-4-[1-(2-dimethylamino-acetyl)-piperidin-4-yl]-phenyl}-amide, (PTM-III-42) 4-cyano-1H-imidazole-2-carboxylic acid {2-cyclohex-1-enyl-4-[1-(2-morpholin-4-yl-acetyl)-piperidin-4-yl]-phenyl}-amide, (PTM-III-43) 4-Cyano-1H-imidazole-2-carboxylic acid {4-[1-(3-amino-3-methyl-butyryl)-piperidin-4-yl]-2-cyclohex-1-enyl-phenyl}-amide trifluoroacetic acid salt, (PTM-III-44) 4H-[1,2,4]-triazole-3-carboxylic acid (2-cyclohex-1-enyl-4-piperidin-4-yl-phenyl)-amide bis trifluoroacetic acid salt, (PTM-III-45) 5-Chloro-4H-[1,2,4]-triazole-3-carboxylic acid (2-cyclohex-1-enyl-4-piperidin-4-yl-phenyl)-amide trifluoroacetic acid salt, (PTM-III-46) 5-Cyano-1H-imidazole-2-carboxylic acid [2-cyclohex-1-enyl-4-(cis-2,6-dimethyl-piperidin-4-yl)-phenyl]-amide bis trifluoroacetic acid salt, (PTM-III-47) 5-cyano-1H-imidazole-2-carboxylic acid [2-cyclohex-1-enyl-4-(trans-2,6-dimethyl-piperidin-4-yl)-phenyl]-amide bis trifluoroacetic acid salt, (PTM-III-48) 5-Cyano-1H-imidazole-2-carboxylic acid {2-cyclohex-1-enyl-4-[1-(R)-(+)-(2,3-dihydroxy-propionyl)-piperidin-4-yl]-phenyl}-amide, (PTM-III-49) 5-Cyano-1H-imidazole-2-carboxylic acid [2-cyclohex-1-enyl-4-(1-methoxy-piperidin-4-yl)-phenyl]-amide trifluoroacetic acid salt, (PTM-III-50) 4-Cyano-1H-imidazole-2-carboxylic acid [6-

(4,4-dimethyl-cyclohex-1-enyl)-1',2',3',4',5',6'-hexahydro-[2,4']bipyridinyl-5-yl]-amide trifluoroacetic acid salt, (PTM-III-51) 5-Cyano-1H-imidazole-2-carboxylic acid {4-[1-(2-amino-2-methyl-propionyl)-piperidin-4-yl]-2-cyclohex-1-enyl-phenyl}-amide trifluoroacetic acid salt, (PTM-III-52) 5-Cyano-1H-imidazole-2-carboxylic acid [6-cyclohex-1-enyl-1'-(2-methanesulfonyl-ethyl)-1',2',3',4',5',6'-hexahydro-[2,4']bipyridinyl-5-yl]-amide, (PTM-III-53) 4-Cyano-1H-imidazole-2-carboxylic acid {2-cyclohex-1-enyl-4-[1-(2-methylamino-acetyl)-piperidin-4-yl]-phenyl}-amide, (PTM-III-54) 4-Cyano-1H-imidazole-2-carboxylic acid [1'-(2-dimethylamino-acetyl)-6-(4,4-dimethyl-cyclohex-1-enyl)-1',2',3',4',5',6'-hexahydro-[2,4']bipyridinyl-5-yl]-amide trifluoroacetic acid salt, (PTM-III-55) 4-Cyano-1H-imidazole-2-carboxylic acid [6-(4,4-dimethyl-cyclohex-1-enyl)-1'-(2-methanesulfonyl-ethyl)-1',2',3',4',5',6'-hexhydro-[2,4']bipyridinyl-5-yl]-amide trifluoroacetic acid salt, or solvates, hydrates, tautomers and pharmaceutically acceptable salts thereof.

In an embodiment, the PTM is represented by Formula PTM-IV (which correspond to Formula I from U.S. Patent Application Publication No. 2009/0054358 A1, which is incorporated herein in its entirety for all purposes):

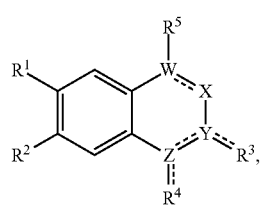

PTM-IV wherein:

W of PTM-IV is C, N, O;

X of PTM-IV can be C, N, absent;

Y of PTM-IV can be C;

Z of PTM-IV can be C, N;

and R groups can be substituted variants of:

$R^1$ of PTM-IV can be H, alkoxy, hydroxyl, heterocyclic alkyl/aryl;

$R^2$ of PTM-IV can be H, F, alkoxy, heterocyclic alkyl/aryl;

$R^3$ of PTM-IV can be H, O, aryl, heteroaryl, C(O) heteroaryl;

$R^4$ of PTM-IV can be H, alkyl, aryl, heteroaryl, CH-heteroaryl, absent;

$R^5$ of PTM-IV can be H, aryl, heteroalkyl/aryl, absent;

the dashed lines between WX, WY, YZ, $YR^3$, and $ZR^4$ of PTM-IV indicating an optionally double bond, wherein the aryl, heteroaryl, heterocyclic alkyl/aryl are optionally substituted; and the PTM-IV is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-IV is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^2$, $R^3$, $R^4$, or $R^5$).

In further embodiments, the PTM is selected from:

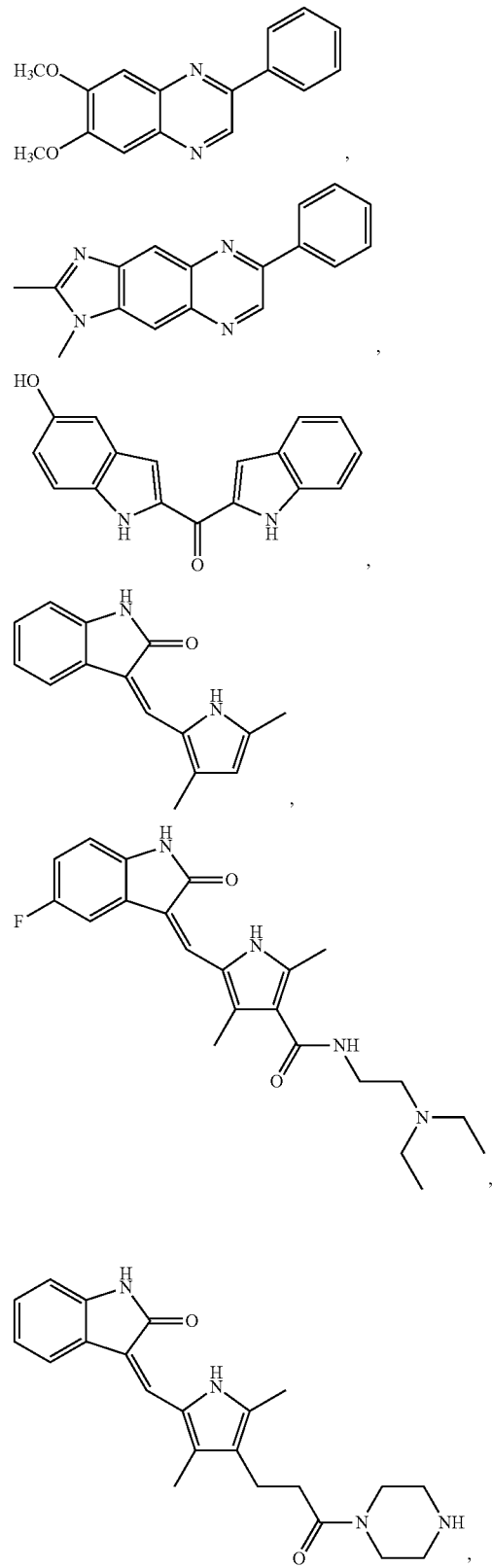

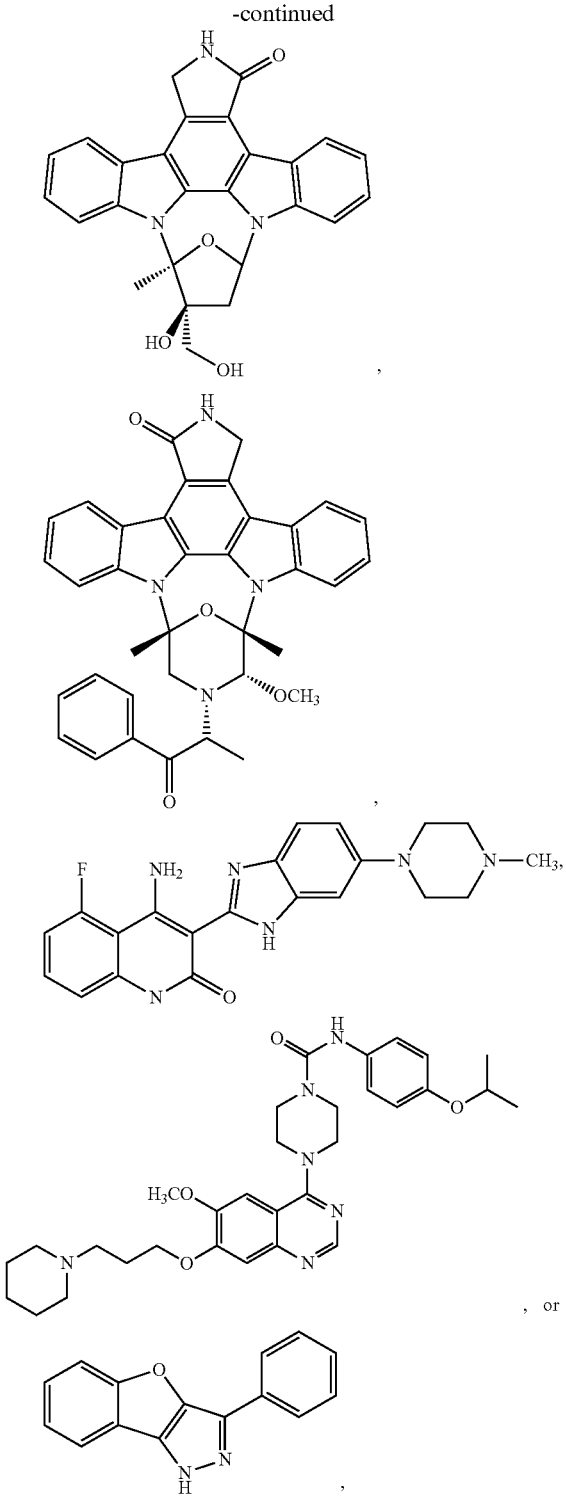

wherein the PTM-IV is covalently joined to a ULM, a chemical linker group (L), a CLM, an ILM, a VLM, MLM, a ULM', a CLM', a ILM', a VLM', a MLM', or combination thereof.

In an embodiment, the PTM is represented by Formula PTM-V (which correspond to Formula I from U.S. Patent Application Publication No. 2013/0274259 A1, which is incorporated herein in its entirety for all purposes):

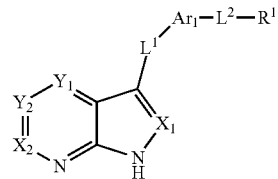

PTM-V or a salt, prodrug, tautomer, or isomer thereof, wherein:

$X_1$ of PTM-V is N or $CR^2$, $X_2$ is N or $CR^6$, $Y_1$ is N or $CR^4$, and $Y_2$ is N or $CR^5$, provided, however, that not more than one of $X_2$, $Y_1$ and $Y_2$ is N;

$L^1$ of PTM-V is selected from the group consisting of optionally substituted lower alkylene, —S—, —O—, —C(O)—, —C(S)—, —S(O)—, —S(O)$_2$—, and —NR'—;

$L^2$ of PTM-V is selected from the group consisting of a bond, optionally substituted lower alkylene, -(alk)$_a$-S-(alk)$_b$-, -(alk)$_a$-O-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)-(alk)$_b$-, -(alk)$_a$-C(S)-(alk)$_b$-, -(alk)$_a$-C(O)NR$^9$-(alk)$_b$-, -(alk)$_a$-OC(O)NR$^9$-(alk)$_b$-, -(alk)$_a$-OC(S)NR$^9$-(alk)$_b$-, -(alk)$_a$-C(S)NR$^9$-(alk)$_b$-, -(alk)$_a$-S(O)-(alk)$_b$-, -(alk)$_a$-S(O)$_2$-(alk)$_b$-, -(alk)$_a$-S(O)$_2$NR$^9$-(alk)$_b$-, -(alk)$_a$-NR$^9$-(alk)$_b$-, -(alk)$_a$-NR$^9$C(O)-(alk)$_b$-, -(alk)$_a$-NR$^9$C(S)-(alk)$_b$-, -(alk)$_a$-NR$^9$C(O)NR$^9$-(alk)$_b$-, -(alk)$_a$-NR$^9$C(S)NR$^9$-(alk)$_b$-, -(alk)$_a$-NR$^9$C(O)O-(alk)$_b$-, -(alk)$_a$-NR$^9$C(S)O-(alk)$_b$-, -(alk)$_a$-NR$^9$S(O)$_2$-(alk)$_b$-, and -(alk)$_a$-NR$^9$S(O)$_2$NR$^9$-(alk)$_b$-, wherein alk is optionally substituted $C_{1-3}$ alkylene and a and b are independently 0 or 1;

$R^1$ of PTM-V is selected from the group consisting of optionally substituted lower alkyl, optionally substituted cycloalkyl, optionally substituted heterocycloalkyl, optionally substituted aryl, and optionally substituted heteroaryl;

$R^2$, $R^4$, $R^5$ and $R^6$ of PTM-V are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —NR$^{10}$R$^{11}$, —NHR$^3$, —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OH, —NR$^3$C(O)OR$^3$, —NHC(S)OR$^3$, —NR$^3$C(S)OH, —NR$^3$C(S)OR$^3$, —NHC(O)NHR$^3$, —NHC(O)NR$^3$R$^3$, —NR$^3$C(O)NH$_2$, —NR$^3$C(O)NHR$^3$, —NR$^3$C(O)NR$^3$R$^3$, —NHC(S)NHR$^3$, —NHC(S)NR$^3$R$^3$, —NR$^3$C(S)NH$_2$, —NR$^3$C(S)NHR$^3$, —NR$^3$C(S)NR$^3$R$^3$, —NHS(O)$_2$NHR$^3$, —NHS(O)$_2$NR$^3$R$^3$, —NR$^3$S(O)$_2$NH$_2$, —NR$^3$S(O)$_2$NHR$^3$, and —NR$^3$S(O)$_2$NR$^3$R$^3$;

$Ar_1$ of PTM-V is a 5 or 6 membered optionally substituted heteroarylene having the structure

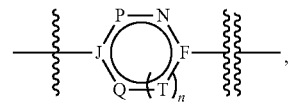

wherein

indicates the point of attachment of L¹ and

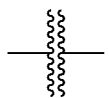

indicates the point of attachment of L², and wherein the indicated N is either =N— or —N=;

n of PTM-V is 0 or 1;

F and J of PTM-V are both C or one of F and J is C and the other of F and J is N;

P and Q of PTM-V are independently selected from CR, N, NR, O or S;

T of PTM-V is selected from CR or N;

wherein:

when n is 1, F and J are C, and P, T and Q are CR, or any one of P, T and Q is N and the other two of P, T and Q are CR, when n is 0 and F and J are both C, then one of P and Q are CR, N or NR and the other of P and Q is C, N, NR, O or S, provided both P and Q are not CR, when n is 0, one of F and J is N and the other of F and J is C, then one of P and Q is N and the other of P and Q is CR or both P and Q are CR, and R of PTM-V is hydrogen or an optional substituent as defined herein for optionally substituted heteroarylene that provides a stable compound;

R³ of PTM-V at each occurrence is independently selected from the group consisting of optionally substituted lower alkyl, optionally substituted lower alkenyl, provided, however, that no alkene carbon thereof is bound to any —C(O)—, —C(S)—, —S(O)—, —S(O)₂, —O—, —S—, or —N— of any of —OR³, —SR³, —C(O)R³, —C(S)R³, —S(O)R³, —S(O)₂R³, —C(O)OR³, —C(S)OR³, —C(O)NHR³, —C(O)NR³R³, —C(S)NHR³, —C(S)NR³R³, —S(O)₂NHR³, —S(O)₂NR³R³, —NHR³, —NHC(O)R³, —NR³C(O)R³, —NHC(S)R³, —NR³C(S)R³, —NHS(O)₂R³, —NR³S(O)₂R³, —NHC(O)OR³, —NR³C(O)OH, —NR³C(O)OR³, —NHC(S)OR³, —NR³C(S)OH, —NR³C(S)OR³, —NHC(O)NHR³, —NHC(O)NR³R³, —NR³C(O)NH₂, —NR³C(O)NHR³, —NR³C(O)NR³R³, —NHC(S)NHR³, —NHC(S)NR³R³, NR³C(S)NH₂, —NR³C(S)NHR³, —NR³C(S)NR³R³, —NHS(O)₂NHR³, —NHS(O)₂NR³R³, —NR³S(O)₂NH₂, —NR³S(O)₂NHR³, or —NR³S(O)₂NR³R³, optionally substituted lower alkynyl, provided, however, that no alkyne carbon thereof is bound to any —C(O)—, —C(S)—, —S(O)—, —S(O)₂, —O—, —S—, or —N— of any of —OR³, —SR³, —C(O)R³, —C(S)R³, —S(O)R³, —S(O)₂R³, —C(O)OR³, —C(S)OR³, —C(O)NHR³, —C(O)NR³R³, —C(S)NHR³, —C(S) NR³R³, —S(O)₂NHR³, —S(O)₂NR³R³, —NHR³, —NHC(O)R³, —NR³C(O)R³, —NHC(S)R³, —NR³C(S)R³, —NHS(O)₂R³, —NR³S(O)₂R³, —NHC(O)OR³, —NR³C(O)OH, —NR³C(O)OR³, —NHC(S)OR³, —NR³C(S)OH, —NR³C(S)OR³, —NHC(O)NHR³, —NHC(O)NR³R³, —NR³C(O)NH₂, —NR³C(O)NHR³, —NR³C(O)NR³R³, —NHC(S)NHR³, —NHC(S)NR³R³, —NR³C(S)NH₂, —NR³C(S)NHR³, —NR³C(S)NR³R³, —NHS(O)₂NHR³, —NHS(O)₂NR³R³, —NR³S(O)₂NH₂, —NR³S(O)₂NHR³, or —NR³S(O)₂NR³R³, optionally substituted cycloalkyl, optionally substituted heterocycloalkyl, optionally substituted aryl, and optionally substituted heteroaryl;

R⁷ of PTM-V is selected from the group consisting of hydrogen, optionally substituted lower alkyl, optionally substituted cycloalkyl, optionally substituted heterocycloalkyl, optionally substituted aryl, optionally substituted heteroaryl, —C(O)R⁸, and —S(O)₂R⁸;

R⁸ of PTM-V is selected from the group consisting of optionally substituted lower alkyl, optionally substituted cycloalkyl, optionally substituted heterocycloalkyl, optionally substituted aryl and optionally substituted heteroaryl;

R⁹ of PTM-V at each occurrence is independently selected from the group consisting of hydrogen, lower alkyl, and lower alkyl substituted with one or more substituents selected from the group consisting of fluoro, —OH, —NH₂, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —NR¹²R¹³, provided, however, that when R⁹ is substituted lower alkyl, any substitution on the alkyl carbon bound to the —N— of NR⁹— is fluoro;

R¹⁰ and R¹¹ of PTM-V at each occurrence are independently selected from the group consisting of optionally substituted lower alkyl, optionally substituted lower alkenyl, provided, however, that no alkene carbon thereof is bound to the nitrogen of NR¹⁰R¹¹, optionally substituted lower alkynyl, provided, however, that no alkyne carbon thereof is bound to the nitrogen of —NR¹⁰R¹¹, optionally substituted cycloalkyl, optionally substituted heterocycloalkyl, optionally substituted aryl, and optionally substituted heteroaryl; or R¹⁰ and R¹¹ of PTM-V together with the nitrogen to which they are attached form a monocyclic 5-7 membered optionally substituted heterocycloalkyl or a monocyclic 5 or 7 membered optionally substituted nitrogen containing heteroaryl;

R¹² and R¹³ of PTM-V combine with the nitrogen to which they are attached to form a 5-7 membered heterocycloalkyl or 5-7 membered heterocycloalkyl substituted with one or more substituents selected from the group consisting of fluoro, —OH, —NH₂, lower alkyl, fluoro substituted lower alkyl, lower alkoxy, fluoro substituted lower alkoxy, lower alkylthio, and fluoro substituted lower alkylthio; and the PTM-V is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-V is covalently joined to a ULM, a chemical linker group (L), a CLM, an ILM, a VLM, MLM, a ULM', a CLM', a ILM', a VLM', a MLM', or combination thereof via an R group (e.g., R, R¹, R², R³, R⁴, R⁵, R⁶, R⁷, R⁸, R⁹, R¹⁰, R¹¹, R¹², or R¹³).

In additional embodiments, the PTM of PTM-V has a structure selected from the following:

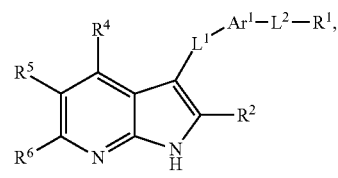

-continued

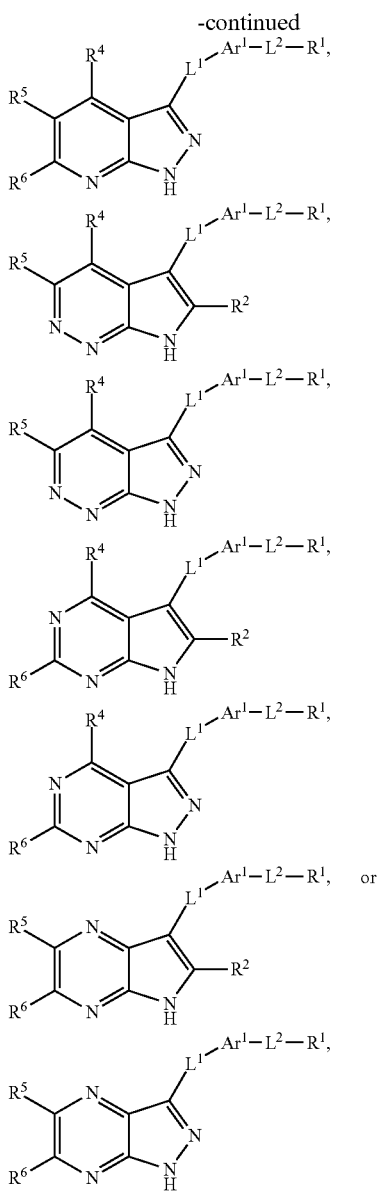

wherein $L^1$, $Ar_1$, $L^2$, $R^1$, $R^2$, $R^4$, $R^5$ and $R^6$ are as defined for Formula PTM-V.

In one embodiment of the methods provided herein, $X_1$ and $X_2$ of Formula PTM-V are N or CH. In another embodiment, $X_1$, $X_2$ and $Y_1$ of PTM-V are N or CH, where in a further embodiment, $Y_2$ is $CR^5$ and $R^5$ is other than hydrogen. In another embodiment, $X_1$, $X_2$ and $Y_2$ of PTM-V are N or CH, where in a further embodiment $Y_1$ is $CR^4$ and $R^4$ is other than hydrogen. In another embodiment, $X_1$, $X_2$ and $Y_1$ of PTM-V are CH, where in a further embodiment, $Y_2$ is $CR^5$ and $R^5$ is other than hydrogen. In another embodiment, $X_1$, $X_2$ and $Y_2$ of PTM-V are CH, where in a further embodiment $Y_1$ is $CR^4$ and $R^4$ is other than hydrogen.

In one embodiment of the methods provided herein, $X_1$, $X_2$, $Y_1$ and $Y_2$ of PTM-V are independently $CR^2$, $CR^6$, $CR^4$ and $CR^5$ respectively, one of $R^4$ or $R^5$ is other than hydrogen, preferably where $R^2$ and $R^6$ are hydrogen. In one embodiment, wherein $X_1$, $X_2$, $Y_1$ and $Y_2$ of PTM-V are independently $CR^2$, $CR^6$, $CR^4$ and $CR^5$ respectively, $R^2$, $R^5$ and $R^6$ are hydrogen and $R^4$ is other than hydrogen. In one embodiment, wherein $X_1$, $X_2$, $Y_1$ and $Y_2$ of PTM-V are independently $CR^2$, $CR^6$, $CR^4$ and $CR^5$ respectively, $R^2$, $R^4$ and $R^6$ are hydrogen and $R^5$ is other than hydrogen.

In one embodiment of the methods provided herein, $X_1$ and $X_2$ of PTM-V are N or CH, preferably wherein both $X_1$ and $X_2$ are CH.

In one embodiment of the methods provided herein, $L^1$ of PTM-V is selected from the group consisting of S, O, lower alkylene, —C(O)—, —C(S)—, —S(O)—, —S(O)$_2$—, and $NR^7$—, wherein lower alkylene is optionally substituted with fluoro, and wherein when $L^2$ is optionally substituted lower alkylene or comprises optionally substituted $C_{1-3}$ alkylene, the alkylene is optionally substituted with fluoro or lower alkyl. In one embodiment, $L^1$ is selected from the group consisting of —S—, —O—, —CH$_2$—, —CF$_2$—, —C(O)—, —C(S)—, —S(O)—, —S(O)$_2$—, and —NH—.

In one embodiment of the methods provided herein, $L^2$ of PTM-V is selected from the group consisting of a bond, optionally substituted lower alkylene, —O-(alk)$_b$-, —OC(O)-(alk)$_b$-, —C(O)O-(alk)$_b$-, —OC(S)-(alk)$_b$-, —C(S)O-(alk)$_b$-, —C(O)-(alk)$_b$-, —C(S)-(alk)$_b$-, —C(O)NR$^9$-(alk)$_b$-, —OC(O)NR$^9$-(alk)$_b$-, —OC(S)NR$^9$-(alk)$_b$-, —C(S)NR$^9$-(alk)$_b$-, —S(O)-(alk)$_b$-, —S(O)$_2$-(alk)$_b$-, S(O)$_2$NR$^9$-(alk)$_b$-, —NR$^9$-(alk)$_b$-, —NR$^9$C(O)-(alk)$_b$-, —NR$^9$C(O)O-(alk)$_b$-, —NR$^9$C(S)-(alk)$_b$-, —NR$^9$C(S)O-(alk)$_b$-, —NR$^9$C(O)NR$^9$-(alk)$_b$-, —NR$^9$C(S)NR$^9$-(alk)$_b$-, —NR$^9$S(O)$_2$-(alk)$_b$-, and —NR$^9$S(O)$_2$NR$^9$-(alk)$_b$-.

In any aspect or embodiments described herein, when $L^1$ of PTM-V is a substituted lower alkylene or when $L^2$ of PTM-V is a substituted lower alkylene or comprises substituted $C_{1-3}$ alkylene, the alkylene is substituted with one or more, preferably 1, 2, or 3 substituents selected from the group consisting of fluoro, —OH, —NH$_2$, lower alkoxy, lower alkylthio, mono-alkylamino, di-alkylamino, and $NR^{12}R^{13}$, wherein the alkyl chain(s) of lower alkoxy, lower alkylthio, mono-alkylamino or di-alkylamino are optionally substituted with one or more, preferably 1, 2, or 3 substituents selected from the group consisting of fluoro, —OH, NH$_2$, lower alkoxy, fluoro substituted lower alkoxy, lower alkylthio, fluoro substituted lower alkylthio, mono-alkylamino, di-alkylamino, or cycloalkylamino.

In one embodiment of the methods provided herein, the variables P, J, Q, T, F, and n of PTM-V are selected to provide structures of $Ar_1$ selected from the group consisting of:

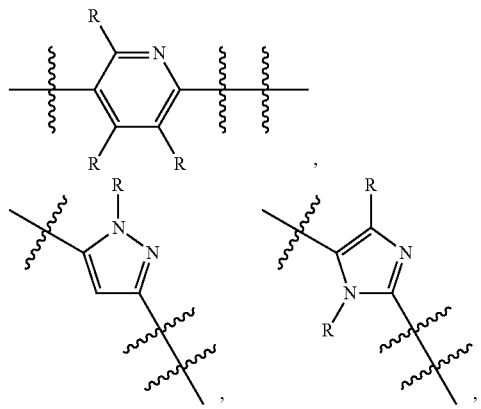

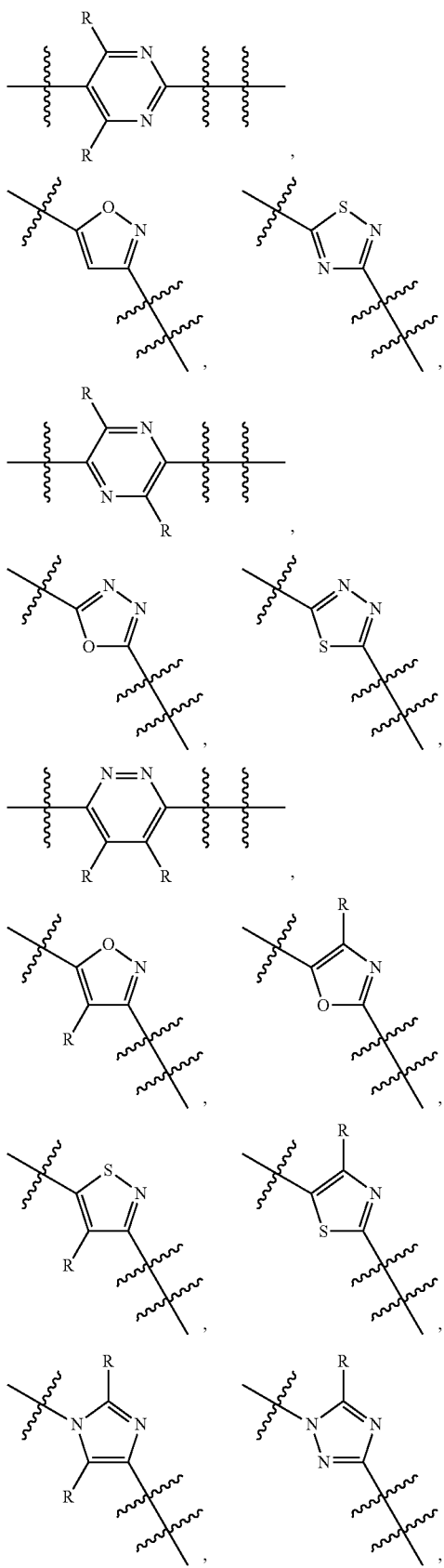

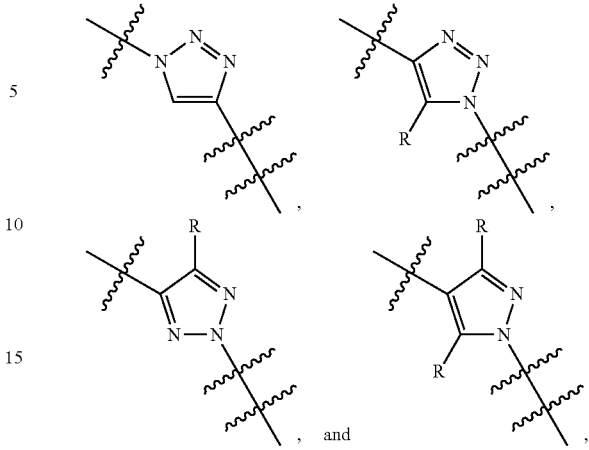

where each R is independently hydrogen or an optional substituent as defined herein for optionally substituted heteroaryl.

In an embodiment, the PTM is represented by Formula PTM-VI (which correspond to Formula I from U.S. Patent Application Publication No. 2014/0329800 A1, which is incorporated herein in its entirety for all purposes):

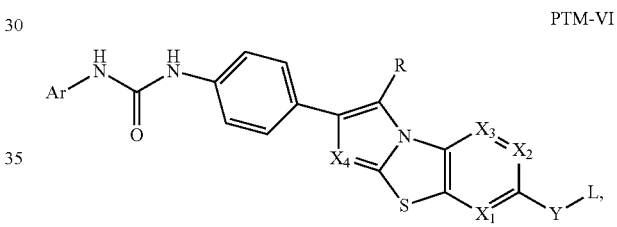

PTM-VI wherein:

Ar of PTM-VI is selected from the group consisting of optionally substituted or unsubstituted aryl, and optionally substituted or unsubstituted heteroaryl, when substituted, the substituents could be one or more groups independently selected from halogen, alkyl, haloalkyl, or hydroxyl alkyl;

L of PTM-VI is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl; when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxylalkyl, alkoxyl, —NHalkylhydroxyl, —NHalkoxyalkyl, —NHalkylamnio, —NHcycloalkyl, —NHcycloalkylalkyl, —NHheterocycloalkyl, —NH heterocycloalkylalkyl, —NHaryl, —NHarylalkyl, —NHheteroaryl, or —NHheteroarylalkyl;

Y of PTM-VI is O, S, $NR_2R_{2'}$ or a direct bond (that means L directly connected with the left heteroaryl);

$X_1$, $X_2$, $X_3$ and $X_4$ of PTM-VI are independently N or $CR_1$, $R_1$ of PTM-VI is H, or —Y-L;

R, $R_2$ and $R_2'$ of PTM-VI are each independently selected from the group consisting of hydrogen, alkyl, cycloalkyl, aryl, heteroaryl, haloalkoxyl, hydroxyl, amino, aminocarbonyl, sulfonamido, cyano, alkynyl, alkoxyl, aryloxyl, carboxylic acid, carboxylic ester or halogen, or $R_2$, $R_2'$ together with the nitrogen atom to which they are attached, form a 3- to 7-membered heterocycloalkyl ring, and the hetero atom could be selected from at least one of O, S or N atoms. The 3- to 7-membered heterocycloalkyl ring could be further optionally substituted with a group independently selected from alkyl, cycloalkyl, methylsulfonyl, ureido, acyl, amido, aminocarbonyl, alkylamino, alkylhydroxyl, heterocycloalkyl, aryl, or heteroaryl. Preferably $R_2$, $R_2'$ and the N could be formed a heterocycle such as

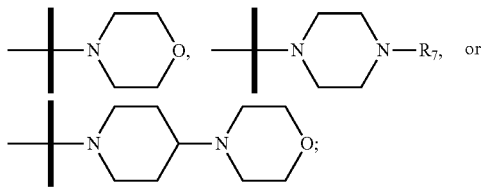

$R_7$ could be the groups independently selected from H, methylsulfonyl, lower alkyl, that is $C_1$-$C_6$ straight chain and branched chain alkyl, such as methyl, ethyl, propyl, 2-propyl, n-butyl, iso-butyl, tert-butyl, pentyl, neopentyl, hexyl, isohexyl; and the PTM-VI is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-VI is covalently joined to a ULM, a chemical linker group (L), a CLM, an ILM, a VLM, MLM, a ULM', a CLM', a ILM', a VLM', a MLM', or combination thereof via an R group (e.g., R, $R_1$, $R_2$, $R_2'$, or $R_7$)

In a preferred embodiment, the PTM of PTM-VI comprises at least one of:

Ar of PTM-VI is

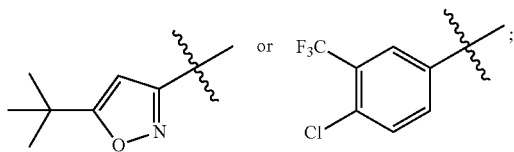

L of PTM-VI is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl, when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxyl alkyl, alkoxyl, —NHalkylhydroxyl, —NHalkoxyalkyl, —NHalkylamnio, —NHcycloalkyl, —NHcycloalkylalkyl, —NHheterocycloalkyl, —NHheterocycloalkylalkyl, —NHaryl, —NHarylalkyl, —NHheteroaryl, or —NH heteroarylalkyl;

Y of PTM-VI is O, S, $NR_2R_2'$ or a direct bond;

$X_1$, $X_2$, $X_3$ and $X_4$ of PTM-VI are independently N or $CR_1$, $R_1$ of PTM-VI is H, or —Y-L;

R, $R_2$ and $R_2'$ of PTM-VI are each independently selected from the group consisting of hydrogen, alkyl, cycloalkyl, aryl, heteroaryl, haloalkoxyl, hydroxyl, amino, amido, aminocarbonyl, sulfonamido, cyano, alkynyl, alkoxyl, aryloxyl, carboxylic acid, carboxylic ester or halogen, or $R_2$, $R_2'$ together with the nitrogen atom to which they are attached, form a 3- to 7-membered heterocycloalkyl ring, and the hetero atom could be selected from at least one of O, S or N atoms. The 3- to 7-membered heterocycloalkyl ring could be further optionally substituted with a group independently selected from alkyl, cycloalkyl, methylsulfonyl, ureido, acyl, amido, aminocarbonyl, alkylamino, alkylhydroxyl, heterocycloalkyl, aryl, or heteroaryl. Preferably $R_2$, $R_2'$ and the N could be formed a heterocycle such as

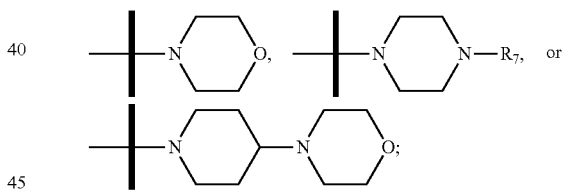

and $R_7$ of PTM-VI is independently selected from H, methylsulfonyl, lower alkyl, that is $C_1$-$C_6$ straight chain and branched chain alkyl, such as methyl, ethyl, propyl, 2-propyl, n-butyl, iso-butyl, tert-butyl, pentyl, neopentyl, hexyl, isohexyl.

In certain embodiments, the PTM of PTM-VI is selected from the group consisting of:

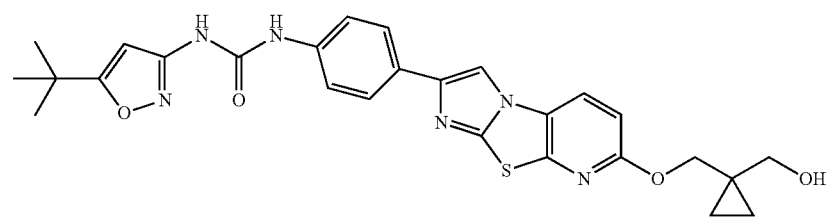

-continued
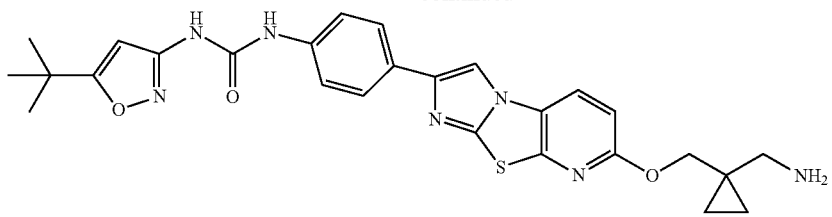
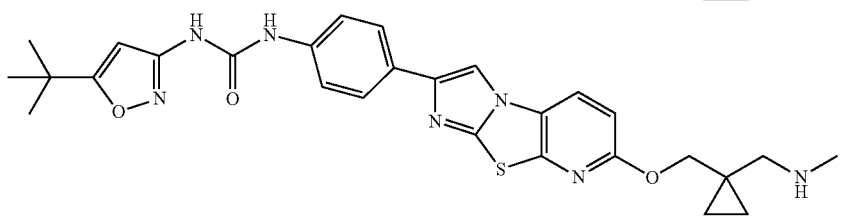
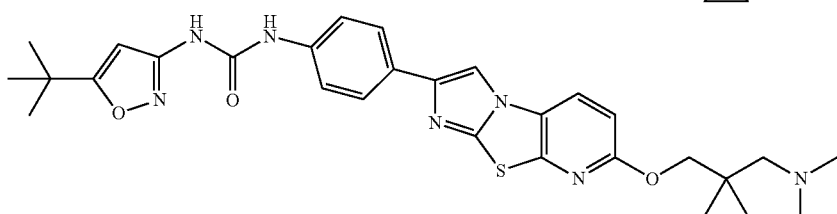
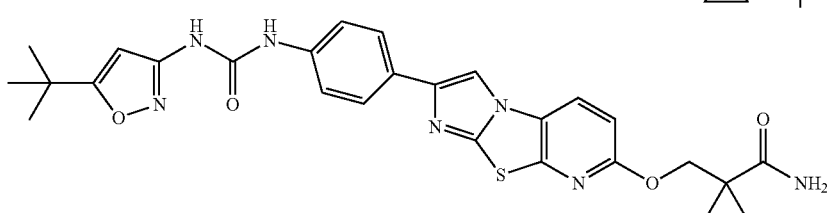
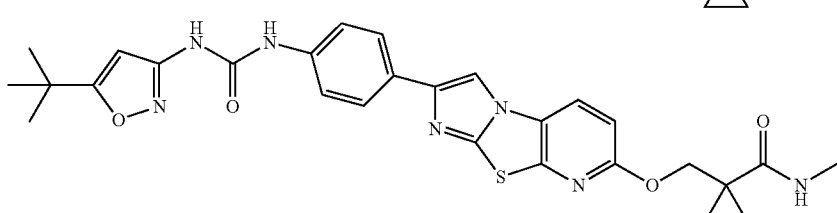
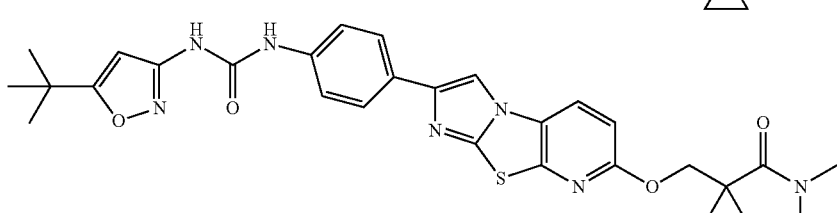
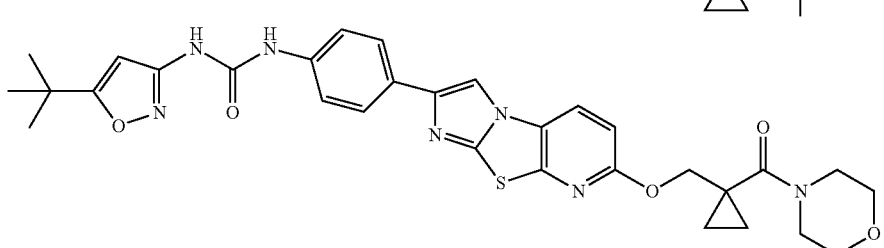
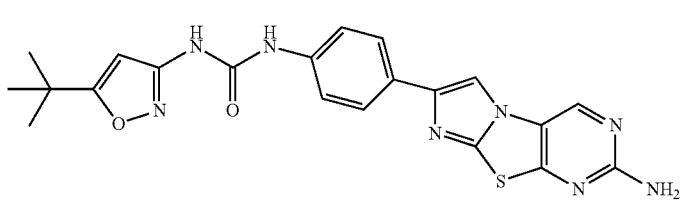

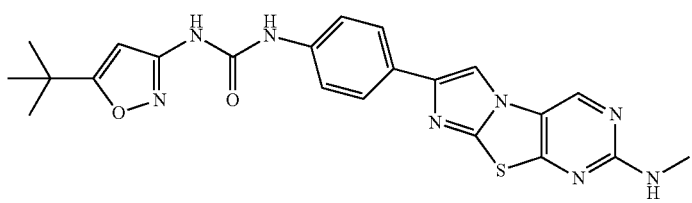
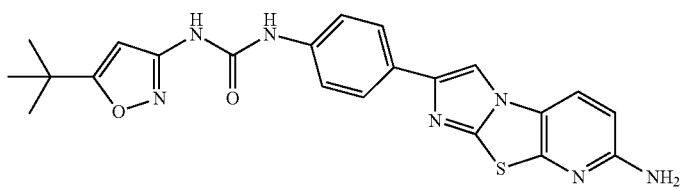
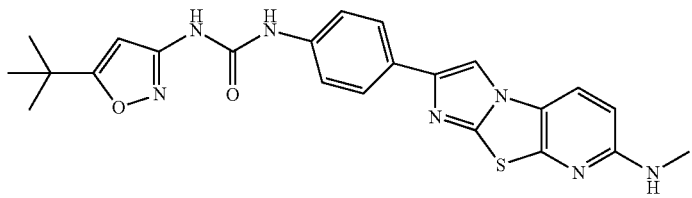
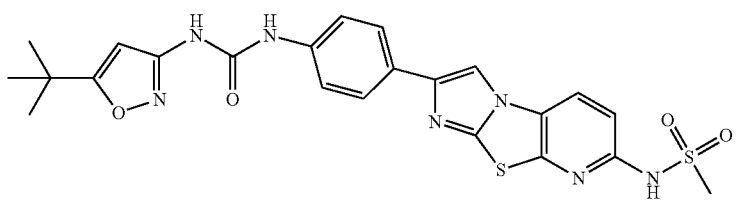
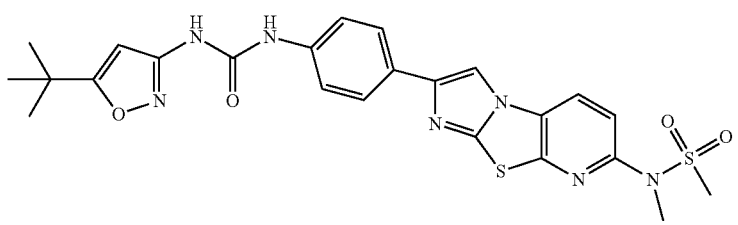
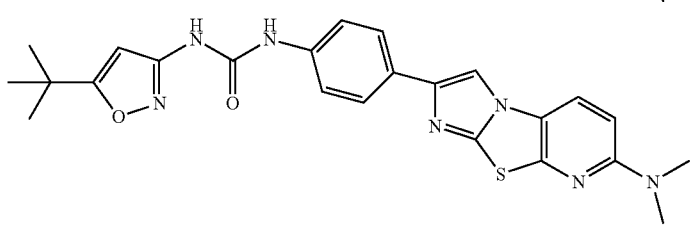
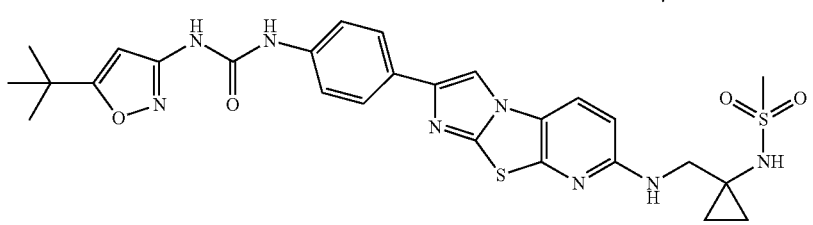
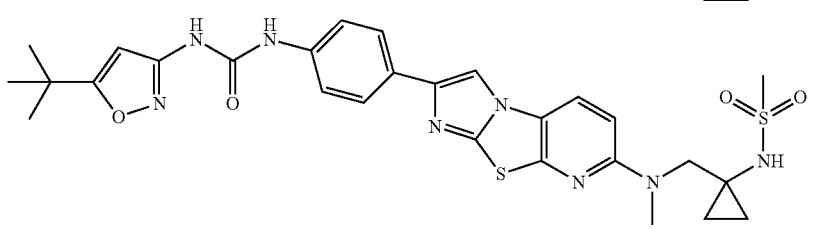

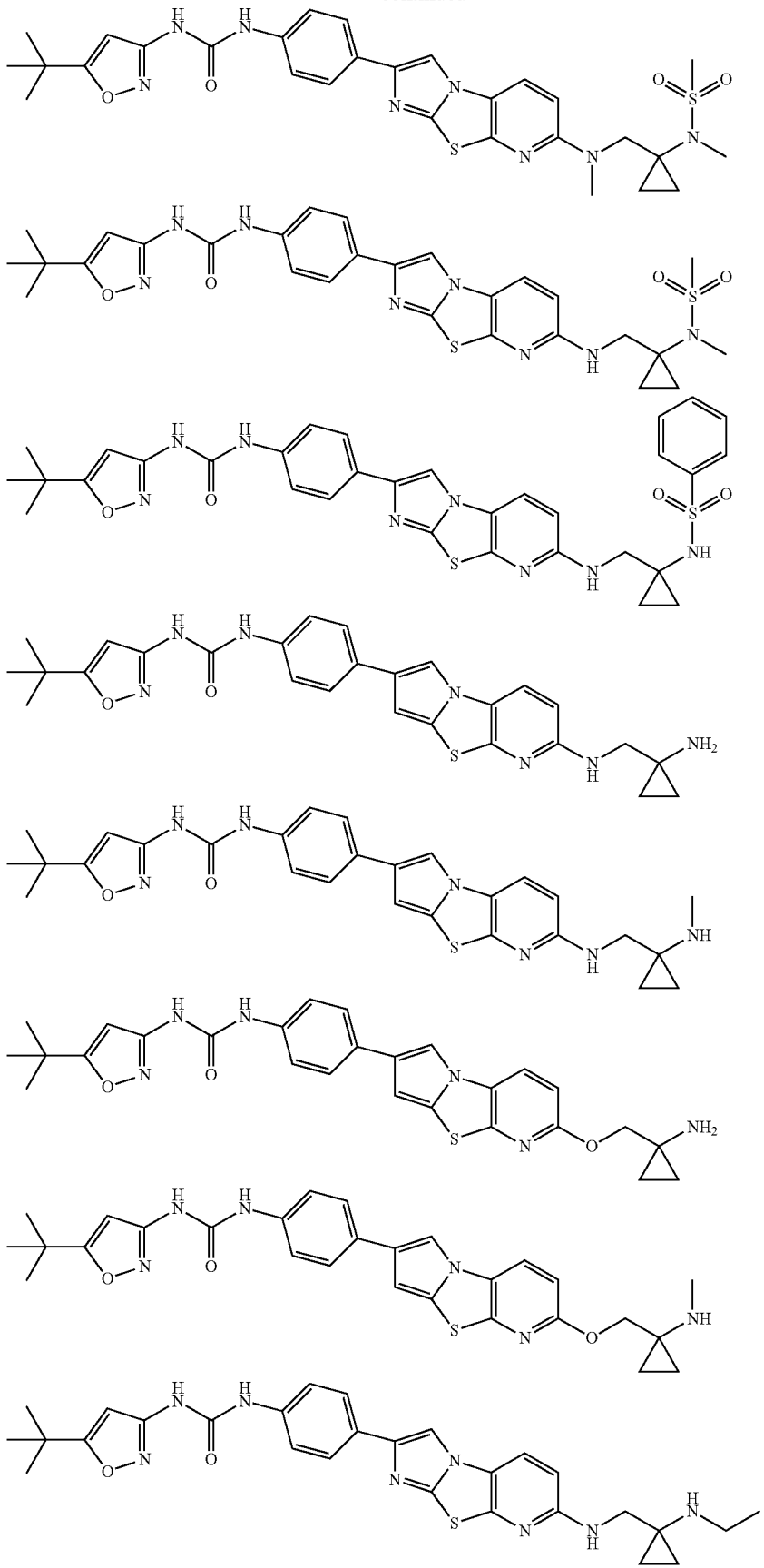

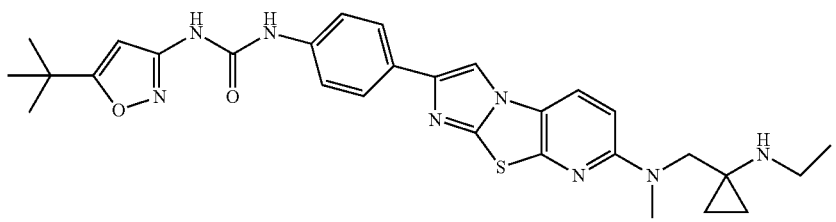
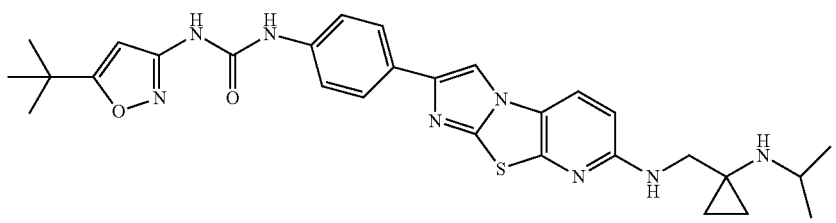
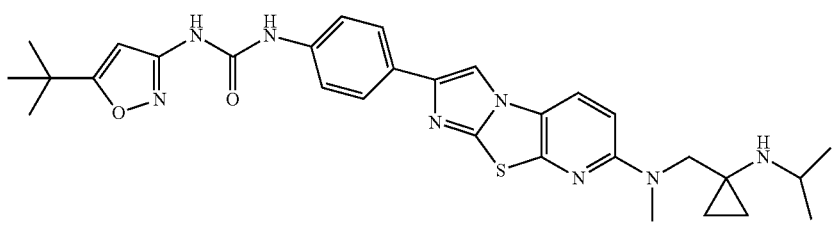
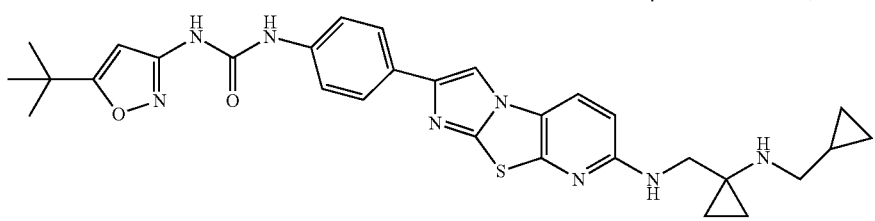
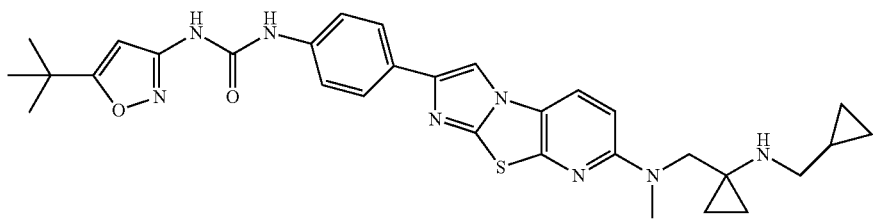
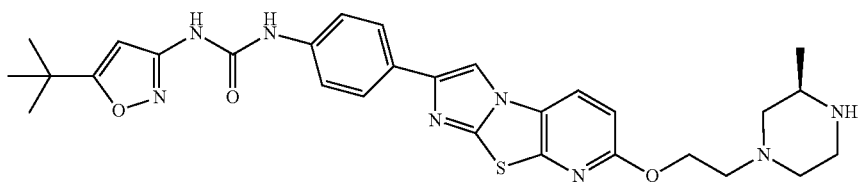
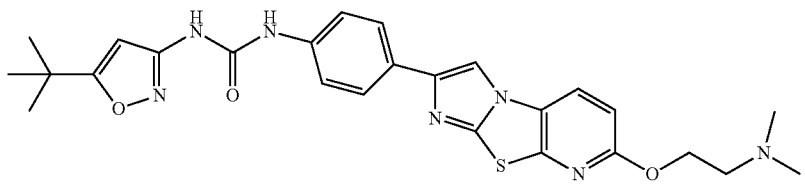
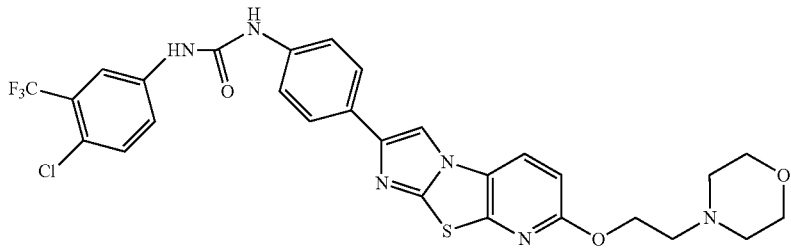

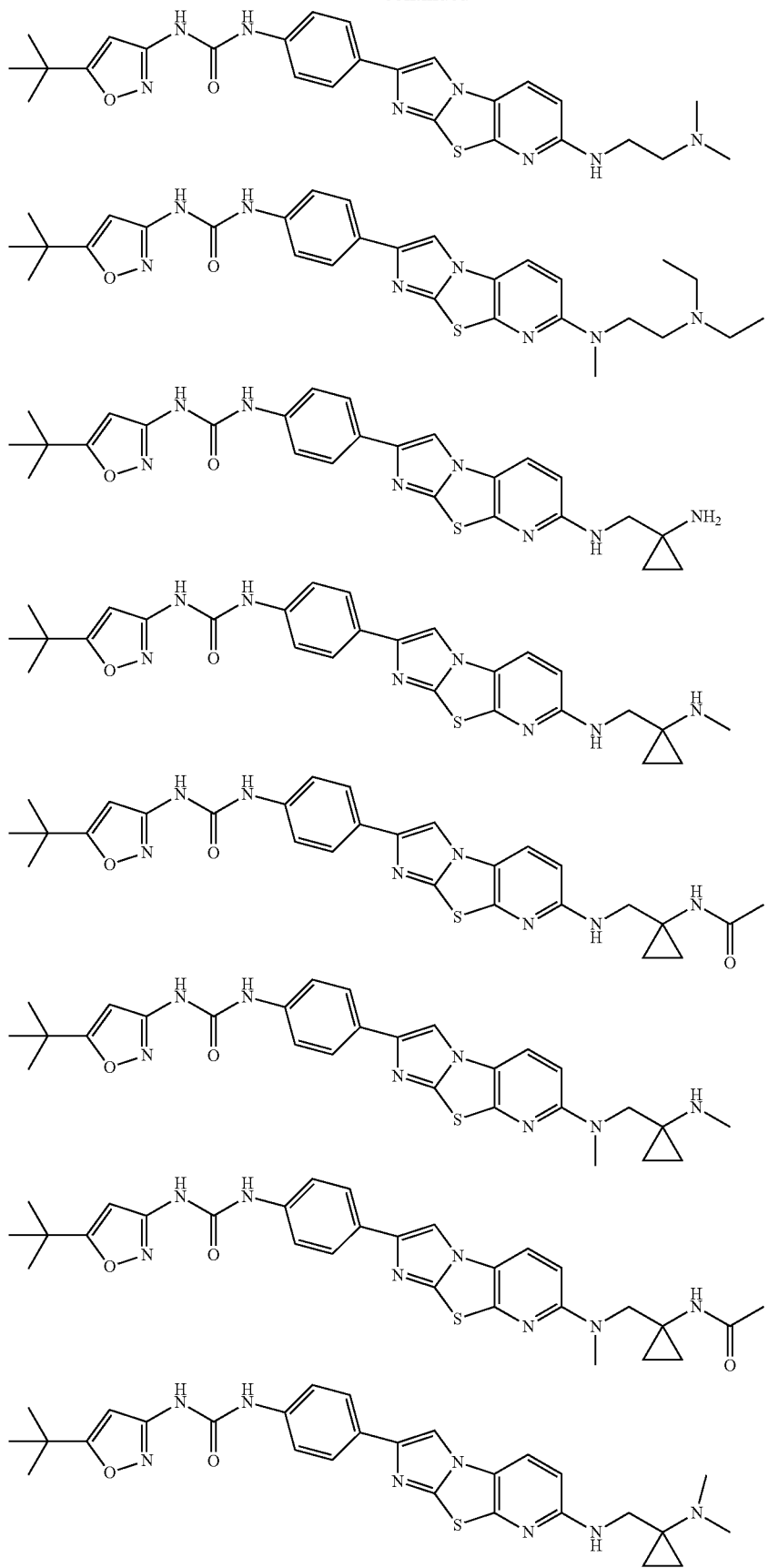

-continued
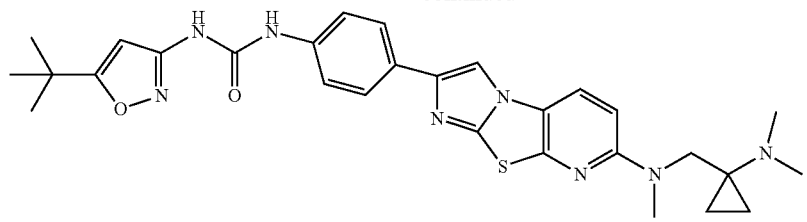
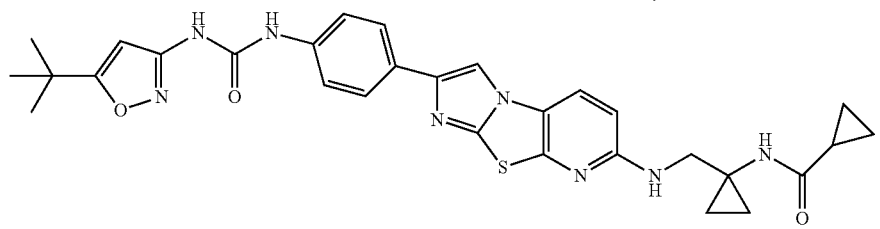
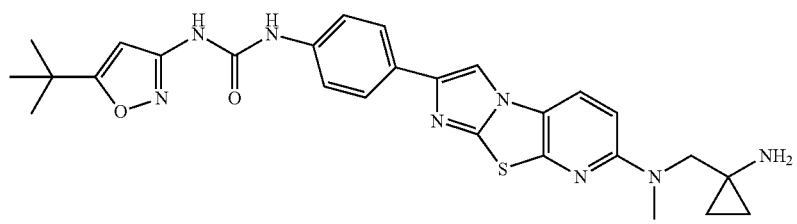
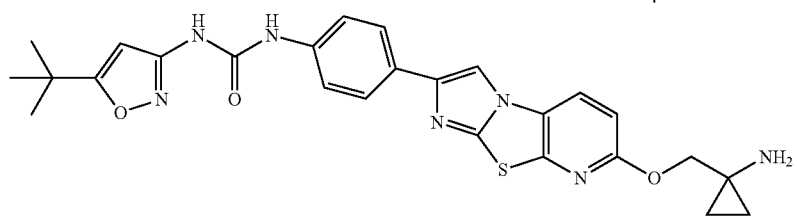
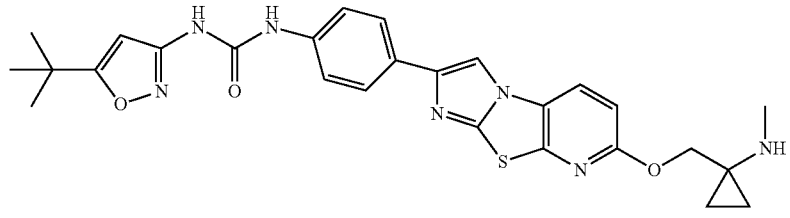
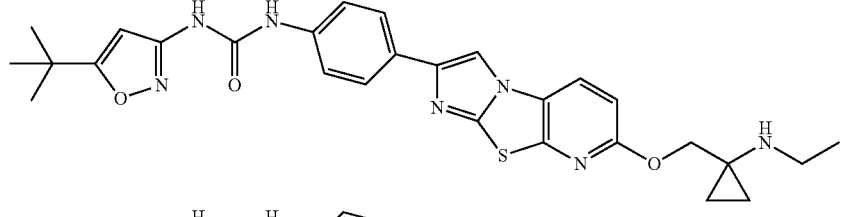
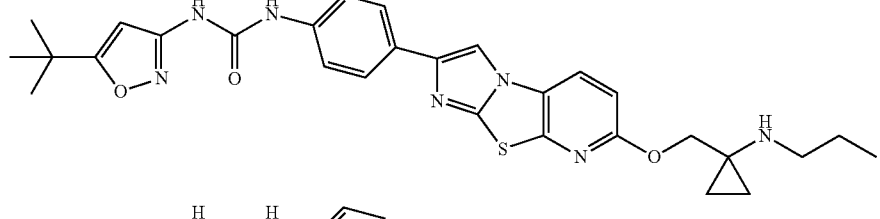
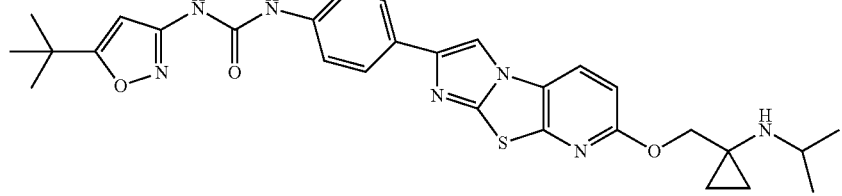

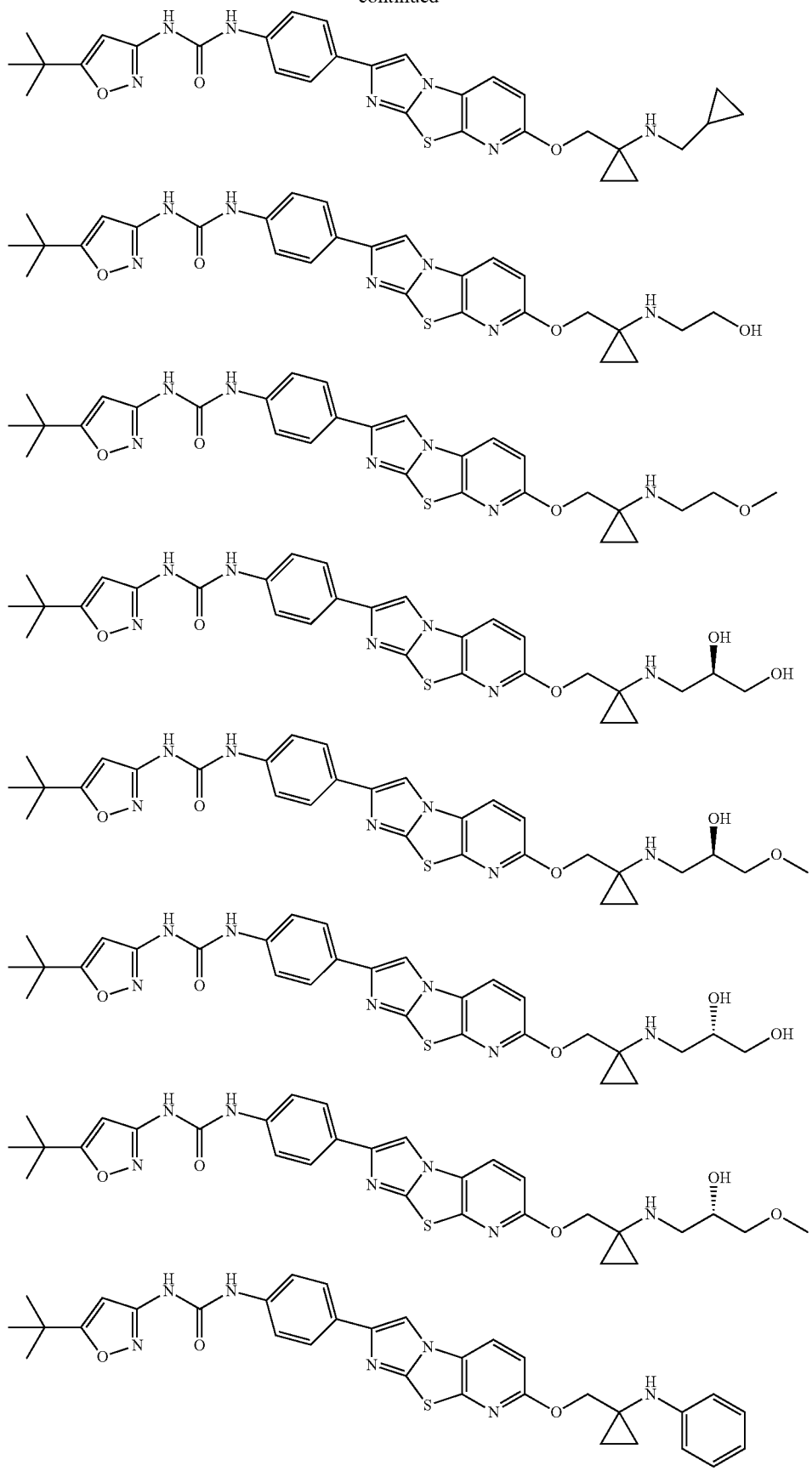

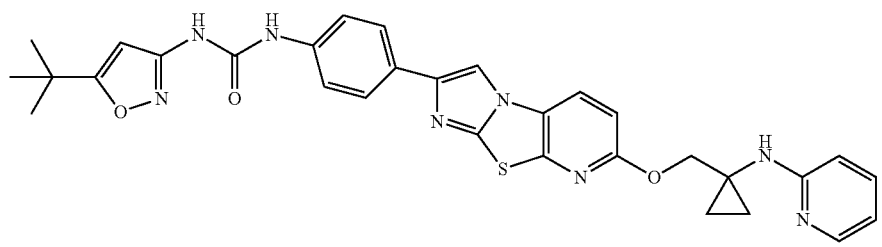
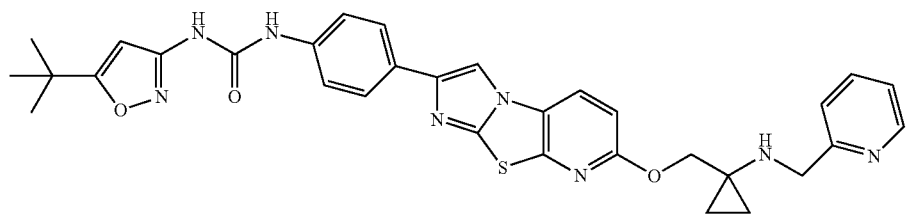
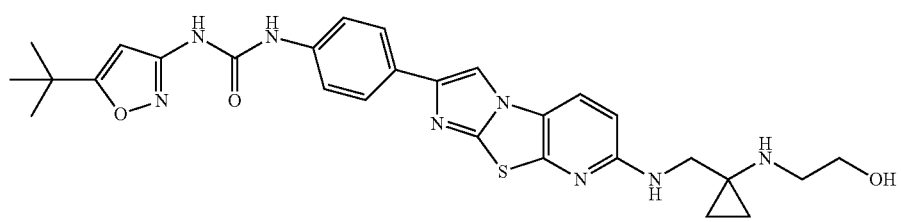
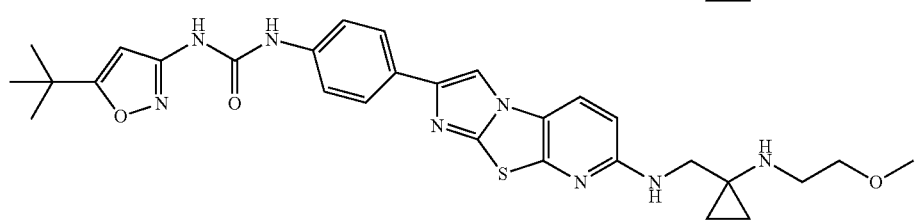
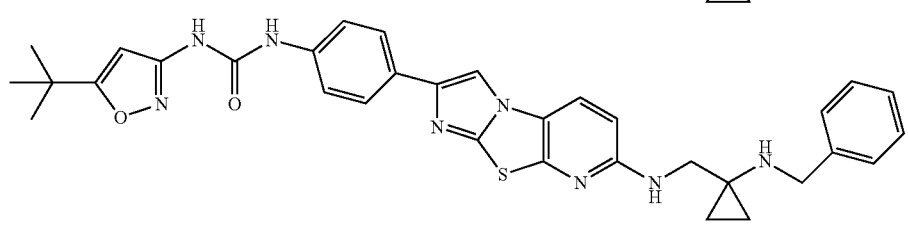
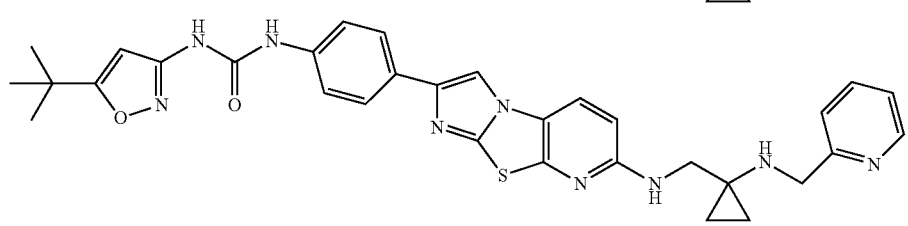
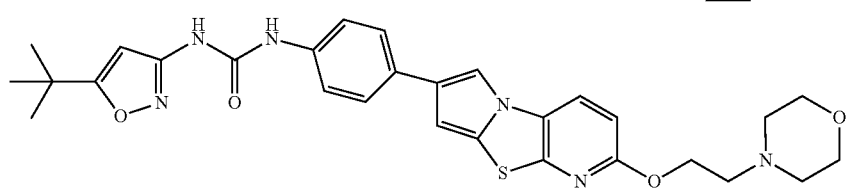
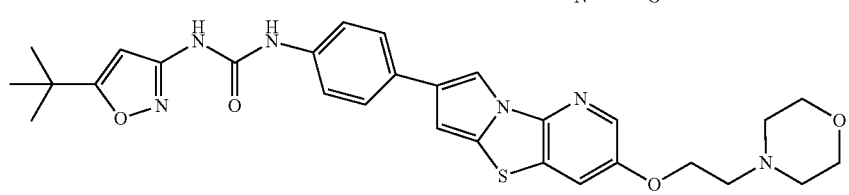

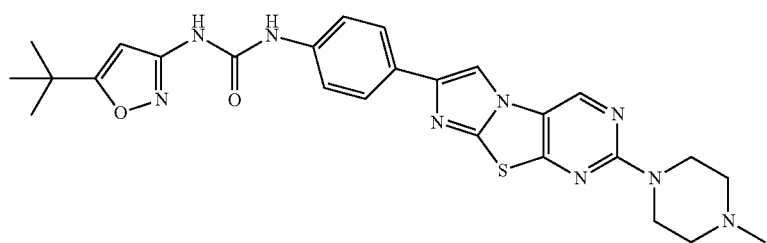
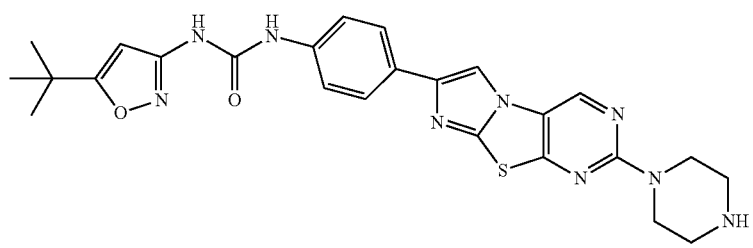
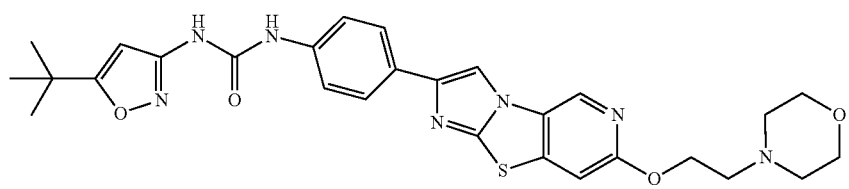
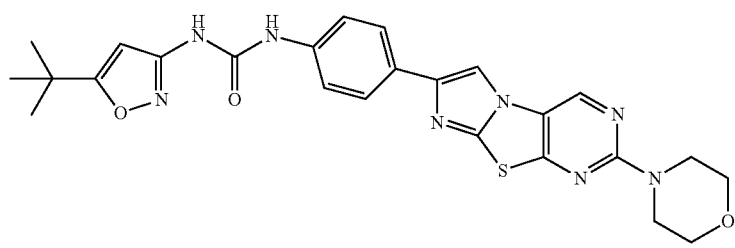
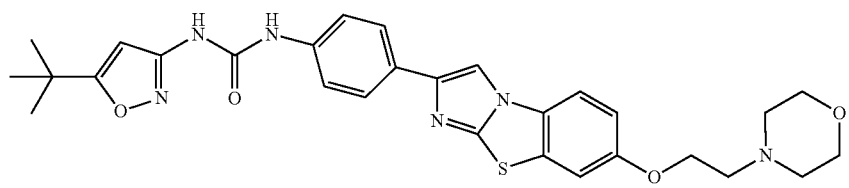
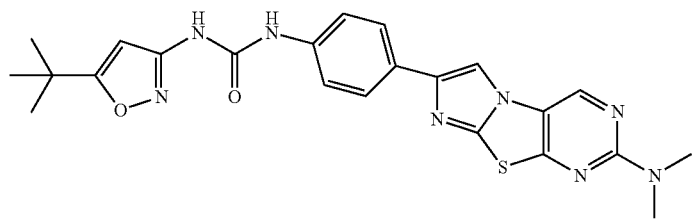
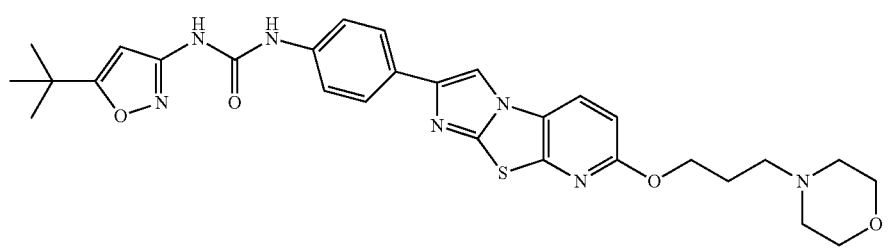

-continued
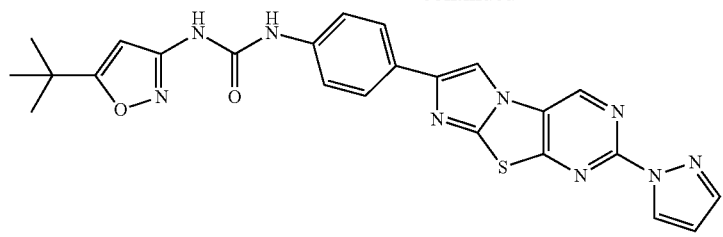
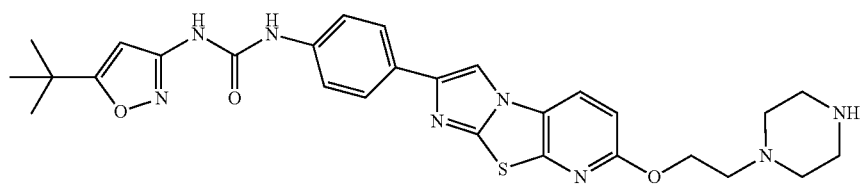
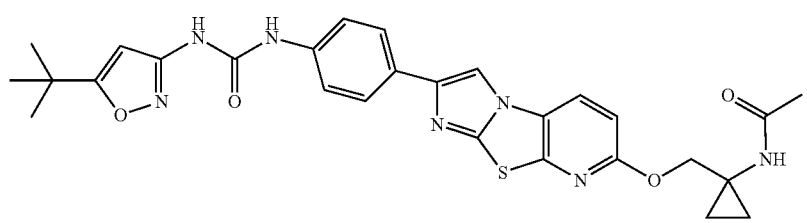
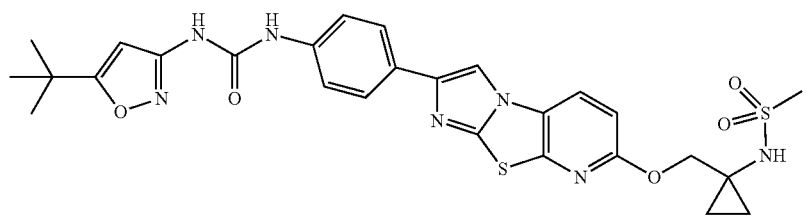
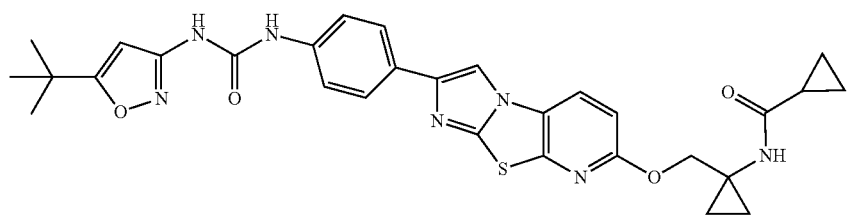
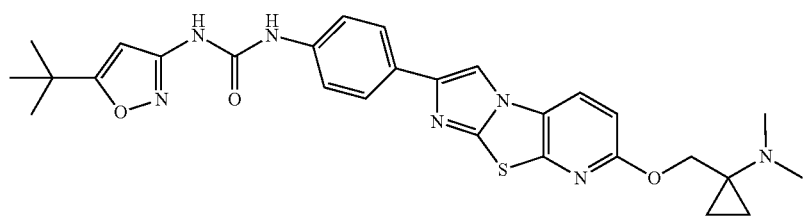
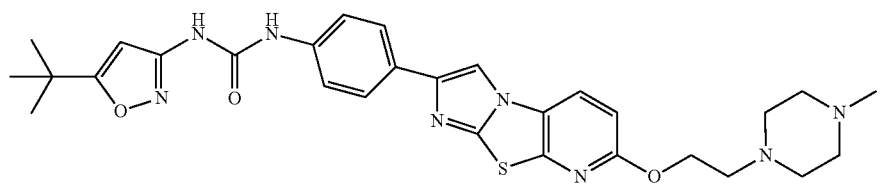
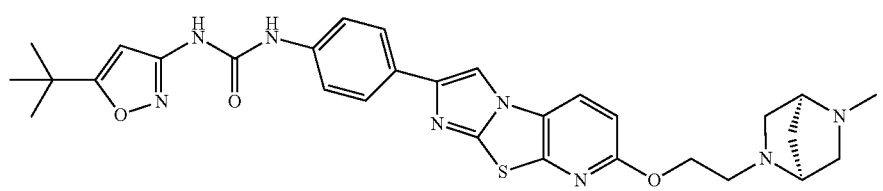

-continued
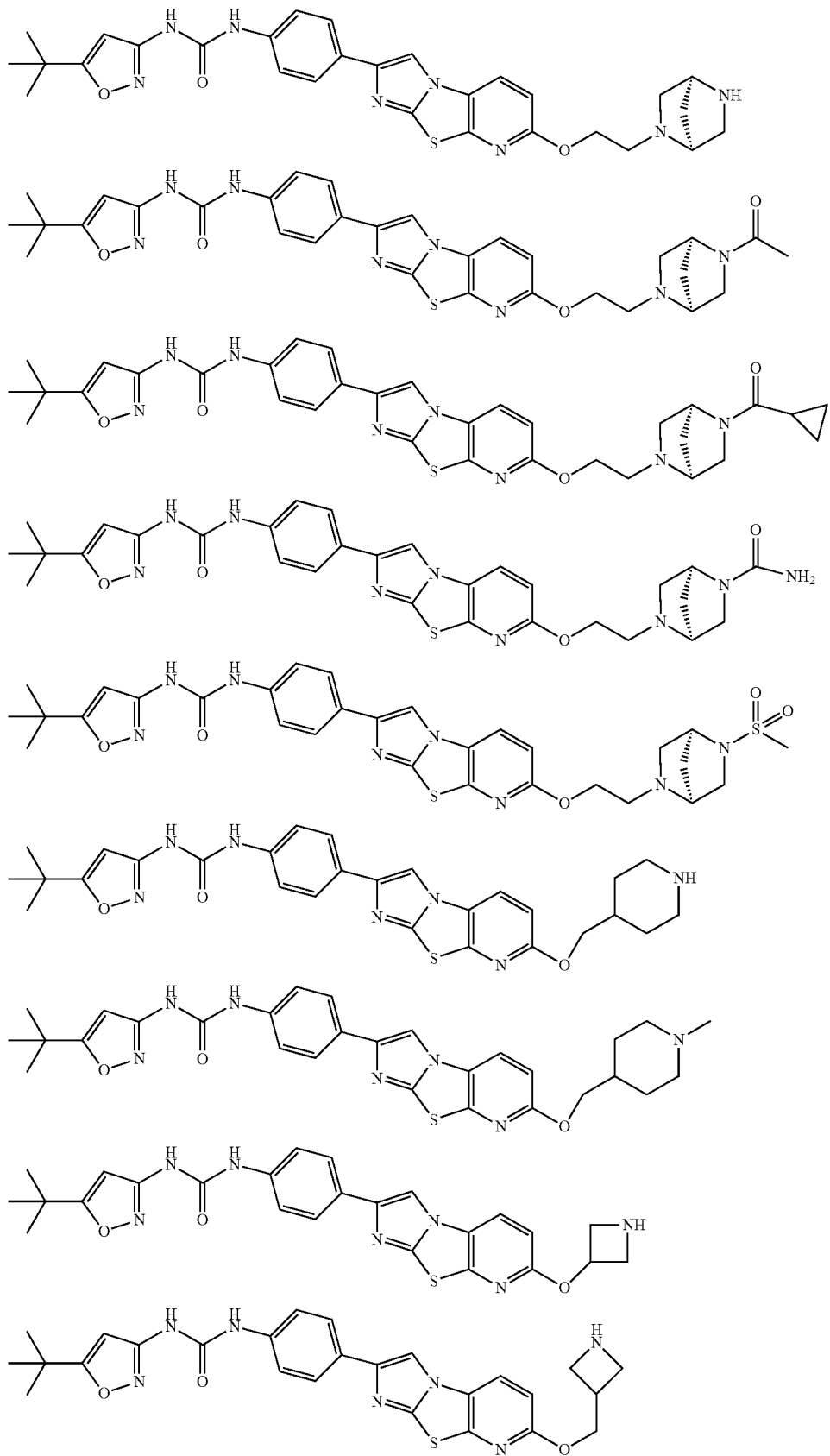

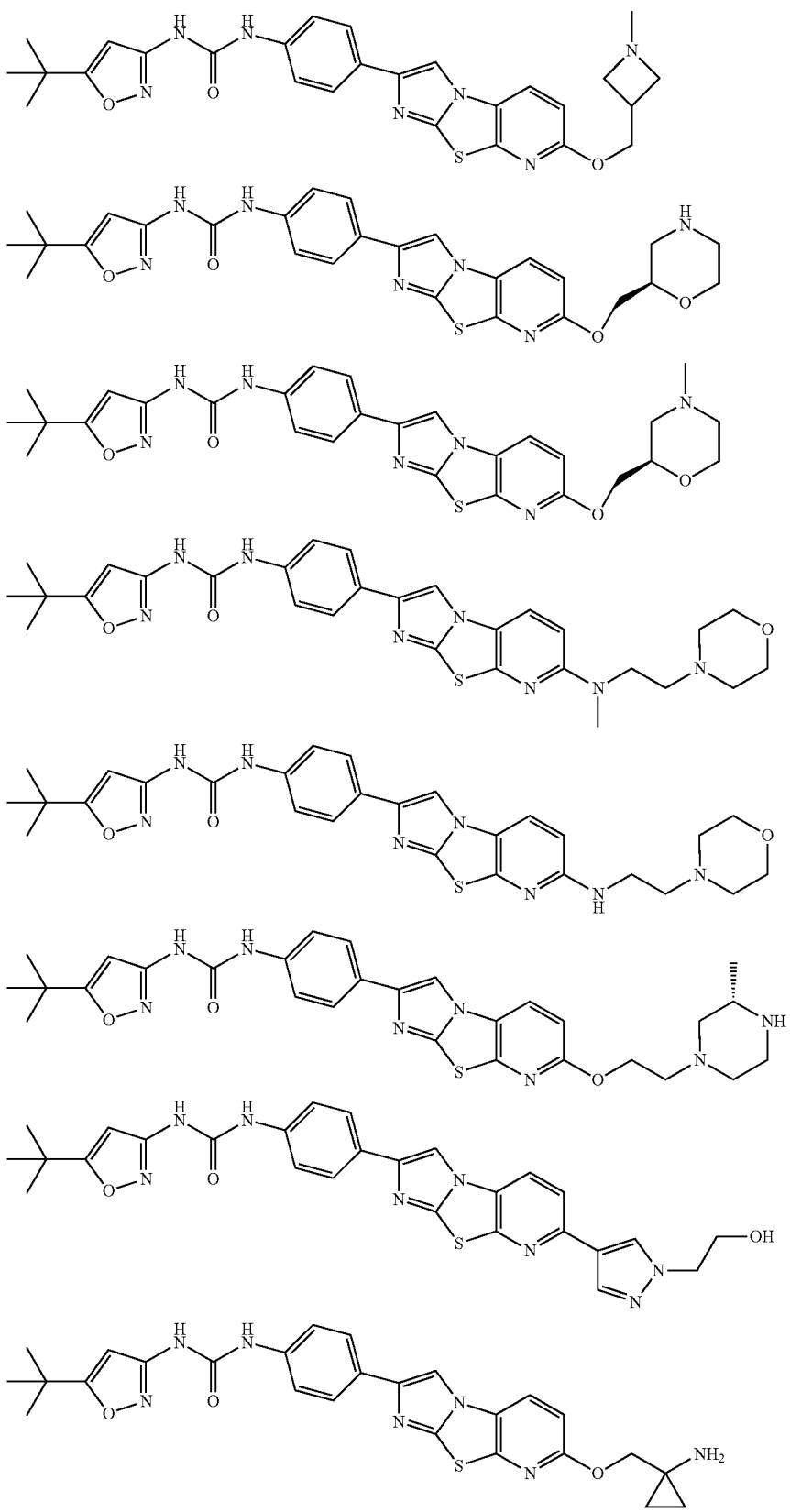

-continued
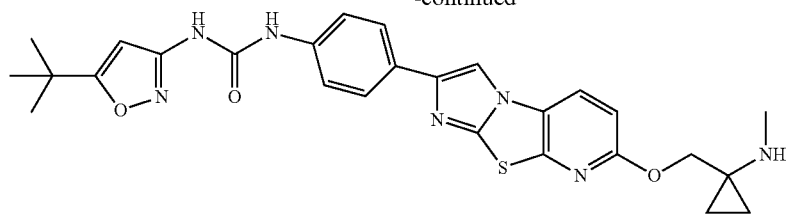
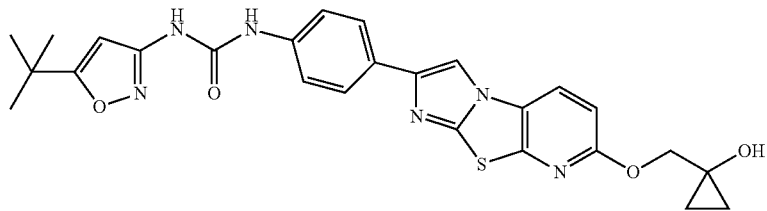
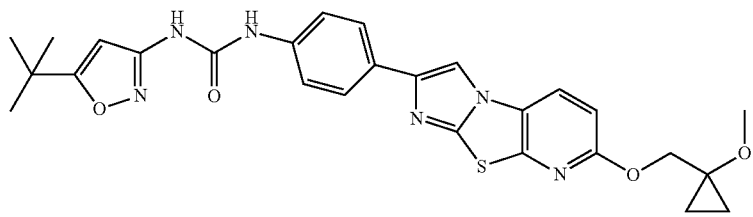
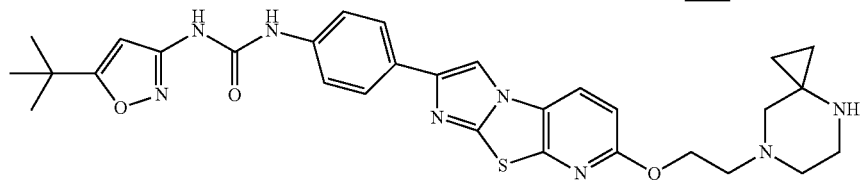
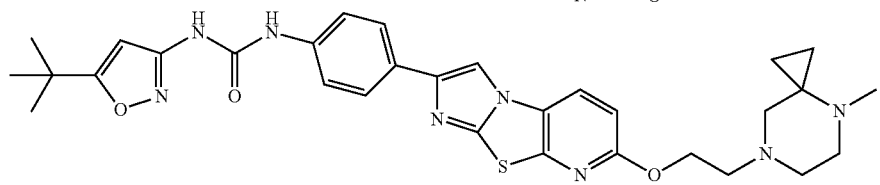
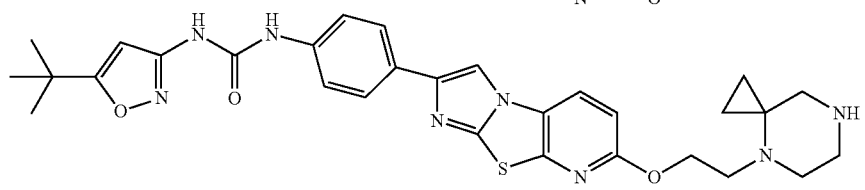
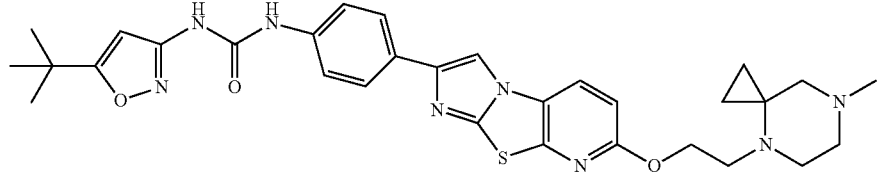
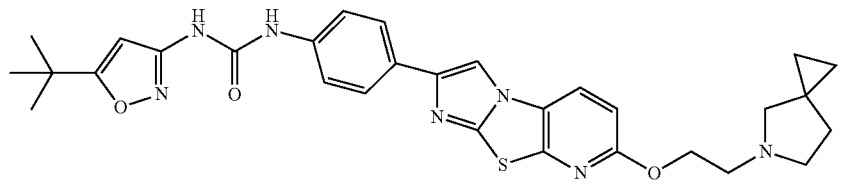
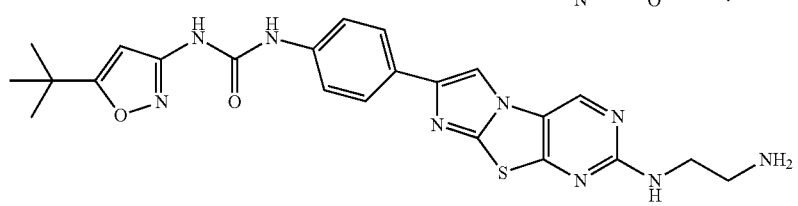

-continued
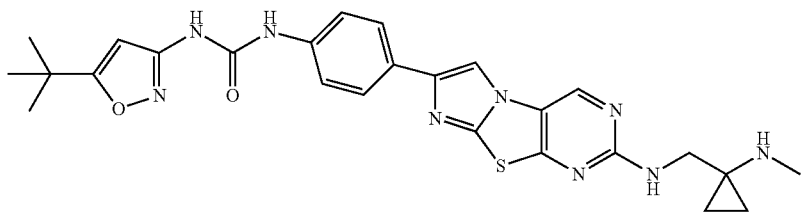
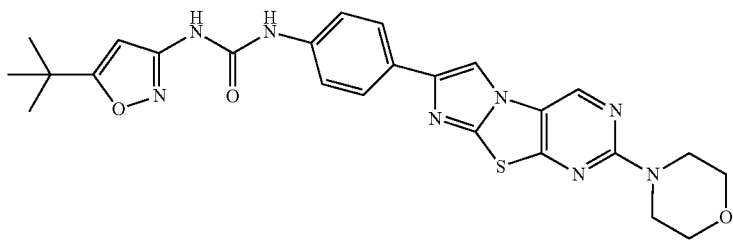
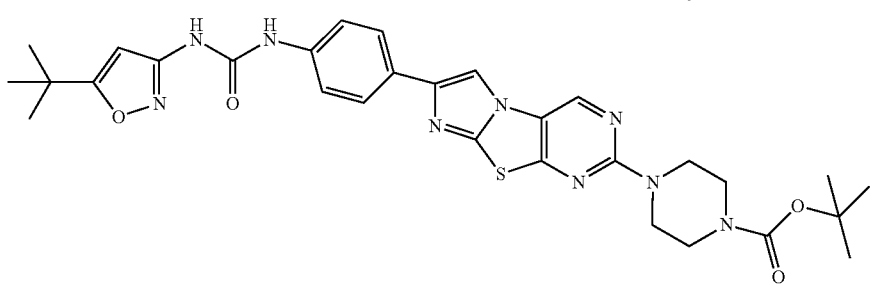
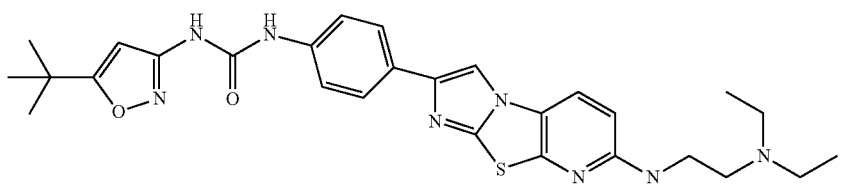
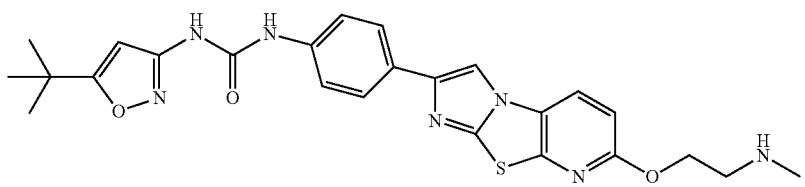
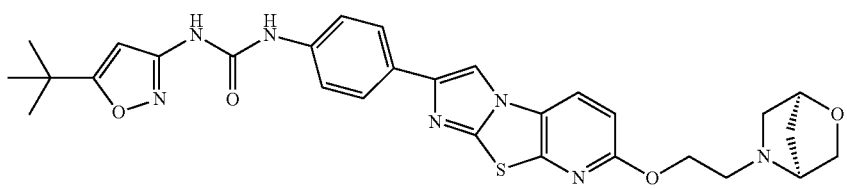
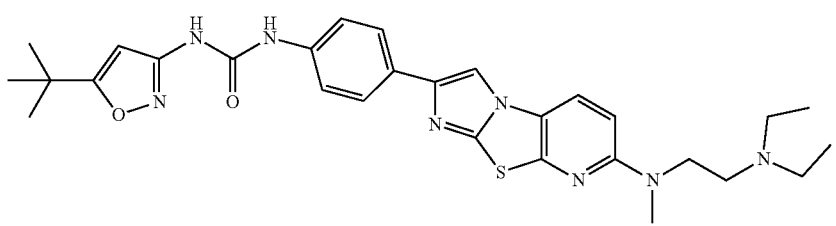
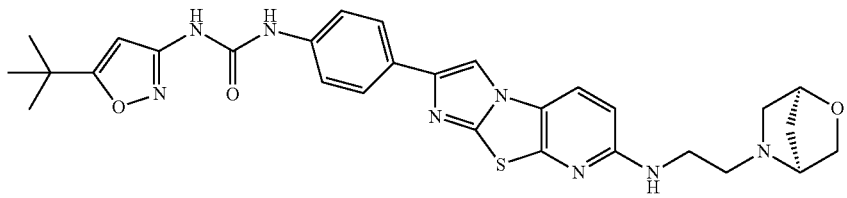

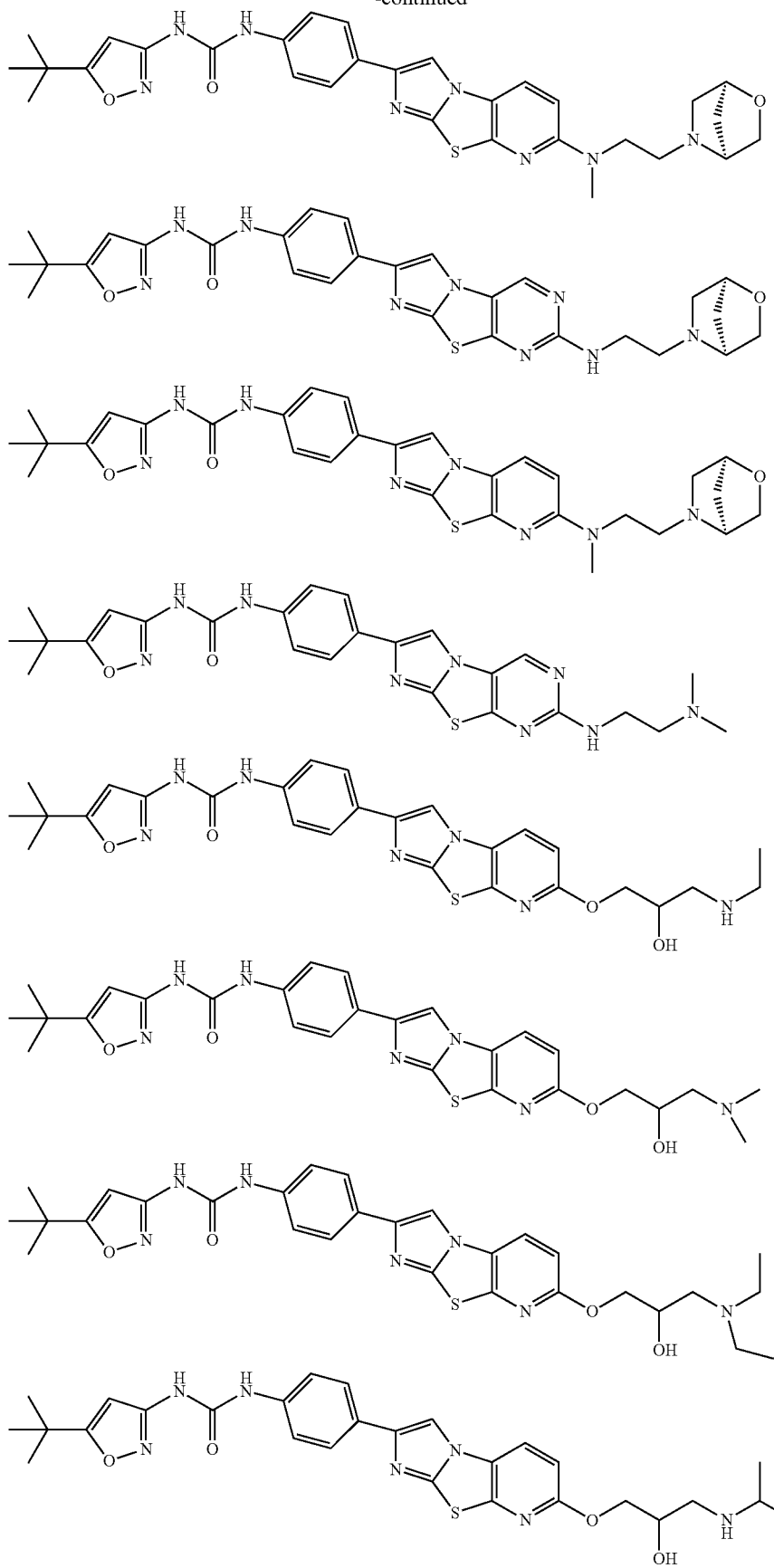

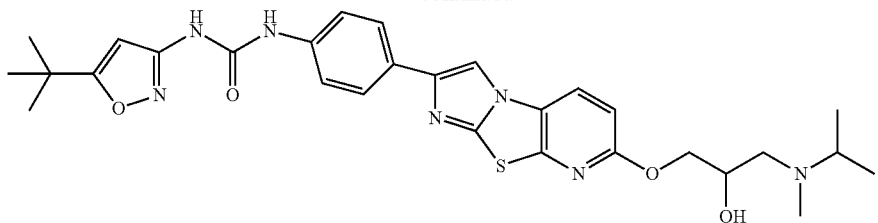
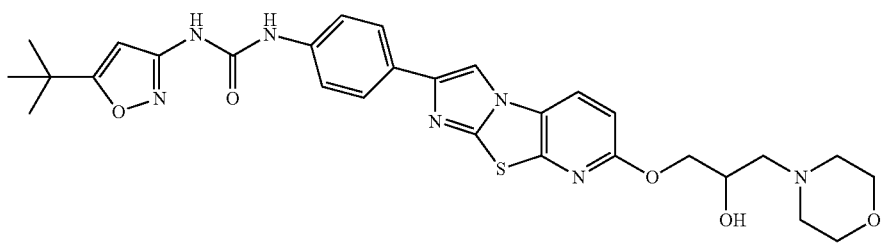
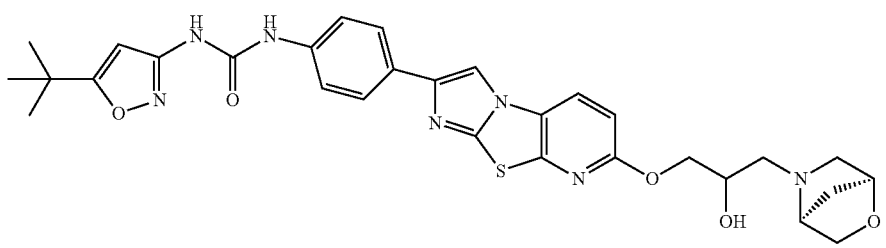
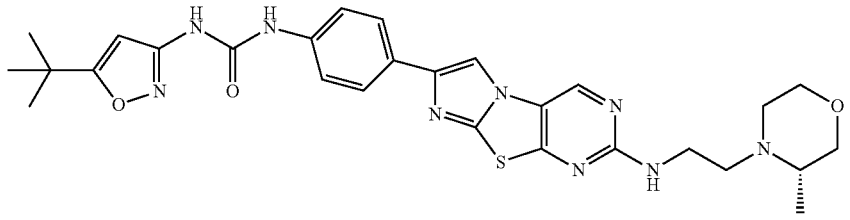
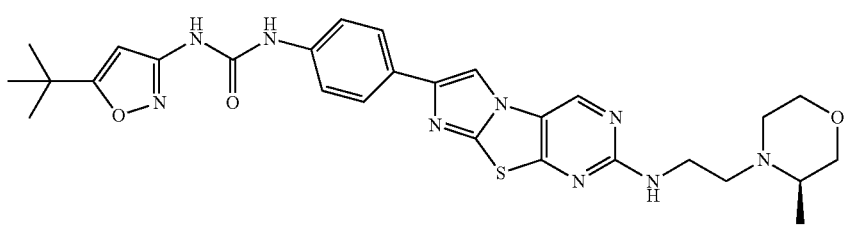
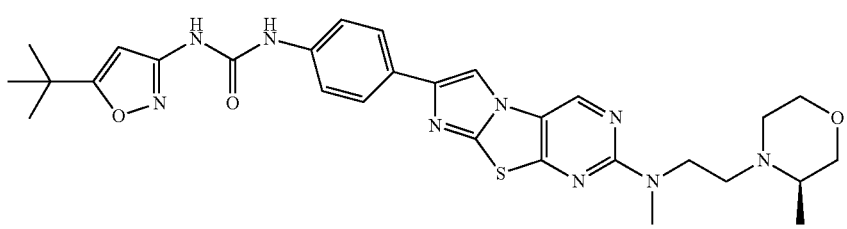

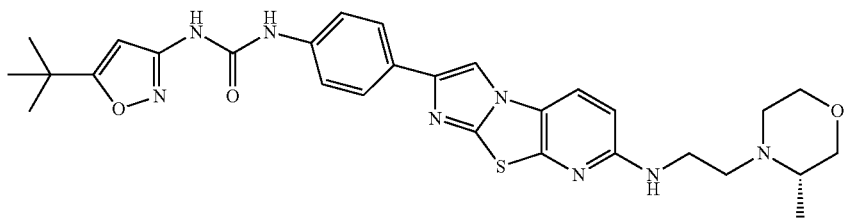
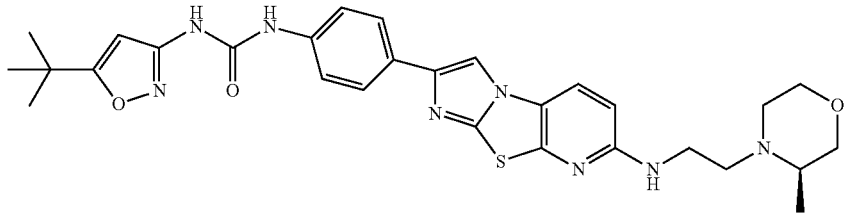
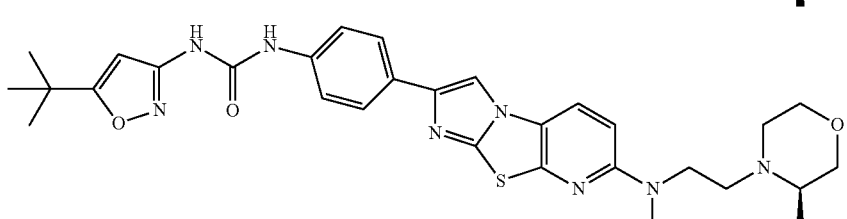
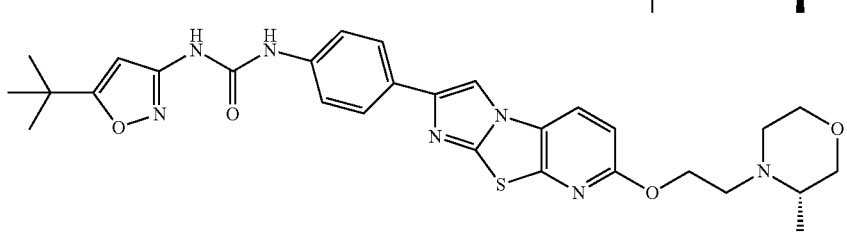
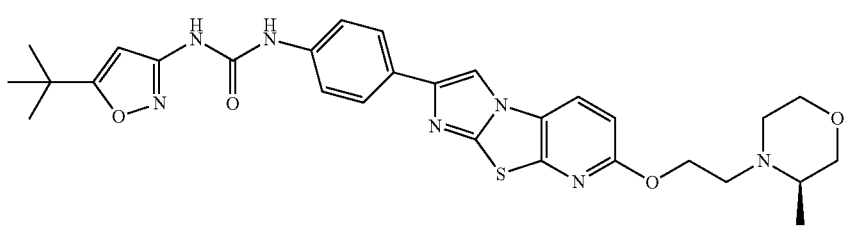
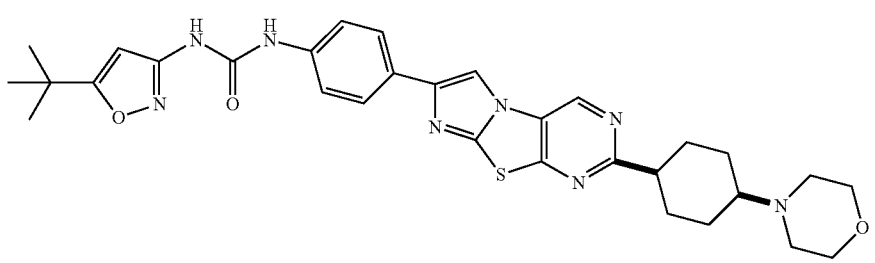

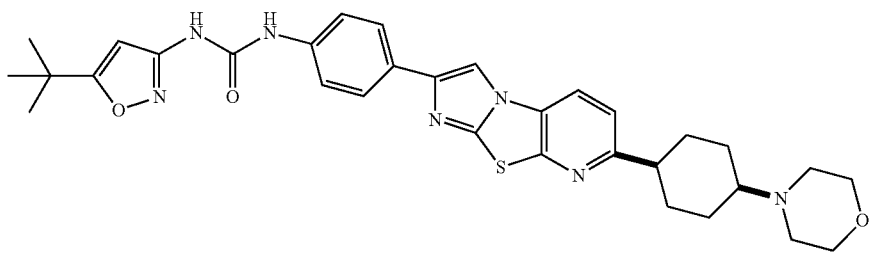
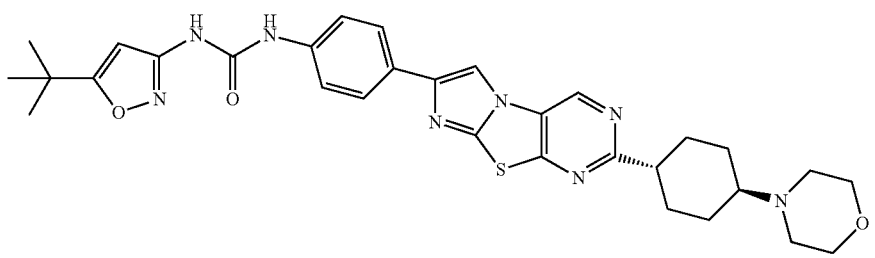
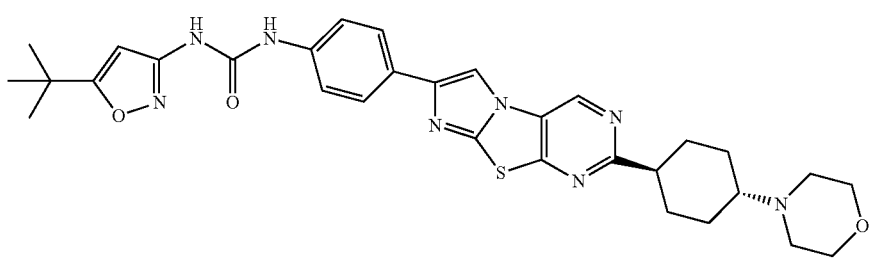
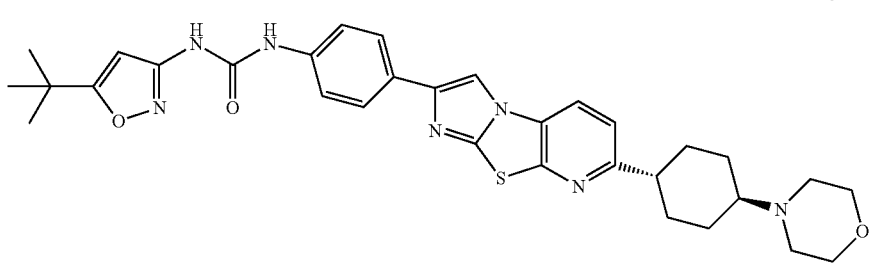
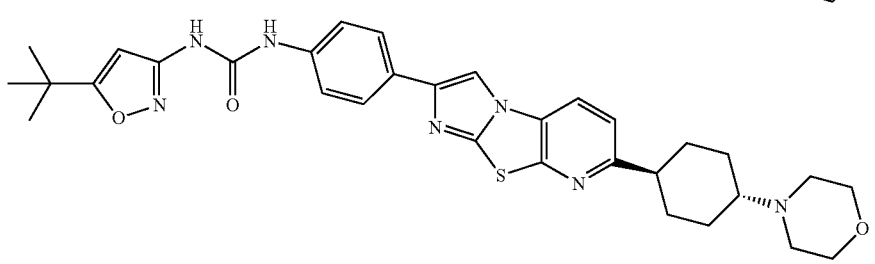
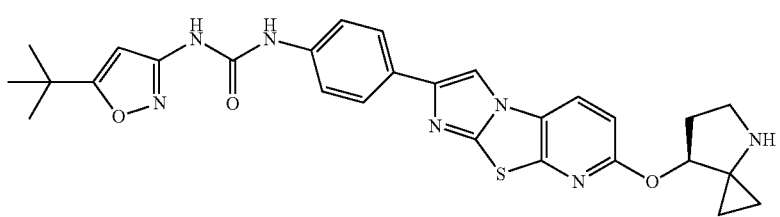
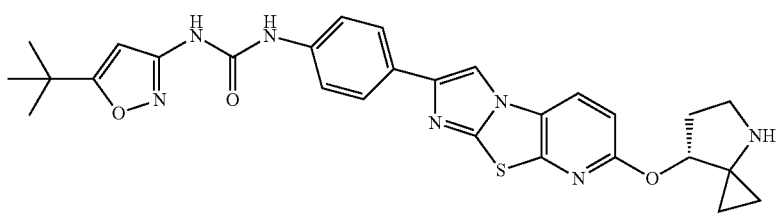

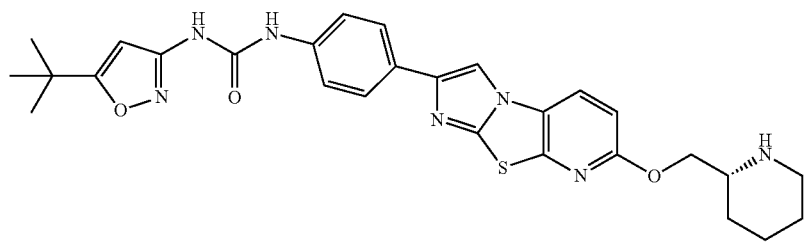
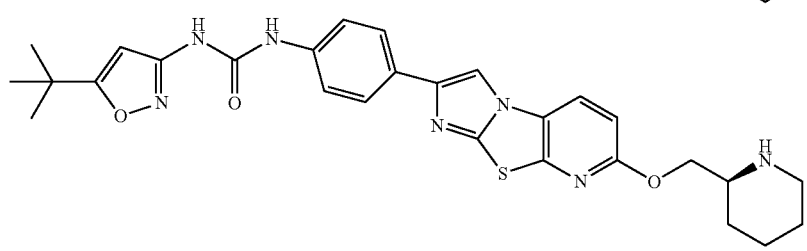
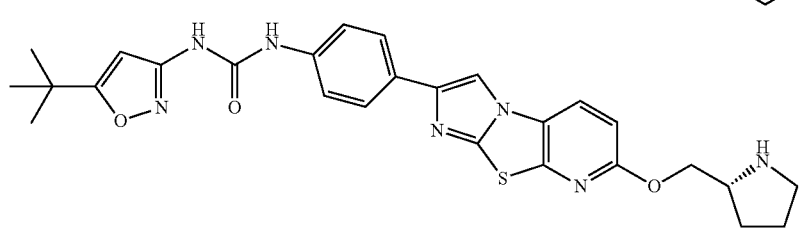
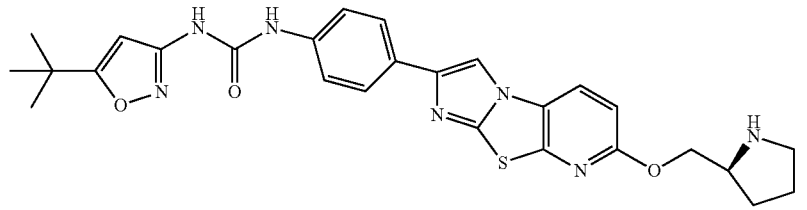
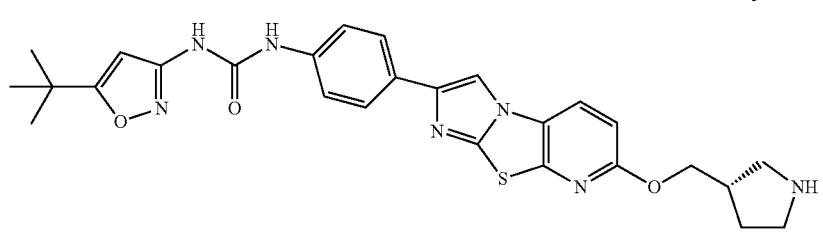
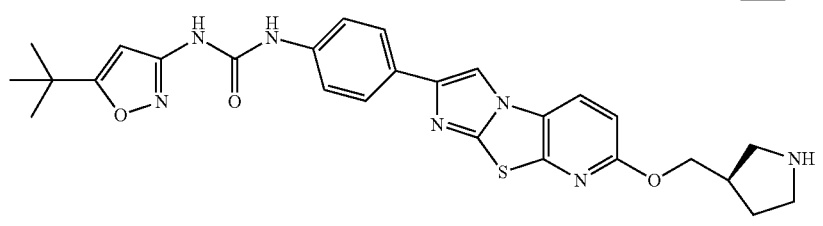
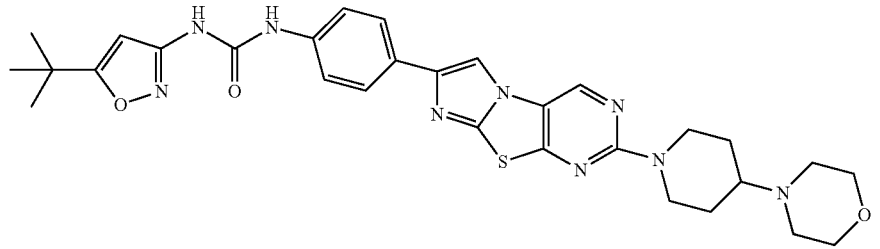

-continued

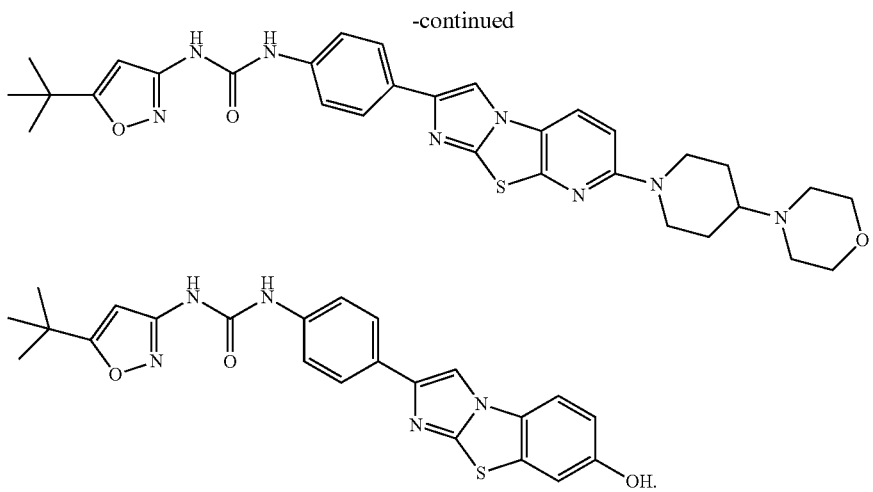

In an embodiment, the PTM is represented by Formula PTM-VII (which correspond to Formula I from U.S. Patent Application Publication No. 2015/0259288 A1, which is incorporated herein in its entirety for all purposes):

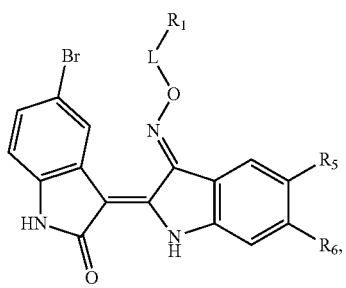

PTM-VII wherein:

L of PTM-VII is a bond, substituted or unsubstituted alkylene, or substituted or unsubstituted heteroalkylene;

$R^1$ of PTM-VII is hydrogen, halogen, —$CF_3$, —$CCl_3$, —$CBr_3$, —$CI_3$, —$OCF_3$, —$OCCl_3$, —$OCBr_3$, —$OCl_3$, —CN, —OH, —$NH_2$, —COOH, —C(O)$OR_4$, —$CONH_2$, —$NO_2$, —SH, —$NHNH_2$, —$NR^2R^3$, —$OR^4$, —$SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R_2$ and $R_3$ of PTM-VII are optionally joined together to form a substituted or unsubstituted heterocycloalkyl or substituted or unsubstituted heteroaryl. $R^4$ of PTM-VII is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R_5$ and $R_6$ of PTM-VII are independently hydrogen, halogen, —$CF_3$, —$CCl_3$, —$CBr_3$, —$CI_3$, —$OCF_3$, —$OCCl_3$, —$OCBr_3$, —$OCl_3$, —CN, —OH, —$NH_2$, —COOH, —C(O)$OR_9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^7$ and $R^8$ of PTM-VII are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, or $R^7$ and $R^8$ are optionally joined together to form a substituted or unsubstituted heterocycloalkyl or substituted or unsubstituted heteroaryl;

$R^9$ of PTM-VII is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

the PTM-VII is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-VII is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^8$, or $R^9$).

In some embodiment, L of PTM-VII may be a bond or substituted or unsubstituted alkylene. In other embodiments, L of PTM-VII is substituted or unsubstituted alkylene. L of PTM-VII may be an unsubstituted alkylene. L of PTM-VII may be an unsubstituted $C_1$-$C_8$ alkylene. L of PTM-VII may be an unsubstituted $C_1$-$C_4$ alkylene. L of PTM-VII may be an unsubstituted $C_2$ alkylene. L of PTM-VII may be an unsubstituted methylene. In certain embodiments, L of PTM-VII is a bond. In an embodiment, L of PTM-VII is independently a bond or $R^{47}$-substituted or unsubstituted alkylene. L may be a substituted or unsubstituted heteroalkylene. L of PTM-VII may be a substituted or unsubstituted 2 to 8 membered heteroalkylene. L of PTM-VII may be substituted or unsubstituted 2 to 6 membered heteroalkylene. L of PTM-VII may be an unsubstituted heteroalkylene. L of PTM-VII may be an unsubstituted 2 to 8 membered heteroalkylene. L of PTM-VII may be an unsubstituted 2 to 6 membered heteroalkylene.

$R^{47}$ of PTM-VII is independently oxo, halogen, —$CF_3$, —CN, —OH, —NH, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCF_3$, —$OCHF_2$, $R^{48}$-substituted or unsubstituted alkyl, $R^{48}$-substituted or unsubstituted heteroalkyl, $R^{48}$-substituted or unsubstituted cycloalkyl, $R^{48}$-substituted or unsubstituted heterocycloalkyl, $R^{48}$-substituted or unsubstituted aryl, or $R^{48}$-substituted or unsubstituted heteroaryl.

$R^{48}$ of PTM-VII is independently oxo, halogen, —$CF_3$, —$CN$, —$OH$, —$NH_2$, —$COOH$, —$CONH_2$, —$NO_2$, —$SH$, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCF_3$, —$OCHF_2$, $R^{49}$-substituted or unsubstituted alkyl, $R^{49}$-substituted or unsubstituted heteroalkyl, $R^{49}$-substituted or unsubstituted cycloalkyl, $R^{49}$-substituted or unsubstituted heterocycloalkyl, $R^{49}$-substituted or unsubstituted aryl, or $R^{49}$-substituted or unsubstituted heteroaryl In any embodiment or aspect described herein, $R^1$ of PTM-VII is halogen, —$CF_3$, —$CCl_3$, —$CBr_3$, —$CI_3$, —$OCF_3$, —$OCCl_3$, —$OCBr_3$, —$OCl_3$, —$CN$, —$OH$, —$NH_2$, —$COOH$, —$C(O)OR^4$, —$CONH_2$, —$NO_2$, —$SH$, —$NHNH_2$, —$NR^2R^3$, —$OR^4$, —$SR^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In any embodiment or aspect described herein, $R^1$ is —$NR^2R^3$. In any embodiment or aspect described herein, $R^1$ is a substituted alkyl. In any embodiment or aspect described herein, $R^1$ may be a substituted $C_1$-$C_8$ alkyl. In any embodiment or aspect described herein, $R^1$ is a substituted $C_1$-$C_4$ alkyl. In any embodiment or aspect described herein, $R^1$ may be a substituted ethyl. In any embodiment or aspect described herein, $R^1$ is a substituted methyl. In any embodiment or aspect described herein, $R^1$ is not hydrogen. In any embodiment or aspect described herein, $R^1$ is not —$OH$. In embodiments, $R^1$ is not —$NH_2$.

In any embodiment or aspects described herein, $R^1$ of PTM-VII is independently hydrogen, halogen, —$CF_3$, —$CN$, —$OH$, —$NH_2$, —$COOH$, —$CONH_2$, —$NO_2$, —$SH$, —$NHNH_2$, —$OCF_3$, —$OCHF_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In any embodiments or aspects described herein, $R^1$ of PTM-VII is independently halogen, —$CF_3$, —$CN$, —$OH$, —$NH_2$, —$COOH$, —$CONH_2$, —$NO_2$, —$SH$, —$NHNH_2$, —$OCF_3$, —$OCHF_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In any embodiment or aspect described herein, $R^1$ of PTM-VII is: a substituted or unsubstituted $C_1$-$C_{20}$ alkyl; $R^{20}$-substituted or unsubstituted $C_1$-$C_{20}$ alkyl; a substituted or unsubstituted $C_1$-$C_{10}$ alkyl; $R^{20}$-a substituted or unsubstituted $C_1$-$C_{10}$ alkyl; a substituted or unsubstituted $C_1$-$C_8$ alkyl; $R^{20}$-substituted or unsubstituted $C_1$-$C_8$ alkyl; a substituted or unsubstituted $C_1$-$C_5$ alkyl; or $R^{20}$-substituted or unsubstituted $C_1$-$C_5$ alkyl.

In any embodiment or aspect described herein, $R^1$ of PTM-VII is: a substituted or unsubstituted 2 to 20 membered heteroalkyl; a $R^{20}$-substituted or unsubstituted 2 to 20 membered heteroalkyl; a substituted or unsubstituted 2 to 10 membered heteroalkyl; a $R^{20}$-substituted or unsubstituted 2 to 10 membered heteroalkyl; a substituted or unsubstituted 2 to 8 membered heteroalkyl; a $R^{20}$-substituted or unsubstituted 2 to 8 membered heteroalkyl; a substituted or unsubstituted 2 to 6 membered heteroalkyl; or a $R^{20}$-substituted or unsubstituted 2 to 6 membered heteroalkyl.

In any embodiments or aspects described herein, $R^1$ of PTM-VII is: a substituted or unsubstituted 3 to 20 membered cycloalkyl; $R^{20}$-substituted or unsubstituted 3 to 20 membered cycloalkyl; a substituted or unsubstituted 3 to 10 membered cycloalkyl; $R^{20}$-substituted or unsubstituted 3 to 10 membered cycloalkyl; a substituted or unsubstituted 3 to 8 membered cycloalkyl; $R^{20}$-substituted or unsubstituted 3 to 8 membered cycloalkyl; a substituted or unsubstituted 3 to 6 membered cycloalkyl; $R^{20}$-substituted or unsubstituted 3 to 6 membered cycloalkyl; a substituted or unsubstituted 5 membered cycloalkyl; $R^{20}$-substituted or unsubstituted 5 membered cycloalkyl; a substituted or unsubstituted 6 membered cycloalkyl; or $R^{20}$-substituted or unsubstituted 6 membered cycloalkyl.

In any aspect or embodiment described herein, $R^1$ of PTM-VII is substituted or unsubstituted 3 to 20 membered heterocycloalkyl; $R^{20}$-substituted or unsubstituted 3 to 20 membered heterocycloalkyl; a substituted or unsubstituted 3 to 10 membered heterocycloalkyl; $R^{20}$-substituted or unsubstituted 3 to 10 membered heterocycloalkyl; a substituted or unsubstituted 3 to 8 membered heterocycloalkyl; $R^{20}$-substituted or unsubstituted 3 to 8 membered heterocycloalkyl; a substituted or unsubstituted 3 to 6 membered heterocycloalkyl; $R^{20}$-substituted or unsubstituted 3 to 6 membered heterocycloalkyl; a substituted or unsubstituted 5 membered heterocycloalkyl $R^{20}$-substituted or unsubstituted 5 membered heterocycloalkyl; a substituted or unsubstituted 6 membered heterocycloalkyl; or $R^{20}$-substituted or unsubstituted 6 membered heterocycloalkyl.

In any embodiment or aspect described herein, $R^1$ of PTM-VII is substituted or unsubstituted 5 to 10 membered aryl; $R^{20}$-substituted or unsubstituted 5 to 10 membered aryl; a substituted or unsubstituted 5 to 8 membered aryl; $R^{20}$-substituted or unsubstituted 5 to 8 membered aryl; a substituted or unsubstituted 6 membered aryl; or $R^{20}$-substituted or unsubstituted 6 membered aryl.

In any embodiment or aspect described herein, $R^1$ of PTM-VII is substituted or unsubstituted 5 to 10 membered heteroaryl; $R^{20}$-substituted or unsubstituted 5 to 10 membered heteroaryl; a substituted or unsubstituted 5 to 8 membered heteroaryl; $R^{20}$-substituted or unsubstituted 5 to 8 membered heteroaryl; a substituted or unsubstituted 6 membered heteroaryl; or $R^{20}$-substituted or unsubstituted 6 membered heteroaryl.

$R^{20}$ of PTM-VII is independently oxo, halogen, —$CF_3$, —$CN$, —$OH$, —$NH_2$, —$COOH$, —$CONH_2$, —$NO_2$, —$SH$, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCF_3$, —$OCHF_2$, $R^{21}$-substituted or unsubstituted alkyl, $R^{21}$-substituted or unsubstituted heteroalkyl, R.sup.$^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

$R^{21}$ of PTM-VII is independently oxo, halogen, —$CF_3$, —$CN$, —$OH$, —$NH_2$, —$COOH$, —$CONH_2$, —$NO_2$, —$SH$, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCF_3$, —$OCHF_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In any embodiment or aspect described herein, $R^2$ of PTM-VII is independently substituted or unsubstituted alkyl; substituted or unsubstituted $C_1$-$C_8$ alkyl; substituted $C_1$-$C_8$ alkyl; unsubstituted $C_1$-$C_8$ alkyl; substituted or unsubstituted $C_1$-$C_4$ alkyl; substituted $C_1$-$C_4$ alkyl; unsubstituted $C_1$-$C_4$ alkyl; —OH substituted or unsubstituted $C_1$-$C_4$ alkyl; substituted or unsubstituted methyl; substituted or unsubstituted ethyl; substituted or unsubstituted propyl; $R^{23}$-substituted or unsubstituted alkyl; $R^{23}$-substituted or unsubstituted heteroalkyl; $R^{23}$-substituted or unsubstituted cycloalkyl; $R^{23}$-substituted or unsubstituted heterocycloalkyl; $R^{23}$-substituted or unsubstituted aryl; or $R^{23}$-substituted or unsubstituted heteroaryl.

In any embodiments or aspects herein, $R^2$ of PTM-VII is substituted or unsubstituted $C_1$-$C_{20}$ alkyl; $R^{23}$-substituted or unsubstituted $C^1$-$C^{20}$ alkyl; substituted or unsubstituted $C^1$-$C^{10}$ alkyl; $R^{23}$-substituted or unsubstituted $C^1$-$C^{10}$ alkyl; substituted or unsubstituted $C^1$-$C^8$ alkyl; $R^{23}$-substituted or unsubstituted $C^1$-$C^8$ alkyl; substituted or unsubstituted $C^1$-$C^5$ alkyl; or $R^{23}$-substituted or unsubstituted $C^1$-$C^5$ alkyl.

In any embodiments or aspects herein, $R^2$ of PTM-VII is substituted or unsubstituted 2 to 20 membered heteroalkyl; $R^{23}$-substituted or unsubstituted 2 to 20 membered heteroalkyl; substituted or unsubstituted 2 to 10 membered heteroalkyl; $R^{23}$-substituted or unsubstituted 2 to 10 membered heteroalkyl; substituted or unsubstituted 2 to 8 membered heteroalkyl; $R^{23}$-substituted or unsubstituted 2 to 8 membered heteroalkyl; substituted or unsubstituted 2 to 6 membered heteroalkyl; or $R^{23}$-substituted or unsubstituted 2 to 6 membered heteroalkyl.

In any embodiment or aspect described herein, $R^2$ of PTM-VII is substituted or unsubstituted 3 to 20 membered cycloalkyl; $R^{23}$-substituted or unsubstituted 3 to 20 membered cycloalkyl; substituted or unsubstituted 3 to 10 membered cycloalkyl; $R^{23}$-substituted or unsubstituted 3 to 10 membered cycloalkyl; substituted or unsubstituted 3 to 8 membered cycloalkyl; $R^{23}$-substituted or unsubstituted 3 to 8 membered cycloalkyl; substituted or unsubstituted 3 to 6 membered cycloalkyl; $R^{23}$-substituted or unsubstituted 3 to 6 membered cycloalkyl; substituted or unsubstituted 5 membered cycloalkyl; $R^{23}$-substituted or unsubstituted 5 membered cycloalkyl; substituted or unsubstituted 6 membered cycloalkyl; or $R^{23}$-substituted or unsubstituted 6 membered cycloalkyl.

In any embodiment or aspect described herein, $R^2$ of PTM-VII is substituted or unsubstituted 3 to 20 membered heterocycloalkyl; $R^{23}$-substituted or unsubstituted 3 to 20 membered heterocycloalkyl; substituted or unsubstituted 3 to 10 membered heterocycloalkyl; $R^{23}$-substituted or unsubstituted 3 to 10 membered heterocycloalkyl; substituted or unsubstituted 3 to 8 membered heterocycloalkyl; $R^{23}$-substituted or unsubstituted 3 to 8 membered heterocycloalkyl; substituted or unsubstituted 3 to 6 membered heterocycloalkyl; $R^{23}$-substituted or unsubstituted 3 to 6 membered heterocycloalkyl; substituted or unsubstituted 5 membered heterocycloalkyl; $R^{23}$-substituted or unsubstituted 5 membered heterocycloalkyl; substituted or unsubstituted 6 membered heterocycloalkyl; or $R^{23}$-substituted or unsubstituted 6 membered heterocycloalkyl.

In any embodiment or aspect described herein, $R^2$ of PTM-VII is substituted or unsubstituted 5 to 10 membered aryl; $R^{23}$-substituted or unsubstituted 5 to 10 membered aryl; substituted or unsubstituted 5 to 8 membered aryl; $R^{23}$-substituted or unsubstituted 5 to 8 membered aryl; substituted or unsubstituted 6 membered aryl; or $R^{23}$-substituted or unsubstituted 6 membered aryl.

In any embodiment or aspect described herein, $R^2$ of PTM-VII is substituted or unsubstituted 5 to 10 membered heteroaryl; $R^{23}$-substituted or unsubstituted 5 to 10 membered heteroaryl; substituted or unsubstituted 5 to 8 membered heteroaryl; $R^{23}$-substituted or unsubstituted 5 to 8 membered heteroaryl; substituted or unsubstituted 6 membered heteroaryl; or $R^{23}$-substituted or unsubstituted 6 membered heteroaryl.

$R^{23}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl. $R^{23}$ may independently be —OH. $R^{23}$ may independently be unsubstituted methyl. $R^{23}$ may independently be $R^{24}$-substituted or unsubstituted heteroalkyl. $R^{23}$ may independently be $R^{24}$-substituted or unsubstituted alkyl. $R^{23}$ may independently be $R^{24}$-substituted or unsubstituted $C_1$-$C_4$ alkyl.

$R^{24}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl. $R^{24}$ may independently be —OH.

In any embodiments or aspects described herein, $R^3$ of PTM-VII is independently substituted or unsubstituted alkyl; independently be substituted or unsubstituted $C_1$-$C_8$ alkyl; substituted $C_1$-$C_8$ alkyl; unsubstituted $C_1$-$C_8$ alkyl; substituted or unsubstituted $C_1$-$C_4$ alkyl; substituted $C_1$-$C_4$ alkyl; unsubstituted $C_1$-$C_4$ alkyl; —OH substituted or unsubstituted $C_1$-$C_4$ alkyl; substituted or unsubstituted methyl; substituted or unsubstituted ethyl; substituted or unsubstituted propyl; $R^{26}$-substituted or unsubstituted alkyl; $R^{26}$-substituted or unsubstituted heteroalkyl; $R^{26}$-substituted or unsubstituted cycloalkyl; $R^{26}$-substituted or unsubstituted heterocycloalkyl, $R^{26}$-substituted or unsubstituted aryl, or $R^{26}$-substituted or unsubstituted heteroaryl.

In any embodiments or aspects described herein, $R^3$ of PTM-VII is substituted or unsubstituted $C_1$-$C_{20}$ alkyl; $R^{26}$-substituted or unsubstituted $C_1$-$C_{20}$ alkyl; substituted or unsubstituted $C_1$-$C_{10}$ alkyl; $R^{26}$-substituted or unsubstituted $C_1$-$C_{10}$ alkyl; substituted or unsubstituted $C_1$-$C_8$ alkyl; $R^{26}$-substituted or unsubstituted $C_1$-$C_8$ alkyl; substituted or unsubstituted $C_1$-$C_5$ alkyl; or $R^{26}$-substituted or unsubstituted $C_1$-$C_5$ alkyl.

In any embodiment or aspect described herein, $R^3$ of PTM-VII is substituted or unsubstituted 2 to 20 membered heteroalkyl; $R^{26}$-substituted or unsubstituted 2 to 20 membered heteroalkyl; substituted or unsubstituted 2 to 10 membered heteroalkyl; $R^{26}$-substituted or unsubstituted 2 to 10 membered heteroalkyl; substituted or unsubstituted 2 to 8 membered heteroalkyl; $R^{26}$-substituted or unsubstituted 2 to 8 membered heteroalkyl; substituted or unsubstituted 2 to 6 membered heteroalkyl; or $R^{26}$-substituted or unsubstituted 2 to 6 membered heteroalkyl.

In any embodiment or aspect described herein, $R^3$ of PTM-VII is substituted or unsubstituted 3 to 20 membered cycloalkyl; $R^{26}$-substituted or unsubstituted 3 to 20 membered cycloalkyl; substituted or unsubstituted 3 to 10 membered cycloalkyl; $R^{26}$-substituted or unsubstituted 3 to 10 membered cycloalkyl; substituted or unsubstituted 3 to 8 membered cycloalkyl; $R^{26}$-substituted or unsubstituted 3 to 8 membered cycloalkyl; substituted or unsubstituted 3 to 6 membered cycloalkyl; $R^{26}$-substituted or unsubstituted 3 to 6 membered cycloalkyl; substituted or unsubstituted 5 membered cycloalkyl; R26-substituted or unsubstituted 5 membered cycloalkyl; substituted or unsubstituted 6 membered cycloalkyl; or $R^{26}$-substituted or unsubstituted 6 membered cycloalkyl.

In any embodiment or aspect described herein, $R^3$ of PTM-VII is substituted or unsubstituted 3 to 20 membered heterocycloalkyl; $R^{26}$-substituted or unsubstituted 3 to 20 membered heterocycloalkyl; substituted or unsubstituted 3 to 10 membered heterocycloalkyl; $R^{26}$-substituted or unsubstituted 3 to 10 membered heterocycloalkyl; substituted or unsubstituted 3 to 8 membered heterocycloalkyl; $R^{26}$-substituted or unsubstituted 3 to 8 membered heterocycloalkyl; substituted or unsubstituted 3 to 6 membered heterocycloalkyl; $R^{26}$-substituted or unsubstituted 3 to 6 membered heterocycloalkyl; substituted or unsubstituted 5 membered heterocycloalkyl; $R^{26}$-substituted or unsubstituted 5 membered heterocycloalkyl; substituted or unsubstituted 6 membered heterocycloalkyl; or $R^{26}$-substituted or unsubstituted 6 membered heterocycloalkyl.

In any embodiment or aspect described herein, $R^3$ of PTM-VII is substituted or unsubstituted 5 to 10 membered aryl; $R^{26}$-substituted or unsubstituted 5 to 10 membered aryl; substituted or unsubstituted 5 to 8 membered aryl; $R^{26}$-substituted or unsubstituted 5 to 8 membered aryl; substituted or unsubstituted 6 membered aryl' or $R^{26}$-substituted or unsubstituted 6 membered aryl.

In any embodiment or aspect described herein, $R^3$ of PTM-VII is substituted or unsubstituted 5 to 10 membered heteroaryl; $R^{26}$-substituted or unsubstituted 5 to 10 membered heteroaryl; substituted or unsubstituted 5 to 8 membered heteroaryl; $R^{26}$-substituted or unsubstituted 5 to 8 membered heteroaryl; substituted or unsubstituted 6 membered heteroaryl; or $R^{26}$-substituted or unsubstituted 6 membered heteroaryl.

$R^{26}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl. $R^{26}$ may independently be —OH. $R^{26}$ may independently be unsubstituted methyl. $R^{23}$ may independently be $R^{24}$-substituted or unsubstituted heteroalkyl. $R^{26}$ may independently be $R^{27}$-substituted or unsubstituted alkyl. $R^{26}$ may independently be $R^{27}$-substituted or unsubstituted $C_1$-$C_4$ alkyl.

$R^{27}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl. $R^{27}$ may independently be —OH.

In any embodiment or aspects described herein, $R^2$ and $R^3$ of PTM-VII are joined together to form: a substituted or unsubstituted heterocycloalkyl or substituted or unsubstituted heteroaryl; a substituted or unsubstituted heterocycloalkyl; a substituted or unsubstituted 3 to 8 membered heterocycloalkyl; a substituted 3 to 8 membered heterocycloalkyl; a substituted or unsubstituted 5 to 7 membered heterocycloalkyl; a substituted 5 to 7 membered heterocycloalkyl; a substituted or unsubstituted 4 membered heterocycloalkyl; a substituted or unsubstituted 5 membered heterocycloalkyl; or a substituted or unsubstituted 6 membered heterocycloalkyl.

In any embodiment or aspect described herein; $R^2$ and $R^3$ of PTM-VII may be joined together to form: $R^{23}$-substituted or unsubstituted 5 to 7 membered heterocycloalkyl; $R^{23}$-substituted or unsubstituted 4 membered heterocycloalkyl; $R^{23}$-substituted or unsubstituted 5 to 7 membered heterocycloalkyl, wherein $R^{23}$ is independently a substituted or unsubstituted alkyl or substituted or unsubstituted heteroalkyl; or $R^{23}$-substituted 5 to 7 membered heterocycloalkyl, wherein $R^{23}$ is independently a substituted or unsubstituted $C_1$-$C_8$ alkyl or substituted or unsubstituted 2 to 8 membered heteroalkyl.

In any embodiment or aspect described herein, $R^2$ and $R^3$ of PTM-VII are joined together to form: a substituted or unsubstituted pyrrolidinyl; a substituted or unsubstituted piperazinyl; $R^{23}$-substituted or unsubstituted pyrrolidinyl; or $R^{23}$-substituted or unsubstituted piperazinyl; wherein $R^{23}$ is as described herein, including embodiments thereof.

In any embodiment or aspect described herein, $R^4$ of PTM-VII is independently $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

In any embodiment or aspect described herein, $R^{29}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{20}$-substituted or unsubstituted alkyl, $R^{30}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{30}$-substituted or unsubstituted heteroaryl.

In any embodiment or aspect described herein, $R^{30}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCHF_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

$R^5$ of PTM-VII may independently be hydrogen, halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —COOH, —$C(O)OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In any embodiment or aspect described herein, $R^5$ is independently —F. In any embodiment or aspect described herein, $R^5$ is independently —Cl. In any embodiment or aspect described herein, $R^5$ is independently —I. In any embodiment or aspect described herein, $R^5$ is independently —Br. In any embodiment or aspect described herein, $R^5$ is —$NR^7R^8$.

In any embodiment or aspect described herein, $R^5$ of PTM-VII is —$C(O)OCH_3$. In any embodiment or aspect described herein, $R^5$ of PTM-VII is —$OCH_3$. In any embodiment or aspect described herein, $R^5$ of PTM-VII is —$OCH(CH_3)_2$. In any embodiment or aspect described herein, $R^5$ of PTM-VII is —CN. In any embodiment or aspect described herein, $R^5$ of PTM-VII is —$NO_2$. In embodiments, $R^5$ is —$NH_2$. In any embodiment or aspect described herein, $R^5$ of PTM-VII is halogen. In any embodiment or aspect described herein, $R^5$ of PTM-VII is independently hydrogen. In any embodiment or aspect described herein, $R^5$ of PTM-VII is independently unsubstituted methyl. In any embodiment or aspect described herein, $R^5$ of PTM-VII is independently —$OCF_3$. In any embodiment or aspect described herein, $R^5$ of PTM-VII is independently —NHAc. In any embodiment or aspect described herein, $R^5$ of PTM-VII is independently —OH. In any embodiment or aspect described herein, $R^5$ of PTM-VII is unsubstituted alkyl. $R^5$ of PTM-VII may be unsubstituted $C_1$-$C_8$ alkyl. In any embodiment or aspect described herein, $R^5$ of PTM-VII is unsubstituted $C_1$-$C_4$ alkyl. $R^5$ of PTM-VII may be unsubstituted ethyl. In any embodiment or aspect described herein, $R^5$ of PTM-VII is an unsubstituted methyl. In any embodiment or aspect described herein, $R^5$ is independently hydrogen, halogen, —$CF_3$, —CN, —OH, —$NH_2$, —COOH, —$CONH_2$, —$NO_2$, —SH, —$NHNH_2$, —$OCF_3$, —$OCHF_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In any embodiment or aspect described herein, $R^5$ is independently halogen, —$CF_3$, —CN, —OH, —$NH_2$, —COOH, —$CONH_2$, —$NO_2$, —SH, —$NHNH_2$, —$OCF_3$, —$OCHF_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. In embodiments $R^5$ is not hydrogen.

Each $R^{32}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

Each $R^{33}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

$R^6$ of PTM-VII may independently be hydrogen, halogen, —$CF_3$, —$CCl_3$, —$CBr_3$, —$CI_3$, —$OCF_3$, —$OCCl_3$, —$OCBr_3$, —$OCI_3$, —CN, —OH, —$NH_2$, —COOH, —$C(O)OR^9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^6$ is independently —F. In any embodiment or aspect described herein, $R^6$ is independently —Cl. In any embodiment or aspect described herein, $R^6$ is independently —I. In any embodiment or aspect described herein, $R^6$ is independently —Br. In any embodiment or aspect described herein, $R^6$ is —$NR^7R^8$.

In any embodiment or aspect described herein, $R^6$ of PTM-VII is —$C(O)OCH_3$. In any embodiment or aspect described herein, $R^6$ is —$OCH_3$. In any embodiment or aspect described herein, $R^6$ is —$OCH(CH3)_2$. In any embodiment or aspect described herein, $R^6$ is —CN. In any embodiment or aspect described herein, $R^6$ is —$NO_2$. In any embodiment or aspect described herein, $R^6$ is —$NH_2$. In any embodiment or aspect described herein, $R^6$ is halogen. In any embodiment or aspect described herein, $R^6$ is independently hydrogen. In any embodiment or aspect described herein, $R^6$ is independently unsubstituted methyl. In any embodiment or aspect described herein, $R^6$ is independently —$OCF_3$. In any embodiment or aspect described herein, $R^6$ is independently —NHAc. In any embodiment or aspect described herein, $R^6$ of PTM-VII is independently —OH. In any embodiment or aspect described herein, $R^6$ of PTM-VII is unsubstituted alkyl. $R^6$ may be unsubstituted $C_1$-$C_8$ alkyl. In any embodiment or aspect described herein, $R^6$ of PTM-VII is unsubstituted $C_1$-$C_4$ alkyl. $R^6$ of PTM-VII may be unsubstituted ethyl. In any embodiment or aspect described herein, $R^6$ of PTM-VII is an unsubstituted methyl. In any embodiment or aspect described herein, $R^6$ of PTM-VII is independently hydrogen, halogen, —$CF_3$, —CN, —OH, —$NH_2$, —COOH, —$CONH_2$, —$NO_2$, —SH, —$NHNH_2$, —$OCF_3$, —$OCHF_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. In embodiments, $R^6$ of PTM-VII is independently halogen, —$CF_3$, —CN, —OH, —$NH_2$, —COOH, —$CONH_2$, —$NO_2$, —SH, —$NHNH_2$, —$OCF_3$, —$OCHF_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. In any embodiment or aspect described herein, $R^5$ and $R^6$ of PTM-VII are independently hydrogen. In any embodiment or aspect described herein, $R^6$ of PTM-VII is hydrogen. In any embodiment or aspect described herein, $R^6$ of PTM-VII is not hydrogen.

Each $R^{35}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCHF_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

Each $R^{36}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

In any embodiment or aspect described herein, $R^7$ of PTM-VII is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

$R^{38}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl. $R^{38}$ may independently be —OH. $R^{38}$ may independently be unsubstituted methyl. $R^{38}$ may independently be $R^{39}$-substituted or unsubstituted heteroalkyl. $R^{38}$ may independently be $R^{39}$-substituted or unsubstituted alkyl. $R^{38}$ may independently be $R^{39}$-substituted or unsubstituted $C_1$-$C_4$ alkyl.

$R^{39}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

In embodiments, $R^8$ of PTM-VII is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{41}$-substituted or unsubstituted alkyl, $R_{41}$-substituted or unsubstituted heteroalkyl, $R^{41}$-substituted or unsubstituted cycloalkyl, $R_{41}$-substituted or unsubstituted heterocycloalkyl, $R^{41}$-substituted or unsubstituted aryl, or $R^{41}$-substituted or unsubstituted heteroaryl.

$R^{41}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl.

$R^{42}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, —$S(O)_2CHCH_2$, —$NHS(O)_2CHCH_2$, $R^{43}$-substituted or unsubstituted alkyl, $R^{43}$-substituted or unsubstituted heteroalkyl, $R^{43}$-substituted or unsubstituted cycloalkyl, $R^{43}$-substituted or unsubstituted heterocycloalkyl, $R^{43}$-substituted or unsubstituted aryl, or $R^{43}$-substituted or unsubstituted heteroaryl.

In embodiments, $R^7$ and $R^8$ of PTM-VII are joined together to form: a substituted or unsubstituted heterocycloalkyl or substituted or unsubstituted heteroaryl; a substituted or unsubstituted heterocycloalkyl; a substituted or unsubstituted 3 to 8 membered heterocycloalkyl; a substituted 3 to 8 membered heterocycloalkyl; a substituted or unsubstituted 5 to 7 membered heterocycloalkyl; a substituted 5 to 7 membered heterocycloalkyl; an $R^{38}$-substituted 5 to 7 membered heterocycloalkyl, wherein $R^{38}$ is as described herein above; an $R^{38}$-substituted 5 to 7 membered heterocycloalkyl, wherein $R^{38}$ is independently a substituted or unsubstituted alkyl or substituted or unsubstituted heteroalkyl; an $R^{38}$-substituted 5 to 7 membered heterocycloalkyl, wherein $R^{38}$ is independently a substituted or unsubstituted $C_1$-$C_8$ alkyl or substituted or unsubstituted 2 to 8 membered heteroalkyl; a substituted or unsubstituted pyrrolidinyl; or a substituted or unsubstituted piperazinyl.

In embodiments, $R^9$ of PTM-VII is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{44}$-substituted or unsubstituted alkyl, $R^{44}$-substituted or unsubstituted heteroalkyl, $R^{44}$-substituted or unsubstituted cycloalkyl, $R^{44}$-substituted or unsubstituted heterocycloalkyl, $R^{44}$-substituted or unsubstituted aryl, or $R^{44}$-substituted or unsubstituted heteroaryl.

$R^{44}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{45}$-substituted or unsubstituted alkyl, $R^{45}$-substituted or unsubstituted heteroalkyl, $R^{45}$-substituted or unsubstituted cycloalkyl, $R^{45}$-substituted or unsubstituted heterocycloalkyl, $R^{45}$-substituted or unsubstituted aryl, or $R^{45}$-substituted or unsubstituted heteroaryl.

$R^{45}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, $R^{46}$-substituted or unsubstituted alkyl, $R^{46}$-substituted or unsubstituted heteroalkyl, $R^{46}$-substituted or unsubstituted cycloalkyl, $R^{46}$-substituted or unsubstituted heterocycloalkyl, $R^{46}$-substituted or unsubstituted aryl, or $R^{46}$-substituted or unsubstituted heteroaryl.

Each $R^{22}$, $R^{25}$, $R^{28}$, $R^{31}$, $R^{34}$, $R^{37}$, $R^{40}$, $R^{43}$, $R^{46}$, and $R^{49}$ of PTM-VII is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, or unsubstituted heteroaryl.
In certain embodiments, the PTM of PTM-VII is selected from the group consisting of:
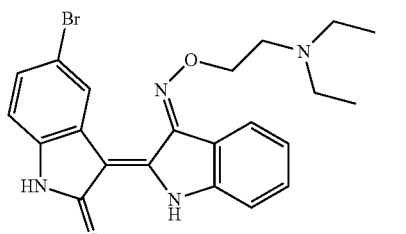,
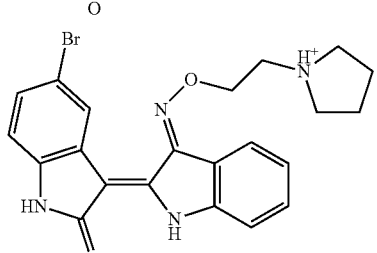,
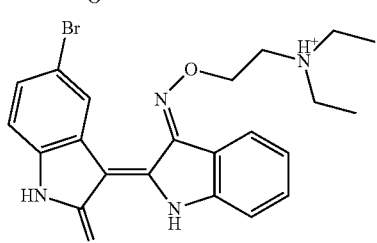,
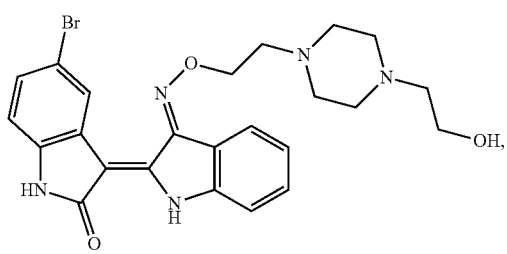,
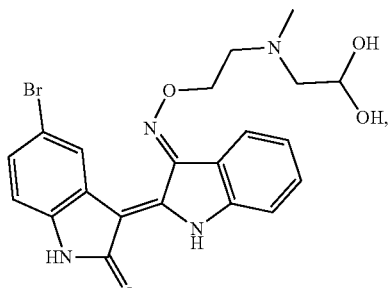,
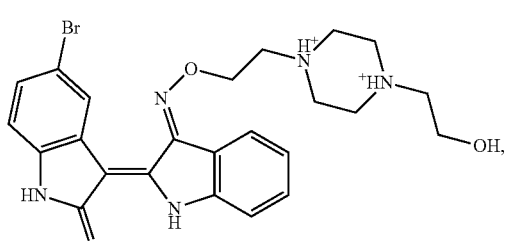,
-continued
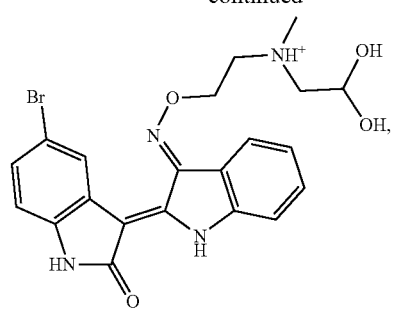,
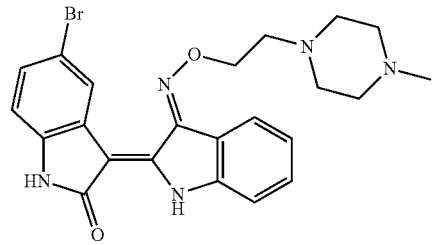,
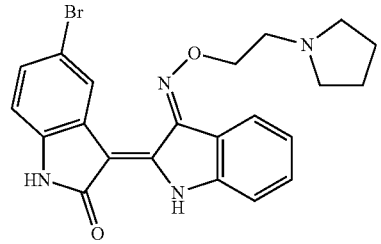,
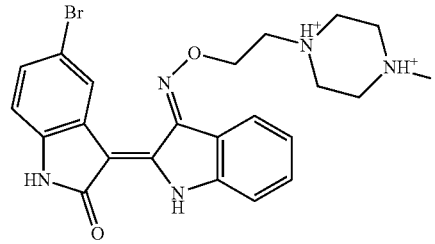,
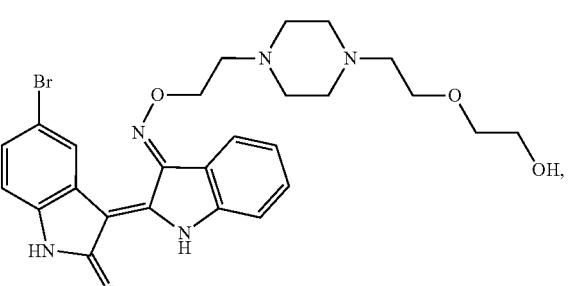,
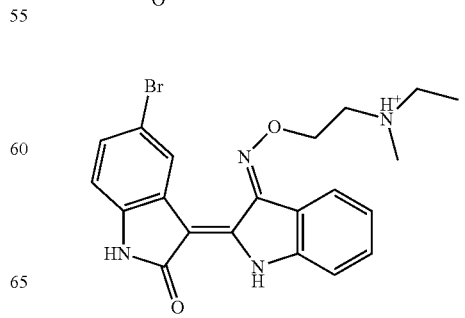, 509
-continued
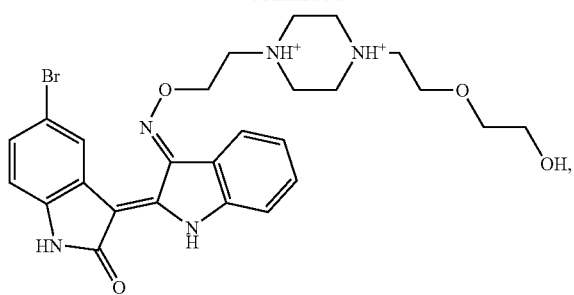
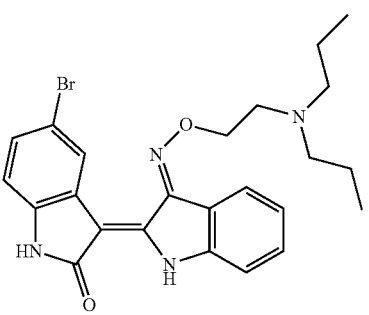
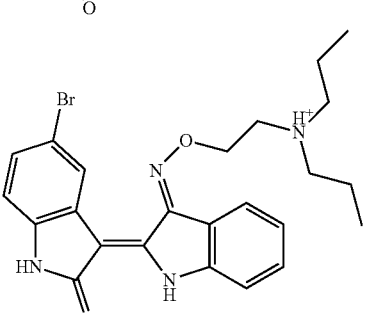
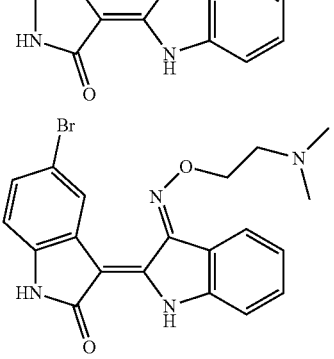
510
-continued
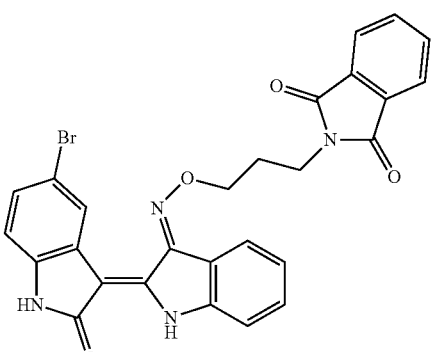
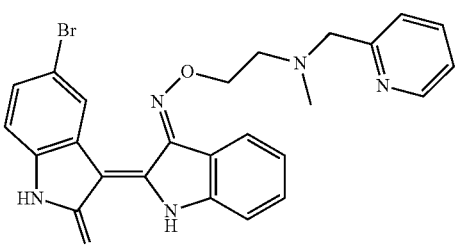
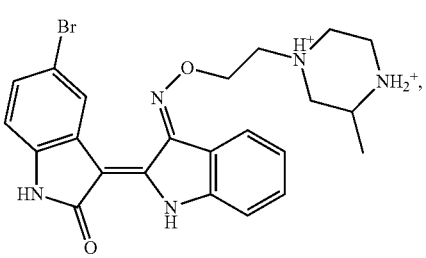
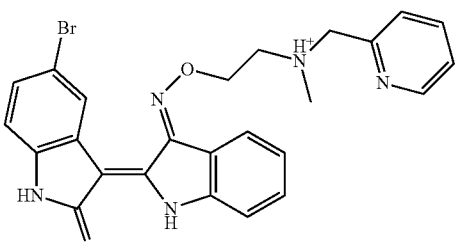
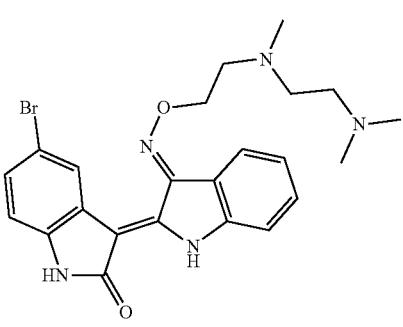

511
-continued
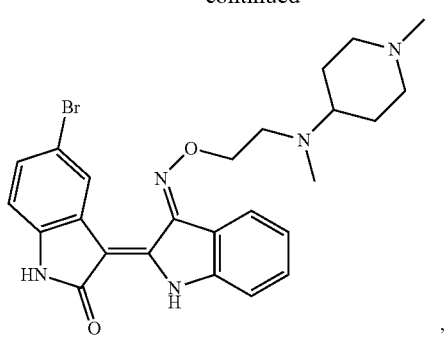
,
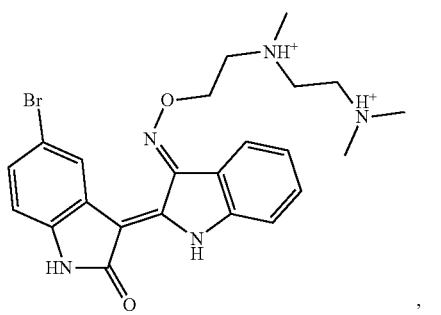
,
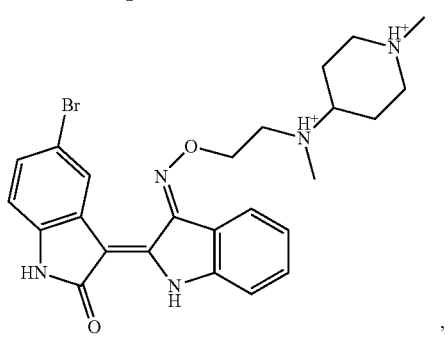
,
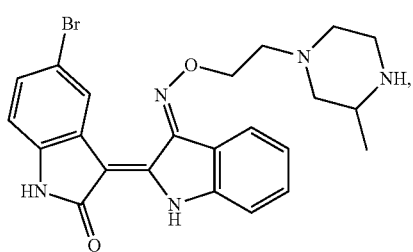
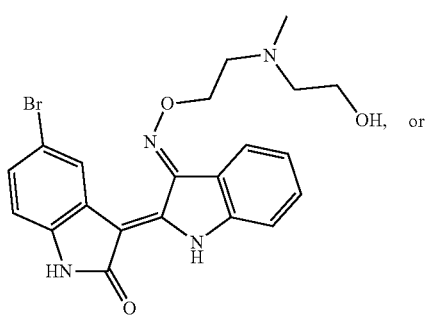
OH, or
512
-continued
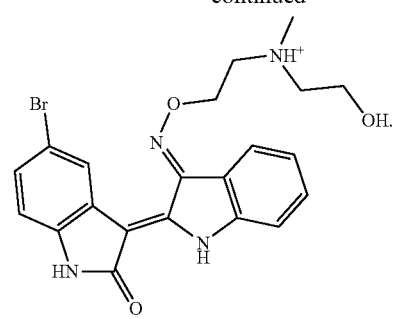
.
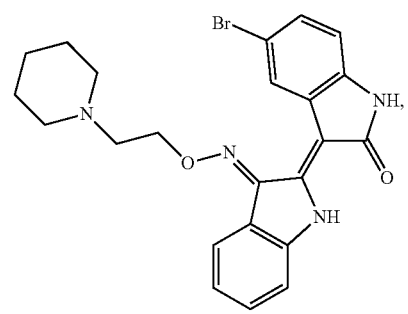
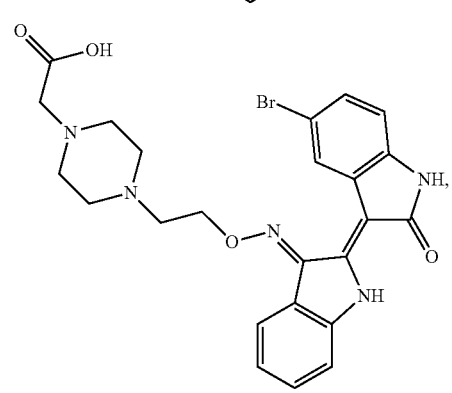
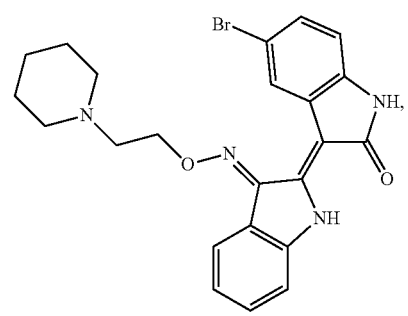
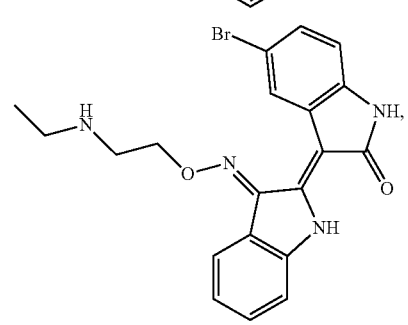

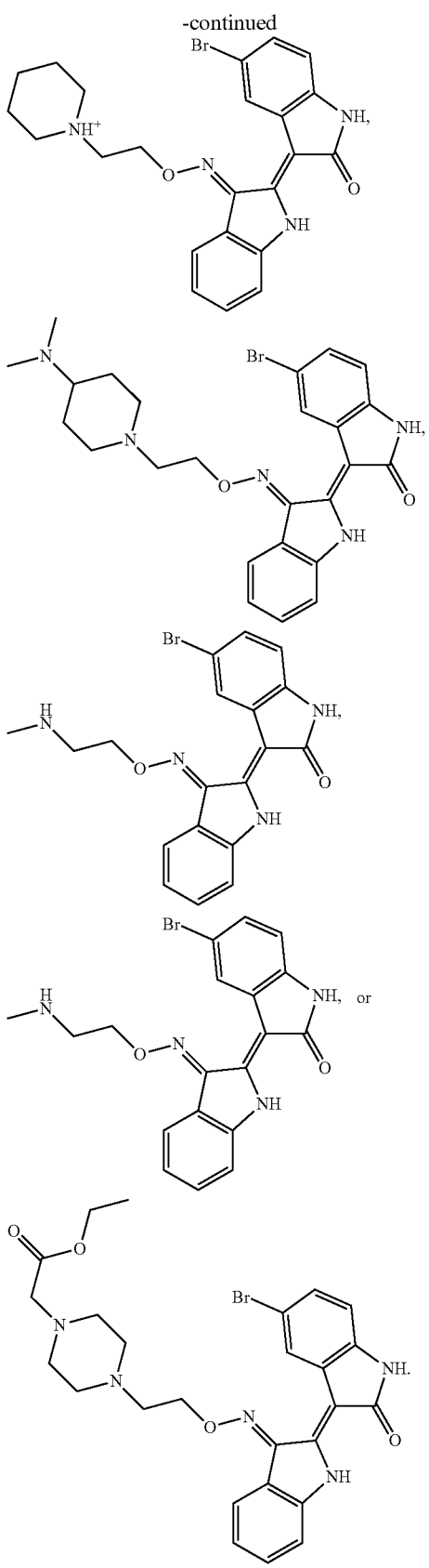

U.S. Patent Application Publication No. 2015/0045339 A1, which is incorporated herein in its entirety for all purposes):

PTM-VIII wherein:

$R^1$ of PTM-VIII is a hydrogen atom or a substituted or unsubstituted $C_{1-6}$ alkyl group;

$R^2$ of PTM-VIII is a hydrogen atom, a substituted or unsubstituted $C_{1-6}$ alkyl group, a substituted or unsubstituted $C_{2-6}$ alkenyl group, or a substituted or unsubstituted $C_{2-6}$ alkynyl group;

$R^3$ of PTM-VIII is a hydrogen atom, a substituted or unsubstituted $C_{1-6}$ alkyl group, a substituted or unsubstituted $C_{2-6}$ alkenyl group, or a substituted or unsubstituted $C_{2-6}$ alkynyl group;

or $R^2$ and $R^3$ of PTM-VIII may bind together to form an atomic bond;

$R^4$ of PTM-VIII is a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, or an imino protecting group;

m of $R^5$ of PTM-VIII are the same or different, and is a hydrogen atom or a substituted or unsubstituted $C_{1-6}$ alkyl group;

m of $R^6$ of PTM-VIII are the same or different, and is a hydrogen atom or a substituted or unsubstituted $C_{1-6}$ alkyl group;

or $R^5$ and $R^6$ of PTM-VIII binding to the same carbon atom may bind together to form: a substituted or unsubstituted $C_{2-6}$ alkylene group; an substituted or unsubstituted O-($C_{1-6}$ alkylene) group, a substitute or unsubstituted N($R^{13}$)—($C_{1-6}$ alkylene) group, wherein $R^{13}$ is a hydrogen atom, a substituted or unsubstituted $C_{1-6}$ alkyl group or an imino protecting group; a substituted or unsubstituted ($C_{1-3}$ alkylene)-O—($C_{1-3}$ alkylene) group; a substitute or unsubstituted ($C_{1-3}$ alkylene)-N($R^{13}$)—($C_{1-3}$ alkylene) group, wherein $R^{13}$ is a hydrogen atom, a substituted or unsubstituted $C_{1-6}$ alkyl group or an imino protecting group;

n of $R^7$ of PTM-VIII are the same or different, and is a hydrogen atom or a substitute or unsubstituted $C_{1-6}$ alkyl group;

n of $R^8$ of PTM-VIII are the same or different, and is a hydrogen atom or a substitute or unsubstituted $C_{1-6}$ alkyl group;

or $R^7$ and $R^8$ of PTM-VIII binding to the same carbon atom may bind together to form: a substituted or unsubstituted $C_{2-6}$ alkylene group; an substituted or unsubstituted O—($C_{1-6}$ alkylene) group; a substituted or unsubstituted N($R^{14}$)—($C_{1-6}$ alkylene) group, wherein $R^{14}$ is a hydrogen atom, a substituted or unsubstituted $C_{1-6}$ alkyl group, or an imino protecting group; a substituted or unsubstituted ($C_{1-3}$ alkylene)-O—($C_{1-3}$ alkylene) group; or a substituted or unsubstituted ($C_{1-3}$ alkylene)-N($R^{14}$)—($C_{1-3}$ alkylene) group which may be substituted, wherein $R^{14}$ is a hydrogen atom, a substituted or unsubstituted $C_{1-6}$ alkyl group, or an imino protecting group;

In an embodiment, the PTM is represented by Formula PTM-VIII (which correspond to General Formula 1 from $R^9$ of PTM-VIII is: a substituted or unsubstituted $C_{1-6}$ alkyl group; a substituted or unsubstituted $C_{3-8}$ cycloalkyl; a substituted or unsubstituted aryl group; a substituted or unsubstituted $C_{1-6}$ alkoxy group; a substituted or unsubstituted heterocyclic group; $N(R15)(R16)$ wherein $R^{15}$ is a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, or a substituted or unsubstituted $C_{3-8}$ cycloalkyl group, and $R^{16}$ is a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, a substituted or unsubstituted aryl group, or a substituted or unsubstituted heterocyclic group, or $R^{15}$ and $R^{16}$ may form a substituted or unsubstituted cyclic amino group together with the nitrogen atom to which they bind;

$R^{10}$ of PTM-VIII is a hydrogen atom, a halogen atom, a substituted or unsubstituted $C_{1-6}$ alkyl group, a substituted or unsubstituted $C_{3-8}$ cycloalkyl group, a substituted or unsubstituted aryl group, a substituted or unsubstituted $C_{1-6}$ alkoxy group, or a substituted or unsubstituted heterocyclic group;

$R^{11}$ of PTM-VIII is a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, or a substituted or unsubstituted $C_{3-8}$ cycloalkyl group;

$R^{12}$ of PTM-VIII is a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, a substituted or unsubstituted aryl group, a substituted or unsubstituted heterocyclic group, or a substituted or unsubstituted carbamoyl group;

$X^1$ of PTM-VIII represents a group represented by $-X^4-X^5-$, wherein $X^4$ is a substituted or unsubstituted divalent alicyclic hydrocarbon, a substituted or unsubstituted divalent aromatic hydrocarbon group, a substituted or unsubstituted divalent heterocyclic group, or a group represented by

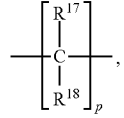

wherein p of $R^{17}$ are the same or different, and is a hydrogen atom or a substituted or unsubstituted $C_{1-6}$ alkyl group, or one $R^{17}$ selected from p of $R^{17}$ may bind with $R^4$ to form: a substituted or unsubstituted $C_{1-6}$ alkylene group: a substituted or unsubstituted $(C_{1-3}$ alkylene)-O group: a substituted or unsubstituted $(C_{1-3}$ alkylene)-N$(R^{19})$ group, wherein $R^{19}$ is a hydrogen atom, substituted or unsubstituted a $C_{1-6}$ alkyl group, or an imino protecting group; a substituted or unsubstituted $(C_{1-3}$ alkylene)-O—$(C_{1-3}$ alkylene) group; a substituted or unsubstituted $(C_{1-3}$ alkylene)-N$(R^{19})$—$(C_{1-3}$ alkylene) group, wherein $R^{19}$ is a hydrogen atom, substituted or unsubstituted a $C_{1-6}$ alkyl group, or an imino protecting group; p of $R^{18}$ are the same or different, and is a hydrogen atom or a substituted or unsubstituted $C_{1-6}$ alkyl group; or $R^{17}$ and $R^{18}$ binding to the same carbon atom may bind together to form: a substituted or unsubstituted $C_{2-6}$ alkylene group, a substituted or unsubstituted O—$(C_{1-6}$ alkylene); a substituted or unsubstituted N$(R^{20})$—$(C_{1-6}$ alkylene) group, wherein $R^{20}$ is a hydrogen atom; a substituted or unsubstituted $C_{1-6}$ alkyl group or an imino protecting group; a substituted or unsubstituted $(C_{1-3}$ alkylene)-O—$(C_{1-3}$ alkylene) group; a substituted or unsubstituted $(C_{1-3}$ alkylene)-N$(R^{20})$—$(C_{1-3}$ alkylene), wherein $R^{20}$ is a hydrogen atom; a substituted or unsubstituted $C_{1-6}$ alkyl group or an imino protecting group; and p represents an integer of 1 to 6; or an atomic bond; and $X^5$ is an oxygen atom, N$(R^{21})$ wherein $R^{21}$ is a hydrogen atom, a substituted or unsubstituted $C_{1-6}$ alkyl group, a substituted or unsubstituted $C_{2-6}$ alkenyl group, a substituted or unsubstitute $C_{2-6}$ alkynyl group or an imino protecting group, or $R^{21}$ may bind with $R^4$ to form a substitute or unsubstituted $C_{1-6}$ alkylene group; C(=O); C(=O)—N$(R^{21})$ wherein $R^{21}$ is a hydrogen atom, a substituted or unsubstituted $C_{1-6}$ alkyl group, a substituted or unsubstituted $C_{2-6}$ alkenyl group, a substituted or unsubstitute $C_{2-6}$ alkynyl group or an imino protecting group; or an atomic bond;

$X^2$ of PTM-VIII is a bond, a substituted or unsubstituted $C_{1-6}$ alkyl group, a substituted or unsubstituted $C_{1-6}$ alkylene group, a substituted or unsubstituted divalent alicyclic hydrocarbon group, a substituted or unsubstituted divalent aromatic hydrocarbon, or a substituted or unsubstituted divalent heterocyclic group;

$X^3$ of PTM-VIII is a substituted or unsubstituted $C_{1-6}$ alkylene group, a substituted or unsubstituted $C_{2-6}$ alkenylene group, a substituted or unsubstituted $C_{2-6}$ alkynylene group, a substituted or unsubstituted O—$(C_{1-6}$ alkylene) group, a substituted or unsubstituted $S(O)_q$—$(C_{1-6}$ alkylene) group wherein q represents 0, 1 or 2; a substituted or unsubstituted N$(R^{22})$—$(C_{1-6}$ alkylene) group wherein $R^{22}$ is a hydrogen atom, a substituted or unsubstitute $C_{1-6}$ alkyl group, a substituted or unsubstituted $C_{2-6}$ alkenyl group, a substitute or unsubstituted $C_{2-6}$ alkynyl group or an imino protecting group; N$(R^{22})$—C(=O) wherein $R^{22}$ is a hydrogen atom, a substituted or unsubstitute $C_{1-6}$ alkyl group, a substituted or unsubstituted $C_{2-6}$ alkenyl group, a substitute or unsubstituted $C_{2-6}$ alkynyl group or an imino protecting group; or an atomic bond;

$Z^1$ of PTM-VIII is a nitrogen atom or C$(R^{23})$ wherein $R^{23}$ is a hydrogen atom, a halogen atom, a substituted or unsubstituted $C_{1-6}$ alkyl group, a substituted or unsubstituted $C_{3-8}$ cycloalkyl group, a substituted or unsubstituted aryl group, a substituted or unsubstituted $C_{1-6}$ alkoxy group or substituted or unsubstituted a heterocyclic group;

m of PTM-VIII is an integer of 0, 1, 2, 3, 4, 5, or 6;

n of PTM-VIII is an integer of 0, 1, 2, 3, 4, 5, or 6); and the PTM-VIII is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM-VIII is covalently joined to a ULM, a chemical linker group (L), a CLM, an ILM, a VLM, MLM, a ULM', a CLM', a ILM', a VLM', a MLM', or combination thereof via an R group (e.g., $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, or $R^{23}$).

In any embodiment or aspect described herein, $Z^1$ of PTM-VIII is nitrogen atom.

In any embodiment or aspect described herein, $X^3$ of PTM-VIII is s a substitute or unsubstituted $C_{2-6}$ alkynylene group or N$(R^{22})$—C(=O), wherein $R^{22}$ is a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group or an imino protecting group.

In any aspect or embodiment described herein, $X^3$ of PTM-VIII ethynylene group.

In any embodiment or aspect described herein, R' of PTM-VIII is a hydrogen atom, and $R^2$ is a substitute or unsubstituted $C_{1-6}$ alkyl group.

In any embodiment or aspect described herein, R' PTM-VIII is a hydrogen atom, and $R^2$ is a $C_{1-6}$ alkyl group substituted with a di($C_{1-6}$alkyl)amino group.

In any embodiment or aspect described herein, $R^9$ of PTM-VIII is $N(R^{15})(R^{16})$ therein $R^{15}$ is a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group or a substituted or unsubstituted $C_{3-8}$ cycloalkyl group, and $R^{16}$ is a substituted or unsubstituted $C_{1-6}$ alkyl group, a substituted or unsubstituted. $C_{2-6}$ alkenyl group, a substituted or unsubstituted $C_{2-6}$ alkynyl group, a substituted or unsubstituted $C_{3-8}$ cycloalkyl group, a substituted or unsubstituted aryl group or a substituted or unsubstituted heterocyclic group, or $R^{15}$ and $R^{16}$ may form a substitute or unsubstitute cyclic amino group together with the nitrogen atom to which they bind.

In any embodiment or aspect described herein, $R^{15}$ of PTM-VIII is a hydrogen atom, and $R^{16}$ is a substituted or unsubstituted $C_{1-6}$ alkyl group.

In any embodiment or aspect described herein, $R^{11}$ of PTM-VIII is a hydrogen atom, and $R^{12}$ is a substituted or unsubstituted aryl group or a substituted or unsubstituted heterocyclic group.

In any embodiment or aspect described herein, $R^{11}$ of PTM-VIII is a hydrogen atom, and $R^{12}$ is substituted or unsubstituted phenyl group, a substituted or unsubstituted pyridyl group, a substituted or unsubstituted pyrazolyl group, substituted or unsubstituted thienyl group, a substituted or unsubstituted oxazolyl group, a substituted or unsubstituted thiazolyl group, a substituted or unsubstituted isothiazolyl group, a substituted or unsubstituted indazolyl group, a substituted or unsubstituted pyrazolopyridinyl group, a substituted or unsubstituted quinolyl group, a substituted or unsubstituted isoquinolyl group, a substituted or unsubstituted cinnolinyl group, a substituted or unsubstituted phthalazinyl group, a substituted or unsubstituted quinoxalinyl group, a substituted or unsubstituted benzofuranyl group or a substituted or unsubstituted benzothiazolyl group.

In any aspect or embodiment described herein, $R^4$ of PTM-VIII is a hydrogen atom or a substituted or unsubstituted $C_{1-6}$ alkyl group.

In any aspect or embodiment described herein, $R^4$ of PTM-VIII is a hydrogen atom or methyl group.

In any aspect or embodiment described herein, $X^2$ of PTM-VIII is a substituted or unsubstituted $C_{1-6}$ alkylene group or a substituted or unsubstituted divalent alicyclic hydrocarbon group.

In any aspect or embodiment described herein, $X^2$ of PTM-VIII is a group represented by —$X^4$—$X^5$—, wherein $X^4$ is a group represented by

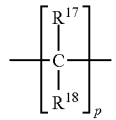

and p of $R^{17}$ are the same or different and is a hydrogen atom or a substituted or unsubstituted $C_{1-6}$ alkyl group, p of $R^{18}$ are the same or different and is a hydrogen atom or a substituted or unsubstituted $C_{1-6}$ alkyl group, and p is an integer of 1, 2, 3, 4, 5, or 6, and $X^5$ is C(=O)—N($R^{21}$) wherein $R^{21}$ is a hydrogen atom.

In any aspect or embodiment described herein, $R^3$ of PTM-VIII is a hydrogen atom or a substituted or unsubstituted $C_{1-6}$ alkyl group.

In any embodiment or aspect described herein, at east one of $R^3$, $R^6$, $R^7$ and $R^8$ of PTM-VIII is a hydrogen atom.

In any aspect or embodiment described herein, $R^{10}$ of PTM-VIII is a hydrogen atom.

In any aspect or embodiment described herein, the PTM of PTM-VIII is selected from the group consisting of: (S,E)-N-(3-(2-(4-(Dimethylamino)-N-methyl-2-butenamido)propanamido)phenyl)-4-(propylamino)-2-((2-(pyridin-4-yl)ethyl)amino)pyrimidine-5-carboxamide [PTM-VIII-1]; (S,E)-2-((4-Carbamoylphenyl)amino)-N-(3-(2-(4-(dimethylamino)-N-methyl-2-butenamido)propanamido) phenyl)-4-(propylamino)pyrimidine-5-carboxamide [PTM-VIII-2]; (E)-2-((4-Carbamoylphenyl)amino)-N-(3-(2-(4-(dimethylamino)-N-methyl-2-butenamido)actamido) cyclohexyl)-4-(propylamino)pyrimidine-5-carboxamide [PTM-VIII-3]; (S,E)-2-((4-Carbamoylphenyl)amino)-N-(3-(2-(4-(diethylamino)-N-methyl-2-butenamido)propanamido)phenyl)-4-(propylamino)pyrimidine-5-carboxamide [PTM-VIII-4]; (S,E)-2-((4-Carbamoylphenyl)amino)-N-(3-(2-(4-(dimethylamino)-N-methyl-2-butenamido)propaneamido)propyl)-4-(propylamino)pyrimidine-5-carboxamide [PTM-VIII-5]; (S,E)-N-(3-(2-(4-(Dimethylamino)-N-methyl-2-butenamido)propanamido)phenyl)-2-(isoquinolin-6-ylamino)-4-(propylamino)pyrimidine-5-carboxamide [PTM-VIII-6]; (S,E)-2-(Cinnolin-6-ylamino)-N-(3-(2-(4-(dimethylamino)-N-methyl-2-butenamido)propanamido) phenyl)-4-(propylamino)pyrimidine-5-carboxamide [PTM-VIII-7]; (S,E)-4-(Dimethylamino)-N-(1-((5-(2-((3-fluorophenyl)amino)-4-(propylamino)pyrimidin-5-yl)-4-pentyn-1-yl)amino)-1-oxopropan-2-yl)-N-methyl-2-butenamide [PTM-VIII-8]; (S,E)-N-(1-((5-(2-((3-Cyanophenyl)amino)-4-(propylamino)pyrimidin-5-yl)-4-pentyn-1-yl)amino)-1-oxopropan-2-yl)-4-(dimethylamino)-N-methyl-2-butenamide [PTM-VIII-9]; (S,E)-4-((5-(5-(2-(4-(Dimethylamino)-N-methyl-2-butenamido) propaneamido)-1-pentyn-1-yl)-4-(propylamino)pyrimidin-2-yl)amino)benzamide IPTM-VIII-101; (S,E)-N-(1-((5-(2-((4-Cyanophenyl)amino)-4-(propylamino)pyrimidin-5-yl)-4-pentyn-1-yl)amino)-1-oxopropan-2-yl)-4-(dimethylamino)-N-methyl-2-butenamide [PTM-VIII-11]; (E)-4-(Dimethylamino)-N-(2-((5-(2-((4-fluorophenyl) amino)-4-(propylamino)pyrimidin-5-yl)-4-pentyn-1-yl) amino)-2-oxoethyl)-N-methyl-2-butenamide [PTM-VIII-12]; (E)-N-(2-((5-(2-((4-Cyanophenyl)amino)-4-(propylamino)pyrimidin-5-yl)-4-pentyn-1-yl)amino)-2-oxoethyl)-4-(dimethylamino)-N-methyl-2-butenamide [PTM-VIII-13]; (S,E)-4-(Dimethylamino)-N-(1-((5-(2-(3-fluorophenyl)amino)-4-(propylamino)pyrimidin-5-yl)-4-pentyn-1-yl)amino)-1-oxobutan-2-yl)-N-methyl-2-butenamide [PTM-VIII-14]; (S,E)-4-(Dimethylamino)-N-(1-((5-(2-((3-fluoro-4-methoxyphenyl)amino)-4-(propylamino) pyrimidin-5-yl)-4-pentyn-1-yl)amino)-1-oxopropan-2-yl)-N-methyl-2-butenamide [PTM-VIII-15]; (S,E)-4-(Dimethylamino)-N-(1-((5-(2-((6-fluoropyridin-3-yl) amino)-4-(propylamino)pyrimidin-5-yl)-4-pentyn-1-yl) amino)-1-oxopropan-2-yl)-N-methyl-2-butenamide [PTM-VIII-16]; (S,E)-4-(Dimethylamino)-N-(1-((5-(2-((6-fluoropyridin-3-yl)amino)-4-(4-methoxyphenyl)amino) pyrimidin-5-yl)-4-pentyn-1-yl)amino)-1-oxopropan-2-yl)-N-methyl-2-butenamide [PTM-VIII-17]; (E)-4-(Dimethylamino)-N-(2-((5-(2-((3-fluorophenyl)amino)-4-(propylamino)pyrimidin-5-yl)-4-pentyn-1-yl)amino)-2- oxoethyl)-N-methyl-2-butenamide [PTM-VIII-18]; (S,E)-N-(5-(2-((4-Cyanophenyl)amino)-4-(propylamino)pyrimidin-5-yl)-4-pentyn-1-yl)-1-(4-(dimethylamino)-2-butenoyl)pyrrolidine-2-carboxamide [PTM-VHII-19]; (S,E)-N-(1-((5-(4-(Cyclopropylamino)-2-((3-fluoro-4-methoxyphenyl)amino)pyrimidin-5-yl)-4-pentyn-1-yl)amino)-1-oxopropan-2-yl)-4-(dimethylamino)-N-methyl-2-butenamide [PTM-VIII-20]; (S,E)-4-(Dimethylamino)-N-(1-((5-(2-((3-fluoro-4-methoxyphenyl)amino)-4-((3-fluoropropyl)amino)pyrimidin-5-yl)-4-pentyn-1-yl)amino)-1-oxopropan-2-yl)-N-methyl-2-butenamide [PTM-V 11-21]; (S,E)-N-(1-((5-(2-((4-Cyanophenyl)amino)-4-(propylamino)pyrimidin-5-yl)-4-pentyn-1-yl)amino)-3-hydroxy-1-oxopropan-2-yl)-4-(dimethylamino)-N-methyl-2-butenamide [PTM-VIII-22]; (2S,4R)-1-(E)-4-(Dimethylamino)-2-butenoyl)-N-(5-(2-((3-fluorophenyl)amino)-4-(propylamino)pyrimidin-5-yl)-4-pentyn-1-yl)-4-hydroxypyrrolidine-2-carboxamide [PTM-VIII-23]; (2S,4S)-1-((E)-4-(Dimethylamino)-2-butenoyl)-4-fluoro-N-(5-(2-((3-fluorophenyl)amino)-4-(methylamino)pyrimidin-5-y)-4-pentyn-1-yl)pyrrolidine-2-carboxamide [PTM-VIII-24]; (2S,4S)-1-((E)-4-(Dimethylamino)-2-butenoyl)-N-(5-(2-((3-fluorophenyl)amino)-4-(methylamino)pyrimidin-5-yl)-4-pentyn-1-yl)-4-methoxypyrrolidine-2-carboxamide [PTM-VIII-25]; (2S,4S)-1-((E)-4-(Dimethylamino)-2-butenoyl)-4-fluoro-N-(5-(2-((4-fluorophenyl)amino)-4-(methylamino)pyrimidin-5-yl)-4-pentyn-1-yl)pyrrolidine-2-carboxamide [PTM-VIII-26]; (2S,4R)-1-((E)-4-(Dimethylamino)-2-butenoyl)-4-fluoro-N-(5-(2-((4-fluorophenyl)amino)-4-(methylamino)pyrimidin-5-yl)-4-pentyn-1-yl)pyrrolidine-2-carboxamide [PTM-VIII-27]; (2S,4S)-1-((E)-4-(Dimethylamino)-2-butenoyl)-N-(5-(2-(4-fluorophenyl)amino)-4-(methylamino)pyrimidin-5-yl)-4-pentyn-1-yl)-4-methoxypyrrolidine-2-carboxamide [PTM-VIII-28]; (2S,4R)-1-((E)-4-(Dimethylamino)-2-butenoyl)-N-(5-(2-((4-fluorophenyl)amino)-4-(methylamino)pyrimidin-5-yl)-4-pentyn-1-yl)-4-methoxypyrrolidine-2-carboxamide [PTM-VIII-29]; (S,E)-1-(4-(Dimethylamino)-2-butenoyl)-N-(5-(2-((4-fluorophenyl)amino)-4-(methylamino)pyrimidin-5-yl)-4-pentyn-1-yl)azetidine-2-carboxamide [PTM-VIII-30]; (2S,4S)—N-(5-(2-((4-Cyanophenyl)amino)-4-(methylamino)pyrimidin-5-yl)-4-pentyn-1-yl)-1-((E)-4-(dimethylamino)-2-butenoyl)-4-fluoropyrrolidine-2-carboxamide [PTM-VIII-31]; (E)-N-(2-((5-(2-((4-Cyanophenyl)amino)-4-(methylamino)pyrimidin-5-yl)-4-pentyn-1-yl)amino)-2-oxoethyl)-4-(dimethylamino)-N-methyl-2-butenamide [PTM-VIII-32]; (S,E)-4-(Dimethylamino)-N-(1-((3-((2-((3-fluorophenyl)amino)-4-(propylamino)pyrimidin-5-yl)ethynyl)phenyl)amino)-1-oxopropan-2-yl)-N-methyl-2-butenamide [PTM-VIII-33]; (S,E)-4-((5-((3-(2-(4-(Dimethylamino)-N-methyl-2-butenamido)propanamido)phenyl)ethynyl)-4-(propylamino)pyrimidin-2-yl)amino)benzamide [PTM-VIII-34]; (S,E)-N-(1-((5-(2-((4-Cyanophenyl)amino)-4-(pyrrolidin-1-yl)pyrimidin-5-yl)-4-pentyn-1-yl)amino)-1-oxopropan-2-yl)-4-(dimethylamino)-N-methyl-2-butenamide [PTM-VIII-35]J; (S,E)-4-(Dimethylamino)-N-(1-((5-(2-((2-fluoropyridin-4-yl)amino)-4-(pyrrolidin-1-yl)pyrimidin-5-yl)-4-pentyn-1-yl)amino)-1-oxopropan-2-yl)-N-methyl-2-butenamide [PTM-VIII-36]; (S,E)-4-(Dimethylamino)-N-(1-((5-(2-((2-fluoropyridin-4-yl)amino)-4-(propylamino)pyrimidin-5-yl)-4-pentyn-1-yl)amino)-1-oxopropan-2-yl)-N-methyl-2-butenamide [PTM-VIII-37]; (S,E)-N-(1-((5-(4-(Cyclopropylamino)-2-((2-fluoropyridin-4-yl)amino)pyrimidin-5-yl)-4-pentyn-1-yl)amino)-1-oxopropan-2-yl)-4-(dimethylamino)-N-methyl-2-butenamide [PTM-VIII-38]; (S,E)-4-(Dimethylamino)-N-methyl-N-(1-((5-(2-((3-methylisothiazol-5-yl)amino)-4-(propylamino)pyrimidin-5-yl)-4-pentyn-1-yl)amino)-1-oxopropan-2-yl)-2-butenamide [PTM-VIII-39]; (S,E)-4-(Dimethylamino)-N-(1-((5-(4-(3-methoxypropyl)amino)-2-((2-methoxypyridin-4-yl)amino)pyrimidin-5-yl)-4-pentyn-1-yl)amino)-1-oxopropan-2-yl)-N-methyl-2-butenamide [PTM-VIII-40]; (S,E)-1-(4-(Dimethylamino)-2-butenoyl)-N-(5-(4-((3-methoxypropyl)amino)-2-((methoxypyridin-4-yl)amino)pyrimidin-5-yl)-4-pentyn-1-yl)pyrrolidine-2-carboxamide [PTM-VIII-41]; (2S,4S)-1-((E)-4-(Dimethylamino)-2-butenoyl)-4-fluoro-N-(5-(4-((3-methoxypropyl)amino)-2-((methoxypyridin-4-yl)amino)pyrimidin-5-yl)-4-pentyn-1-yl)pyrrolidine-2-carboxamide [PTM-VIII-42]; (S,E)-1-(4-(Dimethylamino)-2-butenoyl)-N-(5-(2-((2-methoxypyridin-4-yl)amino)-4-(propylamino)pyrimidin-5-yl)-4-pentyn-1-yl)pyrrolidine-2-carboxamide [PTM-VIII-43]; (2S,4S)-1-((E)-4-(Dimethylamino)-2-butenoyl)-4-fluoro-N-(5-(2-((2-methoxypyridin-4-yl)amino)-4-(propylamino)pyrimidin-5-yl)-4-pentyn-1-yl)pyrrolidine-2-carboxamide [PTM-VIII-44]; (E)-4-(Dimethylamino)-N-(2-((5-(2-((2-methoxypyridin-4-y)amino)-4-(propylamino)pyrimidin-5-yl)-4-pentyn-1-yl)amino)-2-oxoethyl)-N-methyl-2-butenamide [PTM-VIII-45]; (S,E)-4-(Dimethylamino)-N-(1-((5-(2-((3-fluorophenyl)amino)-4-((4-methoxyphenyl)amino)pyrimidin-5-yl)-4-pentyn-1-yl)amino)-1-oxopropan-2-yl)-N-methyl-2-butenamide [PTM-VIII-46]; (S,E)-4-(Dimethylamino)-N-(1-((5-(2-((3-fluorophenyl)amino)-4-morpholinopyrimidin-5-yl)-4-pentyn-1l-yl)amino)-1-oxopropan-2-yl)-N-methyl-2-butenamide [PTM-VIII-47]; (E)-4-(Dimethylamino)-N-(2-((5-(2-((4-fluorophenyl)amino)-4-(3-fluoropropyl)amino)pyrimidin-5-yl)-4-pentyn-1-yl)amino)-2-oxoethyl)-N-methyl-2-butenamide [PTM-VIII-48]; (S,E)-N-(1-(5-(2-((4-Cyanophenyl)amino)-4-(cyclopropylamino)pyrimidin-5-yl)-4-pentyn-1-yl)amino)-1-oxopropan-2-yl)-4-(dimethylamino))-N-methyl-2-butenamide [PTM-VIII-49]; (S,E)-N-(1-((5-(2-((4-Cyanophenyl)amino)-4-((3-fluoropropyl)amino)pyrimidin-5-yl)-4-pentyn-1-yl)amino)-1-oxopropan-2-yl)-4-(dimethylamino))-N-methyl-2-butenamide [PTM-VIII-50]; (S,E)-4-(Dimethylamino))-N-(1-((5-(4-(ethylamino)-2-((1-methyl-1H-indazol-5-yl)amino)pyrimidin-5-yl)-4-pentyn-1-yl)amino)-1-oxopropan-2-yl)-N-methyl-2-butenamide [PTM-VIII-51]; (S,E)-N-(1-((5-(4-(Cyclopropylamino)-2-((1-methyl-1H-indazol-5-yl)amino)pyrimidin-5-yl)-4-pentyn-1-yl)amino)-1-oxopropan-2-yl)-4-(dimethylamino))-N-methyl-2-butenamide [PTM-VIII-52]; (S,E)-4-(Dimethylamino))-N-methyl-N-(1-((5-(2-((1-methyl-1H-indazol-5-yl)amino)-4-(methylamino)pyrimidin-5-yl)-4-pentyn-1-yl)amino)-1-oxopropan-2-yl)-2-butenamide [PTM-VIII-53]; (S,E)-N-(5-(2-((1H-Indazol-5-yl)amino)-4-(methylamino)pyrimidin-5-yl)-4-pentyn-1-yl)-1-(4-(dimethylamino)-2-butenoyl)pyrrolidine-2-carboxamide [PTM-VIII-54]; (S,E)-N-(5-(2-((1H-Indazol-5-yl)amino)-4-(ethylamino)pyrimidin-5-yl)-4-pentyn-1-yl)-1-(4-(dimethylamino)-2-butenoyl)pyrrolidine-2-carboxamide [PTM-VIII-55]; (S,E)-N-(5-(2-((1H-Indazol-5-yl)amino)-4-((3-methoxypropyl)amino)pyrimidin-5-yl)-4-pentyn-1-yl)-1-(4-(dimethylamino)-2-butenoyl)pyrrolidine-2-carboxamide [PTM-VIII-56]; (E)-4-(Dimethylamino)-N—((S)-1-(((1S,3R)-3-((2-((3-fluorophenyl)amino)-4-(propylamino)pyrimidin-5-yl)ethynyl)cyclohexyl)amino)-1-oxopropan-2-yl)-N-methyl-2-butenamide [PTM-VIII-57]; (E)-4-(Dimethylamino)-N—((S)-1-(((1S,3R)-3-((2-((3-fluorophenyl)amino)-4-(propylamino)pyrimidin-5-yl)ethynyl)cyclobutyl)amino)-1-oxopropan-2-yl)-N-methyl-2-butenamide [PTM-VIII-58]; (E)-N—((S)-1-(((1S,3R)-3-((2-((4-Cyanophenyl)amino)-4-(methylamino)pyrimidin-5-yl)

ethynyl)cyclobutyl)amino)-1-oxopropan-2-yl)-4-(dimethylamino)-N-methyl-2-butenamide [PTM-VIII-59]; (E)-4-(Dimethylamino)-N—((S)-1-(((1S,3R)-3-((2-((3-fluorophenyl)amino)-4-(methylamino)pyrimidin-5-yl)ethynyl)cyclobutyl)amino)-1-oxopropan-2-yl)-N-methyl-2-butenamide [PTM-VHII-60]; (E)-N—((S)-1-(((1S,3R)-3-((2-((4-Cyanophenyl)amino)-4-(methylamino)pyrimidin-5-yl)ethynyl)cyclobutyl)amino)-1-oxopropan-2-yl)-4-(dimethylamino)-N-methyl-2-butenamide [PTM-VIII-61]; (E)-N—(S)-1-(((1S,3R)-3-((2-((3-Cyanophenyl)amino)-4-(methylamino)pyrimidin-5-yl)ethynyl)cyclobutyl)amino)-1-oxopropan-2-yl)-4-(dimethylamino)-N-methyl-2-butenamide [PTM-VIII-62]; (E)-4-(Dimethylamino)-N—(S)-1-(((1S,3R)-3-((2-((3-fluoro-4-methoxyphenyl)amino)-4-(methylamino)pyrimidin-5-yl)ethynyl)cyclobutyl)amino)-1-oxopropan-2-yl)-N-methyl-2-butenamide [PTM-VIII-63]; (E)-4-(Dimethylamino)-N—((S)-1-(((1S,3R)-3-((2-((4-fluorophenyl)amino)-4-(methylamino)pyrimidin-5-yl)ethynyl)cyclobutyl)amino)-1-oxopropan-2-yl)-N-methyl-2-butenamide [PTM-VIII-64]; (E)-N—((S)-1-(((1S,3R)-3-((2-((3-Cyanophenyl)amino)-4-(cyclopropylamino)pyrimidin-5-yl)ethynyl)cyclobutyl)amino)-1-oxopropan-2-yl)-4-(dimethylamino)-N-methyl-2-butenamide [PTM-VIII-65]; (E)-4-(Dimethylamino)-N—((S)-1-(((1S*,3R*)-3-((2-((2-fluoropyridin-4y)amino)-4 (propylamino)pyrimidin-5-yl) ethynyl)cyclobutyl)amino)-1-oxopropan-2-yl)-N-methyl-2-butenamide [PTM-VIII-66]; (E)-4-(Dimethylamino)-N—((S)-1-(((1S,3R)-3-((2-((2-methoxypyridin-4-yl)amino)-4-(propylamino)pyrimidin-5-yl)ethynyl)cyclobutyl)amino)-1-oxopropan-2-yl)-N-methyl-2-butenamide [PTM-VIII-67]; (E)-N—((S)-1-(((1 S,3R)-3-((2-((4-Cyanophenyl)amino)-4-(methylamino)pyrimidin-5-yl)ethynyl)cyclohexyl)amino)-1-oxopropan-2-yl)-4-(dimethylamino)-N-methyl-2-butenamide [PTM-VIII-68]; (E)-N—((S)-1-(((1 S*,3R*)-3-((2-((4-Cyanophenyl)amino)-4-(cyclopropylamino)pyrimidin-5-yl) ethynyl)cyclobutyl)amino)-1-oxopropan-2-yl)-4-(dimethylamino)-N-methyl-2-butenamide [PTM-VIII-69]; (E)-N—(S)-1-(((1S*,3R*)-3-((4-(Cyclopropylamino)-2(4-fluorophenyl)amino)pyrimidin-5-yl)ethynyl)cyclobutyl) amino)-1-oxopropan-2-yl)-4-(dimethylamino)-N-methyl-2-butenamide [PTM-VIII-70]; (E)-N—((S)-1-(((1S*,3*)-3-((4-(Cyclopropylamino)-2-((3-fluoro-4-methoxyphenyl) amino)pyrimidin-5-yl)ethynyl)cyclobutyl)amino)-1-oxopropan-2-yl)-4-(dimethylamino)-N-methyl-2-butenamide [PTM-VIII-71]; (E)-4-(Dimethylamino)-N—((S)-1-(((1S,3R)-3-((2-((3-fluorophenyl)amino)-4-((3-fluoropropyl)amino)pyrimidin-5-yl)ethynyl)cyclobutyl) amino)-1-oxopropan-2-yl)-N-methyl-2-butenamide [PTM-VIII-72]; (E)-N—((S)-1-(((1S,3R)-3-((2-((4-Cyanophenyl) amino)-4-((3-fluoropropyl)amino)pyrimidin-5-yl)ethynyl) cyclobutyl)amino)-1-oxopropan-2-yl)-4-(dimethylamino)-N-methyl-2-butenamide [PTM-VIII-73]; (E)-4-(Dimethylamino)-N—((S)-1-(((1S,3R)-3-((2-((3-fluorophenyl)amino)-4-((3-methoxypropyl)amino) pyrimidin-5-yl)ethynyl)cyclobutyl)amino)-1-oxopropan-2-yl)-N-methyl-2-butenamide [PTM-VIII-74]; (E)-N—(S)-1-(((1 S,3R)-3-((2-((4-Cyanophenyl)amino)-4-((3-methoxypropyl)amino)pyrimidin-5-yl)ethynyl)cyclobutyl) amino)-1-oxopropan-2-yl)-4-(dimethylamino)-N-methyl-2-butenamide [PTM-VIII-75]; (E)-4-(Dimethylamino)-N—((S)-1-(((1S,3R)-3-((2-((3-fluoro-4-methoxyphenyl) amino)-4-(methylamino)pyrimidin-5-yl)ethynyl) cyclohexyl)amino)-1-oxopropan-2-yl)-N-methyl-2-butenamide [PTM-VIII-76]; (S,E)-4-(Dimethylamino)-N-methyl-N-(1-((5-(2-((2-methylpyridin-4-ylamino)-4-(propylamino)pyrimidin-5-yl)-4-pentyn-1-yl)amino)-1-oxopropan-2-yl)-2-butenamide [PTM-VIII-77]; (S,E)-N-(1-((5-(2-(Benzo[d]thiazol-6-ylamino)-4-(propylamino) pyrimidin-5-yl)-4-pentyn-1-yl)amino)-1-oxopropan-2-yl)-4-(dimethylamino)-N-methyl-2-butenamide [PTM-VIII-78]; (S,E)-1-(4-(Dimethylamino)-2-butenoyl)-N-(5-(2-((1-methyl-1H-indazol-5-yl)amino)-4-(propylamino)pyrimidin-5-yl)-4-pentyn-1-yl)pyrrolidine-2-carboxamide [PTM-VIII-79]; (S,E)-1-(4-(Dimethylamino)-2-butenoyl)-N-(5-(2-((1-methyl-1H-pyrazolo[3,4-b]pyridin-5-yl)amino)-4-(propylamino)pyrimidin-5-yl)-4-pentyn-1-yl)pyrrolidine-2-carboxamide [PTM-VIII-80]; (S,E)-1-(4-(Dimethylamino)-2-butenoyl)-N-(5-(2-((1-(2-methoxyethyl)-1H-pyrazolo[3,4-b]pyridin-5-yl)amino)-4-(propylamino)pyrimidin-5-yl)-4-pentyn-1l-yl)pyrrolidine-2-carboxamide [PTM-VIII-81]; (S,E)-4-(Dimethylamino)-N-methyl-N-(1-((5-(2-((3-methyl-1H-pyrazolo[3,4-b]pyridin-5-yl)amino)-4-(propylamino)pyrimidin-5-yl)-4-pentyn-1-yl)amino)-1-oxopropan-2-yl)-2-butenamide [PTM-VIII-81]; (S,E)-1-(4-(Dimethylamino)-2-butenoyl)-N-(5-(2-((3-methyl-1H-pyrazolo[3,4-b]pyridin-5-ylamino)-4-(propylamino) pyrimidin-5-yl)-4-pentyn-1-yl)pyrrolidine-2-carboxamide [PTM-VIII-83]; or (S,E)-1-(4-(Dimethylamino)-2-butenoyl)-N-(5-(2-((3-methoxy-1H-pyrazolo[3,4-b]pyridin-5-yl)amino)-4-(propylamino)pyrimidin-5-yl)-4-pentyn-1-yl)pyrrolidine-2-carboxamide [PTM-VIII-84].

In any aspect or embodiment described herein, the PTM is represented by Formula PTM-IX:

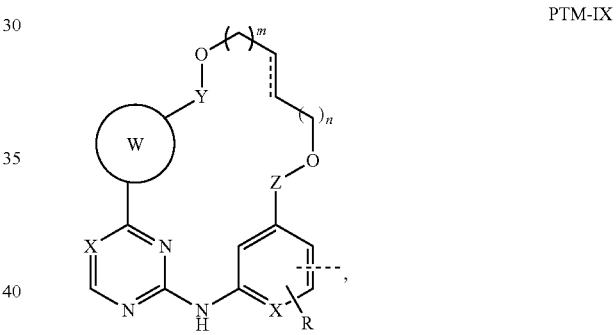

PTM-IX wherein:
W of PTM-IX is an aryl, 5-membered heteroaryl, or 6-membered heteroaryl ring, each optionally substituted with one or more $R_{PTM1}$ groups;
X of PTM-IX is independently selected from C—$R_{PTM1}$ or N;
Y and Z of PTM-IX are independently selected from a bond or $CH_2$;
m and n of PTM-IX are each independently 1 or 2;
$R_{PTM1}$ of PTM-IX is H, halogen, $C_{1-5}$alkyl, CN, OH, or O—$C_{1-5}$alkyl;
=== of PTM-IX indicates either a single or double bond;
each R of PTM-IX is independently selected from H, halogen, $C_{1-5}$alkyl, CN, C(O)—$C_{1-5}$alkyl, C(O)O—$C_{1-5}$alkyl, OH, or O—$C_{1-5}$alkyl, each optionally substituted (e.g., optionally substituted with a cycloalkyl, heterocycle, or aminoalkyl); and of PTM-IX indicates a covalent linkage, optionally through an atom or functional group, to at least one of a linker (L), a ULM, a ULM', a VLM, a VLM', a CLM, a CLM', an ILM, an ILM', a MLM, a MLM', or a combination thereof.

In any aspect or embodiment described herein, wherein the PTM-IX comprises at least one of the following:

W of PTM-IX is phenyl or furan, each optionally substituted with one or more $R_{PTM1}$ groups;

X of PTM-IX is CH;

Y of PTM-IX is $CH_2$;

Z of PTM-IX is $CH_2$;

m and n of PTM-IX are each 1;

R of PTM-IX is H; or a combination thereof.

In any aspect or embodiment described herein, the PTM is represented by chemical structure:

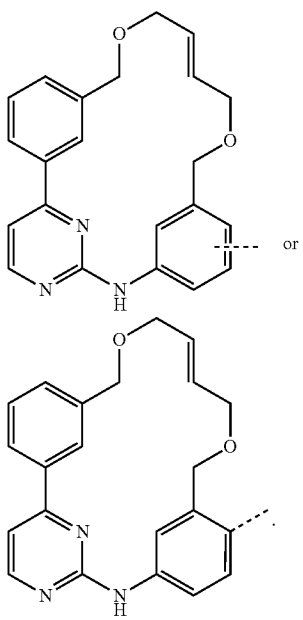

In any aspect or embodiment described herein, the PTM is:

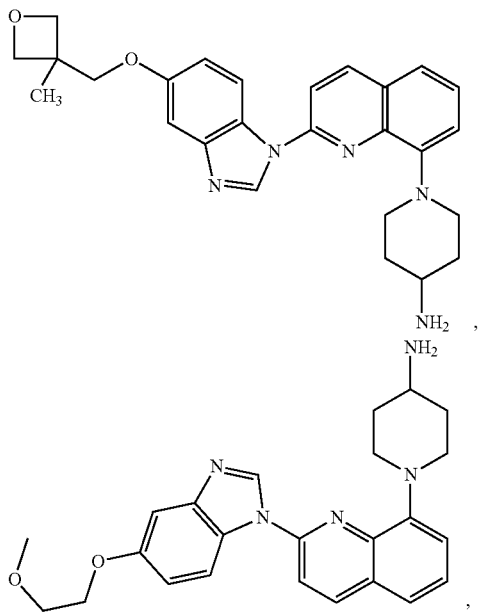

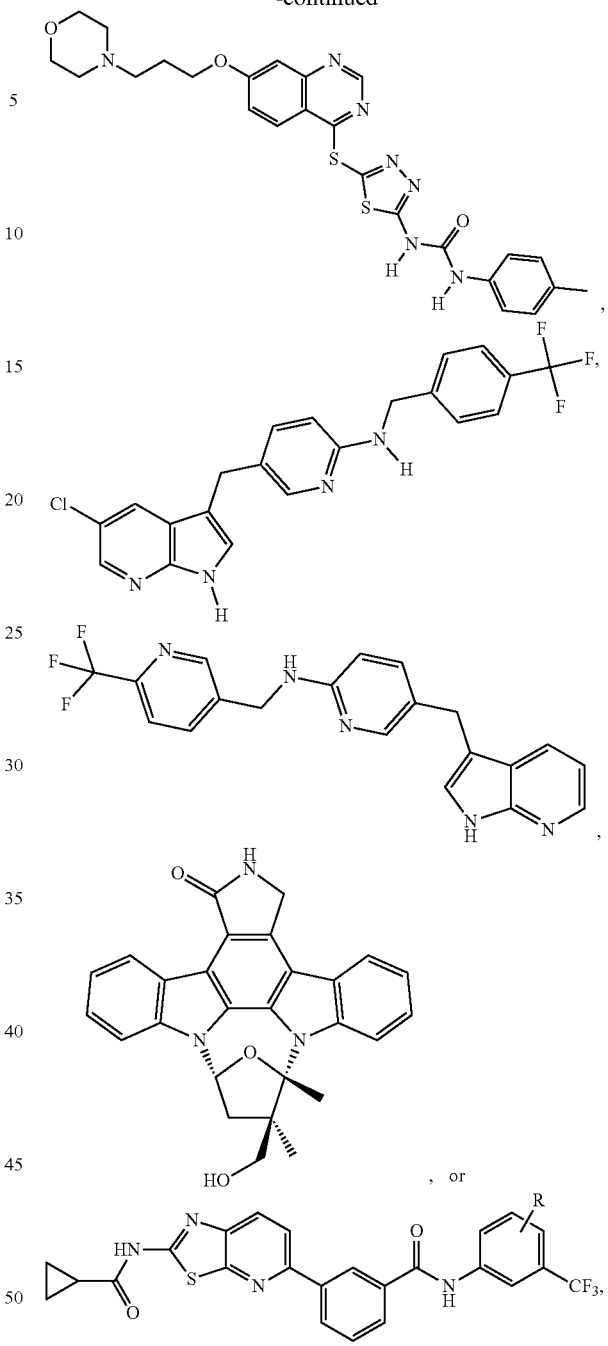

wherein R is 5-(4-methyl-1H-imidazol-1-yl) or 4-(N-(4-ethylpiperazin-1-yl)methyl) [described in Weisberg et el. Mol Cancer Ther. 2010 September; 9(9): 2468-77. Doi: 10.1158/1535-7163.MCT-10-0232].

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure ion may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the disclosure, one or more compounds according to the present disclosure are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the UM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in that patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present disclosure include, for example, asthma, autoimmune diseases such as multiple sclerosis, various cancers or neoplasias, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states (e.g., leukemias, lymphomas, sarcomas, melanomas, and/or carcinomas) and embraces or encompasses the pathological process associated with malignant hematogenous, ascitic and solid tumors. Examples of neoplastic disorders include, but are not limited to, hematopoietic disorders such as, for instance, the myeloproliferative disorders, such as thrombocythemia, essential thrombocytosis (ET), agnogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematoglogical malignancies, including myelodysplasia, multiple myeloma, leukemias and lymphomas. Examples of hematological malignancies include, for instance, leukemias, lymphomas (non-Hodgkin's lymphoma), Hodgkin's disease (also called Hodgkin's lymphoma), and myeloma—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma, (MM). Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia. In embodiments the leukemia is acute myelogenous leukemia (AML), chronic myelogenous leukemia (CML), or precursor B-cell or T-cell acute lymphoblastic Leukemia (ALL).

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs.

Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

In any aspect or embodiment described herein, the disease state or condition is a mutant FLT3-mediated or FLT3-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal FLT3 activity (e.g. kinase activity). The disease state or condition may be selected from the group consisting of acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis. In any embodiment or aspect described herein, the FLT3 mediated disease is selected from axonal degeneration, acute transverse myelitis, amyotrophic lateral sclerosis, infantile spinal muscular atrophy, juvenile spinal muscular atrophy, Creutzfeldt-Jakob disease, subacute sclerosing panencephalitis, organ rejection, bone marrow transplant rejection, non-myeloablative bone marrow transplant rejection, ankylosing spondylitis, aplastic anemia, Behcet's disease, graft-versus-host disease, Graves' disease, autoimmune hemolytic anemia, Wegener's granulomatosis, hyper IgE syndrome, lupus, idiopathic thrombocytopenia purpura, or Myasthenia gravis.

In any aspect or embodiment described herein, the FLT3 disorder or an FLT3 related disorder is a neurologicial disorder, such as one or more of a neurodegenerative disease, for example a disease caused by axonal degeneration. The eeurodegenerative diseases may include, for example, multiple sclerosis; demyelinating core disorders, such as multiple sclerosis, acute transverse myelitis; and disorders of the motor unit such as amyotrophic lateral sclerosis, infantile spinal muscular atrophy and juvenile spinal muscular atrophy); Creutzfeldt-Jakob disease; or Subacute sclerosing panencephalitis.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucleoeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-901525/T), efavirenz (DMP-266), UC-781 (N-[4-chloro-3-(3-methyl-2-butenyloxy)phenyl]-2methyl3-furancarbothiamide), etravirine (TMC 125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-B enzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 342-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present invention, but should not be seen as limiting the present invention in any way.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

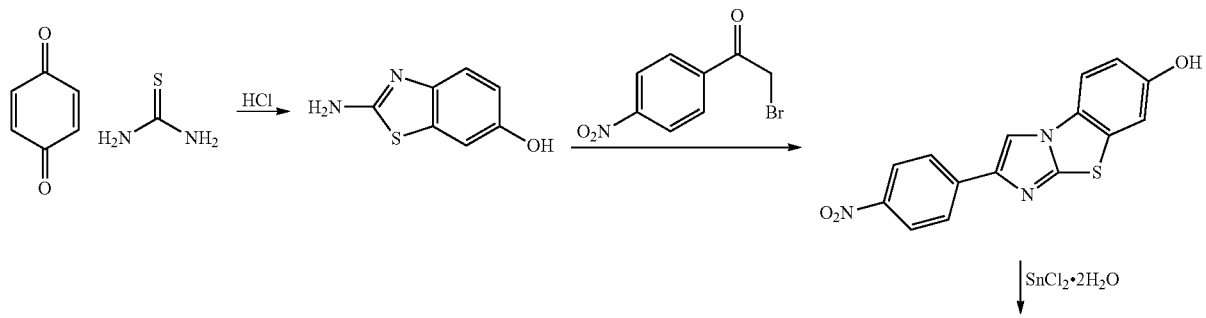

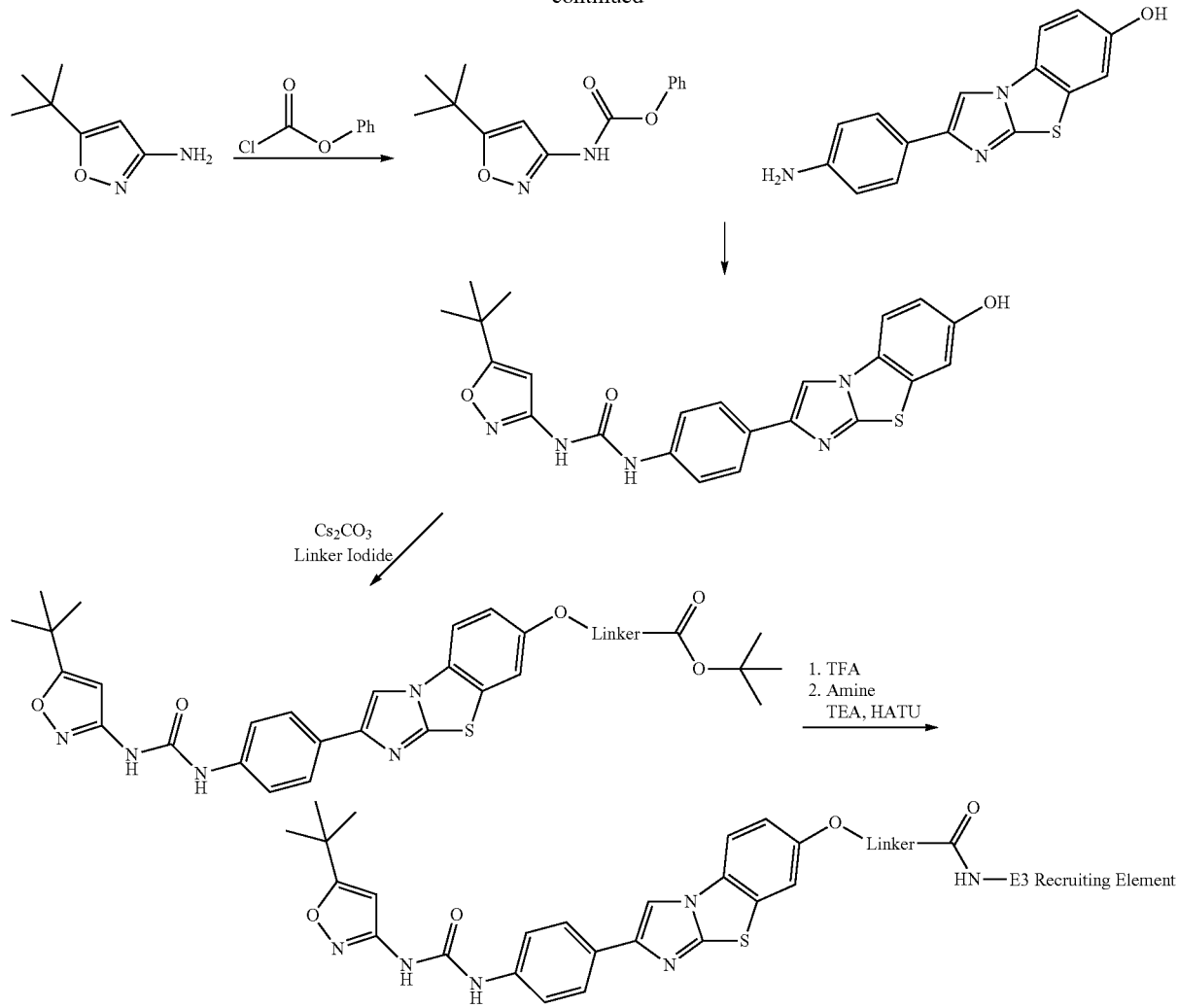

2-amino-1,3-benzothiazol-6-ol

Thiourea (3.8 g) was dissolved in ethanol (50 ml) and conc. HCl (4.5 ml) added. Benzoquinone (10.8 g) was added dropwise as a hot solution of ethanol (50 ml) and the reaction stirred at room temperature overnight. Reaction complete by TLC (10% MeOH/DCM) and LC-MS. Concentrated in vacuo, triturated with hot acetonitrile and washed with ice cold ethanol. Residue dissolved in the minimum amount of water and precipitated by the addition of concentrate HCl. Collected by filtration and dried in vacuo. HCl salt dissolved/suspended in water (150 ml) and treated with saturated sodium bicarbonate solution until pH 7-8. Extracted with ethyl acetate (3×50 ml) and concentrated in vacuo. NMR and LC-MS conform to structure and match literature reports.

2-(4-nitrophenyl)imidazo[2,1-b][1,3]benzothiazol-6-ol 2-amino-1,3-benzothiazol-6-ol (1000 mg), 2-bromo-1-(4-nitrophenyl)ethanone (1615 mg) and NaHCO₃ (757 mg) dissolved in N-butanol (100 ml) and heated to reflux for 3 hours until amine s.m. was consumed by TLC (1:1 ethyl acetate/hexane). Cooled to 0° C. in an ice bath and precipitate collected by filtration—yellow solid. Solid resuspended in water and stirred for 30 minutes and filtered again. Solid resuspended in acetone and stirred for 30 minutes. Product collected as solid by filtration and washed with acetone. Dried in vacuo. NMR and LC-MS conform to structure and match literature reports.

2-(4-aminophenyl)imidazo[2,1-b][1,3]benzothiazol-6-ol 2-(4-nitrophenyl)imidazo[2,1-b][1,3]benzothiazol-6-ol (650 mg) suspended in ethanol (50 ml) and SnCl₂.H₂O (2356 mg) added and reaction heated to reflux overnight. Reaction mixture allowed to cool to room temperature and diluted with water (50 ml) and DCM (100 ml). Neutralised with sat. NaHCO3 and organics separated. Aqueous extracted again with DCM (50 ml). Organics combined, dried over MgSO₄ and concentrated in vacuo to a pale yellow solid. NMR and LC-MS conform to structure and match literature reports.

phenyl N-(5-tert-butylisoxazol-3-yl)carbamate 5-tert-butylisoxazol-3-amine (2 g) dissolved in THF and potassium carbonate (2563 mg) added. Phenyl chloroformate (1.88 ml) added dropwise and reaction stirred at room temperature for 2 hours until no starting material remaining by TLC (DCM). Reaction mixture filtered and filtrate concentrated to 20% volume and treated with water (40 ml) and ethanol (until monophasic) and stirred for 1 hour. Resulting precipitate collected by filtration and dried in vacuo. NMR and LC-MS conform to structure and match literature reports.

1-(5-tert-butylisoxazol-3-yl)-3-[4-(6-hydroxyimidazo[2,1-b][1,3]benzothiazol-2-yl)phenyl]urea 2-(4-aminophenyl)imidazo[2,1-b][1,3]benzothiazol-6-ol (370 mg), phenyl N-(5-tert-butylisoxazol-3-yl)carbamate (377 mg), DMAP (9.6 mg) and TEA (27 µL) were dissolved in DCM. Reaction mixture stirred overnight at reflux then cooled to 0° C. for 30 minutes. Precipitate collected by filtration and washed with ice cold DCM and ice cold hexane and dried in vacuo to give a colourless solid. NMR and LC-MS conform to structure and match literature reports.

Linkers were Introduced Using the Following Generic Conditions.

1-(5-tert-butylisoxazol-3-yl)-3-[4-(6-hydroxyimidazo[2,1-b][1,3]benzothiazol-2-yl)phenyl]urea (1 eq.) was dissolved in dioxane (1 ml per 10 mg starting material) and $Cs_2CO_3$ (1.5 eq.) added followed by linker (1.1 eq.) iodide compounds. The reaction mixture was heated to 100° C. for 4 hours under microwave conditions. The resulting mixture was filtered, concentrated in vacuo and purified by column chromatography eluting with 40-100% ethyl acetate/hexane. NMR and LC-MS conform to structure.

T-Butyl Esters were Cleaved Using the Following Generic Conditions.

T-butyl ester compound was dissolved in 20% TFA in DCM and stirred for 2 hours. The reaction mixture was concentrated in vacuo and used immediately in the next step.

E3 Recruiting Elements were Introduced Using the Following Generic Conditions.

Carboxylic Acid TFA salts (1 eq.), E3 recruiting element amine (1.1 eq.) HATU (1.1 eq) and TEA (5 eq.) were dissolved in DMF and stirred at room temperature overnight. The resulting solution was partitioned between water and ethyl acetate. The organic layer was separated, washed with water and brine, dried over $MgSO_4$ and concentrated in vacuo. The residue was purified by chromatography eluting with 0-10% methanol in DCM. NMR and LC-MS conform to structure.

Examples

Assays and Degradation Data

Protocol for the Cellular Assay of Target Protein Degradation (MV-4-11 Cells, Westernblot).

Figure 2:
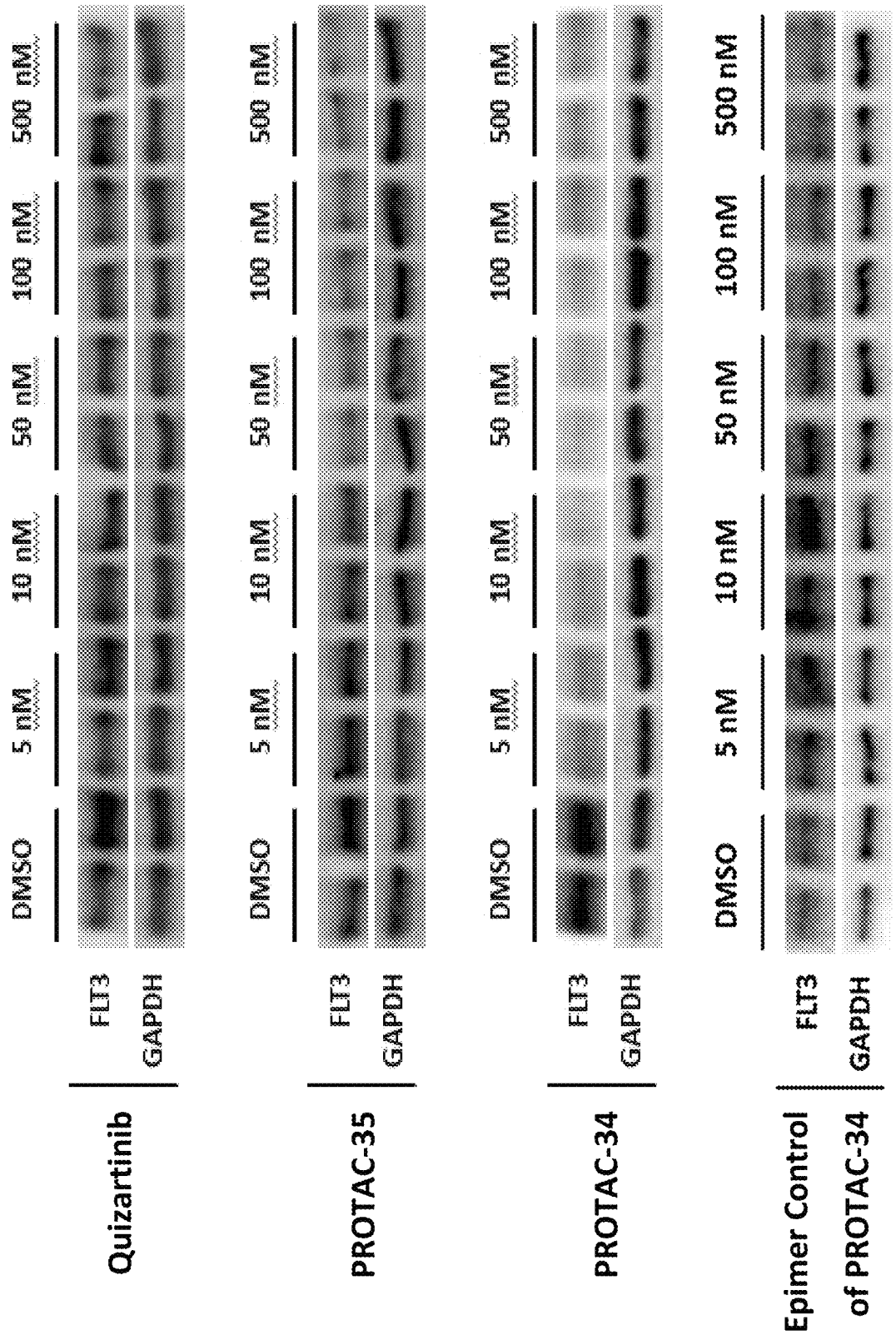
FIG. 2. FLT-3 protein degradation in cells treated with either a bifunctional compound of the present disclosure or Quizartinib is shown.

MV-4-11 cells (approximately 1 million cells per well) were treated with the indicated concentrations (5-500 nm) of compound for 24 hours. The cells were spun down and washed twice with PBS. The cells were suspended by lysis buffer (50 mM Tris (pH7.4), 150 mM NaCl, 1 mM EDTA, 0.5% NP-40, phosphatase and protease inhibitors) and incubated for an additional 30 min at 4° C. for complete lysis. After another centrifugation (13000 rpm for 15 minutes), the supernatants were kept as cell lysates. The protein concentration of the cell lysates was determined via the bicinchoninic acid (BCA) method. Equal amounts (10-20 µg) of protein samples were subjected to 8-15% SDS-PAGE. The proteins were transferred to nitrocellulose membrane and probed with antibodies specific for FLT-3 and GAPDH. As shown in FIG. 2, the exemplary PROTACs were induced protein degradation, whereas Quizartinib did not. Furthermore, PROTAC-34 also demonstrated an ability to induce apoptosis in MV4-11 cells, as shown by cleaved caspase-3 in FIG. 3A and quantified in 3B.

Protocol for the Cell Proliferation Assays (MV-4-11 Cells).

MV-4-11 or Molm 14 cells were seeded in 96-well plates at a density of $1\times10^4$ cells/well and treated with various concentrations of the test compounds for 72 hours. The highest concentration was 500 nM and was serially diluted 5-fold seven times. After incubation, 20 µl/well of CellTiter 96® AQueous One Solution Reagent (Promega®) was added and the plate was incubated an additional 3 hours. The absorbance was measured at 490 nm, and cell viability was calculated by comparing to the absorbance of the vehicle-treated control group using GraphPad Prism 7.

Figure 3A:
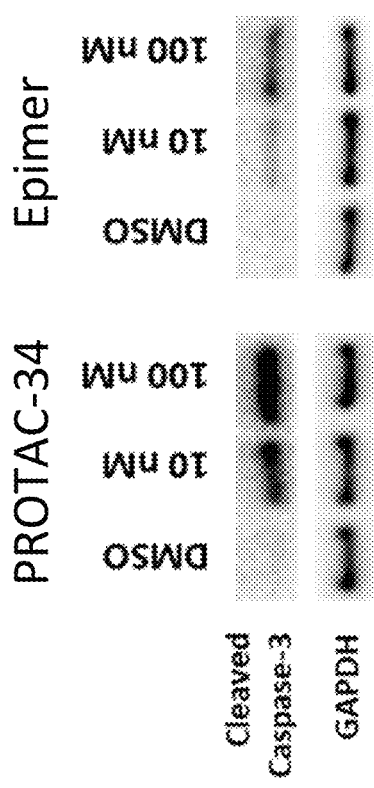
FIGS. 3A and 3B. Bifunctional compound of the present disclosure induced apoptosis as illustrated by caspase-3 cleavage.
Figure 3B:
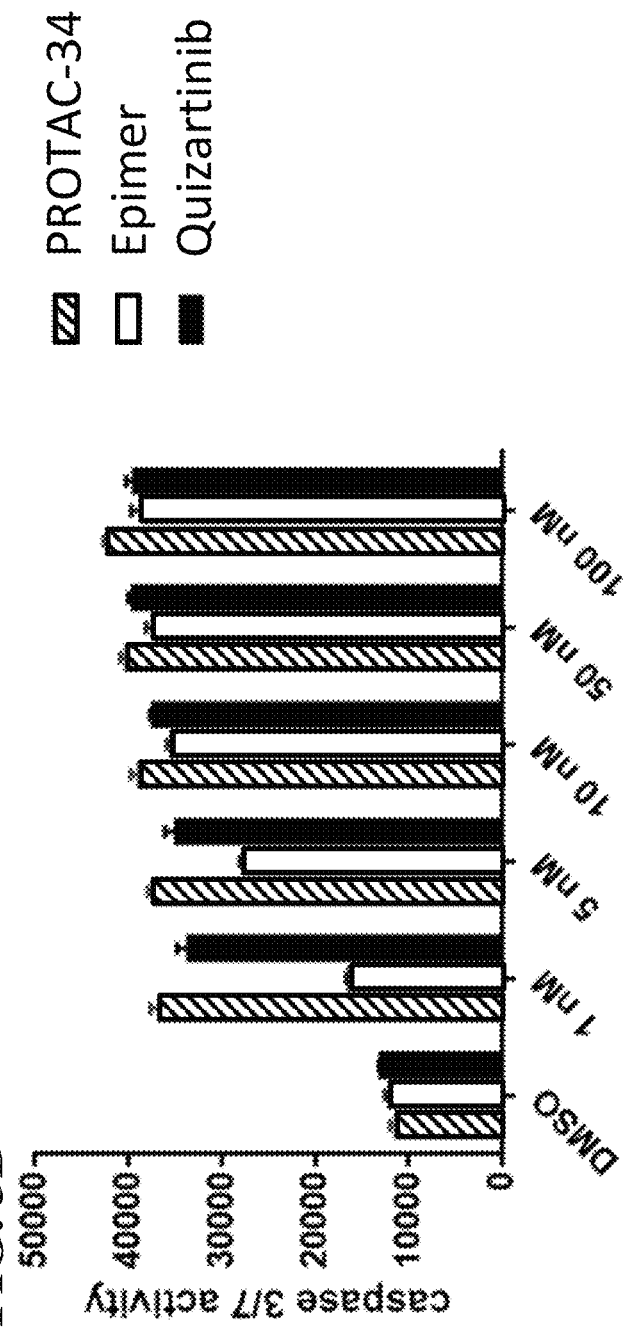
Figure 4A:
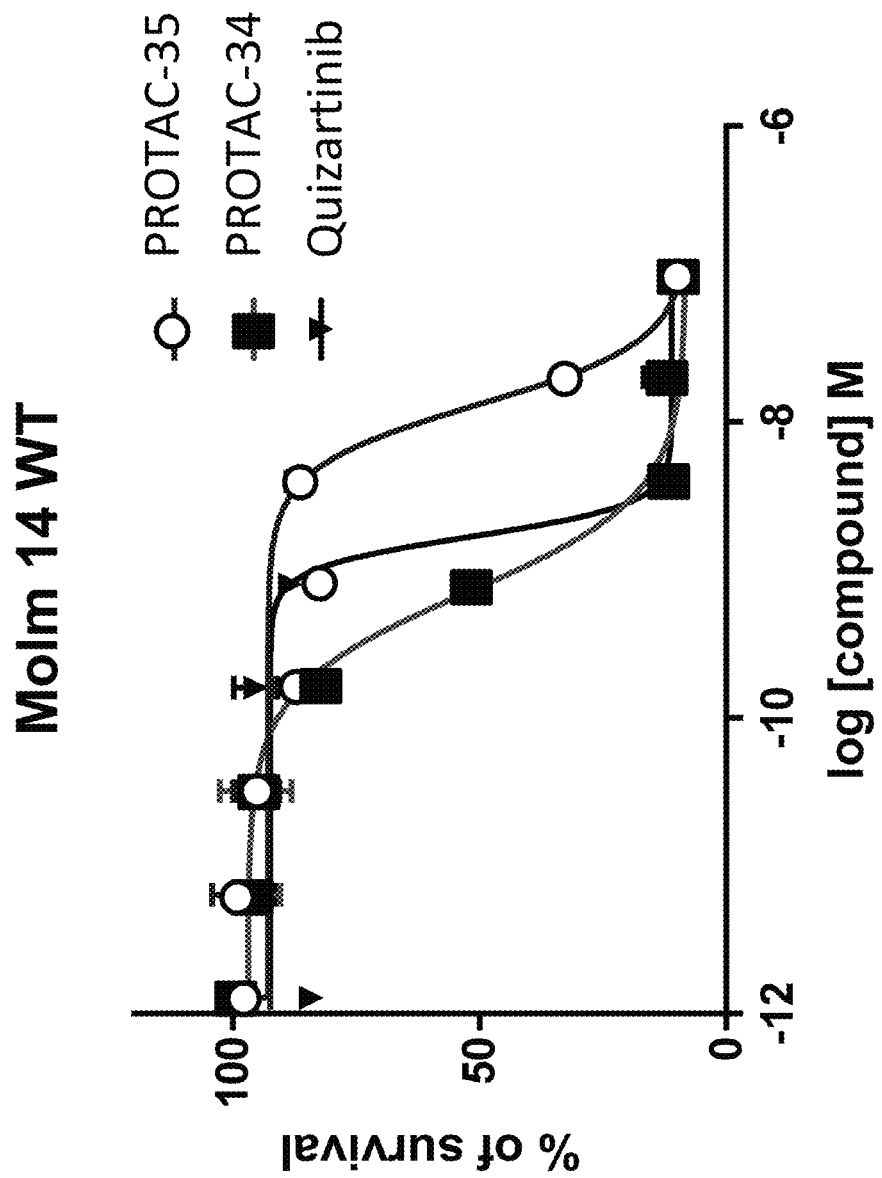
FIGS. 4A, 4B, and 4C. Molm 14 WT (A) and MV4-11 (B and C) cell survival is shown when treated with either a bifunctional compound of the present disclosure or Quizartinib.
Figure 4B:
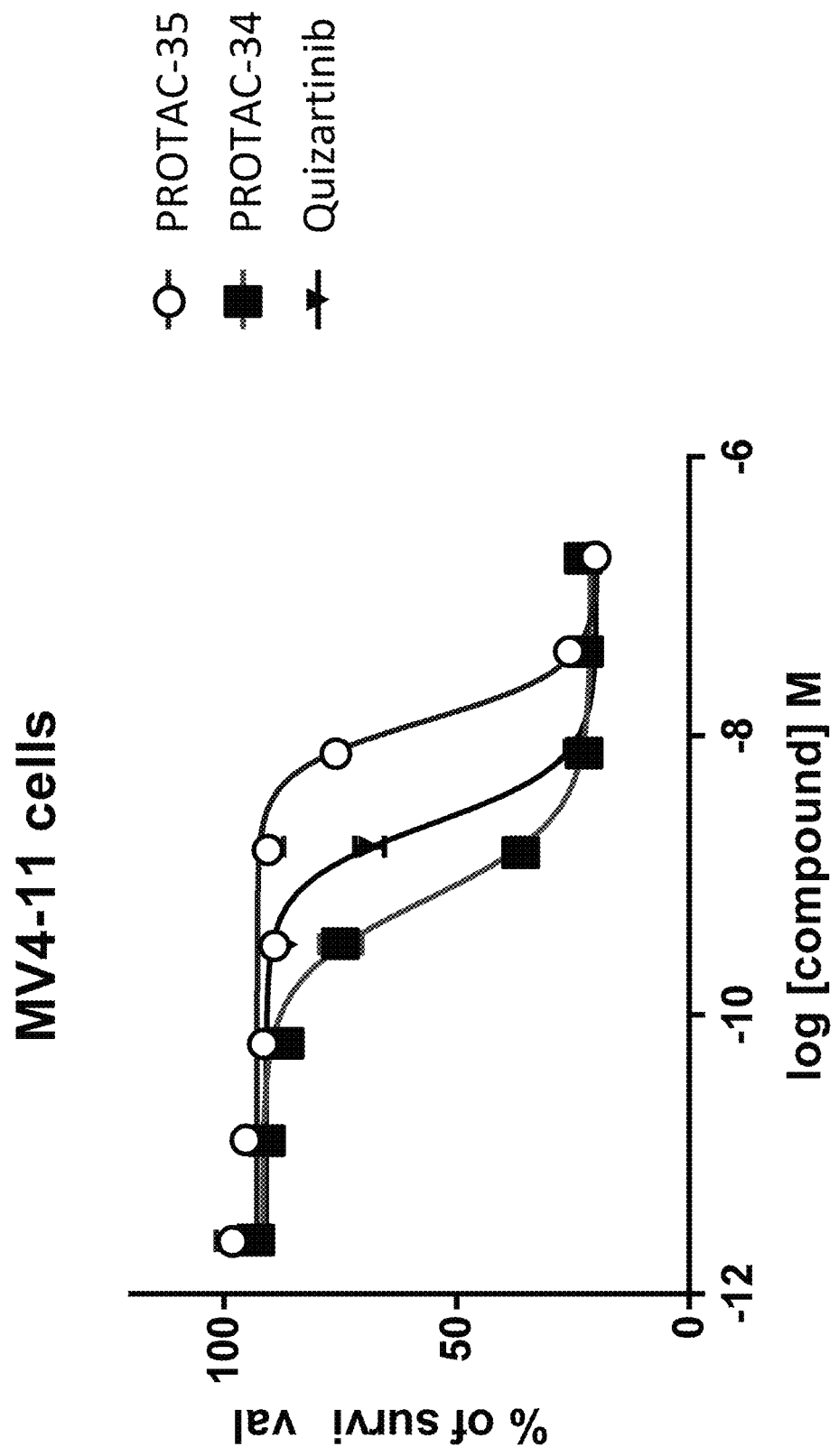
Figure 4C:
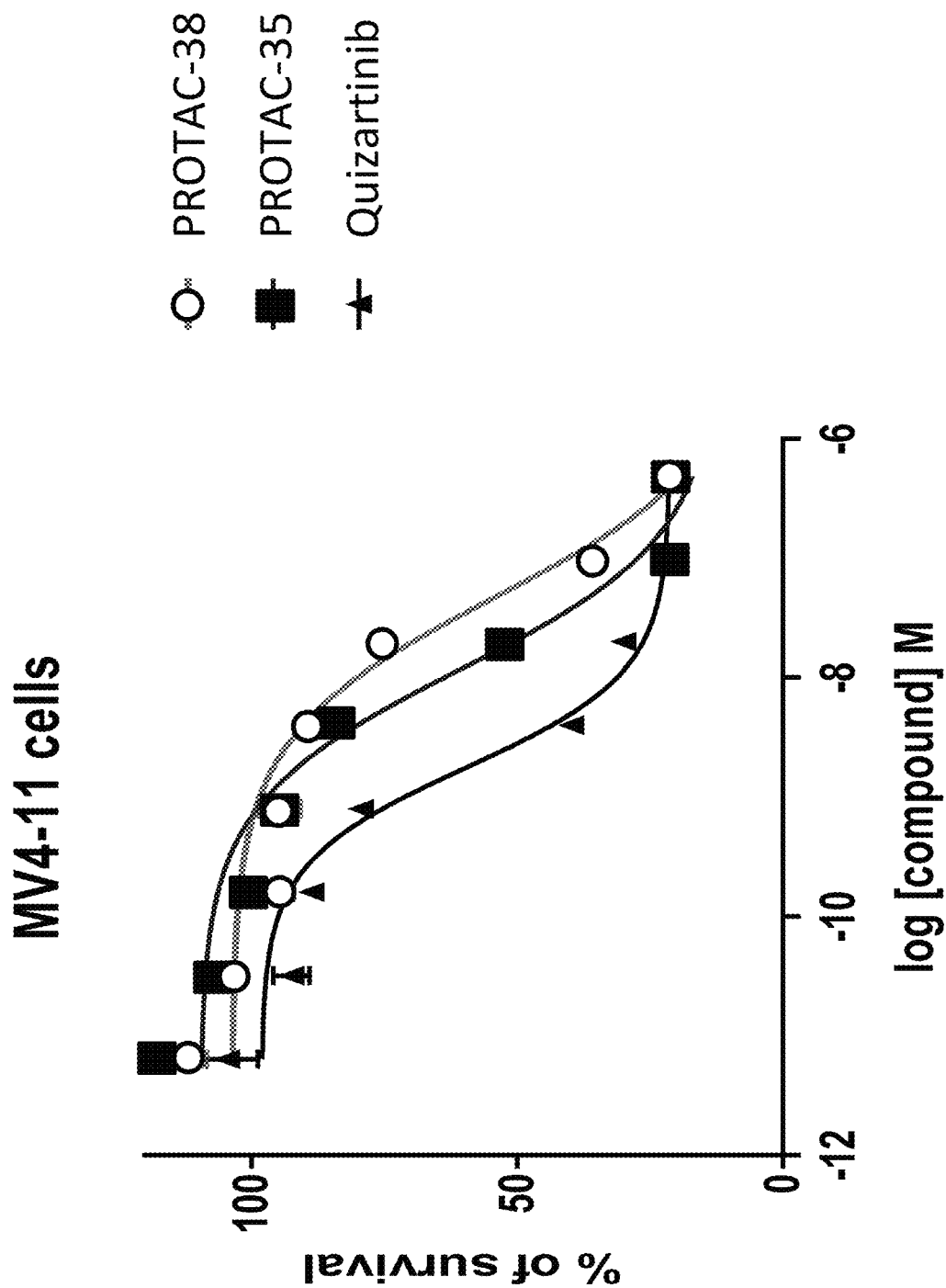

Cell viability/survival is illustrated in FIGS. 4A, 4B and 4C, as determined by a cell proliferation assay. The associated $IC_{50}$ (nM) for exemplary bifunctional compounds of the present disclosure or Quizartinib as a control of FIGS. 2, 4A, 4B, and 4C, is shown in Tables 1 and 2 below. DC50, IC50, MH+, and NMR data for exemplary PROTAC-34 through PROTAC-38 and PROTAC-34-Epimer (structure shown below) is shown in Table 3 below. FLT-3 protein degradation is shown in FIGS. 3A and 3B treated with either exemplary bifunctional compounds of the present disclosure or Quizartinib as a control.

TABLE 1

$IC_{50}$ for MV4-11 cells treated with bifunctional compounds of the present disclosure

| Compounds | $IC_{50}$ (nM) MV4-11 |
| --- | --- |
| PROTAC-35 | 12.91 |
| PROTAC-34 | 0.6723 |
| Quizartinib | 2.338 |

TABLE 2

$IC_{50}$ for MV4-11 cells treated with bifunctional compounds of the present disclosure

| Compounds | $IC_{50}$ (nM) MV4-11 |
| --- | --- |
| PROTAC-38 | 43.01 |
| PROTAC-35 | 11.88 |
| Quizartinib | 1.755 |

PROTAC-34-Epimer has the following chemical structure:

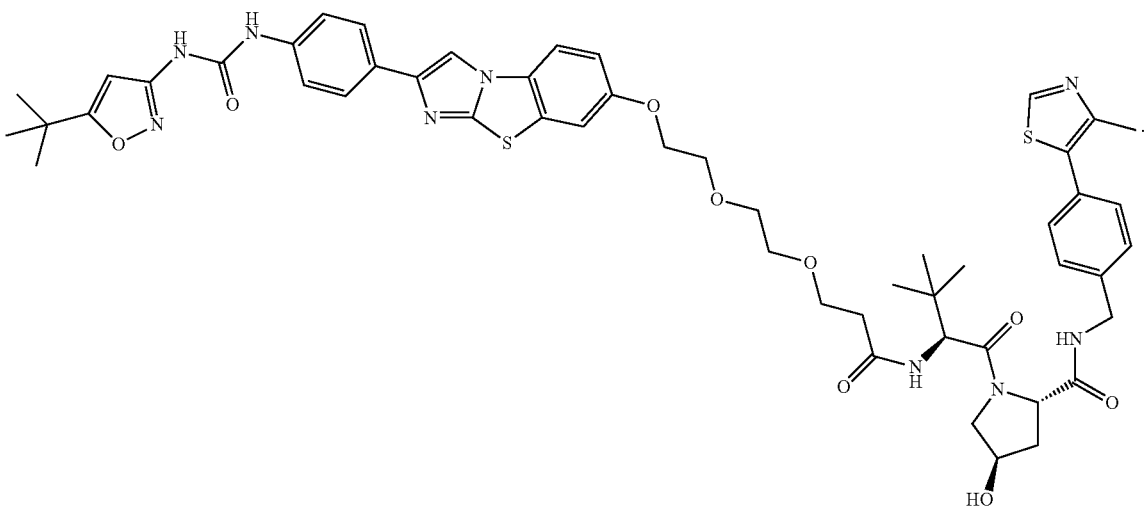 [SMILES: Cc1ncsc1-c1ccc(CNC(=O)[C@@H]2C[C@@H](O)CN2C(=O)[C@@H](NC(=O)CCOCCOCCOc2ccc3c(c2)sc2nc(-c4ccc(NC(=O)Nc5cc(C(C)(C)C)on5)cc4)cn23)C(C)(C)C)cc1]

TABLE 3

Characteristics of Exemlary PROTACs

| Compound | DC$_{50}$ and/or IC$_{50}$ (uM) [cell line] | MH+ (1) | NMR transcript |
|---|---|---|---|
| PROTAC-38 | IC$_{50}$ – 43 nM [MV4-11] No degradation observed | 1090.5712 | |
| PROTAC-35 | IC50$_{50}$ – 11.8 nM [MV4-11] DC$_{50}$~50 nM [MV4-11] | 962.3730 | $^1$H NMR (400 MHz, Chloroform-d) δ 8.69 (s, 1H), 8.58 (s, 1H), 7.85 (s, 1H), 7.49 (d, J = 8.0 Hz, 2H), 7.37-7.15 (m, 8H), 7.06 (d, J = 8.7 Hz, 1H), 6.90 (s, 1H), 6.68 (d, J = 8.8 Hz, 1H), 6.35 (s, 1H), 4.81 (d, J = 8.2 Hz, 1H), 4.59 (m, 4H), 4.29 (dd, J = 14.7, 5.1 Hz, 1H), 4.20-3.94 (m, 3H), 3.86-3.58 (m, 8H), 2.42 (m, 5H), 1.32 (s, 9H), 1.06 (s, 9H). |
| PROTAC-37 | No degradation observed | 1004.4254 | |
| PROTAC-36 | IC$_{50}$ – 240.9 nM [MV4-11] No degradation observed | 890.6568 | |
| PROTAC-34 | IC$_{50}$ – 0.60 nM [MV4-11] DC$_{50}$~5 nM [MV4-11] | 1020.4365 | $^1$H NMR (400 MHz, DMSO-d$_6$) δ 9.54 (s, 1H), 8.94 (s, 1H), 8.90 (s, 1H), 7.94 (d, = 9.4 Hz, 1H), 7.83 (d, J = 8.9 Hz, 1H), 7.74 (d, J = 8.6 Hz, 2H), 7.64 (d, J = 2.5 Hz, 1H), 7.48 (d, J = 8.7 Hz, 2H), 7.36 (q, J = 8.3 Hz, 4H), 7.12 (dd, J = 8.9, 2.5 Hz, 1H), 4.52 (d, J = 9.4 Hz, 1H), 4.45-4.35 (m, 2H), 4.21-4.07 (m, 3H), 3.73 (dd, J = 5.6, 3.6 Hz, 2H), 3.55 (m, 8H), 2.40 (s, 3H), 2.05-1.96 (m, 1H), 1.86 (ddd, J = 12.9, 8.8, 4.6 Hz, 1H), 1.26 (s, 9H), 0.89 (s, 9H). |
| PROTAC-34-Epimer | IC$_{50}$ – 2.27 nM [MV4-11] No degradation observed | 1020.4407 | $^1$H NMR (400 MHz, DMSO-d6) δ 9.50 (s, 1H), 8.93 (s, 1H), 8.85 (s, 1H), 8.57 (s, 1H), 8.18 (s, 1H), 7.96 (d, J = 8.1 Hz, 1H), 7.82 (d, J = 8.9 Hz, 1H), 7.80-7.72 (m, 2H), 7.62 (d, J = 2.5 Hz, 1H), 7.52-7.42 (m, 2H), 7.38 (d, J = 8.3 Hz, 2H), 7.30 (s, 1H), 7.11 (dd, J = 8.9, 2.5 Hz, 1H), 6.49 (s, 1H), 5.08 (d, J = 3.9 Hz, 1H), 4.43-4.24 (m, 4H), 4.21-4.01 (m, 3H), 3.73 (dq, J = 14.5, 4.8 Hz, 3H), 3.57-3.38 (m, 6H), 2.40 (s, 3H), 1.27 (s, 9H), 0.93 (s, 9H). |

Pharmacokinetics of Exemplary Compounds.

Figure 5:
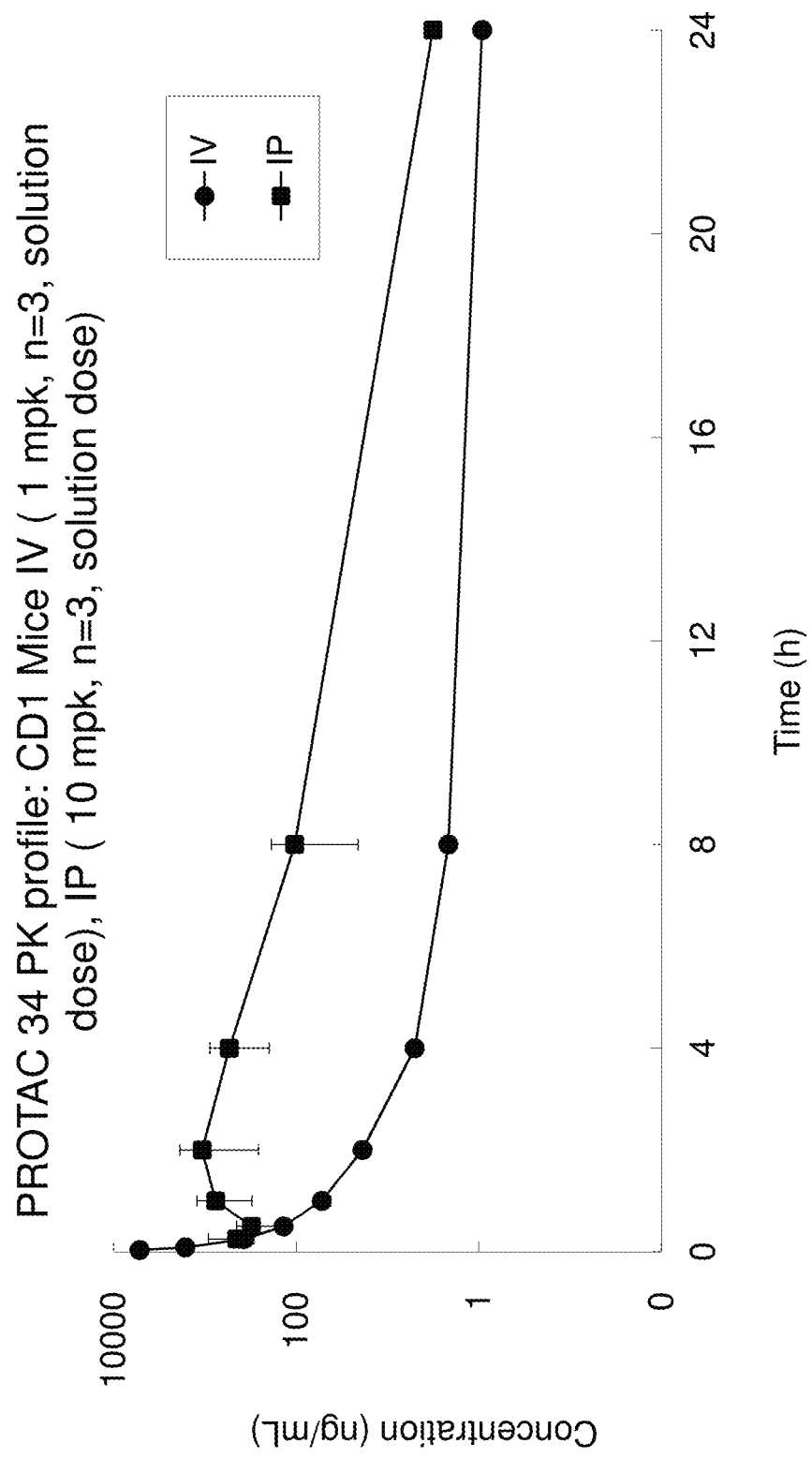
FIG. 5. Pharmacokinetic profile for PROTAC-34 administered by intravenous injection or intraperitoneal injection in CD1 mice.

FIG. 5: PK profile of PROTAC-34 demonstrating exposure in mice when dosed intravenously or intraperitoneally.

In Vitro Kinase Binding Affinity Determination for PROTAC-34.

Figure 6:
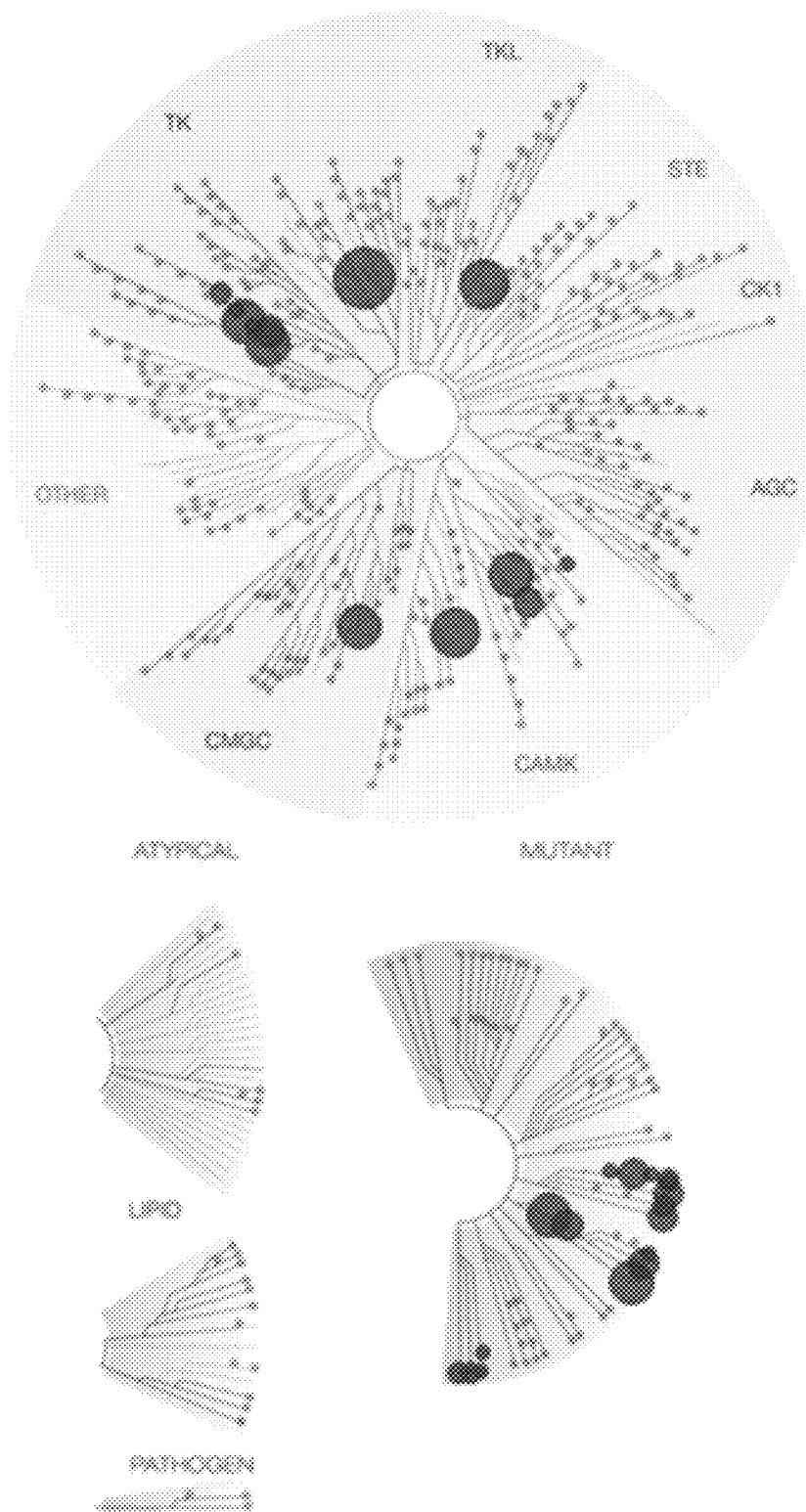
FIG. 6. KINOMEscan™ Dendrogram for PROTAC-34.

In vitro binding activity of PROTAC-34 for kinases was determined using the KINOMEscan™ platform (DiscoverRx Corporation). The compounds were solubilized in DMSO and sent to DiscoverRx Corporation as 10 μM stock solutions. The KINOMEscan™ Dendrogram of FIG. 6 illustrates the kinases that are bound at 1 μM of PROTAC-34. The circles represent kinases which are occupied by PROTAC-34 in a competition assay, wherein the size of the circles represent the percent occupancy. The Dendrogram demonstrates that PROTAC-34 is more selective than Quizartinib.

In Vivo Xenograft Model.

Figure 7A:
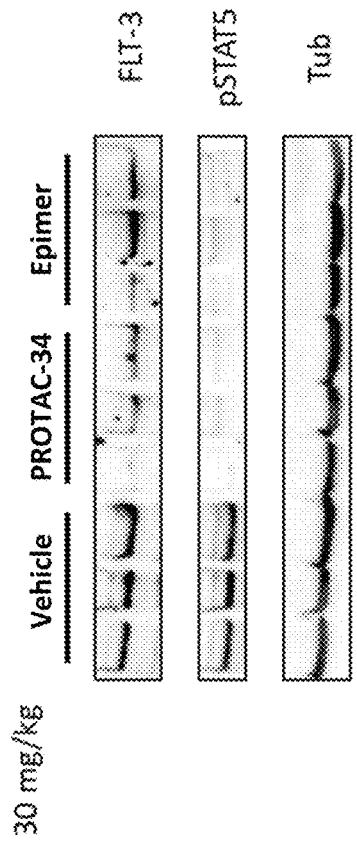
FIGS. 7A and 7B. FLT-3 protein degradation and pSTAT5 status in xenograft tumors from athymic mice treated with a bifunctional compound of the present disclosure is shown in FIG. 7A and quantified in FIG. 7B.
Figure 7B:
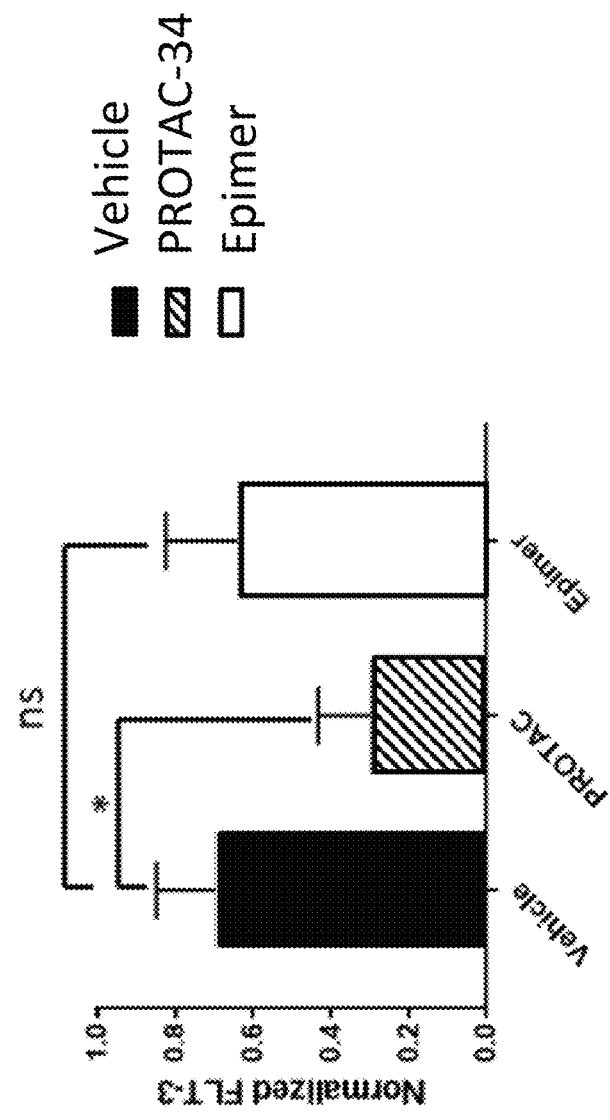

MV4-11 cells were injected subcutaneously into the flank of athymic mice and allowed to proliferate until tumours reached an average of about 200 mm$^3$ at which point mice were treated with vehicle, PROTAC-34 or Epimer control of PROTAC-34 once a day at 30 or 100 mg/kg for 3 days. Mice were sacrificed and tumours collected, and westernblots performed as described above. As shown in FIG. 7A, and quantified in FIG. 7B, PROTAC-34 treatment resulted in a decrease in FLT-3 and pSTAT5, which is involved in angiogenesis and cell motility.

Specific Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative.

In certain embodiments, the description provides the following exemplary FLT3 PROTAC molecules (e.g., PROTAC-1 through PROTAC-38), including salts, prodrugs, polymorphs, analogs, derivatives, and deuterated forms thereof:

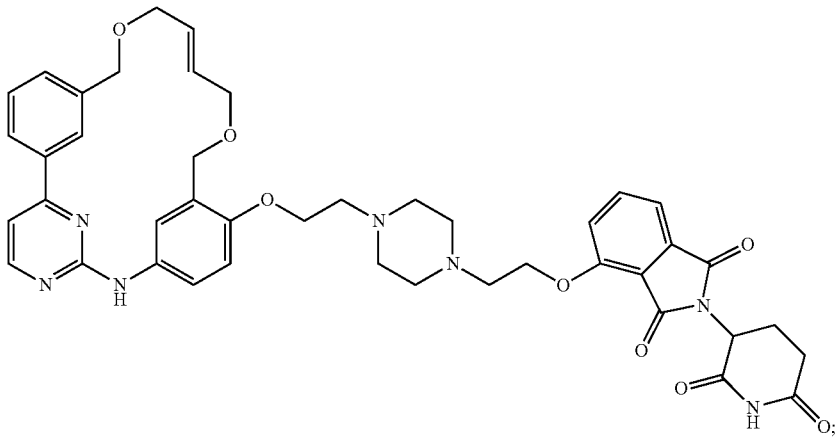

(PROTAC-1)

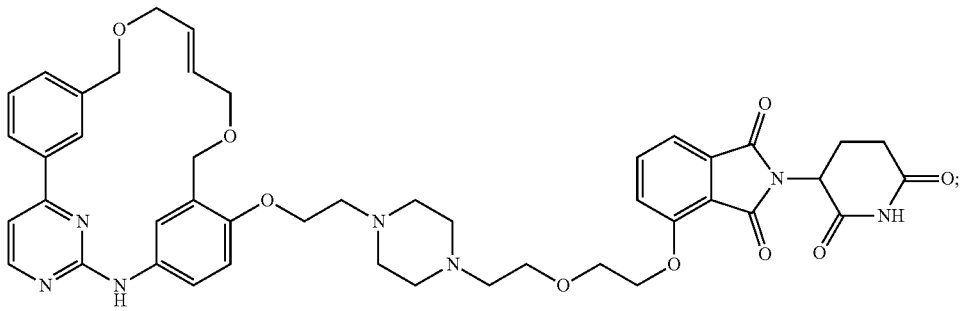

(PROTAC-2)

-continued
(PROTAC-3)
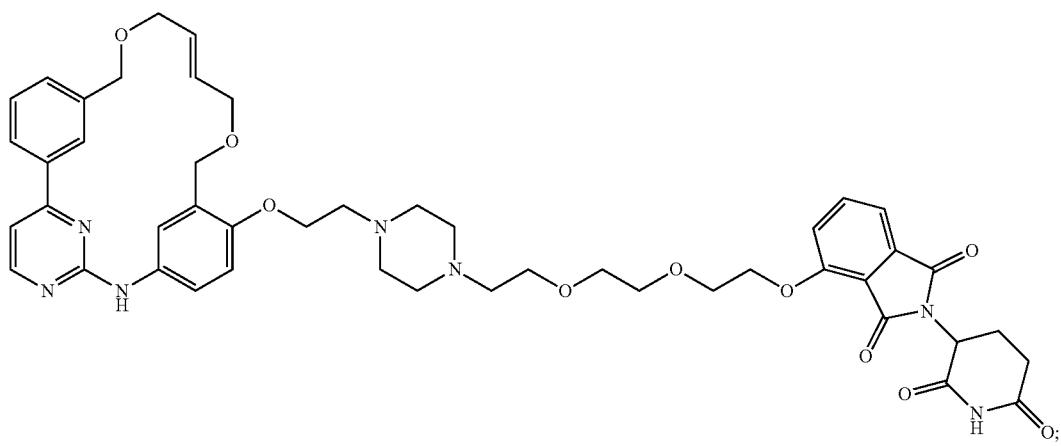
(PROTAC-4)
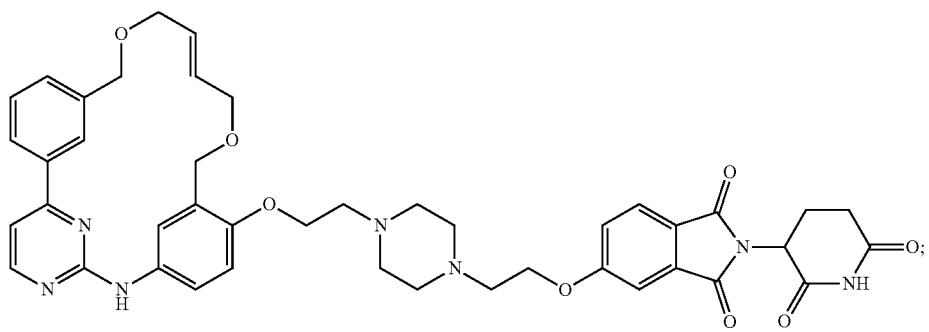
(PROTAC-5)
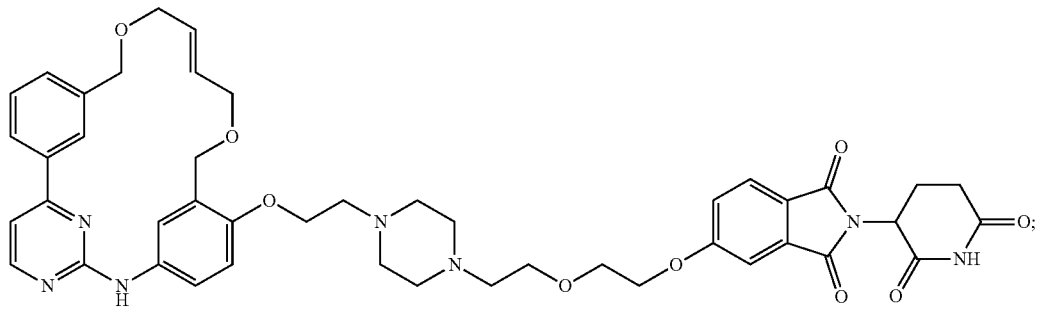
(PROTAC-6)
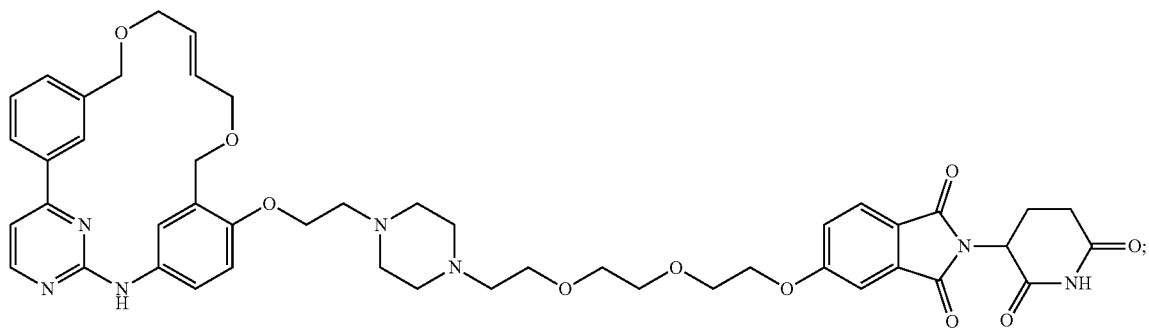

-continued
(PROTAC-7)
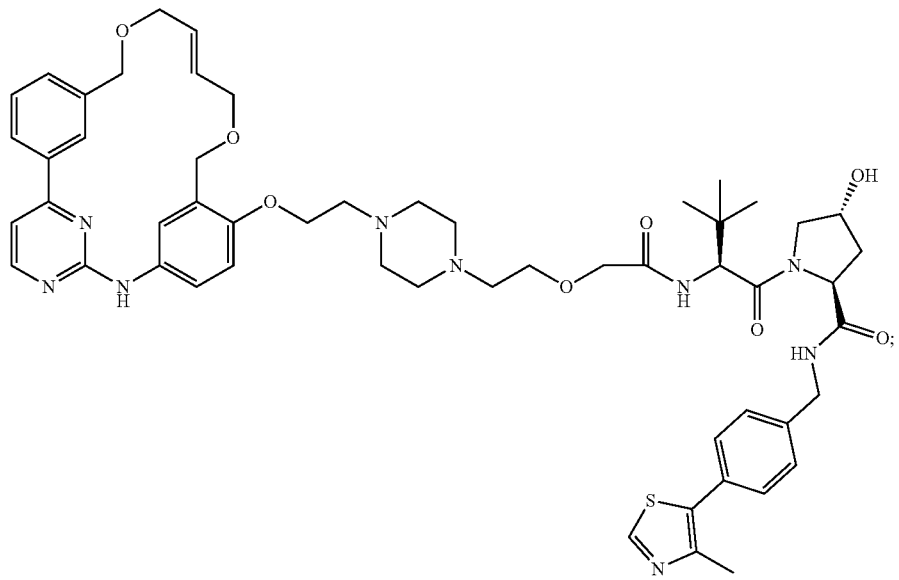
(PROTAC-8)
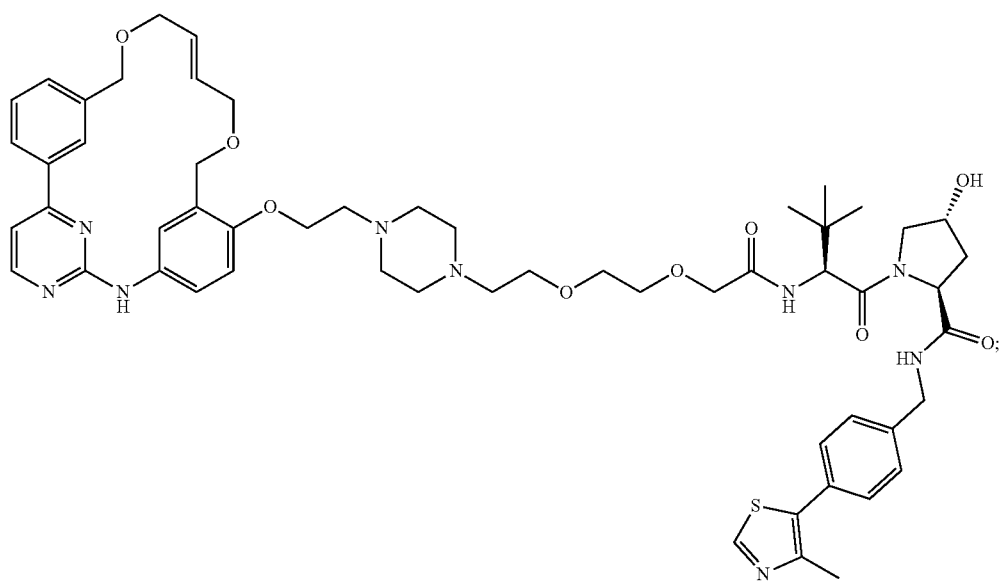

-continued
(PROTAC-9)
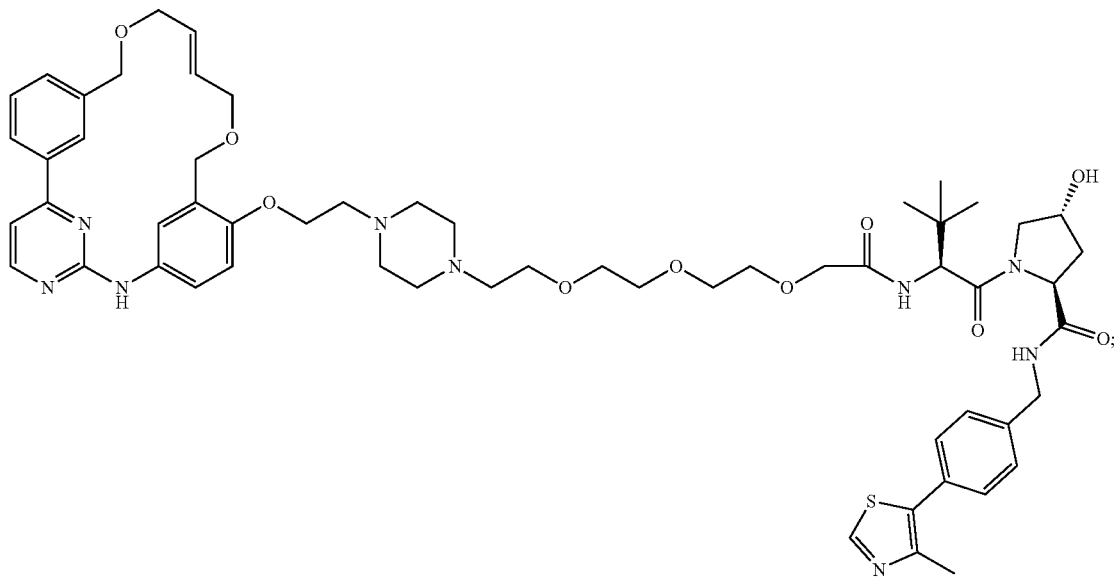
(PROTAC-10)
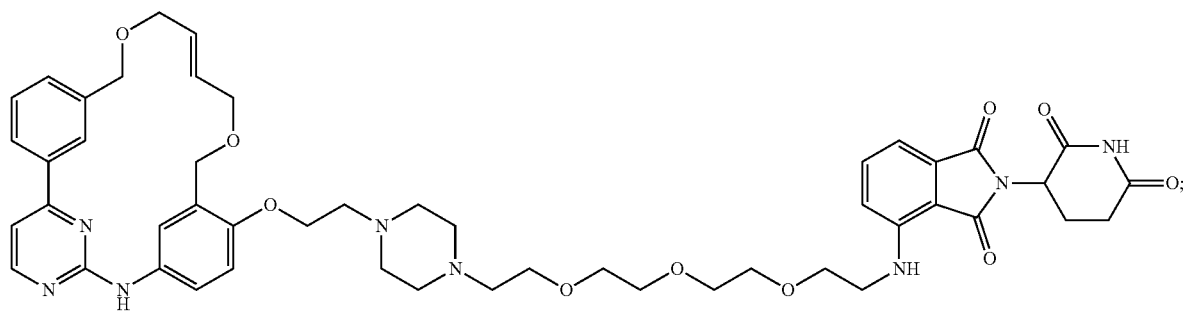
(PROTAC-11)
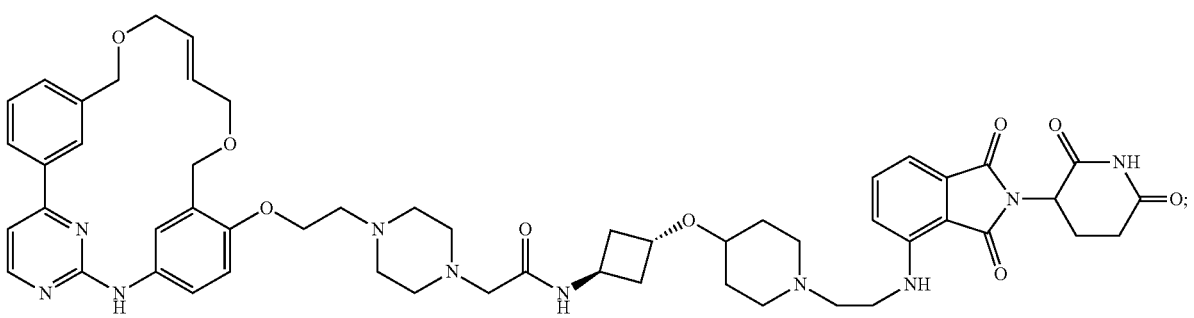
(PROTAC-12)
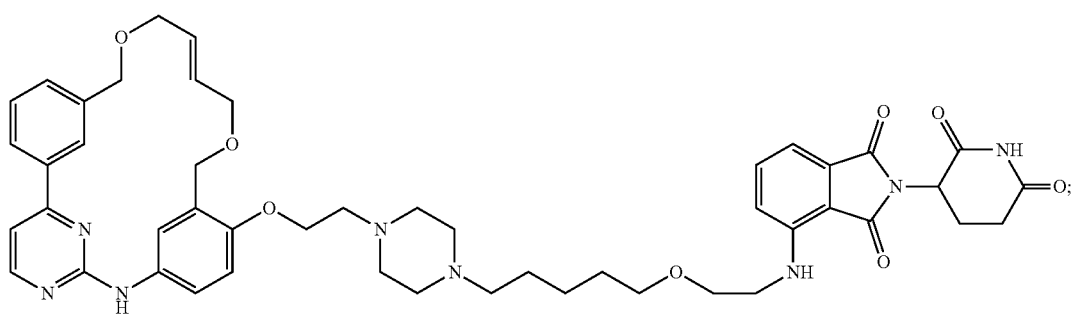

(PROTAC-13)
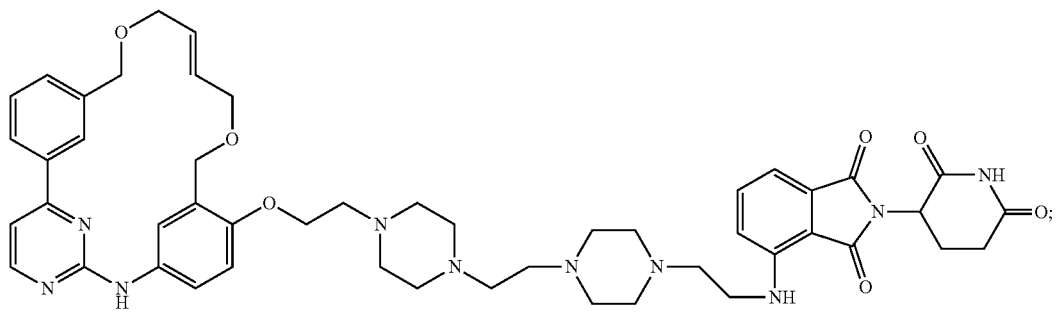
(PROTAC-14)
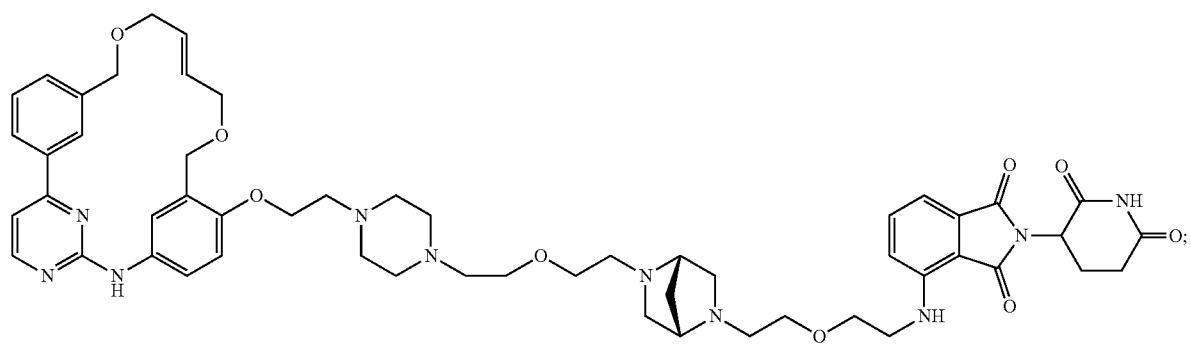
(PROTAC-15)
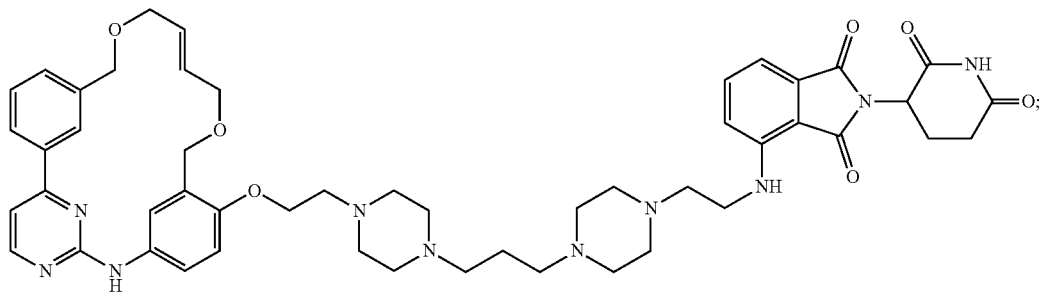
(PROTAC-16)
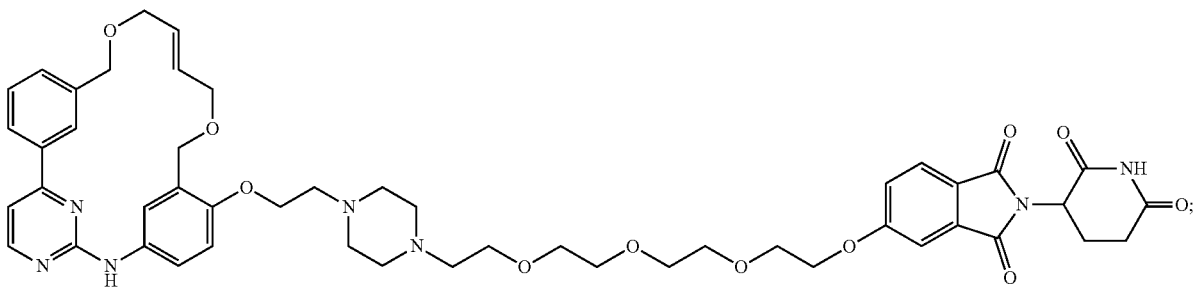

(PROTAC-17)
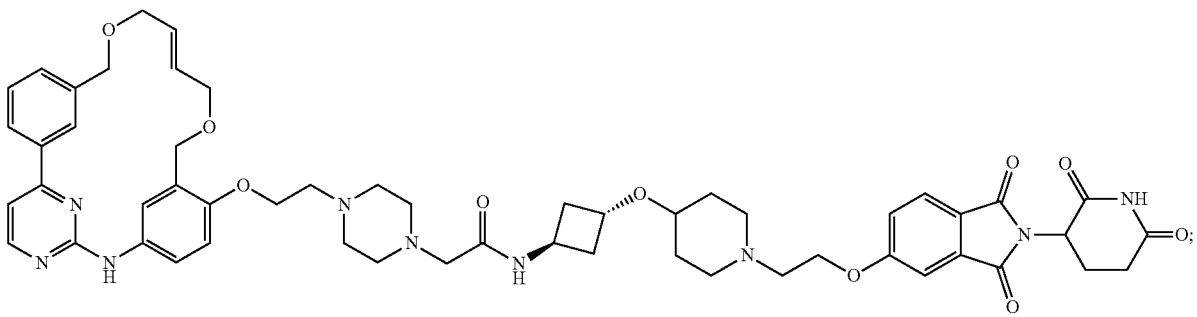
(PROTAC-18)
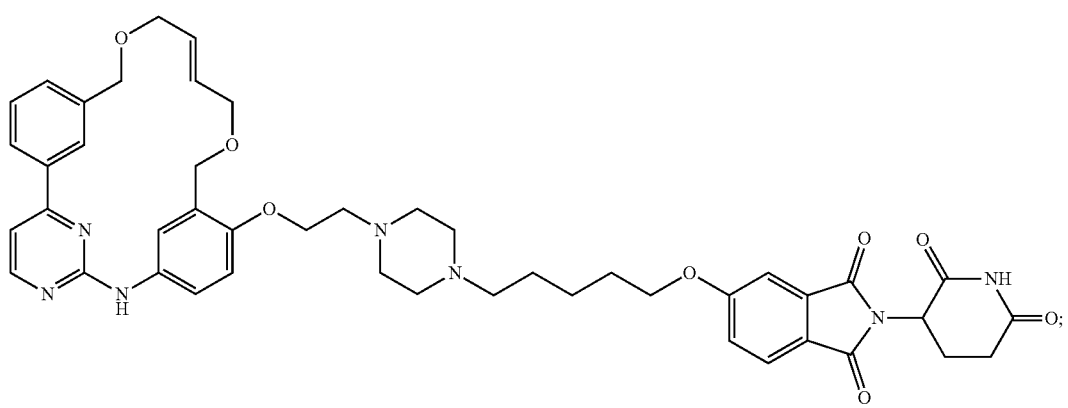
(PROTAC-19)
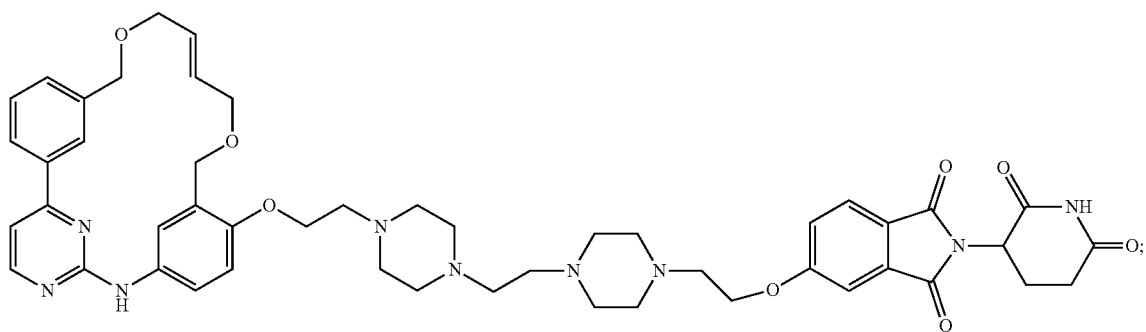
(PROTAC-20)
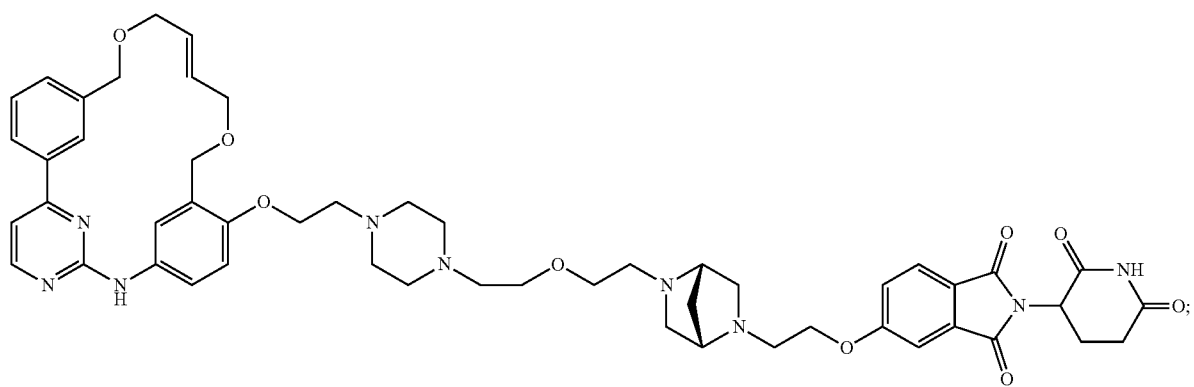

(PROTAC-21)
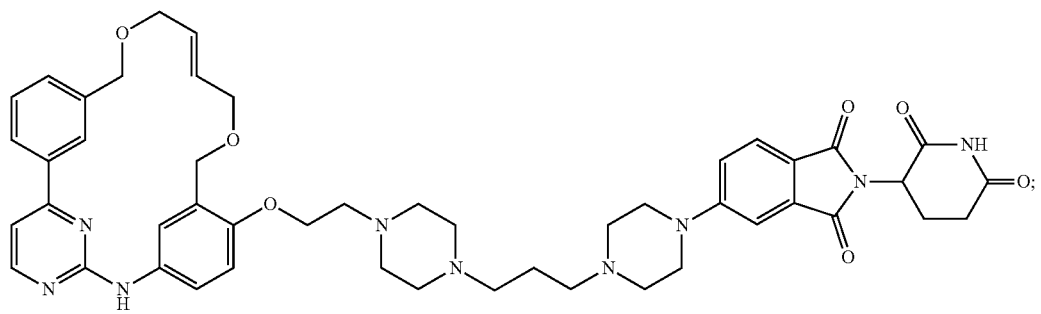
(PROTAC-22)
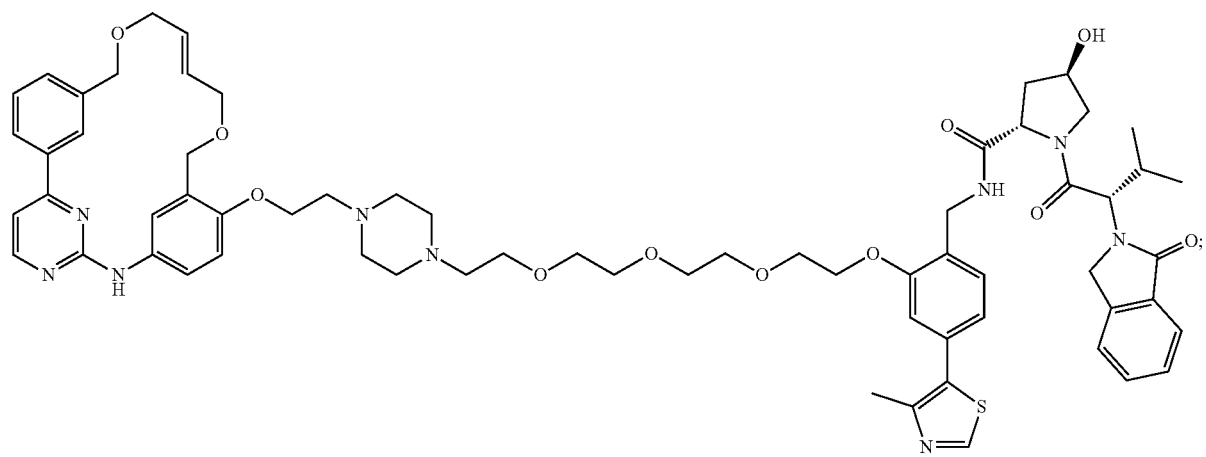
(PROTAC-23)
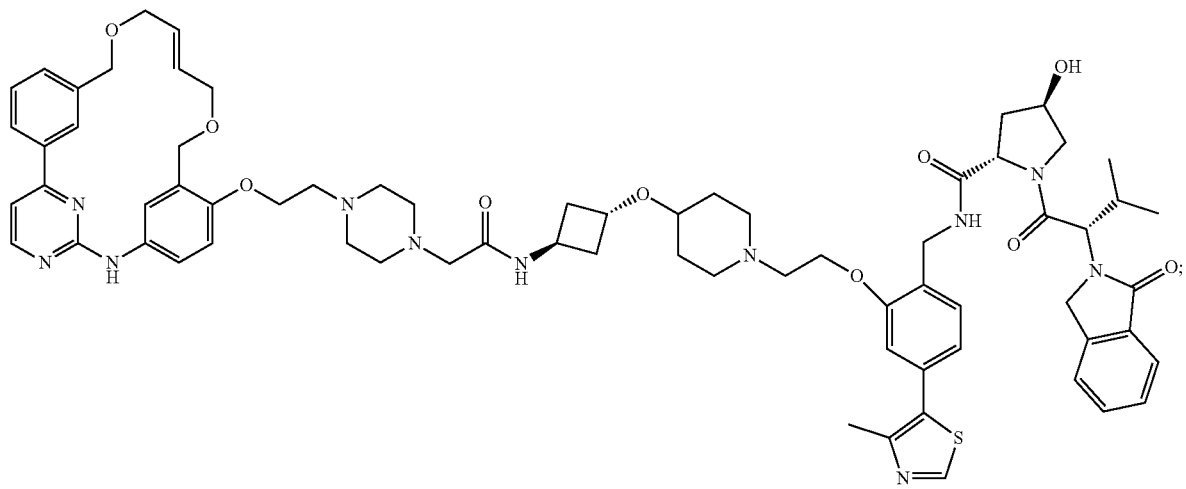

(PROTAC-24)
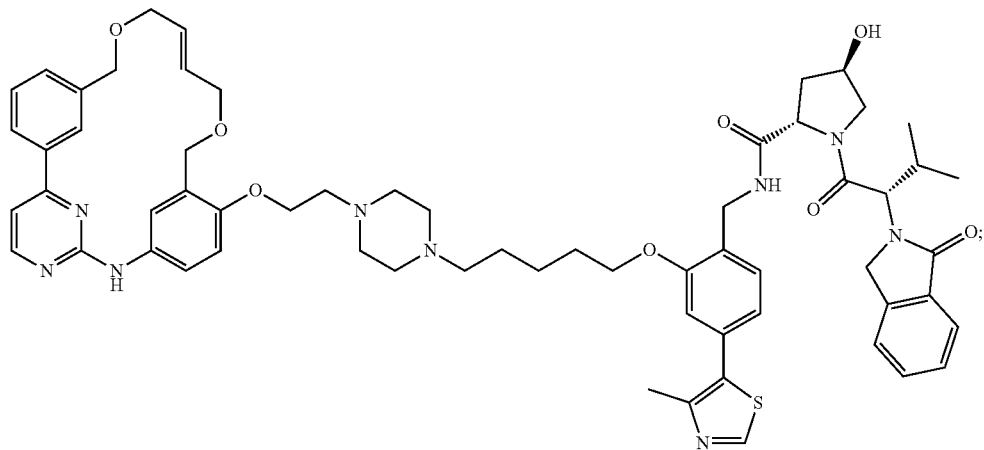
(PROTAC-25)
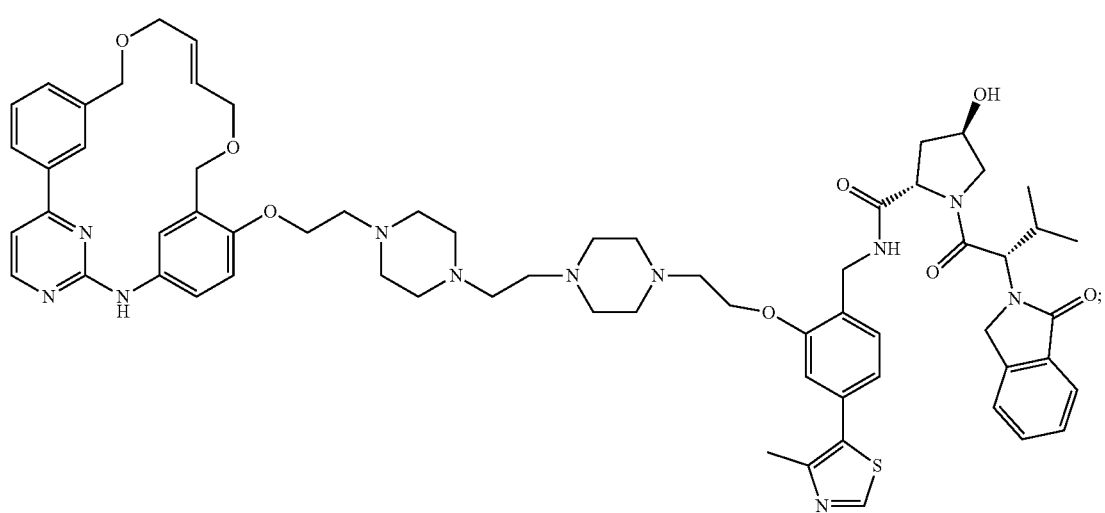
(PROTAC-26)
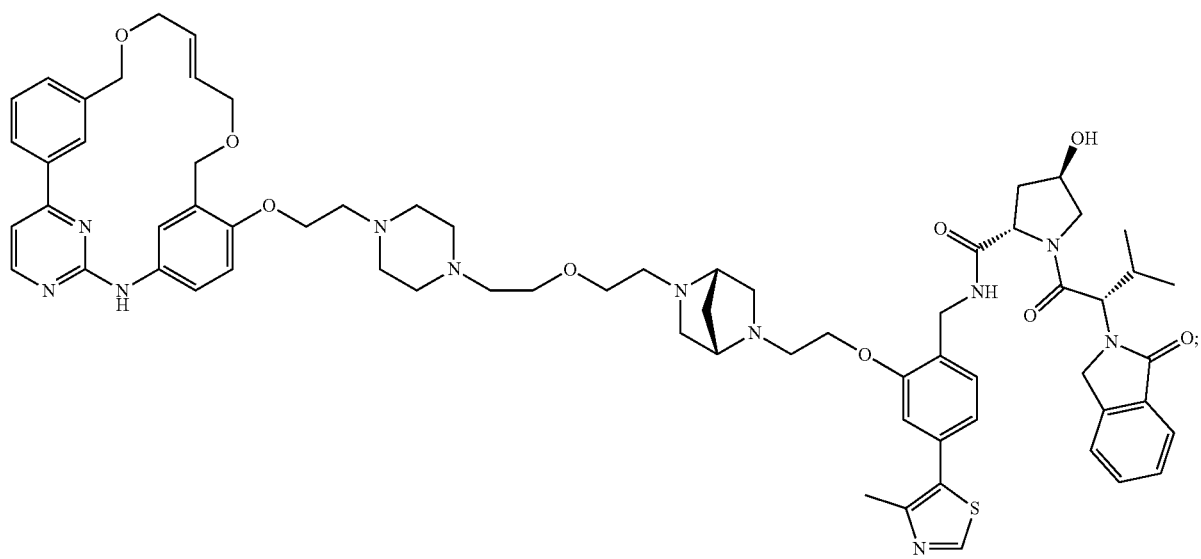

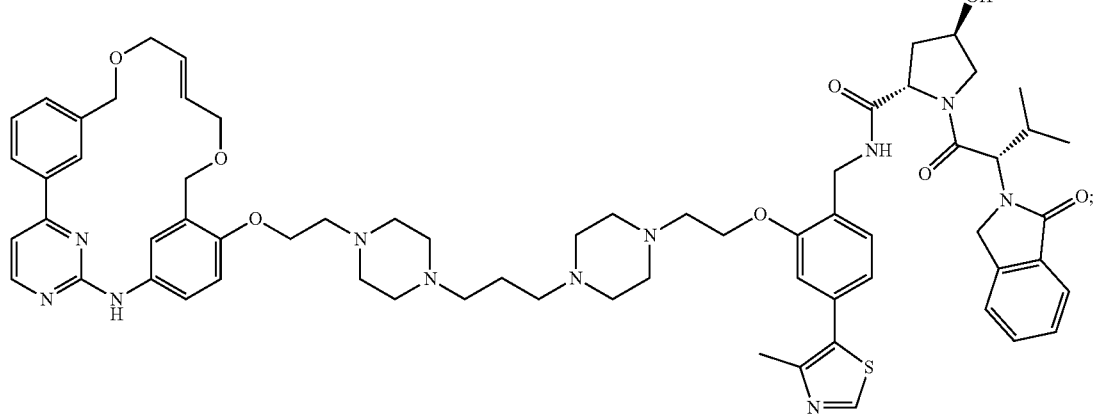
(PROTAC-27)
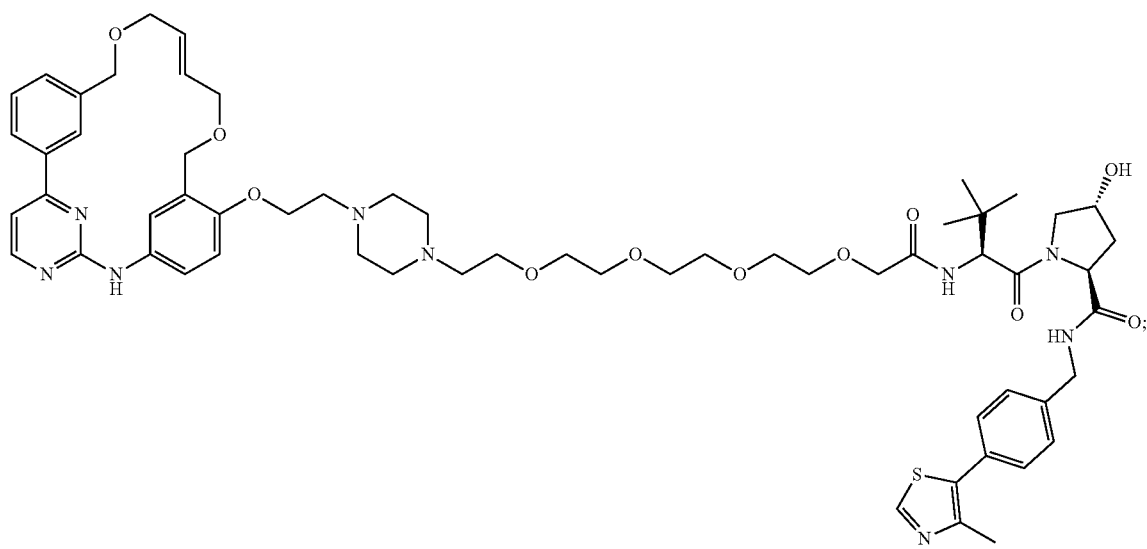
(PROTAC-28)
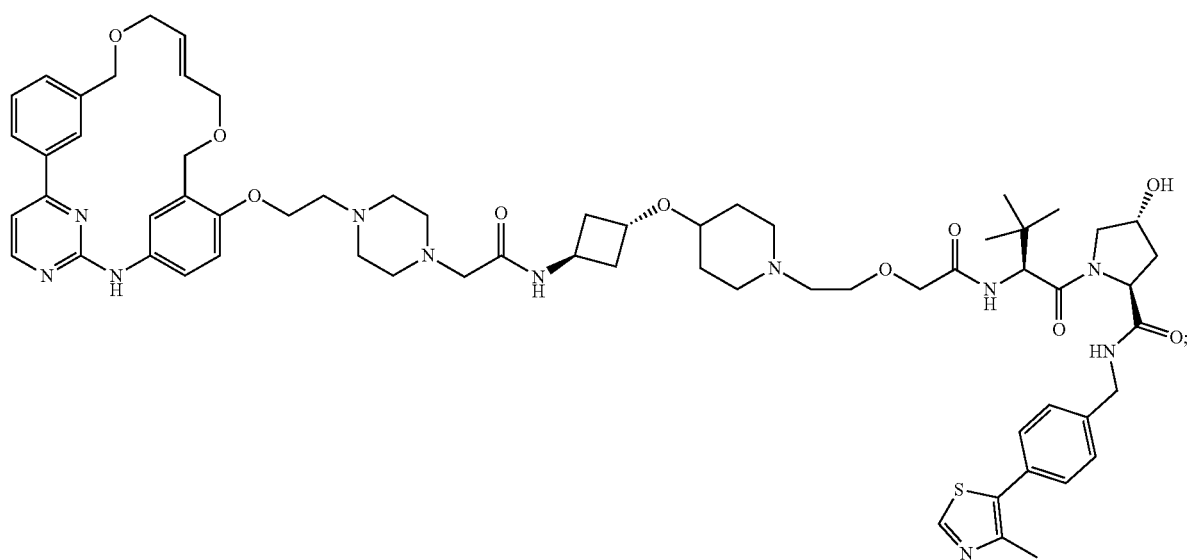
(PROTAC-29)

-continued
(PROTAC-30)
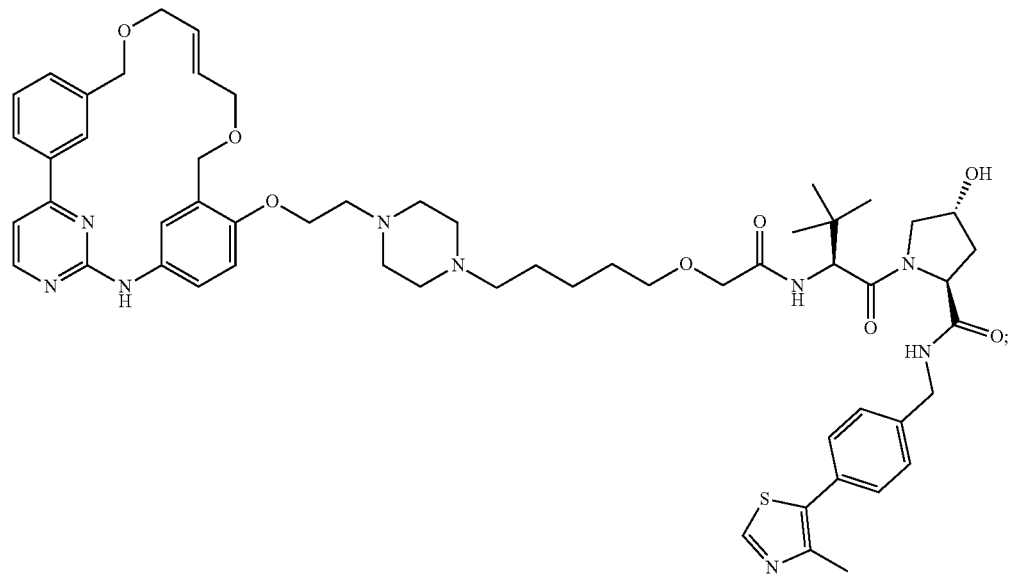
(PROTAC-31)
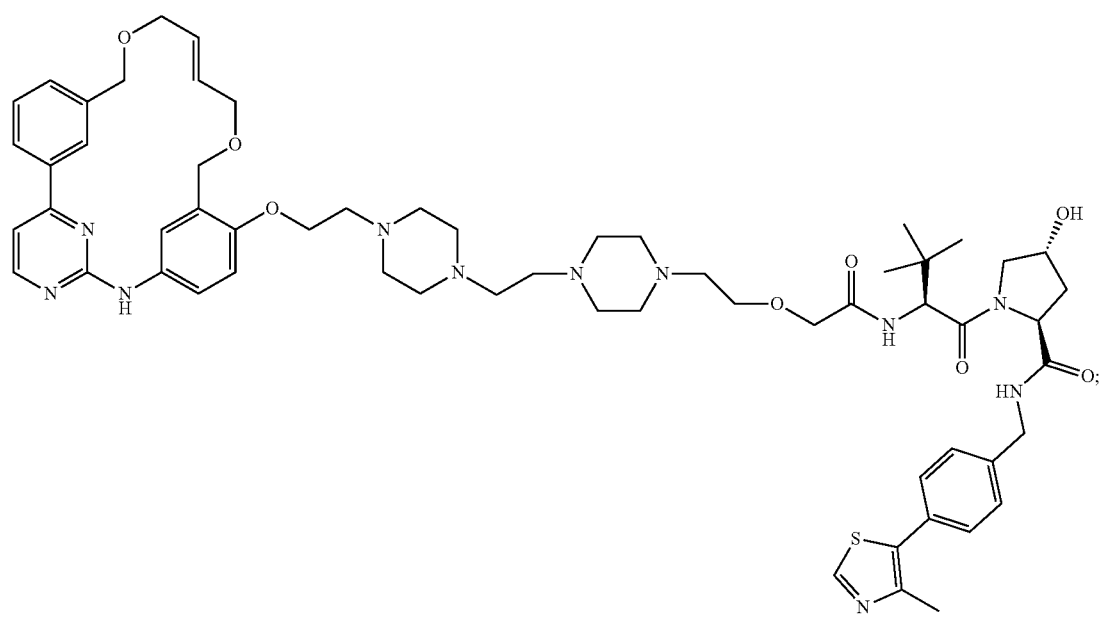

(PROTAC-32)
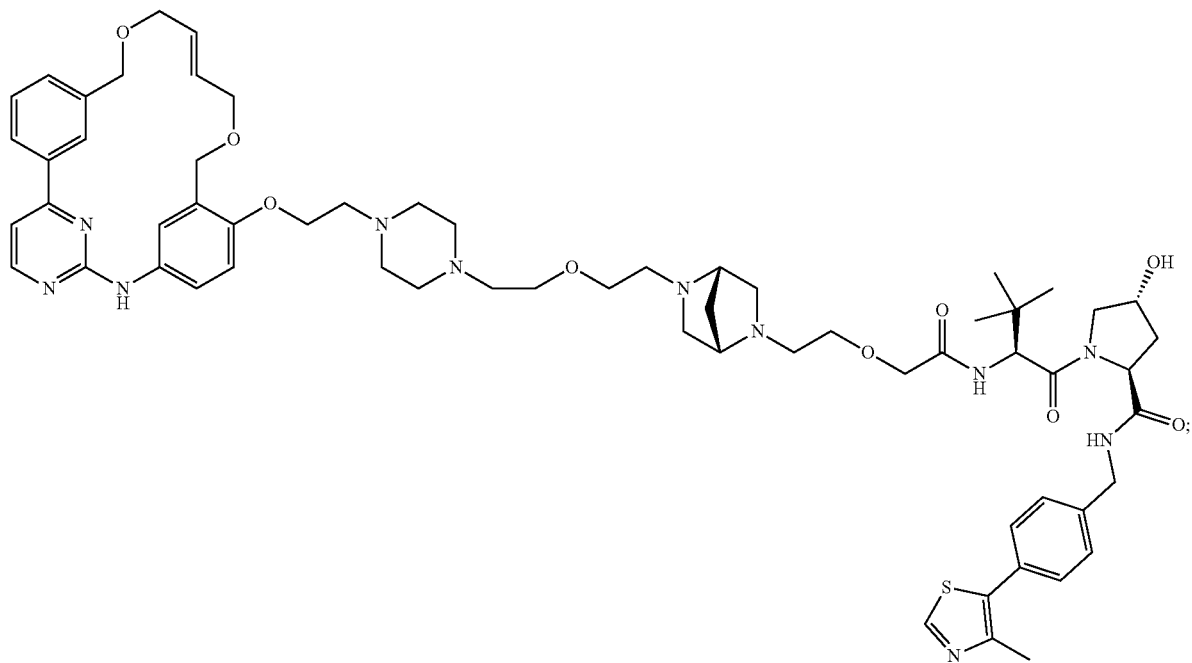
(PROTAC-33)
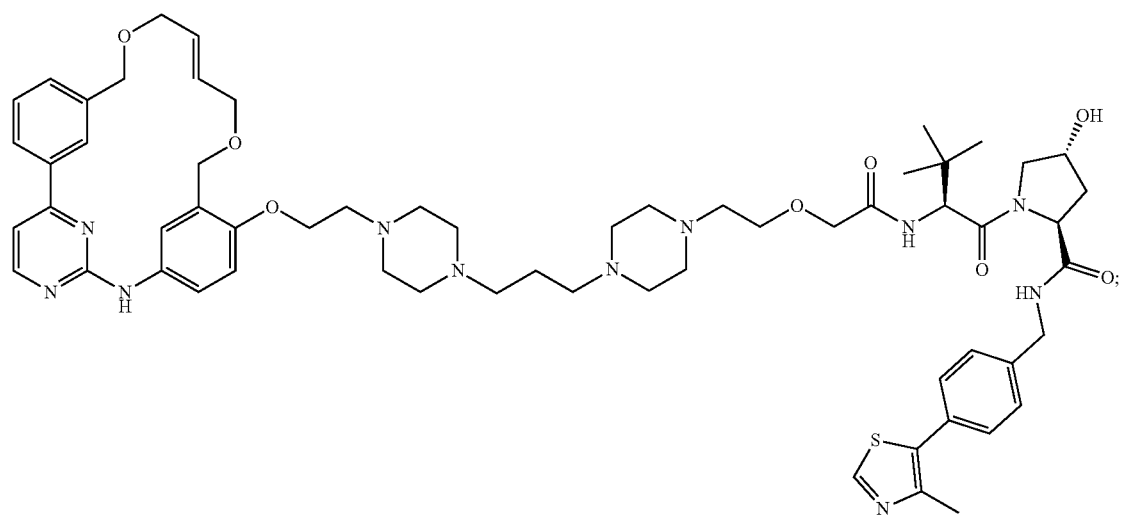

(PROTAC-34)
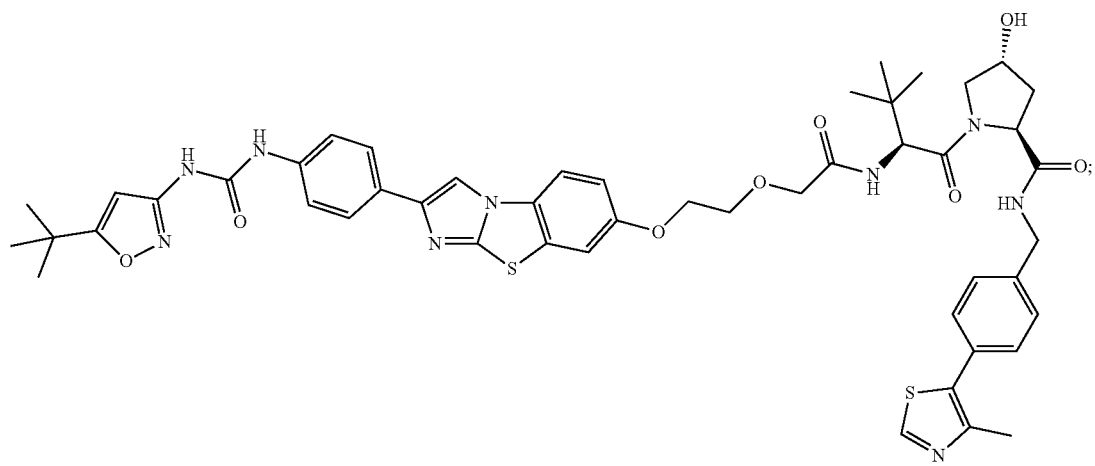
(PROTAC-35)
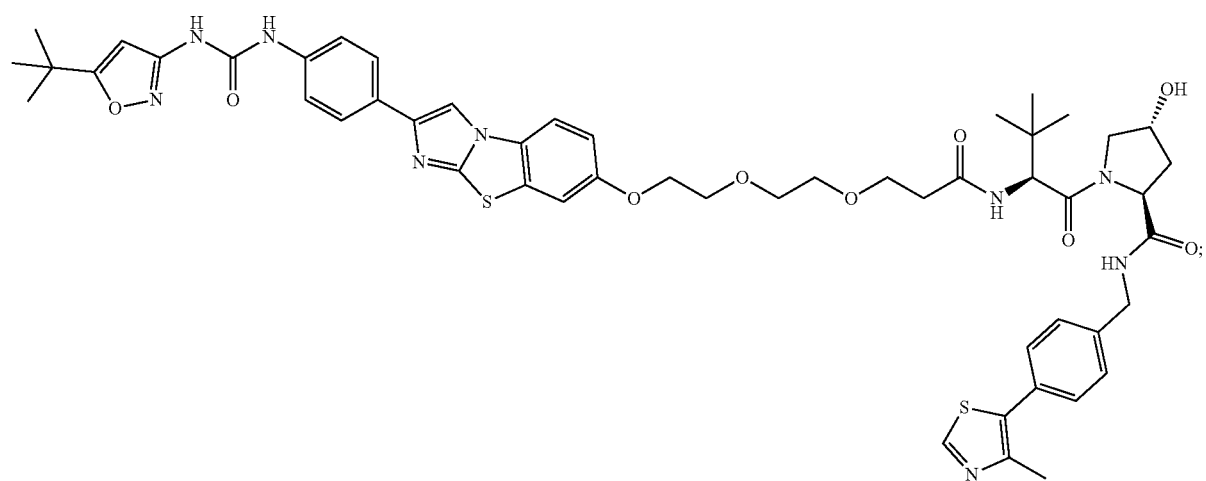
(PROTAC-36)
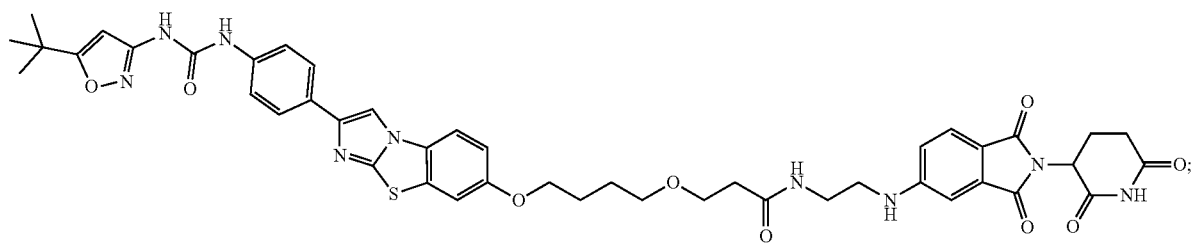

-continued

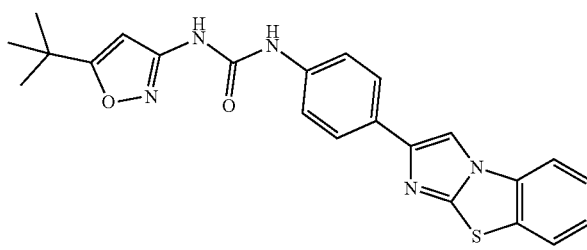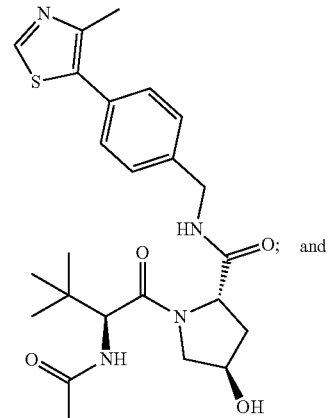

(PROTAC-37)

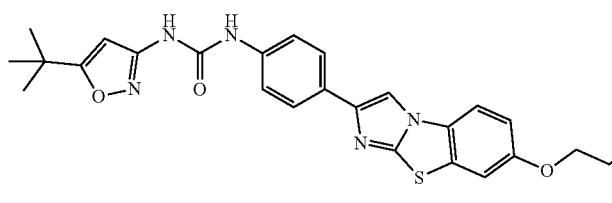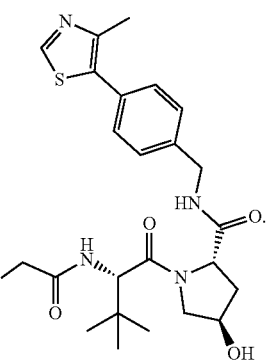

(PROTAC-38)

In certain other embodiments, the description provides exemplary FLT3 PROTAC molecules by selecting a PTM from Table 4 (e.g., a PTM selected from the group consisting of PTM1 through PTM18), a linker from Table 5 (e.g., a linker selected from the group consisting of Linker1 through Linker9), and a ULM from Table 6 (e.g., a linker selected from the group consisting of ULM1 through ULM6), including salts, prodrugs, polymorphs, analogs, derivatives, and deuterated forms thereof:

TABLE 4

Exemplary PTMs

| PTM Number | Chemical Structure |
|---|---|
| PTM1 | 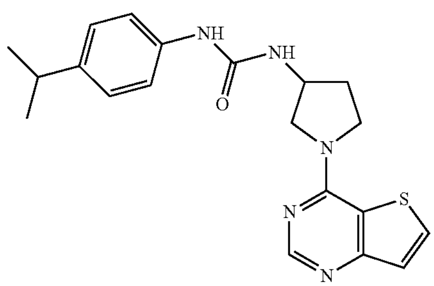 [SMILES: CC(C)c1ccc(NC(=O)NC2CCN(c3ncnc4ccsc34)C2)cc1] |

US 10,806,737 B2
571 572
TABLE 4-continued
Exemplary PTMs
| PTM Number | Chemical Structure |
|---|---|
| PTM2 | 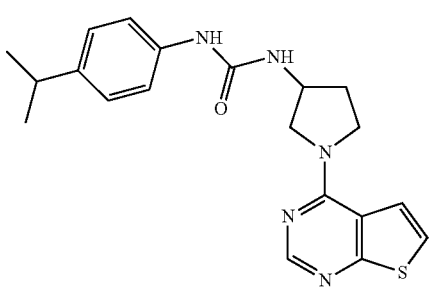 [SMILES: CC(C)c1ccc(NC(=O)NC2CCN(c3ncnc4sccc34)C2)cc1] |
| PTM3 | 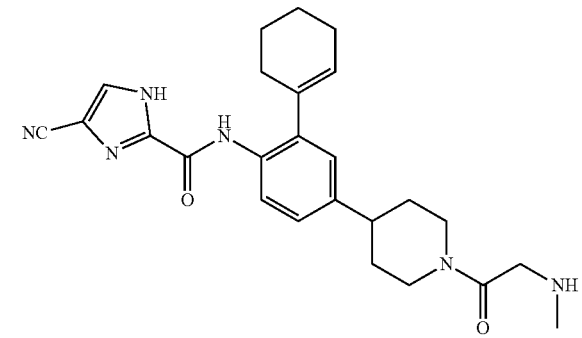 [SMILES: CNCC(=O)N1CCC(c2ccc(NC(=O)c3nc(C#N)c[nH]3)c(C3=CCCCC3)c2)CC1] |
| PTM4 | 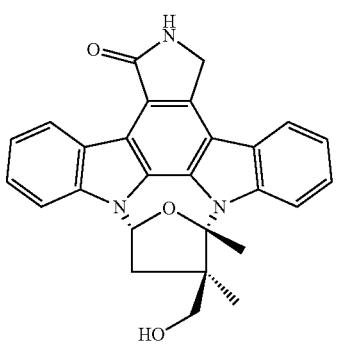 [SMILES: C[C@]1(CO)C[C@H]2O[C@]1(C)n1c3ccccc3c3c4c(c5c6ccccc6n2c5c31)C(=O)NC4] |
| PTM5 | 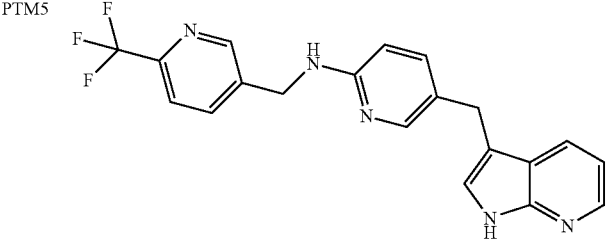 |
| PTM6 | 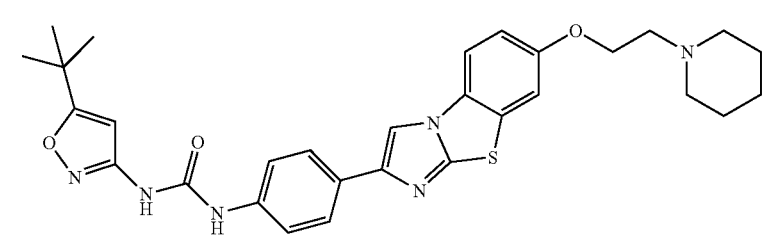 [SMILES: CC(C)(C)c1cc(NC(=O)Nc2ccc(-c3cn4c(n3)sc3cc(OCCN5CCCCC5)ccc34)cc2)no1] |

TABLE 4-continued

Exemplary PTMs

| PTM Number | Chemical Structure |
|---|---|
| PTM7 | 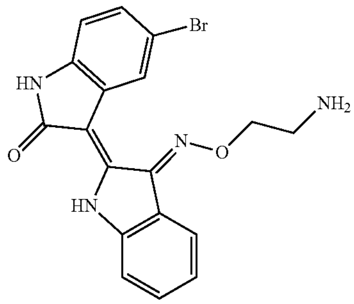 [SMILES: NCCO/N=C1/C(=C2/C(=O)Nc3ccc(Br)cc32)Nc2ccccc21] |
| PTM8 | 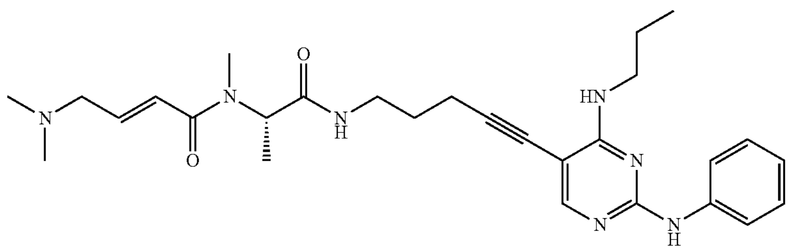 [SMILES: CCCNc1nc(Nc2ccccc2)ncc1C#CCCCNC(=O)[C@H](C)N(C)C(=O)/C=C/CN(C)C] |
| PTM9 | 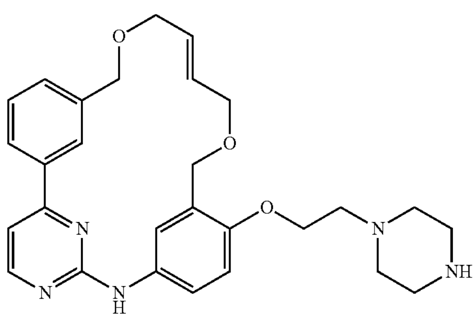 [SMILES: C1=C/COCc2cc(ccc2OCCN2CCNCC2)Nc2nccc(n2)-c2cccc(c2)COC/1] |
| PTM10 | 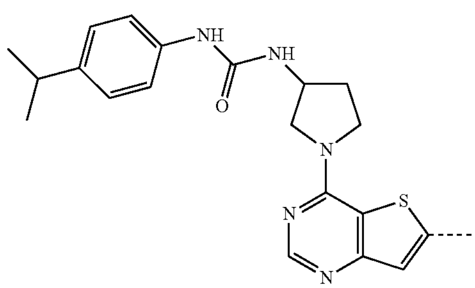 |
| PTM11 | 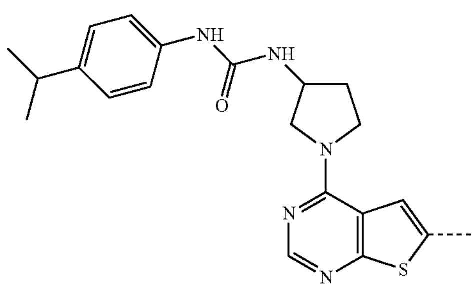 |

TABLE 4-continued
Exemplary PTMs
| PTM Number | Chemical Structure |
|---|---|
| PTM12 | 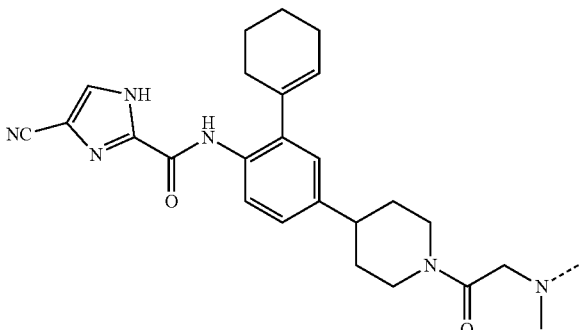 |
| PTM13 | 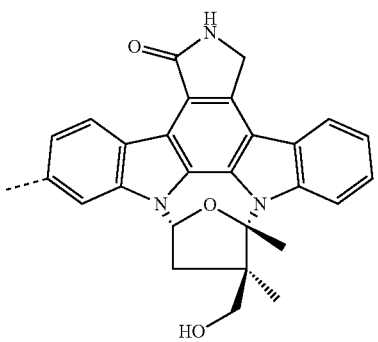 |
| PTM14 | 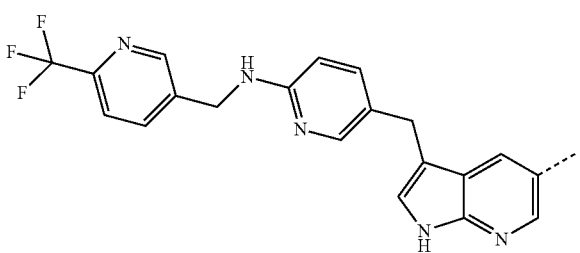 |
| PTM15 | 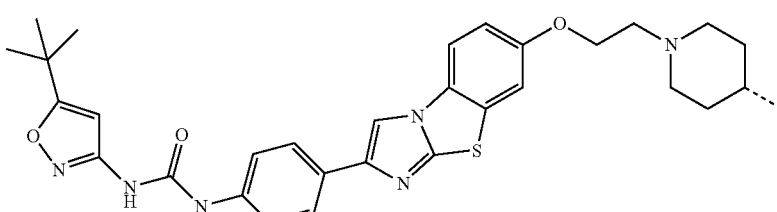 |
| PTM16 | 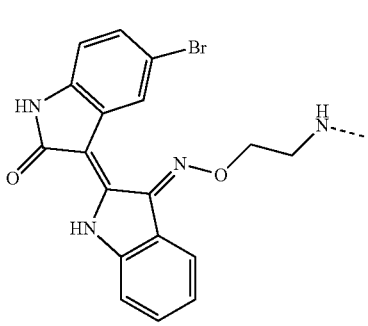 |

TABLE 4-continued
Exemplary PTMs
| PTM Number | Chemical Structure |
|---|---|
| PTM17 | 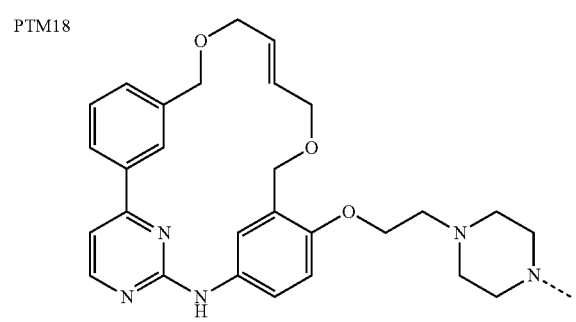 |
| PTM18 | 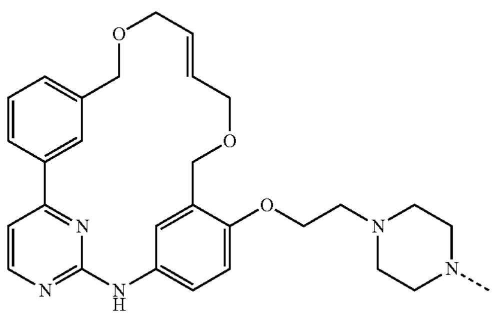 |
TABLE 5
Exemplary Linkers
| Linker Number | Chemical Structure |
|---|---|
| Linker1 | 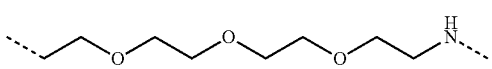 |
| Linker2 | 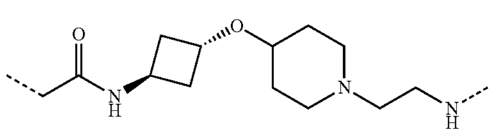 |
| Linker3 | 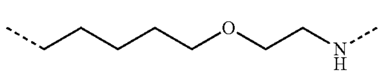 |
| Linker4 | 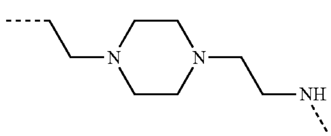 |
| Linker5 | 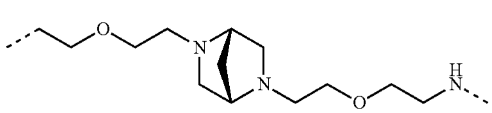 |
TABLE 5-continued
Exemplary Linkers
| Linker Number | Chemical Structure |
|---|---|
| Linker6 | 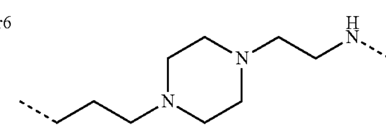 |
| Linker7 | 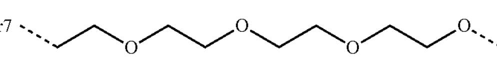 |
| Linker 8 | 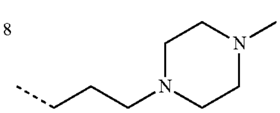 |
| Linker 9 | 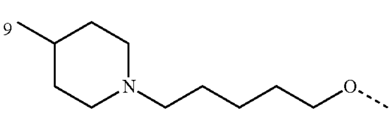 |

TABLE 6

| ULM Number | Structure |
|---|---|
| ULM1 | (structure) |
| ULM2 | (structure) |
| ULM3 | (structure) |
| ULM4 | (structure) |
| ULM5 | (structure) |
| ULM6 | (structure) |

As such, the description provides a compound comprising the structure of any one of compound PROTAC-1 through PROTAC-38, therapeutic compositions comprising the same, and methods of use as described herein.

Additionally, the description provides a compound comprising at least one of a PTM from Table 4 (i.e., a PTM selected from the group consisting of PTM1-PTM18), a linker from Table 5 (i.e., a linker selected from the group consisting of Linker1-Linker9), a ULM from Table 6 (i.e., a ULM selected from the group consisting of ULM1-ULM6), or a combination thereof, including salts, prodrugs, polymorphs, analogs, derivatives, and deuterated forms thereof.

In certain embodiments, the description provides a composition comprising a compound having the structure selected from the group consisting of PROTAC-1 through PROTAC-38, including salts, prodrugs, polymorphs, analogs, derivatives, and deuterated forms thereof.

In other embodiments, the description provides a composition comprising a compound having at least one of a PTM from Table 4 (i.e., a PTM selected from the group consisting of PTM1-PTM18), a linker from Table 5 (i.e., a linker selected from the group consisting of Linker1-Linker9), a ULM from Table 6 (i.e., a ULM selected from the group consisting of ULM1-ULM6), or a combination thereof, including salts, prodrugs, polymorphs, analogs, derivatives, and deuterated forms thereof.

In an aspect, the present disclosure provides a bifunctional compound having the chemical structure:

ULM-L-PTM, or a pharmaceutically acceptable salt, enantiomer, stereoisomer, solvate, polymorph or prodrug thereof, wherein: the ULM is a small molecule E3 ubiquitin ligase binding moiety that binds an E3 ubiquitin ligase; the PTM is a small molecule comprising a FLT3 protein targeting moiety; and the L is a bond or a chemical linking moiety connecting the ULM and the PTM.

In any aspect or embodiment described herein, the E3 ubiquitin ligase binding moiety that targets an E3 ubiquitin ligase selected from the group consisting of Von Hippel-Lindau (VLM), cereblon (CLM), mouse double-minute homolog2 (MLM), and IAP (ILM).

In any aspect or embodiment described herein, the PTM is represented by Formula PTM-I or PTM-II:

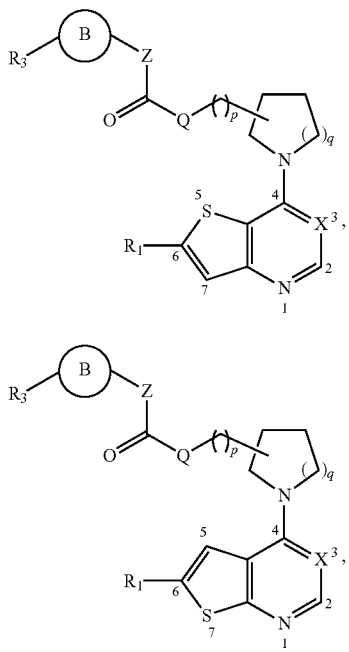

or N-oxides thereof,
wherein:
q of PTM-I or PTM-II is 0, 1 or 2;
p of PTM-I or PTM-II is 0 or 1;
Q of PTM-I or PTM-II is NH, N(alkyl), O, 1 or a direct bond;
X of PTM-I or PTM-II is N or CH;
Z of PTM-I or PTM-II is NH, N(alkyl), or CH2;
B of PTM-I or PTM-II is aryl (wherein said aryl is preferably phenyl), cyclopentadienyl, cycloalkyl (wherein said cycloalkyl is preferably cyclopentanyl, cyclohexanyl, cyclopentenyl or cyclohexenyl), heteroaryl (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or a nine to ten membered benzo-fused heteroaryl (wherein said nine to ten membered benzo-fused heteroaryl is preferably benzothiazolyl, benzooxazolyl, benzoimidazolyl, benzofuranyl, indolyl, quinolinyl, isoquinolinyl, or benzo[b]thiophenyl);
$R_1$ is H,

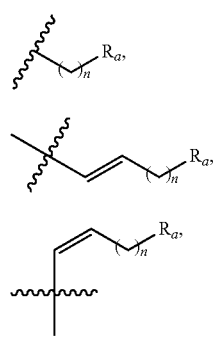

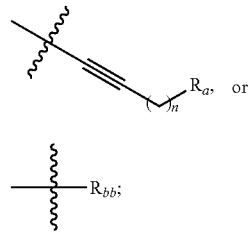

wherein n is 1, 2, 3 or 4;
$R_a$ of PTM-I or PTM-II is hydrogen, heteroaryl optionally substituted with $R_5$ (wherein said heteroaryl is preferably pyrrolyl, furanyl, thiophenyl, imidazolyl, thiazolyl, oxazolyl, pyranyl, thiopyranyl, pyridinyl, pyrimidinyl, triazolyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, triazolyl, or pyrazinyl), hydroxyl, alkylamino, dialkylamino, oxazolidinonyl optionally substituted with $R_5$, pyrrolidinonyl optionally substituted with $R_5$, piperidinonyl optionally substituted with $R_5$, cyclic heterodionyl optionally substituted with $R_5$, heterocyclyl optionally substituted with $R_5$ (wherein said heterocyclyl is preferably pyrrolidinyl, tetrahydrofuranyl, tetrahydrothiophenyl, imidazolidinyl, thiazolidinyl, oxazolidinyl, tetrahydropyranyl, tetrahydrothiopyranyl, thiomorphlinyl, thiomorpholinyl-1, 1-dioxide, piperidinyl, morpholinyl or piperazinyl), —COOR$_y$, —CONR$_w$R$_x$, —N(R$_y$)CON(R$_w$)(R$_x$), —N(R$_w$)C(O)OR$_x$, —N(R$_w$)COR$_y$, —SR$_y$, —SOR$_y$, —SO$_2$R$_y$, —NR$_w$SO$_2$R$_y$, —NR$_w$SO$_2$R$_x$, —SO$_3$R$_y$, or —OSO$_2$NR$_w$R$_x$;
$R_{bb}$ of PTM-I or PTM-II is hydrogen, halogen, aryl, heteroaryl, or heterocyclyl;
$R_5$ of PTM-I or PTM-II is one, two, or three substituents independently selected from: halogen, cyano, trifluoromethyl, amino, hydroxyl, alkoxy, —C(O)alkyl, —SO$_2$alkyl, C(O)N(alkyl)$_2$, alkyl, —C$_{(1-4)}$alkyl-OH, or alkylamino;
$R_w$ and $R_x$ of PTM-I or PTM-II are independently selected from: hydrogen, alkyl, alkenyl, aralkyl (wherein the aryl portion of said aralkyl is preferrably phenyl), or heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or $R_w$ and $R_x$ may optionally be taken together to form a 5 to 7 membered ring, optionally containing a heteromoiety selected from: O, NH, N(alkyl), SO$_2$, SO, or S, preferably selected from the group consisting of:

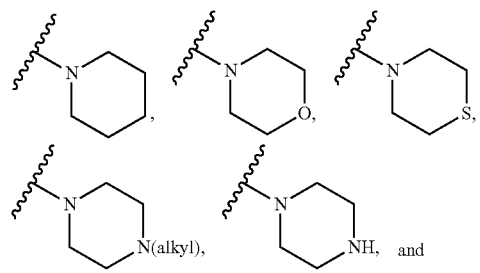

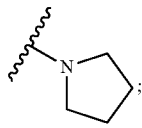

$R_y$ of PTM-I or PTM-II is selected from: hydrogen, alkyl, alkenyl, cycloalkyl (wherein said cycloalkyl is preferably cyclopentanyl or cyclohexanyl), aryl (wherein said aryl is preferably phenyl), aralkyl (wherein the aryl portion of said aralkyl is preferably phenyl), heteroaralkyl (wherein the heteroaryl portion of said heteroaralkyl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl), or heteroaryl (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide, and most preferably pyrrolyl, furanyl, thiophenyl, imidazolyl, thiazolyl, oxazolyl, pyridinyl, pyrimidinyl, or pyrazinyl);

$R_3$ of PTM-I or PTM-II is one or more substituents, optionally present, and independently selected from: alkyl, alkoxy, halogen, alkoxyether, hydroxyl, thio, nitro, cycloalkyl optionally substituted with R4 (wherein said cycloalkyl is preferably cyclopentanyl or cyclohexanyl), heteroaryl optionally substituted with R4 (wherein said heteroaryl is preferably pyrrolyl, furanyl, thiophenyl, imidazolyl, thiazolyl, oxazolyl, pyranyl, thiopyranyl, pyridinyl, pyrimidinyl, pyrazinyl, pyridinyl-N-oxide, or pyrrolyl-N-oxide; and most preferably pyrrolyl, furanyl, thiophenyl, imidazolyl, thiazolyl, oxazolyl, pyridinyl, pyrimidinyl, or pyrazinyl), alkylamino, heterocyclyl optionally substituted with R4 (wherein said heterocyclyl is preferably azapenyl, pyrrolidinyl, tetrahydrofuranyl, tetrahydrothiophenyl, imidazolidinyl, thiazolidinyl, oxazolidinyl, tetrahydropyranyl, tetrahydrothiopyranyl, piperidinyl, morpholinyl, or piperazinyl), partially unsaturated heterocyclyl optionally substituted with $R_4$, (wherein said partially unsaturated heterocyclyl is preferably tetrahydropyridinyl. tetrahydropyrazinyl, dihydrofuranyl, dihydrooxazinyl, dihydropyrrolyl, or dihydroimidazolyl), —O(cycloalkyl), pyrrolidinone optionally substituted with $R_4$, phenoxy optionally substituted with $R_4$, —CN, —OCHF$_2$, —OCF$_3$, —CF$_3$, halogenated alkyl, heteroaryloxy optionally substituted with $R_4$, dialkylamino, —NHSO$_2$alkyl, thioalkyl, or —SO$_2$alkyl; wherein R4 is independently selected from: halogen, cyano, trifluoromethyl, amino, hydroxyl, alkoxy, —C(O)alkyl, —CO$_2$alkyl, —SO$_2$alkyl, —C(O)N(alkyl)$_2$, alkyl, or alkylamino; and the PTM-I or PTM-II is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-III:

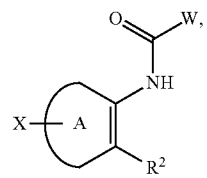

PTM-III wherein:
A of PTM-III is selected from phenyl or pyridyl, either of which may be substituted with one of chloro, fluoro, methyl, —N$_3$, —NH$_2$, —NH(alkyl), —N(alkyl)$_2$, —S(alkyl), O(alkyl), or 4-aminophenyl;

W of PTM-III is selected from pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —Cl, —CN, —NO$_2$, —OMe, or —CF$_3$ substitution, connected to any other carbon;

$R^2$ of PTM-III is selected from cycloalkyl (including cyclohexenyl, cyclopentenyl), thiophenyl, dihydrosulfonopyranyl, phenyl, furanyl, tetrahydropyridyl, or dihydropyranyl, any of which may be independently substituted with one or two of each of the following: chloro, fluoro, and $C_{(1-3)}$alkyl (including 4,4-dimethyl cyclohexenyl, 4-methyl cyclohexenyl, 2-methyl thiophenyl, 3-methyl thiophenyl), with the proviso that tetrahydropyridyl is connected to the ring A through a carbon-carbon bond;

X of PTM-III is selected from:

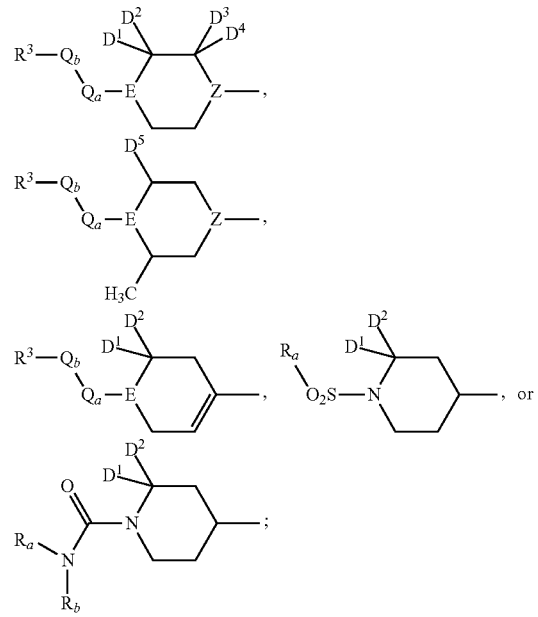

Z of PTM-III is CH or N;
$D^1$ and $D^2$ of PTM-III are each hydrogen or taken together form a double bond to an oxygen;
$D^3$ and $D^4$ of PTM-III are each hydrogen or taken together form a double bond to an oxygen;
$D^5$ of PTM-III is selected from hydrogen or —CH$_3$, wherein said —CH$_3$ may be relatively oriented syn or anti;

$R_a$ and $R_b$ of PTM-III are independently selected from hydrogen, cycloalkyl, haloalkyl, aryl, aralkyl, heteroaryl, or heteroaralkyl; E of PTM-III is selected from N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;

$Q_a$ of PTM-III is selected from being absent, —$CH_2$—, —$CH_2CH_2$—, or C(O);

$Q_b$ of PTM-III is selected from being absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;

$R^3$ of PTM-III is selected from hydrogen, phenyl, hydroxyalkylamino (including 2-hydroxy ethylamino), (hydroxyalkyl)$_2$amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxy eth-2-yl), —COOH, —$CONH_2$, —CN, —$SO_2$-alkyl-$R^4$ (including —$SO_2CH_3$), —$NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); $R^3$ may also be absent, with the proviso that $R^3$ is not absent when E is nitrogen;

$R^4$ of PTM-III is selected from hydrogen, —OH, alkoxy, carboxy, carboxamido, or carbamoyl; and the PTM-III is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-IV:

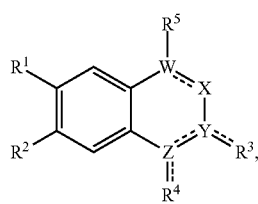

PTM-IV wherein:
W of PTM-IV is C, N, O;
X of PTM-IV can be C, N, absent;
Y of PTM-IV can be C;
Z of PTM-IV can be C, N;

and R groups can be substituted variants of:
$R^1$ of PTM-IV can be H, alkoxy, hydroxyl, heterocyclic alkyl/aryl;
$R^2$ of PTM-IV can be H, F, alkoxy, heterocyclic alkyl/aryl;
$R^3$ of PTM-IV can be H, O, aryl, heteroaryl, C(O) heteroaryl;
$R^4$ of PTM-IV can be H, alkyl, aryl, heteroaryl, CH-heteoaryl, absent;
$R^5$ of PTM-IV can be H, aryl, heteroalkyl/aryl, absent;
the dashed lines between WX, WY, YZ, $YR^3$, and $ZR^4$ of PTM-IV indicating an optionally double bond, wherein the aryl, heteroaryl, heterocyclic alkyl/aryl are optionally substituted; and the PTM-IV is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-V:

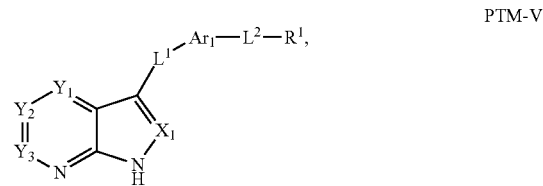

PTM-V wherein:
$X_1$ of PTM-V is N or $CR^2$, $X_2$ is N or $CR^6$, $Y_1$ is N or $CR^4$, and $Y_2$ is N or $CR^5$, provided, however, that not more than one of $X_2$, $Y_1$ and $Y_2$ is N;

$L^1$ of PTM-V is selected from the group consisting of optionally substituted lower alkylene, —S—, —O—, —C(O)—, —C(S)—, —S(O)—, —S(O)$_2$—, and —$NR^7$—;

$L^2$ of PTM-V is selected from the group consisting of a bond, optionally substituted lower alkylene, -(alk)$_a$-S-(alk)$_b$-, -(alk)$_a$-O-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)-(alk)$_b$-, -(alk)$_a$-C(S)-(alk)$_b$-, -(alk)$_a$-C(O)NR$^9$-(alk)$_b$-, -(alk)$_a$-OC(O)NR$^9$-(alk)$_b$-, -(alk)$_a$-OC(S)NR$^9$-(alk)$_b$-, -(alk)$_a$-C(S)NR$^9$-(alk)$_b$-, -(alk)$_a$-S(O)-(alk)$_b$-, -(alk)$_a$-S(O)$_2$-(alk)$_b$-, -(alk)$_a$-S(O)$_2$NR$^9$-(alk)$_b$-, -(alk)$_a$-NR$^9$-(alk)$_b$-, -(alk)$_a$-NR$^9$C(O)-(alk)$_b$-, -(alk)$_a$-NR$^9$C(S)-(alk)$_b$-, -(alk)$_a$-NR$^9$C(O)NR$^9$-(alk)$_b$-, -(alk)$_a$-NR$^9$C(S)NR$^9$-(alk)$_b$-, -(alk)$_a$-NR$^9$C(O)O-(alk)$_b$-, -(alk)$_a$-NR$^9$C(S)O-(alk)$_b$-, -(alk)$_a$-NR$^9$S(O)$_2$-(alk)$_b$-, and -(alk)$_a$-NR$^9$S(O)$_2$NR$^9$-(alk)$_b$-, wherein alk is optionally substituted $C_{1-3}$ alkylene and a and b are independently 0 or 1;

$R^1$ of PTM-V is selected from the group consisting of optionally substituted lower alkyl, optionally substituted cycloalkyl, optionally substituted heterocloalkyl, optionally substituted aryl, and optionally substituted heteroaryl;

$R^2$, $R^4$, $R^5$ and $R^6$ of PTM-V are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —$NH_2$, —$NO_2$, —CN, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —NR$^{10}$R$^{11}$, —NHR$^3$, —OR$^3$, —SR$^3$, —C(O)R$^3$, —C(S)R$^3$, —S(O)R$^3$, —S(O)$_2$R$^3$, —C(O)OR$^3$, —C(S)OR$^3$, C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OH, —NR$^3$C(O)OR$^3$, —NHC(S)OR$^3$, —NR$^3$C(S)OH, —NR$^3$C(S)OR$^3$, —NHC(O)NHR$^3$, —NHC(O)NR$^3$R$^3$, —NR$^3$C(O)NH$_2$, —NR$^3$C(O)NHR$^3$, —NR$^3$C(O)NR$^3$R$^3$, —NHC(S)NHR$^3$, —NHC(S)NR$^3$R$^3$, —NR$^3$C(S)NH$_2$, —NR$^3$C(S)NHR$^3$, —NR$^3$C(S)NR$^3$R$^3$, —NHS(O)$_2$NHR$^3$, —NHS(O)$_2$NR$^3$R$^3$, NR$^3$S(O)$_2$NH$_2$, —NR$^3$S(O)$_2$NHR$^3$, and —NR$^3$S(O)$_2$NR$^3$R$^3$;

Ar$_1$ of PTM-V is a 5 or 6 membered optionally substituted heteroarylene having the structure

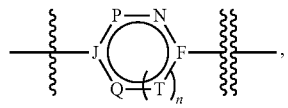

wherein

indicates the point of attachment of L$^1$ and

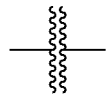

indicates the point of attachment of L$^2$, and wherein the indicated N is either =N— or —N=;
n of PTM-V is 0 or 1;
F and J of PTM-V are both C or one of F and J is C and the other of F and J is N;
P and Q of PTM-V are independently selected from CR, N, NR, O or S;
T of PTM-V is selected from CR or N;
wherein:
 when n is 1, F and J are C, and P, T and Q are CR, or any one of P, T and Q is N and the other two of P, T and Q are CR,
 when n is 0 and F and J are both C, then one of P and Q are CR, N or NR and the other of P and Q is C, N, NR, O or S, provided both P and Q are not CR,
 when n is 0, one of F and J is N and the other of F and J is C, then one of P and Q is N and the other of P and Q is CR or both P and Q are CR, and
R of PTM-V is hydrogen or an optional substituent as defined herein for optionally substituted heteroarylene that provides a stable compound;
R$^3$ of PTM-V at each occurrence is independently selected from the group consisting of optionally substituted lower alkyl, optionally substituted lower alkenyl, provided, however, that no alkene carbon thereof is bound to any —C(O)—, —C(S)—, —S(O)—, —S(O)$_2$—, —O—, —S—, or —N— of any of —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHR$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OH, —NR$^3$C(O)OR$^3$, —NHC(S)OR$^3$, —NR$^3$C(S)OH, —NR$^3$C(S)OR$^3$, —NHC(O)NHR$^3$, —NHC(O)NR$^3$R$^3$, —NR$^3$C(O)NH$_2$, —NR$^3$C(O)NHR$^3$, —NR$^3$C(O)NR$^3$R$^3$, —NHC(S)NHR$^3$, —NHC(S)NR$^3$R$^3$, —NR$^3$C(S)NH$_2$, —NR$^3$C(S)NHR$^3$, —NR$^3$C(S)NR$^3$R$^3$, —NHS(O)$_2$NHR$^3$, —NHS(O)$_2$NR$^3$R$^3$, —NR$^3$S(O)$_2$NH$_2$, —NR$^3$S(O)$_2$NHR$^3$, or —NR$^3$S(O)$_2$NR$^3$R$^3$, optionally substituted lower alkynyl, provided, however, that no alkyne carbon thereof is bound to any —C(O)—, —C(S)—, —S(O)—, —S(O)$_2$—, —O—, —S—, or —N— of any of —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHR$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OH, —NR$^3$C(O)OR$^3$, —NHC(S)OR$^3$, —NR$^3$C(S)OH, —NR$^3$C(S)OR$^3$, —NHC(O)NHR$^3$, —NHC(O)NR$^3$R$^3$, —NR$^3$C(O)NH$_2$, —NR$^3$C(O)NHR$^3$, —NR$^3$C(O)NR$^3$R$^3$, —NHC(S)NHR$^3$, —NHC(S)NR$^3$R$^3$, —NR$^3$C(S)NH$_2$, —NR$^3$C(S)NHR$^3$, —NR$^3$C(S)NR$^3$R$^3$, —NHS(O)$_2$NHR$^3$, —NHS(O)$_2$NR$^3$R$^3$, —NR$^3$S(O)$_2$NH$_2$, —NR$^3$S(O)$_2$NHR$^3$, or —NR$^3$S(O)$_2$NR$^3$R$^3$, optionally substituted cycloalkyl, optionally substituted heterocycloalkyl, optionally substituted aryl, and optionally substituted heteroaryl;

R$^7$ of PTM-V is selected from the group consisting of hydrogen, optionally substituted lower alkyl, optionally substituted cycloalkyl, optionally substituted heterocycloalkyl, optionally substituted aryl, optionally substituted heteroaryl, —C(O)R$^8$, and —S(O)$_2$R$^8$;

R$^8$ of PTM-V is selected from the group consisting of optionally substituted lower alkyl, optionally substituted cycloalkyl, optionally substituted heterocycloalkyl, optionally substituted aryl and optionally substituted heteroaryl;

R$^9$ of PTM-V at each occurrence is independently selected from the group consisting of hydrogen, lower alkyl, and lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —NR$^{12}$R$^{13}$, provided, however, that when R$^9$ is substituted lower alkyl, any substitution on the alkyl carbon bound to the —N— of NR$^9$— is fluoro;

R$^{10}$ and R$^{11}$ of PTM-V at each occurrence are independently selected from the group consisting of optionally substituted lower alkyl, optionally substituted lower alkenyl, provided, however, that no alkene carbon thereof is bound to the nitrogen of NR$^{10}$R$^{11}$ optionally substituted lower alkynyl, provided, however, that no alkyne carbon thereof is bound to the nitrogen of —NR$^{10}$R$^{11}$, optionally substituted cycloalkyl, optionally substituted heterocycloalkyl, optionally substituted aryl, and optionally substituted heteroaryl; or R$^{10}$ and R$^{11}$ of PTM-V together with the nitrogen to which they are attached form a monocyclic 5-7 membered optionally substituted heterocycloalkyl or a monocyclic 5 or 7 membered optionally substituted nitrogen containing heteroaryl;

R[12] and R[13] of PTM-V combine with the nitrogen to which they are attached to form a 5-7 membered heterocycloalkyl or 5-7 membered heterocycloalkyl substituted with one or more substituents selected from the group consisting of fluoro, —OH, —NH$_2$, lower alkyl, fluoro substituted lower alkyl, lower alkoxy, fluoro substituted lower alkoxy, lower alkylthio, and fluoro substituted lower alkylthio; and the PTM-V is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-VI:

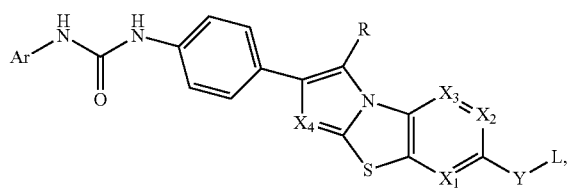

PTM-VI wherein:
Ar of PTM-VI is selected from the group consisting of optionally substituted or unsubstituted aryl, and optionally substituted or unsubstituted heteroaryl, when substituted, the substituents could be one or more groups independently selected from halogen, alkyl, haloalkyl, or hydroxyl alkyl;

L of PTM-VI is H, optionally substituted or unsubstituted alkyl, optionally substituted or unsubstituted cycloalkyl, optionally substituted or unsubstituted cycloalkylalkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkylalkyl, optionally substituted or unsubstituted heteroaryl or optionally substituted or unsubstituted heteroarylalkyl; when substituted, the substituents can be one or more groups independently selected from the group consisting of halo, alkyl, haloalkyl, cycloalkyl, cycloalkylalkyl, heterocycloalkyl, heterocycloalkylalkyl, amino, aminoalkyl, amido, aminocarbonyl, sulfonamido, ureido, cyano, acetyl, acyl, carboxylic acid, hydroxyl, hydroxylalkyl, alkoxyl, —NHalkylhydroxyl, —NHalkoxyalkyl, —NHalkylamino, —NHcycloalkyl, —NHcycloalkylalkyl, —N Hheterocycloalkyl, —NH heterocycloalkylalkyl, —NHaryl, —NHarylalkyl, —NHheteroaryl, or —NHheteroarylalkyl;

Y of PTM-VI is O, S, NR$_2$R$_2$', or a direct bond (that means L directly connected with the left heteroaryl);

X$_1$, X$_2$, X$_3$ and X$_4$ of PTM-VI are independently N or CR$_1$,

R$_1$ of PTM-VI is H, or —Y-L;

R, R$_2$ and R$_2$' of PTM-VI are each independently selected from the group consisting of hydrogen, alkyl, cycloalkyl, aryl, heteroaryl, haloalkoxyl, hydroxyl, amino, aminocarbonyl, sulfonamido, cyano, alkynyl, alkoxyl, aryloxyl, carboxylic acid, carboxylic ester or halogen, or R$_2$, R$_2$' together with the nitrogen atom to which they are attached, form a 3- to 7-membered heterocycloalkyl ring, and the hetero atom could be selected from at least one of O, S or N atoms. The 3- to 7-membered heterocycloalkyl ring could be further optionally substituted with a group independently selected from alkyl, cycloalkyl, methylsulfonyl, ureido, acyl, amido, aminocarbonyl, alkylamino, alkylhydroxyl, heterocycloalkyl, aryl, or heteroaryl. Preferably R$_2$, R$_2$' and the N could be formed a heterocycle such as

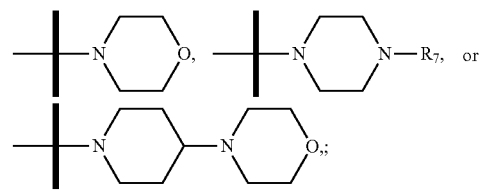

and
R$_7$ of PTM-VI is independently selected from H, methylsulfonyl, lower alkyl, that is C$_1$-C$_6$ straight chain and branched chain alkyl, such as methyl, ethyl, propyl, 2-propyl, n-butyl, iso-butyl, tert-butyl, pentyl, neopentyl, hexyl, isohexyl; and the PTM-VI is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-VII:

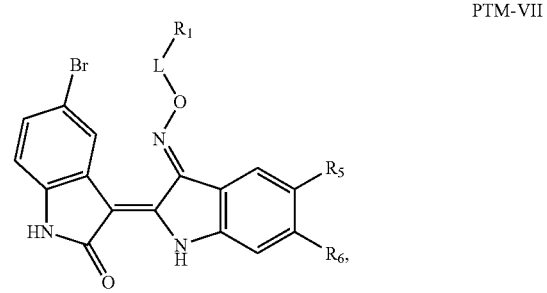

PTM-VII wherein:
L of PTM-VII is a bond, substituted or unsubstituted alkylene, or substituted or unsubstituted heteroalkylene;

R$^1$ of PTM-VII is hydrogen, halogen, —CF$_3$, —CCl$_3$, —CBr$_3$, —CI$_3$, —OCF$_3$, —OCCl$_3$, —OCBr$_3$, —OCl$_3$, —CN, —OH, —NH$_2$, —COOH, —C(O)OR$_4$, —CONH$_2$, —NO$_2$, —SH, —NHNH$_2$, —NR$^2$R$^3$, —OR$^4$, —SR$^4$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. R$^2$ and R$^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R$_2$ and R$_3$ of PTM-VII are optionally joined together to form a substituted or unsubstituted heterocycloalkyl or substituted or unsubstituted heteroaryl. R$^4$ of PTM-VII is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R_5$ and $R_6$ of PTM-VII are independently hydrogen, halogen, —$CF_3$, —$CCl_3$, —$CBr_3$, —$CI_3$, —$OCF_3$, —$OCCl_3$, —$OCBr_3$, —$OCl_3$, —CN, —OH, —$NH_2$, —COOH, —C(O)$OR_9$, —$CONH_2$, —$NO_2$, —SH, —$NHNH_2$, —$NR^7R^8$, —$OR^9$, —$SR^9$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^7$ and $R^8$ of PTM-VII are independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl, or $R^7$ and $R^8$ are optionally joined together to form a substituted or unsubstituted heterocycloalkyl or substituted or unsubstituted heteroaryl;

$R^9$ of PTM-VII is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and the PTM-VII is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-VIII:

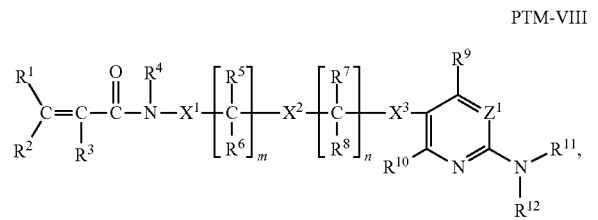

PTM-VIII wherein:
$R^1$ of PTM-VIII is a hydrogen atom or a substituted or unsubstituted $C_{1-6}$ alkyl group;

$R^2$ of PTM-VIII is a hydrogen atom, a substituted or unsubstituted $C_{1-6}$ alkyl group, a substituted or unsubstituted $C_{2-6}$ alkenyl group, or a substituted or unsubstituted $C_{2-6}$ alkynyl group;

$R^3$ of PTM-VIII is a hydrogen atom or a substituted or unsubstituted $C_{1-6}$ alkyl group, a substituted or unsubstituted $C_{2-6}$ alkenyl group, or a substituted or unsubstituted $C_{2-6}$ alkynyl group;

or $R^2$ and $R^3$ of PTM-VIII may bind together to form an atomic bond;

$R^4$ of PTM-VIII is a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, or an imino protecting group;

m of $R^5$ of PTM-VIII are the same or different, and is a hydrogen atom or a substituted or unsubstituted $C_{1-6}$ alkyl group;

m of $R^6$ of PTM-VIII are the same or different, and is a hydrogen atom or a substituted or unsubstituted $C_{1-6}$ alkyl group;

or $R^5$ and $R^6$ of PTM-VIII binding to the same carbon atom may bind together to form: a substituted or unsubstituted $C_{2-6}$ alkylene group; an substituted or unsubstituted O—($C_{1-6}$ alkylene) group, a substitute or unsubstituted N($R^{13}$)—($C_{1-6}$ alkylene) group, wherein $R^{13}$ is a hydrogen atom, a substituted or unsubstituted $C_{1-6}$ alkyl group or an imino protecting group; a substituted or unsubstituted ($C_{1-3}$ alkylene)-O—($C_{1-3}$ alkylene) group; a substitute or unsubstituted ($C_{1-3}$ alkylene)-N($R^{13}$)—($C_{1-3}$ alkylene) group, wherein $R^{13}$ is a hydrogen atom, a substituted or unsubstituted $C_{1-6}$ alkyl group or an imino protecting group;

n of $R^7$ of PTM-VIII are the same or different, and is a hydrogen atom or a substitute or unsubstituted $C_{1-6}$ alkyl group;

n of $R^8$ of PTM-VIII are the same or different, and is a hydrogen atom or a substitute or unsubstituted $C_{1-6}$ alkyl group;

or $R^7$ and $R^8$ of PTM-VIII binding to the same carbon atom may bind together to form: a substituted or unsubstituted $C_{2-6}$ alkylene group; an substituted or unsubstituted O—($C_{1-6}$ alkylene) group; a substituted or unsubstituted N($R^{14}$)—($C_{1-6}$ alkylene) group, wherein $R^{14}$ is a hydrogen atom, a substituted or unsubstituted $C_{1-6}$ alkyl group, or an imino protecting group; a substituted or unsubstituted ($C_{1-3}$ alkylene)-O—($C_{1-3}$ alkylene) group; or a substituted or unsubstituted ($C_{1-3}$ alkylene)-N($R^{14}$)—($C_{1-3}$ alkylene) group which may be substituted, wherein $R^{14}$ is a hydrogen atom, a substituted or unsubstituted $C_{1-6}$ alkyl group, or an imino protecting group;

$R^9$ of PTM-VIII is: a substituted or unsubstituted $C_{1-6}$ alkyl group; a substituted or unsubstituted $C_{3-8}$ cycloalkyl; a substituted or unsubstituted aryl group; a substituted or unsubstituted $C_{1-6}$ alkoxy group; a substituted or unsubstituted heterocyclic group; N($R^{15}$)($R^{16}$) wherein $R^{15}$ is a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, or a substituted or unsubstituted $C_{3-8}$ cycloalkyl group, and $R^{16}$ is a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, a substituted or unsubstituted aryl group, or a substituted or unsubstituted heterocyclic group, or $R^{15}$ and $R^{16}$ may form a substituted or unsubstituted cyclic amino group together with the nitrogen atom to which they bind;

$R^{10}$ of PTM-VIII is a hydrogen atom, a halogen atom, a substituted or unsubstituted $C_{1-6}$ alkyl group, a substituted or unsubstituted $C_{3-8}$ cycloalkyl group, a substituted or unsubstituted aryl group, a substituted or unsubstituted $C_{1-6}$ alkoxy group, or a substituted or unsubstituted heterocyclic group;

$R^{11}$ of PTM-VIII is a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, or a substituted or unsubstituted $C_{3-8}$ cycloalkyl group;

$R^{12}$ of PTM-VIII is a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group, a substituted or unsubstituted aryl group, a substituted or unsubstituted heterocyclic group, or a substituted or unsubstituted carbamoyl group;

X¹ of PTM-VIII represents a group represented by —X⁴—X⁵—, wherein:

X⁴ is a substituted or unsubstituted divalent alicyclic hydrocarbon, a substituted or unsubstituted divalent aromatic hydrocarbon group, a substituted or unsubstituted divalent heterocyclic group, or a group represented by

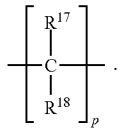

wherein p of $R^{17}$ are the same or different, and is a hydrogen atom or a substituted or unsubstituted $C_{1-6}$ alkyl group, or one $R^{17}$ selected from p of $R^{17}$ may bind with $R^4$ to form: a substituted or unsubstituted $C_{1-6}$ alkylene group: a substituted or unsubstituted ($C_{1-3}$ alkylene)-O group: a substituted or unsubstituted ($C_{1-3}$ alkylene)-N($R^{19}$) group, wherein $R^{19}$ is a hydrogen atom, substituted or unsubstituted a $C_{1-6}$ alkyl group, or an imino protecting group; a substituted or unsubstituted ($C_{1-3}$ alkylene)-O—($C_{1-3}$ alkylene) group; a substituted or unsubstituted ($C_{1-3}$ alkylene)-N($R^{19}$)—($C_{1-3}$ alkylene) group, wherein $R^{19}$ is a hydrogen atom, substituted or unsubstituted a $C_{1-6}$ alkyl group, or an imino protecting group; p of $R^{18}$ are the same or different, and is a hydrogen atom or a substituted or unsubstituted $C_{1-6}$ alkyl group; or $R^{17}$ and $R^{18}$ binding to the same carbon atom may bind together to form: a substituted or unsubstituted $C_{2-6}$ alkylene group, a substituted or unsubstituted O—($C_{1-6}$ alkylene); a substituted or unsubstituted N($R^{20}$)—($C_{1-6}$ alkylene) group, wherein $R^{20}$ is a hydrogen atom; a substituted or unsubstituted $C_{1-6}$ alkyl group or an imino protecting group; a substituted or unsubstituted ($C_{1-3}$ alkylene)-O—($C_{1-3}$ alkylene) group; a substituted or unsubstituted ($C_{1-3}$ alkylene)-N($R^{20}$)—($C_{1-3}$ alkylene), wherein $R^{20}$ is a hydrogen atom; a substituted or unsubstituted $C_{1-6}$ alkyl group or an imino protecting group; and p represents an integer of 1 to 6; or an atomic bond; and X⁵ is an oxygen atom, N($R^{21}$) wherein $R^{21}$ is a hydrogen atom, a substituted or unsubstituted $C_{1-6}$ alkyl group, a substituted or unsubstituted $C_{2-6}$ alkenyl group, a substituted or unsubstitute $C_{2-6}$ alkynyl group or an imino protecting group, or $R^{21}$ may bind with $R^4$ to form a substitute or unsubstituted $C_{1-6}$ alkylene group; C(=O); C(=O)—N($R^{21}$) wherein $R^{21}$ is a hydrogen atom, a substituted or unsubstituted $C_{1-6}$ alkyl group, a substituted or unsubstituted $C_{2-6}$ alkenyl group, a substituted or unsubstitute $C_{2-6}$ alkynyl group or an imino protecting group; or an atomic bond;

X² of PTM-VIII is a substituted or unsubstituted $C_{1-6}$ alkylene group, a substituted or unsubstituted divalent alicyclic hydrocarbon group, a substituted or unsubstituted divalent aromatic hydrocarbon, or a substituted or unsubstituted divalent heterocyclic group;

X³ of PTM-VIII is a substituted or unsubstituted $C_{1-6}$ alkylene group, a substituted or unsubstituted $C_{2-6}$ alkenylene group, a substituted or unsubstituted $C_{2-6}$ alkynylene group, a substituted or unsubstituted O—($C_{1-6}$ alkylene) group, a substituted or unsubstituted $S(O)_q$—($C_{1-6}$ alkylene) group wherein q represents 0, 1 or 2; a substituted or unsubstituted N($R^{22}$)—($C_{1-6}$ alkylene) group wherein $R^{22}$ is a hydrogen atom, a substituted or unsubstitute $C_{1-6}$ alkyl group, a substituted or unsubstituted $C_{2-6}$ alkenyl group, a substitute or unsubstituted $C_{2-6}$ alkynyl group or an imino protecting group; N($R^{22}$)—C(=O) wherein $R^{22}$ is a hydrogen atom, a substituted or unsubstitute $C_{1-6}$ alkyl group, a substituted or unsubstituted $C_{2-6}$ alkenyl group, a substitute or unsubstituted $C_{2-6}$ alkynyl group or an imino protecting group; or an atomic bond;

Z¹ of PTM-VIII is a nitrogen atom or C($R^{23}$) wherein $R^{23}$ is a hydrogen atom, a halogen atom, a substituted or unsubstituted $C_{1-6}$ alkyl group, a substituted or unsubstituted $C_{3-8}$ cycloalkyl group, a substituted or unsubstituted aryl group, a substituted or unsubstituted $C_{1-6}$ alkoxy group or substituted or unsubstituted a heterocyclic group;

m of PTM-VIII is an integer of 0, 1, 2, 3, 4, 5, or 6;

n of PTM-VIII is an integer of 0, 1, 2, 3, 4, 5, or 6); and the PTM-VIII is covalently joined to a ULM, a chemical linker group (L), a CLM, an ILM, a VLM, MLM, a ULM', a CLM', a ILM', a VLM', a MLM', or combination thereof.

In any aspect or embodiment described herein, the PTM is represented by Formula PTM-IX:

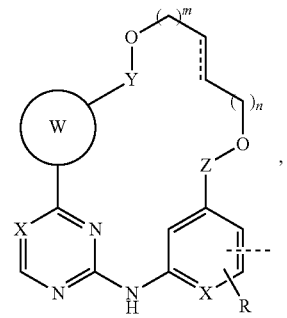

PTM-IX wherein:

W of PTM-IX is an aryl, 5-membered heteroaryl, or 6-membered heteroaryl ring, each optionally substituted with one or more $R_{PTM1}$ groups;

X of PTM-IX is independently selected from C—$R_{PTM1}$ or N;

Y and Z of PTM-IX are independently selected from a bond or CH₂;

m and n of PTM-IX are each independently 1 or 2;

$R_{PTM1}$ of PTM-IX is H, halogen, $C_{1-5}$alkyl, CN, C(O)—$C_{1-5}$alkyl, C(O)O—$C_{1-5}$alkyl, OH, or O—$C_{1-5}$alkyl (e.g., selected from the group consisting of H, halogen, $C_{1-5}$alkyl, CN, OH, or O—$C_{1-5}$alkyl);

=== of PTM-IX indicates either a single or double bond;

each R of PTM-IX is independently selected from H, halogen, $C_{1-5}$alkyl, CN, C(O)—$C_{1-5}$alkyl, C(O)O—$C_{1-5}$alkyl, OH, or O—$C_{1-5}$alkyl, each optionally substituted (e.g., optionally substituted with a cycloalkyl, heterocycle, or aminoalkyl); and ⟿ of PTM-IX indicates a covalent linkage, optionally through an atom or functional group, to at least one of a linker (L), a ULM, a ULM', a VLM, a CLM, a CLM', an ILM, an ILM', a MLM, a MLM', or a combination thereof.

In any aspect or embodiment described herein, the PTM-IX comprises at least one of the following:

W of PTM-IX is phenyl or furan, each optionally substituted with one or more $R_{PTM1}$ groups;

X of PTM-IX is CH;

Y of PTM-IX is $CH_2$;

Z of PTM-IX is $CH_2$;

m and n of PTM-IX are each 1;

R of PTM-IX is H; or a combination thereof.

In any aspect or embodiment described herein, the PTM is selected from:

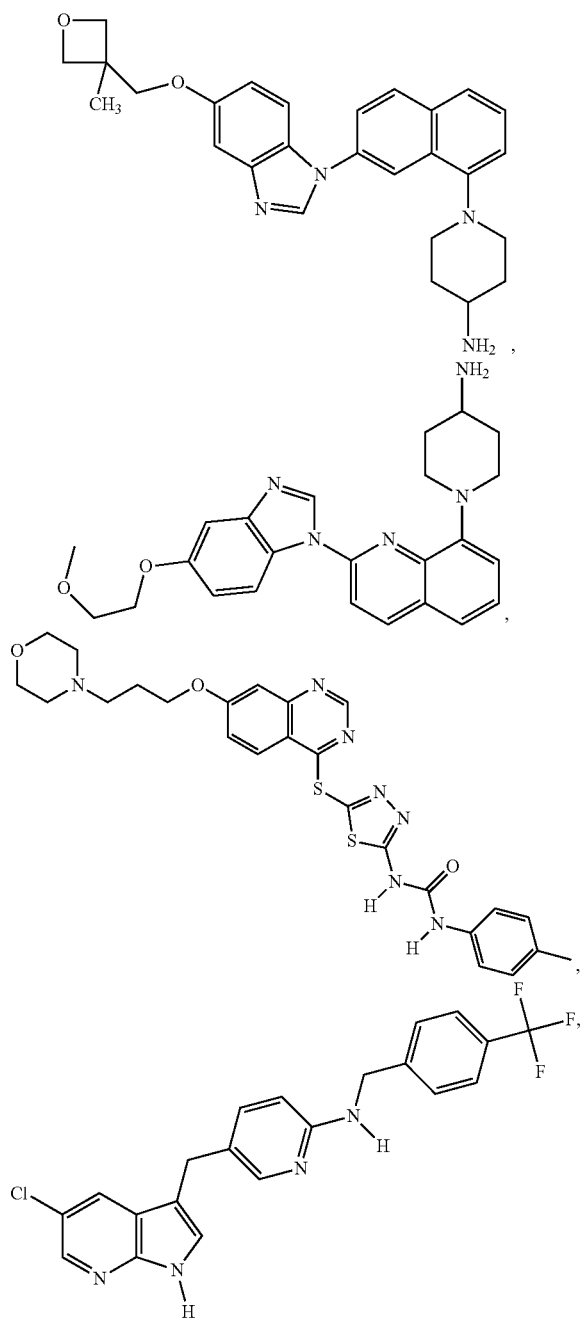

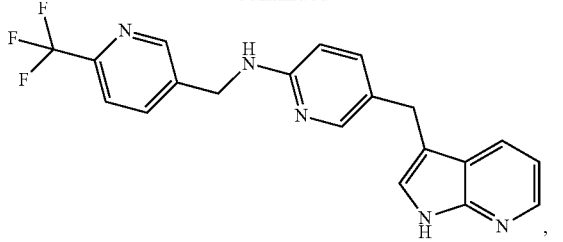

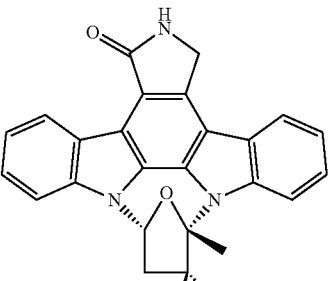

, or

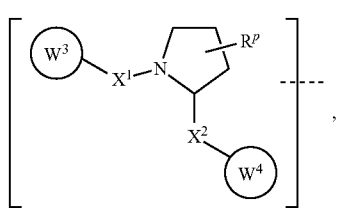

wherein R is 5-(4-methyl-1H-imidazol-1-yl) or 4-(N-(4-ethylpiperazin-1-yl)methyl).

In any aspect or embodiment described herein, the ULM is a Von Hippel-Lindau (VHL) ligase-binding moiety (VLM) with a chemical structure represented by:

wherein:
X¹, X² are each independently selected from the group of a bond, O, $NR^{Y3}$, $CR^{Y3}R^{Y4}$, C=O, C=S, SO, and $SO_2$;
$R^{Y3}$, $R^{Y4}$ are each independently selected from the group of H, linear or branched $C_{1-6}$ alkyl, optionally substituted by 1 or more halo, $C_{1-6}$ alkoxyl optionally substituted by 0-3 $R^P$ groups;
$R^P$ is 0, 1, 2, or 3 groups independently selected from the group H, halo, —OH, $C_{1-3}$ alkyl, C=O;
$W^3$ is selected from the group of an optionally substituted -T-N($R^{1a}R^{1b}$)X³, T-N($R^{1a}R^{1b}$), -T-Aryl, an optionally substituted -T-Heteroaryl, an optionally substituted -T-Heterocycle, an optionally substituted —NR¹-T-Aryl, an optionally substituted —NR¹-T-Heteroaryl or an optionally substituted —NR¹-T-Heterocycle;
X³ is C=O, R¹, $R^{1a}$; $R^{1b}$;
each of R¹, $R^{1a}$, $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;

T is selected from the group of an optionally substituted alkyl, —(CH$_2$)$_n$— group, wherein each one of the methylene groups is optionally substituted with one or two substituents selected from the group of halogen, methyl, a linear or branched C$_1$-C$_6$ alkyl group optionally substituted by 1 or more halogen or —OH groups or an amino acid side chain optionally substituted;

n is 0 to 6;

W$^4$ is

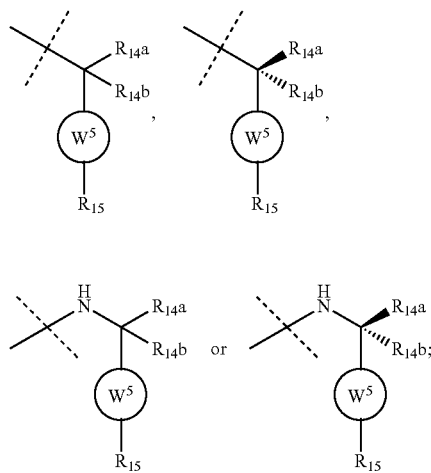

R$_{14a}$, R$_{14b}$, are each independently selected from the group of H, haloalkyl, or optionally substituted alkyl;

W$^5$ is selected from the group of a phenyl or a 5-10 membered heteroaryl;

R$_{15}$ is selected from the group of H, halogen, CN, OH, NO$_2$, N R$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14a}$ SO$_2$R$_{14b}$, optionally substituted alkyl, optionally substituted haloalkyl, optionally substituted haloalkoxy; aryl, heteroaryl, cycloalkyl, or cycloheteroalkyl, each optionally substituted;

and wherein the dashed line indicates the site of attachment of at least one PTM, another ULM (ULM') or a chemical linker moiety coupling at least one PTM or a ULM' or both to ULM.

In any aspect or embodiment described herein, the ULM is a Von Hippel-Lindau (VHL) ligase-binding moiety (VLM) with a chemical structure represented by:

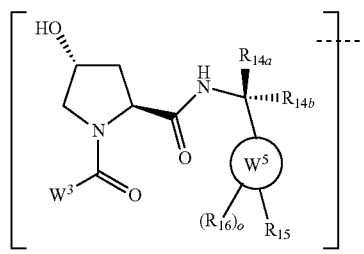

wherein:

W$^3$ is selected from the group of an optionally substituted aryl, optionally substituted heteroaryl, or

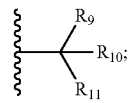

R$_9$ and R$_{10}$ are independently hydrogen, optionally substituted alkyl, optionally substituted cycloalkyl, optionally substituted hydroxyalkyl, optionally substituted heteroaryl, or haloalkyl, or R$_9$, R$_{10}$, and the carbon atom to which they are attached form an optionally substituted cycloalkyl;

R$_{11}$ is selected from the group of an optionally substituted heterocyclic, optionally substituted alkoxy, optionally substituted heteroaryl, optionally substituted aryl,

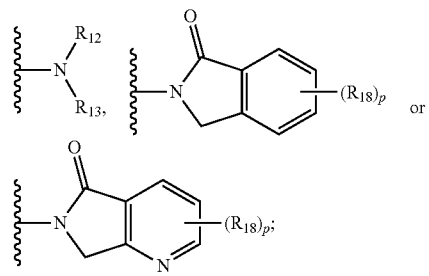

R$_{12}$ is selected from the group of H or optionally substituted alkyl;

R$_{13}$ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

R$_{14a}$, R$_{14b}$, are each independently selected from the group of H, haloalkyl, or optionally substituted alkyl;

W$^5$ is selected from the group of a phenyl or a 5-10 membered heteroaryl,

R$_{15}$ is selected from the group of H, halogen, CN, OH, NO$_2$, N R$_{14a}$R$_{14b}$, OR$_{14a}$, CONR$_{14a}$R$_{14b}$, NR$_{14a}$COR$_{14b}$, SO$_2$NR$_{14a}$R$_{14b}$, NR$_{14a}$ SO$_2$R$_{14b}$, optionally substituted alkyl, optionally substituted haloalkyl, optionally substituted haloalkoxy; aryl, heteroaryl, cycloalkyl, or cycloheteroalkyl, each optionally substituted;

R$_{16}$ is independently selected from the group of halo, optionally substituted alkyl, optionally substituted haloalkyl, hydroxy, or optionally substituted haloalkoxy;

o is 0, 1, 2, 3, or 4;

R$_{18}$ is independently selected from the group of H, halo, optionally substituted alkoxy, cyano, optionally substituted alkyl, haloalkyl, haloalkoxy or a linker; and p is 0, 1, 2, 3, or 4, and wherein the dashed line indicates the site of attachment of at least one PTM, another ULM (ULM') or a chemical linker moiety coupling at least one PTM or a ULM' or both to ULM.

In any aspect or embodiment described herein, the ULM has a chemical structure selected from the group of:

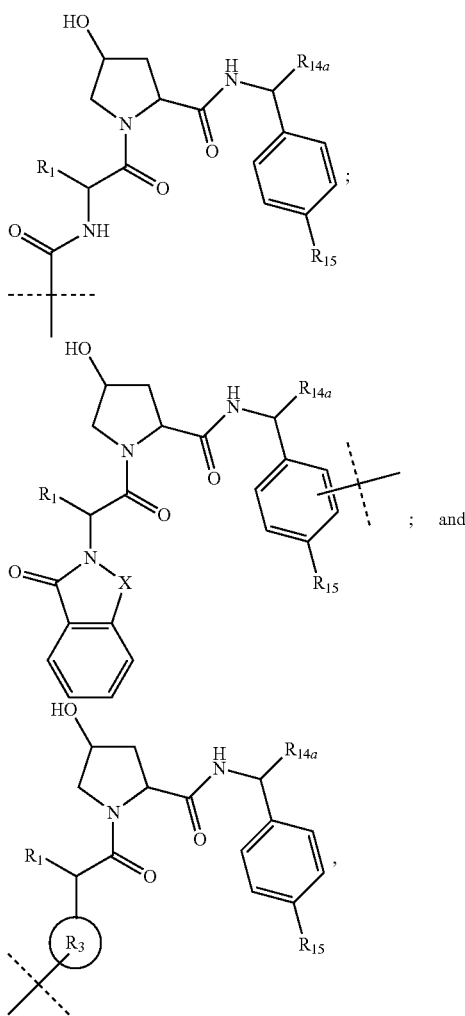

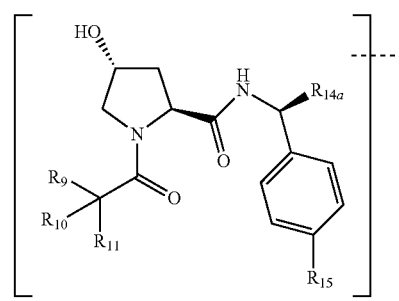

wherein:

R₁ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

R₁₄ₐ is H, haloalkyl, optionally substituted alkyl, methyl, fluoromethyl, hydroxymethyl, ethyl, isopropyl, or cyclopropyl;

R₁₅ is selected from the group consisting of H, halogen, CN, OH, NO₂, optionally substituted heteroaryl, optionally substituted aryl; optionally substituted alkyl, optionally substituted haloalkyl, optionally substituted haloalkoxy, cycloalkyl, or cycloheteroalkyl, each optionally substituted;

X is C, CH₂, or C=O;

R₃ is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to the ULM.

The compound according to any one of claims 1-14, wherein the ULM comprises a group according to the chemical structure:

wherein:

R₁₄ₐ is H, haloalkyl, optionally substituted alkyl, methyl, fluoromethyl, hydroxymethyl, ethyl, isopropyl, or cyclopropyl;

R₉ is H;

R₁₀ is H, ethyl, isopropyl, tert-butyl, sec-butyl, cyclopropyl, cyclobutyl, cyclopentyl, or cyclohexyl;

R₁₁ is

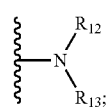

optionally substituted heteroaryl,

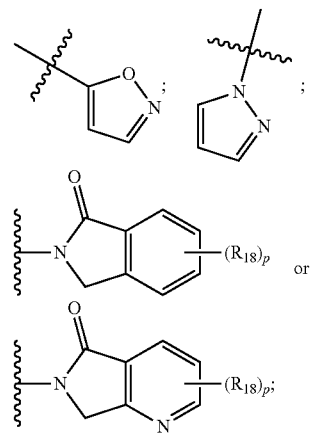

p is 0, 1, 2, 3, or 4; and each R₁₈ is independently halo, optionally substituted alkoxy, cyano, optionally substituted alkyl, haloalkyl, haloalkoxy or a linker;

R₁₂ is H, C=O;

R₁₃ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

R₁₅ is selected from the group consisting of H, halogen, Cl, CN, OH, NO₂, optionally substituted heteroaryl, optionally substituted aryl;

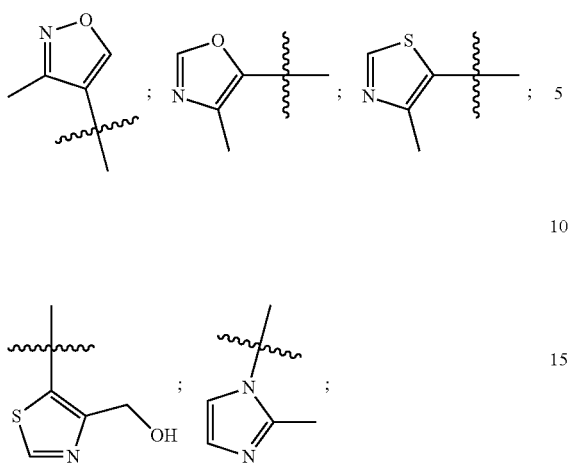

and wherein the dashed line indicates the site of attachment of at least one PTM, another ULM (ULM') or a chemical linker moiety coupling at least one PTM or a ULM' or both to the ULM.

In any aspect or embodiment described herein, the ULM is a cereblon E3 ligase-binding moiety (CLM) selected from the group coinsisting of a thalidomide, lenalidomide, pomalidomide, analogs thereof, isosteres thereof, or derivatives thereof.

In any aspect or embodiment described herein, the CLM has a chemical structure represented by:

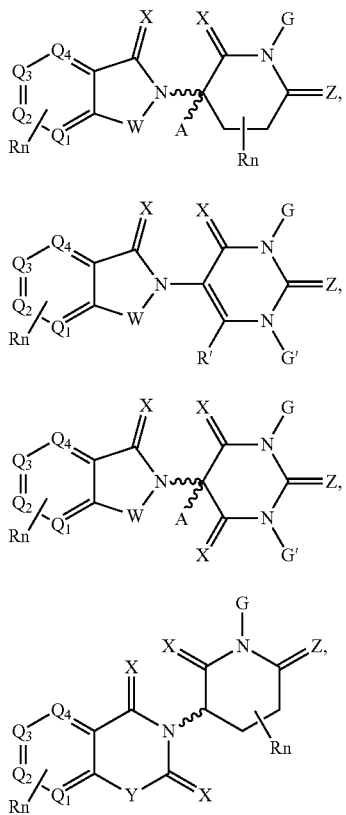

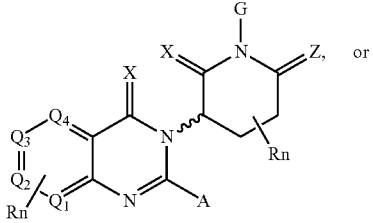

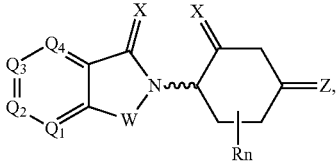

wherein:
W is selected from the group consisting of $CH_2$, CHR, C=O, $SO_2$, NH, and N-alkyl;
each X is independently selected from the group consisting of O, S, and $H_2$,
Y is selected from the group consisting of $CH_2$, —C=CR', NH, N-alkyl, N-aryl, N-hetaryl, N-cycloalkyl, N-heterocyclyl, O, and S;
Z is selected from the group consisting of O, S, and $H_2$;
G and G' are independently selected from the group consisting of H, alkyl (linear, branched), OH, R'OCOOR, R'OCONRR", $CH_2$-heterocyclyl optionally substituted with R', and benzyl optionally substituted with R';
$Q_1$, $Q_2$, $Q_3$, and $Q_4$ represent a carbon C substituted with a group independently selected from R', N or N-oxide;
A is independently selected from the group H, alkyl (linear, branched, optionally substituted), cycloalkyl, Cl and F;
R comprises —CONR'R", —OR', —NR'R", —SR', —$SO_2$R', —$SO_2$NR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —$NR'SO_2NR'R"$, —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2NR'COR"$, —$NO_2$, —$CO_2R'$, —C(C=N—OR')R", —CR', CR'R", —CCR', —S(C=O)(C=N—R')R", —$SF_5$ and —$OCF_3$;
R' and R" are independently selected from the group consisting of a bond, H, alkyl, cycloalkyl, aryl, heteroaryl, heterocyclic, —C(=O)R, heterocyclyl, each of which is optionally substituted;
⁓ represents a bond that may be stereospecific ((R) or (S)) or non-stereospecific; and
$R_a$ comprises a functional group or an atom,
wherein n is an integer from 1-10, and wherein
when n is 1, $R_n$ is modified to be covalently joined to the linker group (L), and
when n is 2, 3, or 4, then one $R_n$ is modified to be covalently joined to the linker group (L), and any other $R_n$ is optionally modified to be covalently joined to a PTM, a CLM, a second CLM having the same chemical structure as the CLM, a CLM', a second linker, or any multiple or combination thereof.

In any aspect or embodiment described herein, the CLM has a chemical structure represented by:

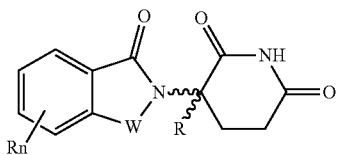

wherein:
W is independently selected from the group CH2, C=O, NH, and N-alkyl;
R is independently selected from a H, methyl, alkyl (e.g. a C1-C6 alkyl (linear, branched, optionally substituted));
 represents a bond that may be stereospecific ((R) or (S)) or non-stereospecific; and
$R_n$ comprises 1-4 independently selected functional groups or atoms, and optionally, one of which is modified to be covalently joined to a PTM, a chemical linker group (L), a CLM (or CLM') or combination thereof.

In any aspect or embodiment described herein, the ULM is a (MDM2) binding moiety (MLM) with a chemical moiety selected from the group consisting of a substituted imidazolines, a substituted spiro-indolinones, a substituted pyrrolidines, a substituted piperidinones, a substituted morpholinones, a substituted pyrrolopyrimidines, a substituted imidazolopyridines, a substituted thiazoloimidazoline, a substituted pyrrolopyrrolidinones, and a substituted isoquinolinones.

In any aspect or embodiment described herein, the ULM is a IAP E3 ubiquitin ligase binding moiety (ILM) comprising the amino acids alanine (A), valine (V), proline (P), and isoleucine (I) or their unnatural mimetics.

In any aspect or embodiment described herein, the ULM is a IAP E3 ubiquitin ligase binding moiety (ILM) comprising a AVPI tetrapeptide fragment or derivative thereof.

In any aspect or embodiment described herein, the linker (L) comprises a chemical structural unit represented by the formula:

$-(A^L)_q-$, wherein:
$(A^L)_q$ is a group that is connected to at least one of a ULM moiety, a PTM moiety, or a combination thereof;
q is an integer greater than or equal to 1;
each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L3}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{3-11}$heterocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and
$R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, CC—$C_{1-8}$alkyl, CCH, CH=CH($C_{1-8}$alkyl), $C(C_{1-8}alkyl)=CH(C_{1-8}alkyl)$, $C(C_{1-8}alkyl)=C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_4$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)$ $SO_2N(C_{1-8}alkyl)_2$, NH $SO_2NH(C_{1-8}alkyl)$, NH $SO_2N(C_{1-8}alkyl)_2$, NH $SO_2NH_2$.

In any aspect or embodiment described herein, the linker (L) comprises a group represented by a general structure selected from the group consisting of:
—N(R)—(CH2)$_m$—O(CH2)$_n$—O(CH2)$_o$—O(CH2)$_p$—O(CH2)$_q$—O(CH2)$_r$-OCH2-,
O—(CH2)$_m$—O(CH2)$_n$—O(CH2)$_o$O(CH2)$_p$—O(CH2)$_q$—O(CH2)$_r$-OCH2-,
O—(CH2)$_m$—O(CH2)$_n$—O(CH2)$_o$O(CH2)$_p$—O(CH2)$_q$—O(CH2)$_r$—O—;
—N(R)—(CH2)$_m$—O(CH2)$_n$—O(CH2)$_o$—O(CH2)$_p$—O(CH2)$_q$—O(CH2)$_r$—O—;
(CH2)$_m$—O(CH2)$_n$—O(CH2)$_o$O(CH2)$_p$—O(CH2)$_q$—O(CH2)$_r$—O—;
(CH2)$_m$—O(CH2)$_n$—O(CH2)$_o$—O(CH2)$_p$—O(CH2)$_q$—O(CH2)$_r$-OCH2-;

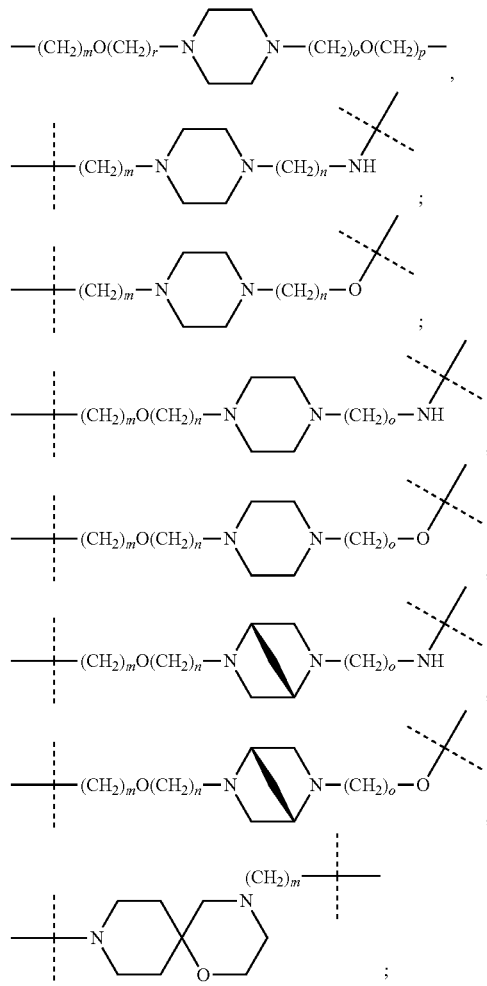

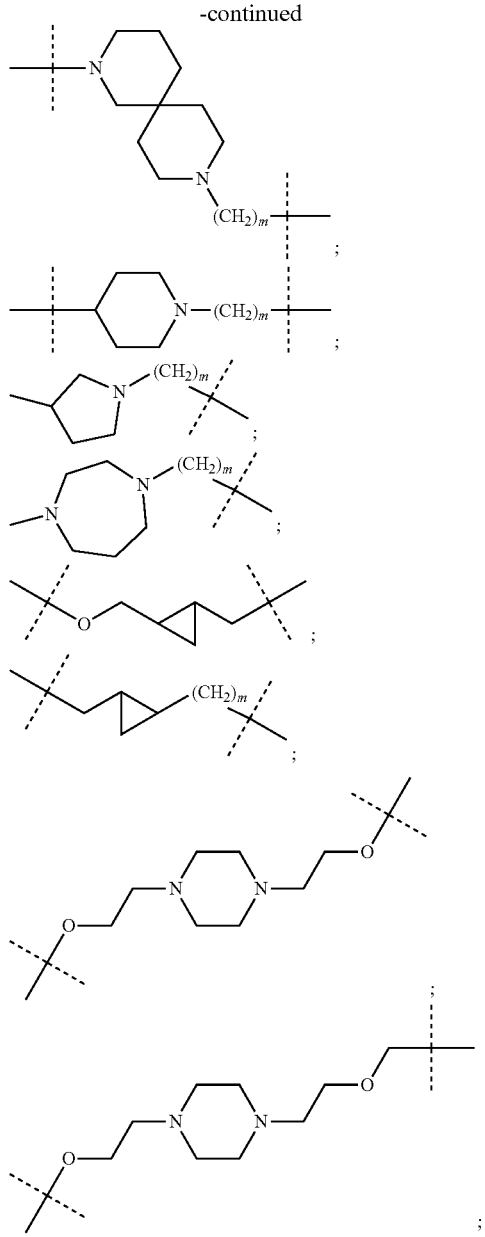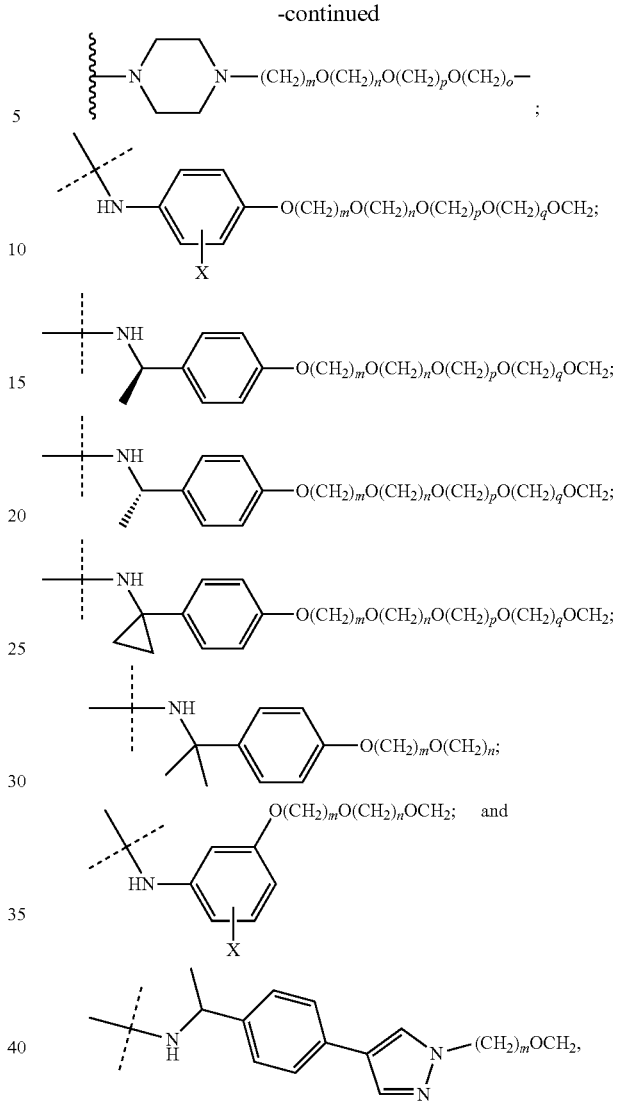
wherein each m, n, o, p, q, and r is independently 0, 1, 2, 3, 4, 5, 6 with the proviso that when the number is zero, there is no N—O or O—O bond, R is selected from the group H, methyl and ethyl, and X is selected from the group H and F;
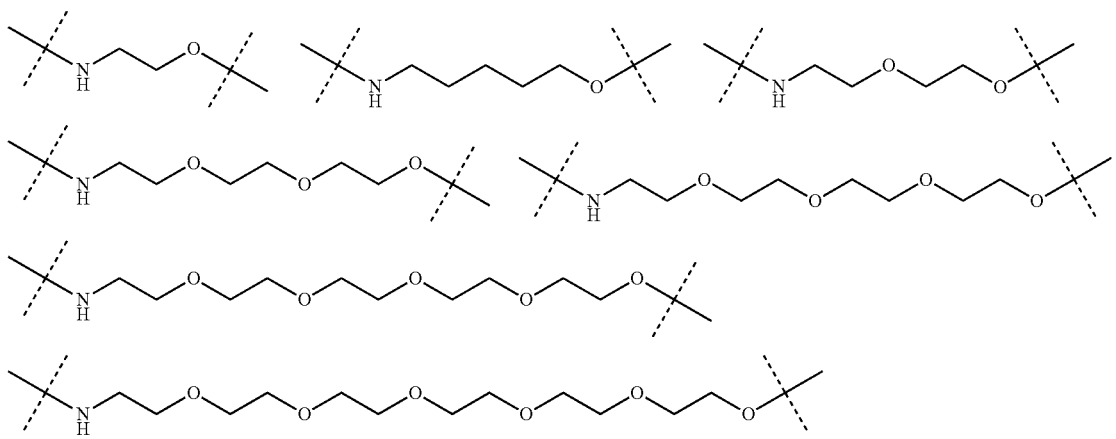

-continued
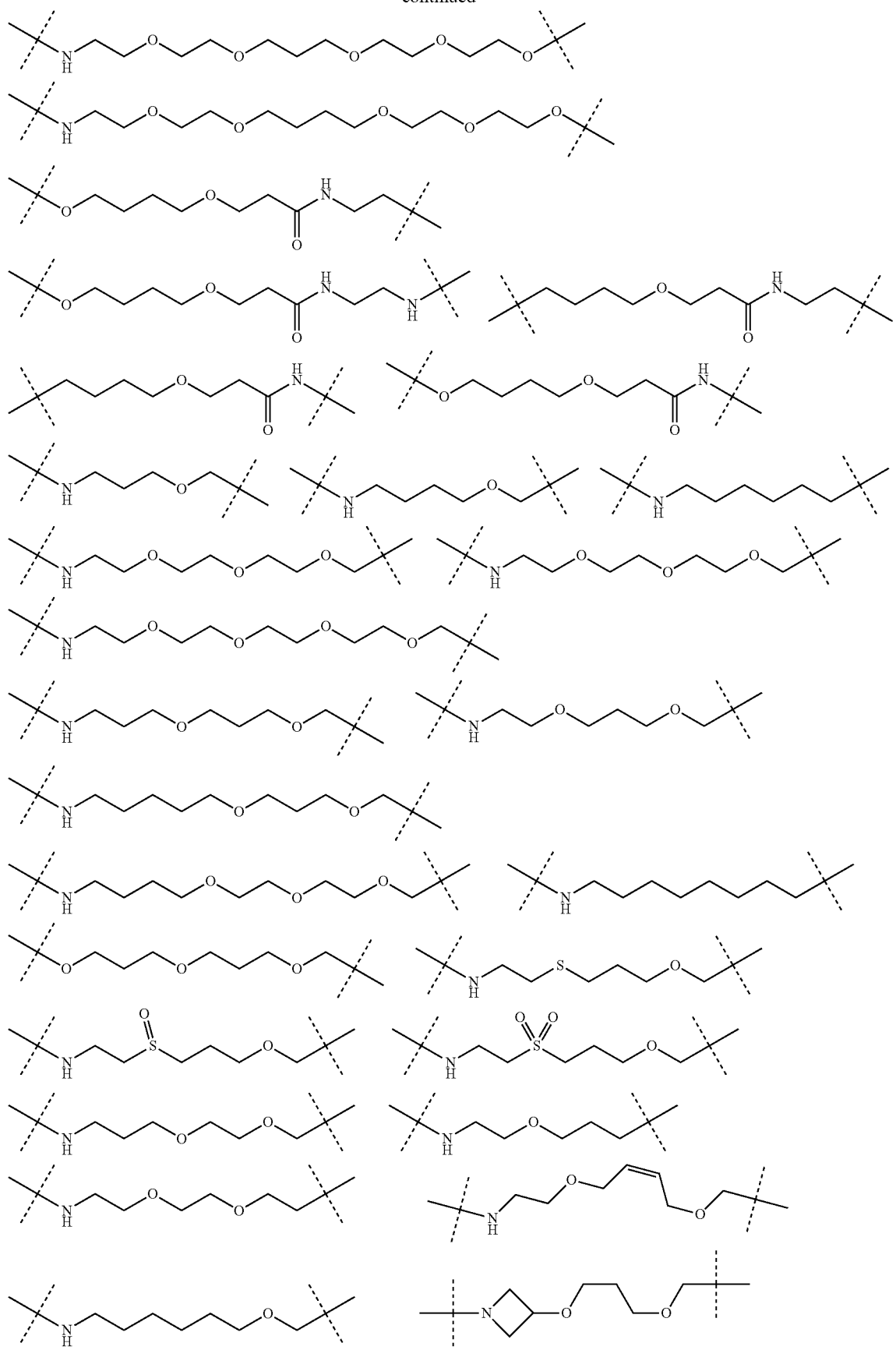

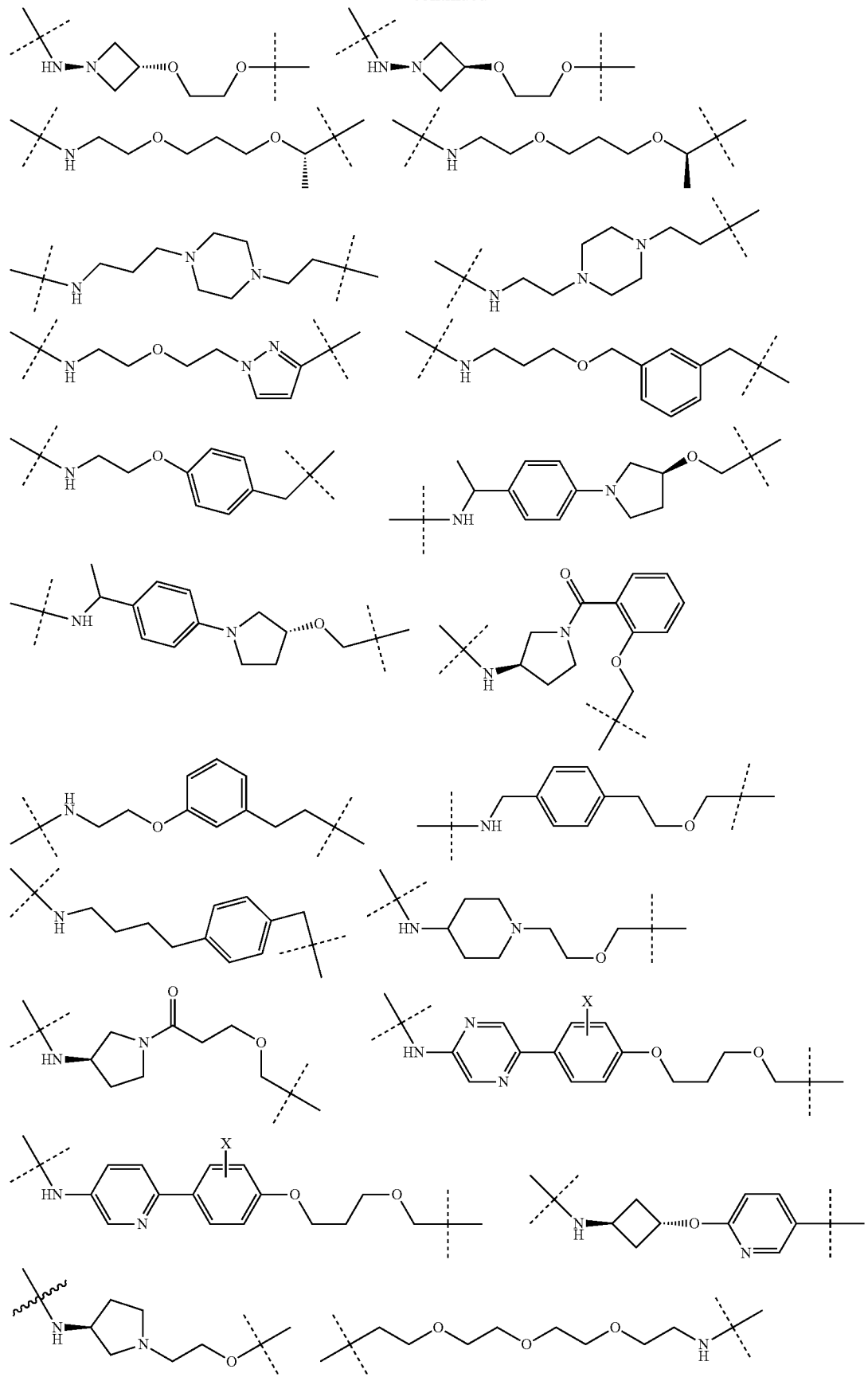

-continued
| 611 | 612 |
|---|---|
| 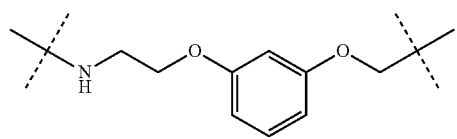 | 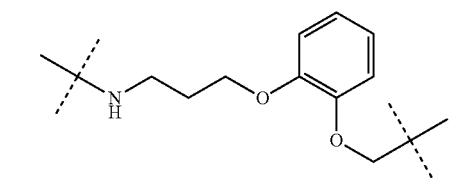 |
| 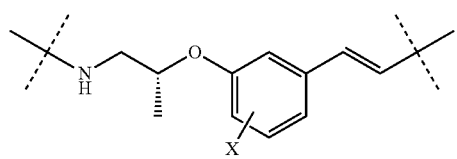 | 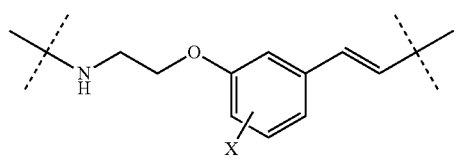 |
| 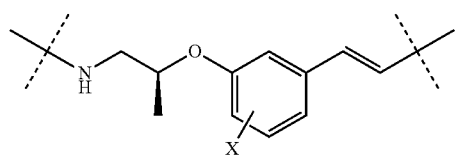 X = H, F | 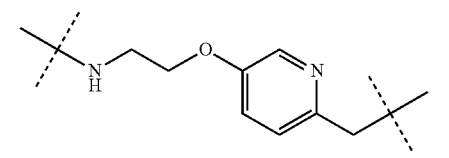 |
| 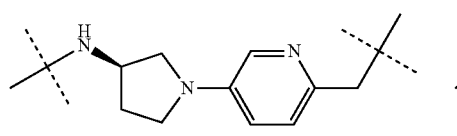 | 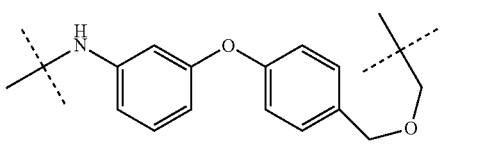 |
| 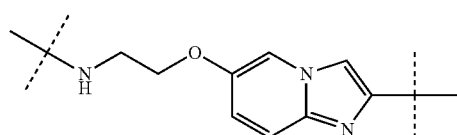 | 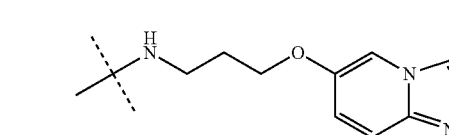 |
| 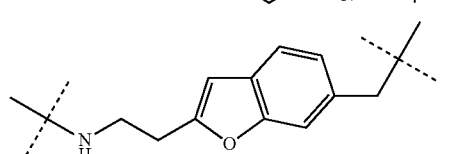 | 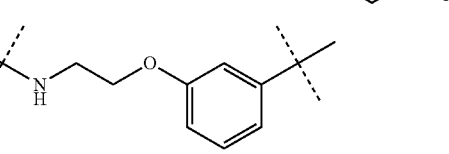 |
| 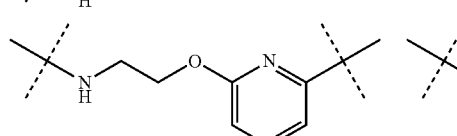 | 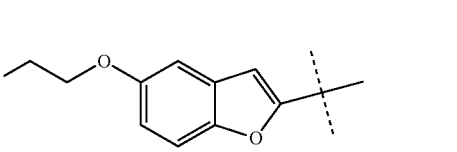 |
| 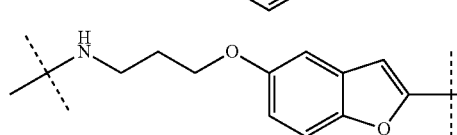 | 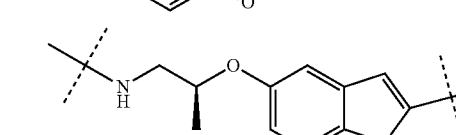 |
| 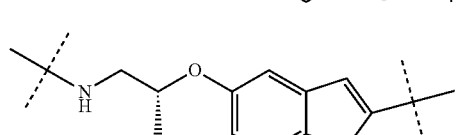 | 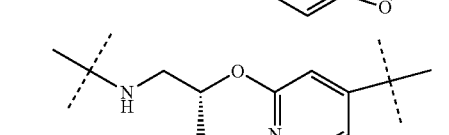 |
| 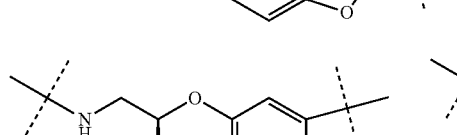 | 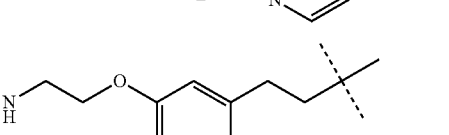 |
| 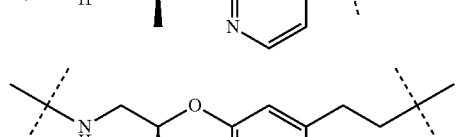 | 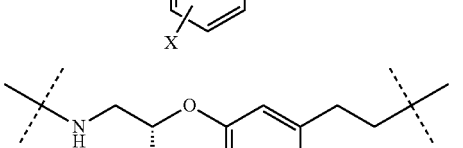 |
| 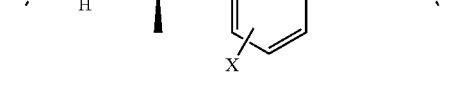 | 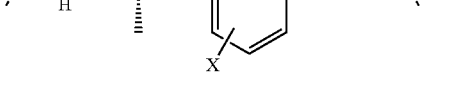 |

613
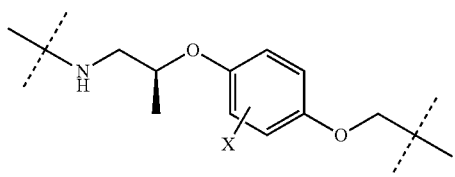
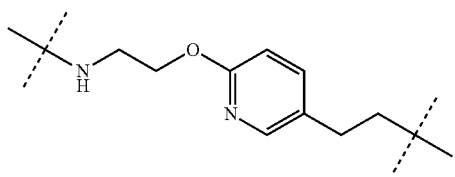
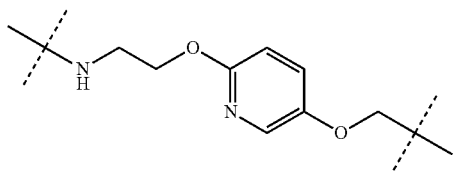
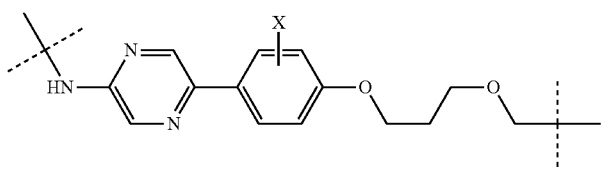
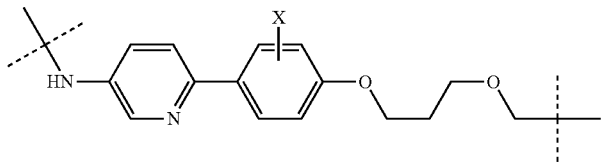
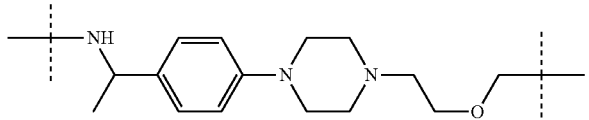
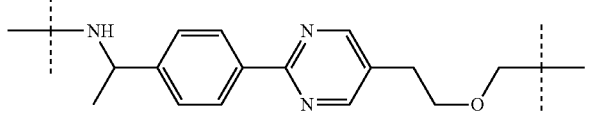
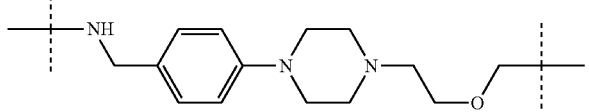
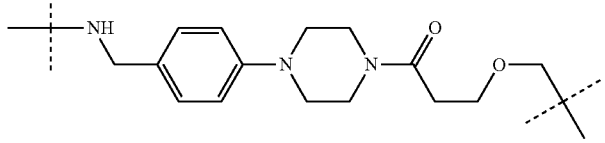
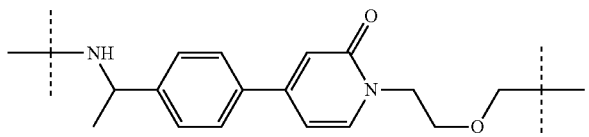
614
-continued
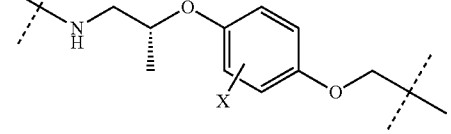
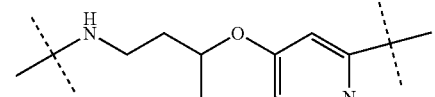
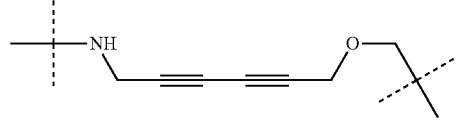

615
616
-continued
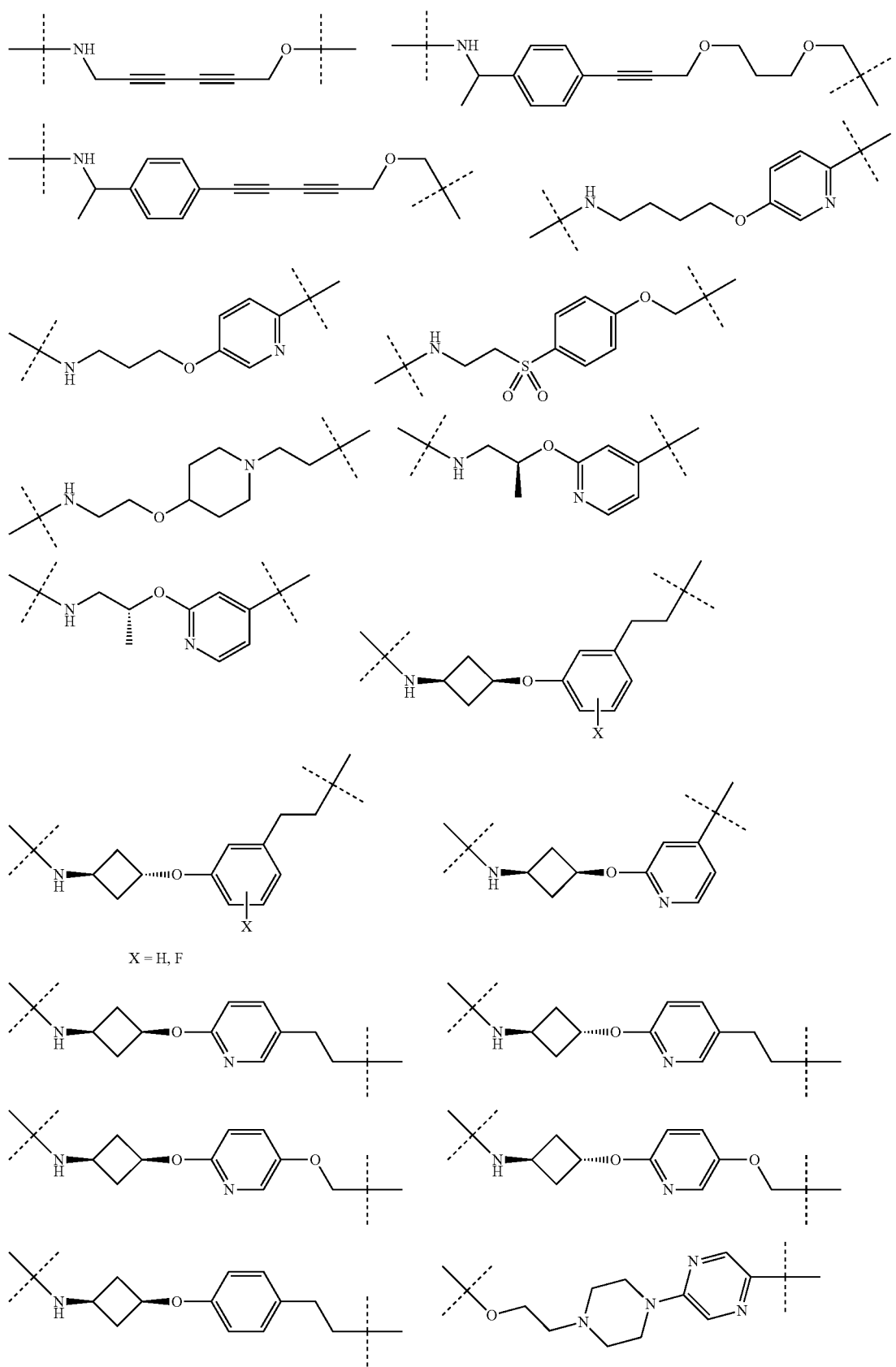
X = H, F 617 618
-continued
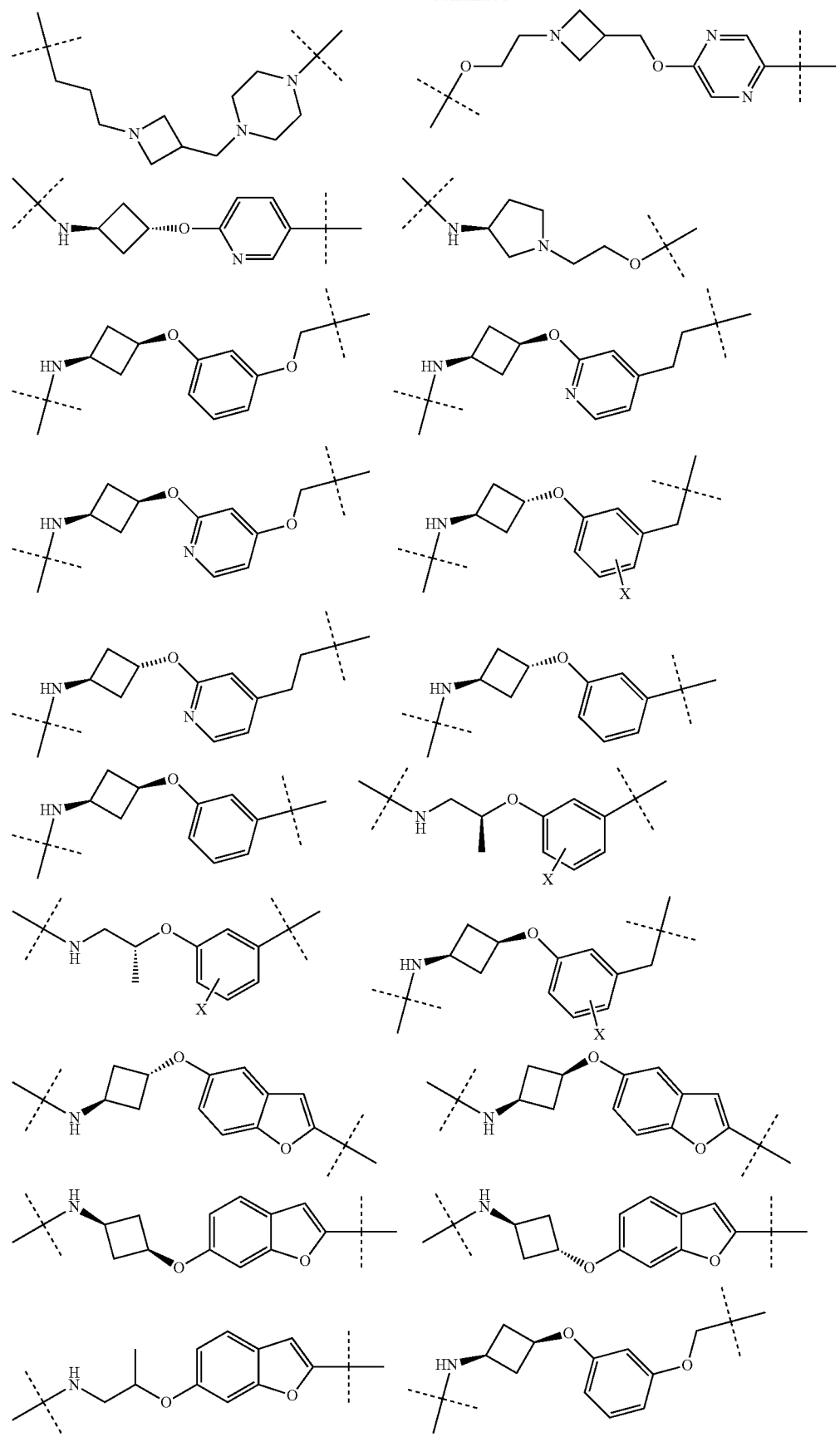

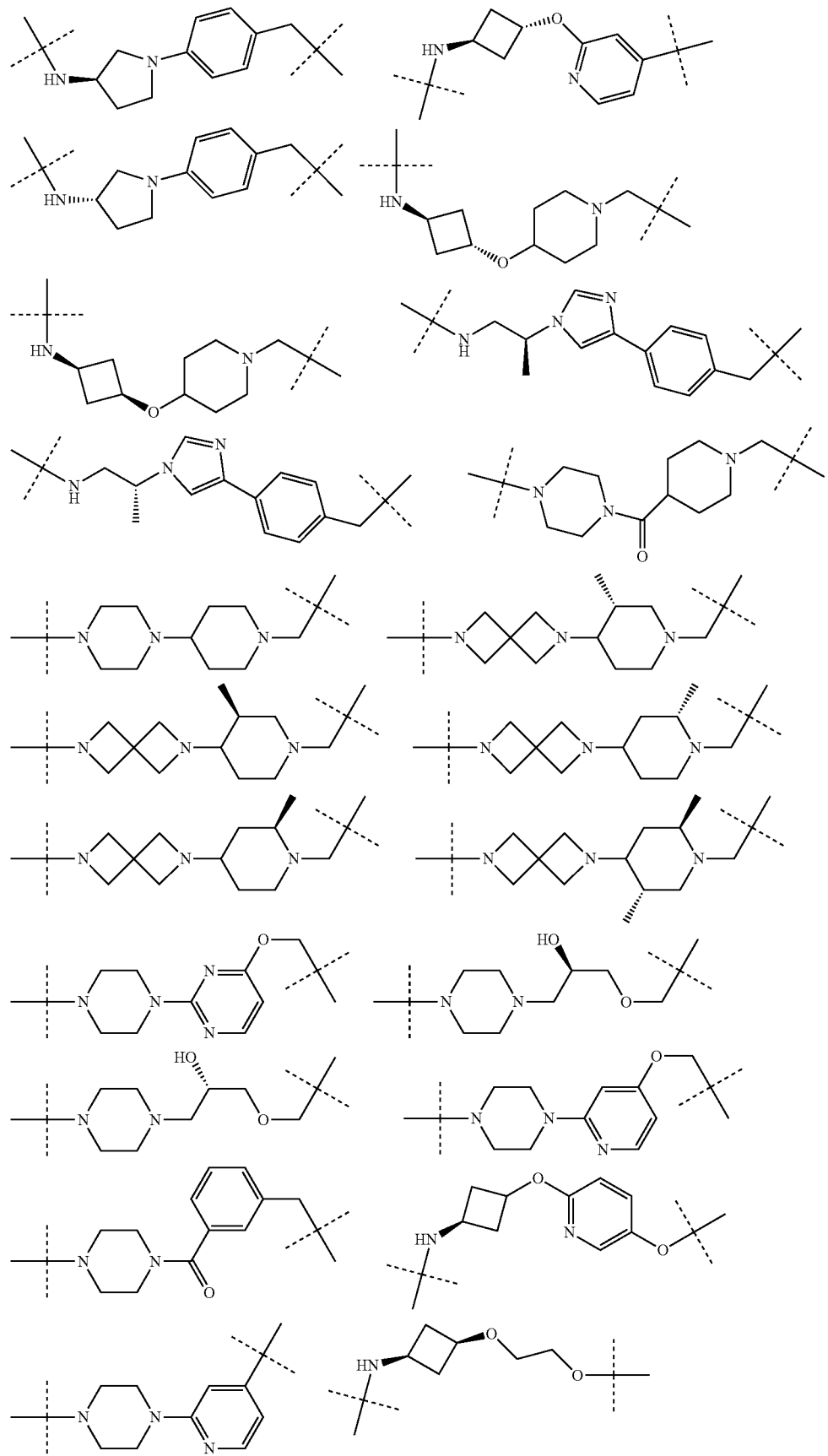

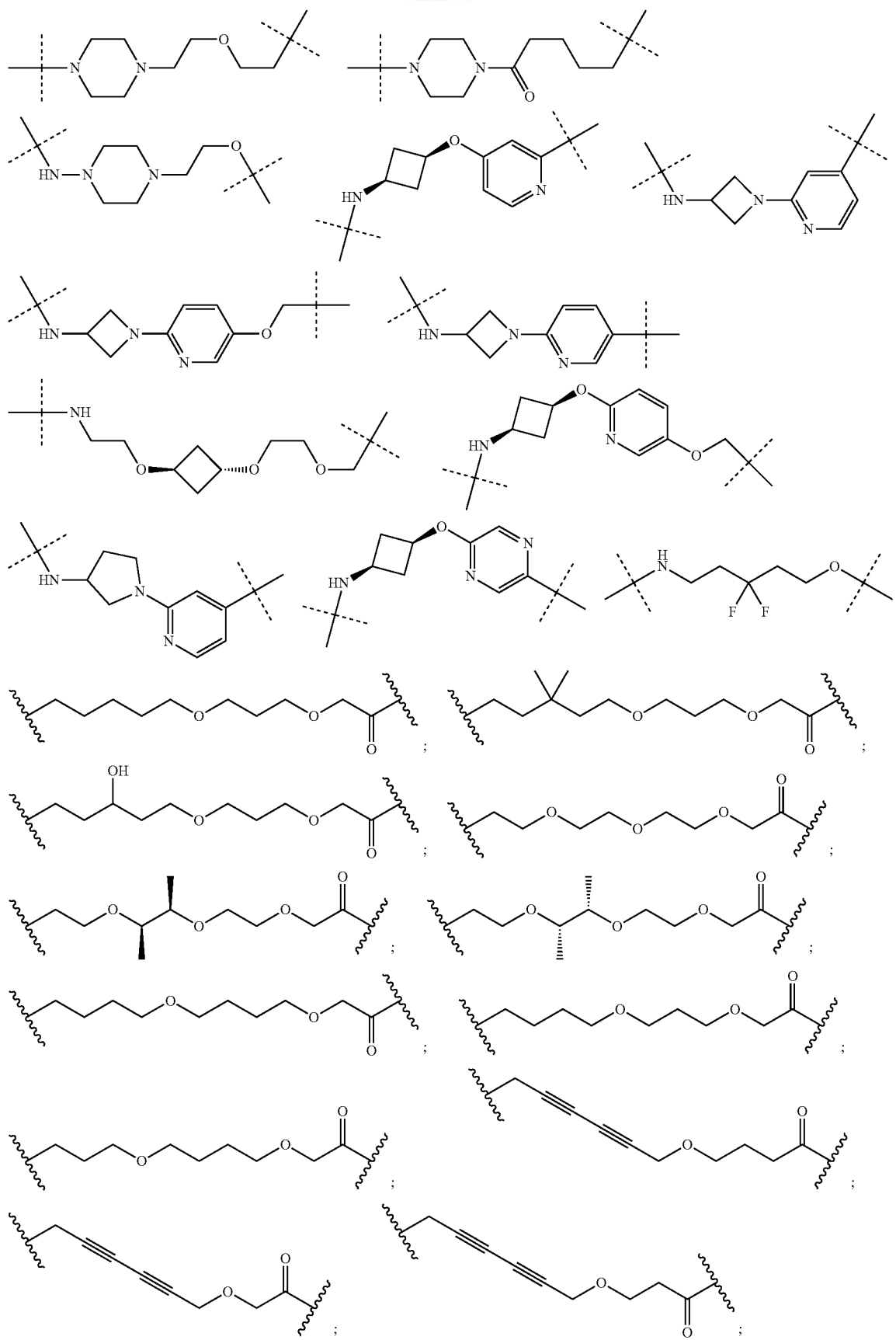

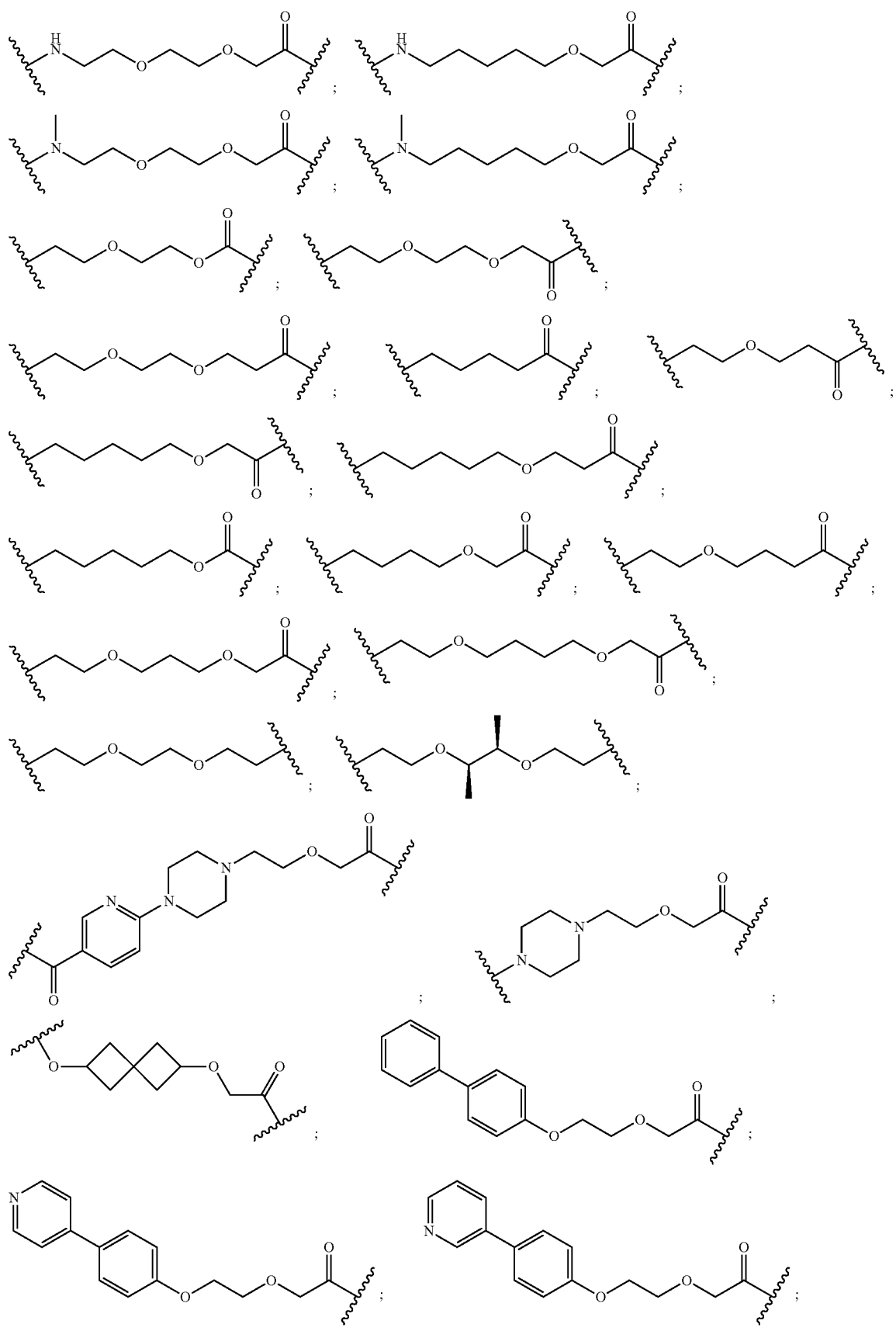

625
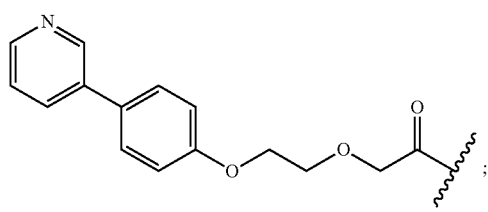
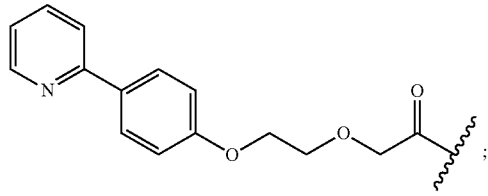
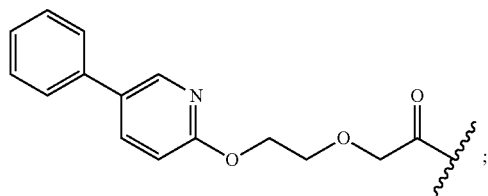
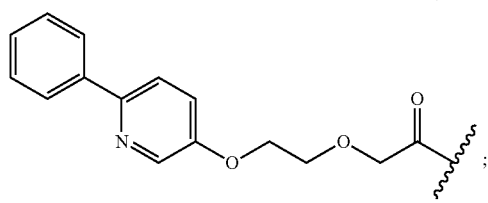
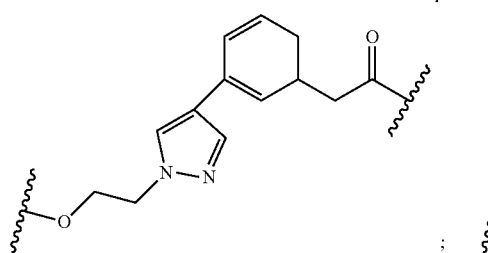
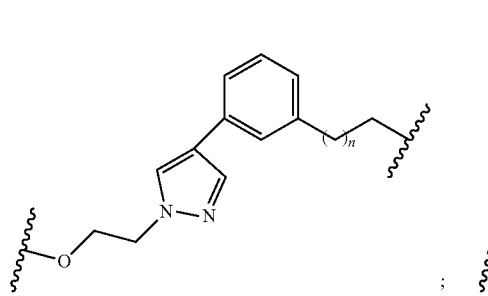
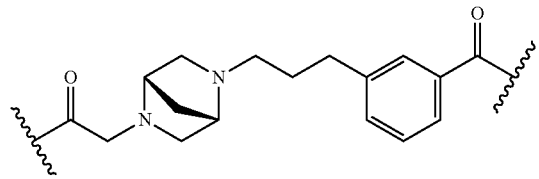
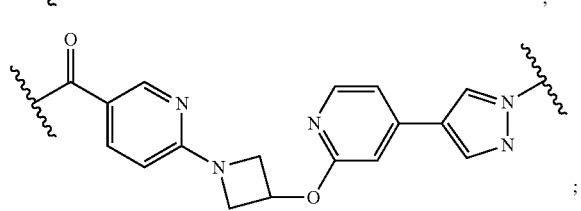
626 -continued
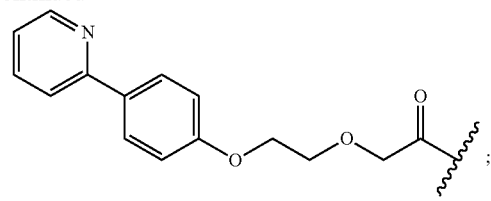
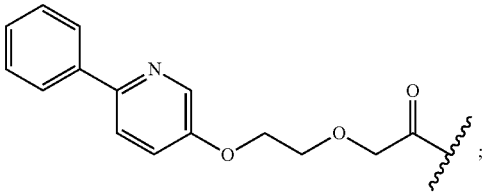
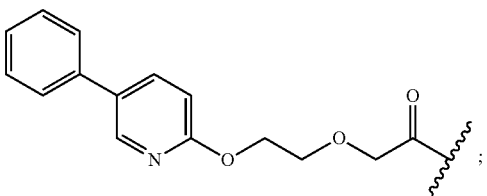
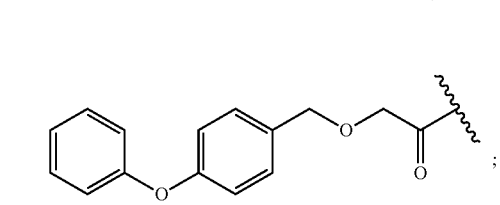
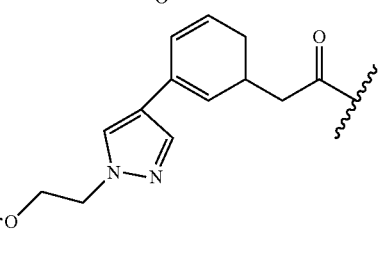
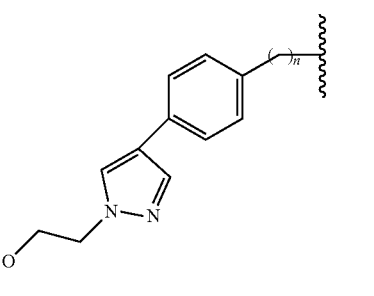
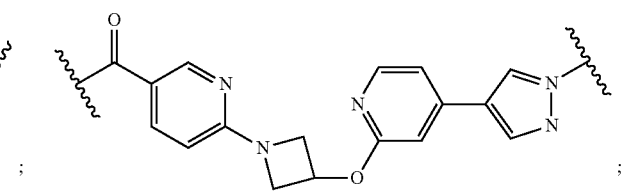

-continued
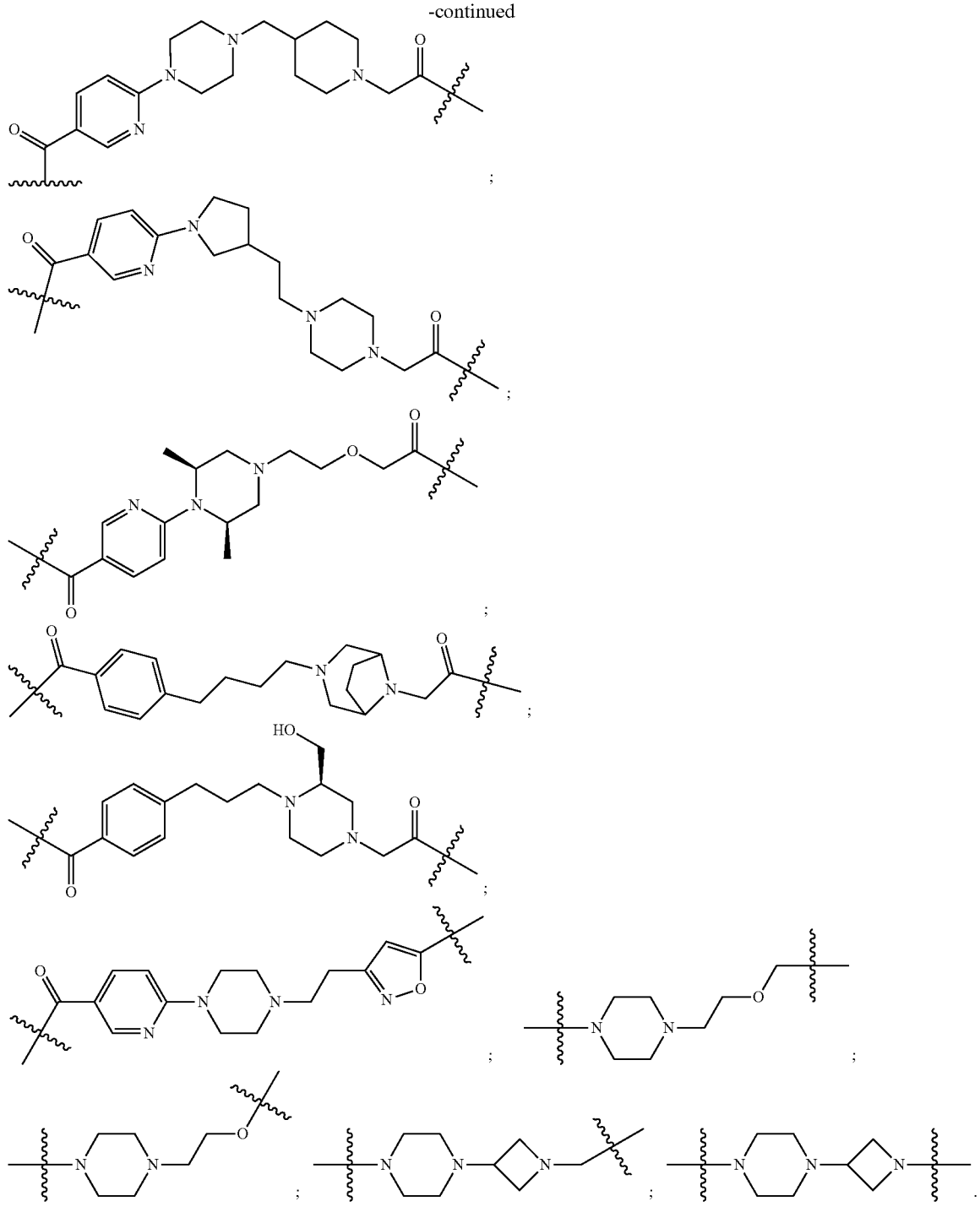
In any aspect or embodiment described herein, the linker (L) is selected from the group consisting of:
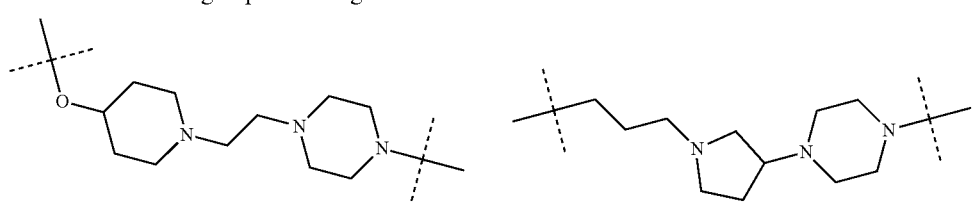

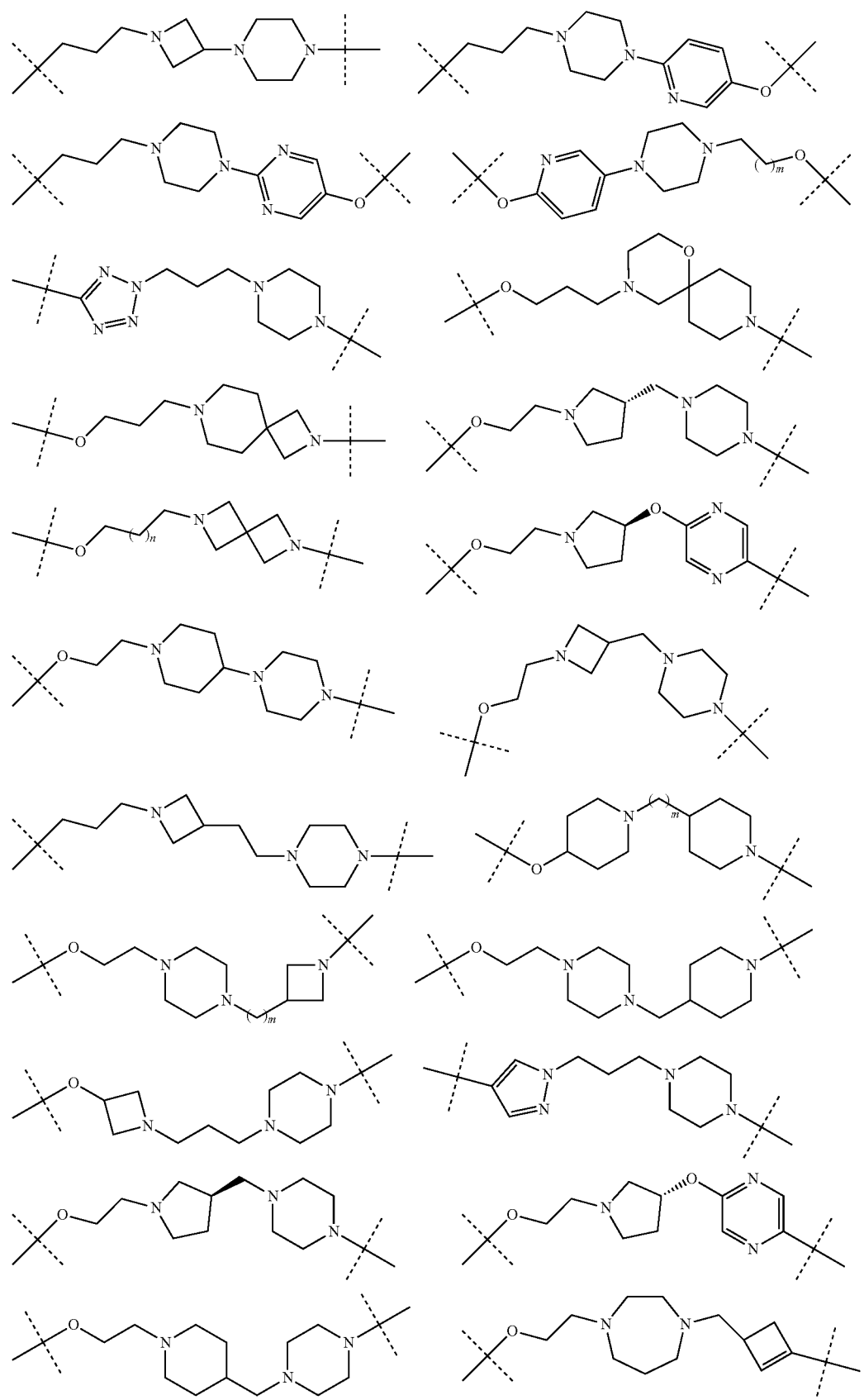

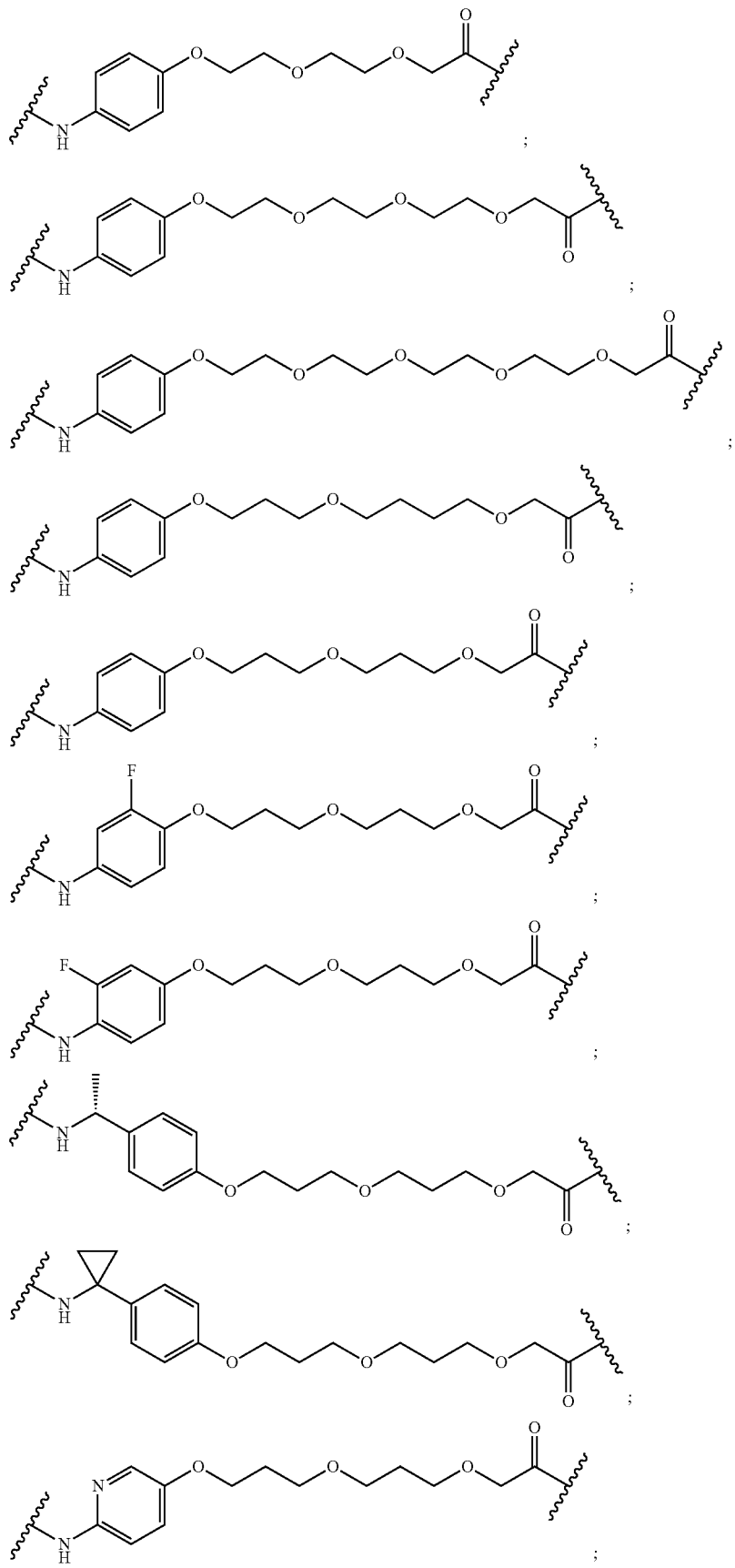

-continued
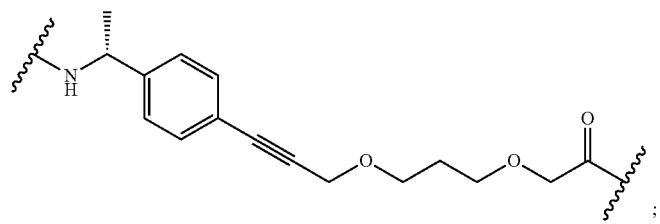
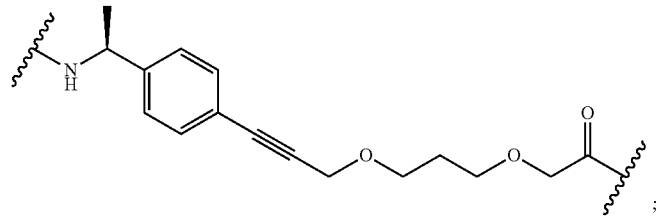
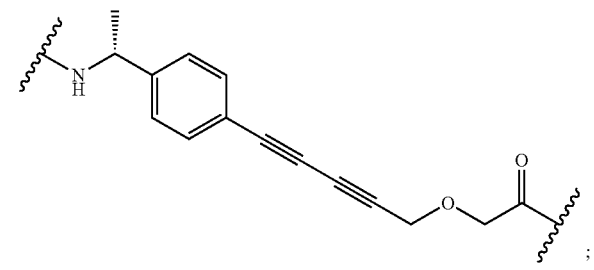
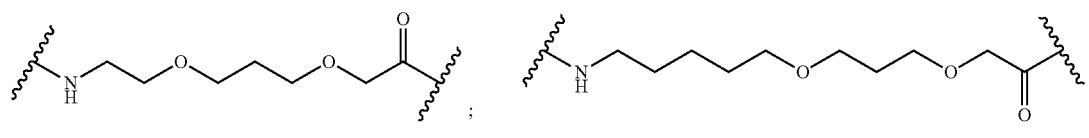
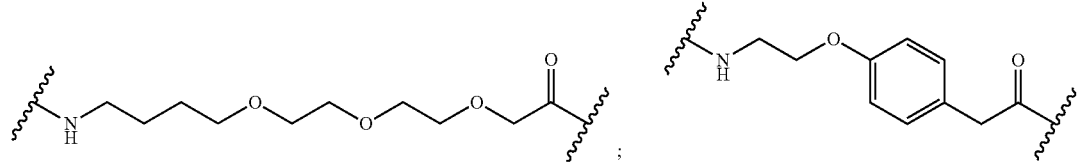
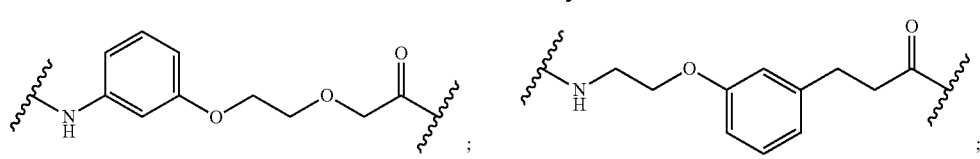
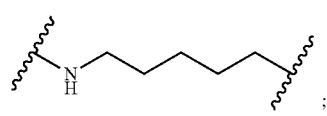
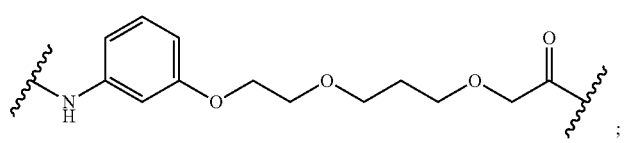
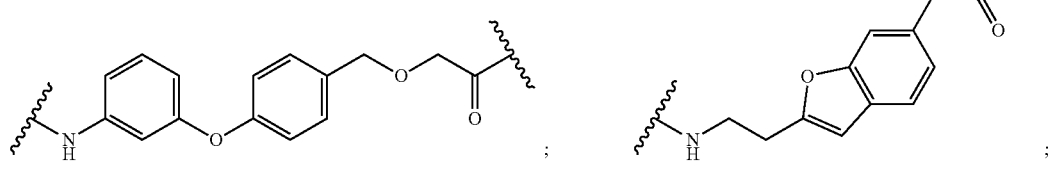

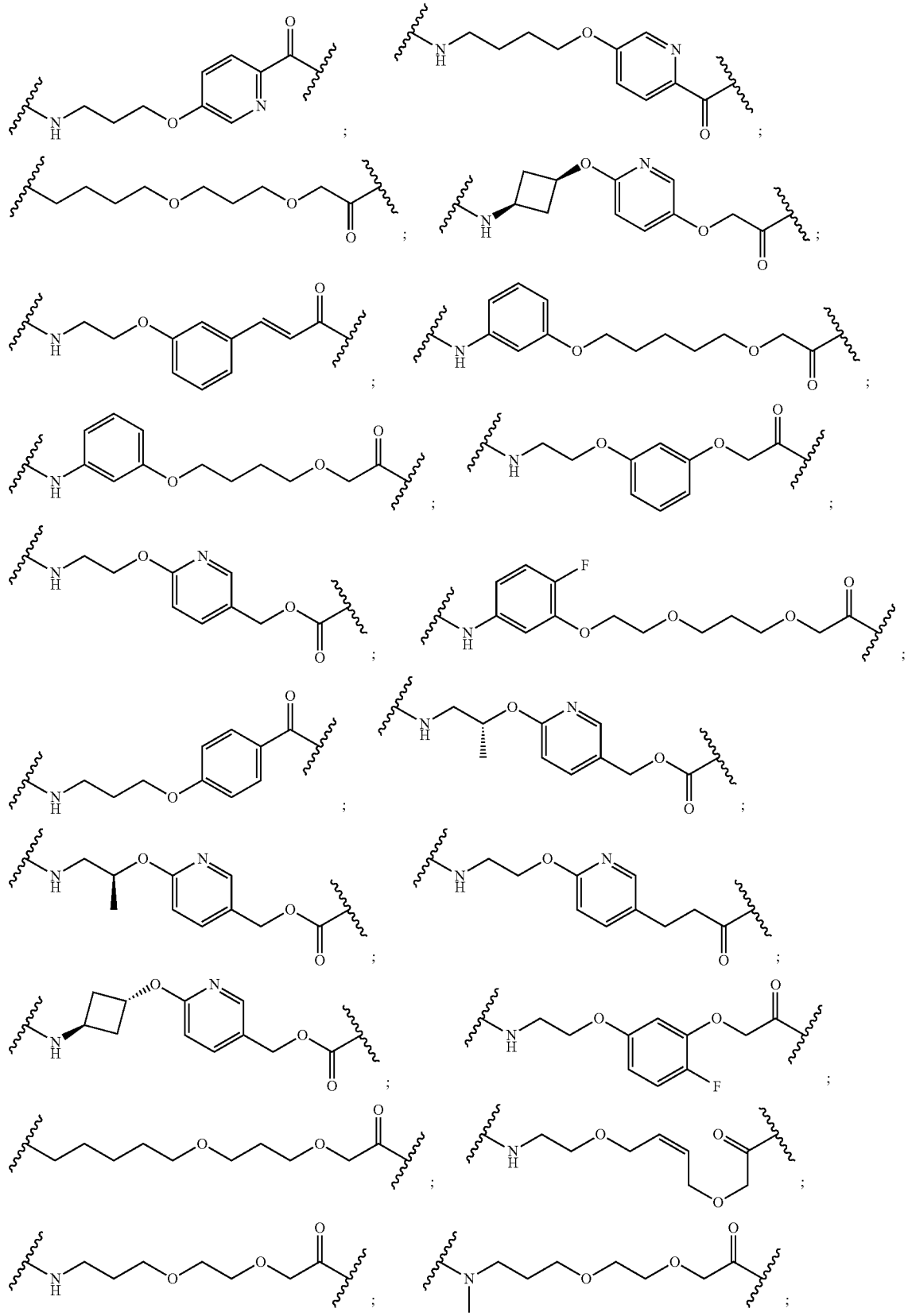

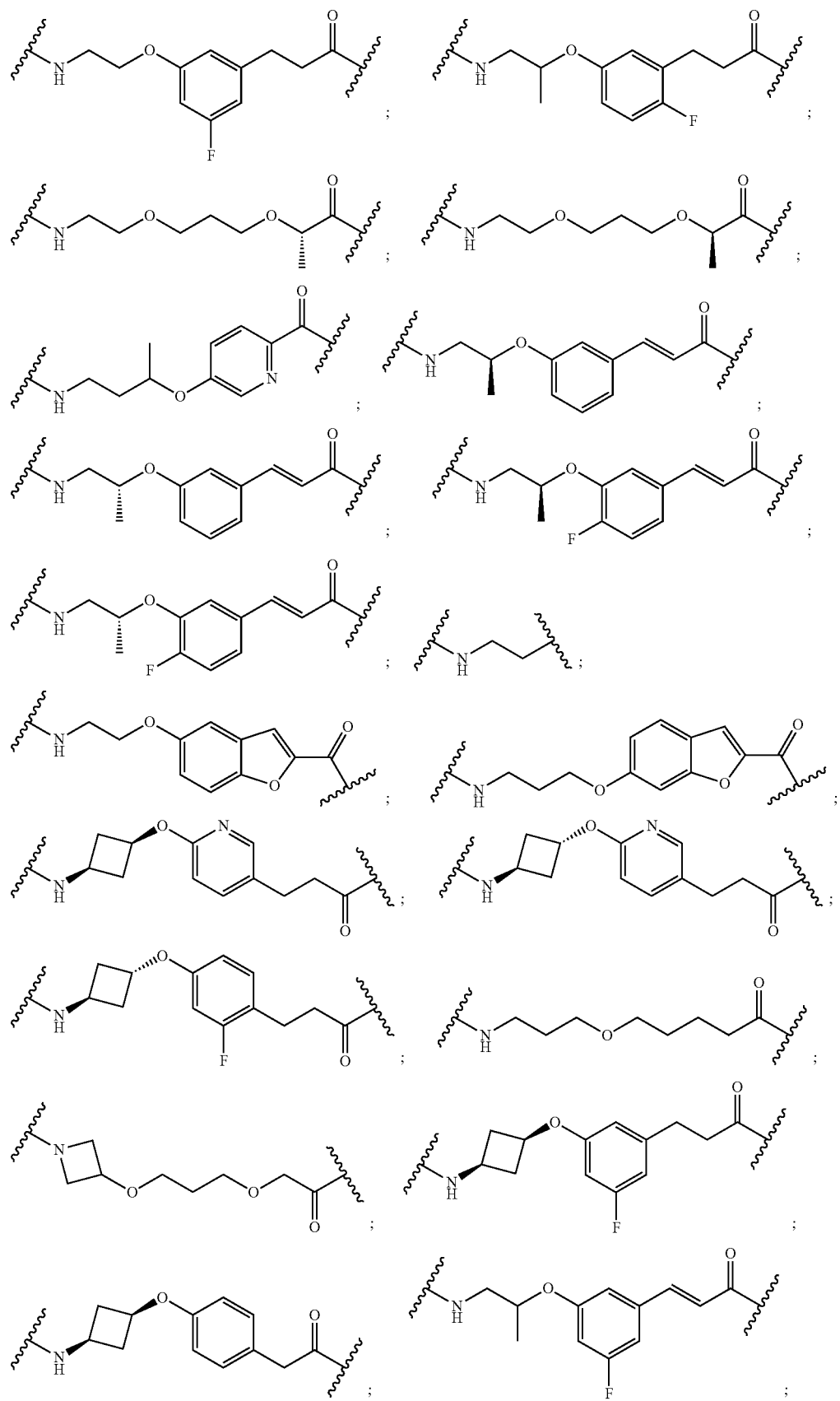

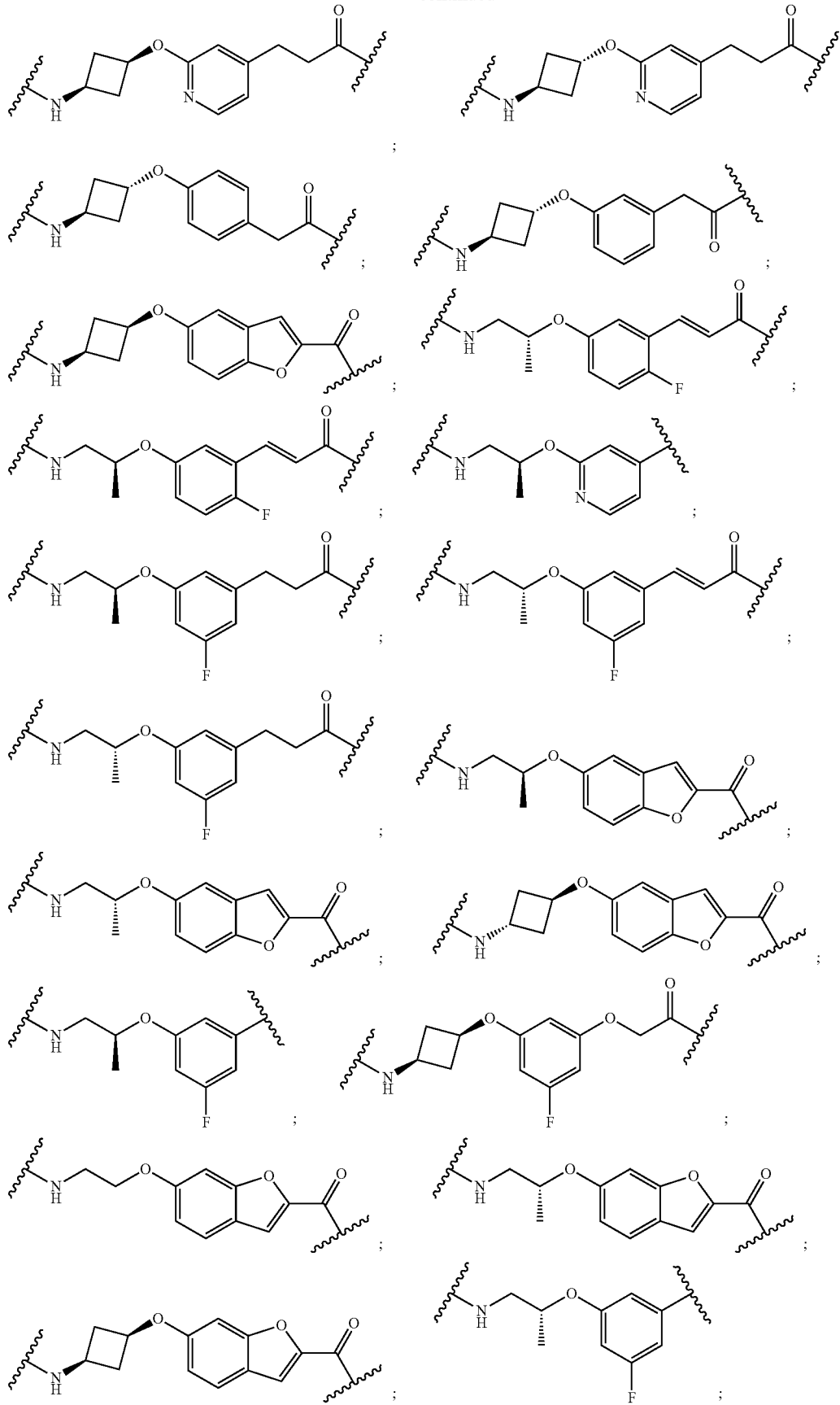

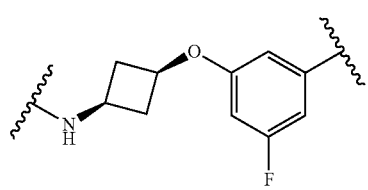
;
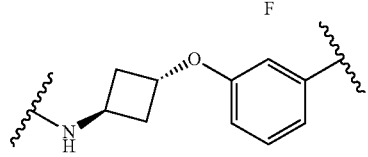
;
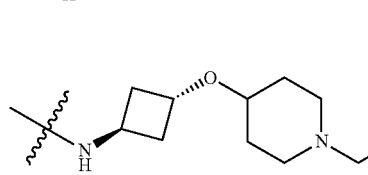
and
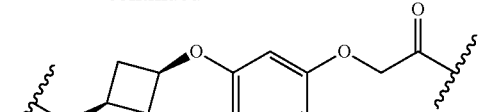
;
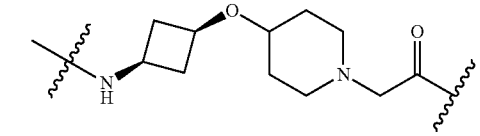
;
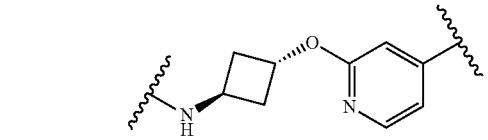
,
wherein each m and n is independently selected from 0, 1, 2, 3, 4, 5 or 6.
In any aspect or embodiment described herein, the linker (L) is selected from the group consisting of:
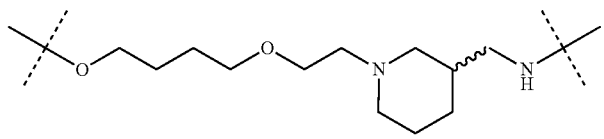
;
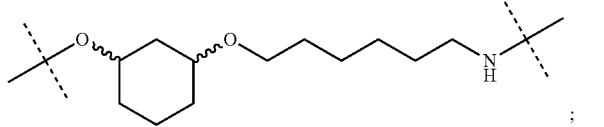
;
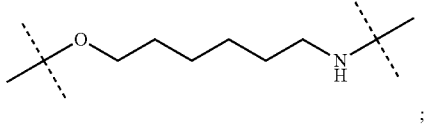
;
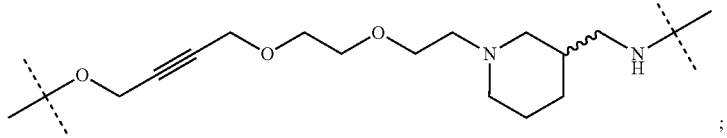
;
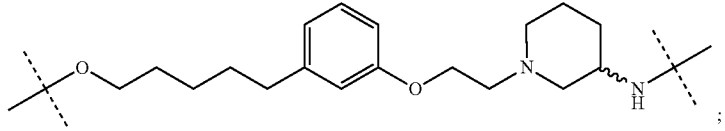
;
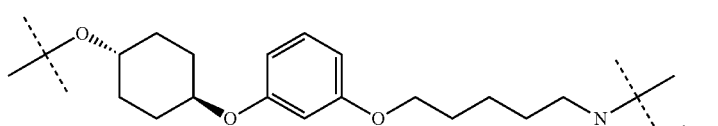
;
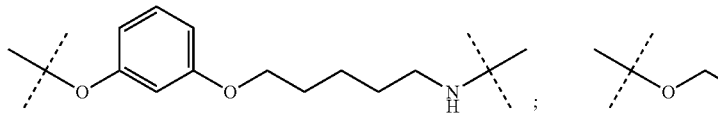
;
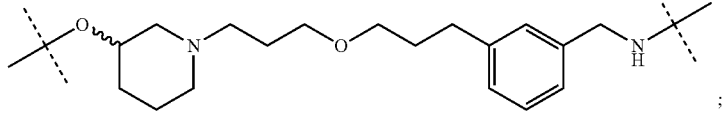
;

643
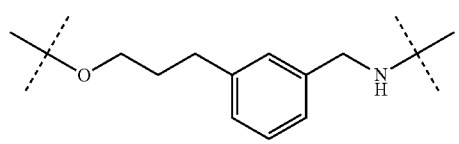

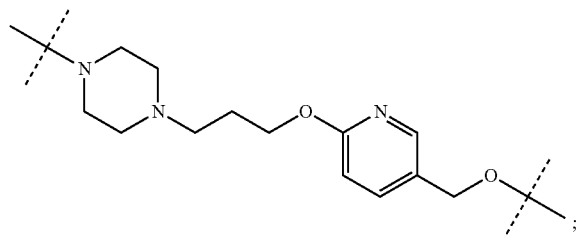
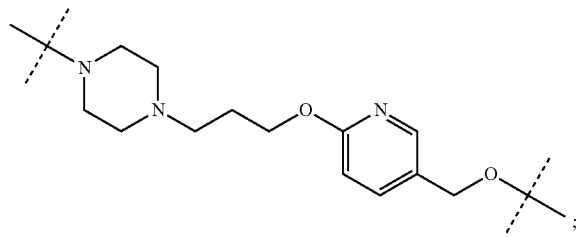
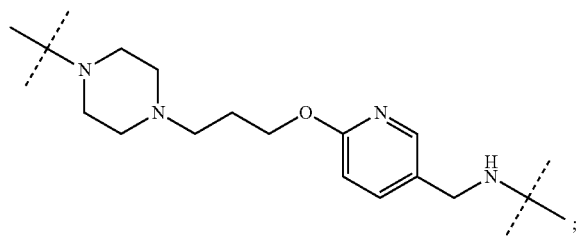
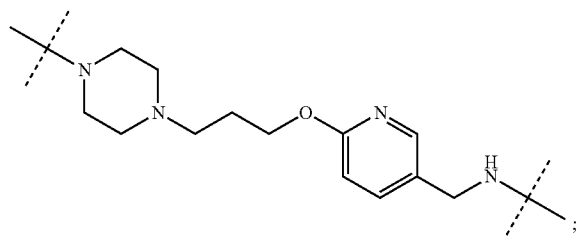
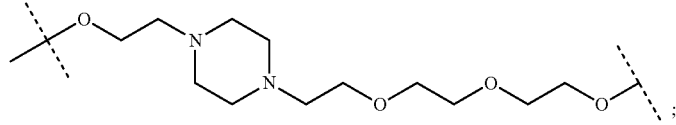
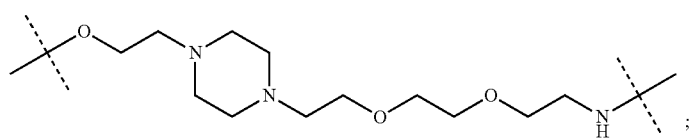
644
-continued
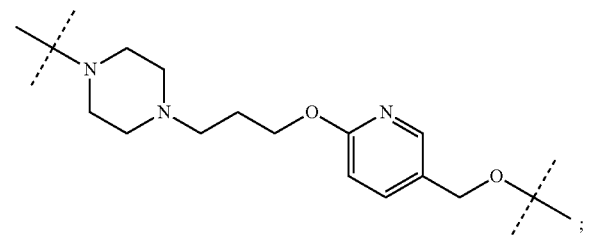
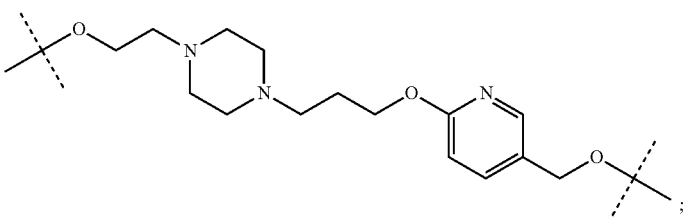
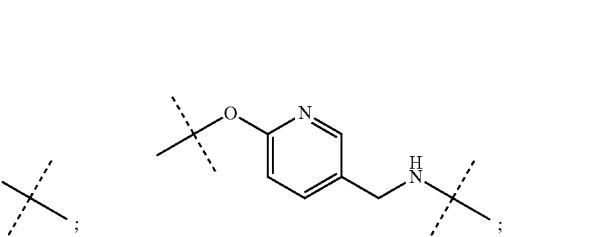
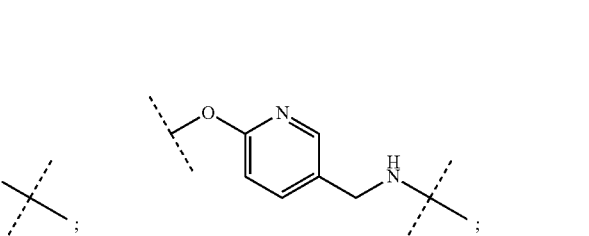
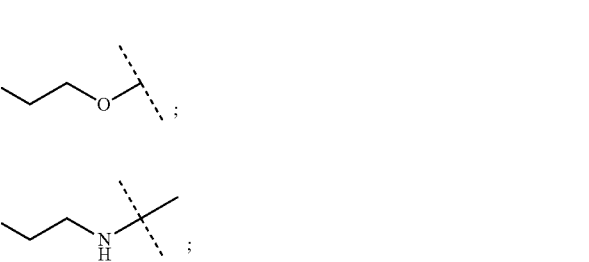

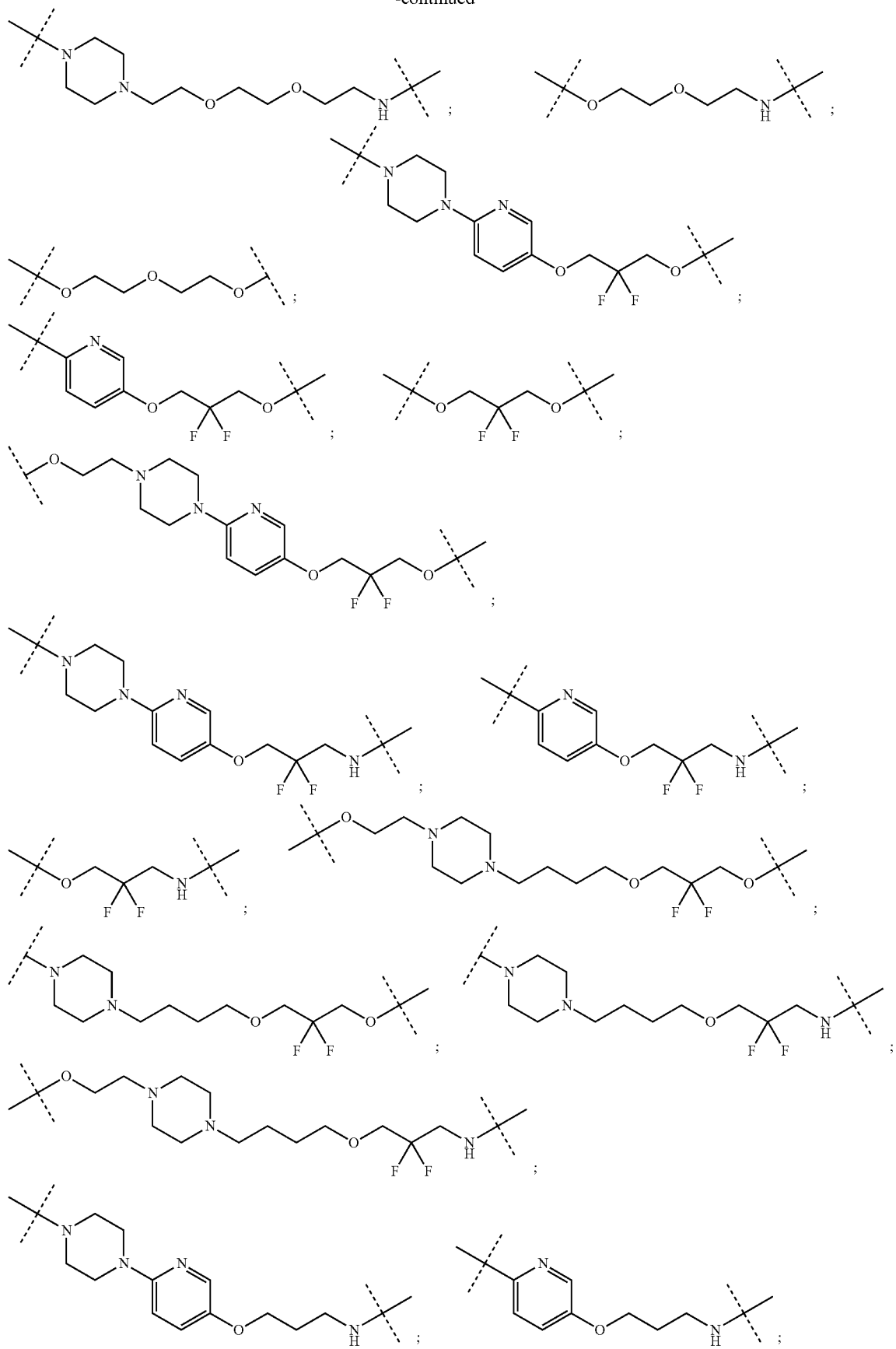

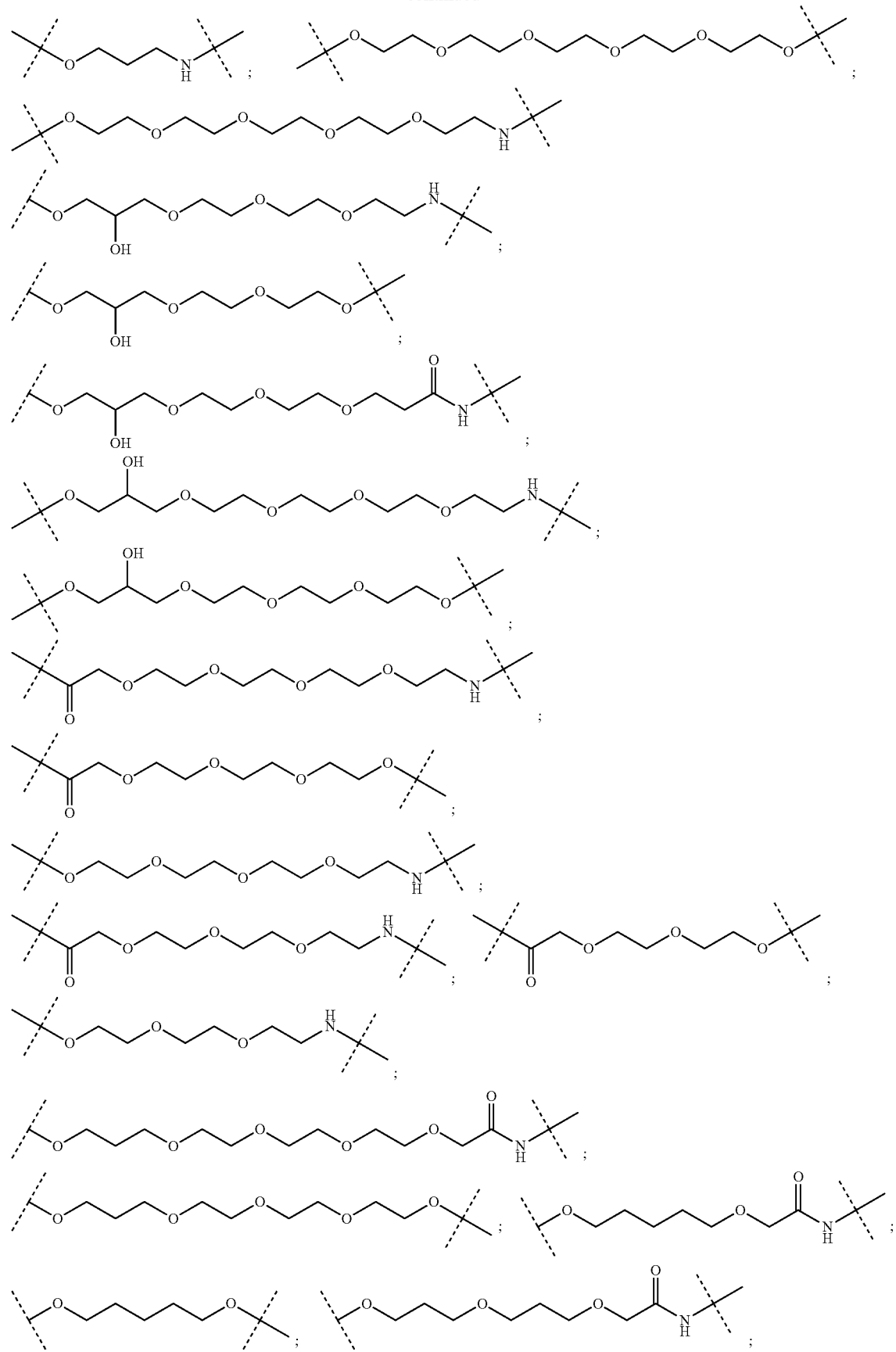

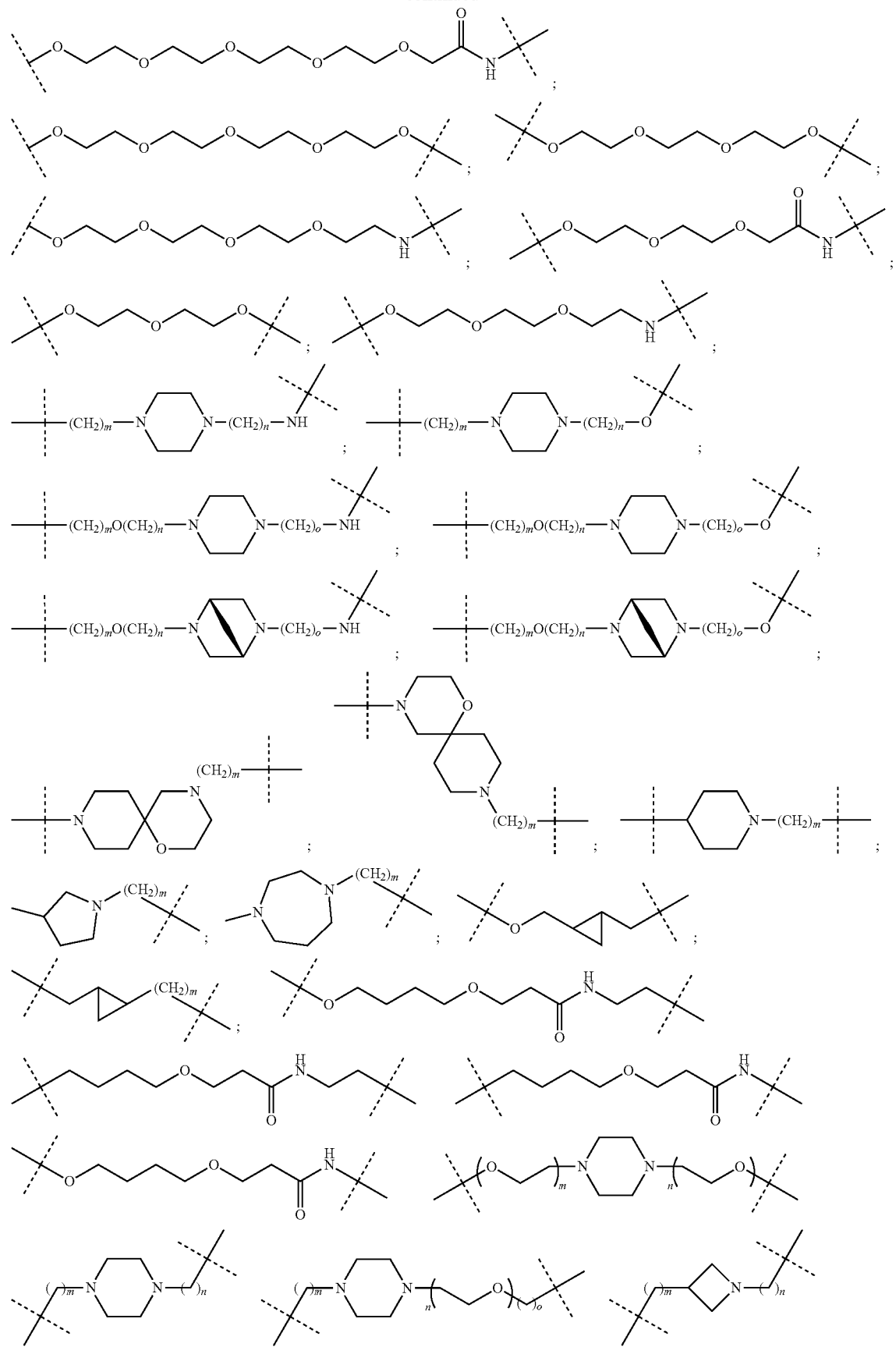

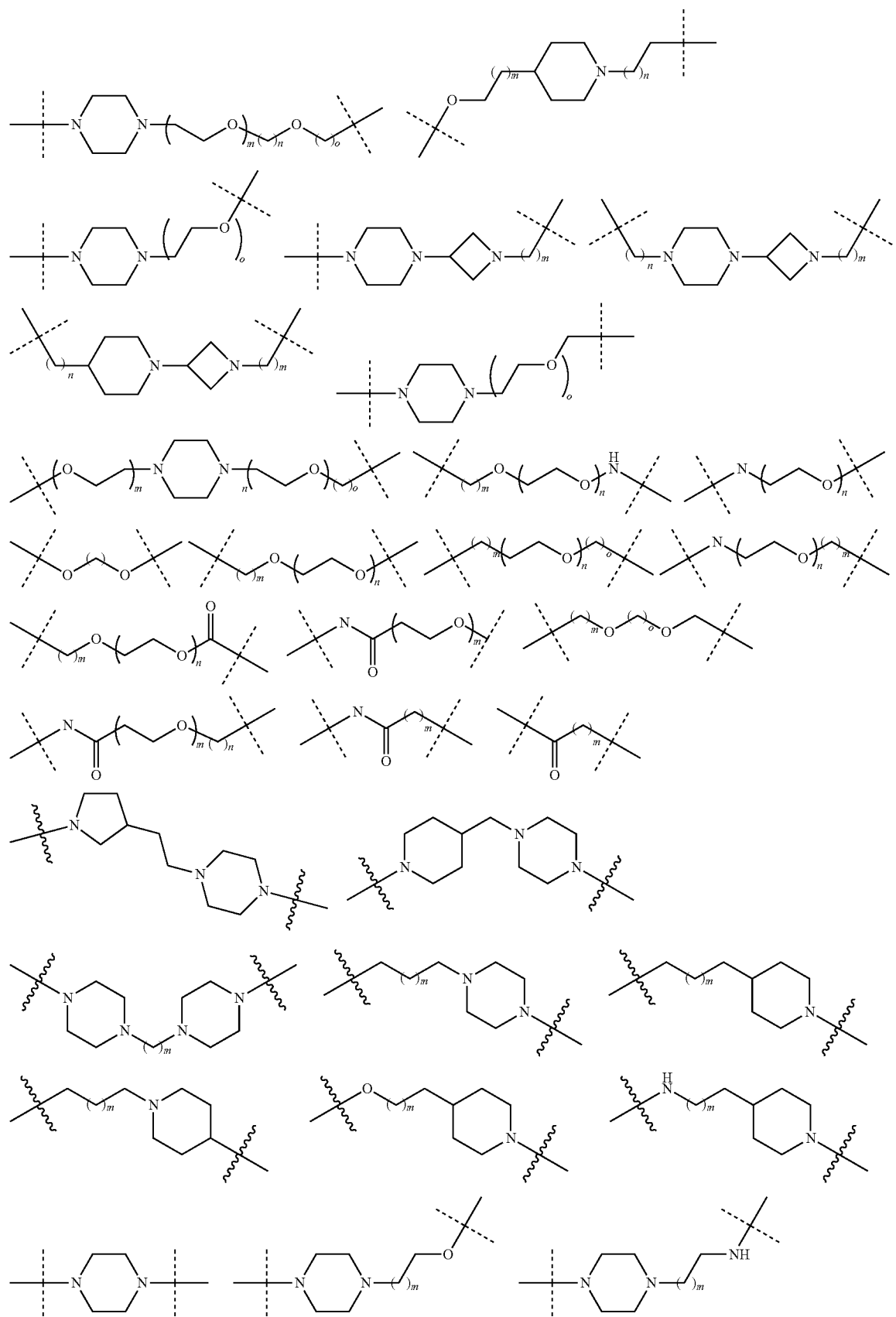

-continued
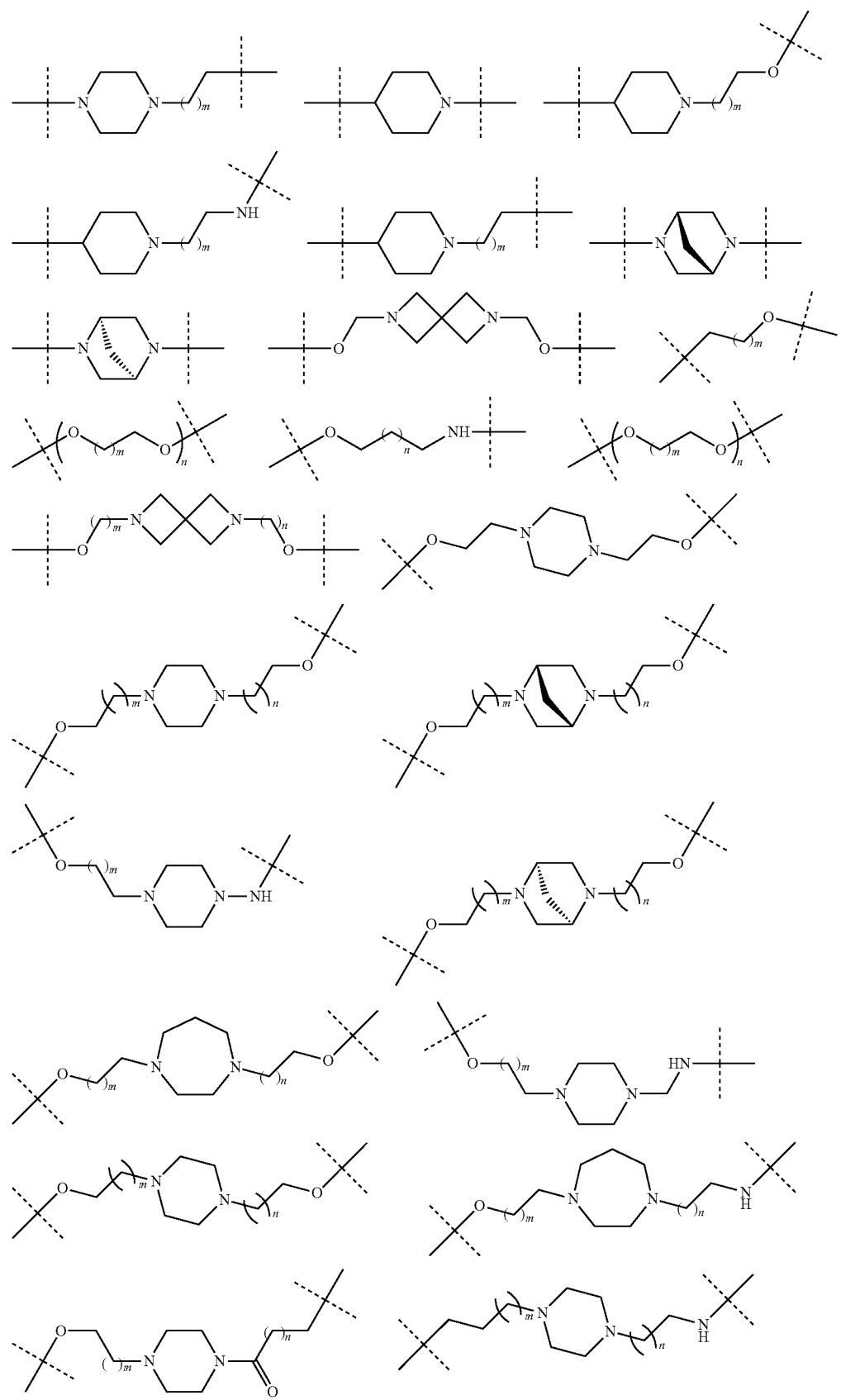

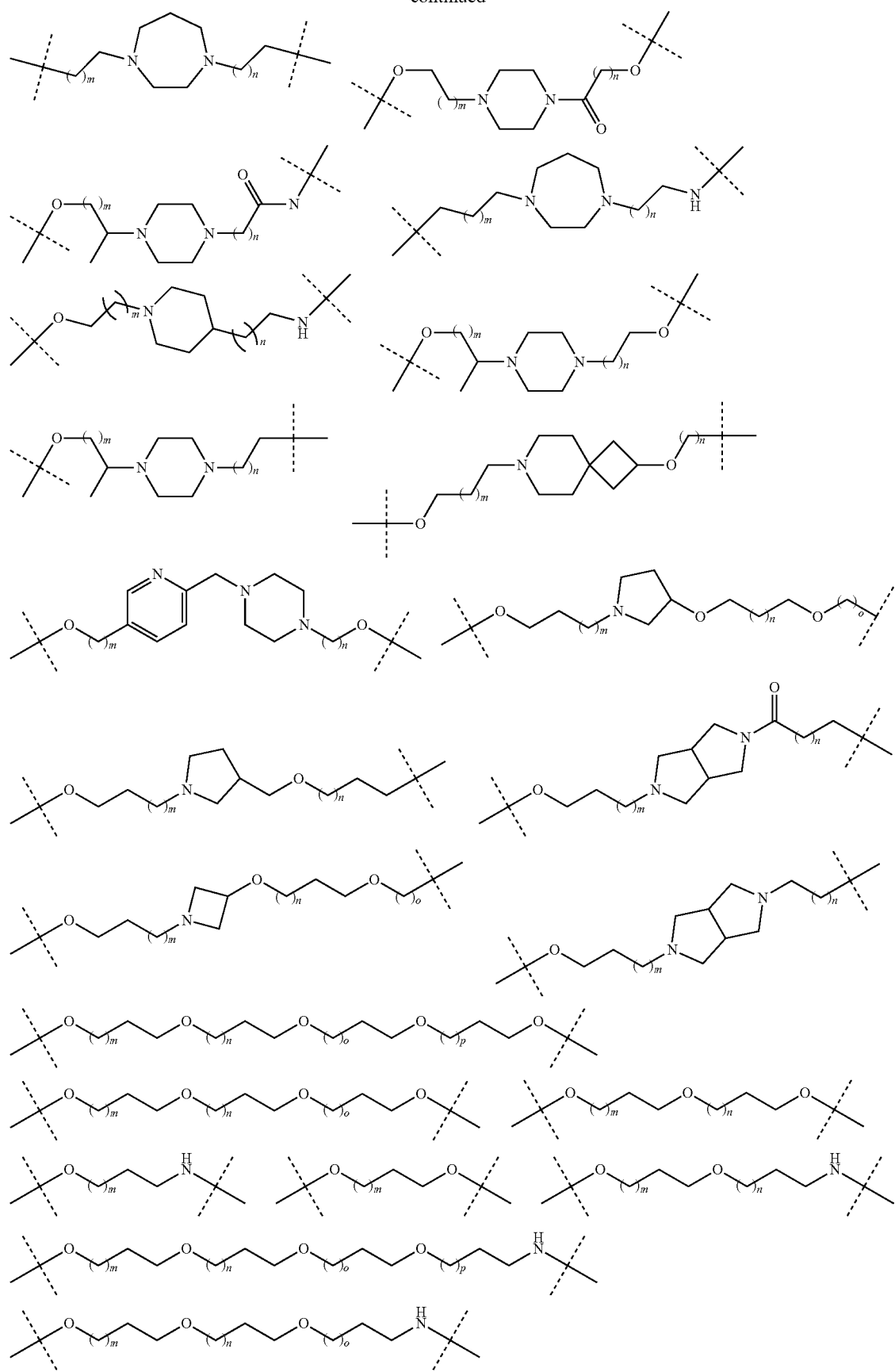

-continued
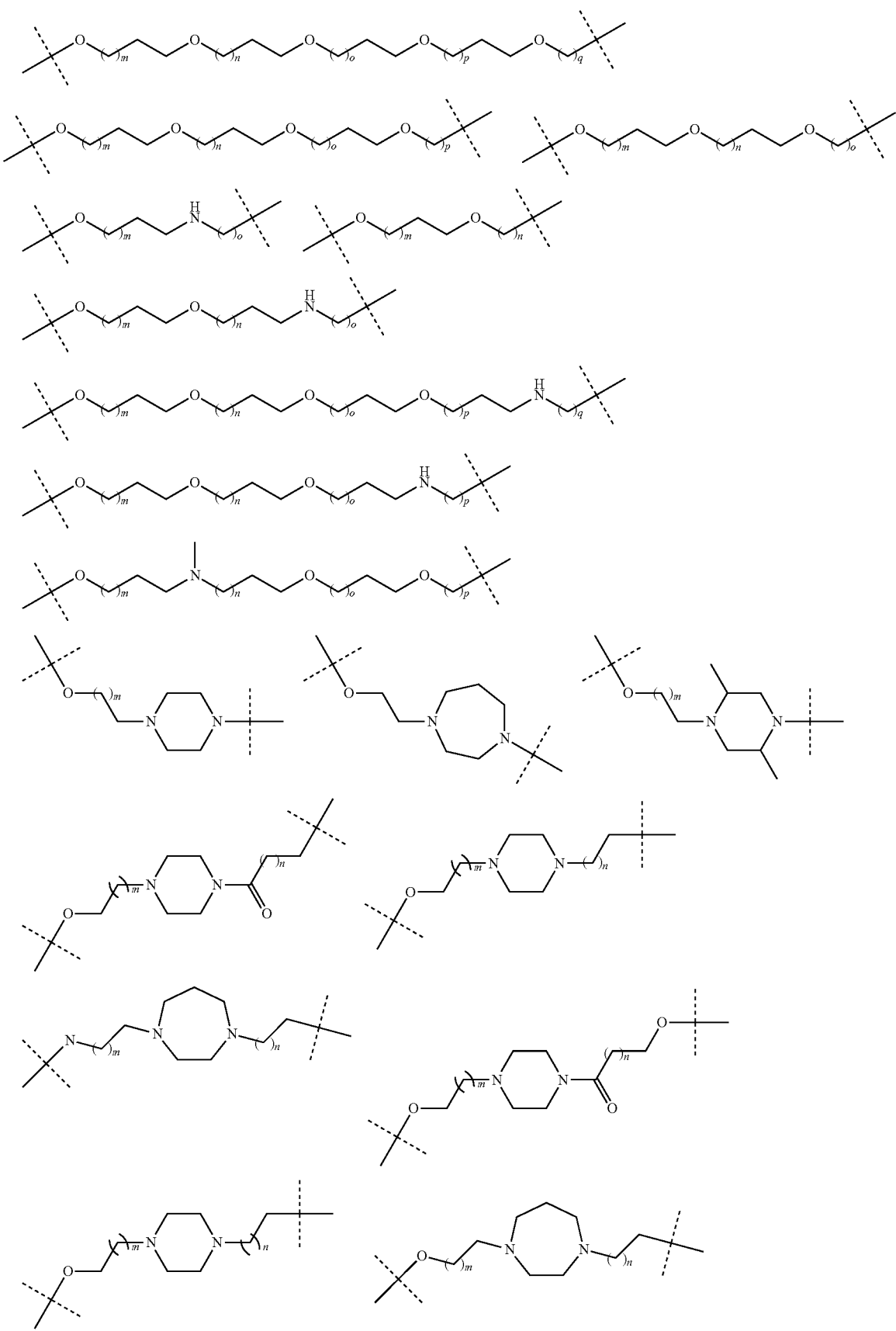

-continued
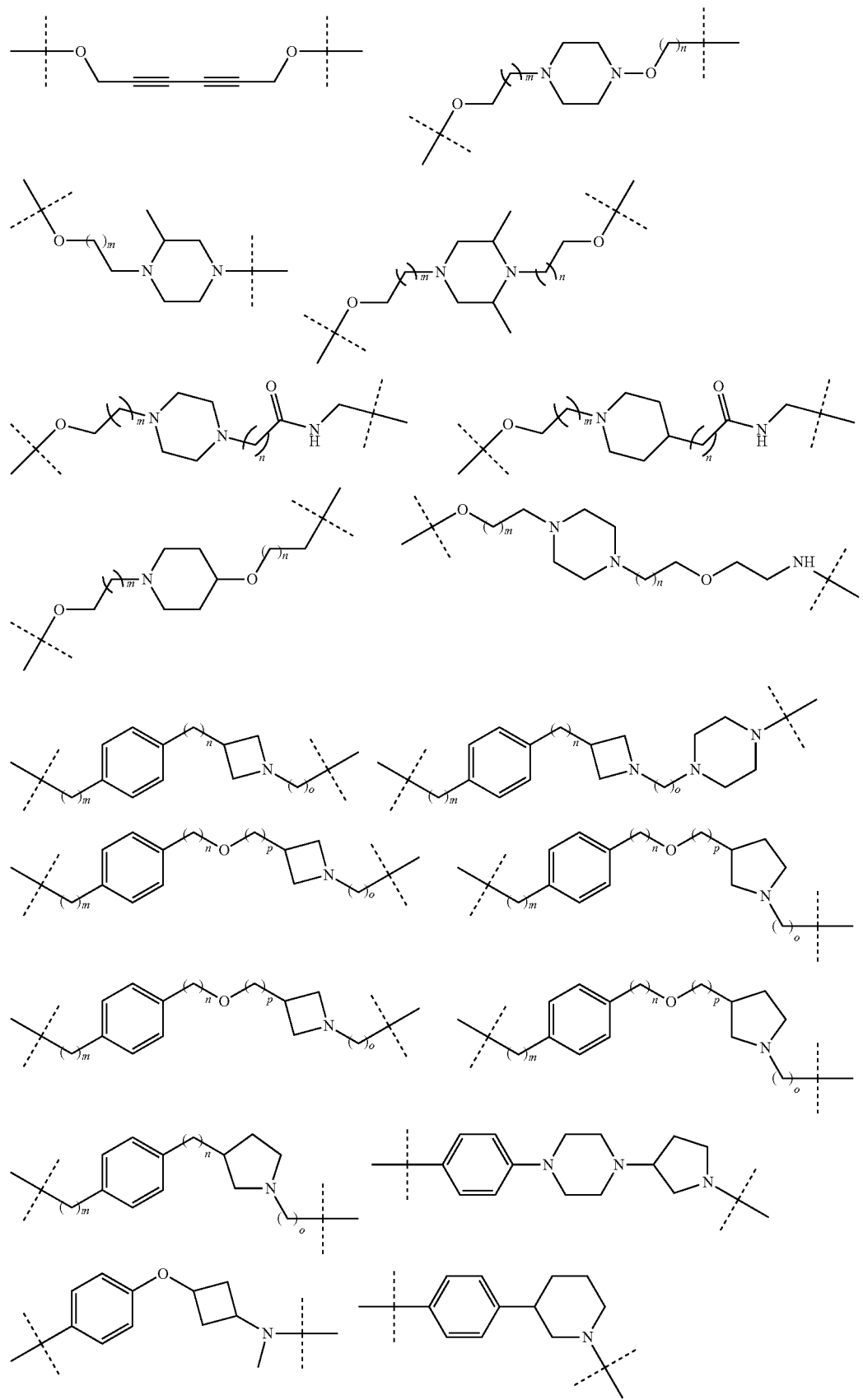

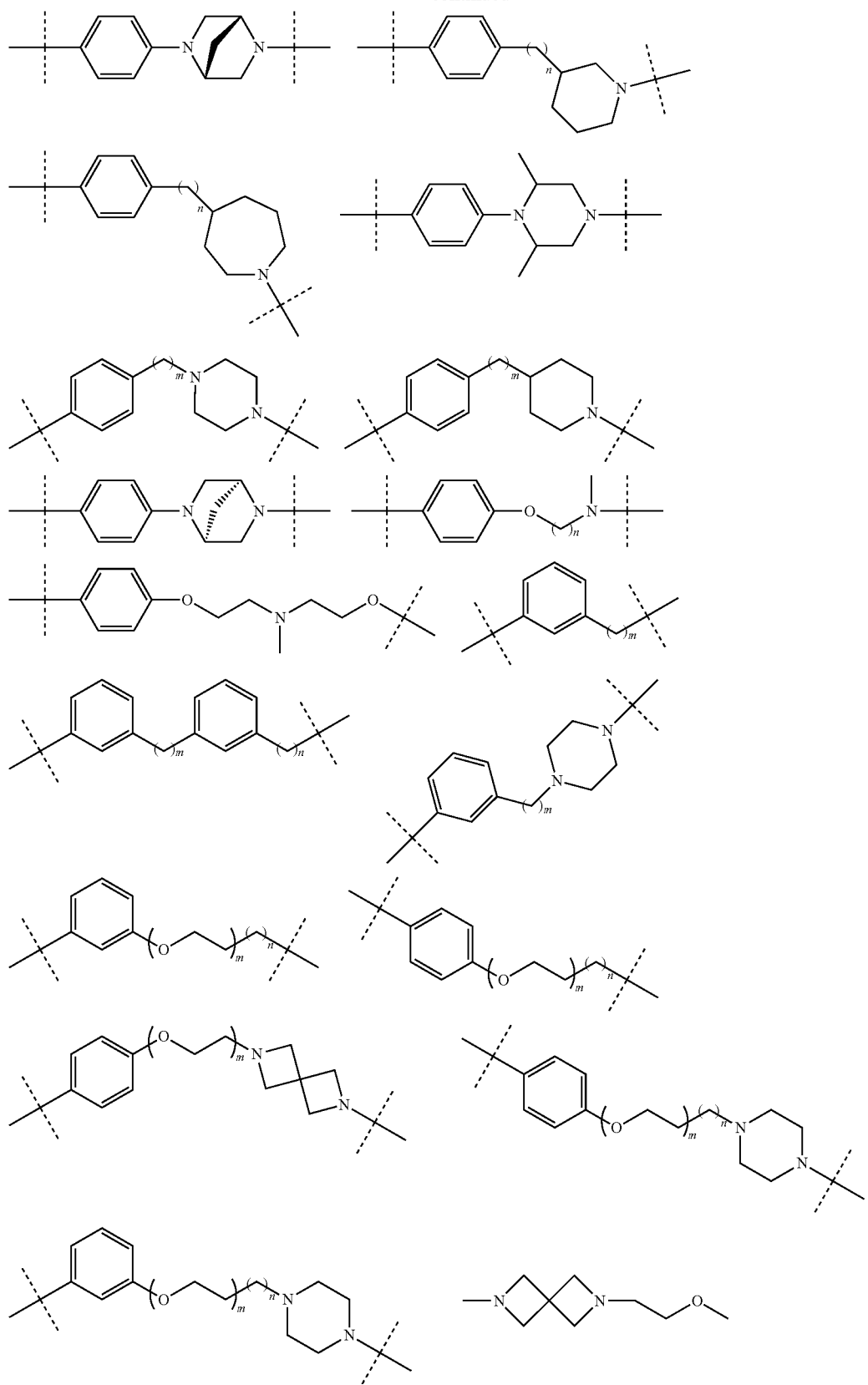

663 664
-continued
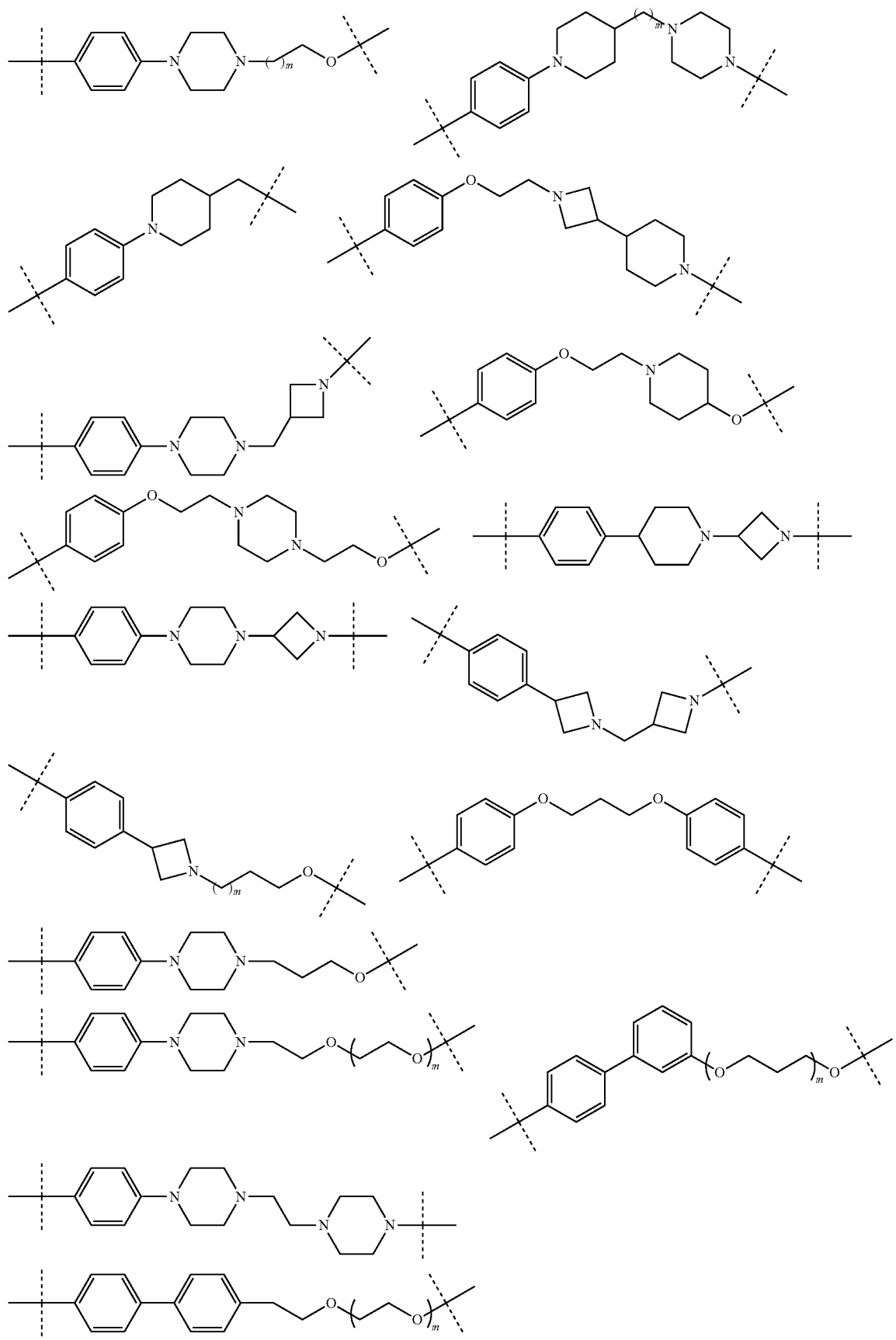

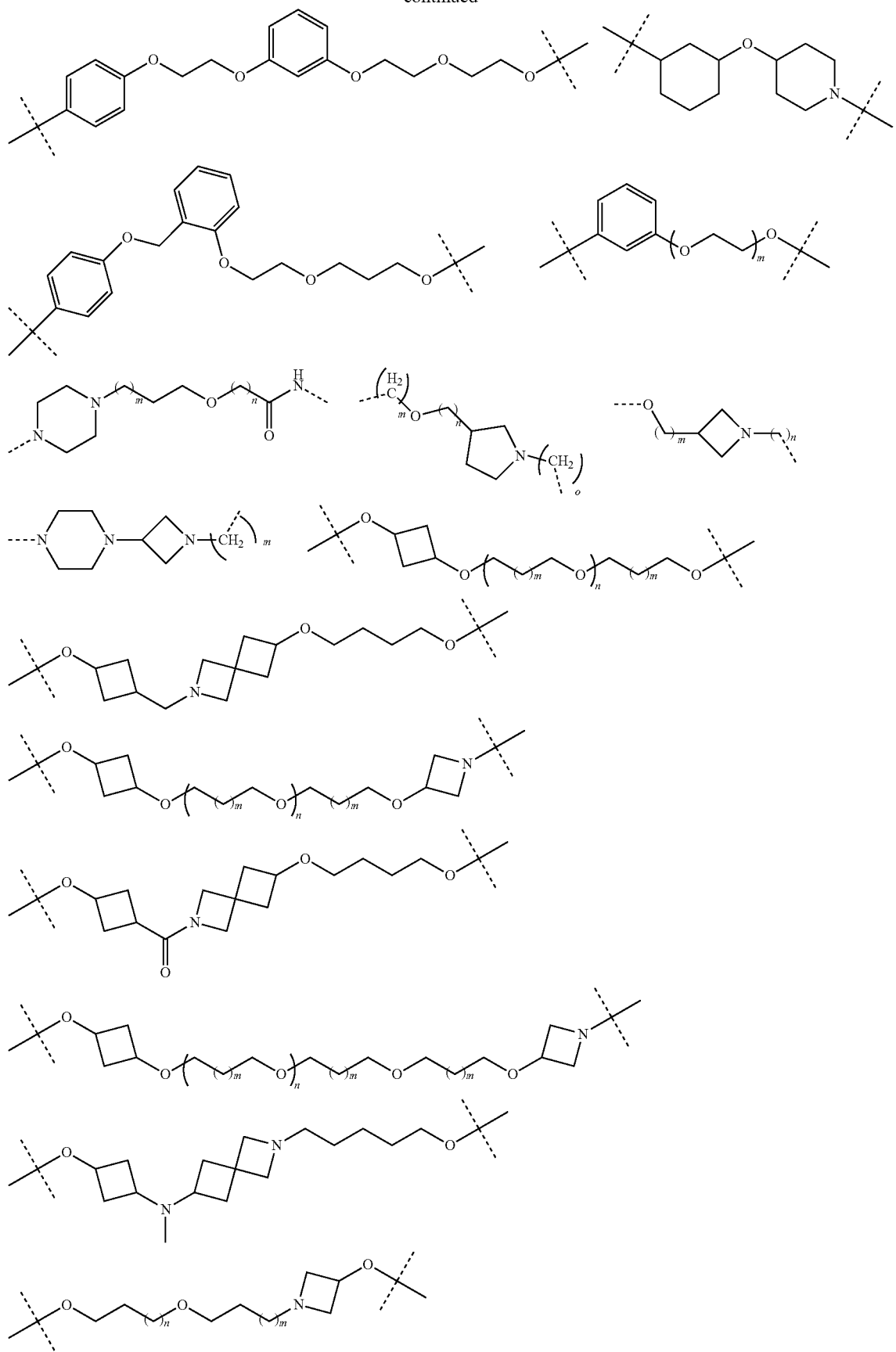

-continued
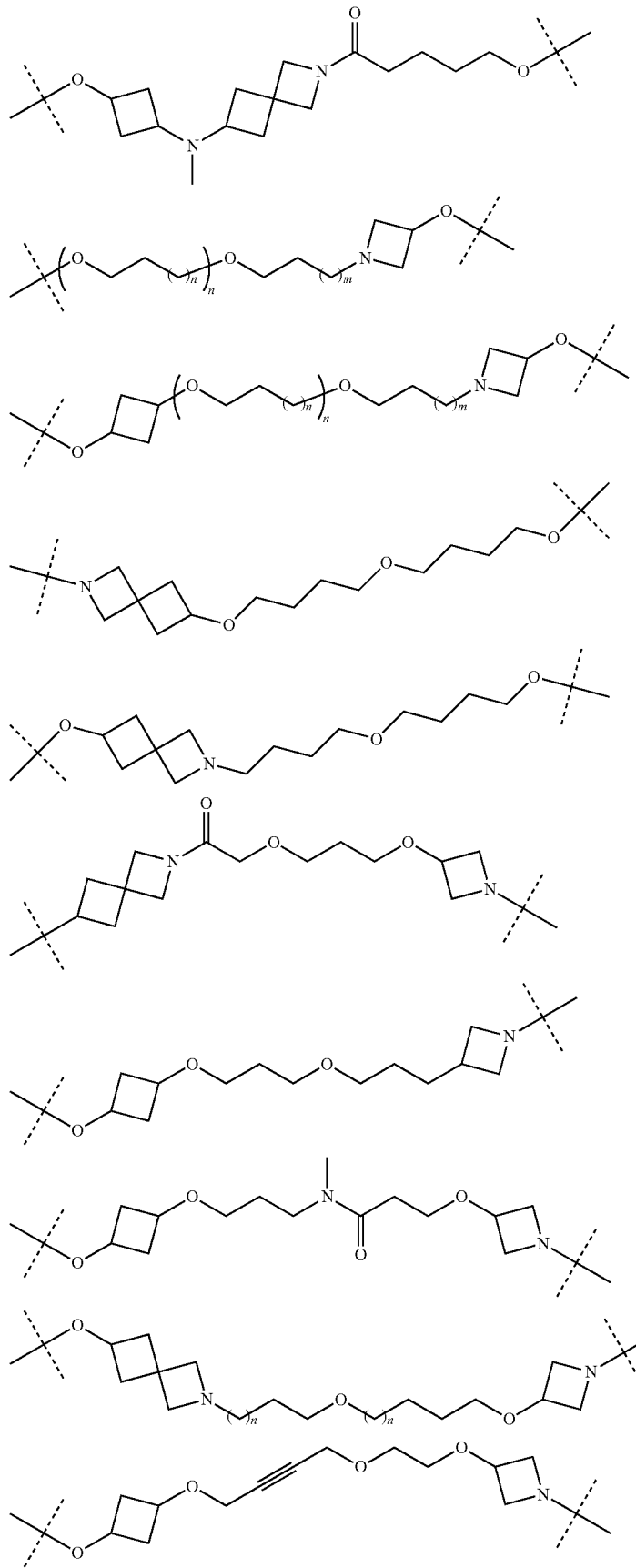

-continued
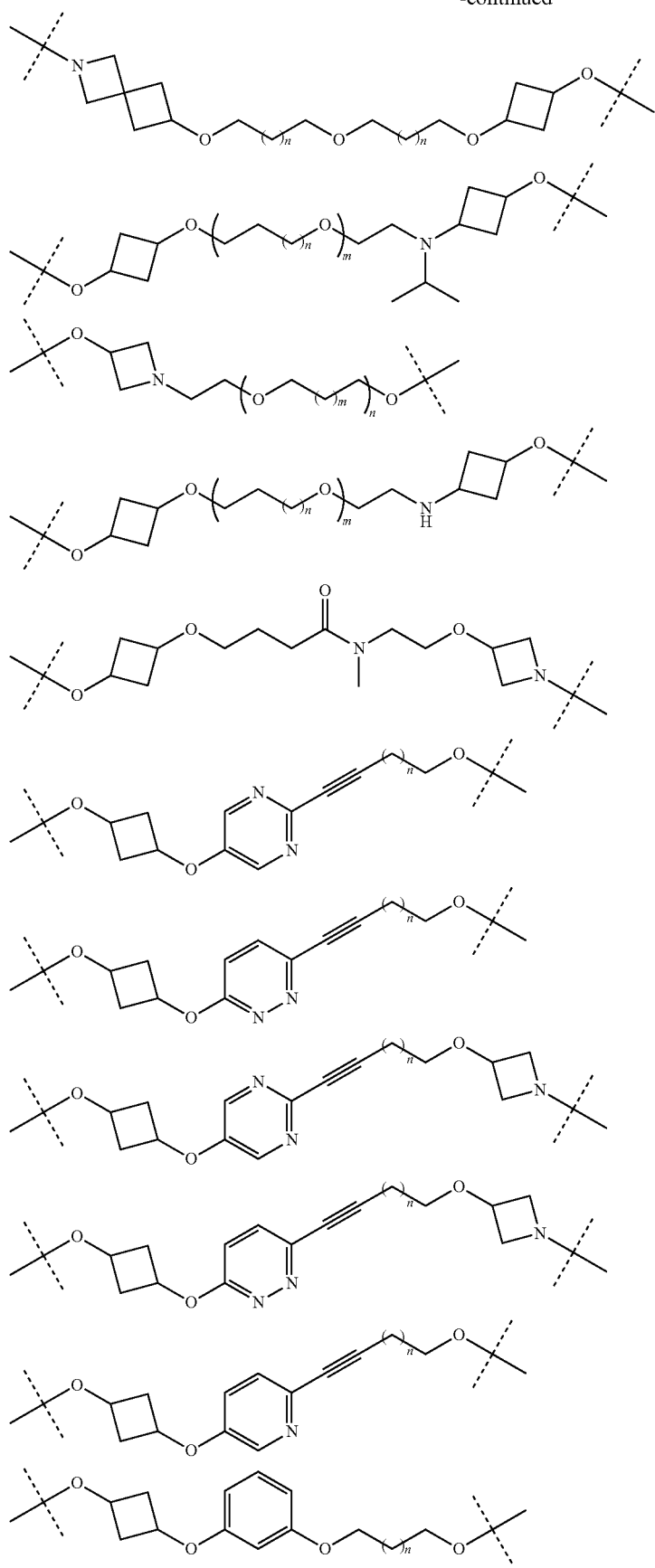

-continued
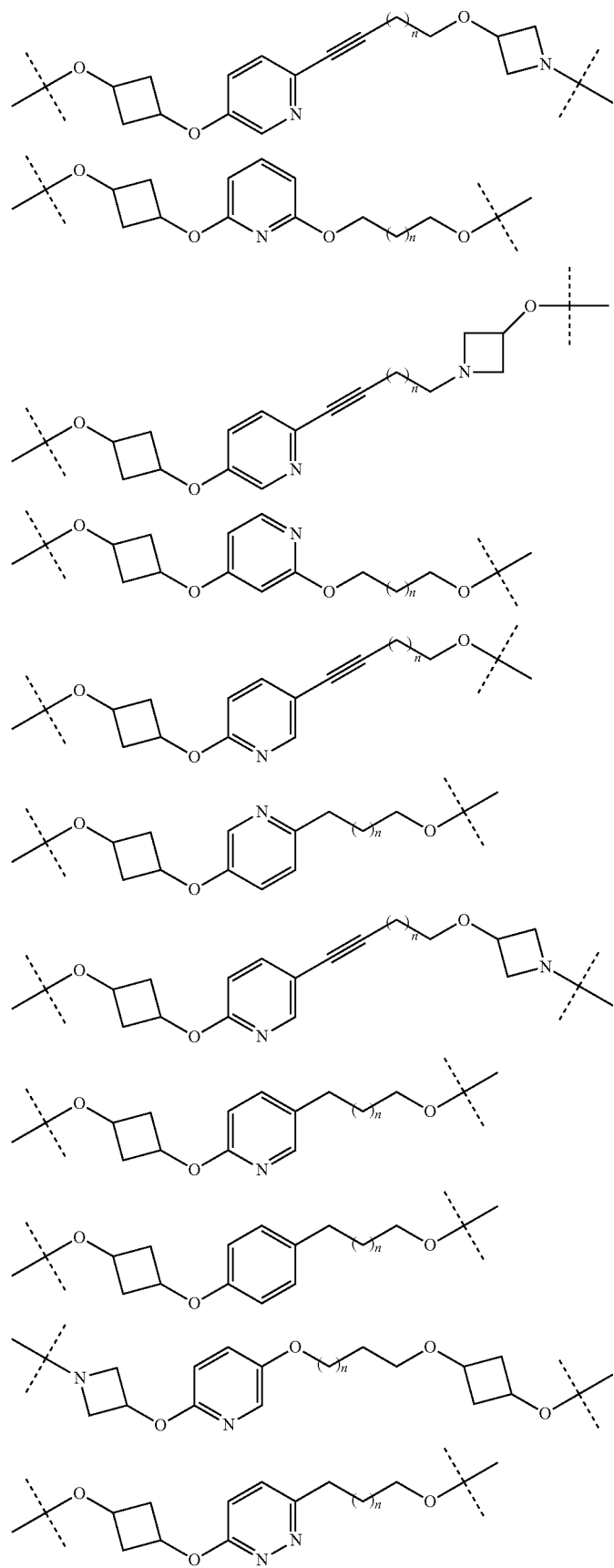

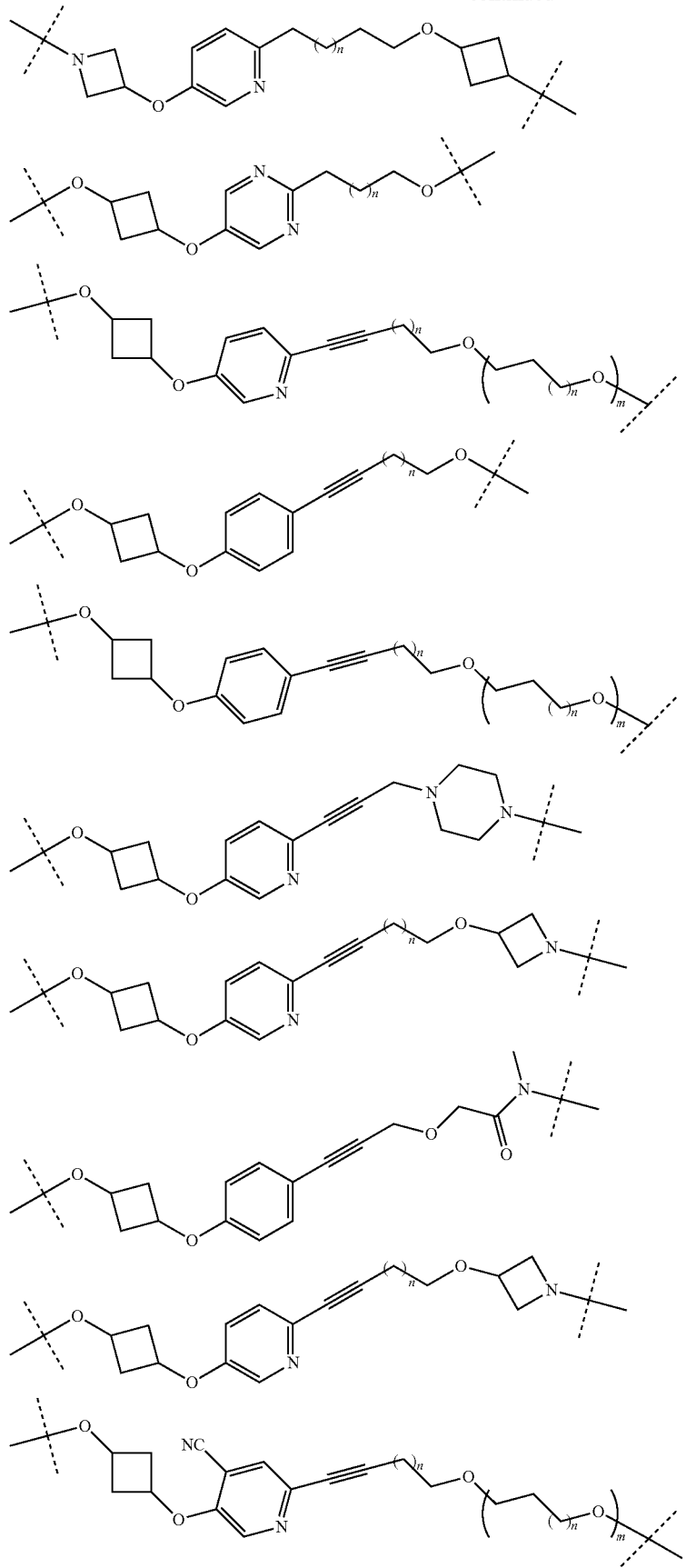

-continued
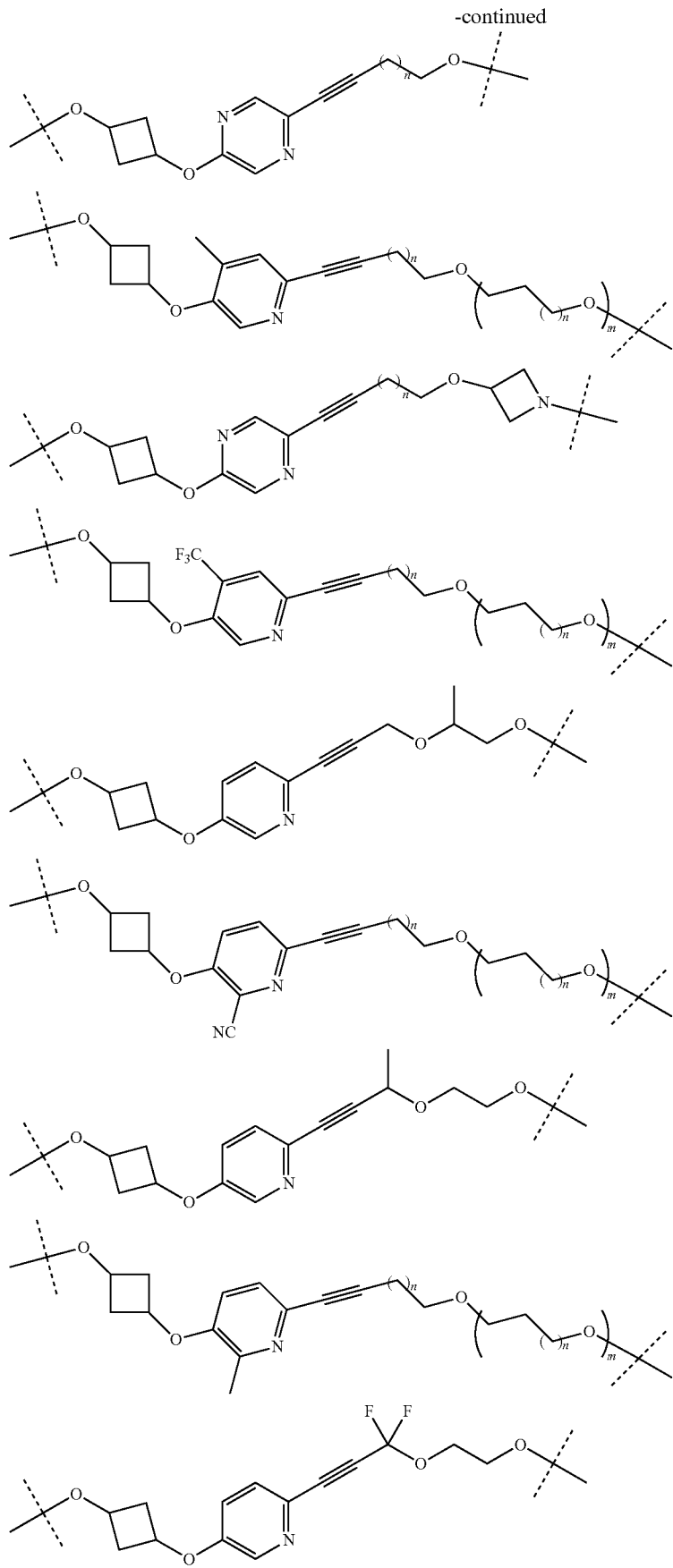

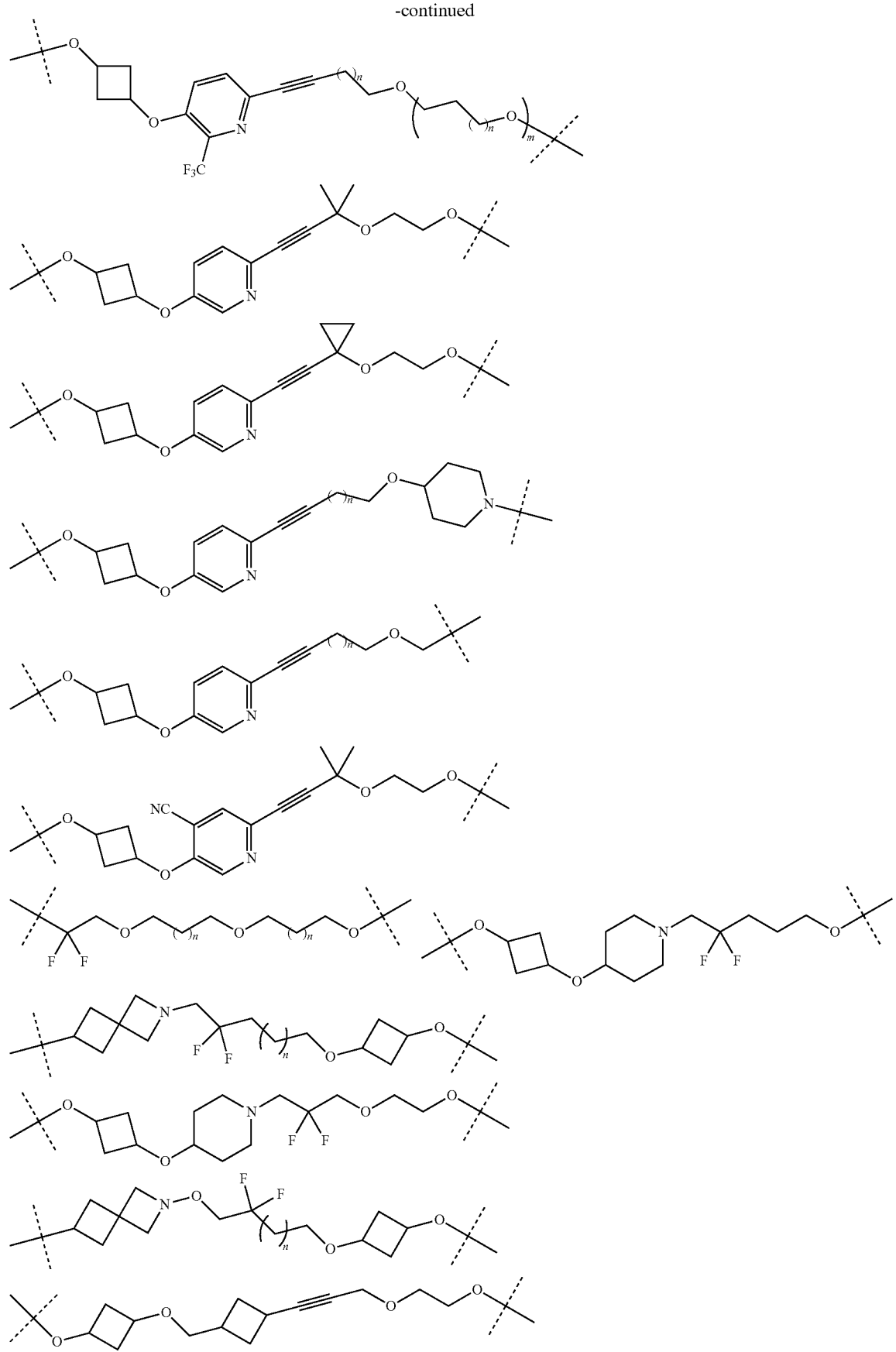

-continued
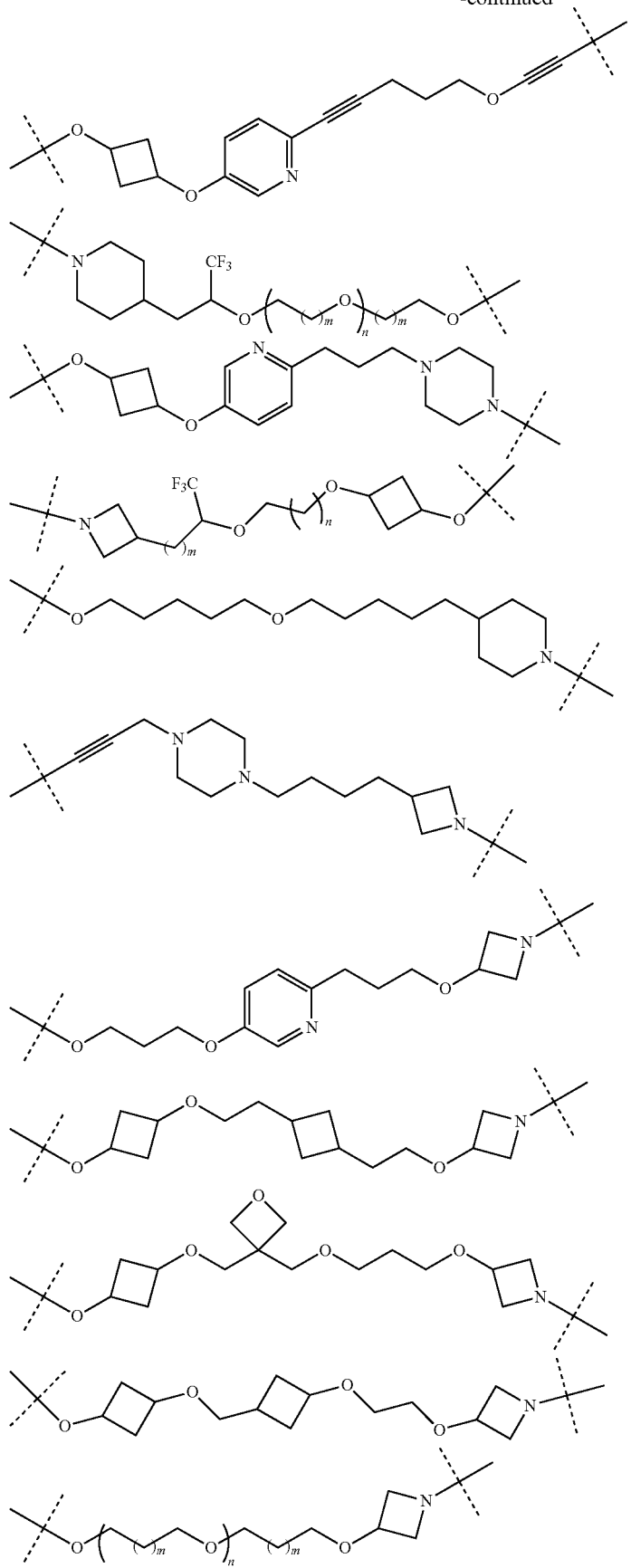

-continued
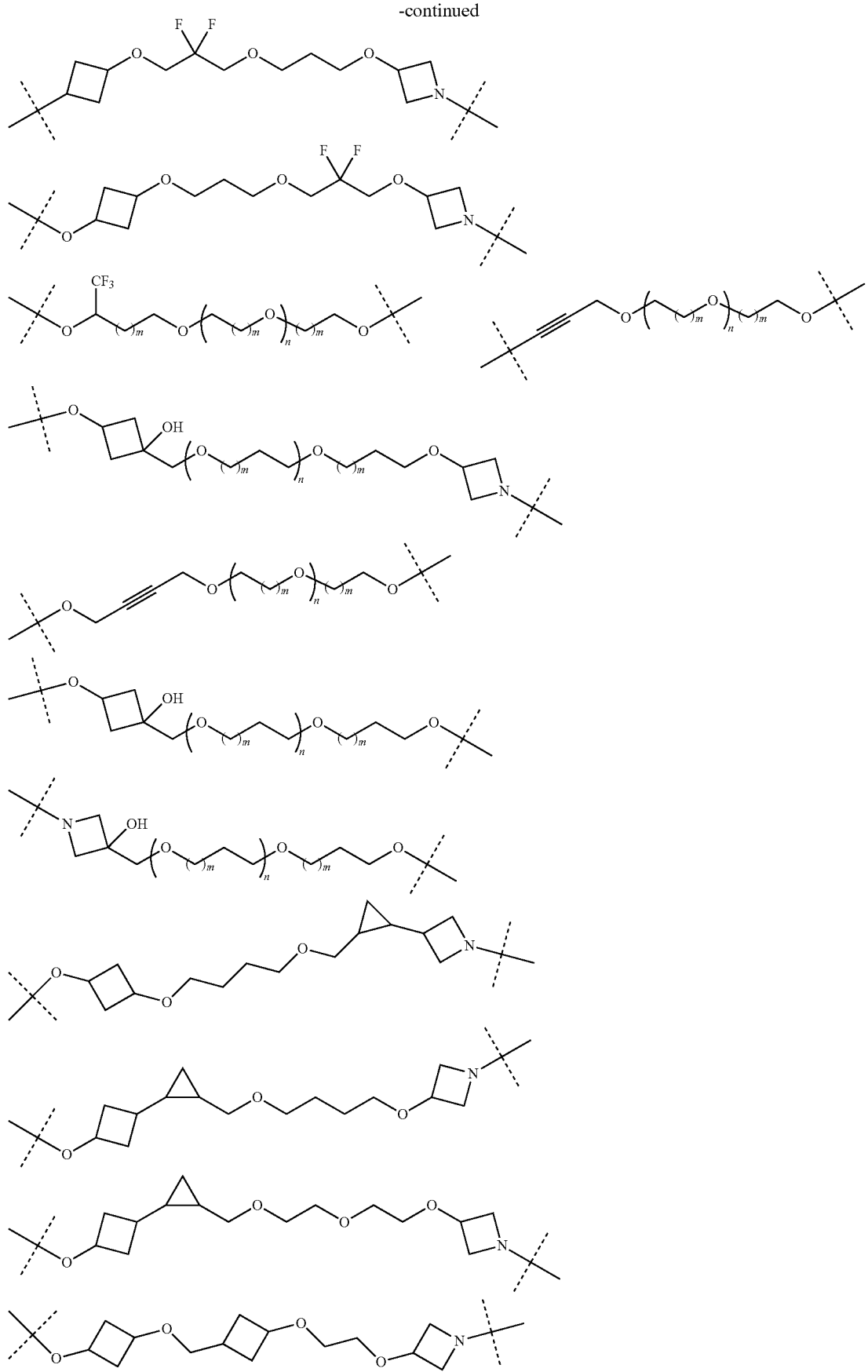

-continued
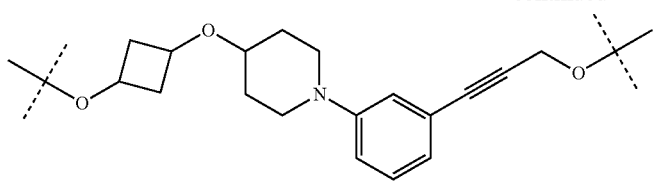
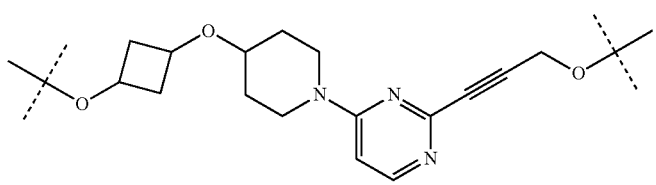
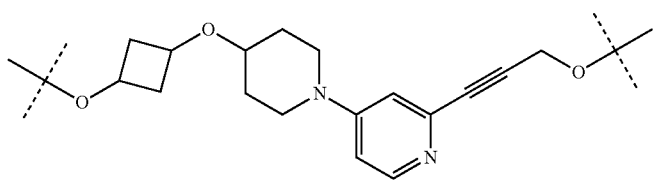
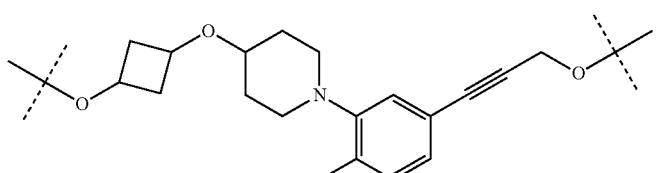
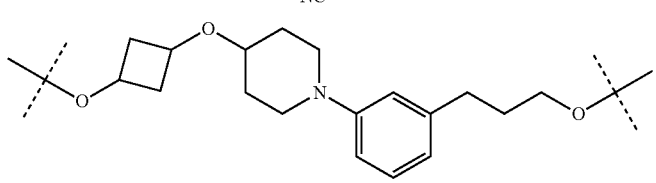
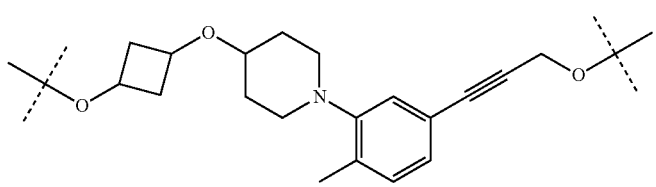
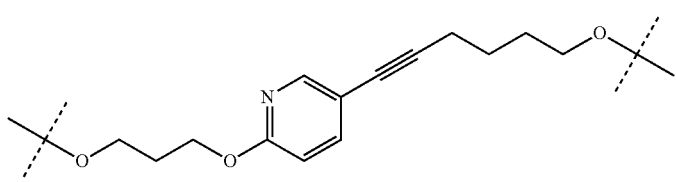
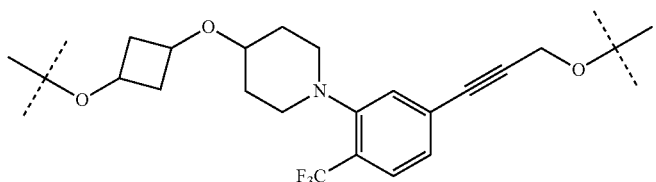
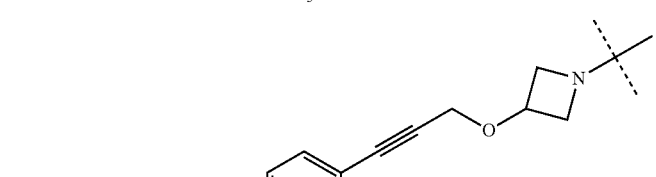

-continued
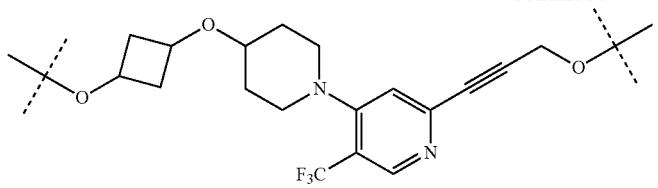
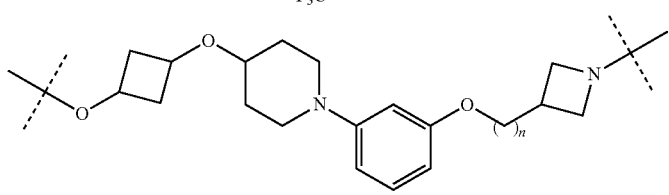
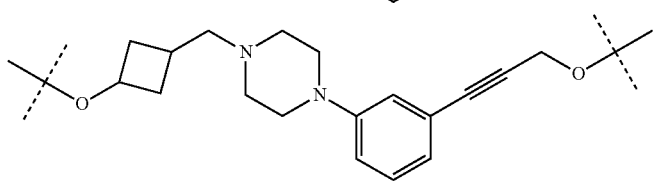
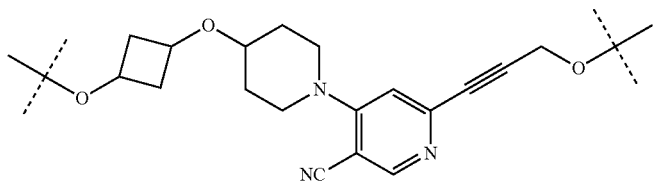
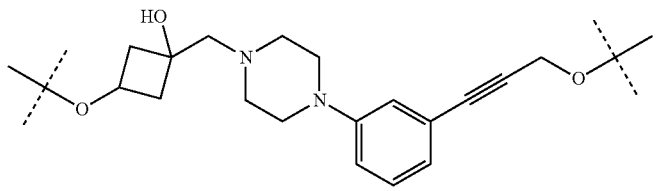
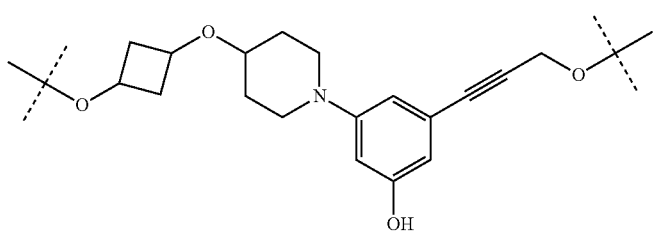
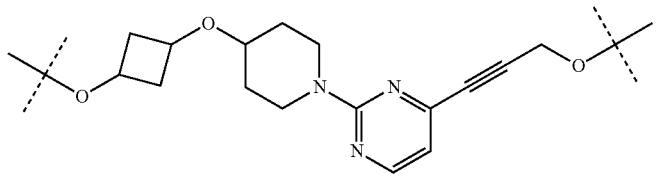
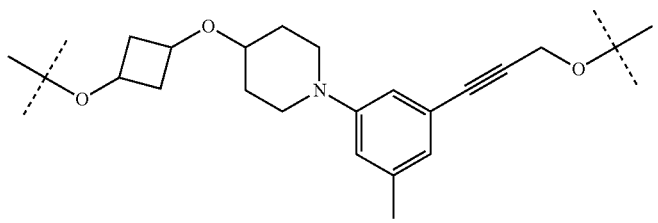
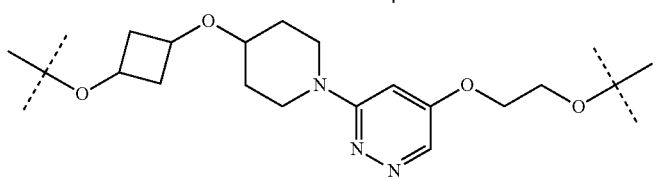

-continued
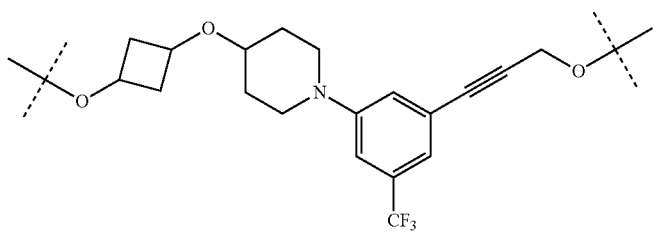
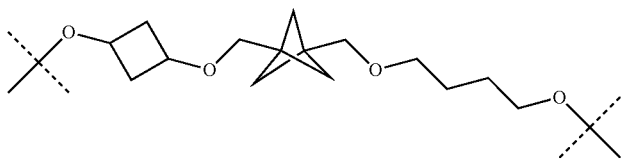
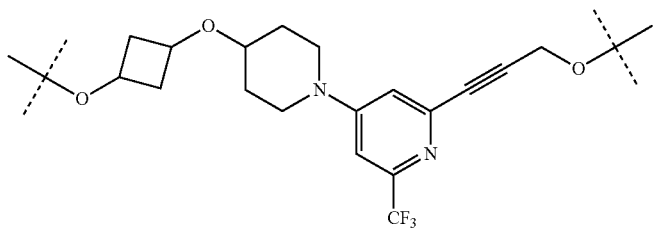
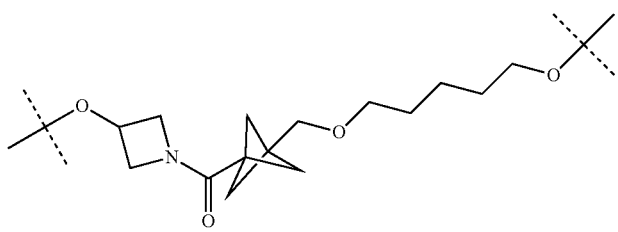
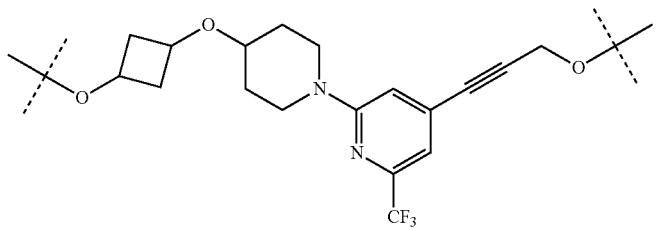
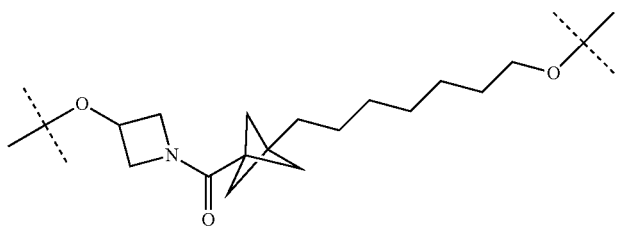
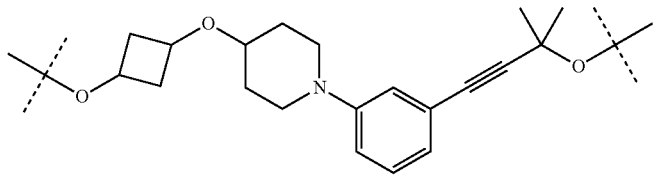
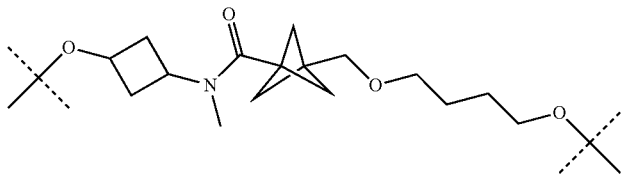

-continued
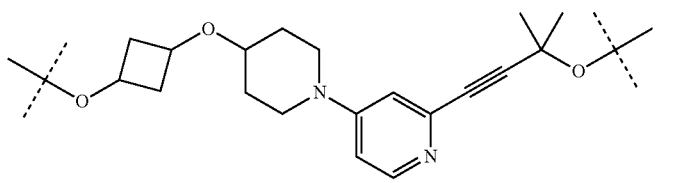
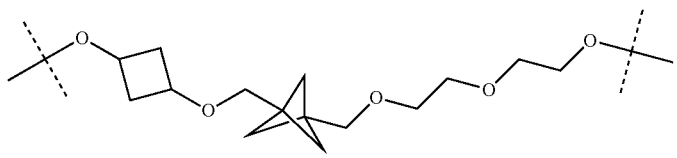
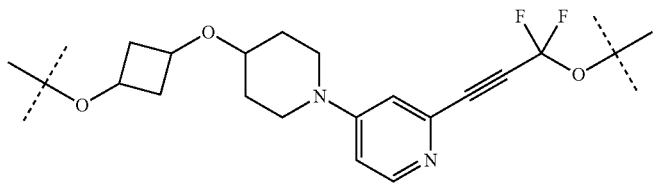
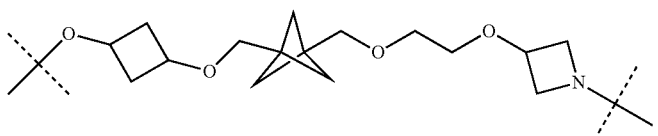
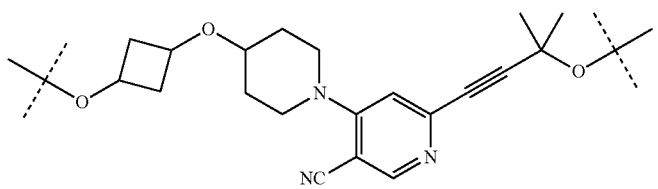
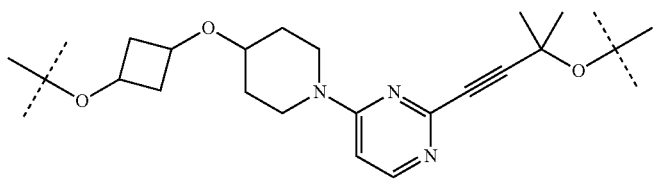
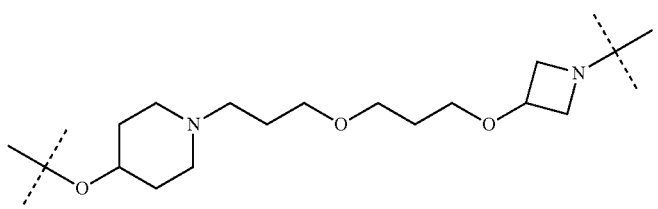
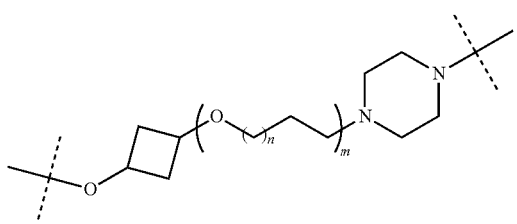
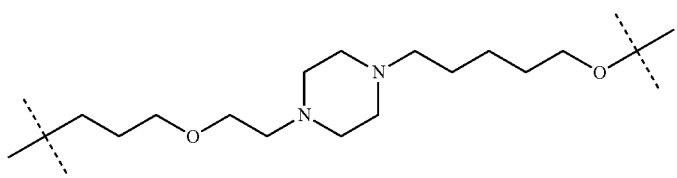

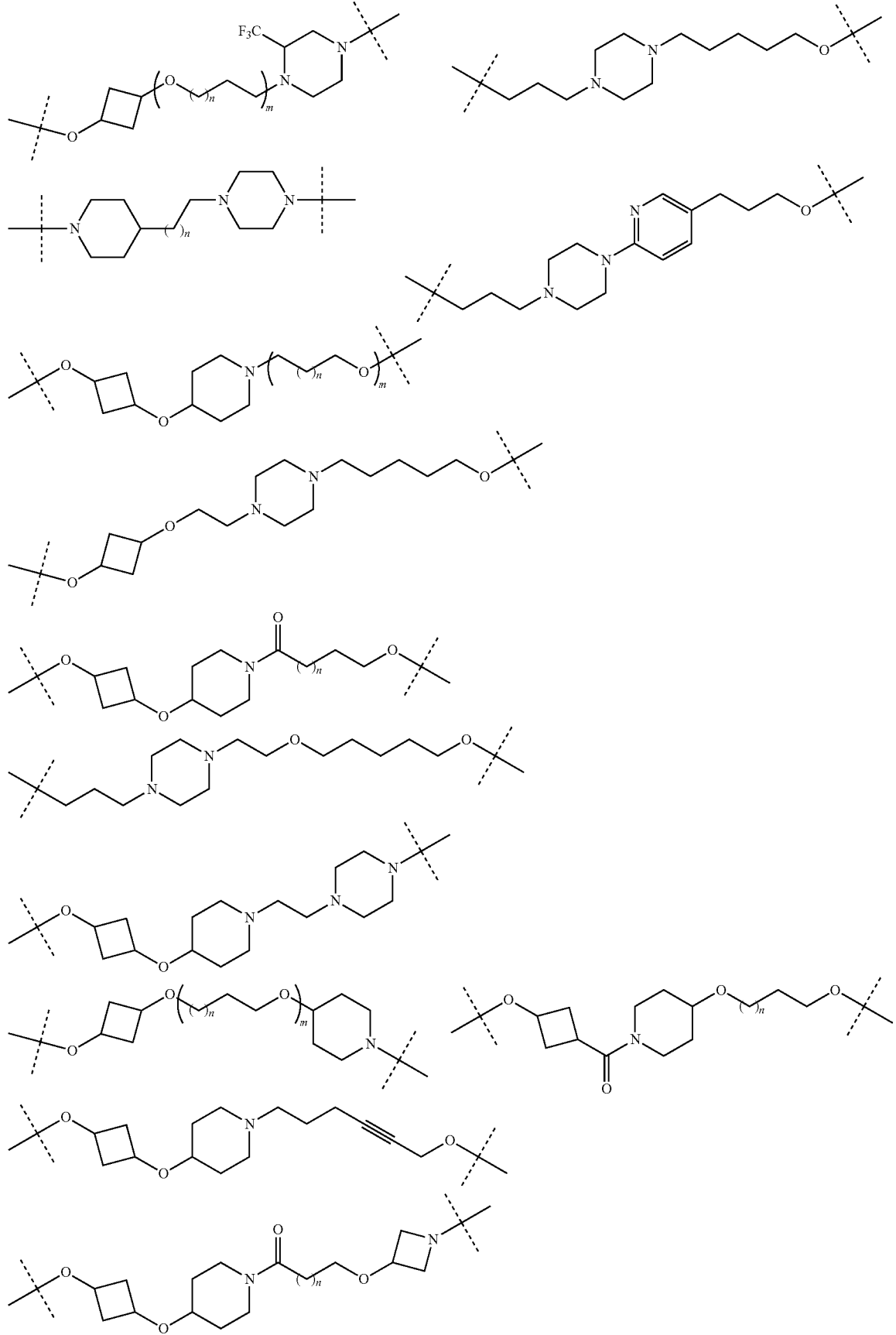

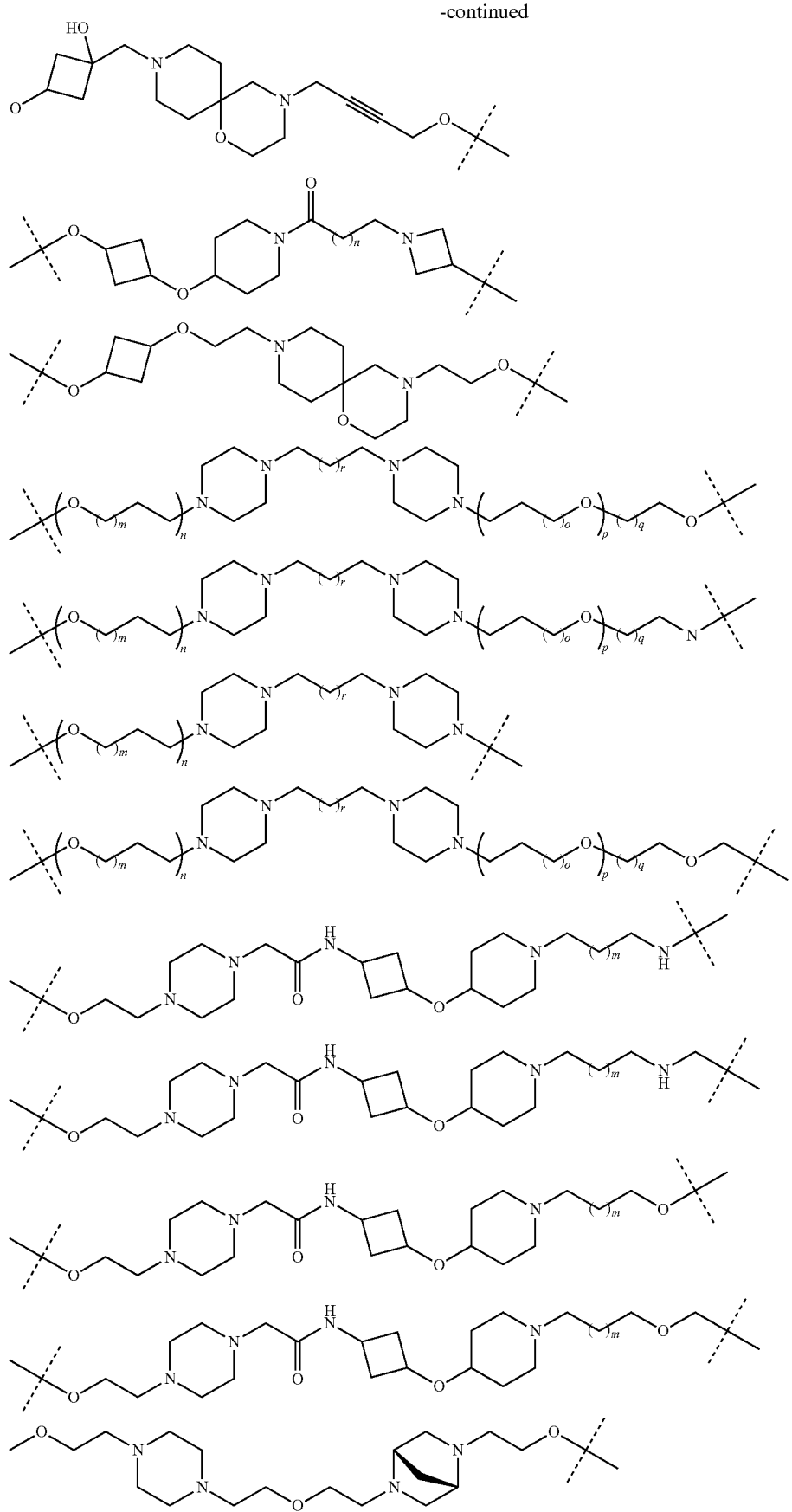

-continued
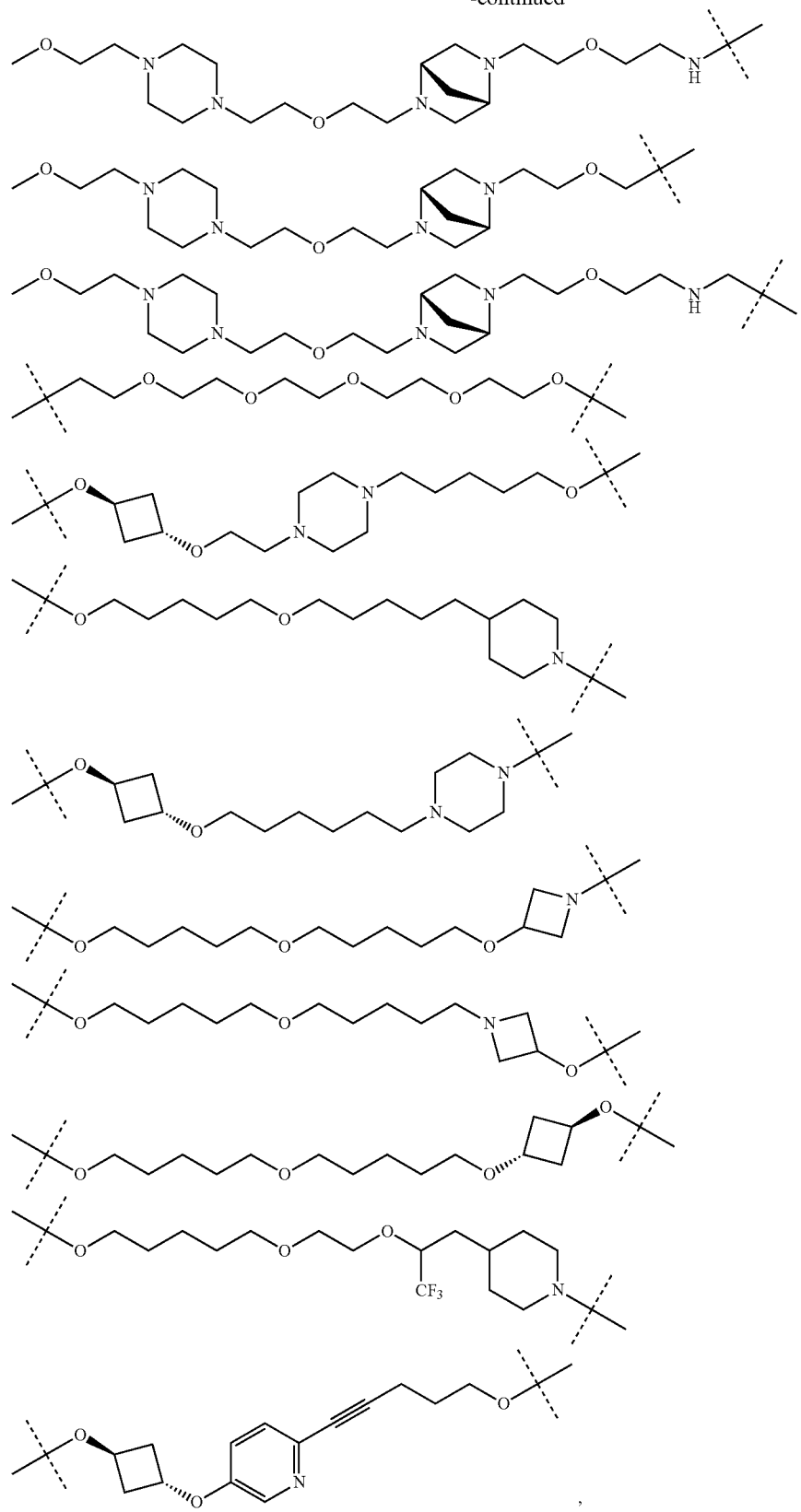
wherein each m, n, o, p, q, and r is independently 0, 1, 2, 3, 4, 5, 6, or 7.
In any aspect or embodiment described herein, the linker (L) is selected from:

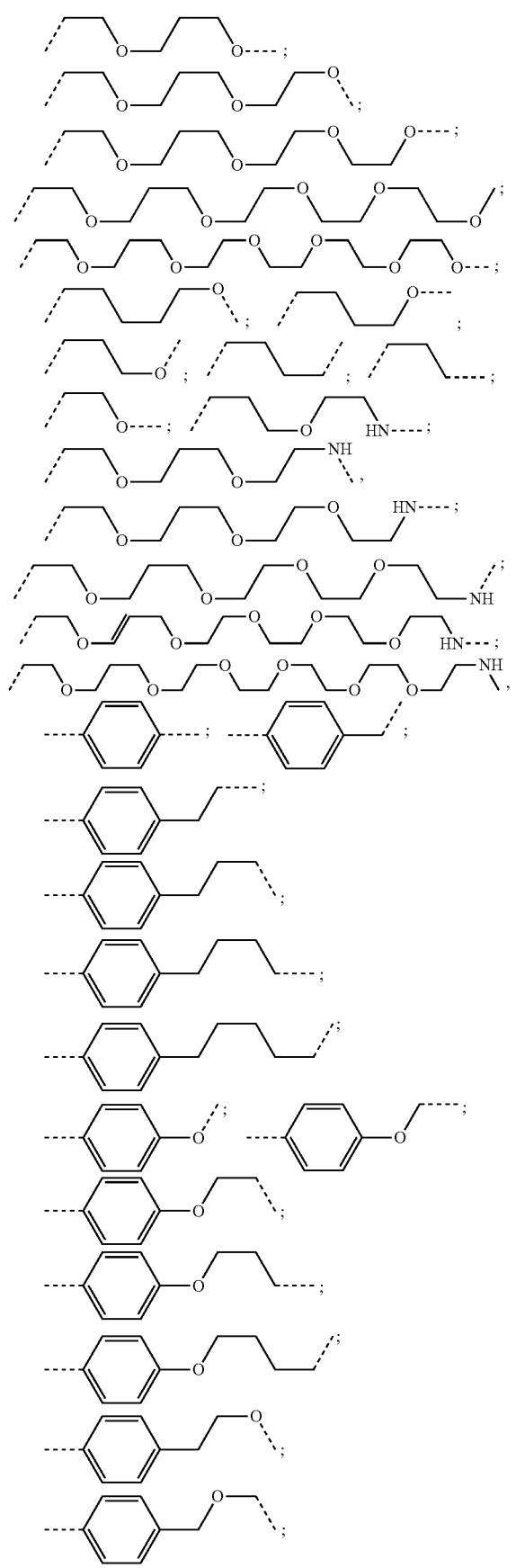
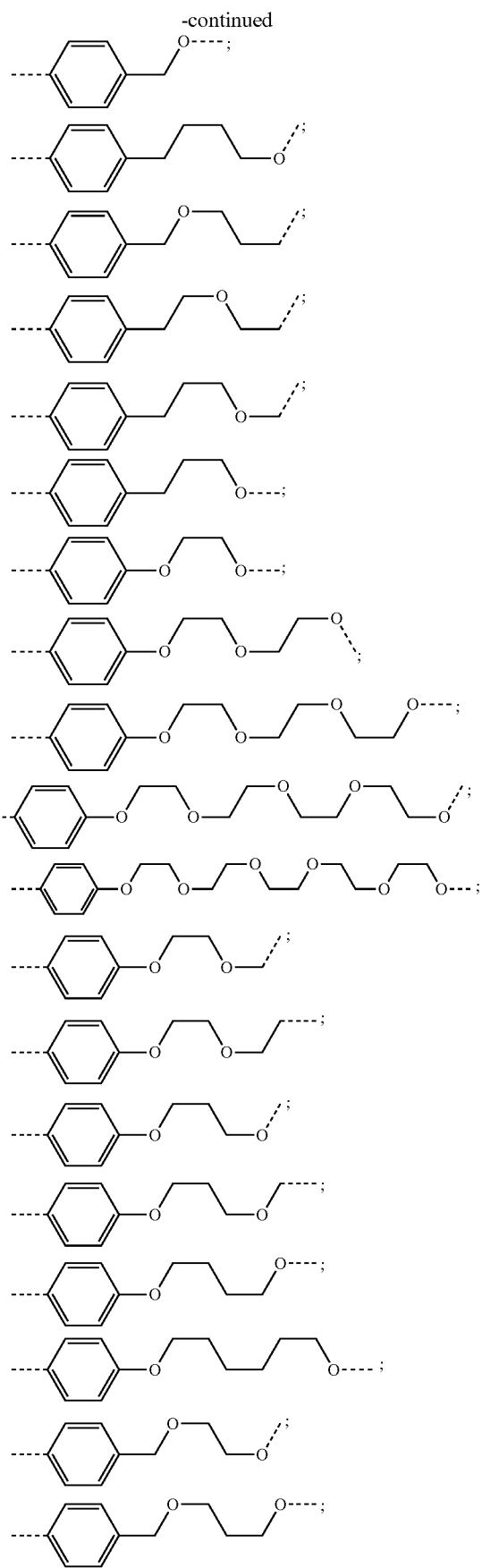

699
-continued
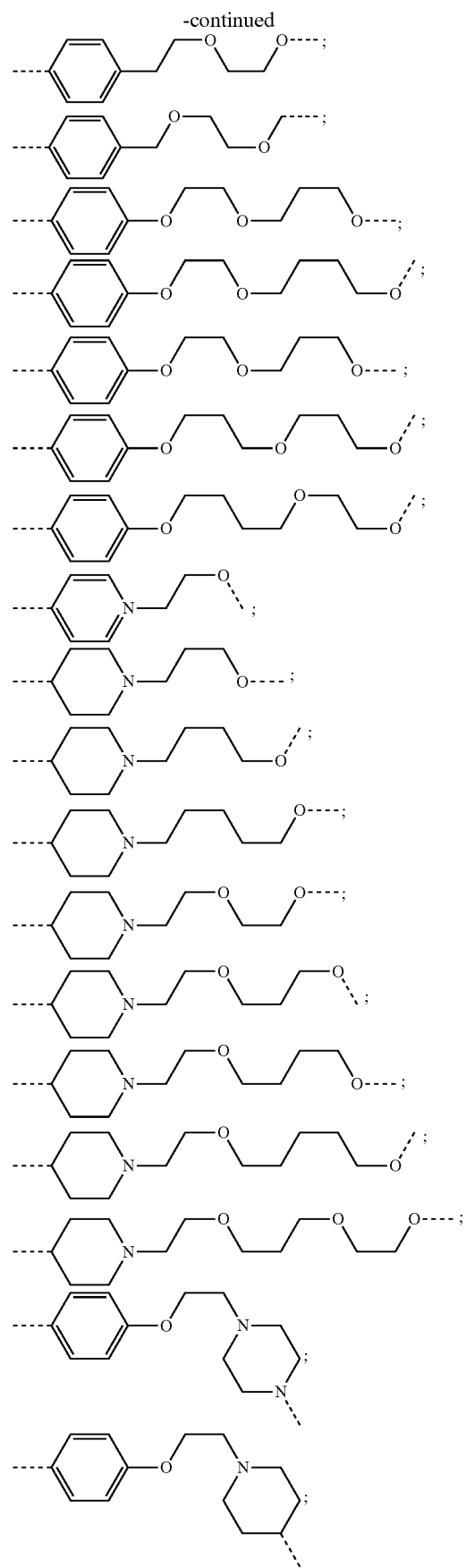
700
-continued
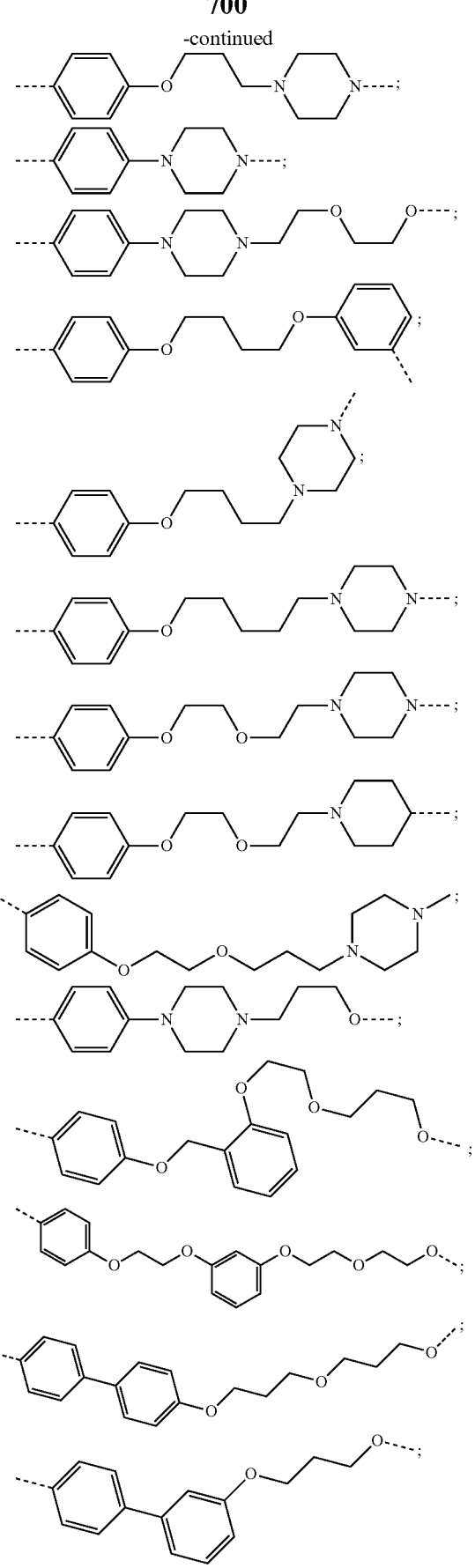

701
-continued
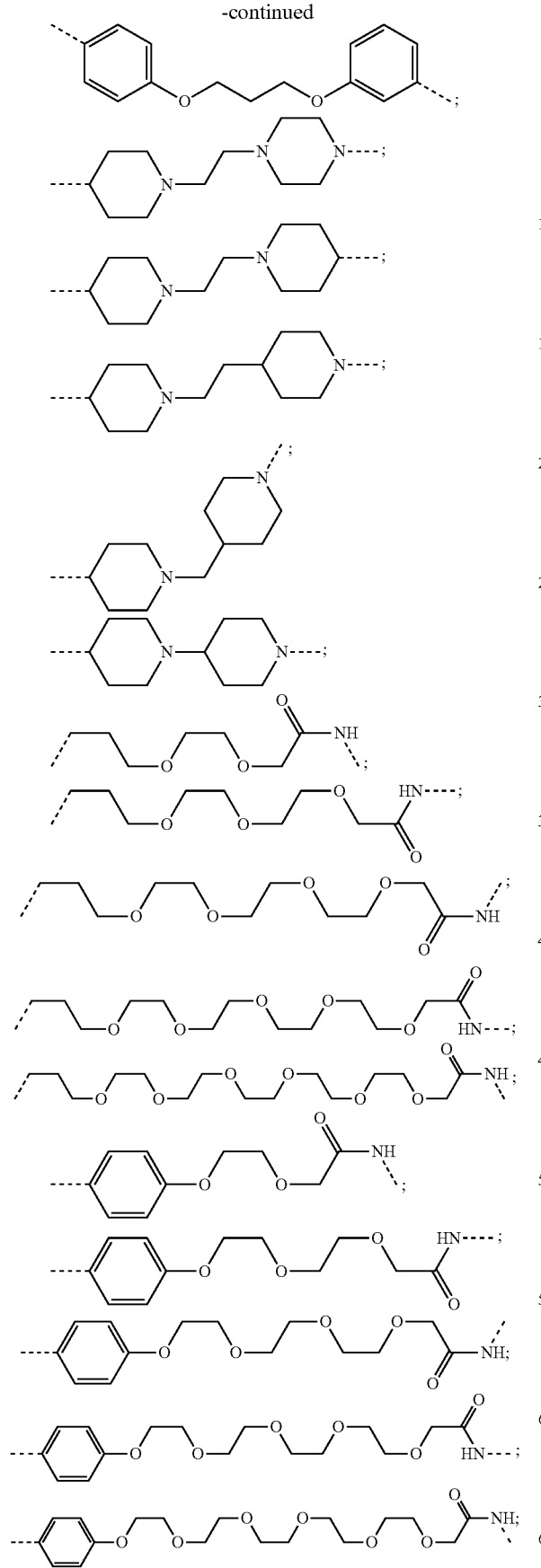
702
-continued
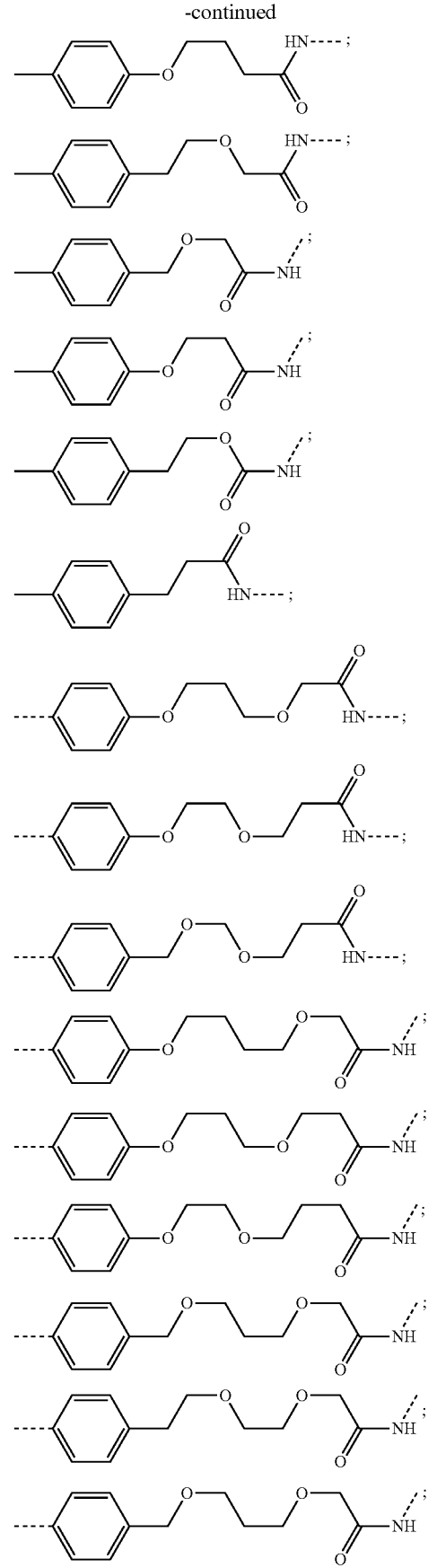

703
-continued
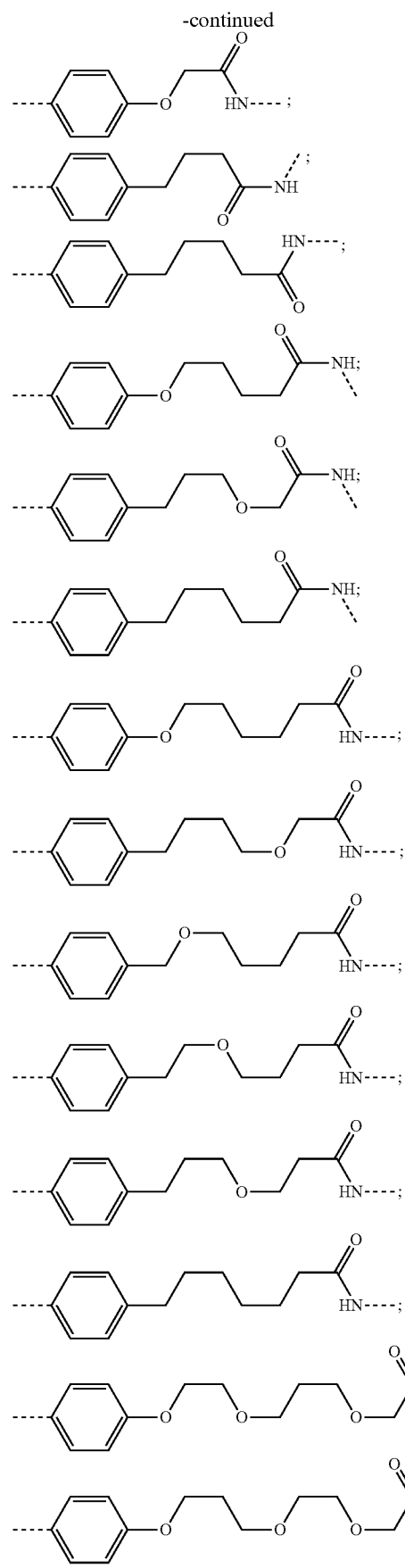
704
-continued
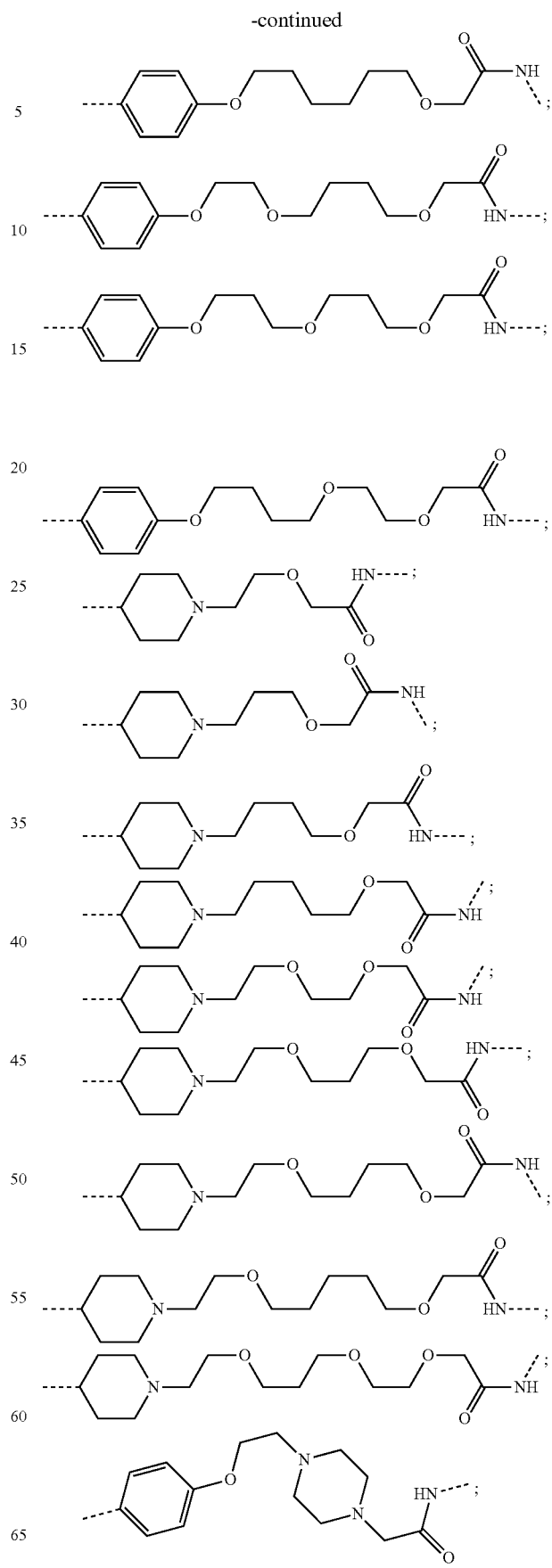

-continued

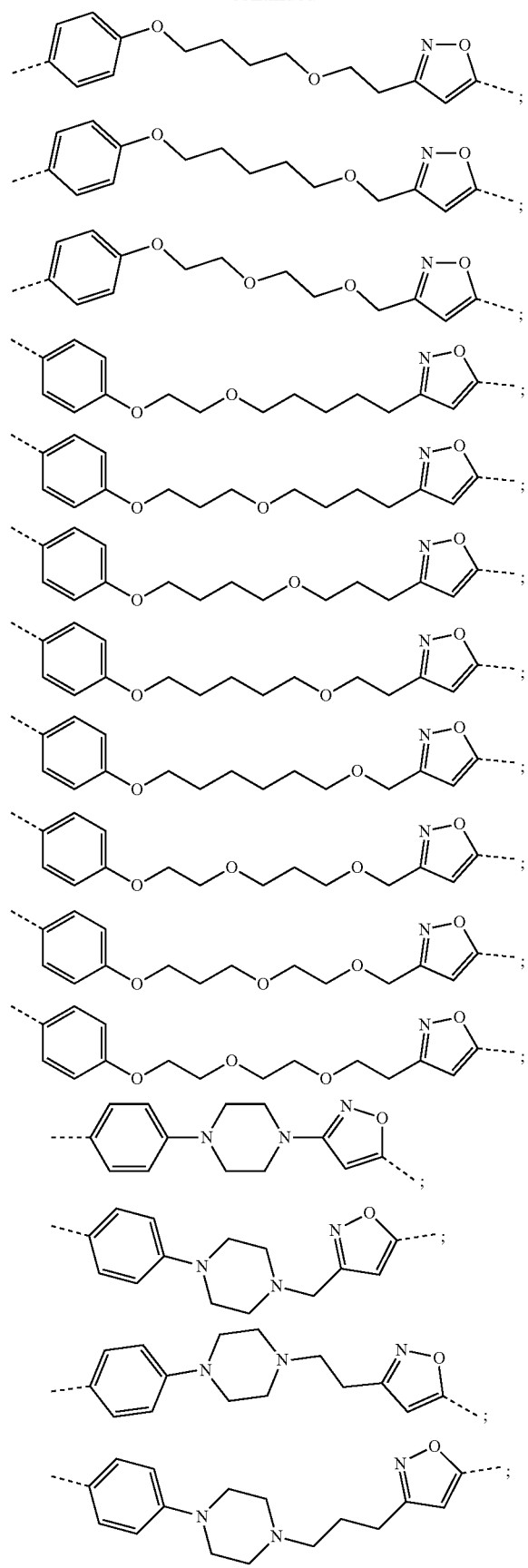
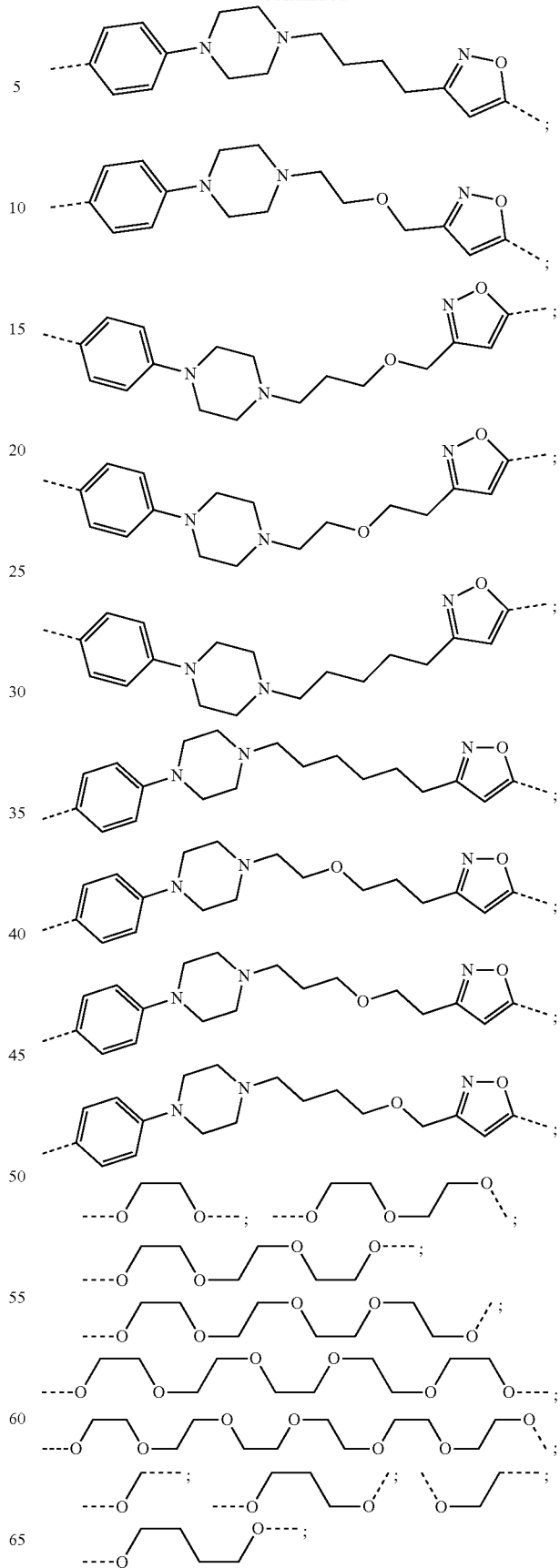

-continued

711
-continued
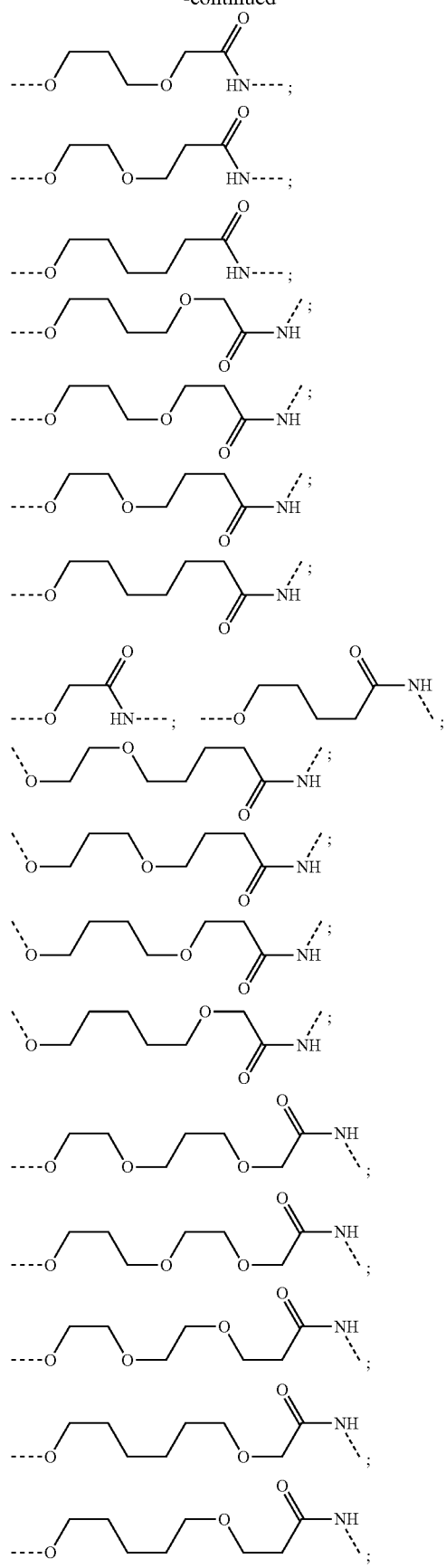
712
-continued
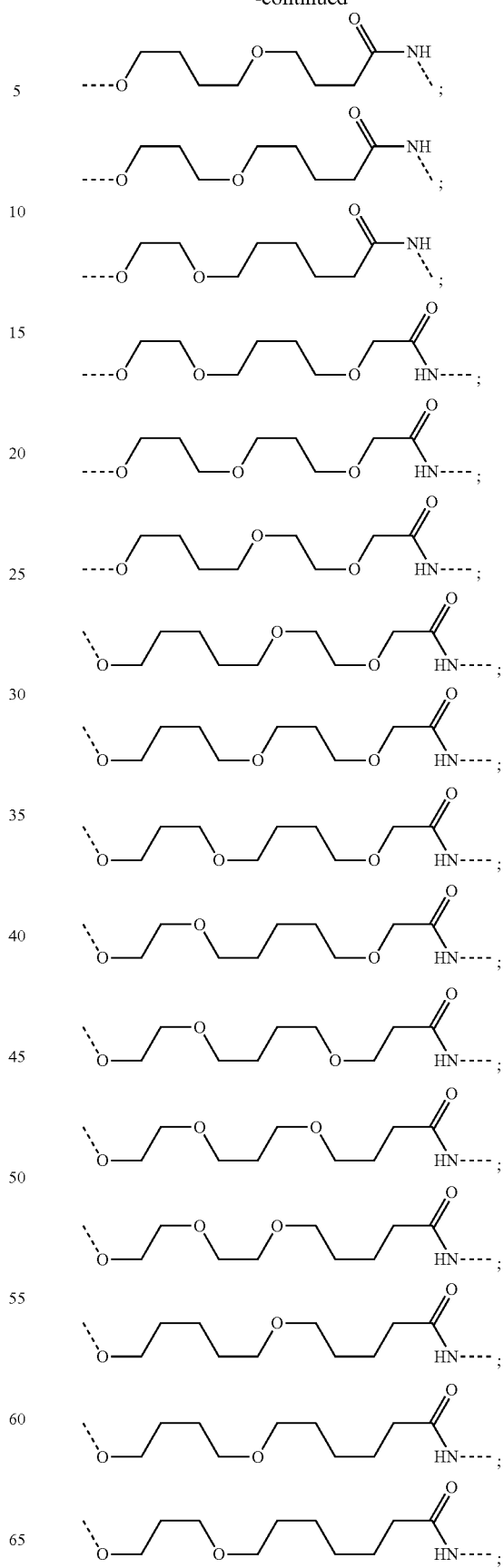

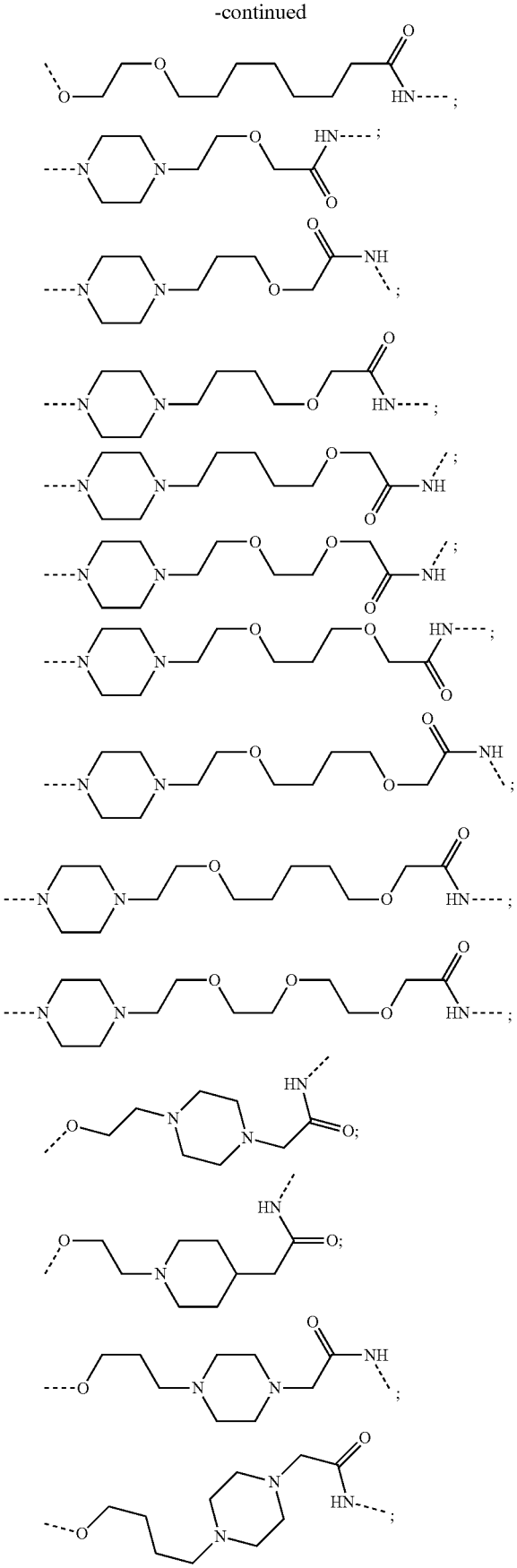
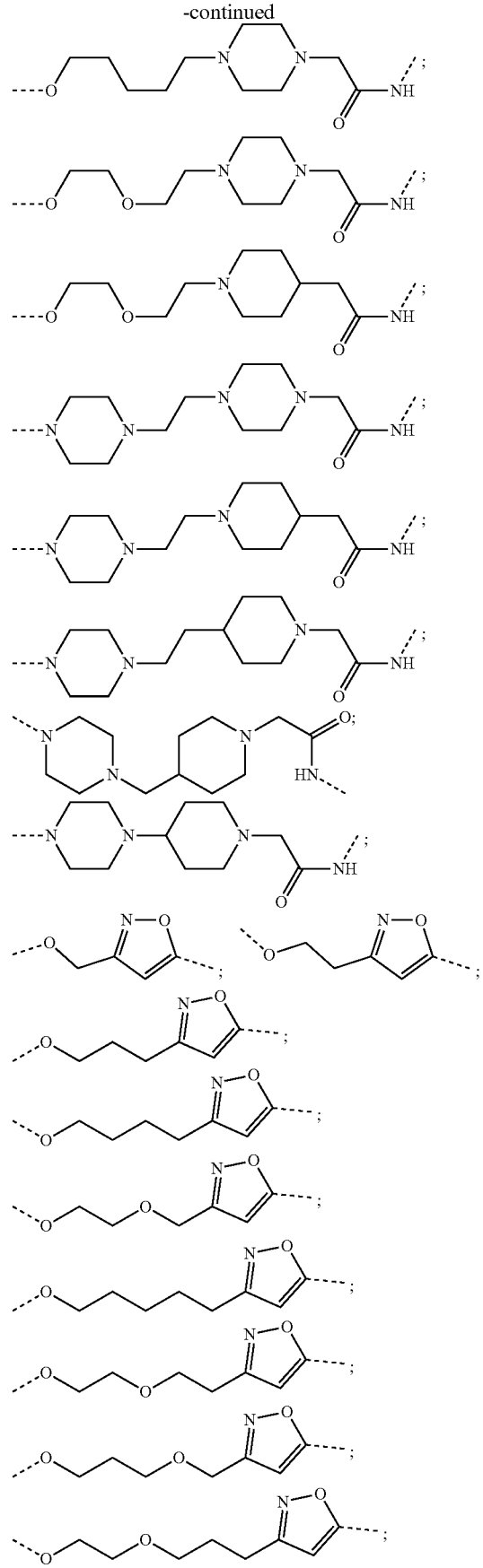

715
-continued

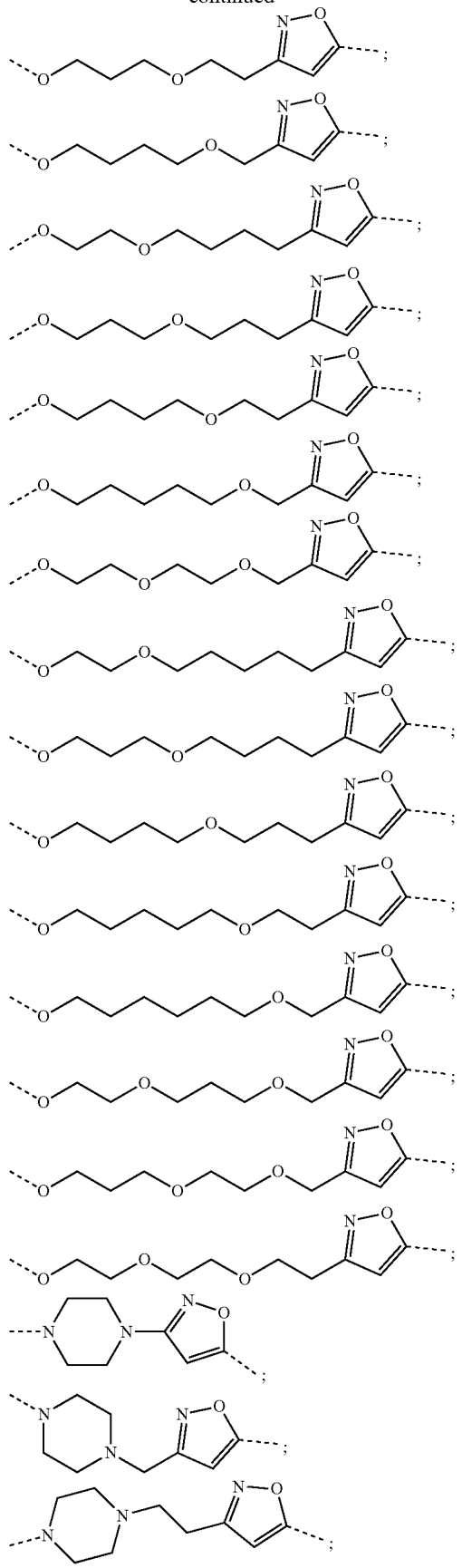

716
-continued

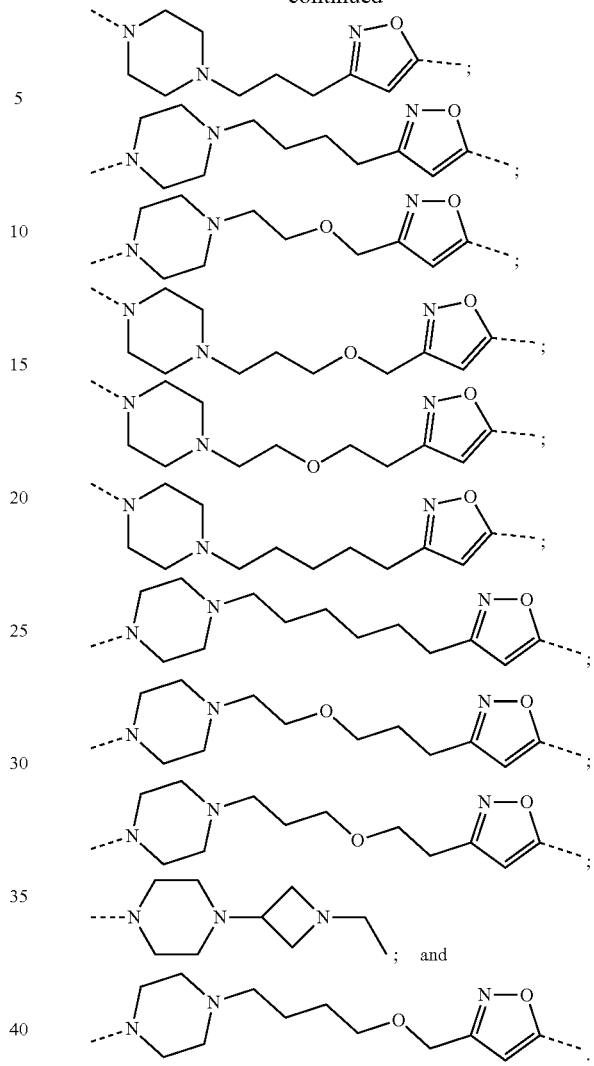

In any aspect or embodiment described herein, the linker (L) comprises the following chemical structure:

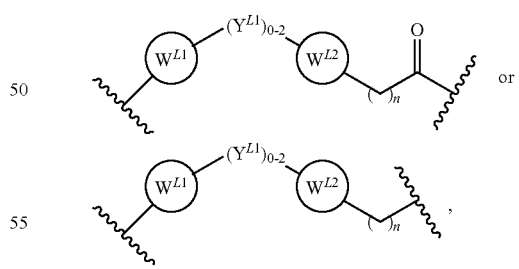

wherein:
W$^{L1}$ and W$^{L2}$ are each independently a 4-8 membered ring with 0-4 heteroatoms, optionally substituted with RQ, each RQ is independently a H, halo, OH, CN, CF3, C1-C6 alkyl (linear, branched, optionally substituted), C1-C6 alkoxy (linear, branched, optionally substituted), or 2 RQ groups taken together with the atom they are attached to, form a 4-8 membered ring system containing 0-4 heteroatoms;

$Y^{L1}$ is each independently a bond, C1-C6 alkyl (linear, branched, optionally substituted) and optionally one or more C atoms are replaced with 0; or C1-C6 alkoxy (linear, branched, optionally substituted);

n is 0-10; and a dashed line indicates the attachment point to the PTM or ULM moieties.

In any aspect or embodiment described herein, the linker (L) comprises the following chemical structure:

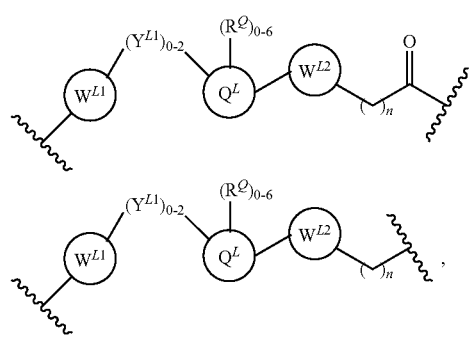

or wherein:

$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C=O, C=S, SO, $SO_2$, $C_1$-$C_6$ alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In any aspect or embodiment described herein, the linker (L) is selected from:

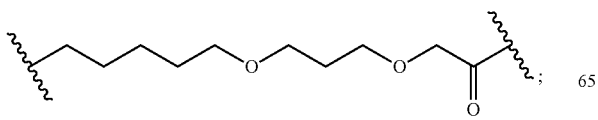

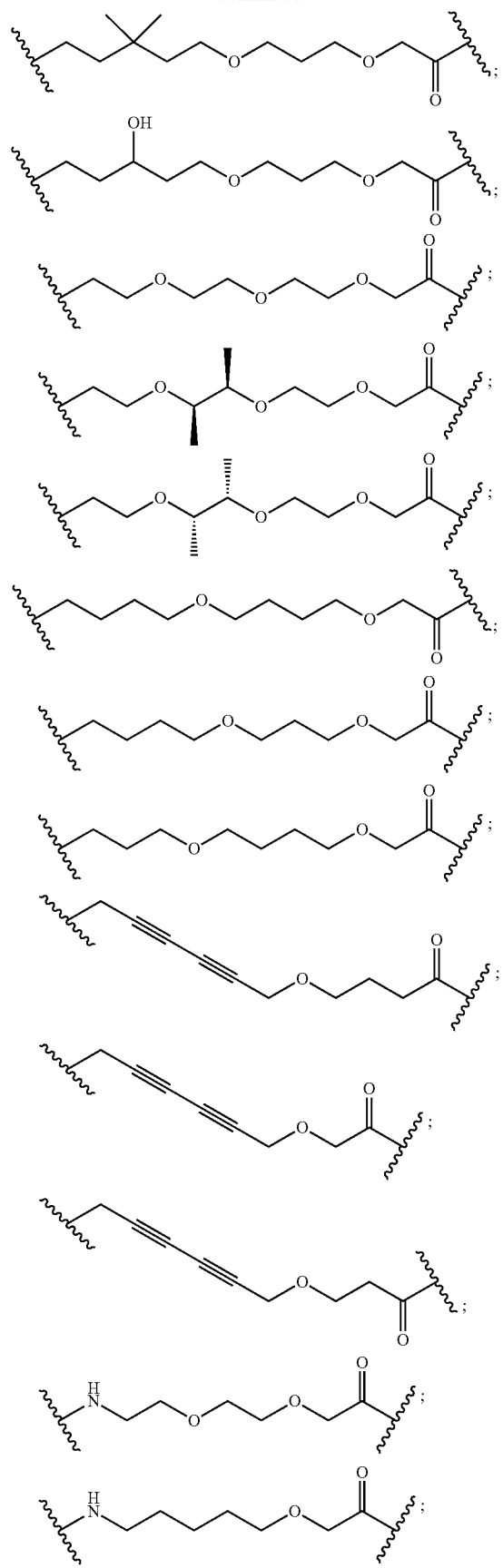

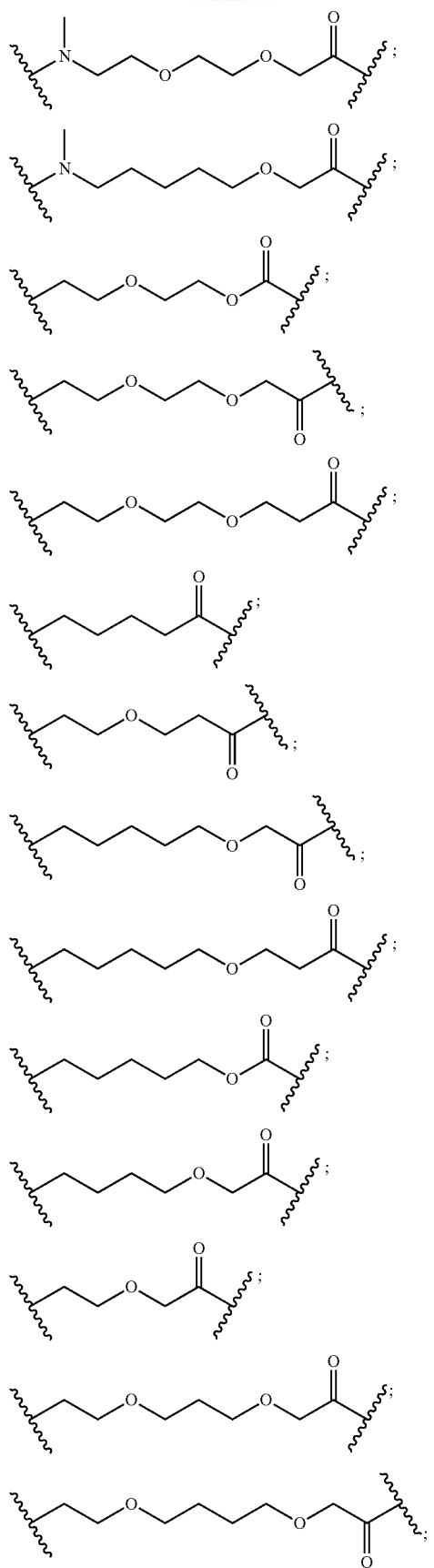
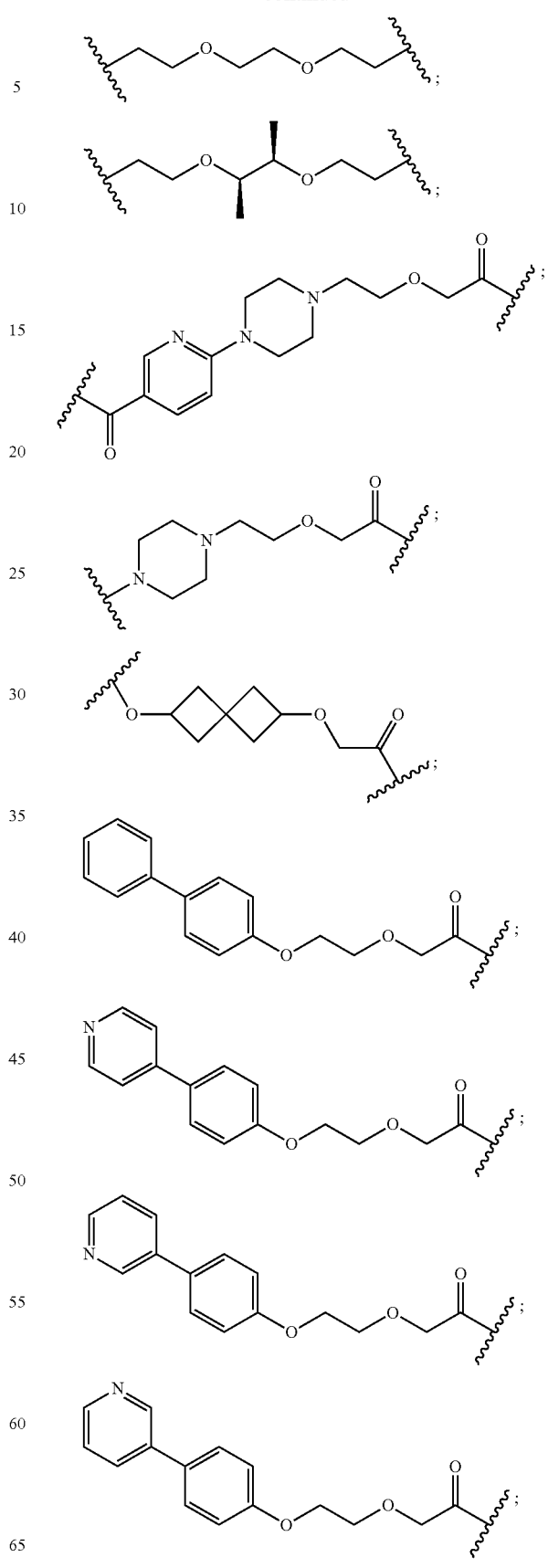

721
-continued
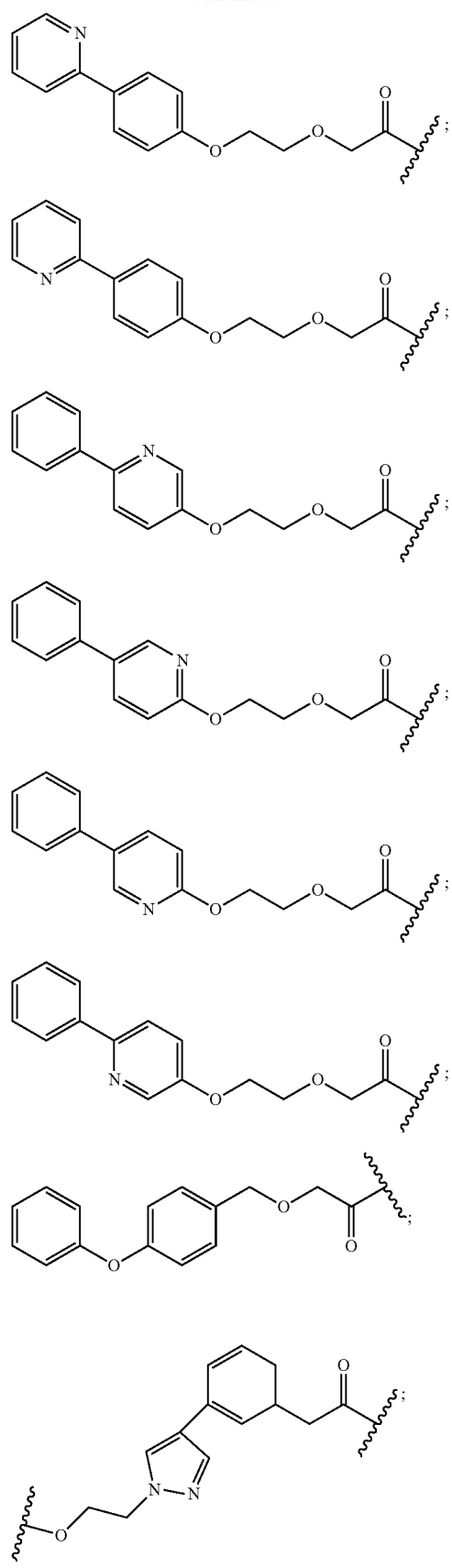
722
-continued
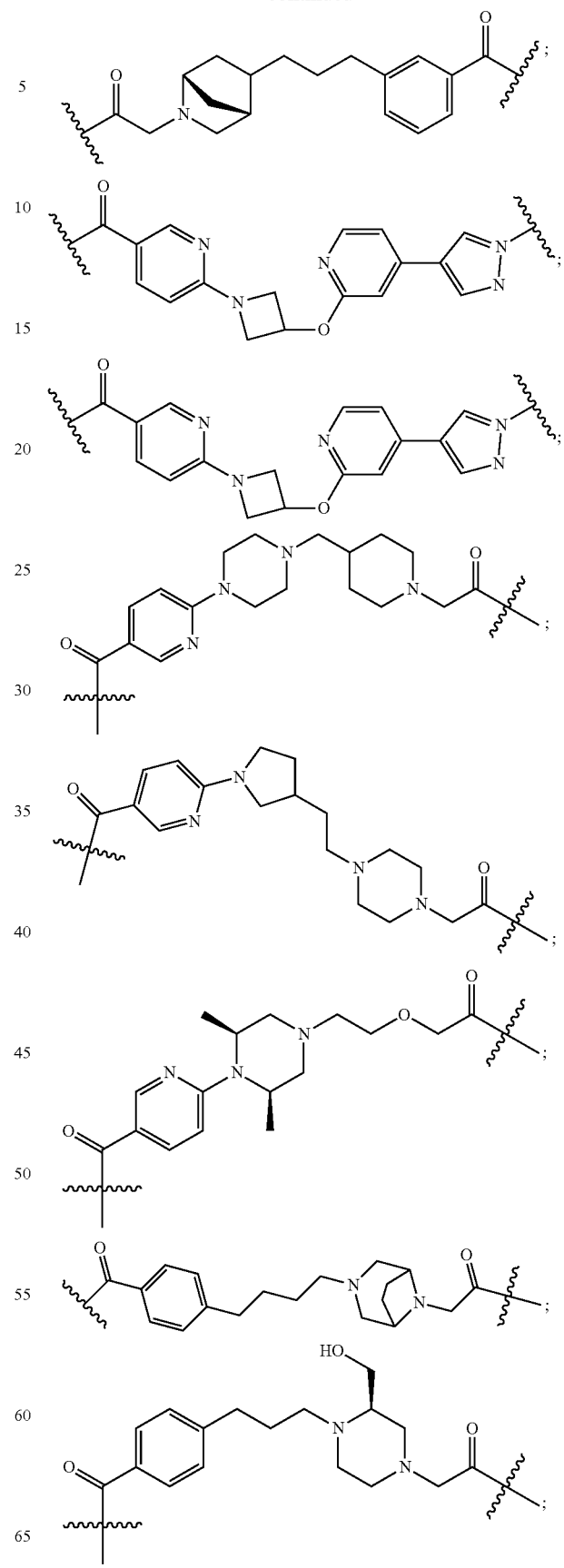

-continued

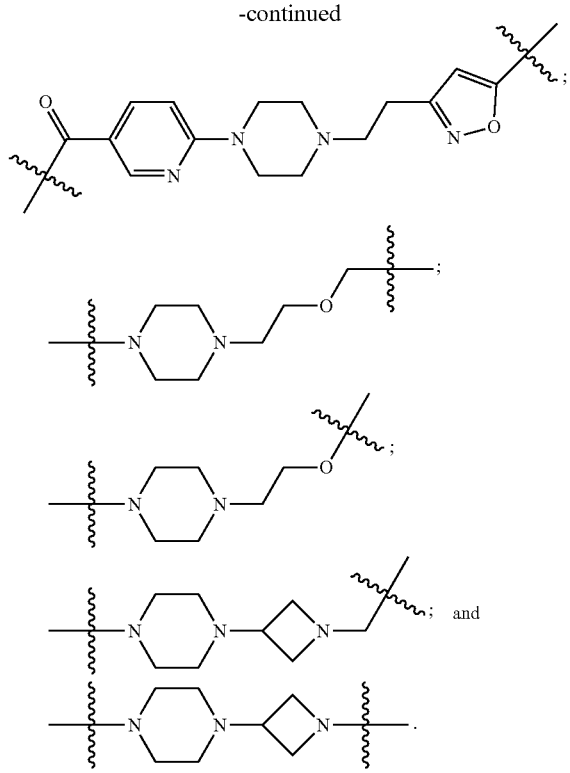

In any aspect or embodiment described herein, the linker (L) is a polyethylenoxy group optionally substituted with aryl or phenyl comprising from 1 to 10 ethylene glycol units.

In any aspect or embodiment described herein, the compound comprises multiple ULMs, multiple PTMs, multiple linkers or any combinations thereof.

In any aspect or embodiment described herein, the compound is selected from the group consisting of PROTAC-1 through PROTAC-38.

In any aspect or embodiments described herein, the compound comprises at least one of a PTM from Table 4 (i.e., the PTM is selected from the group consisting of PTM1-PTM18 [i.e., PTM1, PTM2, PTM3, PTM4, PTM5, PTM6, PTM7, PTM8, PTM9, PTM10, PTM11, PTM12, PTM13, PTM14, PTM15, PTM16, PTM17, PTM18]), a linker from Table 5 (i.e., the linker is selected from the group consisting of Linker1-Linker9 [i.e., Linker1, Linker2, Linker3, Linker4, Linker5, Linker6, Linker1, Linker8, Linker9]), a ULM from Table 6 (i.e., the ULM is selected from the group consisting of ULM1-ULM6 [i.e., ULM1, ULM2, ULM3, ULM4, ULM5, ULM6]), or a combination thereof.

In an additional aspect, the present disclosure provides a composition. The composition comprises an effective amount of a bifunctional compound of the present disclosure, and a pharmaceutically acceptable carrier.

In any aspect or embodiment described herein, the composition further comprises at least one of additional bioactive agent or another bifunctional compound of any of claims 1-28.

In any aspect or embodiment described herein, the additional bioactive agent is anti-cancer agent.

In a further aspect, the present disclosure provides a composition comprising a pharmaceutically acceptable carrier and an effective amount of at least one compound of the present disclosure for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with FLT3 accumulation and aggregation.

In any aspect or embodiment described herein, the disease or disorder is a neoplasia or cancer associated with FLT3 accumulation and aggregation.

In any aspect or embodiment described herein, the disease or disorder is at least one member selected from the group consisting of squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas.

In any aspect or embodiment described herein, the disease or disorder is at least one of T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

What is claimed is:

1. A bifunctional compound having the chemical structure:

ULM-L-PTM, or a pharmaceutically acceptable salt, stereoisomer, solvate, or polymorph thereof,
wherein:
(a) the ULM is a Von Hippel-Lindau E3 ubiquitin ligase binding moiety (VLM) epresented by the chemical structure:

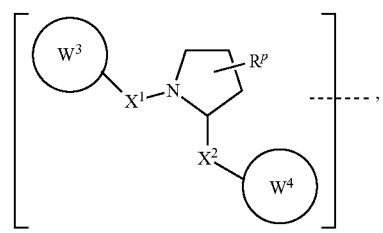

wherein:
$X^1$, $X^2$ of the VLM are each independently selected from the group consisting of a bond, O, $NR^{Y3}$, $CR^{Y3}R^{Y4}$, C=O, C=S, SO, and $SO_2$;
$R^{Y3}$, $R^{Y4}$ of the VLM are each independently selected from the group consisting of H, linear or branched $C_{1-6}$ alkyl, optionally substituted by 1 or more halo, $C_{1-6}$ alkoxyl optionally substituted by 0-3 $R^P$ groups;

$R^P$ of the VLM is 0, 1, 2, or 3 groups each independently selected from the group consisting of H, halo, —OH, $C_{1-3}$ alkyl, and C=O;

$W^3$ of the VLM is an optionally substituted -T-N($R^{1a}R^{1b}$)$X^3$, -T-N($R^{1a}R^{1b}$), -T-Aryl, an optionally substituted -T-Heteroaryl, an optionally substituted -T-Heterocycle, an optionally substituted —$NR^1$-T-Aryl, an optionally substituted —$NR^1$-T-Heteroaryl, or an optionally substituted —$NR^1$-T-Heterocycle;

$X^3$ of the VLM is C=O, $R^1$, $R^{1a}$, or $R^{1b}$;

each of $R^1$, $R^{1a}$, and $R^{1b}$ of the VLM is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}$SO$_2$, N($R^{Y3}R^{Y4}$)C=O, N($R^{Y3}R^{Y4}$)C=S, N($R^{Y3}R^{Y4}$)SO, and N($R^{Y3}R^{Y4}$)SO$_2$;

T of the VLM is selected from the group of an optionally substituted alkyl, —(CH$_2$)$_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n of the VLM is 0 to 6;

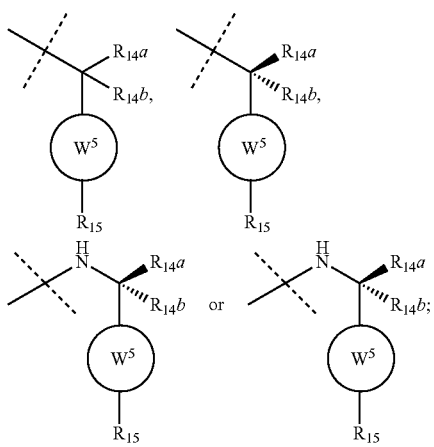

$R_{14a}$, and $R_{14b}$ of the VLM, are each independently selected from the group of H, haloalkyl, or optionally substituted alkyl;

$W^5$ of VLM is a phenyl or a 5-10 membered heteroaryl, $R_{15}$ of the VLM is H, halogen, CN, OH, NO$_2$, N$R_{14a}R_{14b}$, O$R_{14a}$, CON$R_{14a}R_{14b}$, N$R_{14a}$CO$R_{14b}$, SO$_2$N$R_{14a}R_{14b}$, N$R_{14a}$SO$_2R_{14b}$, optionally substituted alkyl, optionally substituted haloalkyl, optionally substituted haloalkoxy; aryl, heteroaryl, cycloalkyl, or cycloheteroalkyl;

o of the VLM is 0, 1, 2, 3, or 4;

each $R_{16}$ of the VLM is independently selected from the group consisting of H, halo, optionally substituted alkyl, optionally substituted haloalkyl, hydroxy, or optionally substituted haloalkoxy;

the dashed line of the VLM chemical structure indicates the site of attachment of the PTM or the chemical linking group;

(b) the L is a chemical linking group represented by the formula -($A^L$)$_q$-, wherein $A^L$ is a chemical moiety and q is an integer from 1-100, and wherein L covalently couples the ULM and the PTM, wherein:

each $A^L$ is independently selected from the group consisting of $CR^{L1}R^{L2}$, O, S, SO, SO$_2$, $NR^{L3}$, SO$_2NR^{L3}$, SON$R^{L3}$, CON$R^{L3}$, $NR^{L3}$CON$R^{L4}$, $NR^{L3}$SO$_2NR^{L4}$, CO, $CR^{L1}$=$CR^{L2}$, C≡C, Si$R^{L1}R^{L2}$, P(O)$R^{L1}$, P(O)O$R^{L1}$, $NR^{L3}$C(=NCN)N$R^{L4}$, $NR^{L3}$C(=NCN), $NR^{L3}$C(=CNO$_2$)N$R^{L4}$, $C_{3-11}$cycloalkyl optionally substituted with 1-6 $R^{L1}$ and/or $R^{L2}$ groups, $C_{3-11}$heteocyclyl optionally substituted with 1-6 $R^{L1}$ and/or $R^{L2}$ groups, aryl optionally substituted with 1-6 $R^{L1}$ and/or $R^{L2}$ groups, heteroaryl optionally substituted with 1-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 1-4 $R^{L5}$ groups; and $R^{L1}$, $R^{L2}$, $R^{L3}$, $R^{L4}$ and $R^{L5}$ are, each independently, H, halo, $C_{1-8}$alkyl, O$C_{1-8}$alkyl, S$C_{1-8}$alkyl, NH$C_{1-8}$alkyl, N($C_{1-8}$alkyl)$_2$, $C_{3-11}$cycloalkyl, aryl, heteroaryl, $C_{3-11}$heterocyclyl, O$C_{3-8}$cycloalkyl, S$C_{3-8}$cycloalkyl, NH$C_{3-8}$cycloalkyl, N($C_{3-8}$cycloalkyl)$_2$, N($C_{3-8}$cycloalkyl)($C_{1-8}$alkyl), OH, NH$_2$, SH, SO$_2C_{1-8}$alkyl, P(O)(O$C_{1-8}$alkyl)($C_{1-8}$alkyl), P(O)(O$C_{1-8}$alkyl)$_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl)$_2$, Si(OH)$_3$, Si($C_{1-8}$alkyl)$_3$, Si(OH)($C_{1-8}$alkyl)$_2$, CO$C_{1-8}$alkyl, CO$_2$H, halogen, CN, CF$_3$, CHF$_2$, CH$_2$F, NO$_2$, SF$_5$, SO$_2$NH$C_{1-8}$alkyl, SO$_2$N($C_{1-8}$alkyl)$_2$, SONH$C_{1-8}$alkyl, SON($C_{1-8}$alkyl)$_2$, CONH$C_{1-8}$alkyl, CON($C_{1-8}$alkyl)$_2$, N($C_{1-8}$alkyl)CONH($C_{1-8}$alkyl), N($C_{1-8}$alkyl)CON($C_{1-8}$alkyl)$_2$, NHCONH($C_{1-8}$alkyl), NHCON($C_{1-8}$alkyl)$_2$, NHCONH$_2$, N($C_{1-8}$alkyl)SO$_2$NH($C_{1-8}$alkyl), N($C_{1-8}$alkyl) SO$_2$N($C_{1-8}$alkyl)$_2$, NH SO$_2$NH($C_{1-8}$alkyl), NH SO$_2$N($C_{1-8}$alkyl)$_2$, NH SO$_2$NH$_2$; and (c) the PTM is a small molecule FLT3 protein targeting moiety represented by Formula PTM-VI:

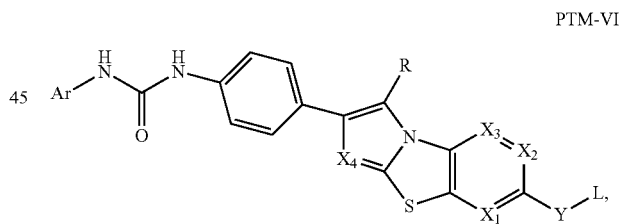

PTM-VI wherein:

Ar of PTM-VI is selected from the group consisting of optionally substituted or unsubstituted aryl, and optionally substituted or unsubstituted heteroaryl, when substituted, the substituents could be one or more groups independently selected from halogen, alkyl, haloalkyl, or hydroxyl alkyl;

L of PTM-VI is H, optionally substituted or unsubstituted alkyl, optionally substituted or unsubstituted cycloalkyl, optionally substituted or unsubstituted cycloalkyl-alkyl, optionally substituted or unsubstituted aryl, optionally substituted or unsubstituted arylalkyl, optionally substituted or unsubstituted sulfonamido, optionally substituted or unsubstituted heterocycloalkyl, optionally substituted or unsubstituted heterocycloalkyl-alkyl, optionally substituted or unsubstituted heteroaryl or optionally substituted or unsubstituted heteroarylalkyl; when substituted, the substituents can be one or more groups independently selected from the group consisting of halo, alkyl, haloalkyl, cycloalkyl, cycloalkyl-alkyl, heterocycloalkyl, heterocycloalkyl-alkyl, amino, aminoalkyl, amido, aminocarbonyl, sulfonamido, ureido, cyano, acetyl, acyl, carboxylic acid, hydroxyl, hydroxylalkyl, alkoxyl, —NH-alkylhydroxyl, —NH-alkoxyalkyl, —NH-alkylamino, —NH-cycloalkyl, —NH-cycloalkyl-alkyl, —NH-heterocyclo-alkyl, —NH-heterocycloalkylalkyl, —NH-aryl, —NH-arylalkyl, —NH-heteroaryl, or —NH-heteroarylalkyl;

Y of PTM-VI is O, $NR_2R_{2'}$ or a direct bond;

$X_1$, $X_2$, $X_3$ and $X_4$ of PTM-VI are independently N or CH

R, $R_2$, and $R_{2'}$ of PTM-VI are each independently selected from the group consisting of hydrogen, alkyl, cycloalkyl, aryl, heteroaryl, haloalkoxyl, hydroxyl, amino, aminocarbonyl, sulfonamido, cyano, alkynyl, alkoxyl, aryloxyl, carboxylic acid, carboxylic ester or halogen, or $R_2$, $R_{2'}$ together with the nitrogen atom to which they are attached, form a 3- to 7-membered heterocycloalkyl ring, and the hetero atom could be selected from at least one of O, S or N atoms, and the 3- to 7-membered heterocycloalkyl ring is further optionally substituted with a group independently selected from alkyl, cycloalkyl, methylsulfonyl, ureido, acyl, amido, aminocarbonyl, alkylamino, alkylhydroxyl, heterocycloalkyl, aryl, or heteroaryl

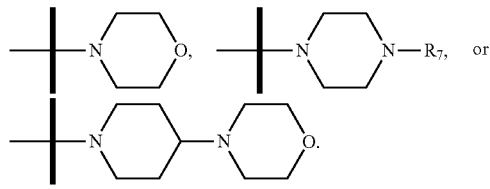

2. The compound according to claim 1, wherein the L has 1-10 optionally substituted ethylene glycol units wherein each O is optionally replaced with an optionally replaced with an optionally substituted N or S atom.

3. The compound according to claim 1, wherein the VLM has a chemical structure represented by:

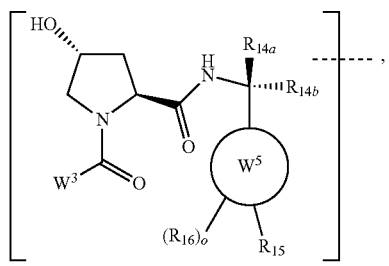

wherein:

$W^3$ of the VLM is an optionally substituted aryl, optionally substituted heteroaryl, or

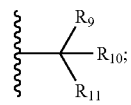

$R_9$ and $R_{10}$ of the VLM are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of the VLM is an optionally substituted heterocyclic, optionally substituted alkoxy, optionally substituted heteroaryl, optionally substituted aryl,

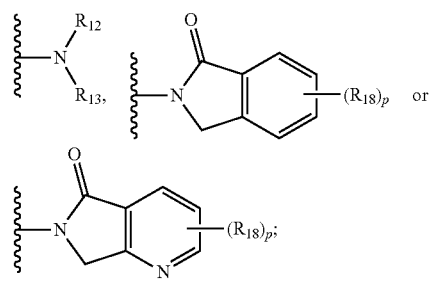

$R_{12}$ of the VLM is H or optionally substituted alkyl;

$R_{13}$ of the VLM is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$ of the VLM are each independently selected from the group consisting of H, haloalkyl, or optionally substituted alkyl;

$W^5$ of the VLM is a phenyl or a 5-10 membered heteroaryl, $R_{15}$ of the VLM is H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; optionally substituted aryl, optionally substituted heteroaryl, optionally substituted cycloalkyl, or optionally substituted cycloheteroalkyl;

$R_{16}$ of the VLM is independently selected from the group of H, halo, optionally substituted alkyl, optionally substituted haloalkyl, hydroxy, or optionally substituted haloalkoxy;

o of the VLM is 0, 1, 2, 3, or 4;

$R_{18}$ of the VLM is independently selected from the group consisting of halo, optionally substituted alkoxy, cyano, optionally substituted alkyl, haloalkyl, or haloalkoxy; and P of the VLM is 0, 1, 2, 3, or 4, and the dashed line indicates the site of attachment of the VLM to the PTM via the chemical linking group.

4. The compound of claim 1, wherein the VLM has a chemical structure selected from the group of:

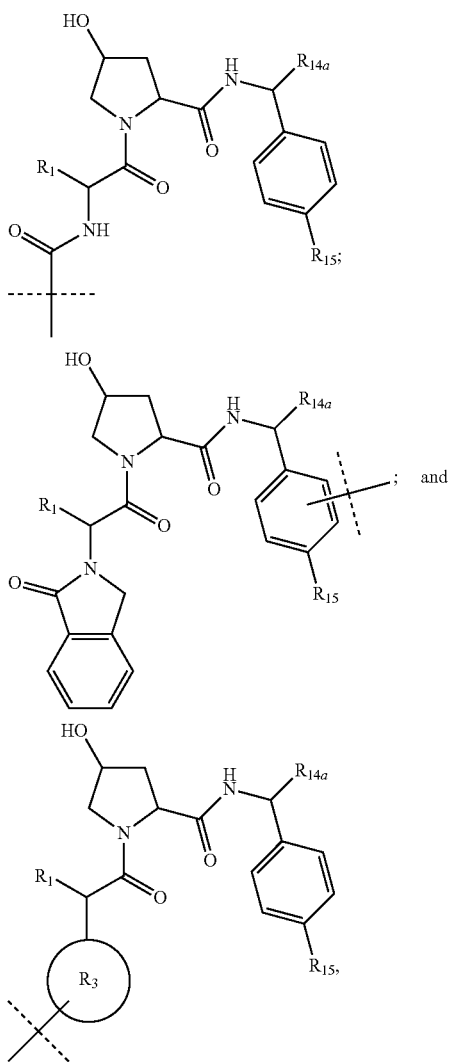

wherein:
R₁ of the VLM is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ of the VLM is H, haloalkyl, optionally substituted alkyl, methyl, fluoromethyl, hydroxymethyl, ethyl, or isopropyl;

$R_{15}$ of the VLM is selected from the group consisting of H, halogen, CN, OH, NO₂, optionally substituted heteroaryl, optionally substituted aryl, optionally substituted alkyl, optionally substituted haloalkyl, optionally substituted haloalkoxy, cycloalkyl, or cycloheteroalkyl;

X of the VLM is C or C=O;

R₃ of the VLM is an optionally substituted 5 or 6 membered heteroaryl; and the dashed line indicates the site of attachment of VLM to the PTM via the chemical linking group.

5. The compound according to claim 1, wherein the VLM has the chemical structure:

wherein:
$R_{14a}$ of the VLM is H, haloalkyl, optionally substituted alkyl, methyl, fluoromethyl, hydroxymethyl, ethyl, or;

R₉ of the VLM is H;

$R_{10}$ of the VLM is H, ethyl, isopropyl, tert-butyl, sec-butyl, cyclopropyl, cyclobutyl, cyclopentyl, or cyclohexyl;

$R_{11}$ of the VLM optionally substituted heteroaryl p of the VLM is 0, 1, 2, 3, or 4; and each $R_{18}$ of the VLM is independently halo, optionally substituted alkoxy, cyano, optionally substituted alkyl, haloalkyl, haloalkoxy or a site of attachment of the PTM or the chemical linker group;

$R_{12}$ of the VLM is H, or C=O;

$R_{13}$ of the VLM is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{15}$ of the VLM is selected from the group consisting of H, halogen, Cl, CN, OH, NO₂, optionally substituted heteroaryl, and optionally substituted aryl;

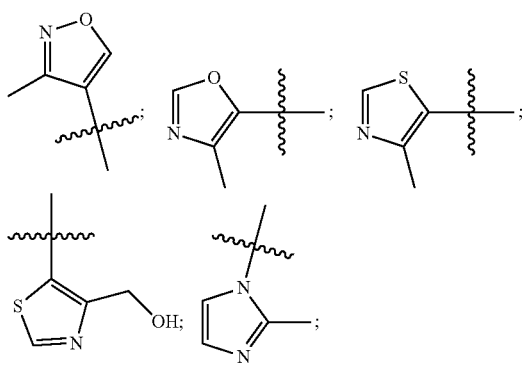

and the dashed line indicates the site of attachment of VLM to the PTM via the chemical linking group.

6. The compound according to claim 1, wherein the chemical linking group is a polyethylenoxy group optionally substituted with aryl or phenyl comprising from 1 to 10 ethylene glycol units.

7. The compound according to claim 1, wherein at least one of:

$R_2$ and $R_2'$ of PTM-VI together with the nitrogen atom to which they are attached form a heterocycle selected from

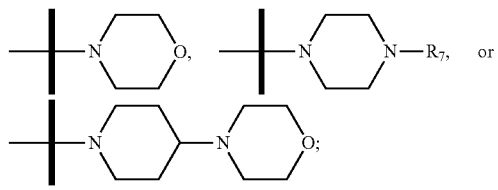

and $R_7$ of PTM-VI is independently selected from a group consisting of H, methylsulfonyl, and linear or branched $C_1$-$C_6$ alkyl.

8. The compound according to claim 1, wherein $R_7$ of PTM-VI is a methyl, ethyl, propyl, 2-propyl, n-butyl, iso-butyl, tert-butyl, pentyl, neopentyl, hexyl, or isohexyl.

9. The compound according to claim 1, wherein the compound is selected from the group consisting of:

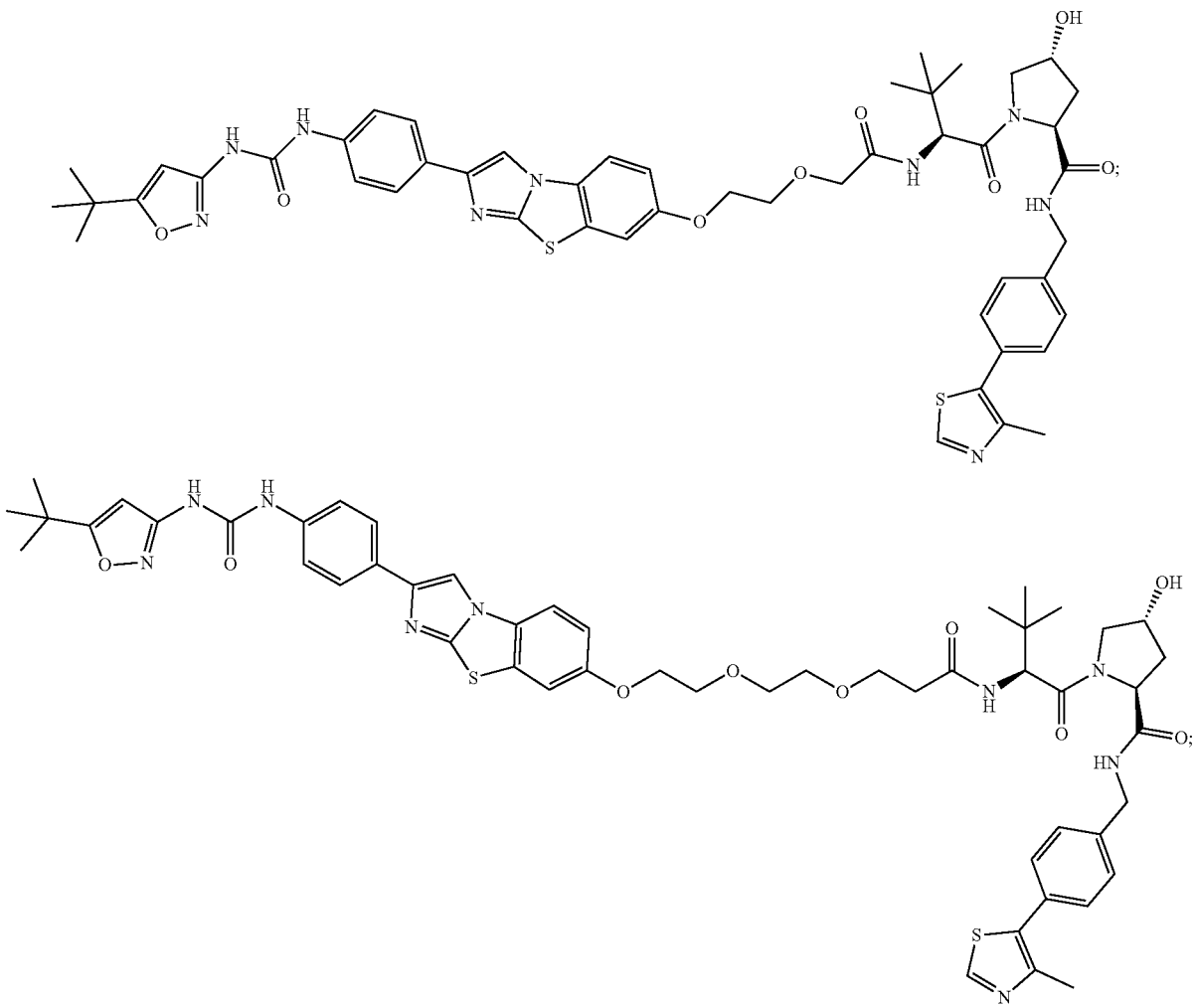

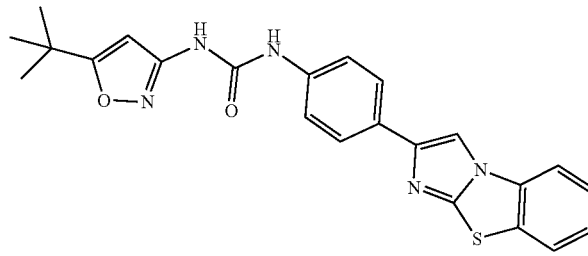
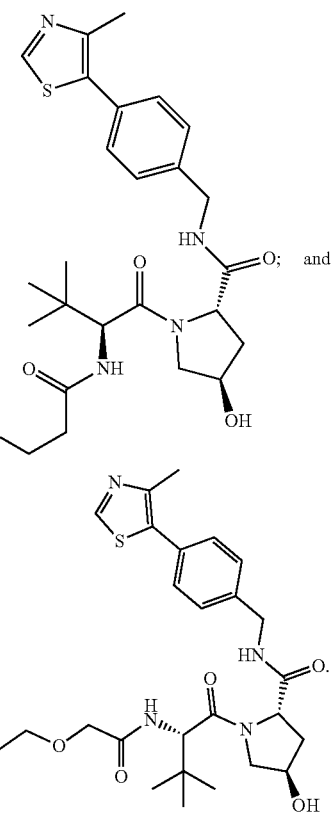
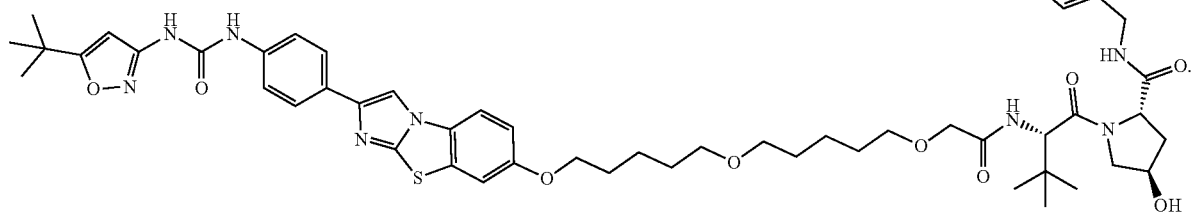
10. The compound according to claim 1, wherein at least one of:
(a) the PTM is selected from the group consisting of:
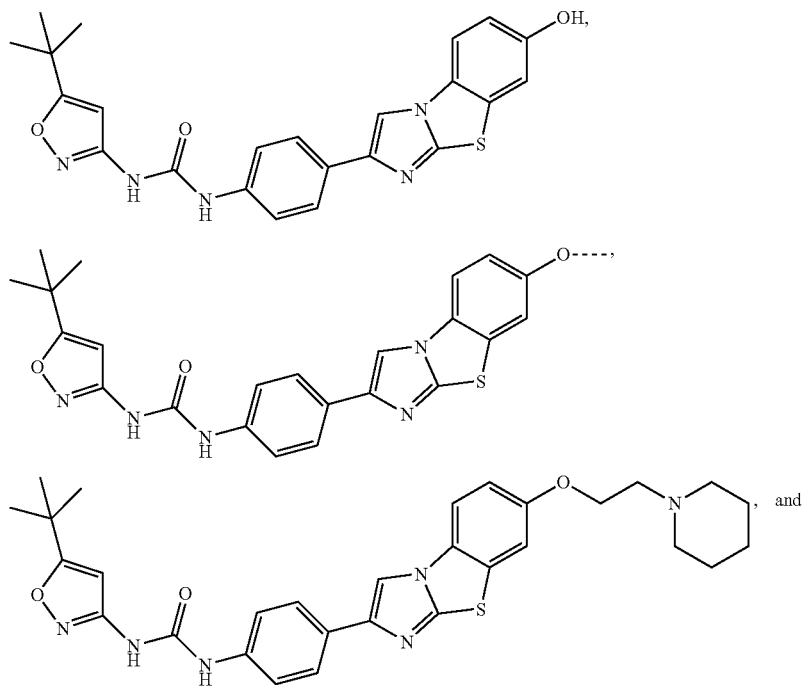

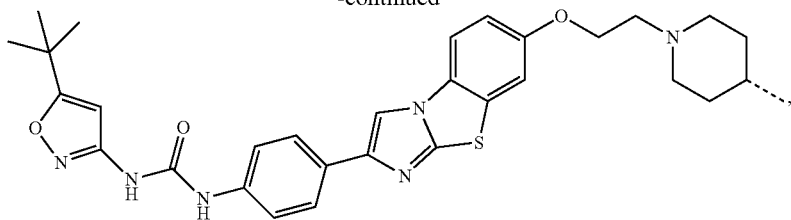
wherein the dashed line indicates the site of attachment of the PTM to the VLM via the chemical linking group;
(b) the linker (L) is selected from the group consisting of:
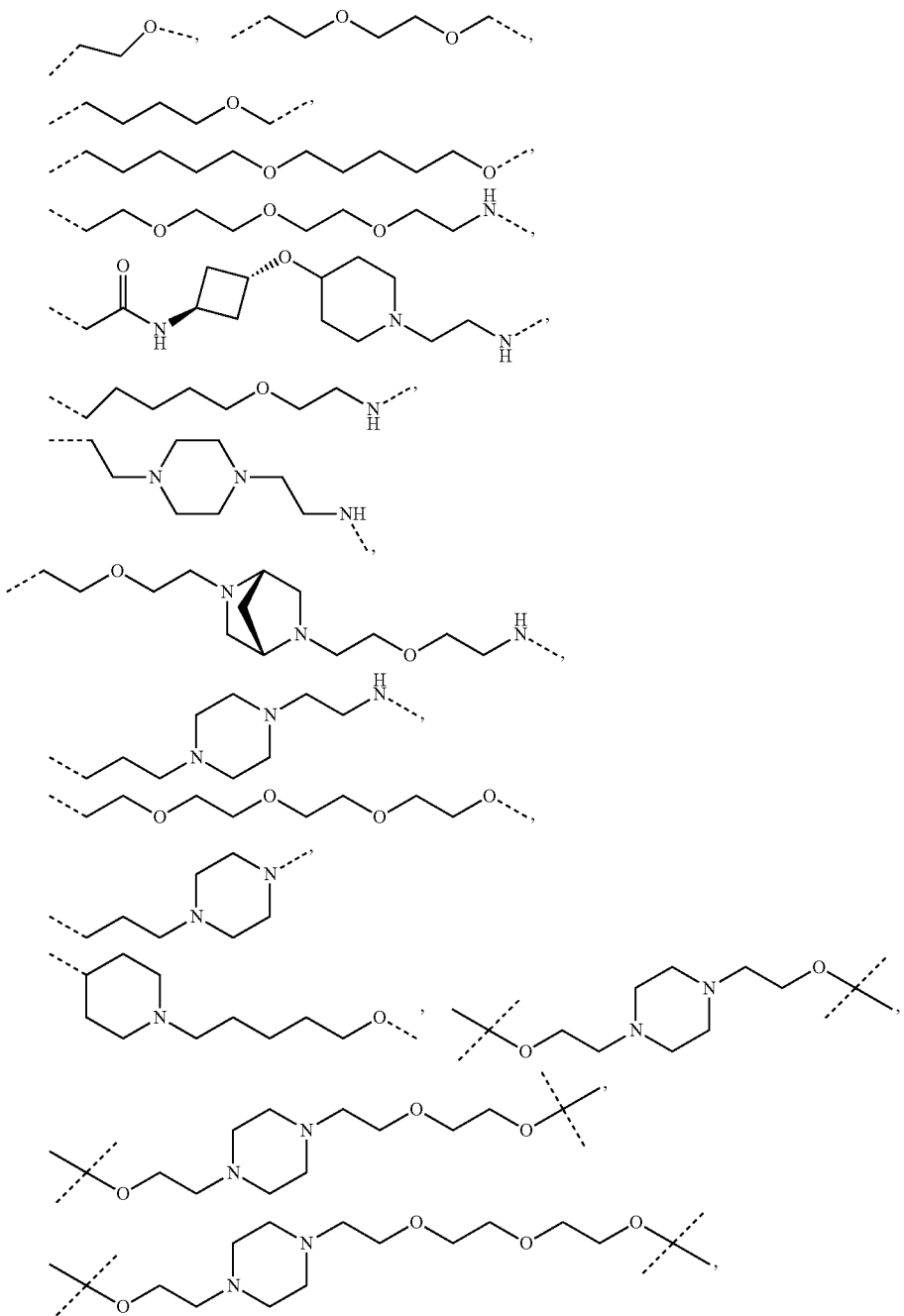

-continued
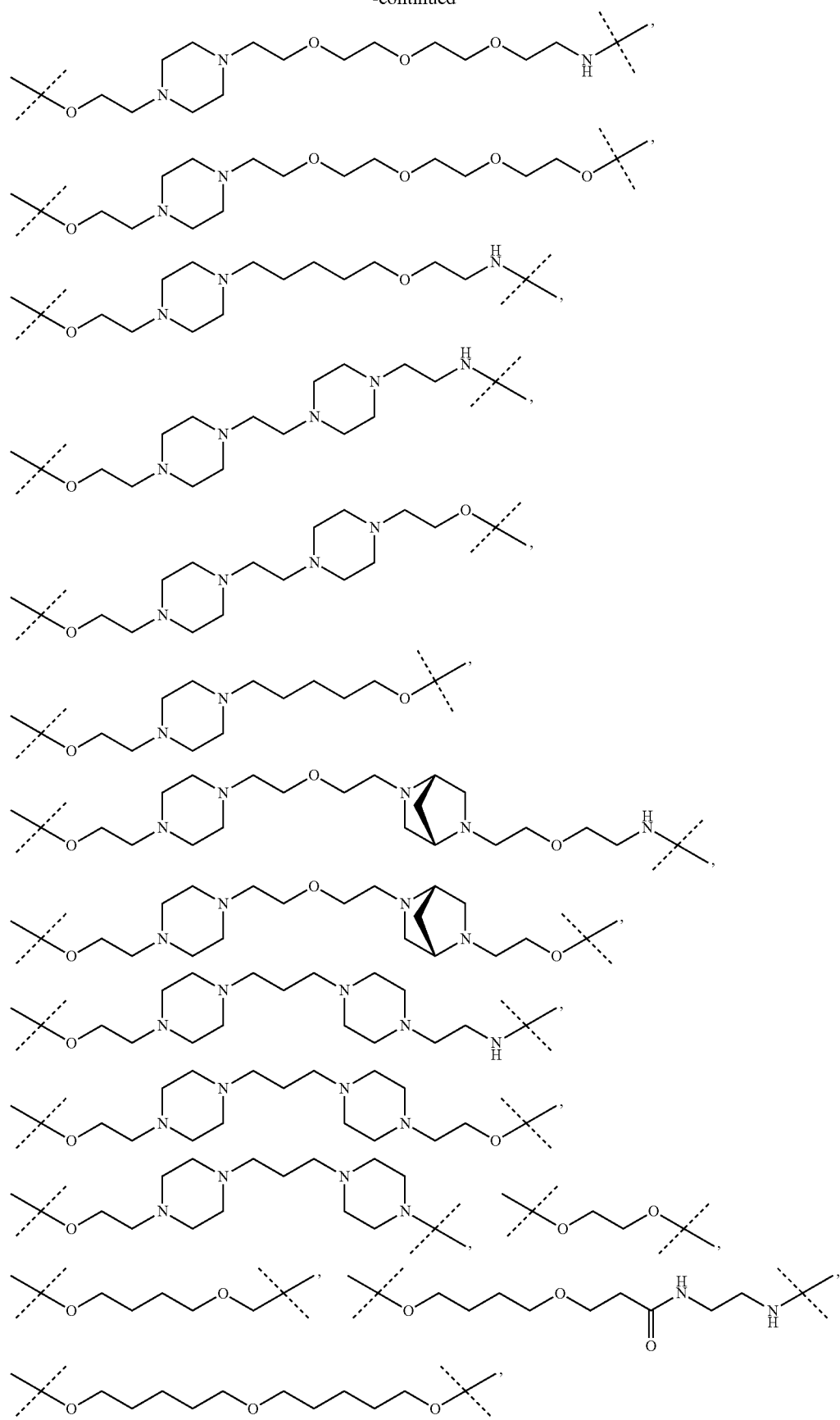

-continued

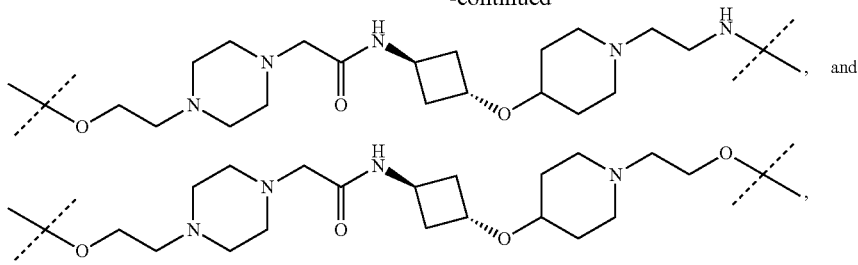

wherein the dashed lines indicate the sites of attachment of the chemical linking group to the VLM and the PTM; and (c) the ULM is selected from the group consisting of:

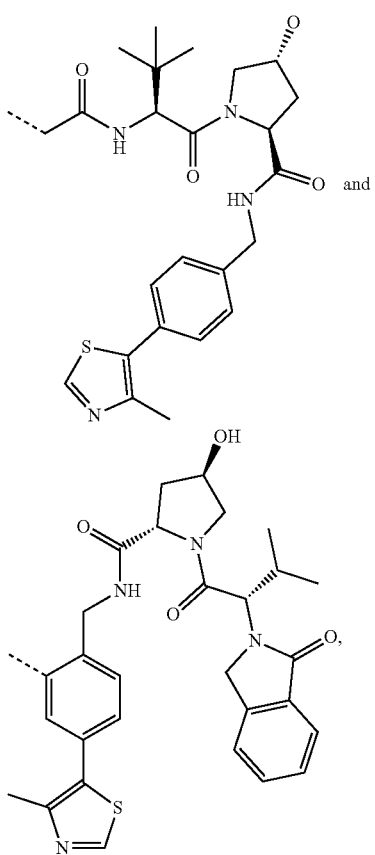

wherein the dashed line indicates the site of attachment of the VLM to the PTM via the chemical linking group.

11. The compound according to claim 1, wherein the PTM is

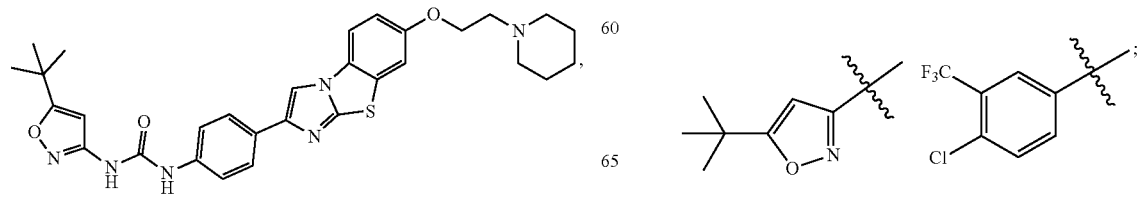

12. A composition comprising an effective amount of a bifunctional compound of claim 1, and a pharmaceutically acceptable carrier.

13. The composition of claim 12, wherein the composition further comprises at least one of additional bioactive agent or another bifunctional compound.

14. The composition of claim 13, wherein the additional bioactive agent is anti-cancer agent.

15. A method for treating a disease or disorder in a subject, the method comprising administering a composition to a subject in need thereof, wherein the composition comprises a pharmaceutically acceptable carrier and an effective amount of at least one compound of claim 1 and the composition is effective in treating or ameliorating at least one symptom of the disease or disorder, wherein the disease or disorder is at least one of T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

16. The compound according to claim 1, wherein at least one of:

Ar of PTM-VI is

L of PTM-VI is the point of attachment to the VLM via the chemical linking group;
Y of PTM-VI is O, NR$_2$R$_2$' or a direct bond;
X$_1$, X$_2$, X$_3$ and X$_4$ of PTM-VI are independently N or CH,
R, R$_2$ and R$_2$' of PTM-VI are each independently selected from the group consisting of hydrogen, alkyl, alkynyl, alkoxyl, carboxylic acid, carboxylic ester or halogen

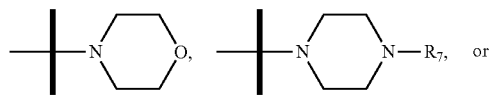

-continued

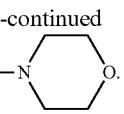

17. The compound according to claim 1, wherein L is selected from:

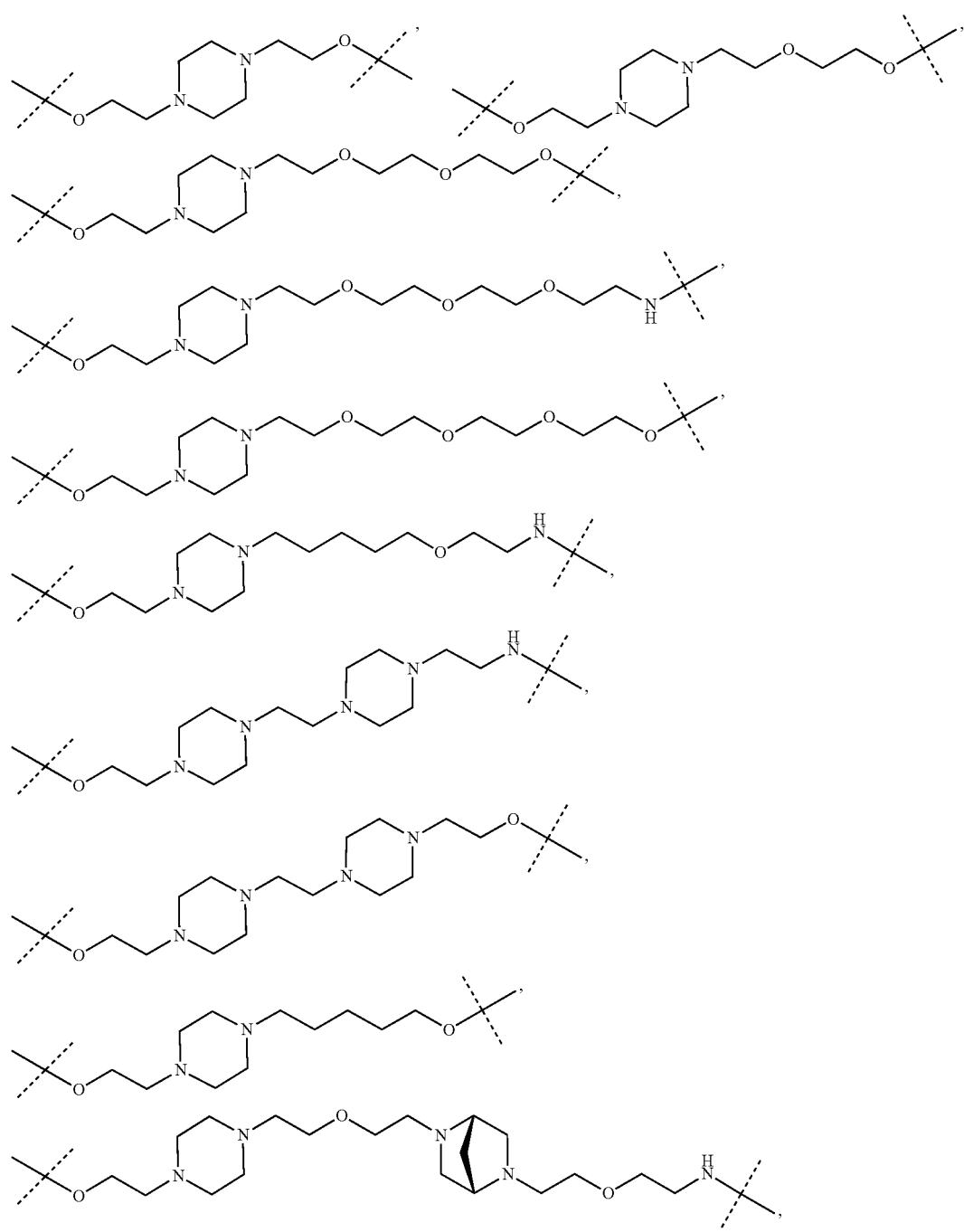

-continued
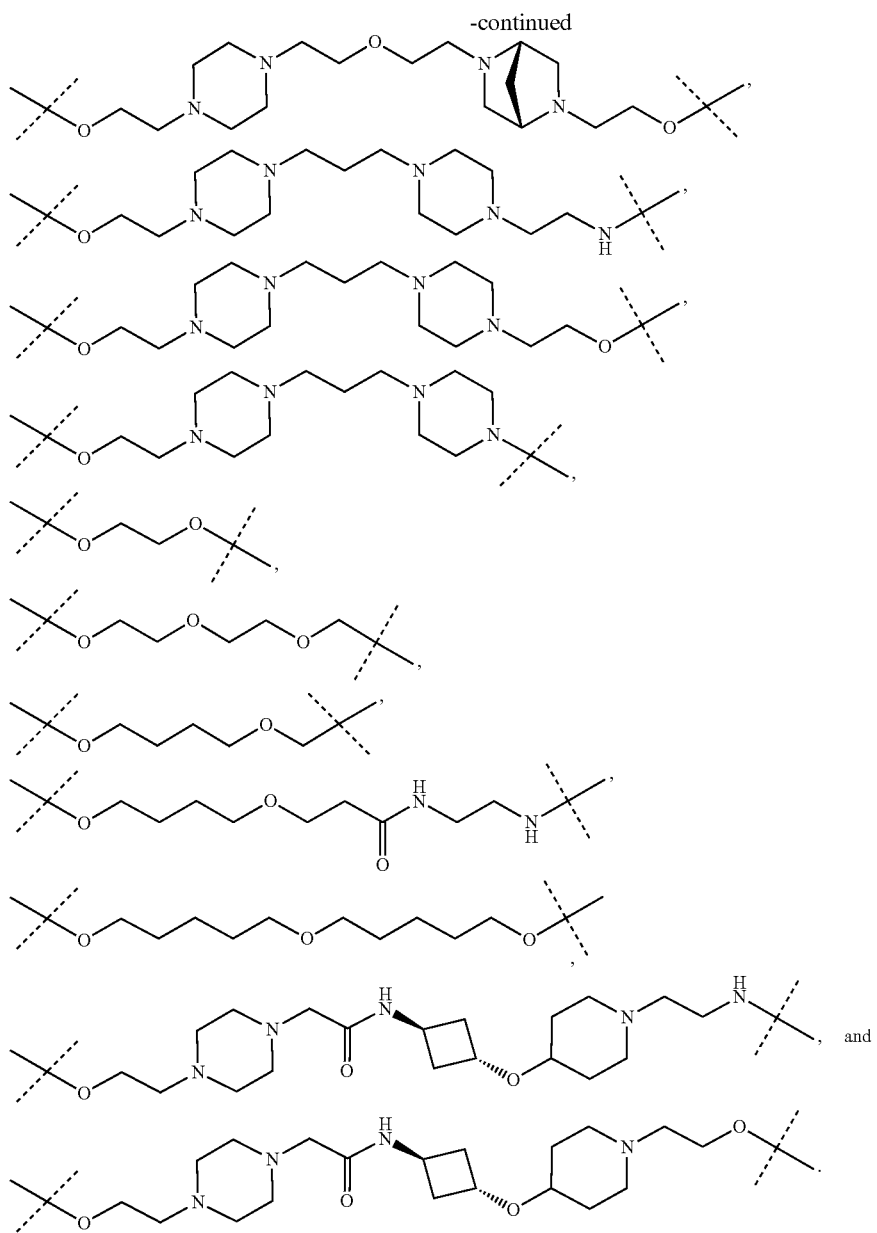
18. The compound according to claim 1, wherein the L has 1 to 6 optionally substitute ethylene glycol units wherein each O is optionally replaced with an optionally substituted N atom.
19. The compound according to claim 1, wherein the L is selected from:
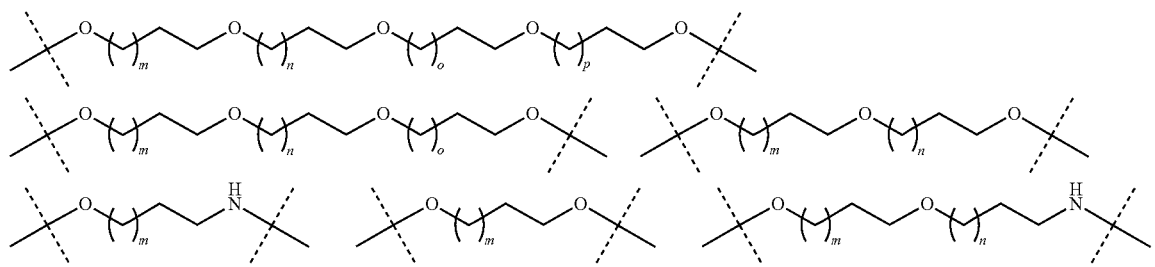

-continued
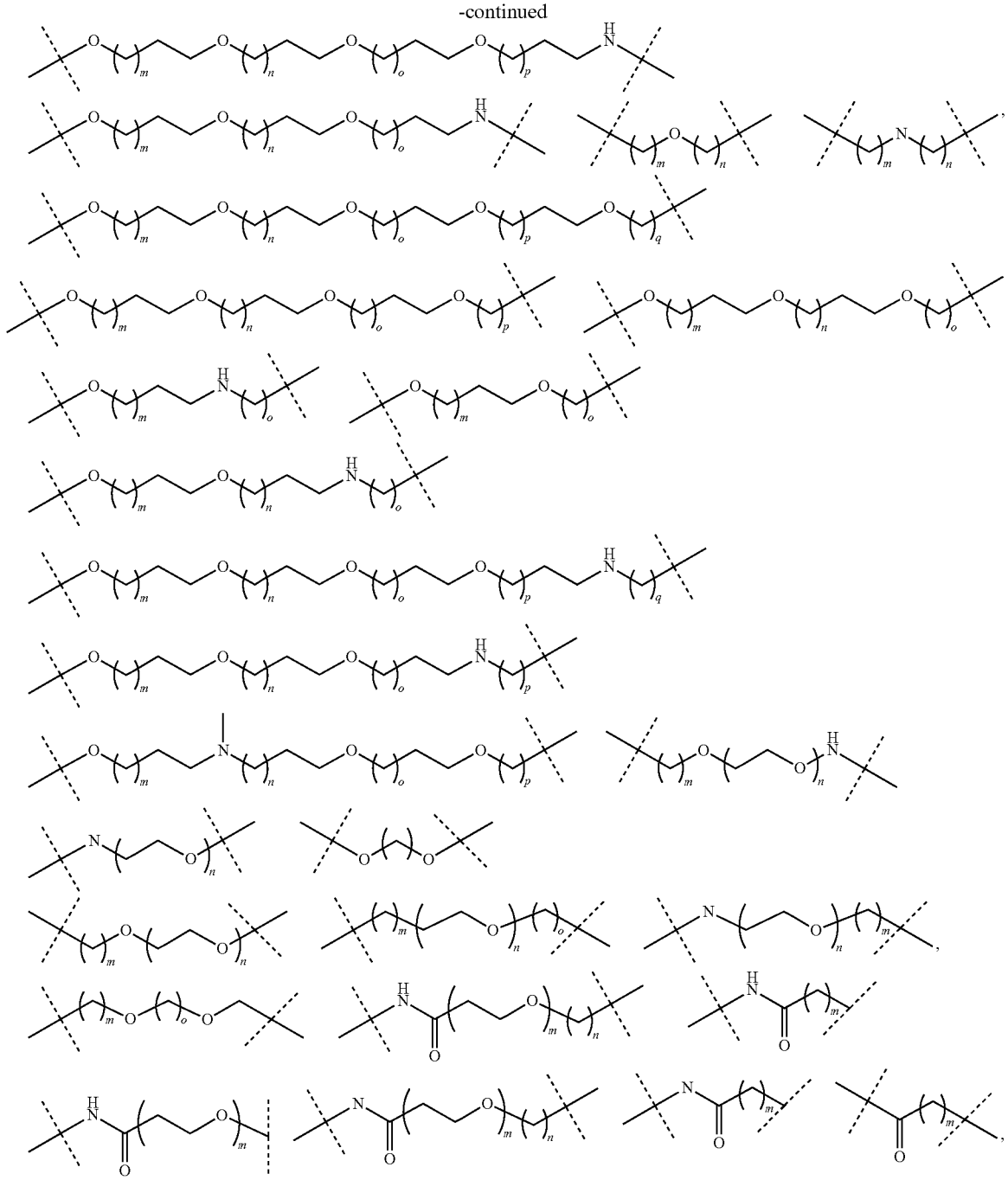
wherein each m, n, o, p, and q is independently 0, 1, 2, 3, 4, 5, 6, or 7.
20. The compound according to claim 1, wherein the L is selected from:
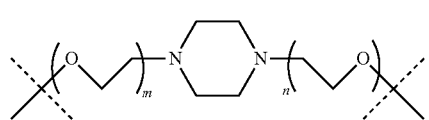
-continued
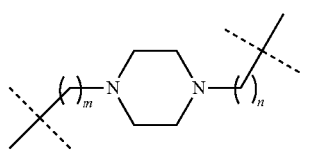

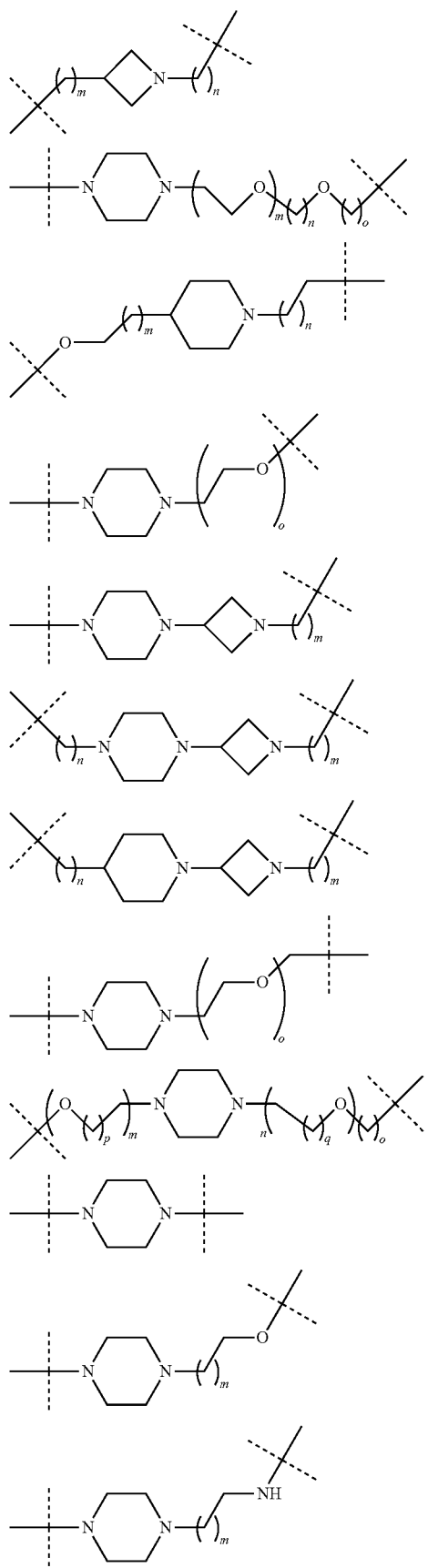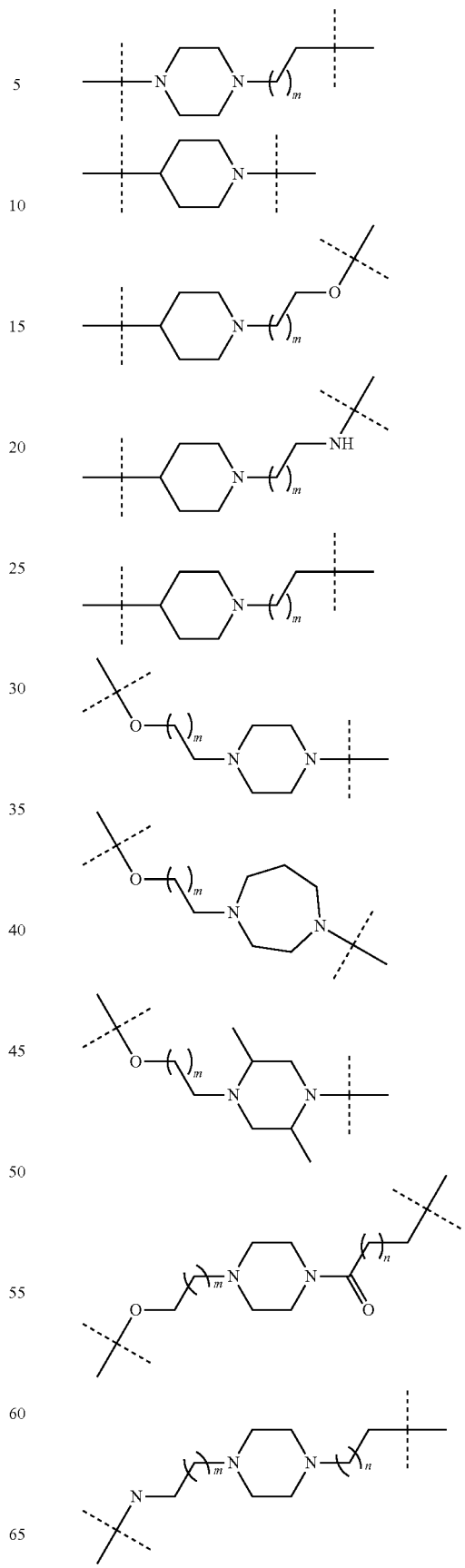

749
-continued
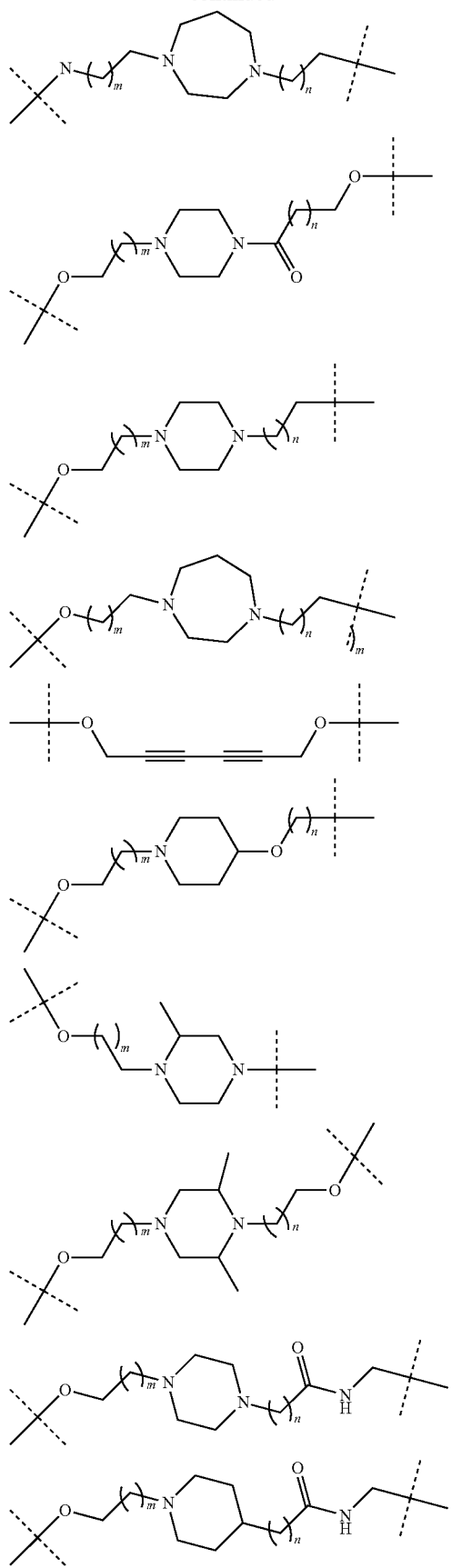
750
-continued
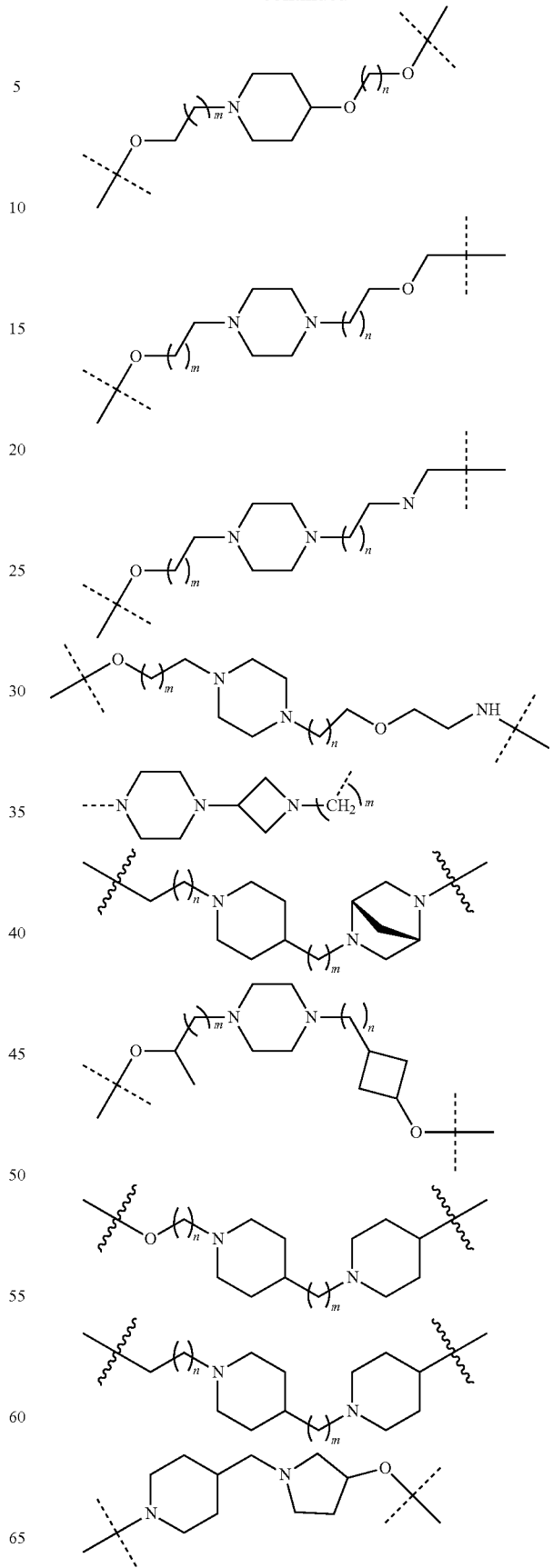

751
-continued
752
-continued
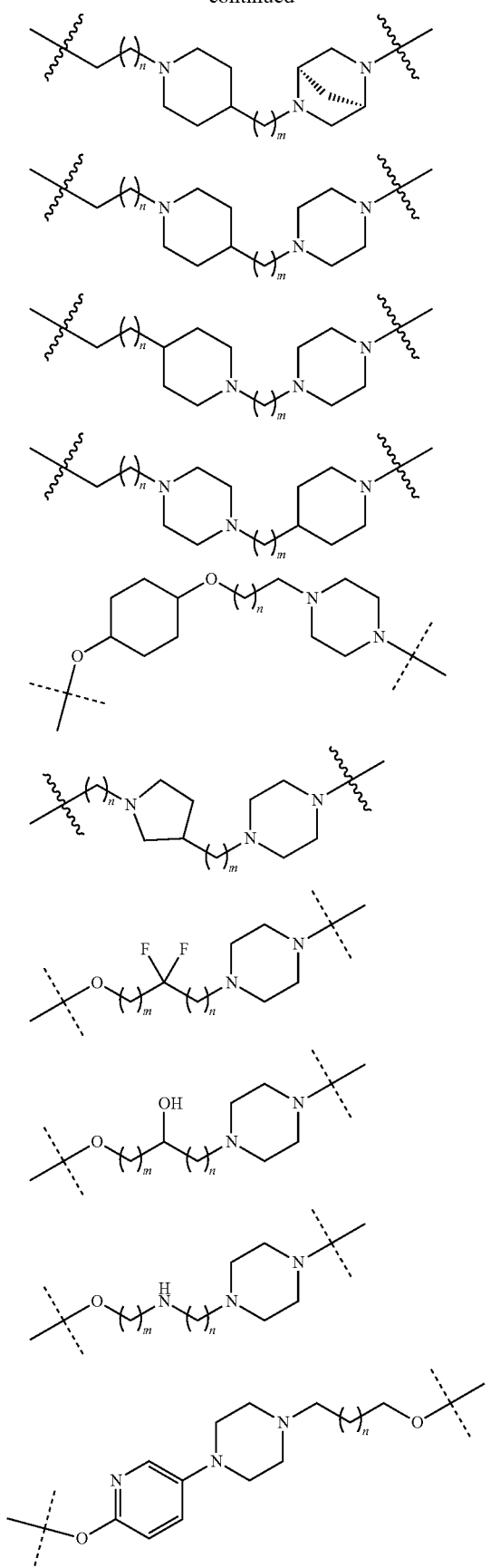
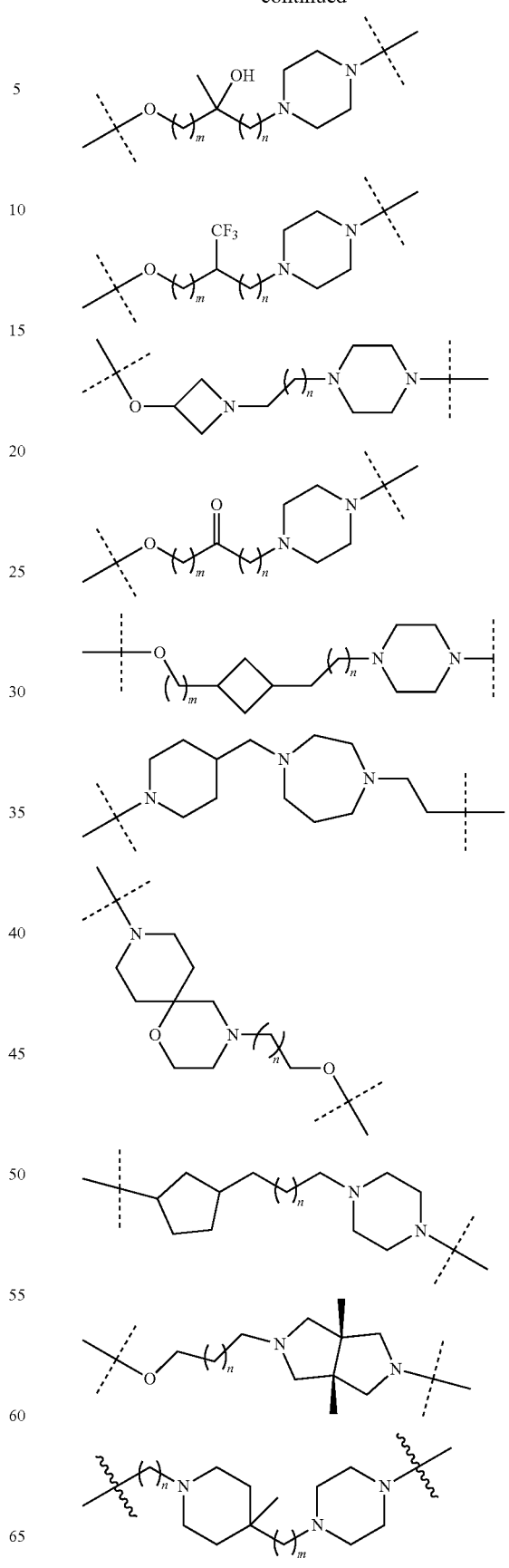

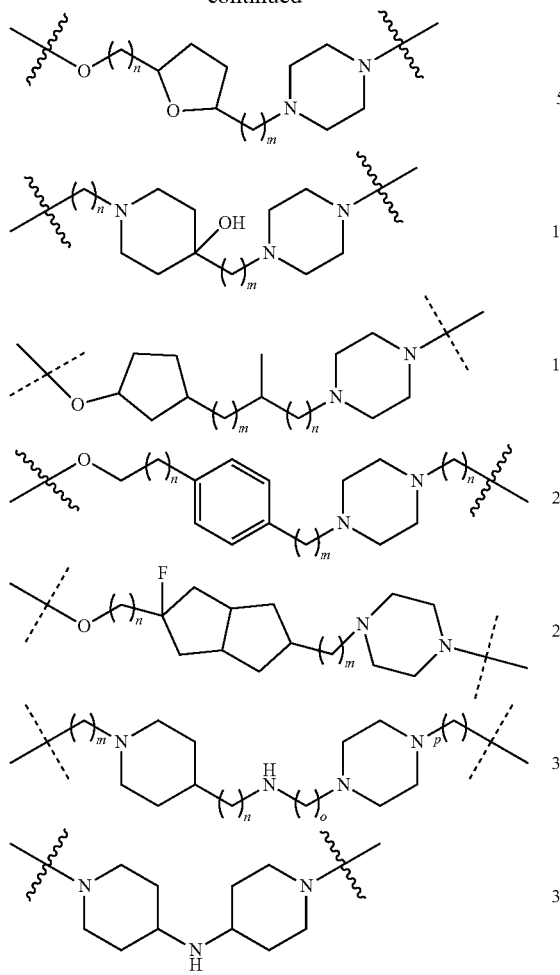

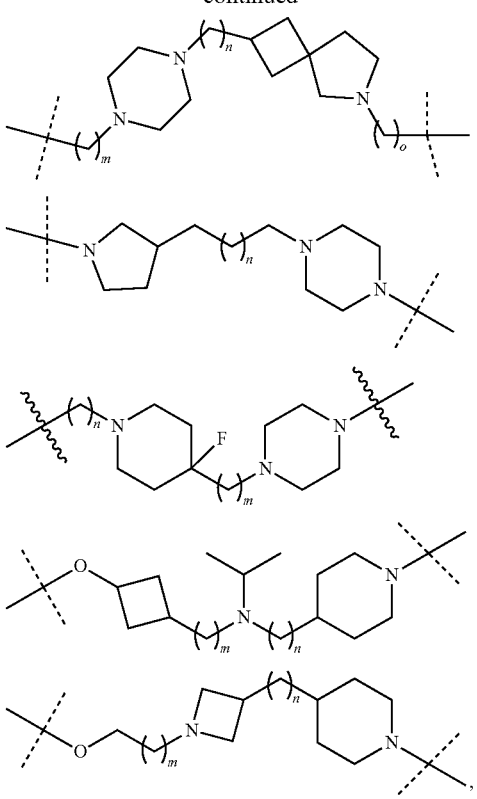

wherein each m, n, o, p, and q is independently 0, 1, 2, 3, 4, 5, 6, or 7.

21. The compound according to claim 1, wherein the L is selected from:

—N(R)—(CH2)$_m$—O(CH2)$_n$—O(CH2)$_o$—O(CH2)$_p$—O(CH2)$_q$—O(CH2)$_r$—OCH2—,

—O—(CH2)$_m$—O(CH2)$_n$—O(CH2)$_o$—O(CH2)$_p$—O(CH2)$_q$—O(CH2)$_r$—OCH2—,

—O—(CH2)$_m$—O(CH2)$_n$—O(CH2)$_o$—O(CH2)$_p$—O(CH2)$_q$—O(CH2)$_r$—O—;

—N(R)—(CH2)$_m$—O(CH2)$_n$—O(CH2)$_o$—O(CH2)$_p$—O(CH2)$_q$—O(CH2)$_r$—O—;

—(CH2)$_m$—O(CH2)$_n$—O(CH2)$_o$—O(CH2)$_p$—O(CH2)$_q$—O(CH2)$_r$—O—;

—(CH2)$_m$—O(CH2)$_n$—O(CH2)$_o$—O(CH2)$_p$—O(CH2)$_q$—O(CH2)$_r$—OCH2—;

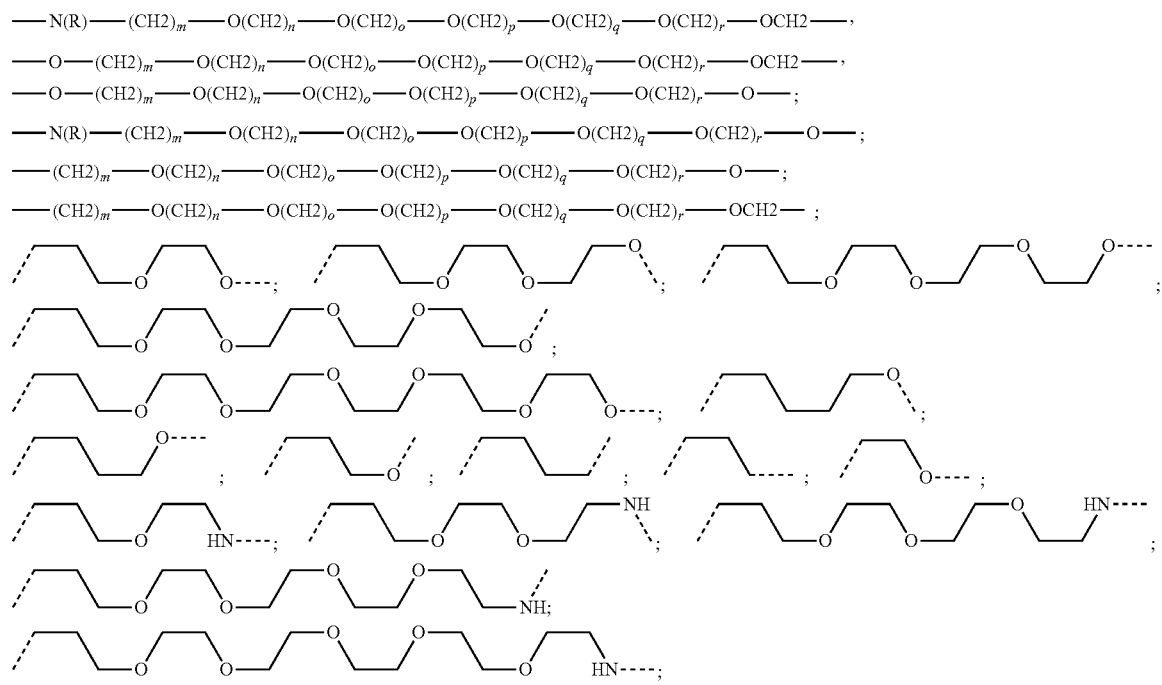

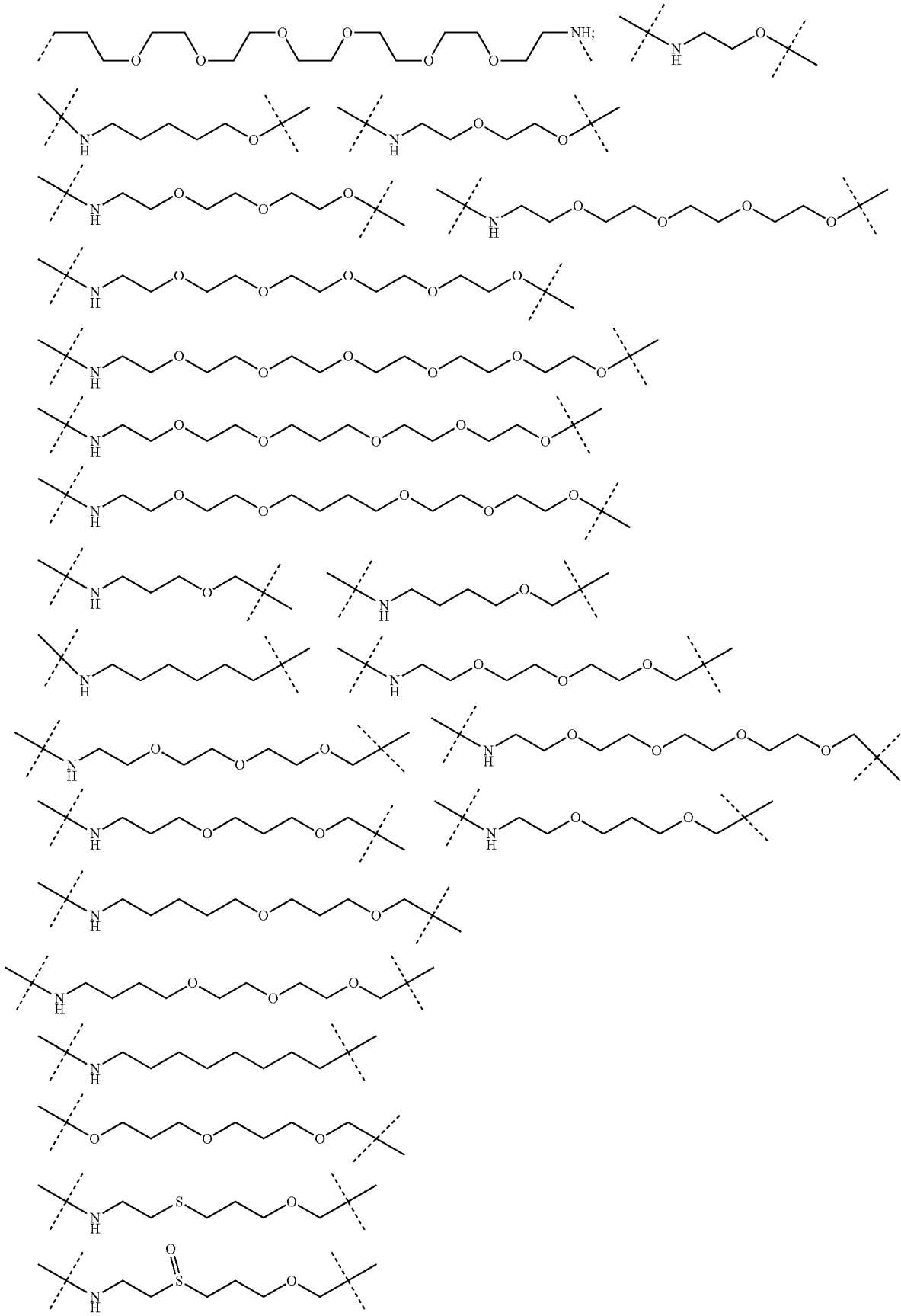

-continued
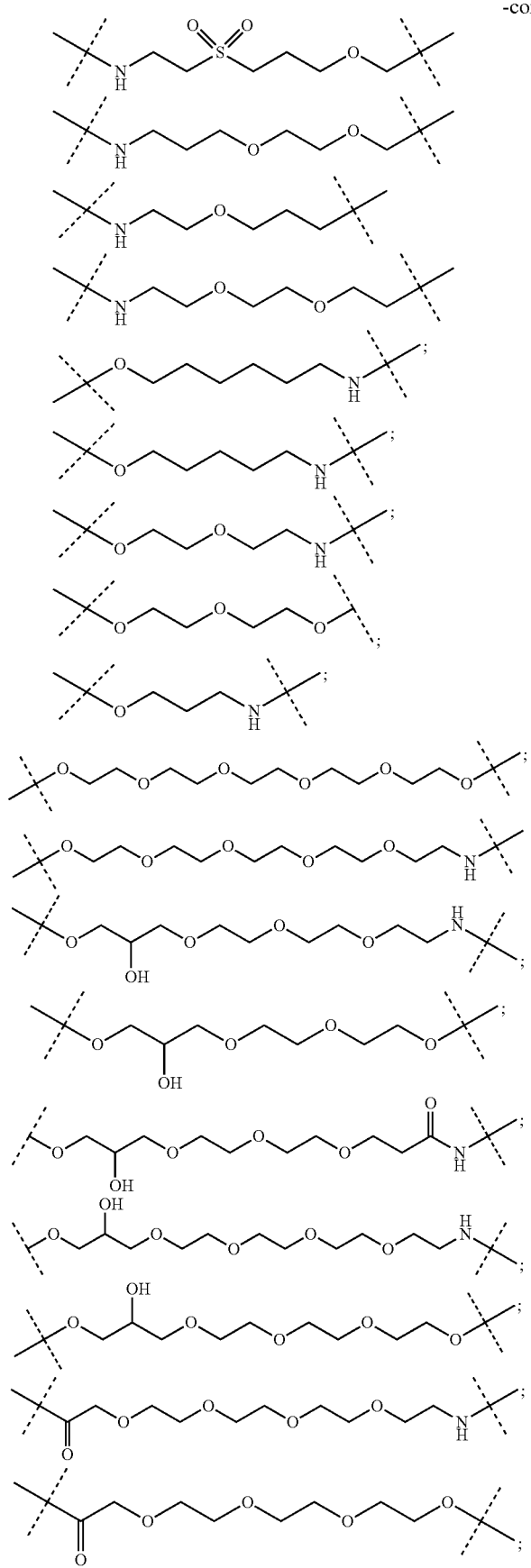

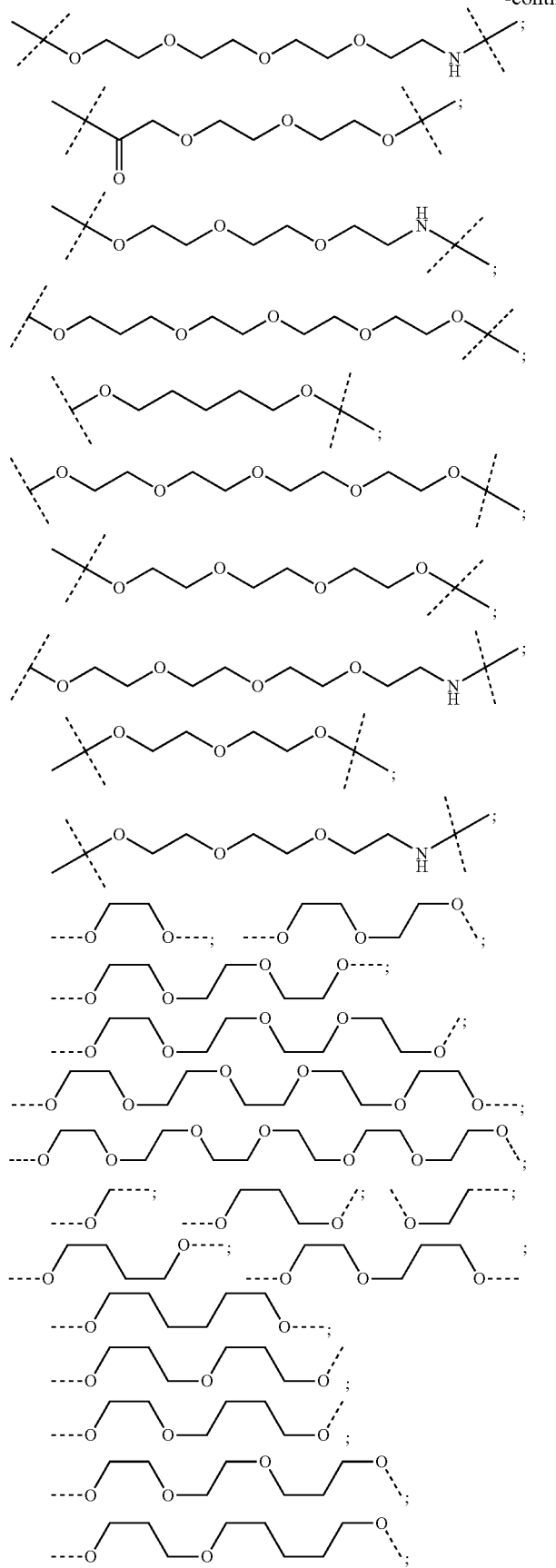

-continued
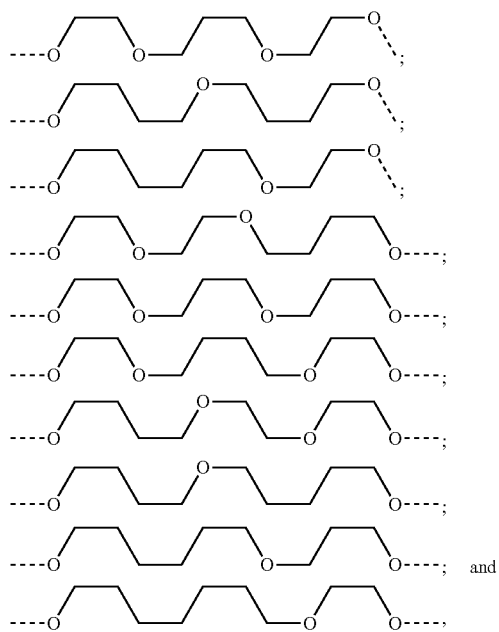
wherein each m, n, o, p, and q and r is independently 0, 1, 2, 3, 4, 5, or 6.
22. The compound according to claim 1, wherein L is selected from:
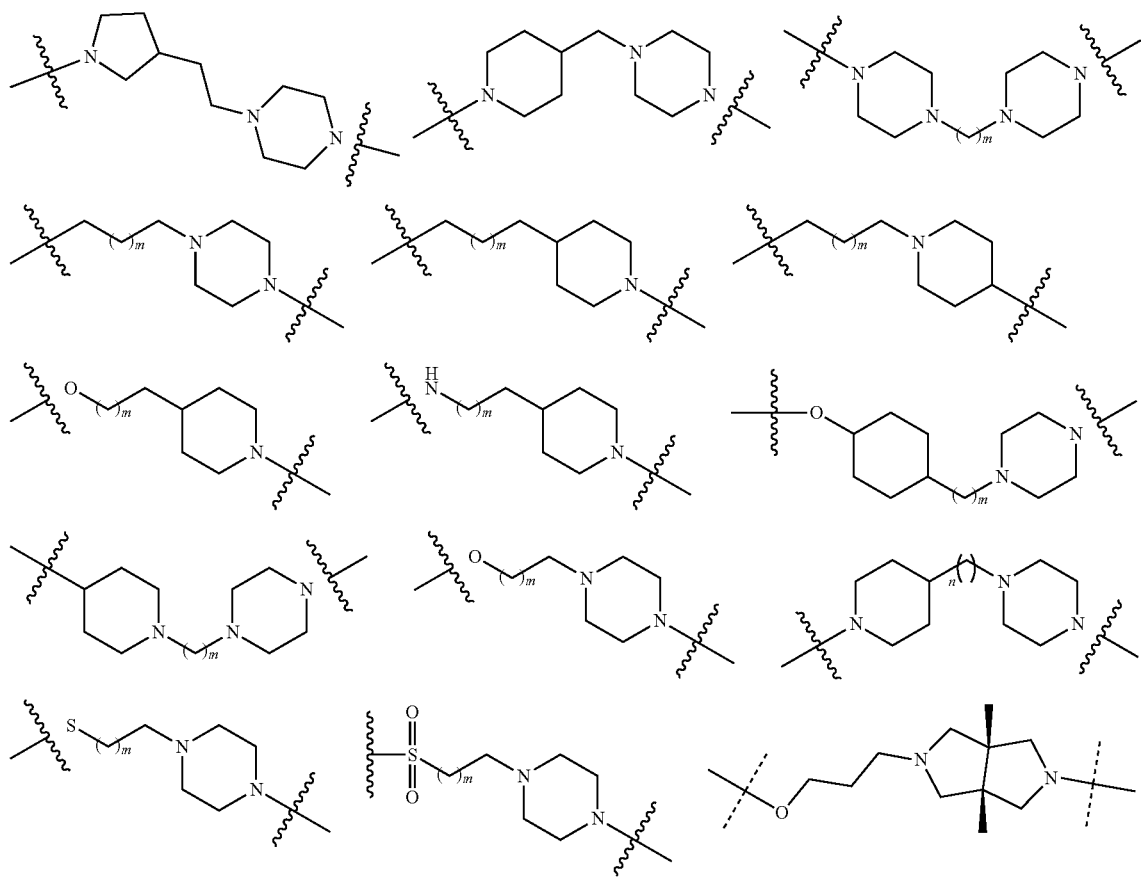

-continued
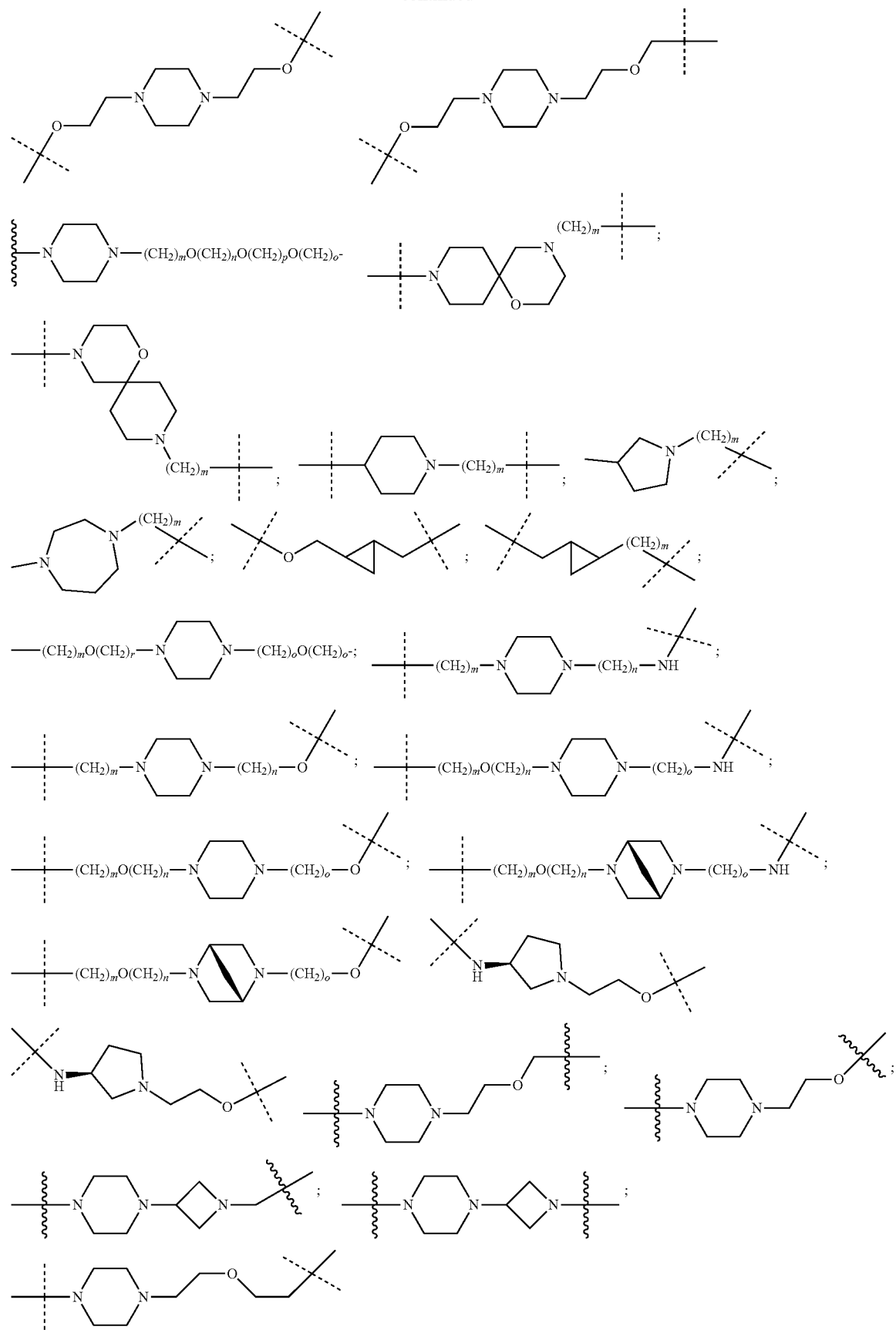

-continued
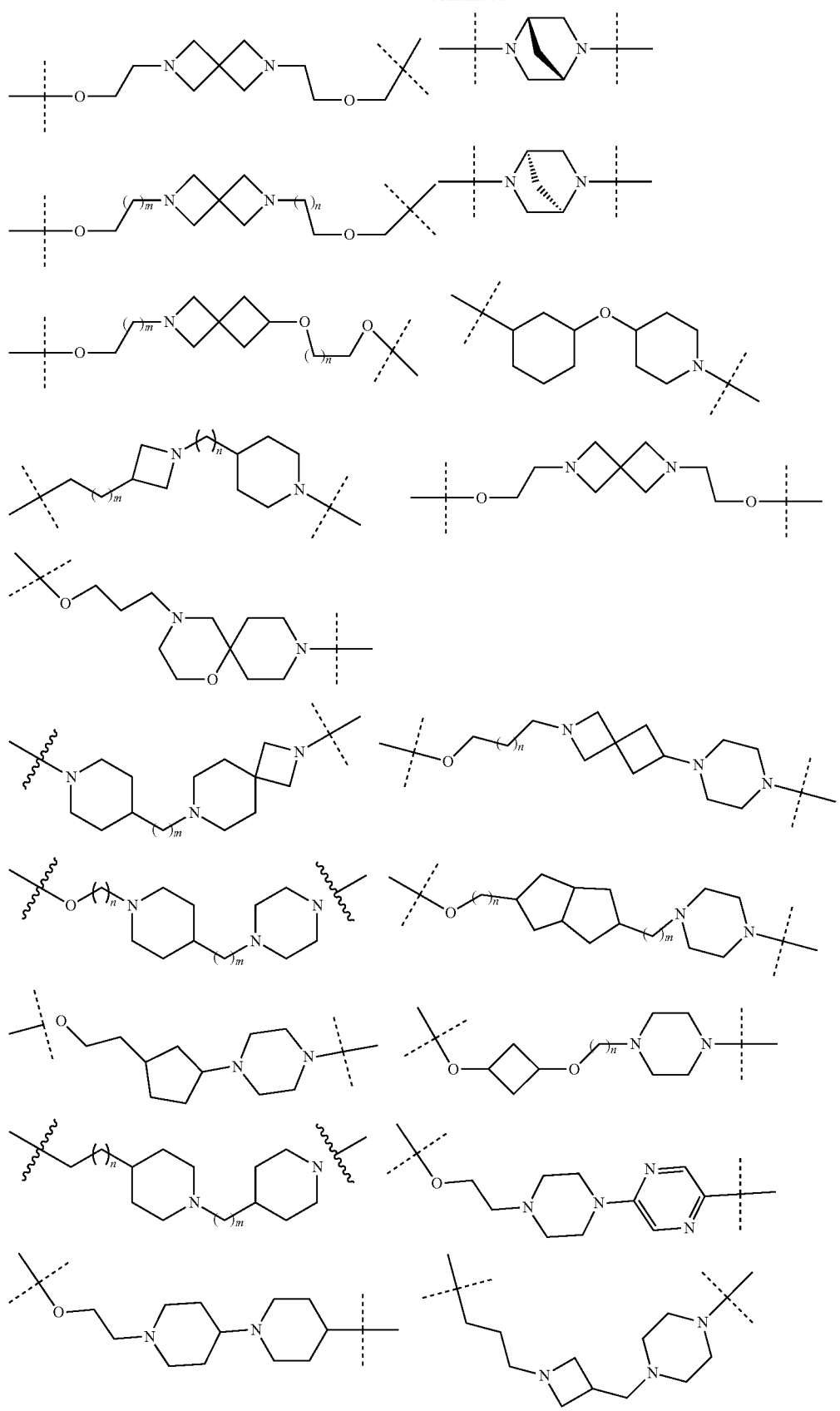

-continued
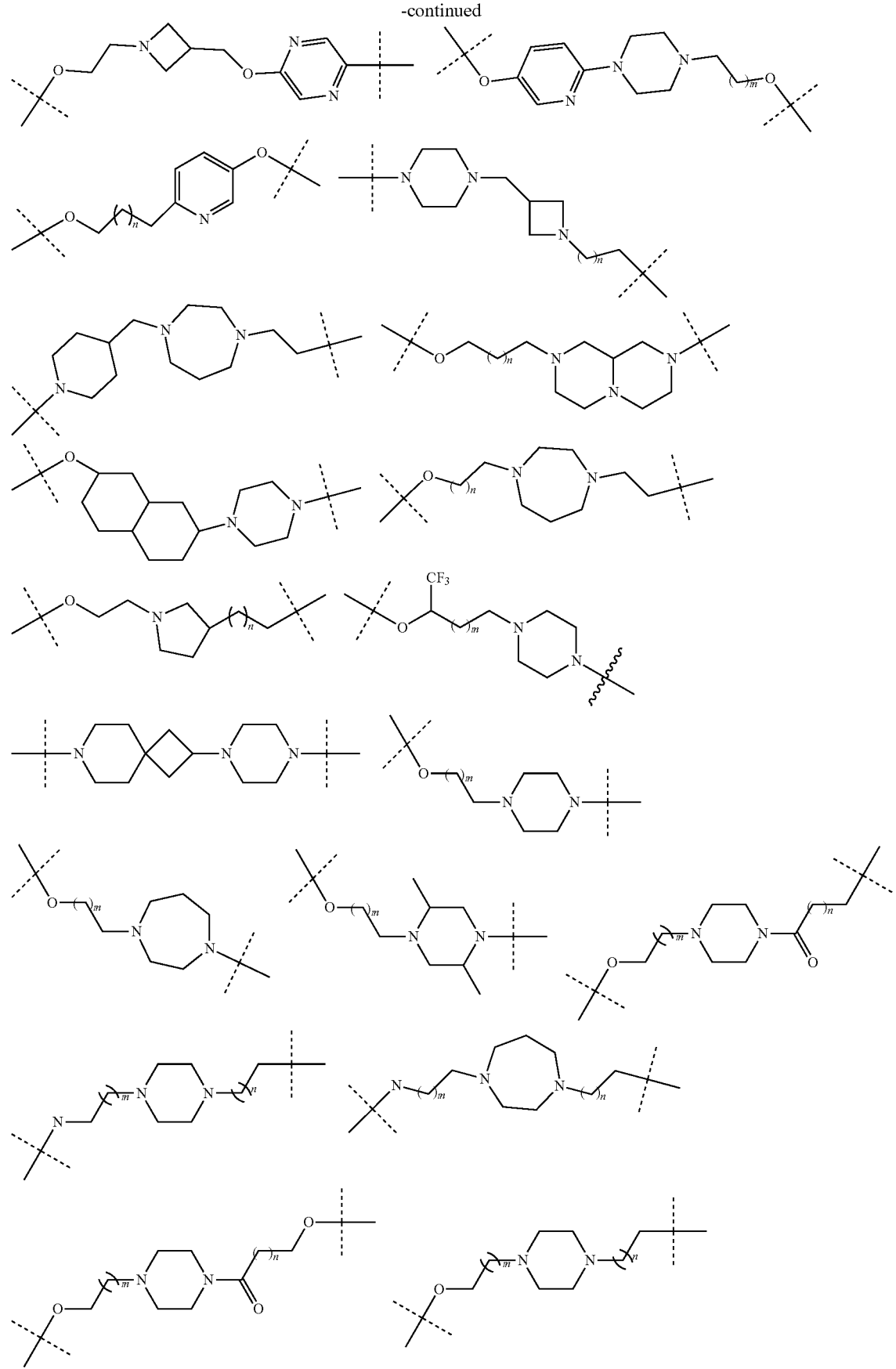

-continued
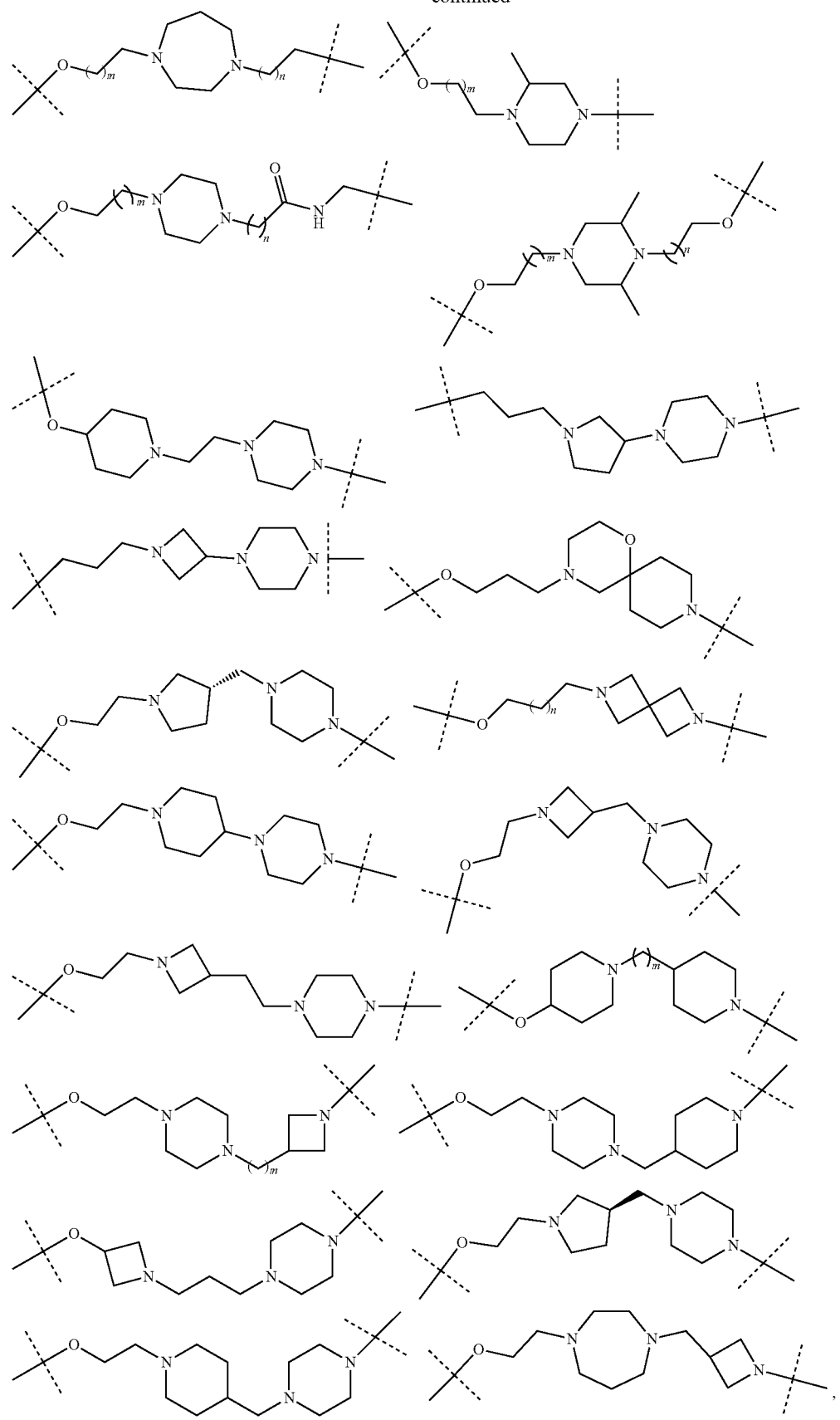

771
wherein each m, n, o, p, q, and r, are independently 0, 1, 2, 3, 4, 5, with the proviso that when the number is zero, there
772
is no N—O or O—O bond, R is selected from the group H, methyl and ethyl, and X is selected from the group H and F;
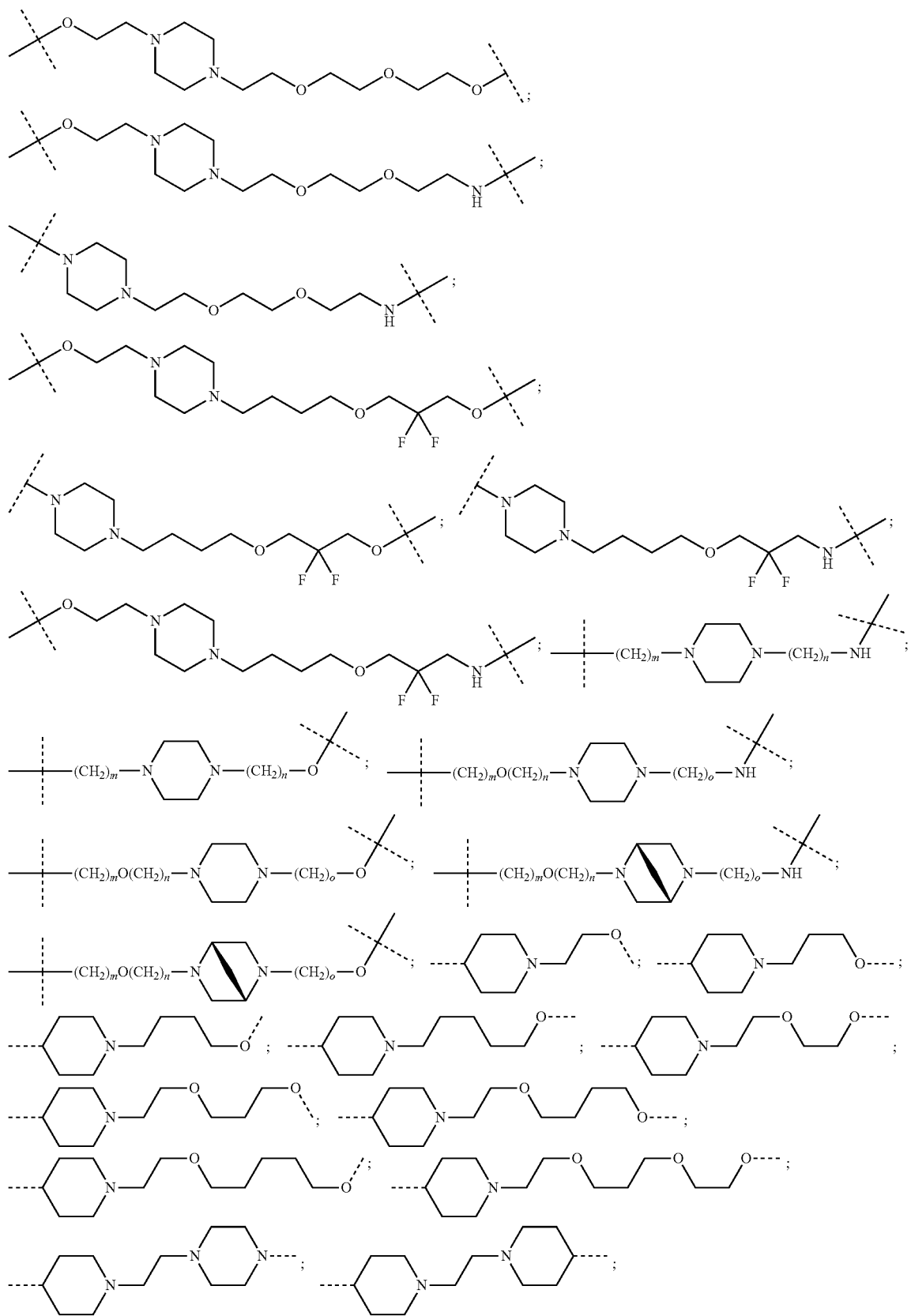

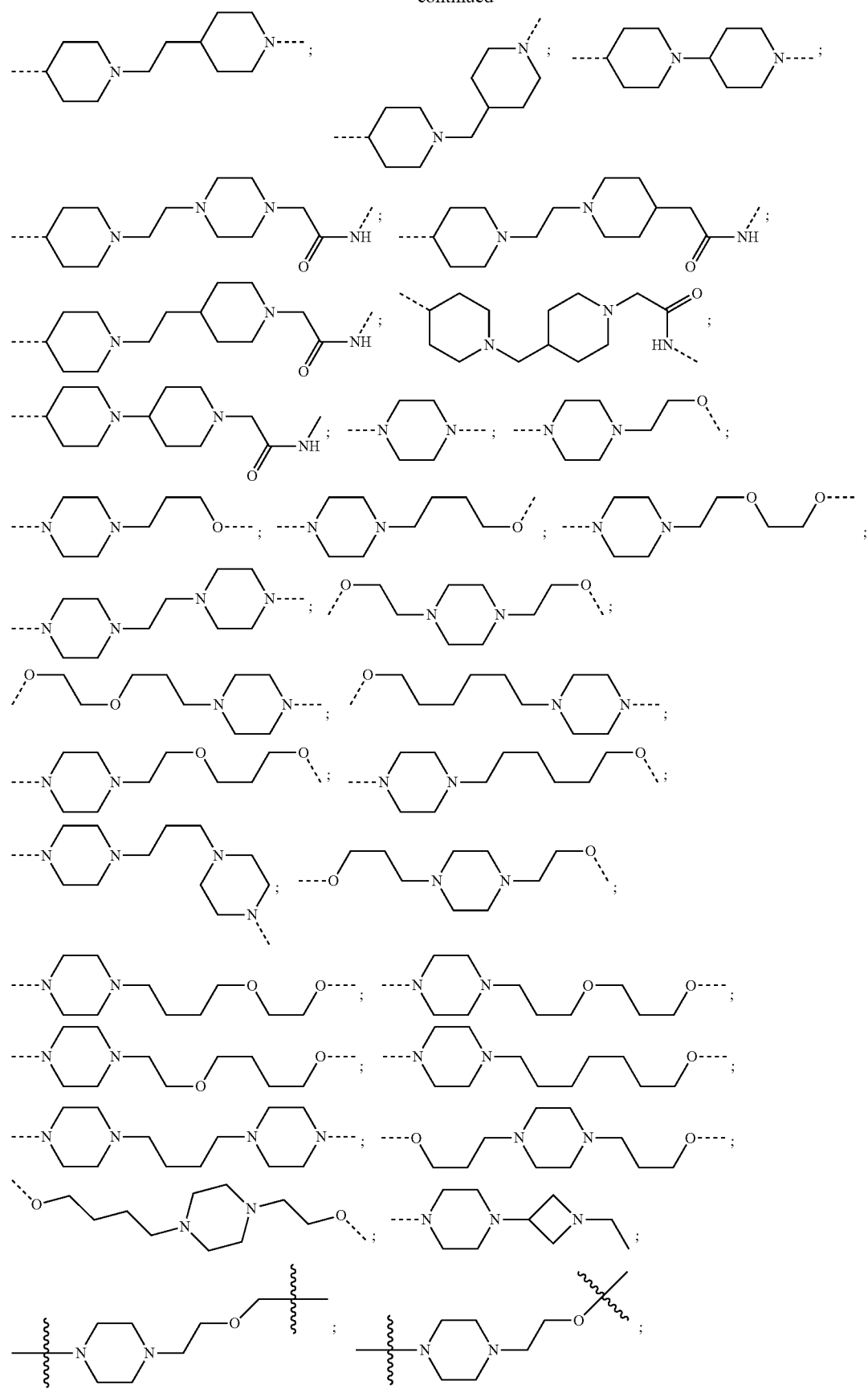

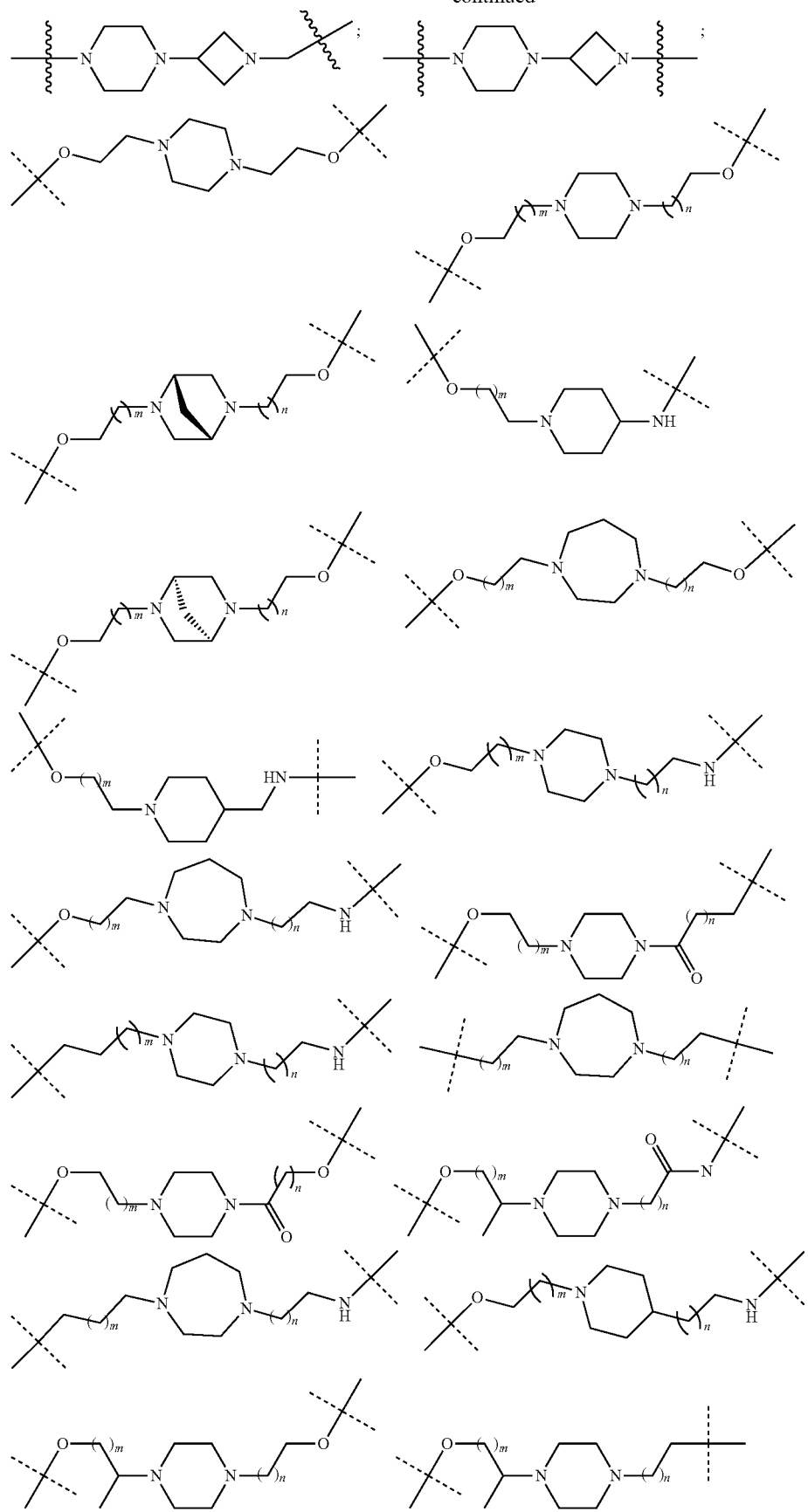

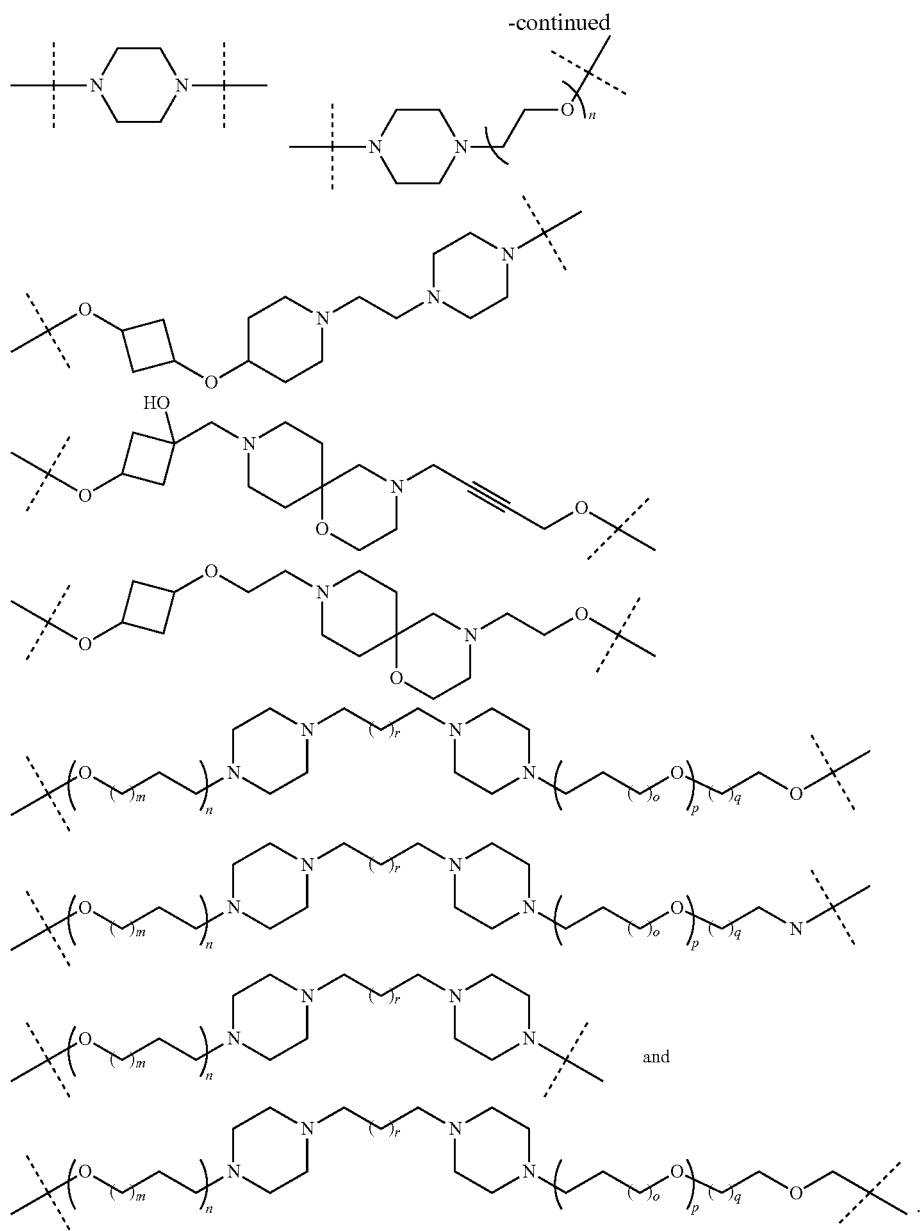
23. The compound according to claim 1, wherein the L is selected from:
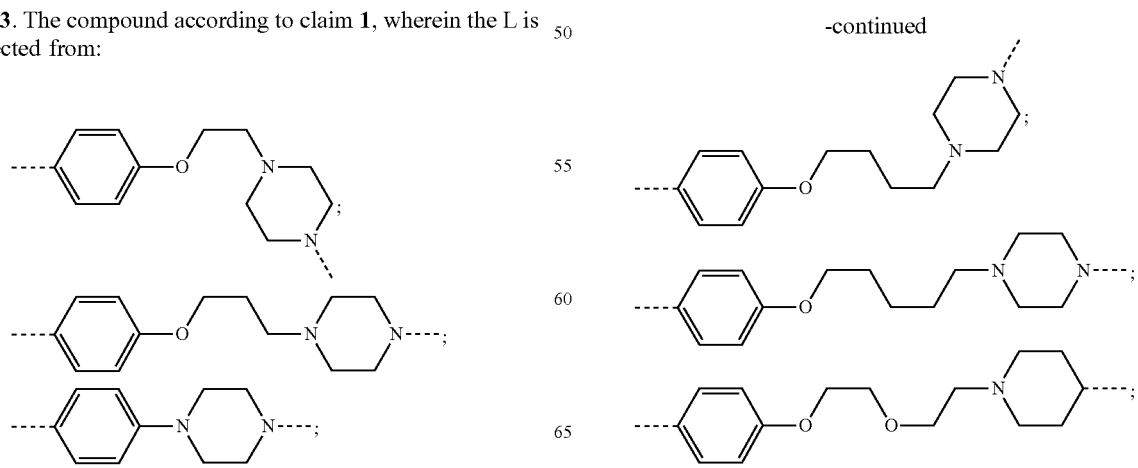

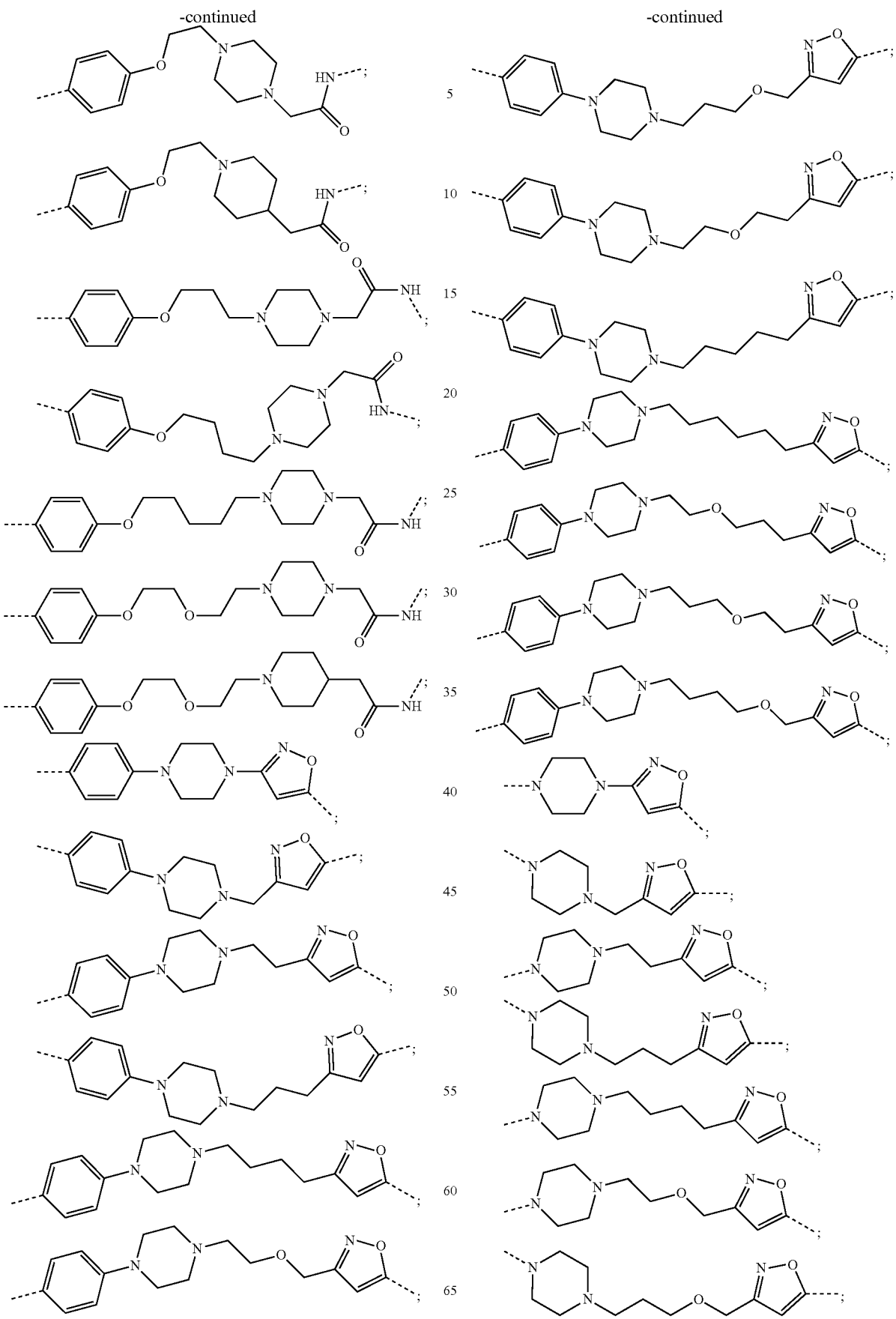

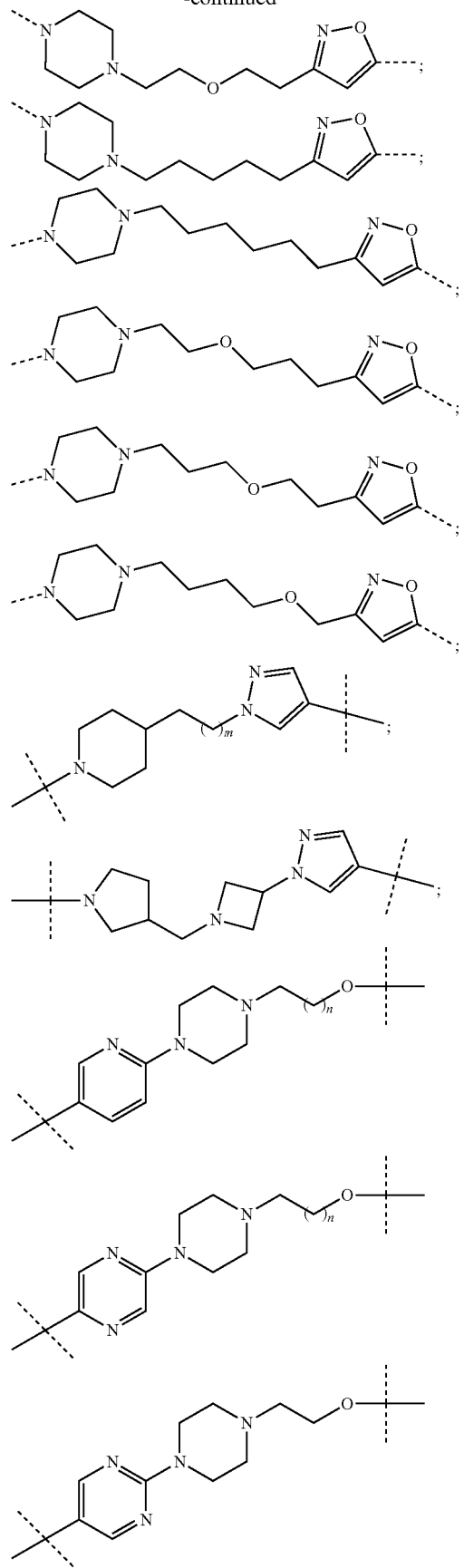
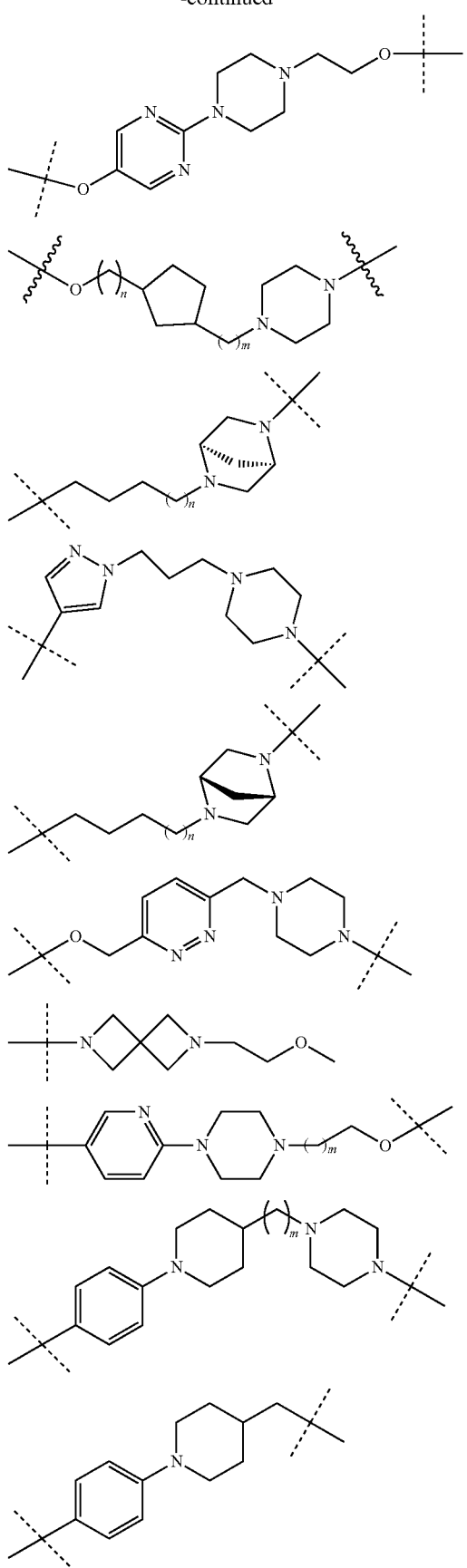

783
-continued
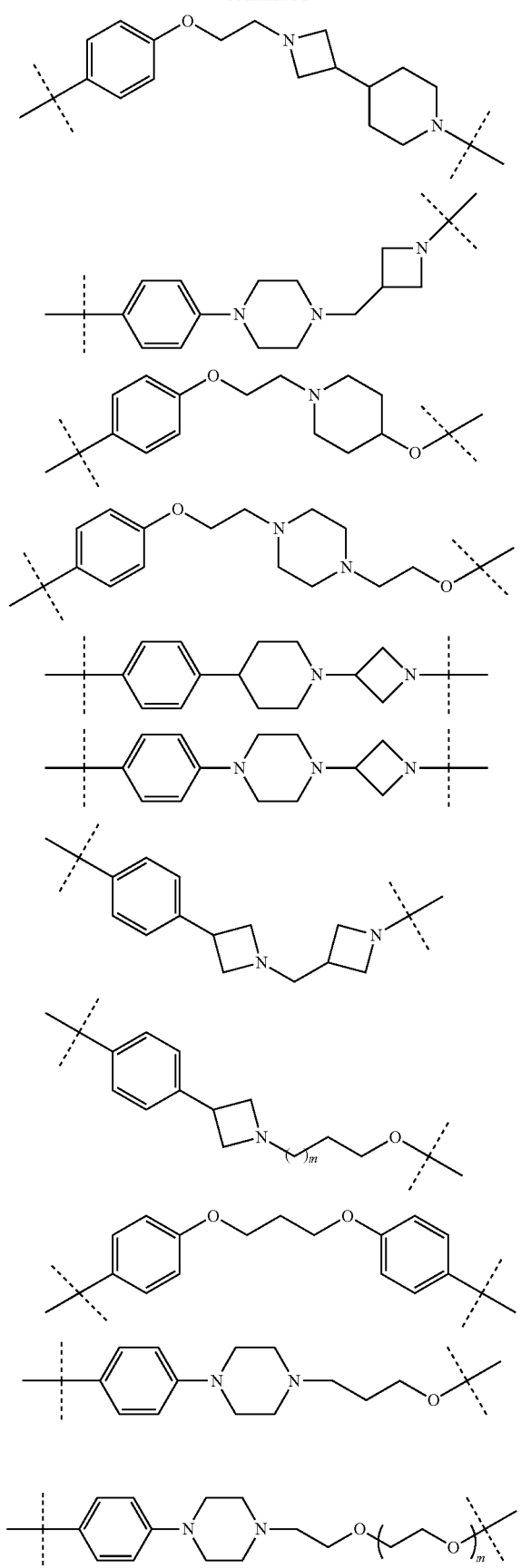
784
-continued
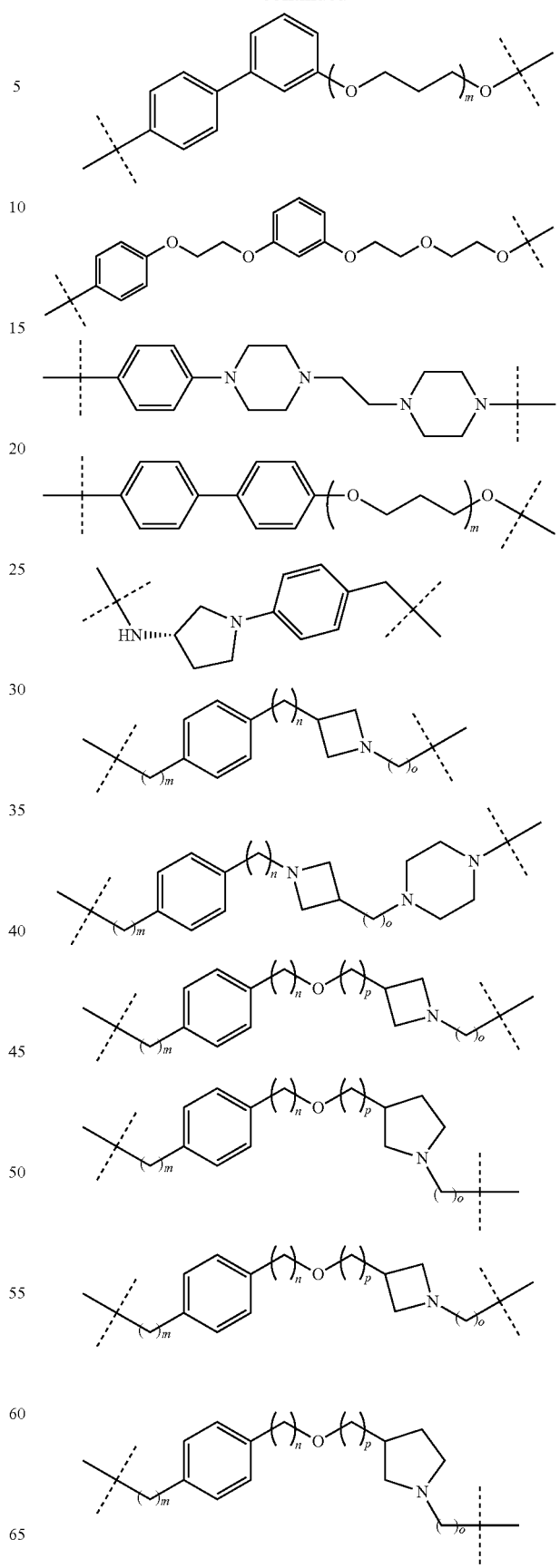

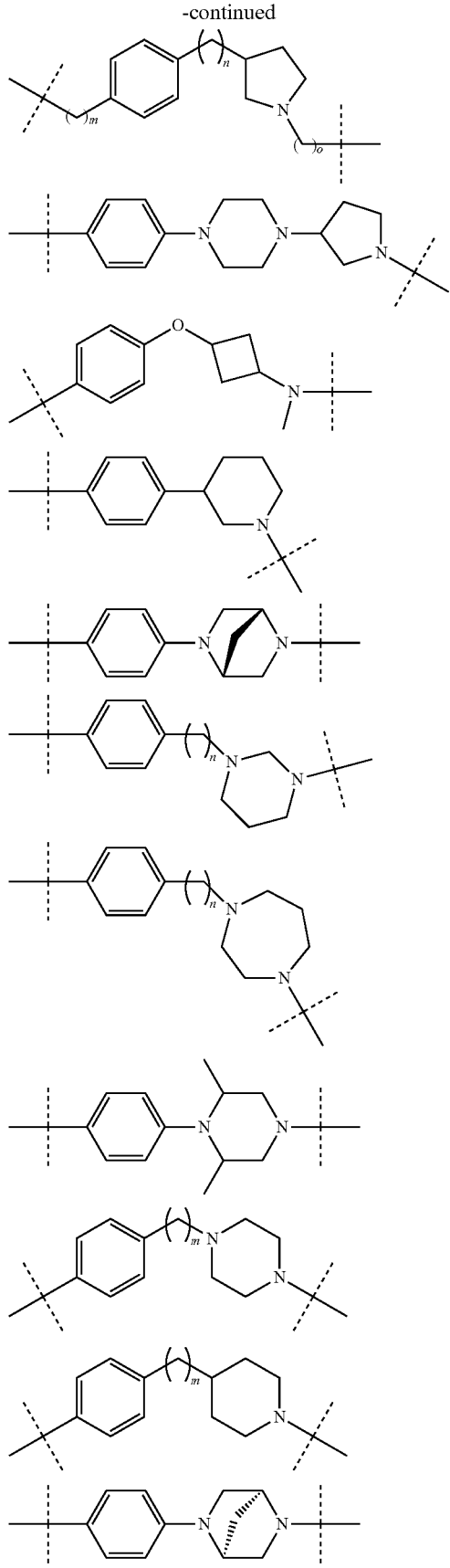
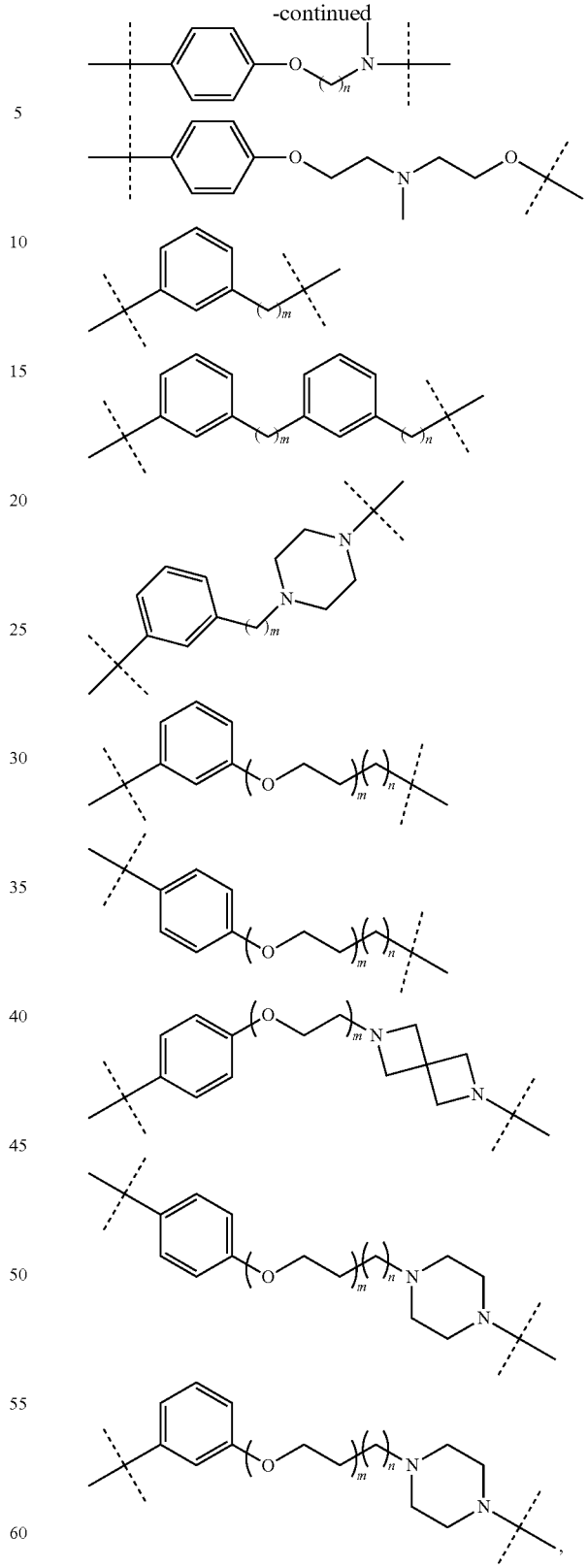
wherein each m and n are independently selected from 0, 1, 2, 3, 4, 5, or 6.
* * * * *